United States Patent
Lairson et al.

(10) Patent No.: US 10,336,735 B2
(45) Date of Patent: Jul. 2, 2019

(54) SMALL MOLECULE INHIBITORS OF FIBROSIS

(71) Applicants: THE CALIFORNIA INSTITUTE FOR BIOMEDICAL RESEARCH, La Jolla, CA (US); THE SCRIPPS RESEARCH INSTITUTE, La Jolla, CA (US)

(72) Inventors: Luke Lairson, San Diego, CA (US); Arnab K. Chatterjee, San Diego, CA (US); Michael Bollong, San Diego, CA (US); Baiyuan Yang, San Diego, CA (US); Peter G. Schultz, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/534,225

(22) PCT Filed: Dec. 9, 2015

(86) PCT No.: PCT/US2015/064814
§ 371 (c)(1),
(2) Date: Jun. 8, 2017

(87) PCT Pub. No.: WO2016/094570
PCT Pub. Date: Jun. 16, 2016

(65) Prior Publication Data
US 2017/0362211 A1   Dec. 21, 2017

Related U.S. Application Data

(60) Provisional application No. 62/090,267, filed on Dec. 10, 2014, provisional application No. 62/117,846, filed on Feb. 18, 2015.

(51) Int. Cl.
| | | |
|---|---|---|
| *A01N 57/00* | (2006.01) | |
| *C07D 403/10* | (2006.01) | |
| *C07D 405/12* | (2006.01) | |
| *C07D 405/14* | (2006.01) | |
| *C07D 495/04* | (2006.01) | |

(52) U.S. Cl.
CPC ......... *C07D 405/14* (2013.01); *C07D 403/10* (2013.01); *C07D 405/12* (2013.01); *C07D 495/04* (2013.01); *A01N 57/00* (2013.01)

(58) Field of Classification Search
USPC ...................................................... 514/384
See application file for complete search history.

(56) References Cited

U.S. PATENT DOCUMENTS

| | | |
|---|---|---|
| 4,267,179 A | 5/1981 | Heeres et al. |
| 4,619,931 A | 10/1986 | Heeres et al. |
| 4,791,111 A | 12/1988 | Heeres et al. |
| 5,521,186 A | 5/1996 | Heeres et al. |
| 6,384,030 B1 | 5/2002 | Meerpoel et al. |
| 6,498,165 B1 | 12/2002 | Armstrong et al. |
| 9,663,499 B2 | 5/2017 | Lairson |
| 2004/0019211 A1 | 1/2004 | Remenar et al. |
| 2010/0092479 A1 | 4/2010 | Johansen et al. |
| 2010/0286114 A1 | 11/2010 | Thomas et al. |
| 2011/0027286 A1 | 2/2011 | Thurston et al. |
| 2011/0183948 A1 | 7/2011 | Levine et al. |
| 2014/0050720 A1 | 2/2014 | Smider et al. |

FOREIGN PATENT DOCUMENTS

| | | |
|---|---|---|
| CN | 1135229 A | 11/1996 |
| EP | 0957101 A1 | 11/1999 |
| WO | WO-9633193 A1 | 10/1996 |
| WO | WO-2012047762 A2 | 4/2012 |
| WO | WO-2013036866 A1 | 3/2013 |
| WO | WO-2014080251 A1 | 5/2014 |
| WO | WO-2014195888 A1 | 12/2014 |
| WO | WO-2014197738 A1 | 12/2014 |

OTHER PUBLICATIONS

International Application No. PCT/US2015/064814 International Report on Patentability dated Jun. 13, 2017.
Arnold, Lee et al.*Pyrrolo*[2,3-d]*pyrimidines containing an extended 5-substituent as potent and selective inhibitors of lck I.* Bioorganic & Medicinal Chemistry Letters 10(19); 2167-2170 (2000).
Burchat, Andrew F. et al. Pyrazolo[3,4-d]pyrimidines Containing an Extended 3-Substituent as Potent Inhibitors of Lck—a Selectivity Insight. Bioorganic & Medicinal Chemistry Letters 12(12); 1687-1690 (Jun. 2002).
Conway, S. P. et al. Pharmacokinetics and safety of itraconazole in patients with cystic fibrosis. Journal of Antimicrobial Chemotherapy, Mar. 24, 2004, vol. 53, No. 5, pp. 841-847.
Co-pending U.S. Appl. No. 15/488,206, filed Apr. 14, 2017.
Fleisher, David et al., Improved Oral drug delivery: solubility limitations overcome by the use of prodrugs.Advanced Drug Delivery Reviews 19(2); 115-130 (May 22, 1996).
Friedman Scott L. et al. Therapy for Fibrotic Diseases: Nearing the Starting Line. Science Translational Medicine 5(167): 1-17 (Jan. 9, 2013).
Heeres, J. et al. Antimycotic Azoles 7. Synthesis and Antifungal Properties of a Series of Novel Triazol-3-Ones, Journal of Medicinal Chemistry 27(7);894-911 (Jul. 1, 1984).
International Application No. PCT/US14/41174 International Preliminary Report on Patentability dated Dec. 17, 2015.
International Application No. PCT/US14/41174 International Search Report and Written Opinion dated Sep. 9, 2014.
International Application No. PCT/US15/64814 International Search Report and Written Opinion dated May 19, 2016.
Kim, James et al. Itraconazole, a Commonly Used Antifungal that Inhibits Hedgehog Pathway Activity and Cancer Growth James. Cell Press Cancer Cell 17;388-399 (Apr. 13, 2010).
Meerpoel, L. et al. Synthesis and in Vitro and in Vivo Structure—Activity Relationships of Novel Antifungal Triazoles for Dermatology, Journal of Medicinal Chemistry, 48(6);2184—(Mar. 24, 2005).
Nacev, Benjamin A. et al. The Antifungal Drug Itraconazole Inhibits Vascular Endothelial Growth Factor Receptor 2 (VEGFR2) Glycosylation, Trafficking, and Signaling in Endothelial Cells. The Journal of Biological Chemistry, 286(51);44045-44056 (Dec. 23, 2011).

(Continued)

*Primary Examiner* — Kathrien A Cruz
(74) *Attorney, Agent, or Firm* — Wilson Sonsini Goodrich & Rosati

(57) ABSTRACT

Described herein are compounds and compositions for the treatment of a fibrotic disease.

15 Claims, No Drawings

(56) References Cited

OTHER PUBLICATIONS

Naranjo, Tonny W. et al. Combined itraconazole-pentoxifylline treatment promptly reduces lung fibrosis induced by chronic pulmonary paracoccidioidomycosis in mice, Pulmonary Pharmacology & Therapeutics, 24(1); 81-91 (2011).

National Center for Biotechnology Information. PubChem Compound Database; CID=59956220, https://pubchem.ncbi.nlm.nih.gov/compound/59956220 (accessed Apr. 28, 2016).

Okada E, Maruyama Y., Viewpoints, Plastic and Reconstructive Surgery, 120(3);814-821(2007).

Pereira da Silva, J. et al. TGF-β plasma levels in chromoblastomycosis patients during itraconazole treatment. Cytokine, 51;202-206 (2010).

PubChem Compound Database; CID=59956220, https://pubchem.ncbi.nlm.nih.gov/compound/59956220 (created Aug. 20, 2012).

Saulnier et al. An Efficient Method for the Synthesis of Guanidino Prodrugs. Bioorg Med Chem Lett 4(16):1985-1990 (1994).

Shi, Wei et al. Itraconazole Side Chain Analogues: Structure—Activity Relationship Studies for Inhibition of Endothelial Cell Proliferation, Vascular Endothelial Growth Factor Receptor 2 (VEGFR2) Glycosylation, and Hedgehog Signaling. J. Med. Chem. 54(20): 7363-7374 (Oct. 27, 2011).

Skov, M. et al. Itraconazole treatment of allergic bronchopulmonary aspergillosis in patients with cystic fibrosis. Allergy, Jul. 11, 2002, vol. 57, No. 8, pp. 723-728.

Strating, J. et al. Itraconazole Inhibits Enterovirus Replication by Targeting the Oxysterol-Binding Protein. Cell Press, 10;600-615 (Feb. 3, 2015).

U.S. Appl. No. 14/895,813 Notice of Allowance dated Mar. 24, 2017.

U.S. Appl. No. 14/895,813 Office Action dated Sep. 29, 2016.

Wheat, L. Joseph, et al. Clinical Practice Guidelines for the Management of Patients with Histoplasmosis: 2007 Update by the Infectious Diseases Society of America, Clinical Infectious Diseases, 45(7);807-825 (Oct. 1, 2007).

Wynn, Thomas A. Fibrotic disease and TH1/TH2 paradigm. Nature Reviews Immunology 4: 583-594 (Aug. 2004).

Yoshiji, H. et al. Vascular endothelial growth factor and receptor interaction is a prerequisite for murine hepatic fibrogenesis. Gut, Sep. 30, 2003, vol. 52, No. 9, pp. 1347-1354.

Chaudhary, N.I. et al. Inhibition of PDGF, VEGF and FGF signaling attenuates fibrosis. Eur. Respir. J. 29(5):976-985(2007).

SMALL MOLECULE INHIBITORS OF FIBROSIS

BACKGROUND OF THE INVENTION

Fibrosis, generally defined as the production of excessive amounts of connective tissue, develops as a consequence of diverse underlying diseases. Chronic inflammation or tissue damage/remodeling are typical fibrosis inducing events. Specific disease examples include idiopathic pulmonary fibrosis (IPF), liver fibrosis associated with the later stages of alcoholic and nonalcoholic liver cirrhosis, kidney fibrosis, cardiac fibrosis, and keloid formation resulting from abnormal wound healing [Wynn, T. A. (2004) Nature Reviews Immunology. 4: 583-594; Friedman, S. L. (2013) Science Translation Medicine. 5(167):1-17]. Additionally, fibrosis is a key pathological feature associated with chronic autoimmune diseases, including rheumatoid arthritis, Crohn's disease, systemic lupus erythematosus, and scleroderma. Diseases representing a dire unmet medical need include idiopathic pulmonary fibrosis (IPF), scleroderma and non-alcoholic steatohepatitis (NASH) related liver fibrosis. The increased incidence of NASH related liver fibrosis is expected to directly parallel those of type 2 diabetes and obesity.

Scleroderma is a rare chronic autoimmune disease characterized by the replacement of normal tissue with dense, thick fibrous tissue. While the exact underlying cause of scleroderma is unknown, the disease generally involves immune cell mediated activation of dermal myofibroblasts leading to the deposition of excessive amounts of extracellular matrix proteins (e.g., type I collagen) that causes a thickening of the skin and in some cases the hardening and eventual failure of multiple organs. At present, there is no cure for scleroderma. Treatment is limited to attempts to manage symptoms and typically requires a combination of approaches. While scleroderma localized to the skin is typically not life threatening, systemic scleroderma affecting multiple internal organs can be a life-threatening disease.

SUMMARY OF THE INVENTION

In one aspect, provided herein are compounds of Formula (I) having the structure:

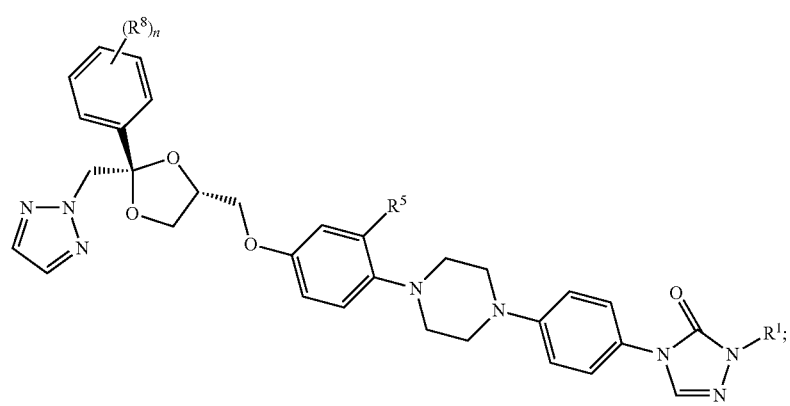

Formula (I)

wherein:

$R^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

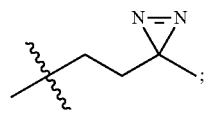

$R^2$ is alkyl, or —NR$^{13}$R$^{14}$;

$R^3$ is —OH, alkyl, or —NR$^{13}$R$^{14}$;

$R^5$ is H, —CN, halogen, haloalkyl, alkyl, —NR$^{13}$R$^{14}$, -alkylene(NR$^{13}$R$^{14}$), and —SO$_2$R$^{13}$;

each $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;

each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached; and n is selected from 0, 1, 2, 3, and 4;

or a pharmaceutically acceptable salt, pharmaceutically acceptable solvate, or pharmaceutically acceptable prodrug thereof.

In another aspect, provided herein are compounds of Formula (Ia) having the structure:

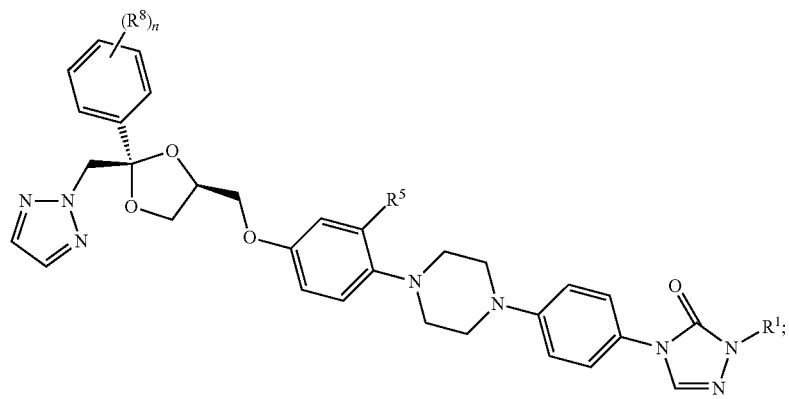

Formula (Ia)

wherein:
R¹ is —CH(CH₃)CH₂CH₂R², —CH(CH₂CH₃)₂, —CH(CH₃)₂, —CH₂CH(CH₃)₂, —CH(CH₂CH₃)CH(R³)CH₃, -alkylene(cycloalkyl), or

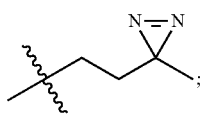

R² is alkyl, or —NR¹³R¹⁴;
R³ is —OH, alkyl, or —NR¹³R¹⁴;
R⁵ is H, —CN, halogen, haloalkyl, alkyl, —NR¹³R¹⁴, -alkylene(NR¹³R¹⁴), and —SO₂R¹³;
each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

In some embodiments is a compound of Formula (I) or (Ia), wherein R¹ is -alkylene(cycloalkyl). In some embodiments is a compound of Formula (I) or (Ia), wherein R¹ is —CH₂-(cycloalkyl). In some embodiments is a compound of Formula (I) or (Ia), wherein R¹ is —CH₂-(cyclopentyl). In some embodiments is a compound of Formula (I) or (Ia), wherein R¹ is —CH(CH₂CH₃)₂. In some embodiments is a compound of Formula (I) or (Ia), wherein R¹ is —CH(CH₃)CH₂R². In some embodiments is a compound of Formula (I) or (Ia), wherein R¹ is —CH(CH₃)CH₂CH₂R² and R² is —CH₃. In some embodiments is a compound of Formula (I) or (Ia), wherein n is 0. In some embodiments is a compound of Formula (I) or (Ia), wherein n is 1. In some embodiments is a compound of Formula (I) or (Ia), wherein n is 1 and R⁸ is halogen, —CN, alkyl, alkoxy, haloalkoxy, or haloalkyl. In some embodiments is a compound of Formula (I) or (Ia), wherein n is 2. In some embodiments is a compound of Formula (I) or (Ia), wherein n is 2 and each R⁸ is independently selected from halogen, —CN, alkyl, alkoxy, haloalkoxy, and haloalkyl. In some embodiments is a compound of Formula (I) or (Ia), wherein n is 2 and each R⁸ is halogen. In some embodiments is a compound of Formula (I) or (Ia), wherein n is 2 and each R⁸ is Cl. In some embodiments is a compound of Formula (I) or (Ia), wherein R⁵ is H. In some embodiments is a compound of Formula (I) or (Ia), wherein R⁵ is halogen. In some embodiments is a compound of Formula (I) or (Ia), wherein R⁵ is F.

In another aspect, provided herein are compounds of Formula (II) having the structure:

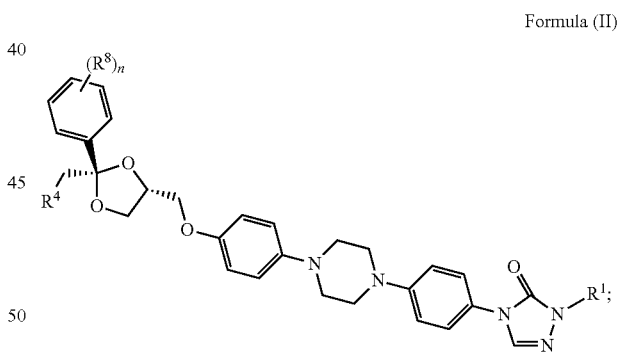

Formula (II)

wherein:
R¹ is —CH(CH₃)CH₂CH₂R², —CH(CH₂CH₃)₂, —CH(CH₃)₂, —CH₂CH(CH₃)₂, —CH(CH₂CH₃)CH(R³)CH₃, -alkylene(cycloalkyl), or

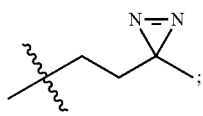 [SMILES: *CCC1(C)N=N1]

R² is H, alkyl, or —NR¹³R¹⁴;
R³ is —OH, alkyl, or —NR¹³R¹⁴;
R⁴ is halogen, alkyl,

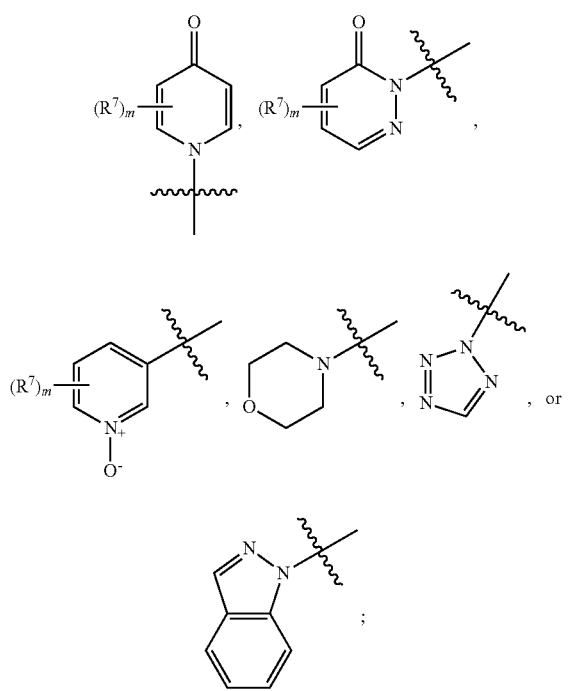

each R⁷ is independently selected from halogen and alkyl;
each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;
n is selected from 0, 1, 2, 3, and 4; and
m is selected from 0, 1, and 2;
or a pharmaceutically acceptable salt, pharmaceutically acceptable solvate, or pharmaceutically acceptable prodrug thereof.

In another aspect, provided herein are compounds of Formula (IIa) having the structure:

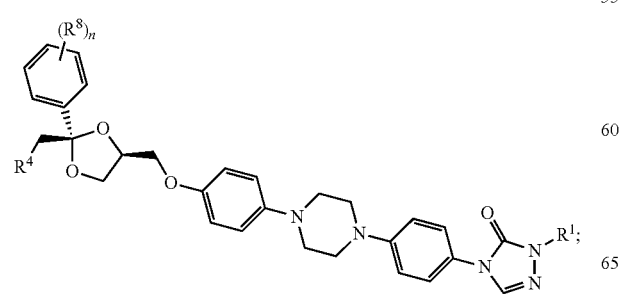

Formula (IIa)

wherein:

R¹ is —CH(CH₃)CH₂CH₂R², —CH(CH₂CH₃)₂, —CH(CH₃)₂, —CH₂CH(CH₃)₂, —CH(CH₂CH₃)CH(R³)CH₃, -alkylene(cycloalkyl), or

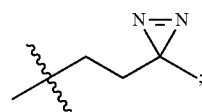

R² is H, alkyl, or —NR¹³R¹⁴;
R³ is —OH, alkyl, or —NR¹³R¹⁴;
R⁴ is halogen, alkyl,

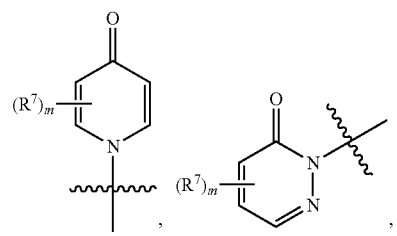

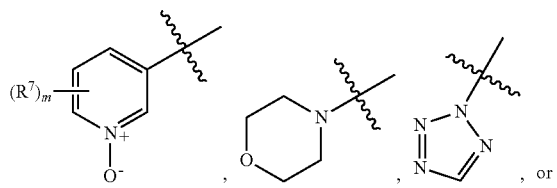

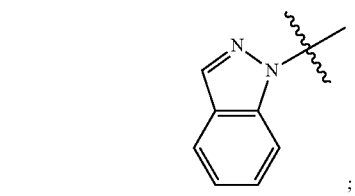

each R⁷ is independently selected from halogen and alkyl;
each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;

each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;

n is selected from 0, 1, 2, 3, and 4; and m is selected from 0, 1, and 2;

or a pharmaceutically acceptable salt, pharmaceutically acceptable solvate, or pharmaceutically acceptable prodrug thereof.

In some embodiments is a compound of Formula (II) or (IIa), wherein $R^4$ is —CH$_3$. In some embodiments is a compound of Formula (II) or (IIa), wherein $R^4$ is

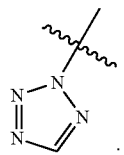

In some embodiments is a compound of Formula (II) or (IIa), wherein $R^1$ is —CH(CH$_2$CH$_3$)$_2$. In some embodiments is a compound of Formula (II) or (IIa), wherein $R^1$ is —CH(CH$_3$)CH$_2$CH$_2$R$^2$. In some embodiments is a compound of Formula (II) or (IIa), wherein $R^1$ is —CH(CH$_3$)CH$_2$CH$_2$R$^2$ and $R^2$ is H. In some embodiments is a compound of Formula (II) or (IIa), wherein $R^1$ is —CH(CH$_3$)CH$_2$CH$_2$R$^2$ and $R^2$ is —CH$_3$.

In another aspect, provided herein are compounds of Formula (III) having the structure:

$R^2$ is H, alkyl, or —NR$^{13}$R$^{14}$;

$R^3$ is —OH, alkyl, or —NR$^{13}$R$^{14}$;

each $R^5$ is independently selected from haloalkyl, -alkylene(NR$^{13}$R$^{14}$), —NR$^{13}$R$^{14}$, and —SO$_2$R$^{13}$;

each $R^6$ is independently selected from halogen, alkyl, and haloalkyl;

each $R^7$ is independently selected from halogen, alkyl, haloalkyl, and —CN;

each $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$) -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent $R^8$ form a heterocyclyl ring;

each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;

Formula (III)

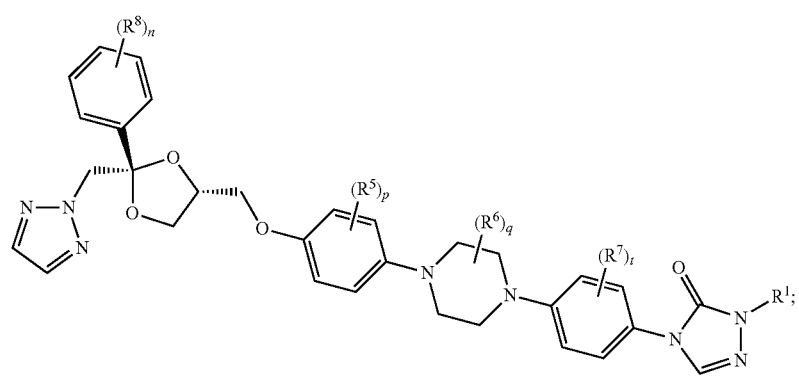

wherein:

$R^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$) CH$_3$, -alkylene(cycloalkyl), or

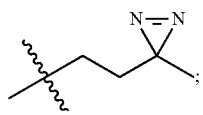

n is selected from 0, 1, 2, 3, and 4;
p is selected from 0, 1, 2, 3, and 4;
q is selected from 0, 1, 2, 3, and 4; and
t is independently selected from 0, 1, 2, 3, and 4;
wherein at least one p, q, or t is not 0;

or a pharmaceutically acceptable salt, pharmaceutically acceptable solvate, or pharmaceutically acceptable prodrug thereof.

In another aspect, provided herein are compounds of Formula (IIIa) having the structure:

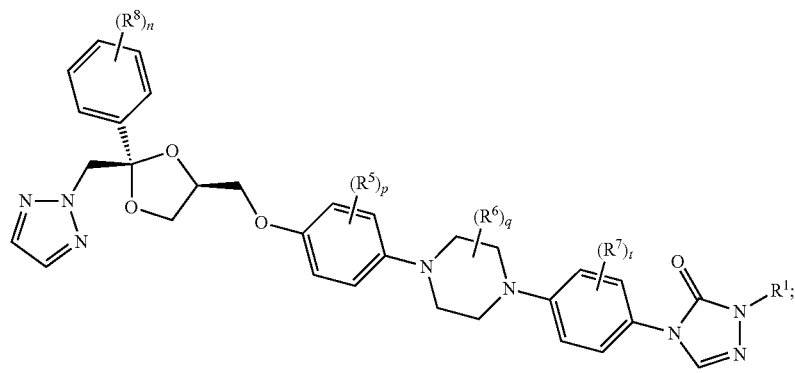

Formula (IIIa)

wherein:
R¹ is —CH(CH₃)CH₂CH₂R², —CH(CH₂CH₃)₂, —CH(CH₃)₂, —CH₂CH(CH₃)₂, —CH(CH₂CH₃)CH(R³)CH₃, -alkylene(cycloalkyl), or

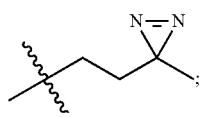

R² is H, alkyl, or —NR¹³R¹⁴;
R³ is —OH, alkyl, or —NR¹³R¹⁴;
each R⁵ is independently selected from haloalkyl, -alkylene(NR¹³R¹⁴), —NR¹³R¹⁴, and —SO₂R¹³;
each R⁶ is independently selected from halogen, alkyl, and haloalkyl;
each R⁷ is independently selected from halogen, alkyl, haloalkyl, and —CN;
each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;
n is selected from 0, 1, 2, 3, and 4;
p is selected from 0, 1, 2, 3, and 4;
q is selected from 0, 1, 2, 3, and 4; and
t is independently selected from 0, 1, 2, 3, and 4;
wherein at least one p, q, or t is not 0;
or a pharmaceutically acceptable salt, pharmaceutically acceptable solvate, or pharmaceutically acceptable prodrug thereof.

In some embodiments is a compound of Formula (III) or (IIIa), wherein p is 1. In some embodiments is a compound of Formula (III) or (IIIa), wherein q is 0. In some embodiments is a compound of Formula (III) or (IIIa), wherein t is 0.

In some embodiments is a compound of Formula (III) or (IIIa), wherein q is 1. In some embodiments is a compound of Formula (III) or (IIIa), wherein q is 1 and R⁶ is alkyl. In some embodiments is a compound of Formula (III) or (IIIa), wherein q is 1 and t is 0. In some embodiments is a compound of Formula (III) or (IIIa), wherein q is 1, R⁶ is alkyl, and t is 0.

In some embodiments is a compound of Formula (III) or (IIIa), wherein t is 1. In some embodiments is a compound of Formula (III) or (IIIa), wherein t is 1 and R⁷ is halogen. In some embodiments is a compound of Formula (III) or (IIIa), wherein t is 1 and q is 0. In some embodiments is a compound of Formula (III) or (IIIa), wherein t is 1, R⁷ is halogen, and q is 0.

In some embodiments is a compound of Formula (III) or (IIIa), wherein p is 0.

In another aspect, provided herein are compounds of Formula (IV) having the structure:

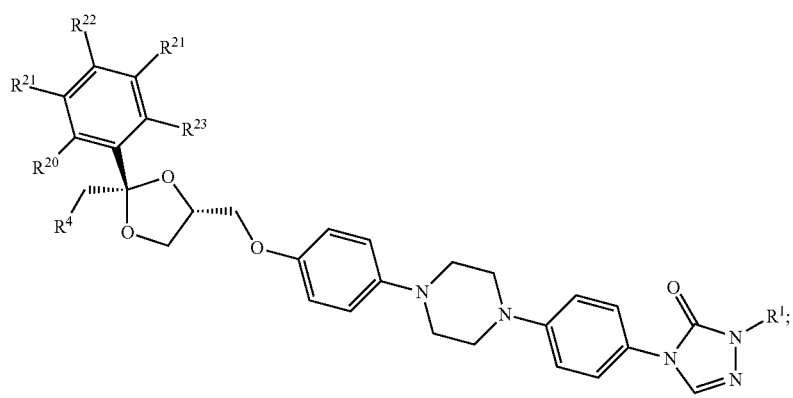

Formula (IV)

wherein:

R¹ is

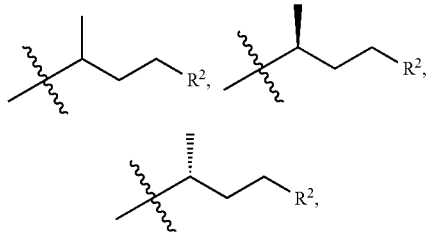

—CH(CH₂CH₃)₂, —CH(CH₃)₂, —CH₂CH(CH₃)₂, —CH(CH₂CH₃)CH(R³)CH₃, -alkylene(cycloalkyl), or

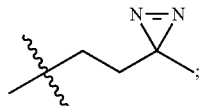 [SMILES: *CCC1(C)N=N1]

$R^2$ is H, alkyl, or —NR¹³R¹⁴;

$R^3$ is —OH, alkyl, or —NR¹³R¹⁴;

$R^4$ is halogen, alkyl,

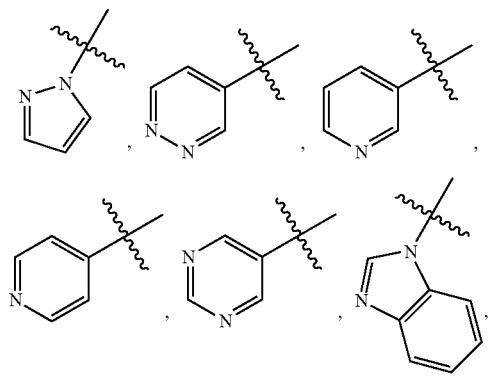

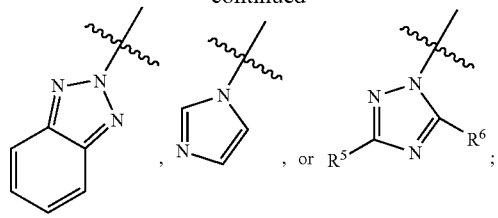

$R^5$ and $R^6$ are independently selected from H, alkyl, halo, and haloalkyl;

each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;

$R^{20}$ and $R^{22}$ are independently selected from H, halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴, wherein at least one of $R^{20}$ and $R^{22}$ is not F or Cl;

each $R^{21}$ is independently selected from H, halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; and $R^{23}$ is H;

or a pharmaceutically acceptable salt, pharmaceutically acceptable solvate, or pharmaceutically acceptable prodrug thereof.

In another aspect, provided herein are compounds of Formula (IVa) having the structure:

Formula (IVa)

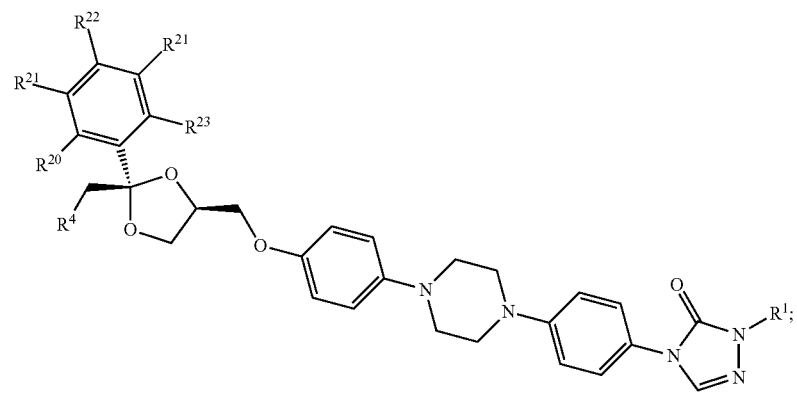

wherein:

R¹ is

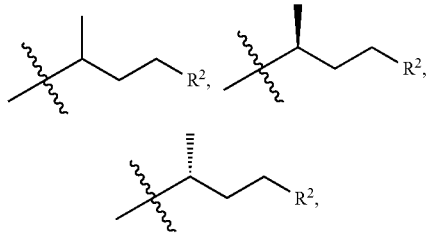

—CH(CH₂CH₃)₂, —CH(CH₃)₂, —CH₂CH(CH₃)₂, —CH(CH₂CH₃)CH(R³)CH₃, -alkylene(cycloalkyl), or

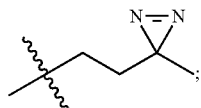 [SMILES: *CCC1(C)N=N1]

R² is H, alkyl, or —NR¹³R¹⁴;
R³ is —OH, alkyl, or —NR¹³R¹⁴;
R⁴ is halogen, alkyl,

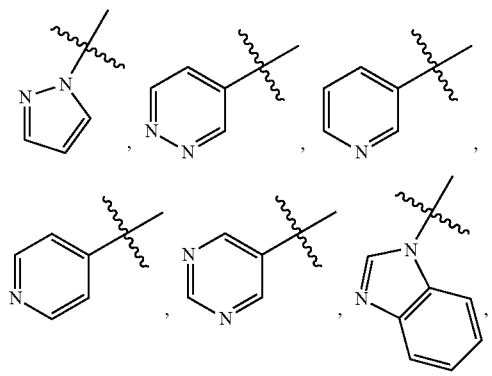

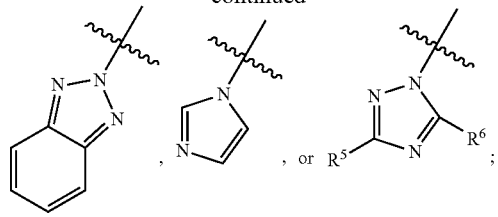

R⁵ and R⁶ are independently selected from H, alkyl, halo, and haloalkyl;

each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;

R²⁰ and R²² are independently selected from H, halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴, wherein at least one of R²⁰ and R²² is not F or Cl;

each R²¹ is independently selected from H, halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; and R²³ is H;

or a pharmaceutically acceptable salt, pharmaceutically acceptable solvate, or pharmaceutically acceptable prodrug thereof.

In another aspect, provided herein are compounds of Formula (IVb) having the structure:

Formula (IVb)

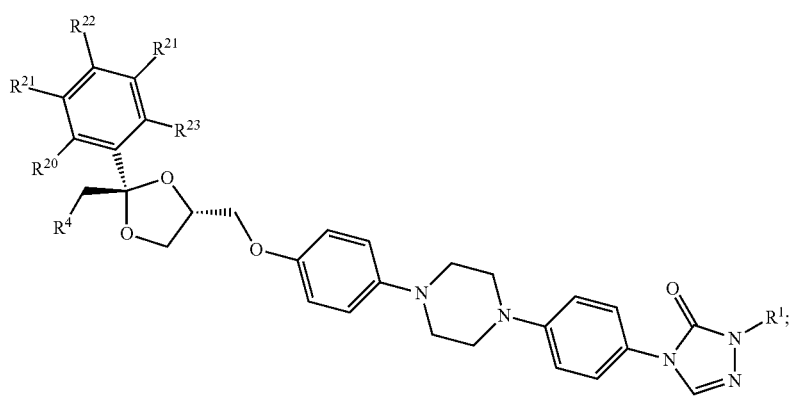

wherein:
R¹ is

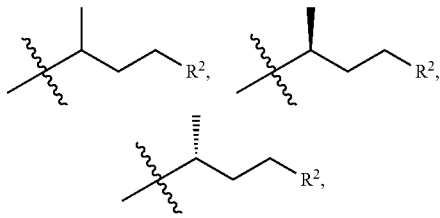

—CH(CH₂CH₃)₂, —CH(CH₃)₂, —CH₂CH(CH₃)₂, —CH(CH₂CH₃)CH(R³)CH₃, -alkylene(cycloalkyl), or

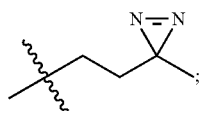 [SMILES: *CCC1(C)N=N1]

R² is H, alkyl, or —NR¹³R¹⁴;
R³ is —OH, alkyl, or —NR¹³R¹⁴;
R⁴ is halogen, alkyl,

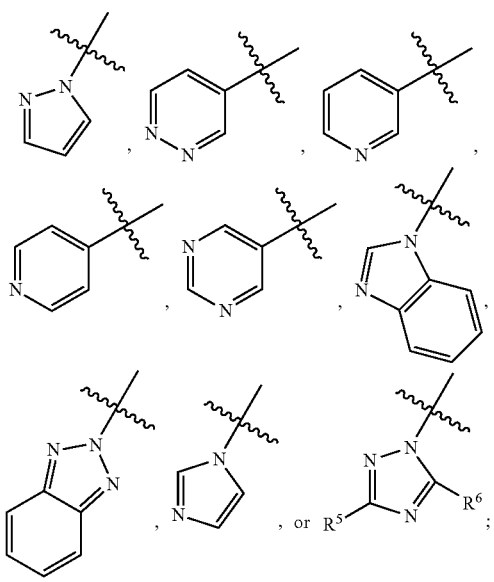

R⁵ and R⁶ are independently selected from H, alkyl, halo, and haloalkyl;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;
R²⁰ and R²² are independently selected from H, halogen, —OH, —NO₂, —N₃, —CN, alkyl, alkoxy, haloalkoxy, haloalkyl, hydroxyalkyl, alkoxyalkyl, -alkylene (NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴, wherein at least one of R²⁰ and R²² is not F or Cl;
each R²¹ is independently selected from H, halogen, —OH, —NO₂, —N₃, —CN, alkyl, alkoxy, haloalkoxy, haloalkyl, hydroxyalkyl, alkoxyalkyl, -alkylene (NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; and
R²³ is H;

or a pharmaceutically acceptable salt, pharmaceutically acceptable solvate, or pharmaceutically acceptable prodrug thereof.

In some embodiments is a compound of Formula (IV), (IVa) or (IVb), wherein R²⁰ and R²² are independently selected from H, halogen, —CN, alkyl, alkoxy, haloalkoxy, haloalkyl, —SO₂R¹³, —SO₂NR¹³R¹⁴, and —C(O) NR¹³R¹⁴; wherein at least one of R²⁰ and R²² is not F or Cl. In some embodiments is a compound of Formula (IV), (IVa) or (IVb), wherein R²⁰ and R²² are independently selected from H, Cl, —CN, —CH₃, —OCH₃, and —CF₃; wherein at least one of R²⁰ and R²² is not Cl. In some embodiments is a compound of Formula (IV), (IVa) or (IVb), wherein each R²¹ is independently selected from H, halogen, —CN, alkyl, alkoxy, and haloalkyl. In some embodiments is a compound of Formula (IV), (IVa) or (IVb), wherein each R²¹ is independently selected from H, Cl, —CN, —CH₃, —OCH₃, and —CF₃. In some embodiments is a compound of Formula (IV), (IVa) or (IVb), wherein R⁴ is

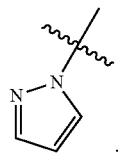

In some embodiments is a compound of Formula (IV), (IVa) or (IVb), wherein R⁴ is

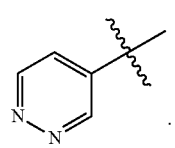 [SMILES: *c1ccnnc1]

In some embodiments is a compound of Formula (IV), (IVa) or (IVb), wherein R⁴ is

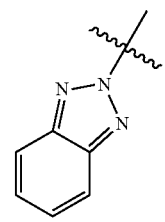

In some embodiments is a compound of Formula (IV), (IVa) or (IVb), wherein $R^1$ is

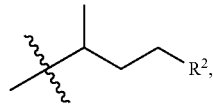

and $R^2$ is H. In some embodiments is a compound of Formula (IV), (IVa) or (IVb), wherein $R^1$ is

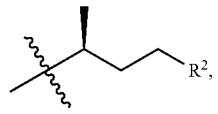

and $R^2$ is H. In some embodiments is a compound of Formula (IV), (IVa) or (IVb), wherein $R^1$ is

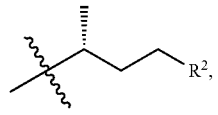

and $R^2$ is H. In some embodiments is a compound of Formula (IV), (IVa) or (IVb), wherein $R^1$ is —CH(CH$_2$CH$_3$)$_2$.

In another aspect, provided herein are compounds of Formula (V) having the structure:

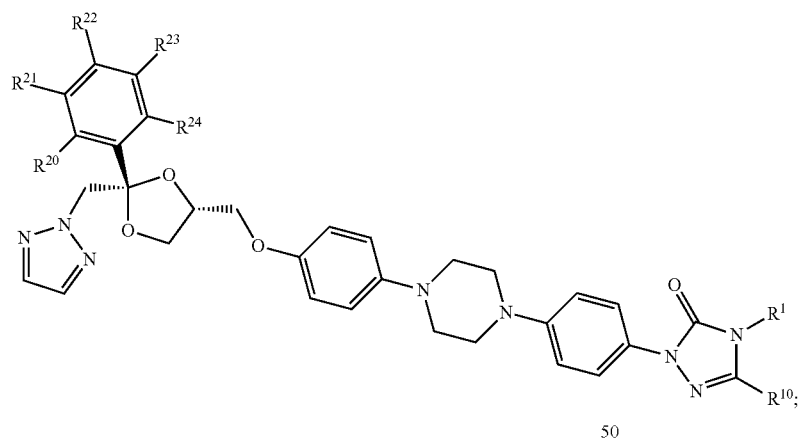

Formula (V)

wherein:
$R^1$ is

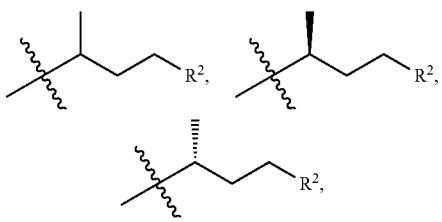

—CH(CH$_3$)CH(R$^3$)CH$_3$, —CH(CH$_3$)C(O)CH$_3$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

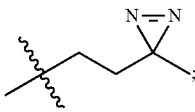

$R^2$ is H, alkyl, or —NR$^{13}$R$^{14}$;
$R^3$ is —OH, alkyl, or —NR$^{13}$R$^{14}$;
$R^{10}$ is H or alkyl;
each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;
$R^{20}$ is selected from H, Cl, Br, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$;
$R^{21}$, $R^{22}$, and $R^{23}$ are independently selected from H, halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; and
$R^{24}$ is H;
or a pharmaceutically acceptable salt, pharmaceutically acceptable solvate, or pharmaceutically acceptable prodrug thereof.

In another aspect, provided herein are compounds of Formula (Va) having the structure:

Formula (Va)

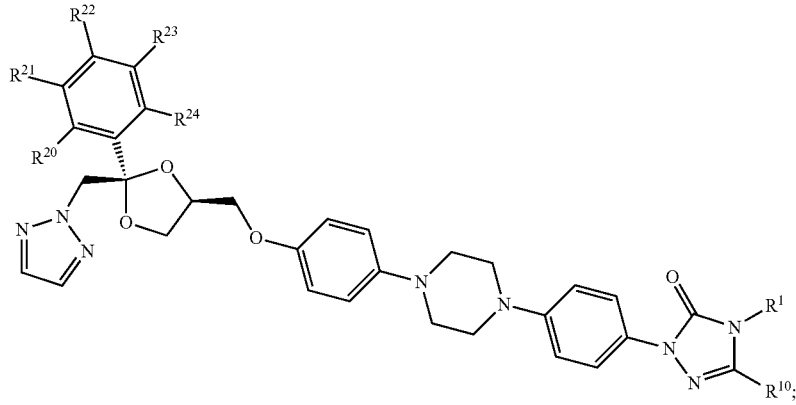

wherein:
R¹ is

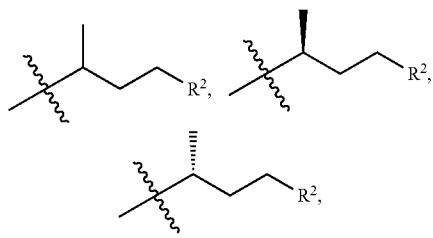

—CH(CH₃)CH(R³)CH₃, —CH(CH₃)C(O)CH₃, —CH(CH₂CH₃)₂, —CH(CH₃)₂, —CH₂CH(CH₃)₂, —CH(CH₂CH₃)CH(R³)CH₃, -alkylene(cycloalkyl), or

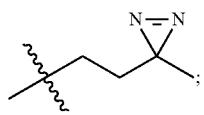

R² is H, alkyl, or —NR¹³R¹⁴;
R³ is —OH, alkyl, or —NR¹³R¹⁴;
R¹⁰ is H or alkyl;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;
R²⁰ is selected from H, Cl, Br, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴;
R²¹, R²², and R²³ are independently selected from H, halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; and
R²⁴ is H;
or a pharmaceutically acceptable salt, pharmaceutically acceptable solvate, or pharmaceutically acceptable prodrug thereof.

In some embodiments is a compound of Formula (V) or (Va), wherein R²¹, R²², and R²³ are independently selected from H, halogen, —CN, alkyl, alkoxy, and haloalkyl. In some embodiments is a compound of Formula (V) or (Va), wherein R²¹, R²², and R²³ are independently selected from H and halogen. In some embodiments is a compound of Formula (V) or (Va), wherein R²⁰ is independently selected from H, Cl, Br, —CN, alkyl, alkoxy, haloalkoxy, and haloalkyl. In some embodiments is a compound of Formula (V) or (Va), wherein R²⁰ is independently selected from H, and Cl.

In another aspect, provided herein are compounds of Formula (VI) having the structure:

Formula (VI)

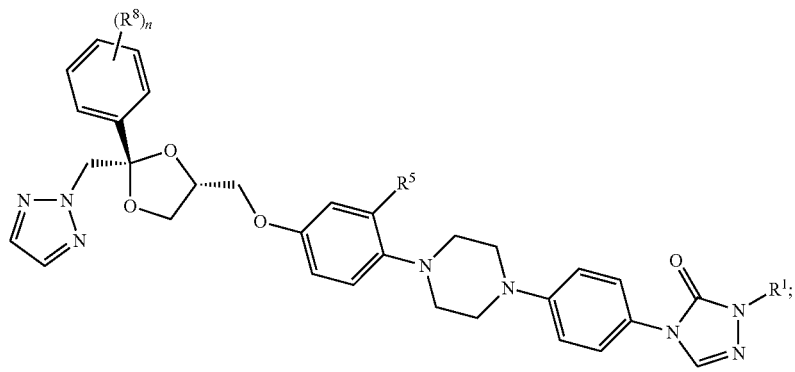

wherein:

R¹ is

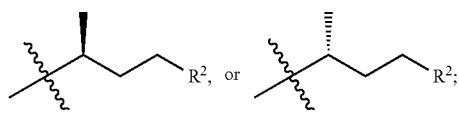

R² is H;

R⁵ is H, —CN, halogen, haloalkyl, alkyl, —NR¹³R¹⁴, -alkylene(NR¹³R¹⁴), and —SO₂R¹³;

each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;

each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached; and n is selected from 0, 1, 2, 3, and 4;

or a pharmaceutically acceptable salt, pharmaceutically acceptable solvate, or pharmaceutically acceptable prodrug thereof.

In another aspect, provided herein are compounds of Formula (VIa) having the structure:

wherein:

R¹ is

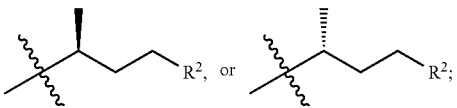

R² is H;

R⁵ is H, —CN, halogen, haloalkyl, alkyl, —NR¹³R¹⁴, -alkylene(NR¹³R¹⁴), and —SO₂R¹³;

each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;

each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached; and n is selected from 0, 1, 2, 3, and 4;

or a pharmaceutically acceptable salt, pharmaceutically acceptable solvate, or pharmaceutically acceptable prodrug thereof.

In another aspect, provided herein are compounds of Formula (VIb) having the structure:

Formula (VIa)

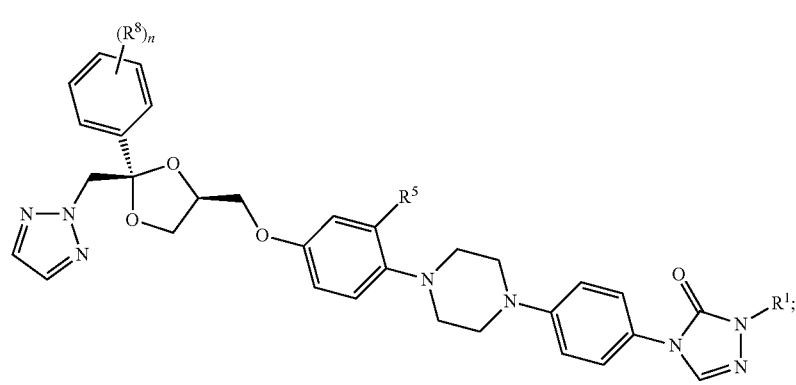

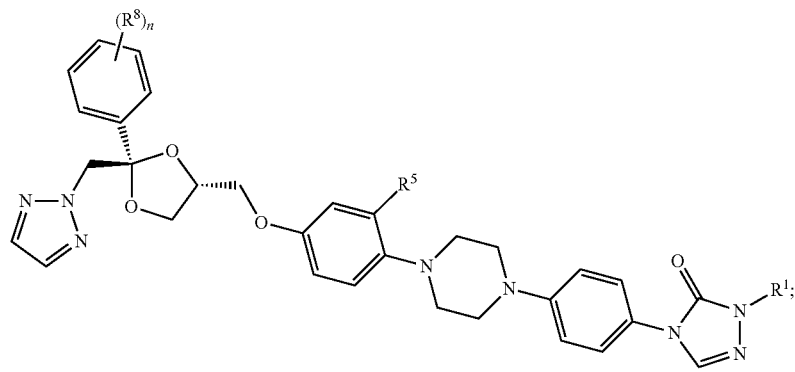

Formula (VIb)

wherein:
R¹ is

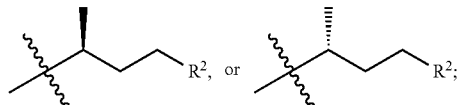

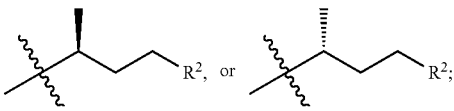

R² is H;
R⁵ is H, —CN, halogen, haloalkyl, alkyl, —NR¹³R¹⁴, -alkylene(NR¹³R¹⁴), and —SO₂R¹³;
each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

In another aspect, provided herein are compounds of Formula (VIc) having the structure:

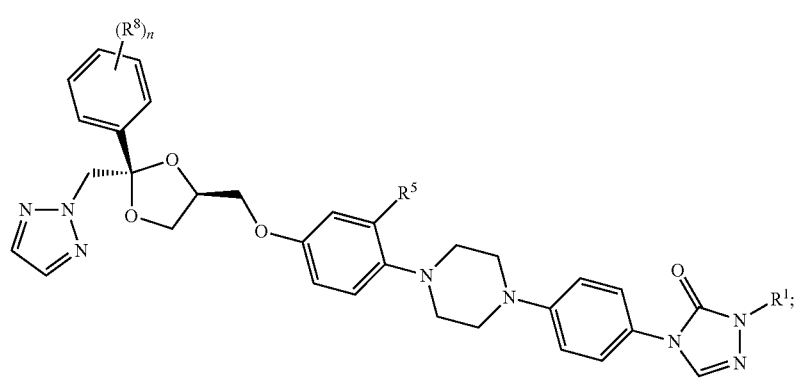

Formula (VIc)

wherein:
R¹ is

R² is H;
R⁵ is H, —CN, halogen, haloalkyl, alkyl, —NR¹³R¹⁴, -alkylene(NR¹³R¹⁴), and —SO₂R¹³;
each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

In some embodiments is a compound of Formula (VI), (VIa), (VIb), or (VIc), wherein n is 0. In some embodiments is a compound of Formula (VI), (VIa), (VIb), or (VIc), wherein n is 1. In some embodiments is a compound of Formula (VI), (VIa), (VIb), or (VIc), wherein $R^8$ is halogen, —CN, alkyl, alkoxy, haloalkoxy, or haloalkyl. In some embodiments is a compound of Formula (VI), (VIa), (VIb), or (VIc), wherein $R^8$ is halogen. In some embodiments is a compound of Formula (VI), (VIa), (VIb), or (VIc), wherein $R^8$ is Cl. In some embodiments is a compound of Formula (VI), (VIa), (VIb), or (VIc), wherein $R^5$ is H. In some embodiments is a compound of Formula (VI), (VIa), (VIb), or (VIc), wherein $R^5$ is halogen. In some embodiments is a compound of Formula (VI), (VIa), (VIb), or (VIc), wherein $R^5$ is F. In some embodiments is a compound of Formula (VI), (VIa), (VIb), or (VIc), wherein $R^1$ is

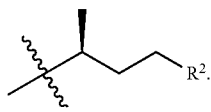

In some embodiments is a compound of Formula (VI), (VIa), (VIb), or (VIc), wherein $R^1$ is

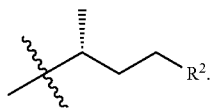

Also provided herein is a pharmaceutical composition comprising a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described above and below, or a pharmaceutically acceptable salt, pharmaceutically acceptable solvate, or pharmaceutically acceptable prodrug thereof, and a pharmaceutically acceptable excipient.

Also provided herein is a method of treating fibrosis, a disorder characterized by fibrosis, or a disorder characterized by fibrosis in a subject comprising administering to the subject a therapeutically effective amount of a compound of Formula (I), (Ia), (II), (IIa), (III), (IIIa), (IV), (IVa), (IVb), (V), (Va), (VI), (VIa), (VIb), or (VIc) as described above and below, or a pharmaceutically acceptable salt, pharmaceutically acceptable solvate, or pharmaceutically acceptable prodrug thereof.

Further provided herein is a method to treat fibrosis using a compound of Formula (I), (Ia), (II), (IIa), (III), (IIIa), (IV), (IVa), (IVb), (V), (Va), (VI), (VIa), (VIb), or (VIc) wherein the fibrosis is liver fibrosis, idiopathic pulmonary fibrosis, kidney fibrosis, or cardiac fibrosis.

Further provided herein is a method to treat liver fibrosis using a compound of Formula (I), (Ia), (II), (IIa), (III), (IIIa), (IV), (IVa), (IVb), (V), (Va), (VI), (VIa), (VIb), or (VIc) wherein the liver fibrosis is associated with the later stages of alcoholic or nonalcoholic liver cirrhosis.

Further provided herein is a method to treat fibrosis using a compound of Formula (I) wherein the fibrosis is idiopathic pulmonary fibrosis.

Further provided herein is a method to treat a disease using a compound of Formula (I), (Ia), (II), (IIa), (III), (IIIa), (IV), (IVa), (IVb), (V), (Va), (VI), (VIa), (VIb), or (VIc) wherein the disease or disorder characterized by fibrosis is a chronic autoimmune disease.

Further provided herein is a method to treat chronic autoimmune disease using a compound of Formula (I), (Ia), (II), (IIa), (III), (IIIa), (IV), (IVa), (IVb), (V), (Va), (VI), (VIa), (VIb), or (VIc) wherein the chronic autoimmune disease is rheumatoid arthritis, scleroderma, Crohn's disease or systemic lupus erythematosus.

Further provided herein is a method to treat chronic autoimmune disease using a compound of Formula (I), (Ia), (II), (IIa), (III), (IIIa), (IV), (IVa), (IVb), (V), (Va), (VI), (VIa), (VIb), or (VIc) wherein the chronic autoimmune disease is scleroderma.

Further provided herein is a method to treat fibrosis using a compound of Formula (I), (Ia), (II), (IIa), (III), (IIIa), (IV), (IVa), (IVb), (V), (Va), (VI), (VIa), (VIb), or (VIc) wherein the fibrosis is keloid formation resulting from abnormal wound healing.

Further provided herein is a method to treat fibrosis using a compound of Formula (I), (Ia), (II), (IIa), (III), (IIIa), (IV), (IVa), (IVb), (V), (Va), (VI), (VIa), (VIb), or (VIc) wherein the fibrosis occurs after organ transplantation.

Also provided herein is a method to treat fibrosis, a disorder characterized by fibrosis, or a disease characterized by fibrosis, the method comprising administering a composition comprising a therapeutically effective amount of a compound described herein in combination with one or more pharmaceutical agents. In certain embodiments described above, the one or more pharmaceutical agents are antifibrotic agents. In certain embodiments described above, the one or more pharmaceutical agents are antifungal agents.

In another aspect, provided herein are compounds of Formula (IX) having the structure:

Formula (IX)

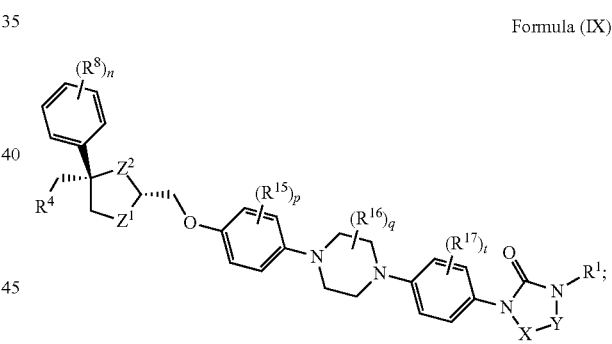

wherein:

—X—Y— is —CH$_2$CH$_2$—, —CH=CH—, —CH=N—, or —N=CH—;

$Z^1$ is selected from O, S, NH, and NR$^{13}$;

$Z^2$ is selected from O, S, CH$_2$, NH, and NR$^{13}$;

$R^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

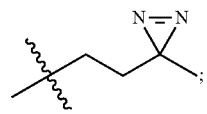

$R^2$ is H, alkyl, or —NR$^{13}$R$^{14}$;

$R^3$ is —OH, alkyl, or —NR$^{13}$R$^{14}$;

$R^4$ is halogen, alkyl,

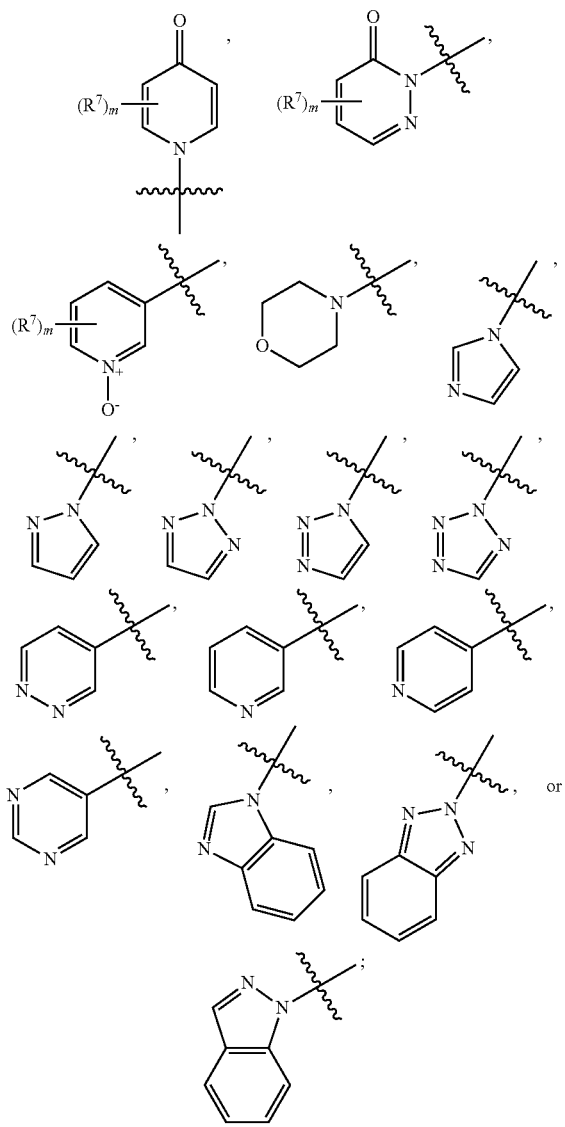

each R[7] is independently selected from halogen and alkyl;
each R[8] is independently selected from halogen, —OH, —NO$_2$, —N$_3$, —CN, alkyl, alkoxy, haloalkoxy, haloalkyl, hydroxyalkyl, alkoxyalkyl, -alkylene(NR[13]R[14]), -alkylene(cycloalkyl), -alkylene(heterocyclyl), cycloalkyl, heterocyclyl, aryl, heteroaryl, —SR[13], —SOR[13], —SO$_2$R[13], —SO$_2$NR[13]R[14], —NR[13]R[14], —NR[13]SO$_2$R[14], —NR[13]C(O)R[14], —NR[13]C(O)OR[14], —NR[13]C(O)NR[13]R[14], —C(O)R[14], —C(O)OR[14], and —C(O)NR[13]R[14]; or two adjacent R[8] form a heterocyclyl ring;
each R[13] and each R[14] is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R[13] and R[14] taken together form a heterocycle with the atoms to which they are attached;
each R[15] is independently selected from haloalkyl, -alkylene(NR[13]R[14]), —NR[13]R[14], and —SO$_2$R[13];
each R[16] is independently selected from halogen, alkyl, and haloalkyl;
each R[17] is independently selected from halogen, alkyl, haloalkyl, and —CN;

n is selected from 0, 1, 2, 3, and 4;
m is selected from 0, 1, and 2;
p is selected from 0, 1, 2, 3, and 4;
q is selected from 0, 1, 2, 3, and 4; and
t is independently selected from 0, 1, 2, 3, and 4;
or a pharmaceutically acceptable salt, pharmaceutically acceptable solvate, pharmaceutically acceptable prodrug, or stereoisomer thereof.

In another aspect, provided herein are compounds of Formula (IXa) having the structure:

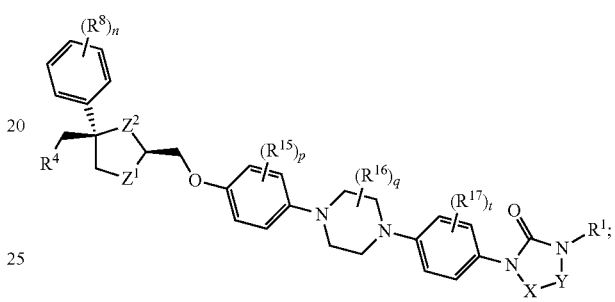

Formula (IXa)

wherein:
—X—Y— is —CH$_2$CH$_2$—, —CH=CH—, —CH=N—, or —N=CH—;
Z$^1$ is selected from O, S, NH, and NR[13];
Z$^2$ is selected from O, S, CH$_2$, NH, and NR[13];
R$^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

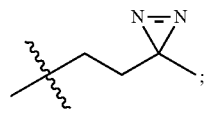

R$^2$ is H, alkyl, or —NR[13]R[14];
R$^3$ is —OH, alkyl, or —NR[13]R[14];
R$^4$ is halogen, alkyl,

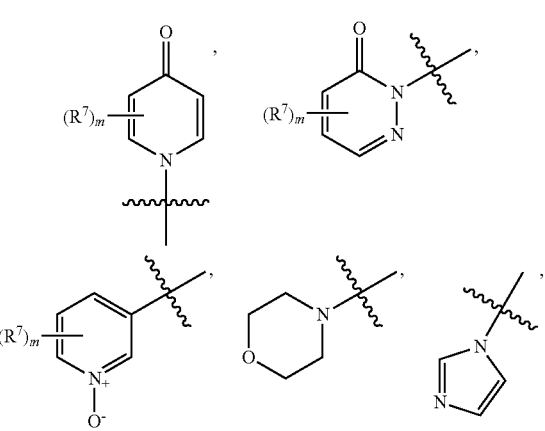

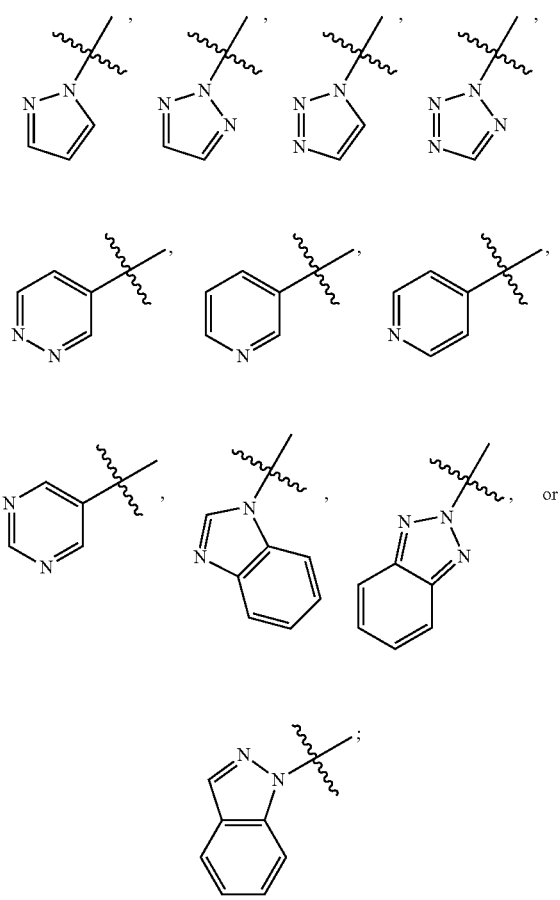

each R[7] is independently selected from halogen and alkyl;
each R[8] is independently selected from halogen, —OH, —NO$_2$, —N$_3$, —CN, alkyl, alkoxy, haloalkoxy, haloalkyl, hydroxyalkyl, alkoxyalkyl, -alkylene(NR[13]R[14]), -alkylene(cycloalkyl), -alkylene(heterocyclyl), cycloalkyl, heterocyclyl, aryl, heteroaryl, —SR[13], —SOR[13], —SO$_2$R[13], —SO$_2$NR[13]R[14], —NR[13]R[14], —NR[13]SO$_2$R[14], —NR[13]C(O)R[14], —NR[13]C(O)OR[14], —NR[13]C(O)NR[13]R[14], —C(O)R[14], —C(O)OR[14], and —C(O)NR[13]R[14]; or two adjacent R[8] form a heterocyclyl ring;
each R[13] and each R[14] is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R[13] and R[14] taken together form a heterocycle with the atoms to which they are attached;
each R[15] is independently selected from haloalkyl, -alkylene(NR[13]R[14]), —NR[13]R[14], and —SO$_2$R[13];
each R[16] is independently selected from halogen, alkyl, and haloalkyl;
each R[17] is independently selected from halogen, alkyl, haloalkyl, and —CN;
n is selected from 0, 1, 2, 3, and 4;
m is selected from 0, 1, and 2;
p is selected from 0, 1, 2, 3, and 4;
q is selected from 0, 1, 2, 3, and 4; and
t is independently selected from 0, 1, 2, 3, and 4;
or a pharmaceutically acceptable salt, pharmaceutically acceptable solvate, pharmaceutically acceptable prodrug, or stereoisomer thereof.

In some embodiments is a compound of Formula (IX) or (IXa), wherein R[4] is

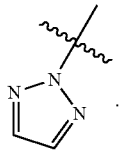

In some embodiments is a compound of Formula (IX) or (IXa), wherein R[4] is

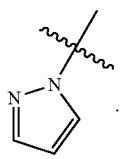 [SMILES: *n1cccn1]

In some embodiments is a compound of Formula (IX) or (IXa), wherein R[4] is

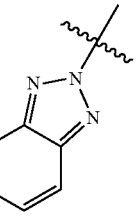

In some embodiments is a compound of Formula (IX) or (IXa), wherein n is 0. In some embodiments is a compound of Formula (IX) or (IXa), wherein n is 1. In some embodiments is a compound of Formula (IX) or (IXa), wherein n is 1 and R[8] is halogen, —CN, alkyl, alkoxy, haloalkoxy, or haloalkyl. In some embodiments is a compound of Formula (IX) or (IXa), wherein n is 2. In some embodiments is a compound of Formula (IX) or (IXa), wherein n is 2 and each R[8] is independently selected from halogen, —CN, alkyl, alkoxy, haloalkoxy, and haloalkyl. In some embodiments is a compound of Formula (IX) or (IXa), wherein n is 2 and each R[8] is halogen. In some embodiments is a compound of Formula (IX) or (IXa), wherein n is 2 and each R[8] is F. In some embodiments is a compound of Formula (IX) or (IXa), wherein R[1] is —CH(CH$_3$)$_2$. In some embodiments is a compound of Formula (IX) or (IXa), wherein R[1] is —CH(CH$_2$CH$_3$)$_2$. In some embodiments is a compound of Formula (IX) or (IXa), wherein R[1] is

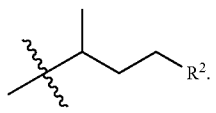

In some embodiments is a compound of Formula (IX) or (IXa), wherein $R^1$ is

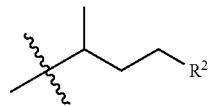

and $R^2$ is H. In some embodiments is a compound of Formula (IX) or (IXa), wherein $R^1$ is

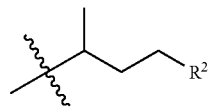

and $R^2$ is —CH$_3$. In some embodiments is a compound of Formula (IX) or (IXa), wherein $R^1$ is

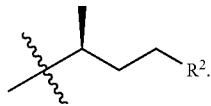

In some embodiments is a compound of Formula (IX) or (IXa), wherein $R^1$ is

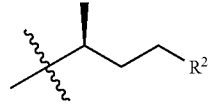

and $R^2$ is H. In some embodiments is a compound of Formula (IX) or (IXa), wherein $R^1$ is and $R^2$ is —CH$_3$. In some embodiments is a compound of Formula (IX) or (IXa), wherein $R^1$ is In some embodiments is a compound of Formula (IX) or (IXa), wherein $R^1$ is and $R^2$ is H. In some embodiments is a compound of Formula (IX) or (IXa), wherein $R^1$ is and $R^2$ is —CH$_3$. In some embodiments is a compound of Formula (IX) or (IXa), wherein p is 0. In some embodiments is a compound of Formula (IX) or (IXa), wherein q is 0. In some embodiments is a compound of Formula (IX) or (IXa), wherein t is 0. In some embodiments is a compound of Formula (IX) or (IXa), wherein $Z^1$ and $Z^2$ are each O. In some embodiments is a compound of Formula (IX) or (IXa), wherein —X—Y— is —CH$_2$CH$_2$—. In some embodiments is a compound of Formula (IX) or (IXa), wherein —X—Y— is —CH=N—.

In another aspect, provided herein are compounds of Formula (X) having the structure:

Formula (X)

wherein:
—X—Y— is —CH$_2$CH$_2$—, —CH=CH—, —CH=N—, or —N=CH—;
Z$^1$ is selected from O, S, NH, and NR$^{13}$;
Z$^2$ is selected from O, S, CH$_2$, NH, and NR$^{13}$;
R$^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

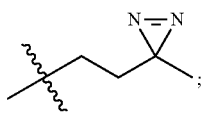

R$^2$ is H, alkyl, or —NR$^{13}$R$^{14}$;
R$^3$ is —OH, alkyl, or —NR$^{13}$R$^{14}$;
each R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;
each R$^{15}$ is independently selected from haloalkyl, -alkylene(NR$^{13}$R$^{14}$), —NR$^{13}$R$^{14}$, and —SO$_2$R$^{13}$;
each R$^{16}$ is independently selected from halogen, alkyl, and haloalkyl;
each R$^{17}$ is independently selected from halogen, alkyl, haloalkyl, and —CN;
n is selected from 0, 1, 2, 3, and 4;
p is selected from 0, 1, 2, 3, and 4;
q is selected from 0, 1, 2, 3, and 4; and
t is independently selected from 0, 1, 2, 3, and 4;
wherein when Z$^1$ and Z$^2$ are both O then —X—Y— is —CH=CH—, —CH=N—, or —N=CH—;
or a pharmaceutically acceptable salt, pharmaceutically acceptable solvate, pharmaceutically acceptable prodrug, or stereoisomer thereof.

In another aspect, provided herein are compounds of Formula (Xa) having the structure:

wherein:
—X—Y— is —CH$_2$CH$_2$—, —CH=CH—, —CH=N—, or —N=CH—;
Z$^1$ is selected from O, S, NH, and NR$^{13}$;
Z$^2$ is selected from O, S, CH$_2$, NH, and NR$^{13}$;
R$^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

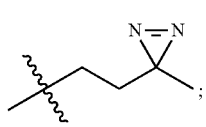

R$^2$ is H, alkyl, or —NR$^{13}$R$^{14}$;
R$^3$ is —OH, alkyl, or —NR$^{13}$R$^{14}$;
each R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;
each R$^{15}$ is independently selected from haloalkyl, -alkylene(NR$^{13}$R$^{14}$), —NR$^{13}$R$^{14}$, and —SO$_2$R$^{13}$;
each R$^{16}$ is independently selected from halogen, alkyl, and haloalkyl;
each R$^{17}$ is independently selected from halogen, alkyl, haloalkyl, and —CN;
n is selected from 0, 1, 2, 3, and 4;
p is selected from 0, 1, 2, 3, and 4;
q is selected from 0, 1, 2, 3, and 4; and
t is independently selected from 0, 1, 2, 3, and 4;
wherein when Z$^1$ and Z$^2$ are both O then —X—Y— is —CH=CH—, —CH=N—, or —N=CH—;
or a pharmaceutically acceptable salt, pharmaceutically acceptable solvate, pharmaceutically acceptable prodrug, or stereoisomer thereof.

Formula (Xa)

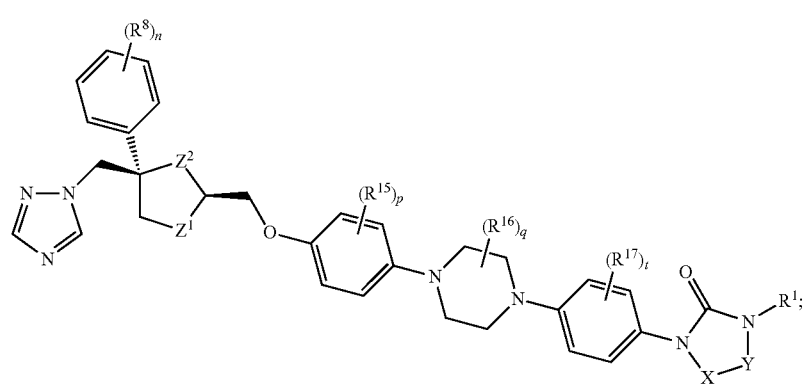

In some embodiments is a compound of Formula (X) or (Xa), wherein n is 0. In some embodiments is a compound of Formula (X) or (Xa), wherein n is 1. In some embodiments is a compound of Formula (X) or (Xa), wherein n is 1 and $R^8$ is halogen, —CN, alkyl, alkoxy, haloalkoxy, or haloalkyl. In some embodiments is a compound of Formula (X) or (Xa), wherein n is 2. In some embodiments is a compound of Formula (X) or (Xa), wherein n is 2 and each $R^8$ is independently selected from halogen, —CN, alkyl, alkoxy, haloalkoxy, and haloalkyl. In some embodiments is a compound of Formula (X) or (Xa), wherein n is 2 and each $R^8$ is halogen. In some embodiments is a compound of Formula (X) or (Xa), wherein n is 2 and each $R^8$ is F. In some embodiments is a compound of Formula (X) or (Xa), wherein $R^1$ is —CH(CH$_3$)$_2$. In some embodiments is a compound of Formula (X) or (Xa), wherein $R^1$ is —CH(CH$_2$CH$_3$)$_2$. In some embodiments is a compound of Formula (X) or (Xa), wherein $R^1$ is

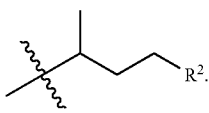

In some embodiments is a compound of Formula (X) or (Xa), wherein $R^1$ is

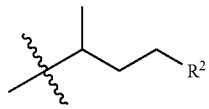

and $R^2$ is H. In some embodiments is a compound of Formula (X) or (Xa), wherein $R^1$ is

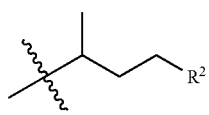

and $R^2$ is —CH$_3$. In some embodiments is a compound of Formula (X) or (Xa), wherein $R^1$ is

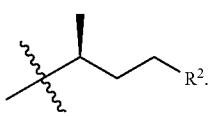

In some embodiments is a compound of Formula (X) or (Xa), wherein $R^1$ is

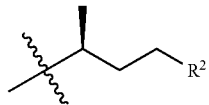

and $R^2$ is H. In some embodiments is a compound of Formula (X) or (Xa), wherein $R^1$ is

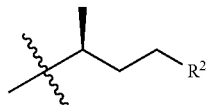

and $R^2$ is —CH$_3$. In some embodiments is a compound of Formula (X) or (Xa), wherein $R^1$ is

In some embodiments is a compound of Formula (X) or (Xa), wherein $R^1$ is

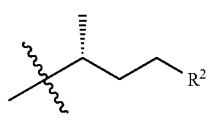

$R^1$ is

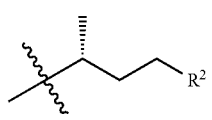

and $R^2$ is —CH$_3$. In some embodiments is a compound of Formula (X) or (Xa), wherein p is 0. In some embodiments is a compound of Formula (X) or (Xa), wherein q is 0. In some embodiments is a compound of Formula (X) or (Xa), wherein t is 0. In some embodiments is a compound of Formula (X) or (Xa), wherein $Z^1$ and $Z^2$ are each O. In some embodiments is a compound of Formula (X) or (Xa), wherein —X—Y— is —CH=N—.

In another aspect, provided herein is a method to treat fibrosis, a disorder characterized by fibrosis, or a disease characterized by fibrosis, the method comprising administering a composition comprising a therapeutically effective amount of a compound of Formula (XI), a pharmaceutically acceptable salt, solvate, polymorph, prodrug, metabolite, N-oxide, stereoisomer, or isomer thereof:

Formula (XI)

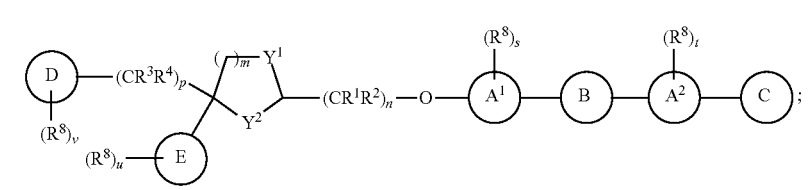

wherein:
A¹ and A² are independently selected from aryl or heteroaryl;
B is

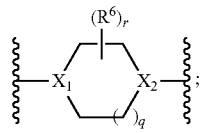

C is optionally substituted 5- or 6-membered heterocyclyl or optionally substituted 5- or 6-membered heteroaryl, wherein the heterocyclyl or the heteroaryl contains 1 to 4 nitrogen atoms;
D is aryl or heteroaryl;
E is aryl, heteroaryl, carbocyclyl, hetercyclyl, or alkyl;
each $R^1$, $R^2$, $R^3$, and $R^4$ is independently selected from H, alkyl, haloalkyl, or alkoxy;
$X_1$ and $X_2$ are independently selected from N and $CR^5$;
$R^5$ is H, OH, alkyl, or alkoxy;
each $R^6$ is independently alkyl, haloalkyl, halo, alkoxy, -alkylene($NR^{13}R^{14}$), or aryl;
each $R^8$ is independently selected from alkyl, cycloalkyl, heterocyclyl, halo, hydroxy, nitrile, azido, nitro, alkoxy, haloalkoxy, haloalkyl, hydroxyalkyl, alkoxyalkyl, -alkylene($NR^{13}R^{14}$), -alkylene(cycloalkyl), -alkylene(heterocyclyl), aryl, heteroaryl, $—SR^{13}$, $—SOR^{13}$, $—SO_2R^{13}$, $—SO_2NR^{13}R^{14}$, $—NR^{13}R^{14}$, $—NR^{13}SO_2R^{14}$, $—NR^{13}C(O)R^{14}$, $—NR^{13}C(O)OR^{14}$, $—NR^{13}C(O)NR^{13}R^{14}$, $—C(O)R^{14}$, $—C(O)OR^{14}$, and $—C(O)NR^{13}R^{14}$; or two adjacent $R^8$ form a heterocyclyl ring;
each $R^{13}$ and $R^{14}$ is independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;
$Y^1$ is selected from O, NH, and $NR^{13}$;
$Y^2$ is selected from O, $CH_2$, NH, and $NR^{13}$;
n is 1, 2, or 3;
m is 1 or 2;
p is 1, 2, 3, or 4;
q is 1, 2, or 3;
r is 0, 1, 2, 3, 4, 5, 6, 7, or 8;
s is 0, 1, 2, 3, or 4;
t is 0, 1, 2, 3, or 4;
u is 0, 1, 2, 3, 4 or 5; and
v is 0, 1, 2, 3, or 4.

In some embodiments described above or below of a compound of Formula (XI), $X_1$ and $X_2$ are N.
In some embodiments described above or below of a compound of Formula (XI), $X_1$ is $CR^5$ and $X_2$ is N.
In some embodiments described above or below of a compound of Formula (XI), $X_1$ is N and $X_2$ is $CR^5$.
In some embodiments described above or below of a compound of Formula (XI), q is 1 and r is 0.
In some embodiments described above or below of a compound of Formula (XI), $A^1$ is aryl.

In some embodiments described above or below of a compound of Formula (XI), $A^1$ is

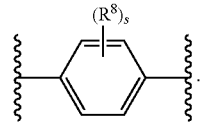

In some embodiments described above or below of a compound of Formula (XI), $A^1$ is

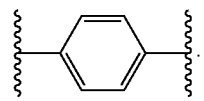

In some embodiments described above or below of a compound of Formula (XI), $A^1$ is heteroaryl.
In some embodiments described above or below of a compound of Formula (XI), $A^2$ is aryl.
In some embodiments described above or below of a compound of Formula (XI), $A^2$ is

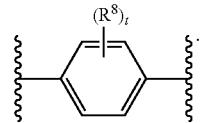

In some embodiments described above or below of a compound of Formula (XI), $A^2$ is

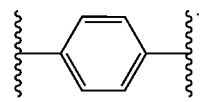

In some embodiments described above or below of a compound of Formula (XI), $A^2$ is heteroaryl.
In some embodiments described above or below of a compound of Formula (XI), $A^2$ is pyridine, pyrazine, pyrimidine, pyridazine, or triazine.
In some embodiments described above or below of a compound of Formula (XI), C is optionally substituted 5- or 6-membered heteroaryl. In other embodiments described above or below of a compound of Formula (XI), C is optionally substituted 5- or 6-membered heterocyclyl.
In some embodiments described above or below of a compound of Formula (XI), C is

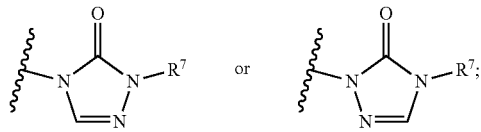

and
$R^7$ is alkyl, haloalkyl, hydroxyalkyl, alkoxyalkyl, -alkylene($NR^{13}R^{14}$), cycloalkyl, heterocyclyl, -alkylene(cycloalkyl), or -alkylene(heterocyclyl).

In some embodiments described above or below of a compound of Formula (XI), C is

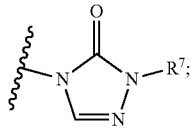

and R⁷ is alkyl, haloalkyl, hydroxyalkyl, alkoxyalkyl, -alkylene(NR¹³R¹⁴), cycloalkyl, heterocyclyl, -alkylene(cycloalkyl), or -alkylene(heterocyclyl).

In some embodiments described above or below of a compound of Formula (XI), C is

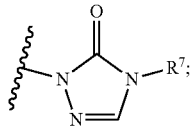

and R⁷ is alkyl, haloalkyl, hydroxyalkyl, alkoxyalkyl, -alkylene(NR¹³R¹⁴), cycloalkyl, heterocyclyl, -alkylene(cycloalkyl), or -alkylene(heterocyclyl).

In some embodiments described above or below of a compound of Formula (XI), E is alkyl.

In some embodiments described above or below of a compound of Formula (XI), E is cycloalkyl.

In some embodiments described above or below of a compound of Formula (XI), E is cyclopropyl, cyclobutyl, cyclopentyl, or cyclohexyl.

In some embodiments described above or below of a compound of Formula (XI), E is heterocyclyl.

In some embodiments described above or below of a compound of Formula (XI), E is aryl.

In some embodiments described above or below of a compound of Formula (XI), E is

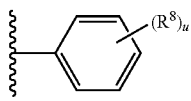

and u is 0, 1, 2, 3, 4, or 5.

In some embodiments described above or below of a compound of Formula (XI), E is heteroaryl.

In some embodiments described above or below of a compound of Formula (XI), E is selected from:

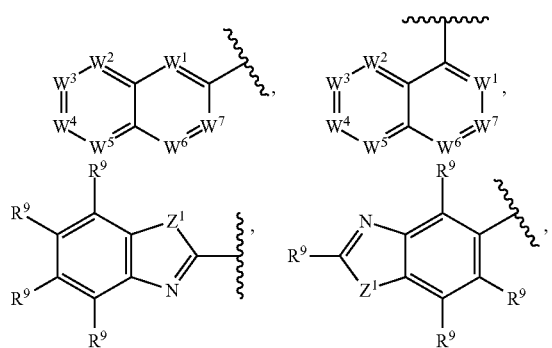

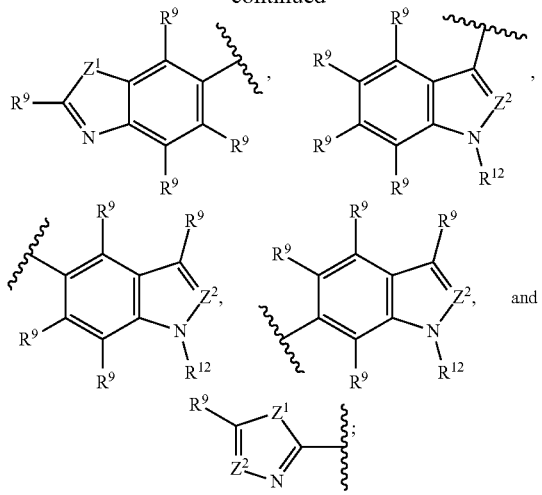

$W^1$, $W^2$, $W^3$, $W^4$, $W^5$, $W^6$, and $W^7$ are independently selected from N and $CR^9$;

$Z^1$ is $NR^{12}$, S, or O;

$Z^2$ is N or $CR^9$;

each $R^9$ is independently selected from H, halogen, CN, $NO_2$, alkyl, —$SR^{10}$, —$OR^{10}$, —$NR^{10}R^{11}$, $NR^{10}C(O)$(alkyl), —$NR^{10}C(O)$(cycloalkyl), —$NR^{10}C(O)$(heterocycloalkyl), —$NR^{10}C(O)$(aryl), —$NR^{10}C(O)$(heteroaryl), —$C(O)NR^{10}R^{11}$, —$C(O)NR^{10}$(cycloalkyl), —$C(O)NR^{10}$(heterocyclo alkyl), —$C(O)NR^{10}$(aryl), —$C(O)NR^{10}$(heteroaryl), —$NR^{10}C(O)NR^{10}R^{11}$, —$NR^{10}C(O)NR^{11}$(cycloalkyl), —$NR^{10}C(O)NR^{11}$(heterocycloalkyl), —$NR^{10}C(O)NR^{11}$(aryl), —$NR^{10}C(O)NR^{11}$(heteroaryl), —$NR^{10}C(O)O$(alkyl), —$NR^{10}C(O)O$(cycloalkyl), —$NR^{10}C(O)O$(heterocycloalkyl), —$NR^{10}C(O)O$(aryl), —$NR^{10}C(O)O$(heteroaryl), —$NR^{10}SO_2$(alkyl), —$NR^{10}SO_2$(cycloalkyl), —$NR^{10}SO_2$(heterocycloalkyl), —$NR^{10}SO_2$(aryl), —$NR^{10}SO_2$(heteroaryl), —$SO_2NR^{10}R^{11}$, —$SO_2NR^{10}$(cycloalkyl), —$SO_2NR^{10}$(heterocycloalkyl), —$SO_2NR^{10}$(aryl), —$SO_2NR^{10}$(heteroaryl), haloalkyl, aryl, and heteroaryl;

each $R^{10}$ and $R^{11}$ is independently selected from H and alkyl; or $R^{10}$ and $R^{11}$ taken together form a heterocycle with the nitrogen to which they are attached; and $R^{12}$ is H, alkyl or haloalkyl.

In some embodiments described above or below of a compound of Formula (XI), D is aryl.

In some embodiments described above or below of a compound of Formula (XI), E is heteroaryl.

In some embodiments described above or below of a compound of Formula (XI), D is selected from:

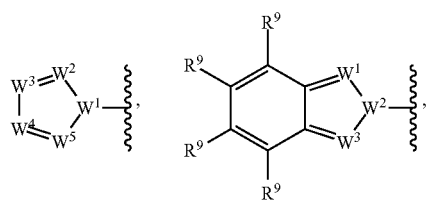

-continued

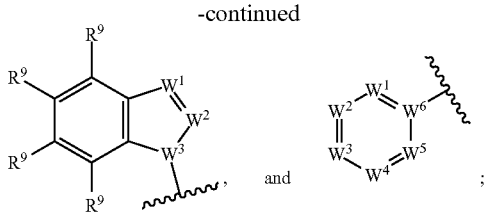

$W^1$, $W^2$, $W^3$, $W^4$, and $W^5$ are independently selected from N and $CR^9$;

$W^6$ is N or C; and each $R^9$ is independently selected from H, halogen, CN, $NO_2$, alkyl, —$SR^{10}$, —$OR^{10}$, —$NR^{10}R^{11}$, $NR^{10}C(O)$(alkyl), —$NR^{10}C(O)$(cycloalkyl), —$NR^{10}C(O)$(heterocycloalkyl), —$NR^{10}C(O)$(aryl), —$NR^{10}C(O)$(heteroaryl), —$C(O)NR^{10}R^{11}$, —$C(O)NR^{10}$(cycloalkyl), —$C(O)NR^{10}$(heterocycloalkyl), —$C(O)NR^{10}$(aryl), —$C(O)NR^{10}$(heteroaryl), —$NR^{10}C(O)NR^{10}R^{11}$, —$NR^{10}C(O)NR^{11}$(cycloalkyl), —$NR^{10}C(O)NR^{11}$(heterocycloalkyl), —$NR^{10}C(O)NR^{11}$(aryl), —$NR^{10}C(O)NR^{11}$(heteroaryl), —$NR^{10}C(O)O$(alkyl), —$NR^{10}C(O)O$(cycloalkyl), —$NR^{10}C(O)O$(heterocycloalkyl), —$NR^{10}C(O)O$(aryl), —$NR^{10}C(O)O$(heteroaryl), —$NR^{10}SO_2$(alkyl), —$NR^{10}SO_2$(cycloalkyl), —$NR^{10}SO_2$(heterocycloalkyl), —$NR^{10}SO_2$(aryl), —$NR^{10}SO_2$(heteroaryl), —$SO_2NR^{10}R^{11}$, —$SO_2NR^{10}$(cycloalkyl), —$SO_2NR^{10}$(heterocycloalkyl), —$SO_2NR^{10}$(aryl), —$SO_2NR^{10}$(heteroaryl), haloalkyl, aryl, and heteroaryl.

In certain embodiments described above or below of a compound of Formula (XI), D is

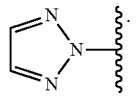

In certain embodiments described above or below of a compound of Formula (XI), D is

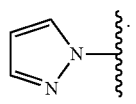

In certain embodiments described above or below of a compound of Formula (XI), D is

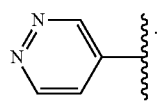 [SMILES: *c1ccnnc1]

In some embodiments described above or below of a compound of Formula (XI), $Y^1$ and $Y^2$ are O.

In some embodiments described above or below of a compound of Formula (XI), m is 1.

In some embodiments described above or below of a compound of Formula (XI), p is 1, 2, or 3.

In some embodiments described above or below of a compound of Formula (XI), p is 1.

In some embodiments described above or below of a compound of Formula (XI), $R^1$, $R^2$, $R^3$, and $R^4$ are hydrogen.

Further provided herein is a method to treat fibrosis using a compound of Formula (XI) wherein the fibrosis is liver fibrosis, idiopathic pulmonary fibrosis, kidney fibrosis, or cardiac fibrosis.

Further provided herein is a method to treat liver fibrosis using a compound of Formula (XI) wherein the liver fibrosis is associated with the later stages of alcoholic or nonalcoholic liver cirrhosis.

Further provided herein is a method to treat fibrosis using a compound of Formula (XI) wherein the fibrosis is idiopathic pulmonary fibrosis.

Further provided herein is a method to treat a disease using a compound of Formula (XI) wherein the disease or disorder characterized by fibrosis is a chronic autoimmune disease.

Further provided herein is a method to treat chronic autoimmune disease using a compound of Formula (XI) wherein the chronic autoimmune disease is rheumatoid arthritis, scleroderma, Crohn's disease or systemic lupus erythematosus.

Further provided herein is a method to treat chronic autoimmune disease using a compound of Formula (XI) wherein the chronic autoimmune disease is scleroderma.

Further provided herein is a method to treat fibrosis using a compound of Formula (XI) wherein the fibrosis is keloid formation resulting from abnormal wound healing.

Further provided herein is a method to treat fibrosis using a compound of Formula (XI) wherein the fibrosis occurs after organ transplantation.

Also provided herein is a method to treat fibrosis, a disorder characterized by fibrosis, or a disease characterized by fibrosis, the method comprising administering a composition comprising a therapeutically effective amount of a compound described herein in combination with one or more pharmaceutical agents. In certain embodiments described above, the one or more pharmaceutical agents are antifibrotic agents. In certain embodiments described above, the one or more pharmaceutical agents are antifungal agents.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Fibrosis represents a critically important yet surprisingly neglected health problem. Nearly 45% of all natural deaths in the Western world are attributed to chronic fibroproliferative diseases. However, there is currently only one clinically approved drug (Pirfenidone) that specifically targets the pathogenesis of fibrosis and is directly indicated for the treatment of a fibrotic disease. Fibrosis affects nearly every tissue in the body and, when highly progressive, can lead to organ malfunction and death. Clearly, the identification of novel anti-fibrotic drugs represents an unmet medical need that would have significant beneficial impact on patients in multiple disease populations. In addition, at present there is no cure for scleroderma and treatment is limited to symptom management.

Fibrosis, generally defined as the production of excessive amounts of connective tissue, develops as a consequence of diverse underlying diseases. Chronic inflammation or tissue damage/remodeling are typical fibrosis inducing events. Fibrosis affects nearly every tissue in the body and, when highly progressive, can lead to organ malfunction and death. Specific disease examples include idiopathic pulmonary fibrosis (IPF); liver fibrosis associated with the later stages of alcoholic and nonalcoholic liver cirrhosis; kidney fibrosis; cardiac fibrosis; and keloid formation resulting from abnormal wound healing. Additionally, fibrosis is a key pathological feature associated with chronic autoimmune diseases, including rheumatoid arthritis, scleroderma, Crohn's disease and systemic lupus erythematosus. As such, fibrosis represents a critically important yet surprisingly neglected health problem. Indeed, nearly 45% of all natural deaths in the Western world are attributed to chronic fibroproliferative diseases. However, at present, there is only one clinically approved drug (Pirfenidone, approved for the treatment of IPF in Europe only) that specifically targets the pathogenesis of fibrosis and is directly indicated for the treatment of a fibrotic disease. Unfortunately, Pirfenidone has significant liver and GI side effects, and patients treated with Pirfenidone are advised to avoid direct sunlight exposure, as it is known to cause photosensitivity reactions leading to rash, dry skin or pruritus. Recently, lysophosphatidic acid 1 (LPA1) antagonists (e.g., AM-152) have been demonstrated to be efficacious in preclinical models of IPF. However, clinical efficacy remains to be demonstrated for AM-152. Clearly, the identification of novel anti-fibrotic drugs represents a major unmet medical need that would have significant beneficial impact on patients in multiple disease populations.

Despite the diversity of diseases and triggers that can initiate a fibrotic process in a given tissue or organ, common biochemical and cellular mechanisms occur in all instances studied to date. Following injury or inflammatory insult, resident fibroblasts (in some cases recruited bone marrow-derived circulating fibrocytes or epithelial cells that have undergone an epithelial-to-mesenchymal transition) are activated and "transdifferentiate" into α-smooth muscle actin (α-SMA) expressing myofibroblasts that secrete the extracellular matrix (ECM) components required for wound repair. In the case of liver fibrosis, a resident pericyte population termed a quiescent hepatic stellate cell (HSC) "transdifferentiates" into a type I collagen producing α-SMA expressing fibrogenic "activated" HSC. Transforming growth factor-β1 (TGF-β1) mediated Smad 3/4 signaling commonly drives the transdifferentiation of resident fibroblasts or HSCs to myofibroblasts or activated HSCs and stimulates production of ECM components in the latter populations. Platelet-derived growth factor (PDGF) also serves as a common pro-fibrotic cytokine that drives cell activation and proliferation.

One therapeutic approach for the treatment of progressive fibrosis diseases is to target one of the multitudes of complex causative immunological processes. This approach is limited by a lack of mechanistic clarity and potential exacerbation of the underlying disease. An attractive alternative approach for the treatment of diverse fibrotic diseases is to directly target the transdifferentiation pathway responsible for interconversion of quiescent fibroblasts and activated pro-fibrotic myofibroblasts. Drugs capable of blocking the conversion of fibroblasts to activated myofibroblasts could be administered prophylactically following injury or insult (e.g., myocardial infaction) or therapeutically in the early stages of disease in organs capable of repair (e.g., liver fibrosis, IPF or scleroderma). Direct suppressors of TGF-β1 production (e.g., Pirfenidone) are not ideal candidates for chronic dosing and are especially undesirable for the treatment of autoimmune diseases, as they have the potential to exacerbate autoimmune responses. Alternatively, drugs capable of inducing the reversion of existing myofibroblasts to a quiescent cell fate would have broad applicability for the treatment of fibrosis in multiple tissue types and could potentially be efficacious at later stages of disease.

High content imaging assays have been established, using primary human lung fibroblasts and primary rodent HSCs, that enable the identification of small molecules that either inhibit myofibroblast formation/activation or induce the reversion of activated myofibroblasts to a quiescent fibroblast state. Conditions, involving serum starvation and subsequent TGF-β treatment, have been identified that facilitate robust in vitro transdifferentiation in a miniaturized (384 well plate) format that is amenable to high throughput small molecule screening. The inhibition assay is based on α-SMA immunofluorescent staining and cell morphology changes associated with fibroblast to myofibroblast transdifferentiation, Using the selective ALK-5 TGF-β1 receptor inhibitor (SB-43154) as a positive control, the inhibition assay has been used to initiate a screen of a collection of ~100,000 small molecules that consists of bioactive small molecules and a diversity set that has been assembled based on 2D and 3D structural diversity and inherent "drug-likeness" properties. Preliminary screening led to the identification of multiple previously identified anti-fibrotic molecules. The majority of these have limited clinical utility, as a result of known off target toxicity issues or demonstrated lack of in vivo efficacy. However, in addition to these, the triazole antifungal agent Itraconazole was identified as a highly efficacious inhibitor of myofibroblast formation (at doses well below those associated with toxicity in fibroblasts or other control cell types).

The activity of Itraconazole was confirmed in vitro by analyzing expression changes in multiple genes associated with fibroblast to myofibroblast transdifferentiation using biochemical methods (i.e., Western blot and RT-PCR). Using pharmacological methods, the mechanistic basis for the anti-fibrotic activity of this molecule has been established as dual inhibition of hedgehog signaling and vascular endothelial growth factor (VEFG) receptor glycosylation/trafficking (neither activity alone is sufficient). Encouragingly, it was established that the activity of Itraconazole translates to both human and rodent cell types, as well as to cells derived from multiple tissue types (e.g., lung, liver, skin, heart). Using Pirfenidone and AM-152 as benchmark control compounds, Itraconazole was demonstrated to have efficacy in both bleomycin-induced lung and carbon tetrachloride-induce liver fibrosis mouse models. As such, the FDA approved drug Itraconazole has been identified as a novel lead for the development of a new class of drugs for the treatment of multiple fibrosis related diseases.

A potential limitation to the use of this drug as an anti-fibrotic, especially for the treatment of liver fibrosis, is a known liver toxicity profile that is associated with coordination of heme iron by N4 of the 1,2,4 triazole moiety, leading to inhibition of P450 enzymes (most notably Cyp3A4), an activity distinct from the VEGF and Hgh activity of itraconazole. As such, medicinal chemistry efforts aimed at identifying optimized Itraconazole analogues with favorable liver toxicity profiles and further improvements in anti-fibrotic efficacy have been initiated. From an initial panel of ~30 Itraconazole analogues, in which the pKa of N4 is reduced or N4 nitrogen is substituted with carbon, several candidate leads have been identified wherein Cyp inhibition activity is eliminated and in vitro anti-fibrotic activity is retained. Notably, the pharmacokinetic properties of these compounds are comparable to those of the parent compound. Based on observed in vitro activity, in vivo efficacy, rodent serum exposure and human exposure data, it is anticipated that a 5-fold improvement in efficacy and/or exposure is desirable for the final clinical candidate. A preliminary structure activity relationship study has revealed that potency enhancement can be achieved by making modifications at sites distal to the triazole substituent. Chemistry efforts are ongoing and will be used to optimize efficacy, exposure ($C_{max}$>5-fold in vitro $EC_{50}$) and toxicity profiles (based on human off-target panel profiling, hERG and AMES in vitro toxicity assays, and Cyp induction/inhibition assays). Reproducible disease modifying activity, i.e., efficacy equal to or greater than that of existing (pirfenidone) or potential future (AM-152) standards of care, will be demonstrated for an optimized Itraconazole analogue, using both lung and liver rodent fibrosis models.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.
"Cyano" or "nitrile" refers to the —CN radical.
"Hydroxy" or "hydroxyl" refers to the —OH radical.
"Nitro" refers to the —$NO_2$ radical.
"Oxo" refers to the =O substituent.
"Oxime" refers to the =N—OH substituent.
"Thioxo" refers to the =S substituent.
"Alkyl" refers to a straight or branched hydrocarbon chain radical, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, vinyl, allyl, propynyl, and the like. Alkyl comprising unsaturations include alkenyl and alkynyl groups. Unless stated otherwise specifically in the specification, an alkyl group may be optionally substituted as described below.

"Alkylene" or "alkylene chain" refers to a straight or branched divalent hydrocarbon chain, as described for alkyl above. Unless stated otherwise specifically in the specification, an alkylene group may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. Illustrative examples of cycloalkyl groups include, but are not limited to, the following moieties:

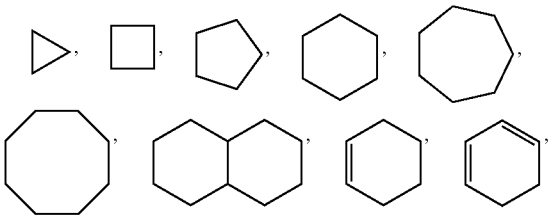

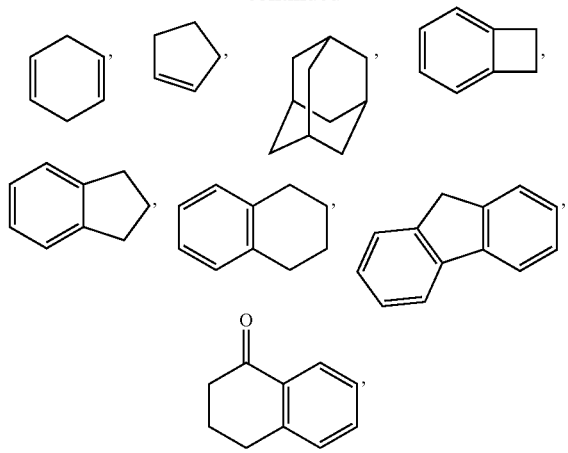

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

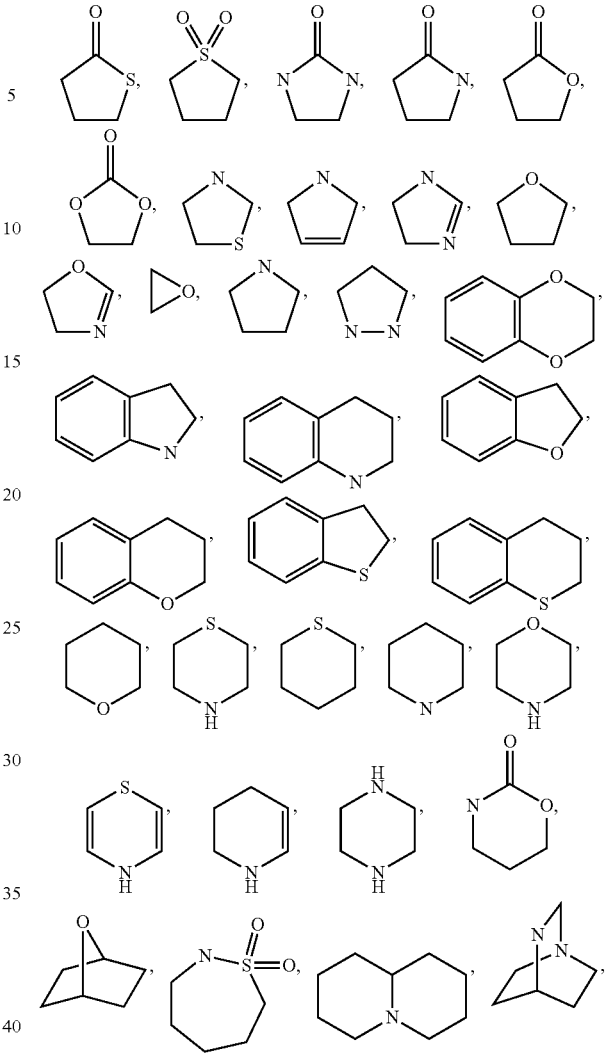

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

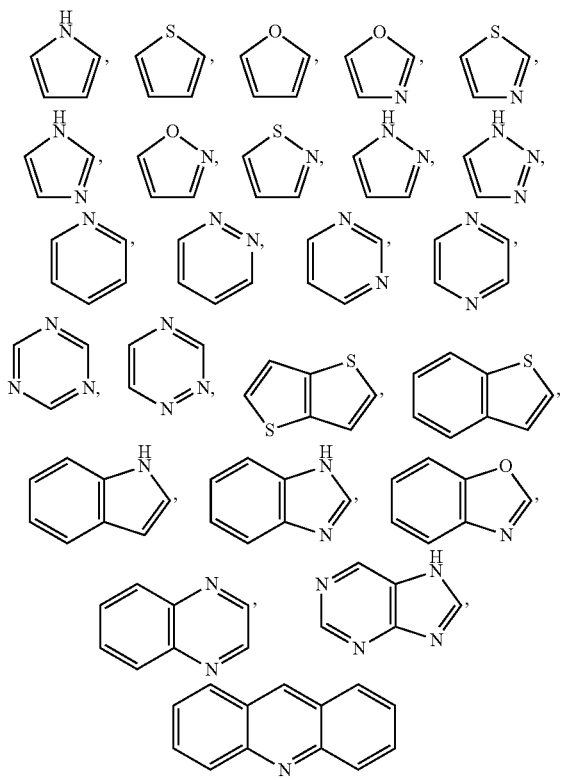

and the like.

The heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl).

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —$CO_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—$N^+R_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NH_2$, —$NR_gC$(=O)$NR_gR_h$, —$NR_gC$(=O)$OR_h$, —$NR_gSO_2R_h$, —$OC$(=O)$NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

Compounds

In one aspect, provided herein are compounds of Formula (I) having the structure:

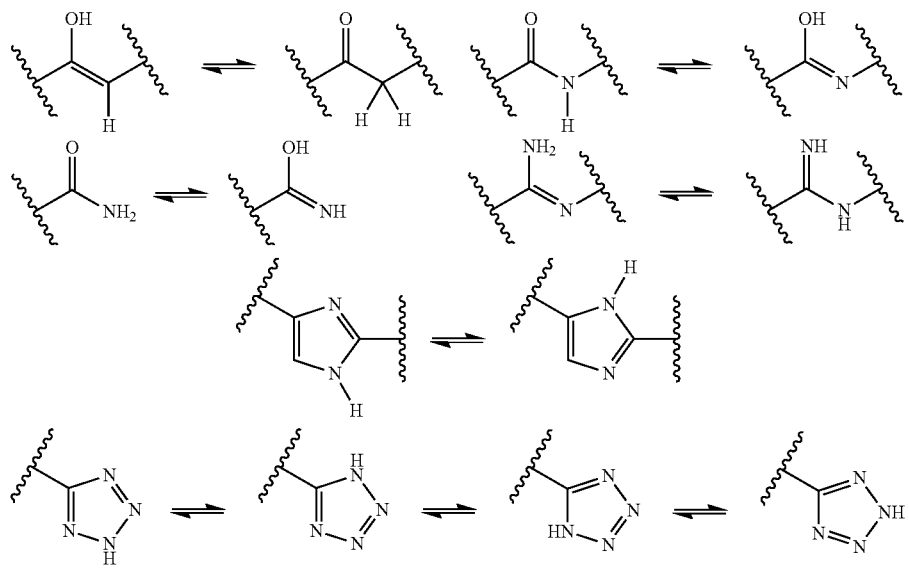

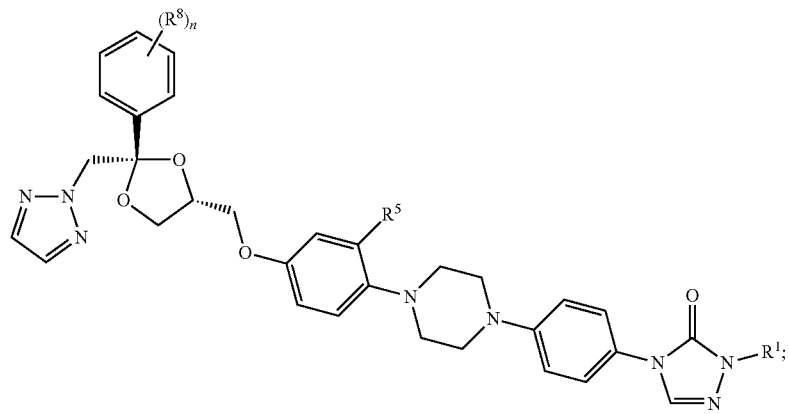

Formula (I)

wherein:
R[1] is —CH(CH$_3$)CH$_2$CH$_2$R[2], —CH(CH$_2$CH$_3$)$_2$, —CH(CH$_3$)$_2$, —CH$_2$CH(CH$_3$)$_2$, —CH(CH$_2$CH$_3$)CH(R[3])CH$_3$, -alkylene(cycloalkyl), or

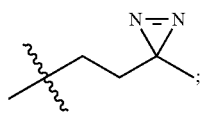 [SMILES: *CCC1(C)N=N1]

R[2] is alkyl, or —NR[13]R[14];
R[3] is —OH, alkyl, or —NR[13]R[14];
R[5] is H, —CN, halogen, haloalkyl, alkyl, —NR[13]R[14], -alkylene(NR[13]R[14]), and —SO$_2$R[13];
each R[8] is independently selected from halogen, —OH, —NO$_2$, —N$_3$, —CN, alkyl, alkoxy, haloalkoxy, haloalkyl, hydroxyalkyl, alkoxyalkyl, -alkylene(NR[13]R[14]), -alkylene(cycloalkyl), -alkylene(heterocyclyl), cycloalkyl, heterocyclyl, aryl, heteroaryl, —SR[13], —SOR[13], —SO$_2$R[13], —SO$_2$N[13]R[14], —NR[13]R[14], —NR[13]SO$_2$R[14], —NR[13]C(O)R[14], —NR[13]C(O)OR[14], —NR[13]C(O)NR[13]R[14], —C(O)R[14], —C(O)OR[14], and —C(O)NR[13]R[14]; or two adjacent R[8] form a heterocyclyl ring;
each R[13] and each R[14] is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R[13] and R[14] taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

In some embodiments is a compound of Formula (I), wherein R[1] is —CH(CH$_3$)CH$_2$CH$_2$R[2]. In some embodiments is a compound of Formula (I), wherein R[1] is —CH(CH$_3$)CH$_2$CH$_2$R[2], and R[2] is alkyl. In some embodiments is a compound of Formula (I), wherein R[1] is —CH(CH$_3$)CH$_2$CH$_2$R[2], and R[2] is methyl. In some embodiments is a compound of Formula (I), wherein R[1] is —CH(CH$_3$)CH$_2$CH$_2$R[2], and R[2] is ethyl. In some embodiments is a compound of Formula (I), wherein R[1] is —CH(CH$_3$)CH$_2$CH$_2$R[2], and R[2] is isopropyl. In some embodiments is a compound of Formula (I), wherein R[1] is —CH(CH$_3$)CH$_2$CH$_2$R[2], and R[2] is —NR[13]R[14]. In some embodiments is a compound of Formula (I), wherein R[1] is —CH(CH$_3$)CH$_2$CH$_2$R[2], and R[2] is —NH$_2$. In some embodiments is a compound of Formula (I), wherein R[1] is —CH(CH$_3$)CH$_2$CH$_2$R[2], and R[2] is —NHCH$_3$. In some embodiments is a compound of Formula (I), wherein R[1] is —CH(CH$_3$)CH$_2$CH$_2$R[2], and R[2] is —N(CH$_3$)$_2$.

In some embodiments is a compound of Formula (I), wherein R[1] is —CH(CH$_2$CH$_3$)$_2$. In some embodiments is a compound of Formula (I), wherein R[1] is —CH(CH$_3$)$_2$. In some embodiments is a compound of Formula (I), wherein R[1] is —CH(CH$_2$CH$_3$)CH(R[3])CH$_3$. In some embodiments is a compound of Formula (I), wherein R[1] is —CH(CH$_2$CH$_3$)CH(R[3])CH$_3$, and R[3] is —OH. In some embodiments is a compound of Formula (I), wherein R[1] is —CH(CH$_2$CH$_3$)CH(R[3])CH$_3$, and R[3] is alkyl. In some embodiments is a compound of Formula (I), wherein R[1] is —CH(CH$_2$CH$_3$)CH(R[3])CH$_3$, and R[3] is methyl. In some embodiments is a compound of Formula (I), wherein R[1] is —CH(CH$_2$CH$_3$)CH(R[3])CH$_3$, and R[3] is ethyl. In some embodiments is a compound of Formula (I), wherein R[1] is —CH(CH$_2$CH$_3$)CH(R[3])CH$_3$, and R[3] is —NR[13]R[14]. In some embodiments is a compound of Formula (I), wherein R[1] is —CH(CH$_2$CH$_3$)CH(R[3])CH$_3$, and R[3] is —NH$_2$. In some embodiments is a compound of Formula (I), wherein R[1] is —CH(CH$_2$CH$_3$)CH(R[3])CH$_3$, and R[3] is —NHCH$_3$. In some embodiments is a compound of Formula (I), wherein R[1] is —CH(CH$_2$CH$_3$)CH(R[3])CH$_3$, and R[3] is —N(CH$_3$)$_2$. In some embodiments is a compound of Formula (I), wherein R[1] is -alkylene(cycloalkyl). In some embodiments is a compound of Formula (I), wherein R[1] is —CH$_2$CH$_2$(cycloalkyl). In some embodiments is a compound of Formula (I), wherein R[1] is —CH$_2$(cycloalkyl). In some embodiments is a compound of Formula (I), wherein R[1] is —CH$_2$(cyclobutyl). In some embodiments is a compound of Formula (I), wherein R[1] is —CH$_2$(cyclopentyl). In some embodiments is a compound of Formula (I), wherein R[1] is —CH$_2$(cyclohexyl). In some embodiments is a compound of Formula (I), wherein R[1] is

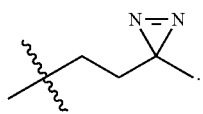

In some embodiments described above or below is a compound of Formula (I), wherein R[5] is H. In some embodiments described above or below is a compound of Formula (I), wherein R⁵ is —CN. In some embodiments described above or below is a compound of Formula (I), wherein R⁵ is halogen. In some embodiments described above or below is a compound of Formula (I), wherein R⁵ is F. In some embodiments described above or below is a compound of Formula (I), wherein R⁵ is Cl. In some embodiments described above or below is a compound of Formula (I), wherein R⁵ is alkyl. In some embodiments described above or below is a compound of Formula (I), wherein R⁵ is methyl. In some embodiments described above or below is a compound of Formula (I), wherein R⁵ is ethyl. In some embodiments described above or below is a compound of Formula (I), wherein R⁵ is —NR¹³R¹⁴. In some embodiments described above or below is a compound of Formula (I), wherein R⁵ is —NH₂. In some embodiments described above or below is a compound of Formula (I), wherein R⁵ is -alkylene(NR¹³R¹⁴). In some embodiments described above or below is a compound of Formula (I), wherein R⁵ is -alkylene(NH₂). In some embodiments described above or below is a compound of Formula (I), wherein R⁵ is —CH₂NH₂.

In some embodiments described above or below is a compound of Formula (I), wherein n is 0.

In some embodiments described above or below is a compound of Formula (I), wherein n is 1. In some embodiments described above or below is a compound of Formula (I), wherein n is 1 and R⁸ is selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, or —C(O)NR¹³R¹⁴. In some embodiments described above or below is a compound of Formula (I), wherein n is 1 and R⁸ is selected from halogen, —CN, alkyl, alkoxy, haloalkoxy, or haloalkyl. In some embodiments described above or below is a compound of Formula (I), wherein n is 1 and R⁸ is halogen. In some embodiments described above or below is a compound of Formula (I), wherein n is 1 and R⁸ is F. In some embodiments described above or below is a compound of Formula (I), wherein n is 1 and R⁸ is Cl. In some embodiments described above or below is a compound of Formula (I), wherein n is 1 and R⁸ is —CN. In some embodiments described above or below is a compound of Formula (I), wherein n is 1 and R⁸ is alkyl. In some embodiments described above or below is a compound of Formula (I), wherein n is 1 and R⁸ is methyl. In some embodiments described above or below is a compound of Formula (I), wherein n is 1 and R⁸ is ethyl. In some embodiments described above or below is a compound of Formula (I), wherein n is 1 and R⁸ is alkoxy. In some embodiments described above or below is a compound of Formula (I), wherein n is 1 and R⁸ is methoxy. In some embodiments described above or below is a compound of Formula (I), wherein n is 1 and R⁸ is ethoxy. In some embodiments described above or below is a compound of Formula (I), wherein n is 1 and R⁸ is haloalkoxy. In some embodiments described above or below is a compound of Formula (I), wherein n is 1 and R⁸ is —OCF₃. In some embodiments described above or below is a compound of Formula (I), wherein n is 1 and R⁸ is haloalkyl. In some embodiments described above or below is a compound of Formula (I), wherein n is 1 and R⁸ is —CF₃.

In some embodiments described above or below is a compound of Formula (I), wherein n is 2. In some embodiments described above or below is a compound of Formula (I), wherein n is 2 and R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴),-alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴. In some embodiments described above or below is a compound of Formula (I), wherein n is 2 and R⁸ is independently selected from halogen, —CN, alkyl, alkoxy, haloalkoxy, and haloalkyl. In some embodiments described above or below is a compound of Formula (I), wherein n is 2 and R⁸ is halogen. In some embodiments described above or below is a compound of Formula (I), wherein n is 2 and each R⁸ is F. In some embodiments described above or below is a compound of Formula (I), wherein n is 2 and each R⁸ is Cl. In some embodiments described above or below is a compound of Formula (I), wherein n is 2 and R⁸ is independently selected from halogen and —CN. In some embodiments described above or below is a compound of Formula (I), wherein n is 2 and R⁸ is independently selected from halogen and alkyl. In some embodiments described above or below is a compound of Formula (I), wherein n is 2 and R⁸ is independently selected from —CN and alkyl. In some embodiments described above or below is a compound of Formula (I), wherein n is 2 and two adjacent R⁸ form a heterocyclyl ring.

In another embodiment is a compound of Formula (I) having the structure:

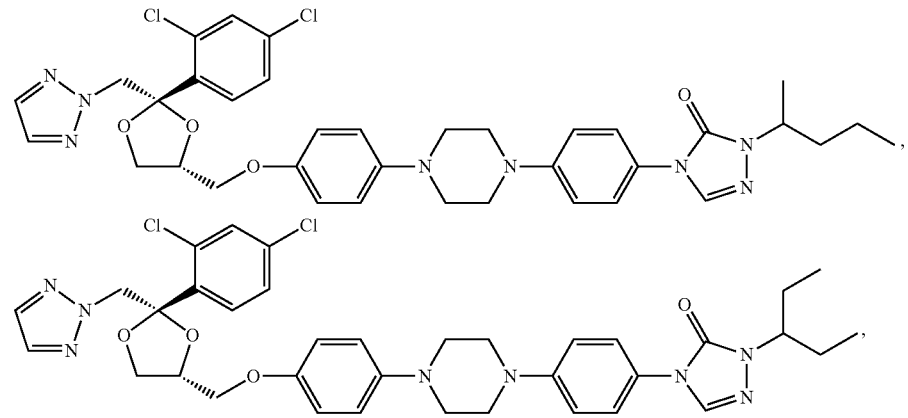

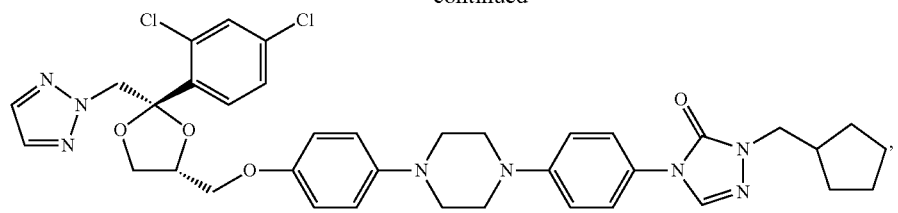
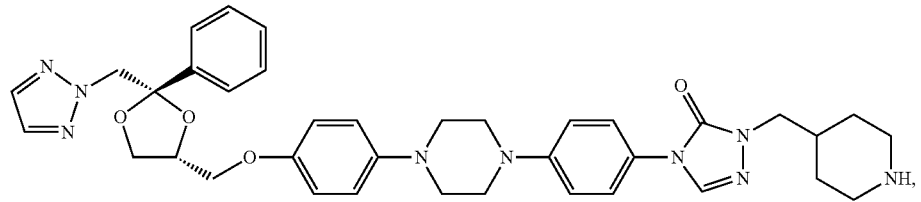
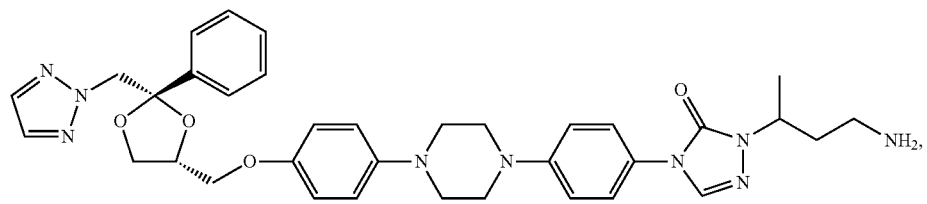
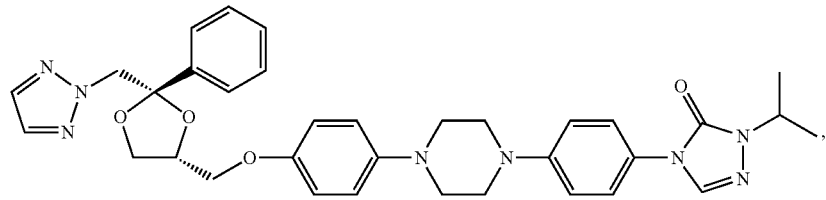
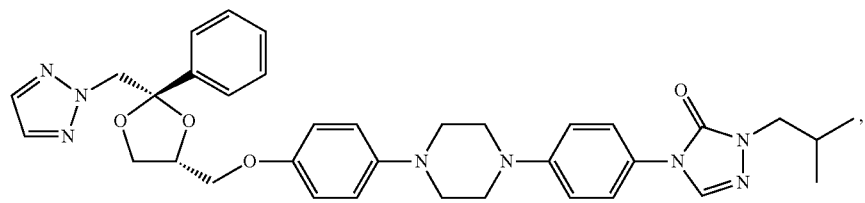
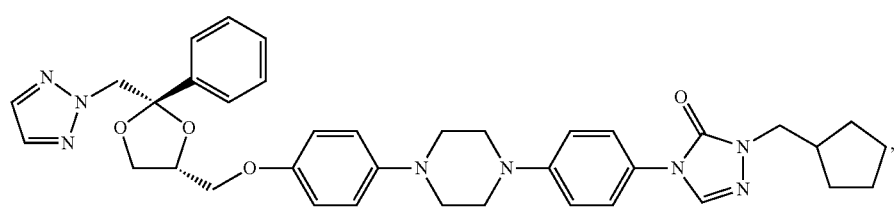
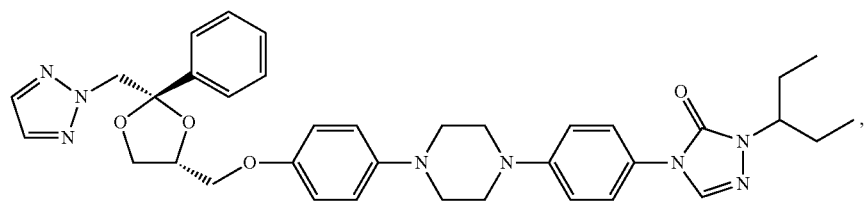
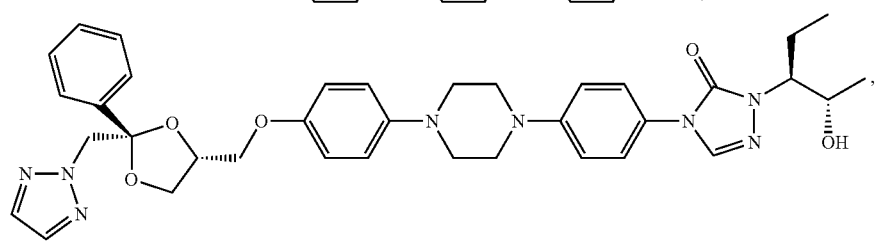

-continued
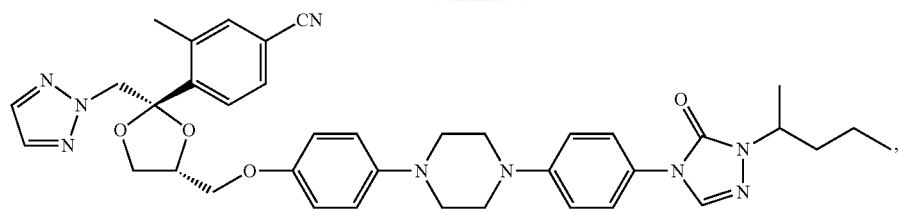
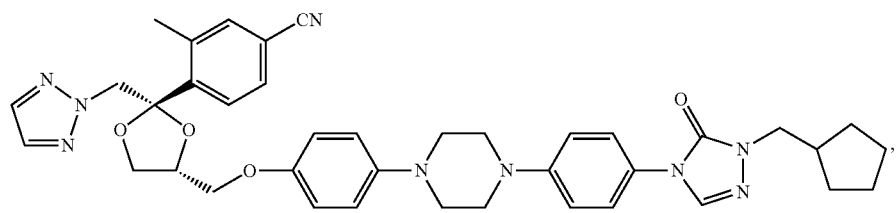
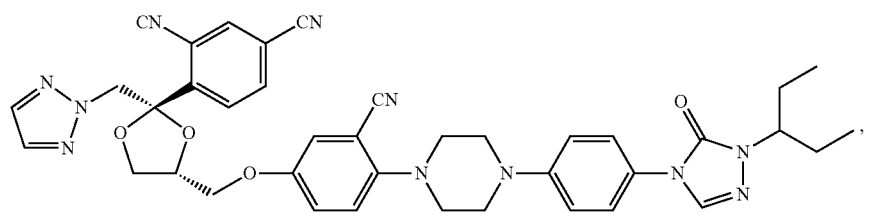
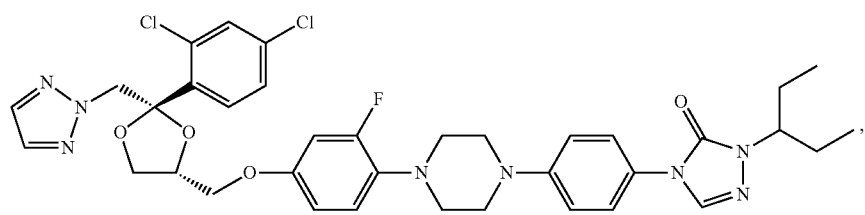
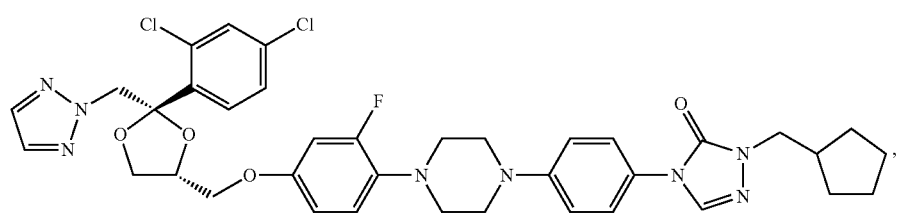
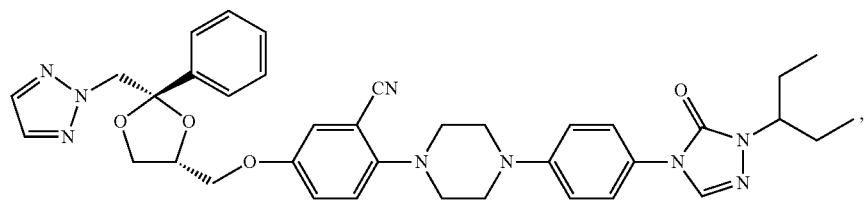
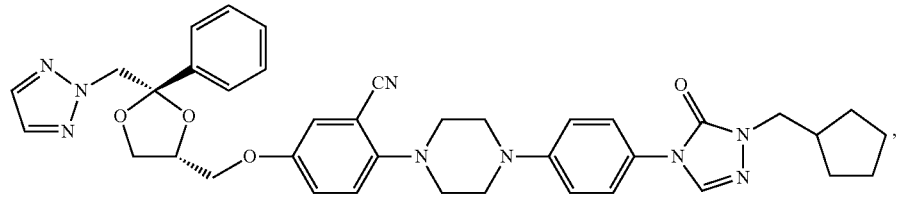

-continued
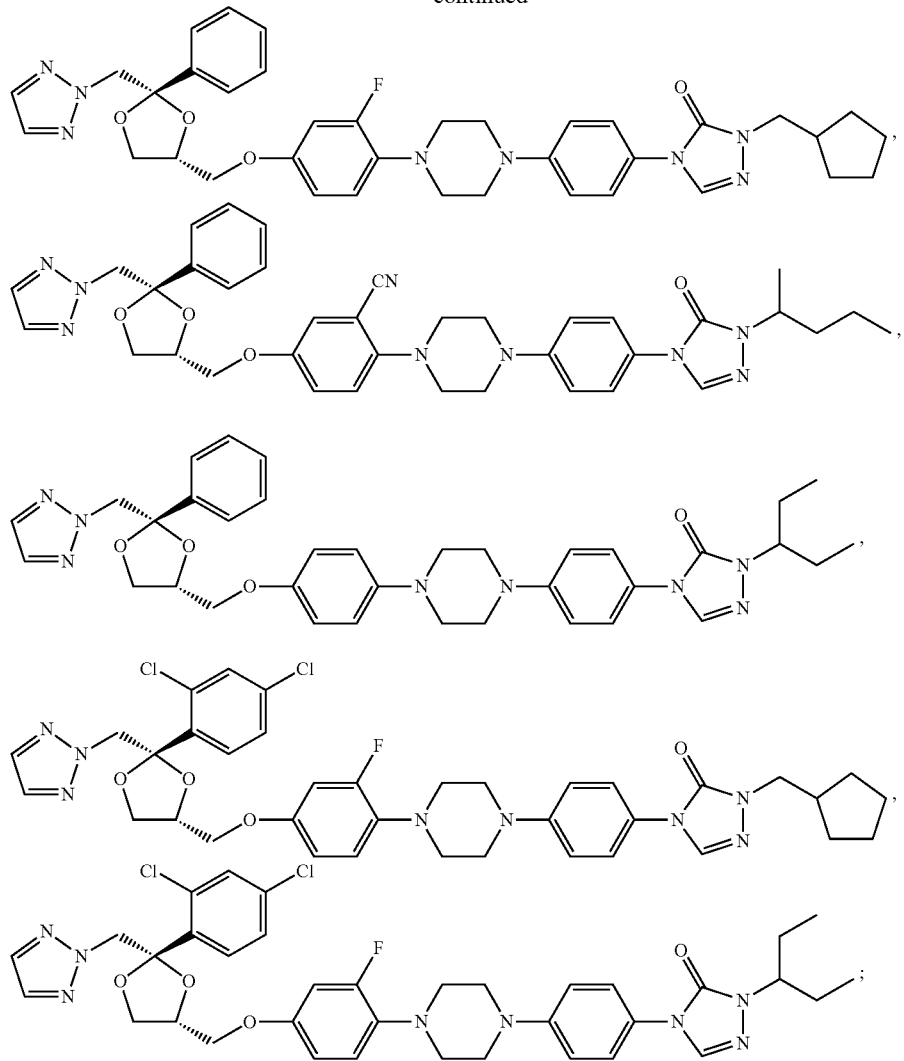
or a pharmaceutically acceptable salt, pharmaceutically acceptable solvate, or pharmaceutically acceptable prodrug thereof.
In another aspect, provided herein are compounds of Formula (Ia) having the structure:
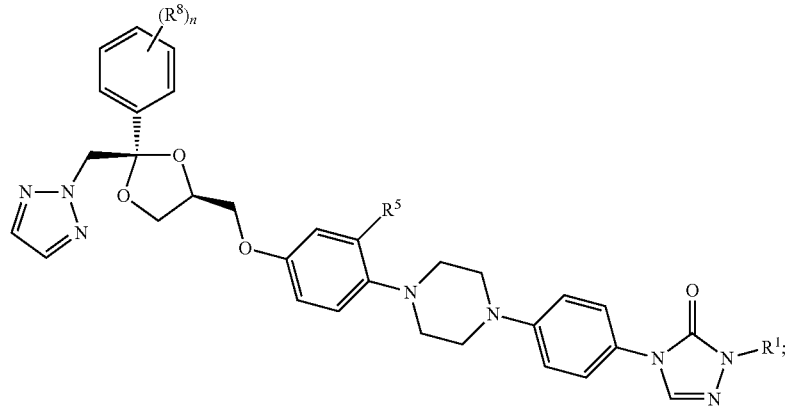
Formula (Ia)

wherein:

$R^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

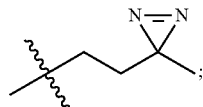
;

$R^2$ is alkyl, or —NR$^{13}$R$^{14}$;

$R^3$ is —OH, alkyl, or —NR$^{13}$R$^{14}$;

$R^5$ is H, —CN, halogen, haloalkyl, alkyl, —NR$^{13}$R$^{14}$, -alkylene(NR$^{13}$R$^{14}$), and —SO$_2$R$^{13}$;

each $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$),-alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent $R^8$ form a heterocyclyl ring;

each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached; and n is selected from 0, 1, 2, 3, and 4;

or a pharmaceutically acceptable salt, pharmaceutically acceptable solvate, or pharmaceutically acceptable prodrug thereof.

In some embodiments is a compound of Formula (Ia), wherein $R^1$ is —CH(CH$_3$)CH$_2$CH$_2$R$^2$. In some embodiments is a compound of Formula (Ia), wherein $R^1$ is —CH(CH$_3$)CH$_2$CH$_2$R$^2$, and $R^2$ is alkyl. In some embodiments is a compound of Formula (Ia), wherein $R^1$ is —CH(CH$_3$)CH$_2$CH$_2$R$^2$, and $R^2$ is methyl. In some embodiments is a compound of Formula (Ia), wherein $R^1$ is —CH(CH$_3$)CH$_2$CH$_2$R$^2$, and $R^2$ is ethyl. In some embodiments is a compound of Formula (Ia), wherein $R^1$ is —CH(CH$_3$)CH$_2$CH$_2$R$^2$, and $R^2$ is isopropyl. In some embodiments is a compound of Formula (Ia), wherein $R^1$ is —CH(CH$_3$)CH$_2$CH$_2$R$^2$, and $R^2$ is —NR$^{13}$R$^{14}$. In some embodiments is a compound of Formula (Ia), wherein $R^1$ is —CH(CH$_3$)CH$_2$CH$_2$R$^2$, and $R^2$ is —NH$_2$. In some embodiments is a compound of Formula (Ia), wherein $R^1$ is —CH(CH$_3$)CH$_2$CH$_2$R$^2$, and $R^2$ is —NHCH$_3$. In some embodiments is a compound of Formula (Ia), wherein $R^1$ is —CH(CH$_3$)CH$_2$CH$_2$R$^2$, and $R^2$ is —N(CH$_3$)$_2$.

In some embodiments is a compound of Formula (Ia), wherein $R^1$ is —CH(CH$_2$CH$_3$)$_2$. In some embodiments is a compound of Formula (Ia), wherein $R^1$ is —CH(CH$_3$)$_2$. In some embodiments is a compound of Formula (Ia), wherein $R^1$ is —CH(CH$_2$CH$_3$)CH(R$^3$)CH$_3$. In some embodiments is a compound of Formula (Ia), wherein $R^1$ is —CH(CH$_2$CH$_3$)CH(R$^3$)CH$_3$, and $R^3$ is —OH. In some embodiments is a compound of Formula (Ia), wherein $R^1$ is —CH(CH$_2$CH$_3$)CH(R$^3$)CH$_3$, and $R^3$ is alkyl. In some embodiments is a compound of Formula (Ia), wherein $R^1$ is —CH(CH$_2$CH$_3$)CH(R$^3$)CH$_3$, and $R^3$ is methyl. In some embodiments is a compound of Formula (Ia), wherein $R^1$ is —CH(CH$_2$CH$_3$)CH(R$^3$)CH$_3$, and $R^3$ is ethyl. In some embodiments is a compound of Formula (Ia), wherein $R^1$ is —CH(CH$_2$CH$_3$)CH(R$^3$)CH$_3$, and $R^3$ is —NR$^{13}$R$^{14}$. In some embodiments is a compound of Formula (Ia), wherein $R^1$ is —CH(CH$_2$CH$_3$)CH(R$^3$)CH$_3$, and $R^3$ is —NH$_2$. In some embodiments is a compound of Formula (Ia), wherein $R^1$ is —CH(CH$_2$CH$_3$)CH(R$^3$)CH$_3$, and $R^3$ is —NHCH$_3$. In some embodiments is a compound of Formula (Ia), wherein $R^1$ is —CH(CH$_2$CH$_3$)CH(R$^3$)CH$_3$, and $R^3$ is —N(CH$_3$)$_2$. In some embodiments is a compound of Formula (Ia), wherein $R^1$ is -alkylene(cycloalkyl). In some embodiments is a compound of Formula (Ia), wherein $R^1$ is —CH$_2$CH$_2$(cycloalkyl). In some embodiments is a compound of Formula (Ia), wherein $R^1$ is —CH$_2$(cycloalkyl). In some embodiments is a compound of Formula (Ia), wherein $R^1$ is —CH$_2$(cyclobutyl). In some embodiments is a compound of Formula (Ia), wherein $R^1$ is —CH$_2$(cyclopentyl). In some embodiments is a compound of Formula (Ia), wherein $R^1$ is —CH$_2$(cyclohexyl). In some embodiments is a compound of Formula (Ia), wherein $R^1$ is

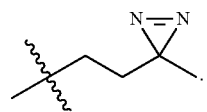 [SMILES: *CCC1(C)N=N1]
.

In some embodiments described above or below is a compound of Formula (Ia), wherein $R^5$ is H. In some embodiments described above or below is a compound of Formula (Ia), wherein $R^5$ is —CN. In some embodiments described above or below is a compound of Formula (Ia), wherein $R^5$ is halogen. In some embodiments described above or below is a compound of Formula (a), wherein $R^5$ is F. In some embodiments described above or below is a compound of Formula (Ia), wherein $R^5$ is Cl. In some embodiments described above or below is a compound of Formula (Ia), wherein $R^5$ is alkyl. In some embodiments described above or below is a compound of Formula (Ia), wherein $R^5$ is methyl. In some embodiments described above or below is a compound of Formula (Ia), wherein $R^5$ is ethyl. In some embodiments described above or below is a compound of Formula (Ia), wherein $R^5$ is —NR$^{13}$R$^{14}$. In some embodiments described above or below is a compound of Formula (Ia), wherein $R^5$ is —NH$_2$. In some embodiments described above or below is a compound of Formula (Ia), wherein $R^5$ is -alkylene(NR$^{13}$R$^{14}$). In some embodiments described above or below is a compound of Formula (Ia), wherein $R^5$ is -alkylene(NH$_2$). In some embodiments described above or below is a compound of Formula (Ia), wherein $R^5$ is —CH$_2$NH$_2$.

In some embodiments described above or below is a compound of Formula (Ia), wherein n is 0.

In some embodiments described above or below is a compound of Formula (Ia), wherein n is 1. In some embodiments described above or below is a compound of Formula (Ia), wherein n is 1 and $R^8$ is selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, or —C(O)NR$^{13}$R$^{14}$. In some embodiments described above or below is a compound of Formula (Ia), wherein n is 1 and $R^8$ is selected from halogen, —CN, alkyl, alkoxy, haloalkoxy, or haloalkyl. In some embodiments described above or below is a compound of Formula (Ia), wherein n is 1 and R⁸ is halogen. In some embodiments described above or below is a compound of Formula (Ia), wherein n is 1 and R⁸ is F. In some embodiments described above or below is a compound of Formula (Ia), wherein n is 1 and R⁸ is Cl. In some embodiments described above or below is a compound of Formula (Ia), wherein n is 1 and R⁸ is —CN. In some embodiments described above or below is a compound of Formula (Ia), wherein n is 1 and R⁸ is alkyl. In some embodiments described above or below is a compound of Formula (Ia), wherein n is 1 and R⁸ is methyl. In some embodiments described above or below is a compound of Formula (Ia), wherein n is 1 and R⁸ is ethyl. In some embodiments described above or below is a compound of Formula (Ia), wherein n is 1 and R⁸ is alkoxy. In some embodiments described above or below is a compound of Formula (Ia), wherein n is 1 and R⁸ is methoxy. In some embodiments described above or below is a compound of Formula (Ia), wherein n is 1 and R⁸ is ethoxy. In some embodiments described above or below is a compound of Formula (Ia), wherein n is 1 and R⁸ is haloalkoxy. In some embodiments described above or below is a compound of Formula (Ia), wherein n is 1 and R⁸ is —OCF₃. In some embodiments described above or below is a compound of Formula (Ia), wherein n is 1 and R⁸ is haloalkyl. In some embodiments described above or below is a compound of Formula (Ia), wherein n is 1 and R⁸ is —CF₃.

In some embodiments described above or below is a compound of Formula (Ia), wherein n is 2. In some embodiments described above or below is a compound of Formula (Ia), wherein n is 2 and R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴. In some embodiments described above or below is a compound of Formula (Ia), wherein n is 2 and R⁸ is independently selected from halogen, —CN, alkyl, alkoxy, haloalkoxy, and haloalkyl. In some embodiments described above or below is a compound of Formula (Ia), wherein n is 2 and R⁸ is halogen. In some embodiments described above or below is a compound of Formula (Ia), wherein n is 2 and each R⁸ is F. In some embodiments described above or below is a compound of Formula (Ia), wherein n is 2 and each R⁸ is Cl. In some embodiments described above or below is a compound of Formula (Ia), wherein n is 2 and R⁸ is independently selected from halogen and —CN. In some embodiments described above or below is a compound of Formula (Ia), wherein n is 2 and R⁸ is independently selected from halogen and alkyl. In some embodiments described above or below is a compound of Formula (Ia), wherein n is 2 and R⁸ is independently selected from —CN and alkyl. In some embodiments described above or below is a compound of Formula (Ia), wherein n is 2 and two adjacent R⁸ form a heterocyclyl ring.

In another embodiment is a compound of Formula (Ia) having the structure:

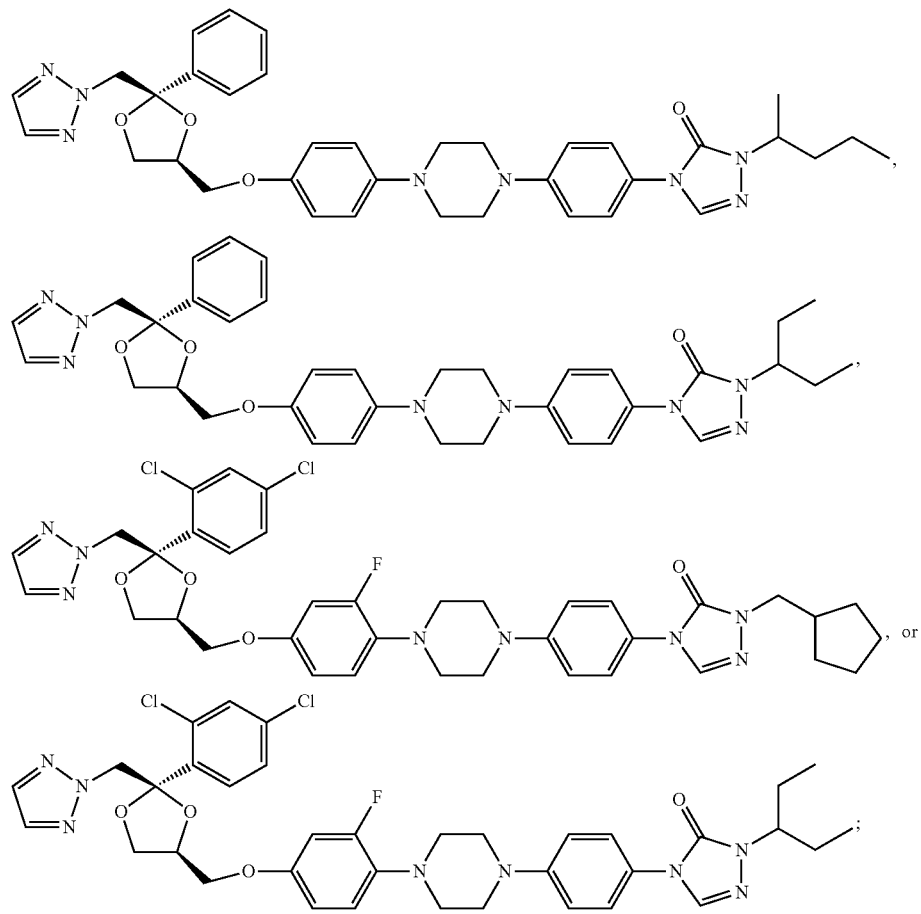

or a pharmaceutically acceptable salt, pharmaceutically acceptable solvate, or pharmaceutically acceptable prodrug thereof.

In another aspect, provided herein are compounds of Formula (II) having the structure:

Formula (II)

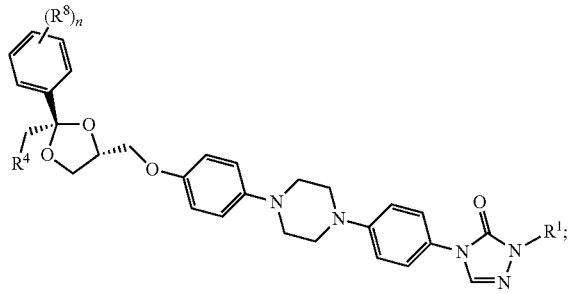

wherein:
R$^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

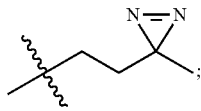 [SMILES: *CCC1(C)N=N1]

R$^2$ is alkyl, or —NR$^{13}$R$^{14}$;
R$^3$ is —OH, alkyl, or —NR$^{13}$R$^{14}$;
R$^5$ is H, —CN, halogen, haloalkyl, alkyl, —NR$^{13}$R$^{14}$, -alkylene(NR$^{13}$R$^{14}$), and —SO$_2$R$^{13}$;
each R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

In some embodiments is a compound of Formula (II), wherein R$^4$ is halogen. In some embodiments is a compound of Formula (II), wherein R$^4$ is F. In some embodiments is a compound of Formula (II), wherein R$^4$ is Cl. In some embodiments is a compound of Formula (II), wherein R$^4$ is alkyl. In some embodiments is a compound of Formula (II), wherein R$^4$ is methyl. In some embodiments is a compound of Formula (II), wherein R$^4$ is ethyl. In some embodiments is a compound of Formula (II), wherein R$^4$ is

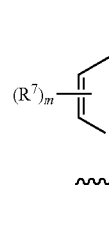

In some embodiments is a compound of Formula (II), wherein R$^4$ is

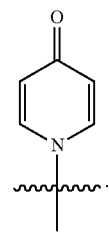

In some embodiments is a compound of Formula (II), wherein R$^4$ is

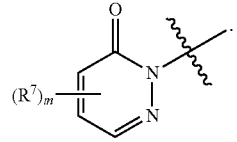

In some embodiments is a compound of Formula (II), wherein R$^4$ is

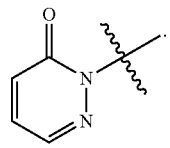 [SMILES: *n1ncccc1=O]

In some embodiments is a compound of Formula (II), wherein R$^4$ is

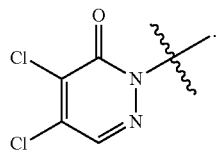

In some embodiments is a compound of Formula (II), wherein R$^4$ is

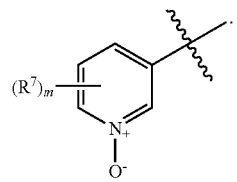

In some embodiments is a compound of Formula (II), wherein R$^4$ is

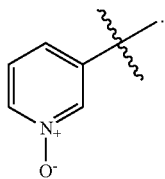 [SMILES: *c1ccc[n+]([O-])c1]

In some embodiments is a compound of Formula (II), wherein $R^4$ is

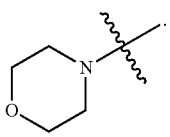 [SMILES: *N1CCOCC1]

In some embodiments is a compound of Formula (II), wherein $R^4$ is

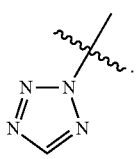

In some embodiments is a compound of Formula (II), wherein $R^4$ is

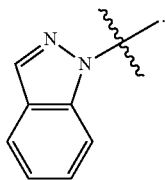 [SMILES: *n1ncc2ccccc21]

In some embodiments is a compound of Formula (II), wherein $R^1$ is —CH(CH$_3$)CH$_2$CH$_2$R$^2$. In some embodiments is a compound of Formula (II), wherein $R^1$ is —CH(CH$_3$)CH$_2$CH$_2$R$^2$, and $R^2$ is H. In some embodiments is a compound of Formula (II), wherein $R^1$ is —CH(CH$_3$)CH$_2$CH$_2$R$^2$, and $R^2$ is alkyl. In some embodiments is a compound of Formula (II), wherein $R^1$ is —CH(CH$_3$)CH$_2$CH$_2$R$^2$, and $R^2$ is methyl. In some embodiments is a compound of Formula (II), wherein $R^1$ is —CH(CH$_3$)CH$_2$CH$_2$R$^2$, and $R^2$ is ethyl. In some embodiments is a compound of Formula (II), wherein $R^1$ is —CH(CH$_3$)CH$_2$CH$_2$R$^2$, and $R^2$ is isopropyl. In some embodiments is a compound of Formula (II), wherein $R^1$ is —CH(CH$_3$)CH$_2$CH$_2$R$^2$, and $R^2$ is —NR$^{13}$R$^{14}$. In some embodiments is a compound of Formula (II), wherein $R^1$ is —CH(CH$_3$)CH$_2$CH$_2$R$^2$, and $R^2$ is —NH$_2$. In some embodiments is a compound of Formula (II), wherein $R^1$ is —CH(CH$_3$)CH$_2$CH$_2$R$^2$, and $R^2$ is —NHCH$_3$. In some embodiments is a compound of Formula (II), wherein $R^1$ is —CH(CH$_3$)CH$_2$CH$_2$R$^2$, and $R^2$ is —N(CH$_3$)$_2$.

In some embodiments is a compound of Formula (II), wherein $R^1$ is —CH(CH$_2$CH$_3$)$_2$. In some embodiments is a compound of Formula (II), wherein $R^1$ is —CH(CH$_3$)$_2$. In some embodiments is a compound of Formula (II), wherein $R^1$ is —CH(CH$_2$CH$_3$)CH(R$^3$)CH$_3$. In some embodiments is a compound of Formula (II), wherein $R^1$ is —CH(CH$_2$CH$_3$)CH(R$^3$)CH$_3$, and $R^3$ is —OH. In some embodiments is a compound of Formula (II), wherein $R^1$ is —CH(CH$_2$CH$_3$)CH(R$^3$)CH$_3$, and $R^3$ is alkyl. In some embodiments is a compound of Formula (II), wherein $R^1$ is —CH(CH$_2$CH$_3$)CH(R$^3$)CH$_3$, and $R^3$ is methyl. In some embodiments is a compound of Formula (II), wherein $R^1$ is —CH(CH$_2$CH$_3$)CH(R$^3$)CH$_3$, and $R^3$ is ethyl. In some embodiments is a compound of Formula (II), wherein $R^1$ is —CH(CH$_2$CH$_3$)CH(R$^3$)CH$_3$, and $R^3$ is —NR$^{13}$R$^{14}$. In some embodiments is a compound of Formula (II), wherein $R^1$ is —CH(CH$_2$CH$_3$)CH(R$^3$)CH$_3$, and $R^3$ is —NH$_2$. In some embodiments is a compound of Formula (II), wherein $R^1$ is —CH(CH$_2$CH$_3$)CH(R$^3$)CH$_3$, and $R^3$ is —NHCH$_3$. In some embodiments is a compound of Formula (II), wherein $R^1$ is —CH(CH$_2$CH$_3$)CH(R$^3$)CH$_3$, and $R^3$ is —N(CH$_3$)$_2$. In some embodiments is a compound of Formula (II), wherein $R^1$ is -alkylene(cycloalkyl). In some embodiments is a compound of Formula (II), wherein $R^1$ is —CH$_2$CH$_2$(cycloalkyl). In some embodiments is a compound of Formula (II), wherein $R^1$ is —CH$_2$(cycloalkyl). In some embodiments is a compound of Formula (II), wherein $R^1$ is —CH$_2$(cyclobutyl). In some embodiments is a compound of Formula (II), wherein $R^1$ is —CH$_2$(cyclopentyl). In some embodiments is a compound of Formula (II), wherein $R^1$ is —CH$_2$(cyclohexyl). In some embodiments is a compound of Formula (II), wherein $R^1$ is

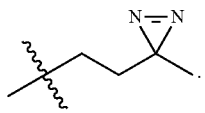

In some embodiments described above or below is a compound of Formula (II), wherein n is 0.

In some embodiments described above or below is a compound of Formula (II), wherein n is 1. In some embodiments described above or below is a compound of Formula (II), wherein n is 1 and $R^8$ is selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, or —C(O)NR$^{13}$R$^{14}$. In some embodiments described above or below is a compound of Formula (II), wherein n is 1 and $R^8$ is selected from halogen, —CN, alkyl, alkoxy, haloalkoxy, or haloalkyl. In some embodiments described above or below is a compound of Formula (II), wherein n is 1 and $R^8$ is halogen. In some embodiments described above or below is a compound of Formula (II), wherein n is 1 and $R^8$ is F. In some embodiments described above or below is a compound of Formula (II), wherein n is 1 and $R^8$ is Cl. In some embodiments described above or below is a compound of Formula (II), wherein n is 1 and $R^8$ is —CN. In some embodiments described above or below is a compound of Formula (II), wherein n is 1 and $R^8$ is alkyl. In some embodiments described above or below is a compound of Formula (II), wherein n is 1 and $R^8$ is methyl. In some embodiments described above or below is a compound of Formula (II), wherein n is 1 and $R^8$ is ethyl. In some embodiments described above or below is a compound of Formula (II), wherein n is 1 and $R^8$ is alkoxy. In some embodiments described above or below is a compound of Formula (II), wherein n is 1 and $R^8$ is methoxy. In some embodiments described above or below is a compound of Formula (II), wherein n is 1 and $R^8$ is ethoxy. In some embodiments described above or below is a compound of Formula (II), wherein n is 1 and $R^8$ is haloalkoxy. In some embodiments described above or below is a compound of Formula (II), wherein n is 1 and $R^8$ is —$OCF_3$. In some embodiments described above or below is a compound of Formula (II), wherein n is 1 and $R^8$ is haloalkyl. In some embodiments described above or below is a compound of Formula (II), wherein n is 1 and $R^8$ is —$CF_3$.

In some embodiments described above or below is a compound of Formula (II), wherein n is 2. In some embodiments described above or below is a compound of Formula (II), wherein n is 2 and $R^8$ is independently selected from halogen, —OH, —$NO_2$, —$N_3$, —CN, alkyl, alkoxy, haloalkoxy, haloalkyl, hydroxyalkyl, alkoxyalkyl, -alkylene ($NR^{13}R^{14}$), -alkylene(cycloalkyl), -alkylene(heterocyclyl), cycloalkyl, heterocyclyl, aryl, heteroaryl, —$SR^{13}$, —$SOR^{13}$, —$SO_2R^{13}$, —$SO_2NR^{13}R^{14}$, —$NR^{13}R^{14}$, —$NR^{13}SO_2R^{14}$, —$NR^{13}C(O)R^{14}$, —$NR^{13}C(O)OR^{14}$, —$NR^{13}C(O)NR^{13}R^{14}$, —$C(O)R^{14}$, —$C(O)OR^{14}$, and —$C(O)NR^{13}R^{14}$.

In some embodiments described above or below is a compound of Formula (II), wherein n is 2 and $R^8$ is independently selected from halogen, —CN, alkyl, alkoxy, haloalkoxy, and haloalkyl. In some embodiments described above or below is a compound of Formula (II), wherein n is 2 and $R^8$ is halogen. In some embodiments described above or below is a compound of Formula (II), wherein n is 2 and each $R^8$ is F. In some embodiments described above or below is a compound of Formula (II), wherein n is 2 and each $R^8$ is Cl. In some embodiments described above or below is a compound of Formula (II), wherein n is 2 and $R^8$ is independently selected from halogen and —CN. In some embodiments described above or below is a compound of Formula (II), wherein n is 2 and $R^8$ is independently selected from halogen and alkyl. In some embodiments described above or below is a compound of Formula (II), wherein n is 2 and $R^8$ is independently selected from —CN and alkyl. In some embodiments described above or below is a compound of Formula (II), wherein n is 2 and two adjacent $R^8$ form a heterocyclyl ring.

In another embodiment is a compound of Formula (II) having the structure:

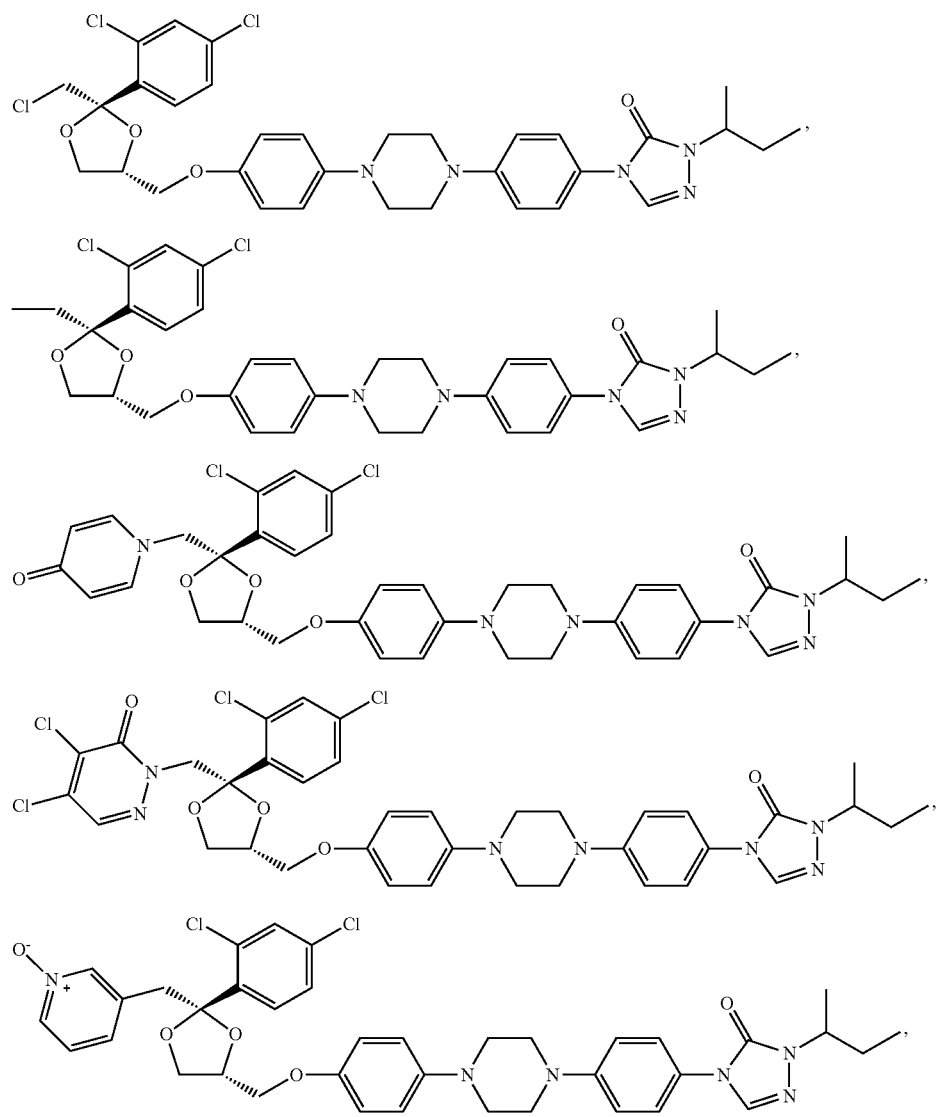

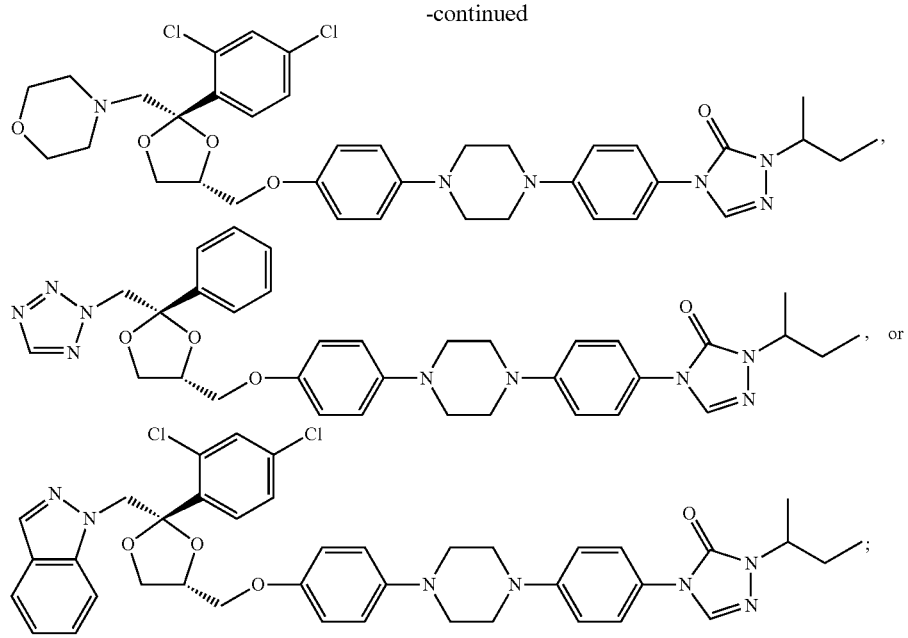

or a pharmaceutically acceptable salt, pharmaceutically acceptable solvate, or pharmaceutically acceptable prodrug thereof.

In another aspect, provided herein are compounds of Formula (IIa) having the structure:

Formula (IIa)

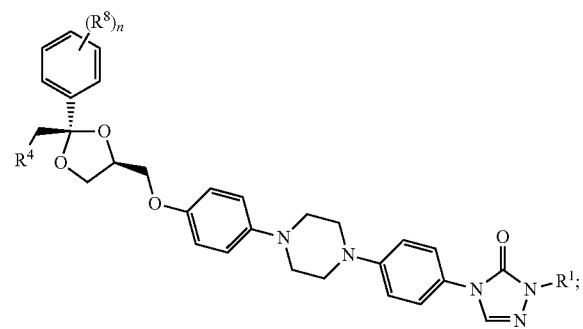

wherein:
$R^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

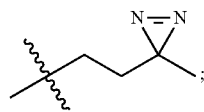

$R^2$ is alkyl, or —NR$^{13}$R$^{14}$;
$R^3$ is —OH, alkyl, or —NR$^{13}$R$^{14}$;
$R^5$ is H, —CN, halogen, haloalkyl, alkyl, —NR$^{13}$R$^{14}$, -alkylene(NR$^{13}$R$^{14}$), and —SO$_2$R$^{13}$;
each $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent $R^8$ form a heterocyclyl ring;
each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

In some embodiments is a compound of Formula (IIa), wherein $R^4$ is halogen. In some embodiments is a compound of Formula (IIa), wherein $R^4$ is F. In some embodiments is a compound of Formula (IIa), wherein $R^4$ is Cl. In some embodiments is a compound of Formula (IIa), wherein $R^4$ is alkyl. In some embodiments is a compound of Formula (IIa), wherein $R^4$ is methyl. In some embodiments is a compound of Formula (IIa), wherein $R^4$ is ethyl. In some embodiments is a compound of Formula (IIa), wherein $R^4$ is

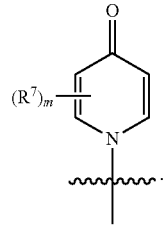

In some embodiments is a compound of Formula (IIa), wherein $R^4$ is

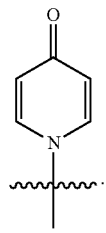

In some embodiments is a compound of Formula (IIa), wherein $R^4$ is

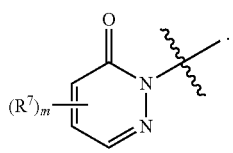

In some embodiments is a compound of Formula (IIa), wherein $R^4$ is

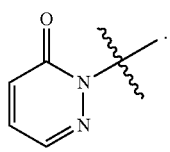 [SMILES: *n1ncccc1=O]

In some embodiments is a compound of Formula (IIa), wherein $R^4$ is

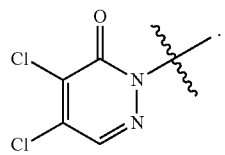 [SMILES: *n1ncc(Cl)c(Cl)c1=O]

In some embodiments is a compound of Formula (IIa), wherein $R^4$ is

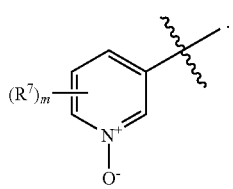

In some embodiments is a compound of Formula (IIa), wherein $R^4$ is

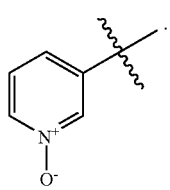 [SMILES: *c1ccc[n+]([O-])c1]

In some embodiments is a compound of Formula (IIa), wherein $R^4$ is

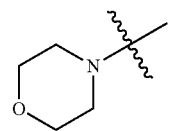

In some embodiments is a compound of Formula (IIa), wherein $R^4$ is

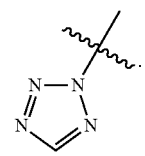

In some embodiments is a compound of Formula (IIa), wherein $R^4$ is

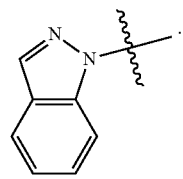 [SMILES: *n1ncc2ccccc21]

In some embodiments is a compound of Formula (IIa), wherein $R^1$ is —CH(CH$_3$)CH$_2$CH$_2$R$^2$. In some embodiments is a compound of Formula (IIa), wherein $R^1$ is —CH(CH$_3$)CH$_2$CH$_2$R$^2$, and $R^2$ is H. In some embodiments is a compound of Formula (IIa), wherein $R^1$ is —CH(CH$_3$)CH$_2$CH$_2$R$^2$, and $R^2$ is alkyl. In some embodiments is a compound of Formula (IIa), wherein $R^1$ is —CH(CH$_3$)CH$_2$CH$_2$R$^2$, and $R^2$ is methyl. In some embodiments is a compound of Formula (IIa), wherein $R^1$ is —CH(CH$_3$)CH$_2$CH$_2$R$^2$, and $R^2$ is ethyl. In some embodiments is a compound of Formula (IIa), wherein $R^1$ is —CH(CH$_3$)CH$_2$CH$_2$R$^2$, and $R^2$ is isopropyl. In some embodiments is a compound of Formula (IIa), wherein $R^1$ is —CH(CH$_3$)CH$_2$CH$_2$R$^2$, and $R^2$ is —NR$^{13}$R$^{14}$. In some embodiments is a compound of Formula (IIa), wherein $R^1$ is —CH(CH$_3$)CH$_2$CH$_2$R$^2$, and $R^2$ is —NH$_2$. In some embodiments is a compound of Formula (IIa), wherein $R^1$ is —CH(CH$_3$)CH$_2$CH$_2$R$^2$, and $R^2$ is —NHCH$_3$. In some embodiments is a compound of Formula (IIa), wherein $R^1$ is —CH(CH$_3$)CH$_2$CH$_2$R$^2$, and $R^2$ is —N(CH$_3$)$_2$.

In some embodiments is a compound of Formula (IIa), wherein $R^1$ is —CH(CH$_2$CH$_3$)$_2$. In some embodiments is a compound of Formula (IIa), wherein $R^1$ is —CH(CH$_3$)$_2$. In some embodiments is a compound of Formula (IIa), wherein $R^1$ is —CH(CH$_2$CH$_3$)CH(R$^3$)CH$_3$. In some embodiments is a compound of Formula (IIa), wherein $R^1$ is —CH(CH$_2$CH$_3$)CH(R$^3$)CH$_3$, and $R^3$ is —OH. In some embodiments is a compound of Formula (IIa), wherein $R^1$ is —CH(CH$_2$CH$_3$)CH(R$^3$)CH$_3$, and $R^3$ is alkyl. In some embodiments is a compound of Formula (IIa), wherein $R^1$ is —CH(CH$_2$CH$_3$)CH(R$^3$)CH$_3$, and $R^3$ is methyl. In some embodiments is a compound of Formula (IIa), wherein $R^1$ is —CH(CH$_2$CH$_3$)CH(R$^3$)CH$_3$, and $R^3$ is ethyl. In some embodiments is a compound of Formula (IIa), wherein $R^1$ is —CH(CH$_2$CH$_3$)CH(R$^3$)CH$_3$, and $R^3$ is —NR$^{13}$R$^{14}$. In some embodiments is a compound of Formula (IIa), wherein $R^1$ is —CH(CH$_2$CH$_3$)CH(R$^3$)CH$_3$, and $R^3$ is —NH$_2$. In some embodiments is a compound of Formula (IIa), wherein $R^1$ is —CH(CH$_2$CH$_3$)CH(R$^3$)CH$_3$, and R$^3$ is —NHCH$_3$. In some embodiments is a compound of Formula (IIa), wherein R$^1$ is —CH(CH$_2$CH$_3$)CH(R$^3$)CH$_3$, and R$^3$ is —N(CH$_3$)$_2$. In some embodiments is a compound of Formula (IIa), wherein R$^1$ is -alkylene(cycloalkyl). In some embodiments is a compound of Formula (IIa), wherein R$^1$ is —CH$_2$CH$_2$(cycloalkyl). In some embodiments is a compound of Formula (IIa), wherein R$^1$ is —CH$_2$(cycloalkyl). In some embodiments is a compound of Formula (IIa), wherein R$^1$ is —CH$_2$(cyclobutyl). In some embodiments is a compound of Formula (IIa), wherein R$^1$ is —CH$_2$(cyclopentyl). In some embodiments is a compound of Formula (IIa), wherein R$^1$ is —CH$_2$(cyclohexyl). In some embodiments is a compound of Formula (IIa), wherein R$^1$ is

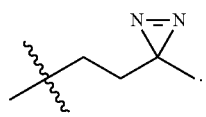

In some embodiments described above or below is a compound of Formula (IIa), wherein n is 0.

In some embodiments described above or below is a compound of Formula (IIa), wherein n is 1. In some embodiments described above or below is a compound of Formula (IIa), wherein n is 1 and R$^8$ is selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, or —C(O)NR$^{13}$R$^{14}$. In some embodiments described above or below is a compound of Formula (IIa), wherein n is 1 and R$^8$ is selected from halogen, —CN, alkyl, alkoxy, haloalkoxy, or haloalkyl. In some embodiments described above or below is a compound of Formula (IIa), wherein n is 1 and R$^8$ is halogen. In some embodiments described above or below is a compound of Formula (IIa), wherein n is 1 and R$^8$ is F. In some embodiments described above or below is a compound of Formula (IIa), wherein n is 1 and R$^8$ is Cl. In some embodiments described above or below is a compound of Formula (IIa), wherein n is 1 and R$^8$ is —CN. In some embodiments described above or below is a compound of Formula (IIa), wherein n is 1 and R$^8$ is alkyl. In some embodiments described above or below is a compound of Formula (IIa), wherein n is 1 and R$^8$ is methyl. In some embodiments described above or below is a compound of Formula (IIa), wherein n is 1 and R$^8$ is ethyl. In some embodiments described above or below is a compound of Formula (IIa), wherein n is 1 and R$^8$ is alkoxy. In some embodiments described above or below is a compound of Formula (IIa), wherein n is 1 and R$^8$ is methoxy. In some embodiments described above or below is a compound of Formula (IIa), wherein n is 1 and R$^8$ is ethoxy. In some embodiments described above or below is a compound of Formula (IIa), wherein n is 1 and R$^8$ is haloalkoxy. In some embodiments described above or below is a compound of Formula (IIa), wherein n is 1 and R$^8$ is —OCF$_3$. In some embodiments described above or below is a compound of Formula (IIa), wherein n is 1 and R$^8$ is haloalkyl. In some embodiments described above or below is a compound of Formula (IIa), wherein n is 1 and R$^8$ is —CF$_3$.

In some embodiments described above or below is a compound of Formula (IIa), wherein n is 2. In some embodiments described above or below is a compound of Formula (IIa), wherein n is 2 and R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$. In some embodiments described above or below is a compound of Formula (IIa), wherein n is 2 and R$^8$ is independently selected from halogen, —CN, alkyl, alkoxy, haloalkoxy, and haloalkyl. In some embodiments described above or below is a compound of Formula (IIa), wherein n is 2 and R$^8$ is halogen. In some embodiments described above or below is a compound of Formula (IIa), wherein n is 2 and each R$^8$ is F. In some embodiments described above or below is a compound of Formula (IIa), wherein n is 2 and each R$^8$ is Cl. In some embodiments described above or below is a compound of Formula (IIa), wherein n is 2 and R$^8$ is independently selected from halogen and —CN. In some embodiments described above or below is a compound of Formula (IIa), wherein n is 2 and R$^8$ is independently selected from halogen and alkyl. In some embodiments described above or below is a compound of Formula (IIa), wherein n is 2 and R$^8$ is independently selected from —CN and alkyl. In some embodiments described above or below is a compound of Formula (IIa), wherein n is 2 and two adjacent R$^8$ form a heterocyclyl ring.

In another aspect, provided herein are compounds of Formula (III) having the structure:

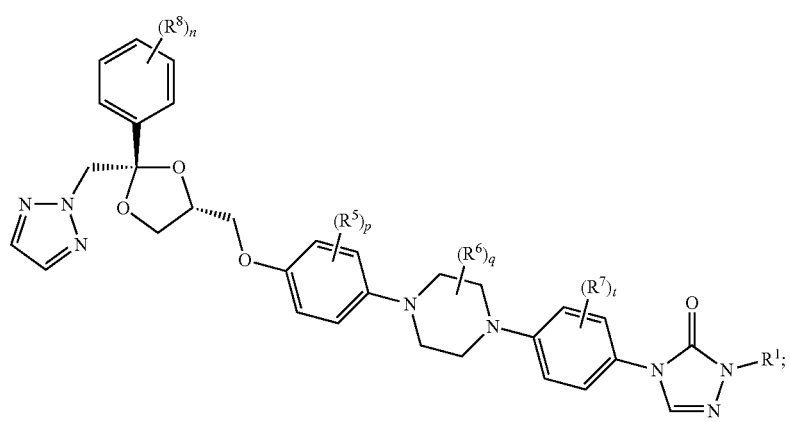

Formula (III)

wherein:

R¹ is —CH(CH₃)CH₂CH₂R², —CH(CH₂CH₃)₂, —CH(CH₃)₂, —CH₂CH(CH₃)₂, —CH(CH₂CH₃)CH(R³)CH₃, -alkylene(cycloalkyl), or

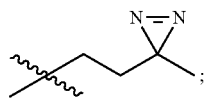

R² is H, alkyl, or —NR¹³R¹⁴;

R³ is —OH, alkyl, or —NR¹³R¹⁴;

each R⁵ is independently selected from haloalkyl, -alkylene(NR¹³R¹⁴), —NR¹³R¹⁴, and —SO₂R¹³;

each R⁶ is independently selected from halogen, alkyl, and haloalkyl;

each R⁷ is independently selected from halogen, alkyl, haloalkyl, and —CN;

each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;

each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;

n is selected from 0, 1, 2, 3, and 4;

p is selected from 0, 1, 2, 3, and 4;

q is selected from 0, 1, 2, 3, and 4; and t is selected from 0, 1, 2, 3, and 4;

wherein at least one p, q, or t is not 0;

or a pharmaceutically acceptable salt, pharmaceutically acceptable solvate, or pharmaceutically acceptable prodrug thereof.

In some embodiments is a compound of Formula (III), wherein R¹ is —CH(CH₃)CH₂CH₂R². In some embodiments is a compound of Formula (III), wherein R¹ is —CH(CH₃)CH₂CH₂R², and R² is H. In some embodiments is a compound of Formula (III), wherein R¹ is —CH(CH₃)CH₂CH₂R², and R² is alkyl. In some embodiments is a compound of Formula (III), wherein R¹ is —CH(CH₃)CH₂CH₂R², and R² is methyl. In some embodiments is a compound of Formula (III), wherein R¹ is —CH(CH₃)CH₂CH₂R², and R² is ethyl. In some embodiments is a compound of Formula (III), wherein R¹ is —CH(CH₃)CH₂CH₂R², and R² is isopropyl. In some embodiments is a compound of Formula (III), wherein R¹ is —CH(CH₃)CH₂CH₂R², and R² is —NR¹³R¹⁴. In some embodiments is a compound of Formula (III), wherein R¹ is —CH(CH₃)CH₂CH₂R², and R² is —NH₂. In some embodiments is a compound of Formula (III), wherein R¹ is —CH(CH₃)CH₂CH₂R², and R² is —NHCH₃. In some embodiments is a compound of Formula (III), wherein R¹ is —CH(CH₃)CH₂CH₂R², and R² is —N(CH₃)₂.

In some embodiments is a compound of Formula (III), wherein R¹ is —CH(CH₂CH₃)₂. In some embodiments is a compound of Formula (III), wherein R¹ is —CH(CH₃)₂. In some embodiments is a compound of Formula (III), wherein R¹ is —CH(CH₂CH₃)CH(R³)CH₃. In some embodiments is a compound of Formula (III), wherein R¹ is —CH(CH₂CH₃)CH(R³)CH₃, and R³ is —OH. In some embodiments is a compound of Formula (III), wherein R¹ is —CH(CH₂CH₃)CH(R³)CH₃, and R³ is alkyl. In some embodiments is a compound of Formula (III), wherein R¹ is —CH(CH₂CH₃)CH(R³)CH₃, and R³ is methyl. In some embodiments is a compound of Formula (III), wherein R¹ is —CH(CH₂CH₃)CH(R³)CH₃, and R³ is ethyl. In some embodiments is a compound of Formula (III), wherein R¹ is —CH(CH₂CH₃)CH(R³)CH₃, and R³ is —NR¹³R¹⁴. In some embodiments is a compound of Formula (III), wherein R¹ is —CH(CH₂CH₃)CH(R³)CH₃, and R³ is —NH₂. In some embodiments is a compound of Formula (III), wherein R¹ is —CH(CH₂CH₃)CH(R³)CH₃, and R³ is —NHCH₃. In some embodiments is a compound of Formula (III), wherein R¹ is —CH(CH₂CH₃)CH(R³)CH₃, and R³ is —N(CH₃)₂. In some embodiments is a compound of Formula (III), wherein R¹ is -alkylene(cycloalkyl). In some embodiments is a compound of Formula (III), wherein R¹ is —CH₂CH₂(cycloalkyl). In some embodiments is a compound of Formula (III), wherein R¹ is —CH₂(cycloalkyl). In some embodiments is a compound of Formula (III), wherein R¹ is —CH₂(cyclobutyl). In some embodiments is a compound of Formula (III), wherein R¹ is —CH₂(cyclopentyl). In some embodiments is a compound of Formula (III), wherein R¹ is —CH₂(cyclohexyl). In some embodiments is a compound of Formula (III), wherein R¹ is

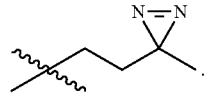 [SMILES: *CCC1(C)N=N1]

In some embodiments described above or below is a compound of Formula (III), wherein n is 0.

In some embodiments described above or below is a compound of Formula (III), wherein n is 1. In some embodiments described above or below is a compound of Formula (III), wherein n is 1 and R⁸ is selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, or —C(O)NR¹³R¹⁴. In some embodiments described above or below is a compound of Formula (III), wherein n is 1 and R⁸ is selected from halogen, —CN, alkyl, alkoxy, haloalkoxy, or haloalkyl. In some embodiments described above or below is a compound of Formula (III), wherein n is 1 and R⁸ is halogen. In some embodiments described above or below is a compound of Formula (III), wherein n is 1 and R⁸ is F. In some embodiments described above or below is a compound of Formula (III), wherein n is 1 and R⁸ is Cl. In some embodiments described above or below is a compound of Formula (III), wherein n is 1 and R⁸ is —CN. In some embodiments described above or below is a compound of Formula (III), wherein n is 1 and R⁸ is alkyl. In some embodiments described above or below is a compound of Formula (III), wherein n is 1 and R⁸ is methyl. In some embodiments described above or below is a compound of Formula (III), wherein n is 1 and R⁸ is ethyl. In some embodiments described above or below is a compound of Formula (III), wherein n is 1 and R⁸ is alkoxy. In some embodiments described above or below is a compound of Formula (III), wherein n is 1 and R⁸ is methoxy. In some embodiments described above or below is a compound of Formula (III), wherein n is 1 and $R^8$ is ethoxy. In some embodiments described above or below is a compound of Formula (III), wherein n is 1 and $R^8$ is haloalkoxy. In some embodiments described above or below is a compound of Formula (III), wherein n is 1 and $R^8$ is —$OCF_3$. In some embodiments described above or below is a compound of Formula (III), wherein n is 1 and $R^8$ is haloalkyl. In some embodiments described above or below is a compound of Formula (III), wherein n is 1 and $R^8$ is —$CF_3$.

In some embodiments described above or below is a compound of Formula (III), wherein n is 2. In some embodiments described above or below is a compound of Formula (III), wherein n is 2 and $R^8$ is independently selected from halogen, —OH, —$NO_2$, —$N_3$, —CN, alkyl, alkoxy, haloalkoxy, haloalkyl, hydroxyalkyl, alkoxyalkyl, -alkylene($NR^{13}R^{14}$), -alkylene(cycloalkyl), -alkylene(heterocyclyl), cycloalkyl, heterocyclyl, aryl, heteroaryl, —$SR^{13}$, —$SOR^{13}$, —$SO_2R^{13}$, —$SO_2NR^{13}R^{14}$, —$NR^{13}R^{14}$, —$NR^{13}SO_2R^{14}$, —$NR^{13}C(O)R^{14}$, —$NR^{13}C(O)OR^{14}$, —$NR^{13}C(O)NR^{13}R^{14}$, —$C(O)R^{14}$, —$C(O)OR^{14}$, and —$C(O)NR^{13}R^{14}$. In some embodiments described above or below is a compound of Formula (III), wherein n is 2 and $R^8$ is independently selected from halogen, —CN, alkyl, alkoxy, haloalkoxy, and haloalkyl. In some embodiments described above or below is a compound of Formula (III), wherein n is 2 and $R^8$ is halogen. In some embodiments described above or below is a compound of Formula (III), wherein n is 2 and each $R^8$ is F. In some embodiments described above or below is a compound of Formula (III), wherein n is 2 and each $R^8$ is Cl. In some embodiments described above or below is a compound of Formula (III), wherein n is 2 and $R^8$ is independently selected from halogen and —CN. In some embodiments described above or below is a compound of Formula (III), wherein n is 2 and $R^8$ is independently selected from halogen and alkyl. In some embodiments described above or below is a compound of Formula (III), wherein n is 2 and $R^8$ is independently selected from —CN and alkyl. In some embodiments described above or below is a compound of Formula (III), wherein n is 2 and two adjacent $R^8$ form a heterocyclyl ring.

In some embodiments described above or below is a compound of Formula (III), wherein each $R^5$ is independently selected from —$CH_2NH_2$, —$CF_3$, and —$SO_2Me$. In some embodiments described above or below is a compound of Formula (III), wherein p is 1 and $R^5$ is selected from —$CH_2NH_2$, —$CF_3$, and —$SO_2Me$. In some embodiments described above or below is a compound of Formula (III), wherein q is 0. In some embodiments described above or below is a compound of Formula (III), wherein t is 0. In some embodiments described above or below is a compound of Formula (III), wherein q is 0, t is 0, p is 1, and $R^5$ is selected from —$CH_2NH_2$, —$CF_3$, and —$SO_2Me$.

In some embodiments described above or below is a compound of Formula (III), wherein q is 1. In some embodiments described above or below is a compound of Formula (III), wherein q is 1 and $R^6$ is alkyl. In some embodiments described above or below is a compound of Formula (III), wherein q is 1, t is 0, and $R^6$ is alkyl. In some embodiments described above or below is a compound of Formula (III), wherein q is 1, t is 0, p is 0, and $R^6$ is alkyl.

In some embodiments described above or below is a compound of Formula (III), wherein t is 1. In some embodiments described above or below is a compound of Formula (III), wherein t is 1 and $R^7$ is halogen. In some embodiments described above or below is a compound of Formula (III), wherein t is 1, q is 0, and $R^6$ is alkyl. In some embodiments described above or below is a compound of Formula (III), wherein t is 1, q is 0, p is 0, and $R^7$ is halogen.

In another embodiment is a compound of Formula (III) having the structure:

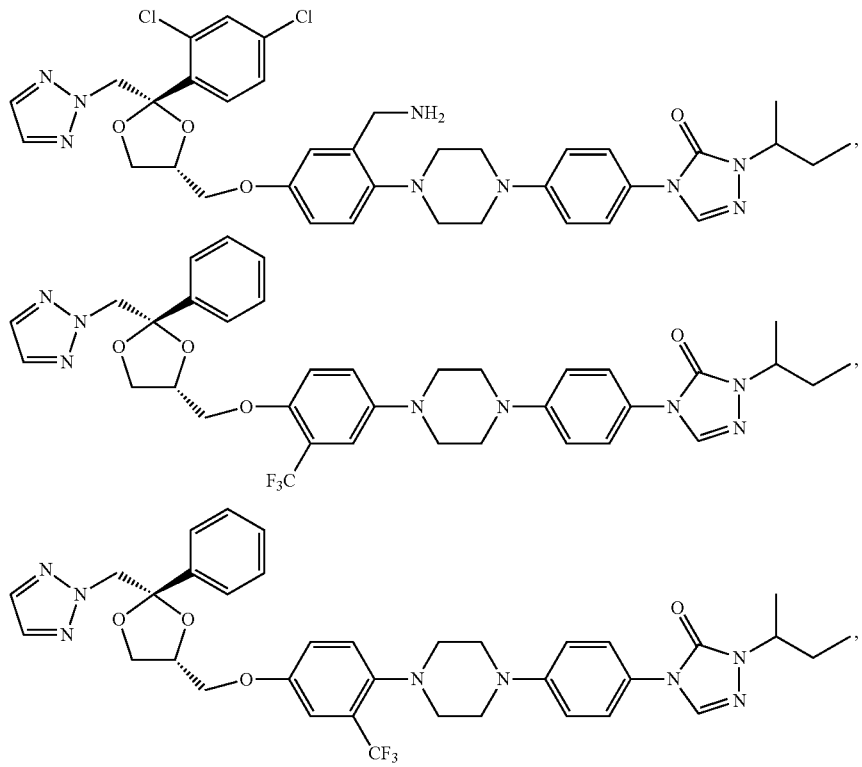

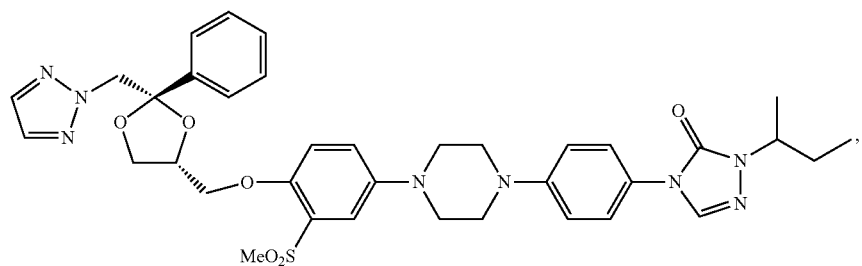
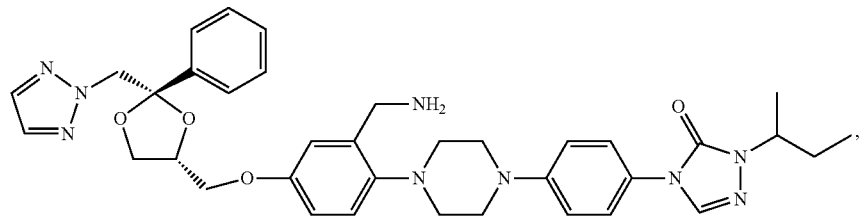
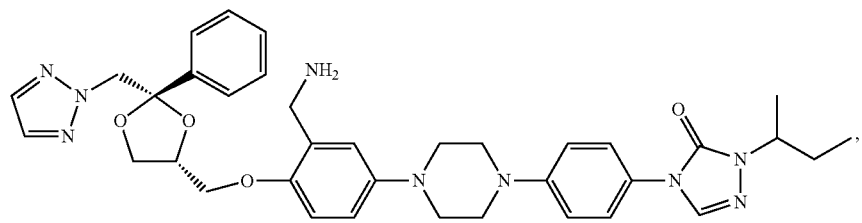
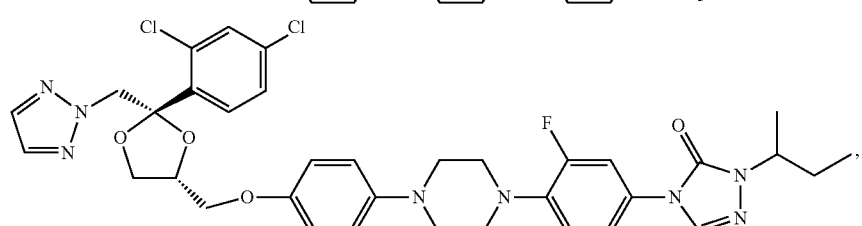
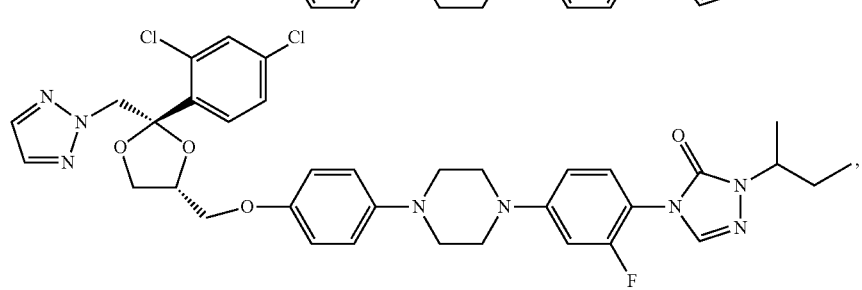
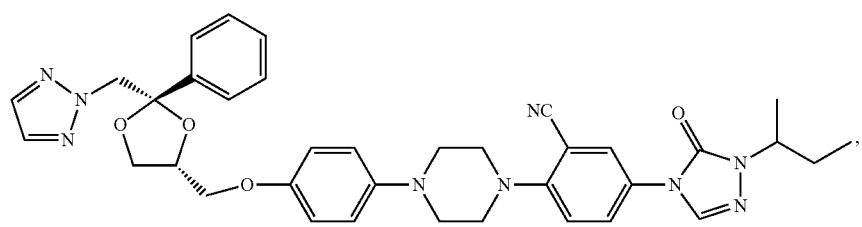
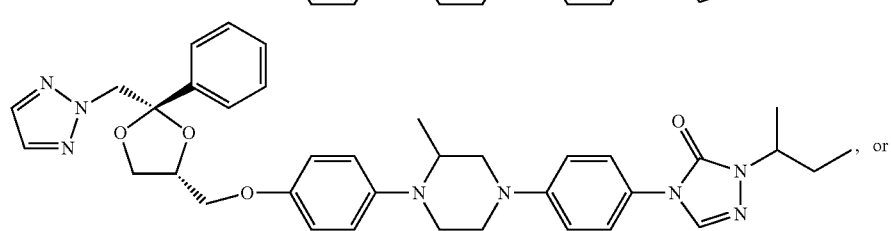

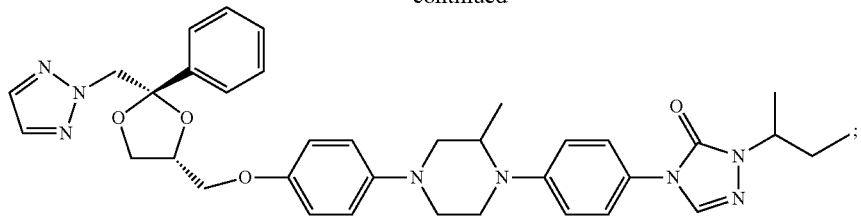

or a pharmaceutically acceptable salt, pharmaceutically acceptable solvate, or pharmaceutically acceptable prodrug thereof.

In another aspect, provided herein are compounds of Formula (IIIa) having the structure:

Formula (IIIa)

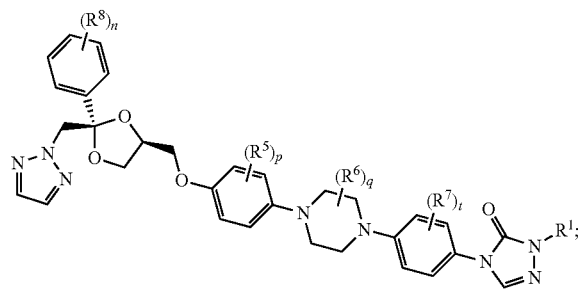

wherein:
R$^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

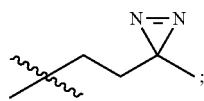 [SMILES: *CCC1(C)N=N1]

R$^2$ is H, alkyl, or —NR$^{13}$R$^{14}$;
R$^3$ is —OH, alkyl, or —NR$^{13}$R$^{14}$;
each R$^5$ is independently selected from haloalkyl, -alkylene(NR$^{13}$R$^{14}$), —NR$^{13}$R$^{14}$, and —SO$_2$R$^{13}$;
each R$^6$ is independently selected from halogen, alkyl, and haloalkyl;
each R$^7$ is independently selected from halogen, alkyl, haloalkyl, and —CN;
each R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;
n is selected from 0, 1, 2, 3, and 4;
p is selected from 0, 1, 2, 3, and 4;
q is selected from 0, 1, 2, 3, and 4; and
t is selected from 0, 1, 2, 3, and 4;
wherein at least one p, q, or t is not 0;
or a pharmaceutically acceptable salt, pharmaceutically acceptable solvate, or pharmaceutically acceptable prodrug thereof.

In some embodiments is a compound of Formula (IIIa), wherein R$^1$ is —CH(CH$_3$)CH$_2$CH$_2$R$^2$. In some embodiments is a compound of Formula (IIIa), wherein R$^1$ is —CH(CH$_3$)CH$_2$CH$_2$R$^2$, and R$^2$ is H. In some embodiments is a compound of Formula (IIIa), wherein R$^1$ is —CH(CH$_3$)CH$_2$CH$_2$R$^2$, and R$^2$ is alkyl. In some embodiments is a compound of Formula (IIIa), wherein R$^1$ is —CH(CH$_3$)CH$_2$CH$_2$R$^2$, and R$^2$ is methyl. In some embodiments is a compound of Formula (IIIa), wherein R$^1$ is —CH(CH$_3$)CH$_2$CH$_2$R$^2$, and R$^2$ is ethyl. In some embodiments is a compound of Formula (IIIa), wherein R$^1$ is —CH(CH$_3$)CH$_2$CH$_2$R$^2$, and R$^2$ is isopropyl. In some embodiments is a compound of Formula (IIIa), wherein R$^1$ is —CH(CH$_3$)CH$_2$CH$_2$R$^2$, and R$^2$ is —NR$^{13}$R$^{14}$. In some embodiments is a compound of Formula (IIIa), wherein R$^1$ is —CH(CH$_3$)CH$_2$CH$_2$R$^2$, and R$^2$ is —NH$_2$. In some embodiments is a compound of Formula (IIIa), wherein R$^1$ is —CH(CH$_3$)CH$_2$CH$_2$R$^2$, and R$^2$ is —NHCH$_3$. In some embodiments is a compound of Formula (IIIa), wherein R$^1$ is —CH(CH$_3$)CH$_2$CH$_2$R$^2$, and R$^2$ is —N(CH$_3$)$_2$.

In some embodiments is a compound of Formula (IIIa), wherein R$^1$ is —CH(CH$_2$CH$_3$)$_2$. In some embodiments is a compound of Formula (IIIa), wherein R$^1$ is —CH(CH$_3$)$_2$. In some embodiments is a compound of Formula (IIIa), wherein R$^1$ is —CH(CH$_2$CH$_3$)CH(R$^3$)CH$_3$. In some embodiments is a compound of Formula (IIIa), wherein R$^1$ is —CH(CH$_2$CH$_3$)CH(R$^3$)CH$_3$, and R$^3$ is —OH. In some embodiments is a compound of Formula (IIIa), wherein R$^1$ is —CH(CH$_2$CH$_3$)CH(R$^3$)CH$_3$, and R$^3$ is alkyl. In some embodiments is a compound of Formula (IIIa), wherein R$^1$ is —CH(CH$_2$CH$_3$)CH(R$^3$)CH$_3$, and R$^3$ is methyl. In some embodiments is a compound of Formula (IIIa), wherein R$^1$ is —CH(CH$_2$CH$_3$)CH(R$^3$)CH$_3$, and R$^3$ is ethyl. In some embodiments is a compound of Formula (IIIa), wherein R$^1$ is —CH(CH$_2$CH$_3$)CH(R$^3$)CH$_3$, and R$^3$ is —NR$^{13}$R$^{14}$. In some embodiments is a compound of Formula (IIIa), wherein R$^1$ is —CH(CH$_2$CH$_3$)CH(R$^3$)CH$_3$, and R$^3$ is —NH$_2$. In some embodiments is a compound of Formula (IIIa), wherein R$^1$ is —CH(CH$_2$CH$_3$)CH(R$^3$)CH$_3$, and R$^3$ is —NHCH$_3$. In some embodiments is a compound of Formula (IIIa), wherein R$^1$ is —CH(CH$_2$CH$_3$)CH(R$^3$)CH$_3$, and R$^3$ is —N(CH$_3$)$_2$. In some embodiments is a compound of Formula (IIIa), wherein R$^1$ is -alkylene(cycloalkyl). In some embodiments is a compound of Formula (IIIa), wherein R$^1$ is —CH$_2$CH$_2$(cycloalkyl). In some embodiments is a compound of Formula (IIIa), wherein R$^1$ is —CH$_2$(cycloalkyl). In some embodiments is a compound of Formula (IIIa), wherein R$^1$ is —CH$_2$(cyclobutyl). In some embodiments is a compound of Formula (IIIa), wherein R$^1$ is —CH$_2$(cyclopentyl). In some embodiments is a compound of Formula (IIIa), wherein R$^1$ is —CH$_2$(cyclohexyl). In some embodiments is a compound of Formula (IIIa), wherein R$^1$ is

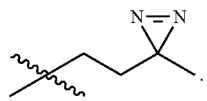 [SMILES: *CCC1(C)N=N1]

In some embodiments described above or below is a compound of Formula (IIIa), wherein n is 0.

In some embodiments described above or below is a compound of Formula (IIIa), wherein n is 1. In some embodiments described above or below is a compound of Formula (IIIa), wherein n is 1 and R$^8$ is selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, or —C(O)NR$^{13}$R$^{14}$. In some embodiments described above or below is a compound of Formula (IIIa), wherein n is 1 and R$^8$ is selected from halogen, —CN, alkyl, alkoxy, haloalkoxy, or haloalkyl. In some embodiments described above or below is a compound of Formula (IIIa), wherein n is 1 and R$^8$ is halogen. In some embodiments described above or below is a compound of Formula (IIIa), wherein n is 1 and R$^8$ is F. In some embodiments described above or below is a compound of Formula (IIIa), wherein n is 1 and R$^8$ is Cl. In some embodiments described above or below is a compound of Formula (IIIa), wherein n is 1 and R$^8$ is —CN. In some embodiments described above or below is a compound of Formula (IIIa), wherein n is 1 and R$^8$ is alkyl. In some embodiments described above or below is a compound of Formula (IIIa), wherein n is 1 and R$^8$ is methyl. In some embodiments described above or below is a compound of Formula (IIIa), wherein n is 1 and R$^8$ is ethyl. In some embodiments described above or below is a compound of Formula (IIIa), wherein n is 1 and R$^8$ is alkoxy. In some embodiments described above or below is a compound of Formula (IIIa), wherein n is 1 and R$^8$ is methoxy. In some embodiments described above or below is a compound of Formula (IIIa), wherein n is 1 and R$^8$ is ethoxy. In some embodiments described above or below is a compound of Formula (IIIa), wherein n is 1 and R$^8$ is haloalkoxy. In some embodiments described above or below is a compound of Formula (IIIa), wherein n is 1 and R$^8$ is —OCF$_3$. In some embodiments described above or below is a compound of Formula (IIIa), wherein n is 1 and R$^8$ is haloalkyl. In some embodiments described above or below is a compound of Formula (IIIa), wherein n is 1 and R$^8$ is —CF$_3$.

In some embodiments described above or below is a compound of Formula (IIIa), wherein n is 2. In some embodiments described above or below is a compound of Formula (IIIa), wherein n is 2 and R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$. In some embodiments described above or below is a compound of Formula (IIIa), wherein n is 2 and R$^8$ is independently selected from halogen, —CN, alkyl, alkoxy, haloalkoxy, and haloalkyl. In some embodiments described above or below is a compound of Formula (IIIa), wherein n is 2 and R$^8$ is halogen. In some embodiments described above or below is a compound of Formula (IIIa), wherein n is 2 and each R$^8$ is F. In some embodiments described above or below is a compound of Formula (IIIa), wherein n is 2 and each R$^8$ is Cl. In some embodiments described above or below is a compound of Formula (IIIa), wherein n is 2 and R$^8$ is independently selected from halogen and —CN. In some embodiments described above or below is a compound of Formula (IIIa), wherein n is 2 and R$^8$ is independently selected from halogen and alkyl. In some embodiments described above or below is a compound of Formula (IIIa), wherein n is 2 and R$^8$ is independently selected from —CN and alkyl. In some embodiments described above or below is a compound of Formula (IIIa), wherein n is 2 and two adjacent R$^8$ form a heterocyclyl ring.

In some embodiments described above or below is a compound of Formula (IIIa), wherein each R$^5$ is independently selected from —CH$_2$NH$_2$, —CF$_3$, and —SO$_2$Me. In some embodiments described above or below is a compound of Formula (IIIa), wherein p is 1 and R$^5$ is selected from —CH$_2$NH$_2$, —CF$_3$, and —SO$_2$Me. In some embodiments described above or below is a compound of Formula (IIIa), wherein q is 0. In some embodiments described above or below is a compound of Formula (IIIa), wherein t is 0. In some embodiments described above or below is a compound of Formula (IIIa), wherein q is 0, t is 0, p is 1, and R$^5$ is selected from —CH$_2$NH$_2$, —CF$_3$, and —SO$_2$Me.

In some embodiments described above or below is a compound of Formula (IIIa), wherein q is 1. In some embodiments described above or below is a compound of Formula (IIIa), wherein q is 1 and R$^6$ is alkyl. In some embodiments described above or below is a compound of Formula (IIIa), wherein q is 1, t is 0, and R$^6$ is alkyl. In some embodiments described above or below is a compound of Formula (IIIa), wherein q is 1, t is 0, p is 0, and R$^6$ is alkyl.

In some embodiments described above or below is a compound of Formula (IIIa), wherein t is 1. In some embodiments described above or below is a compound of Formula (IIIa), wherein t is 1 and R$^7$ is halogen. In some embodiments described above or below is a compound of Formula (IIIa), wherein t is 1, q is 0, and R$^6$ is alkyl. In some embodiments described above or below is a compound of Formula (IIIa), wherein t is 1, q is 0, p is 0, and R$^7$ is halogen.

In another aspect, provided herein are compounds of Formula (IV) having the structure:

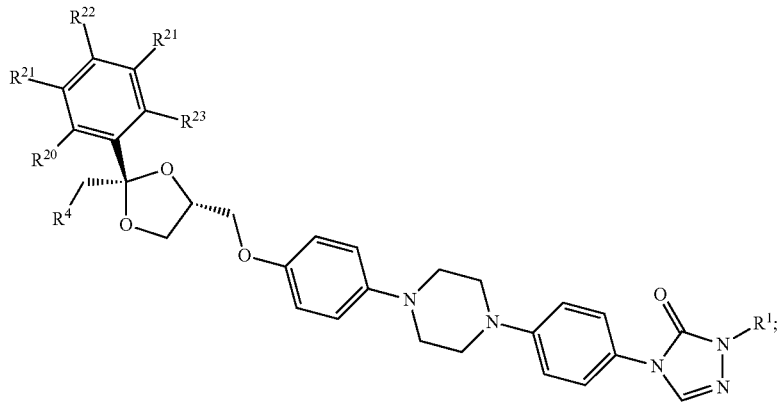

Formula (IV)

wherein:
R¹ is

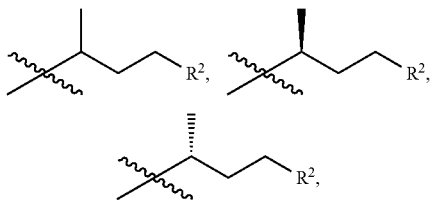

—CH(CH₂CH₃)₂, —CH(CH₃)₂, —CH₂CH(CH₃)₂, —CH(CH₂CH₃)CH(R³)CH₃, -alkylene(cycloalkyl), or

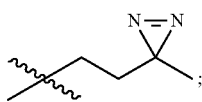 [SMILES: *CCC1(C)N=N1]

$R^2$ is H, alkyl, or —NR$^{13}$R$^{14}$;
$R^3$ is —OH, alkyl, or —NR$^{13}$R$^{14}$;
$R^4$ is halogen, alkyl,

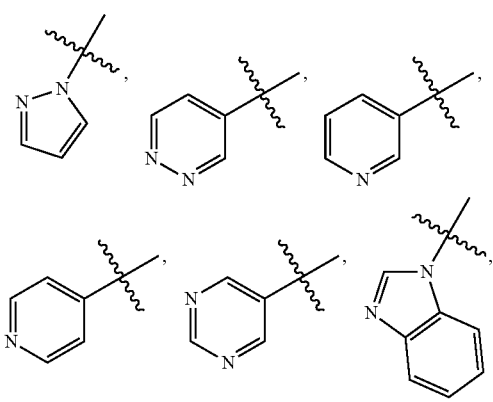

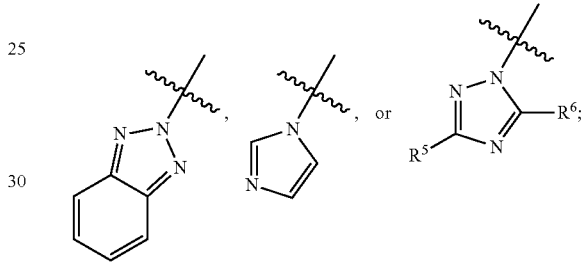

$R^5$ and $R^6$ are independently selected from H, alkyl, halo, and haloalkyl;
each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;
$R^{20}$ and $R^{22}$ are independently selected from H, halogen, —OH, —NO₂, —N₃, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO₂R$^{13}$, —SO₂NR$^{13}$R$^{14}$, —NR$^{13}$R$^{14}$, —NR$^{13}$SO₂R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$, wherein at least one of $R^{20}$ and $R^{22}$ is not F or Cl;
each $R^{21}$ is independently selected from H, halogen, —OH, —NO₂, —N₃, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO₂R$^{13}$, —SO₂NR$^{13}$R$^{14}$, —NR$^{13}$R$^{14}$, —NR$^{13}$SO₂R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; and
$R^{23}$ is H;
or a pharmaceutically acceptable salt, pharmaceutically acceptable solvate, or pharmaceutically acceptable prodrug thereof.

In some embodiments is a compound of Formula (IV), wherein $R^{20}$ and $R^{22}$ are independently selected from H, halogen, —CN, alkyl, alkoxy, haloalkoxy, haloalkyl, —SO$_2$R$^{13}$, —SO$_2$NR$^{13}$R$^{14}$, and —C(O)NR$^{13}$R$^{14}$; wherein at least one of R$^{20}$ and R$^{22}$ is not F or Cl. In some embodiments is a compound of Formula (IV), wherein R$^{20}$ and R$^{22}$ are independently selected from H and halogen; wherein at least one of R$^{20}$ and R$^{22}$ is not F or Cl. In some embodiments is a compound of Formula (IV), wherein R$^{20}$ and R$^{22}$ are independently selected from H and —CN. In some embodiments is a compound of Formula (IV), wherein R$^{20}$ and R$^{22}$ are independently selected from H and alkyl. In some embodiments is a compound of Formula (IV), wherein R$^{20}$ and R$^{22}$ are independently selected from H and alkoxy. In some embodiments is a compound of Formula (IV), wherein R$^{20}$ and R$^{22}$ are independently selected from H and haloalkoxy. In some embodiments is a compound of Formula (IV), wherein R$^{20}$ and R$^{22}$ are independently selected from H and haloalkyl. In some embodiments is a compound of Formula (IV), wherein R$^{20}$ and R$^{22}$ are independently selected from H and —SO$_2$R$^{13}$. In some embodiments is a compound of Formula (IV), wherein R$^{20}$ and R$^{22}$ are independently selected from H and —SO$_2$NR$^{13}$R$^{14}$. In some embodiments is a compound of Formula (IV), wherein R$^{20}$ and R$^{22}$ are independently selected from H and —C(O)NR$^{13}$R$^{14}$. In some embodiments is a compound of Formula (IV), wherein R$^{20}$ and R$^{22}$ are independently selected from —CN and alkyl. In some embodiments is a compound of Formula (IV), wherein R$^{20}$ and R$^{22}$ are independently selected from H, Cl, —CN, —CH$_3$, —OCH$_3$, and —CF$_3$; wherein at least one of R$^{20}$ and R$^{22}$ is not Cl.

In some embodiments is a compound of Formula (IV), wherein R$^{20}$ and R$^{22}$ are each H.

In some embodiments is a compound of Formula (IV), wherein each R$^{21}$ is independently selected from H, halogen, —CN, alkyl, alkoxy, and haloalkyl. In some embodiments is a compound of Formula (IV), wherein each R$^{21}$ is independently selected from H and —CN. In some embodiments is a compound of Formula (IV), wherein each R$^{21}$ is independently selected from H and alkyl. In some embodiments is a compound of Formula (IV), wherein each R$^{21}$ is independently selected from H and alkoxy. In some embodiments is a compound of Formula (IV), wherein each R$^{21}$ is independently selected from H and haloalkoxy. In some embodiments is a compound of Formula (IV), wherein each R$^{21}$ is independently selected from H and haloalkyl. In some embodiments is a compound of Formula (IV), wherein each R$^{21}$ is independently selected from H and —SO$_2$R$^{13}$. In some embodiments is a compound of Formula (IV), wherein each R$^{21}$ is independently selected from H and —SO$_2$NR$^{13}$R$^{14}$. In some embodiments is a compound of Formula (IV), wherein each R$^{21}$ is independently selected from H and —C(O)NR$^{13}$R$^{14}$. In some embodiments is a compound of Formula (IV), wherein each R$^{21}$ is independently selected from —CN and alkyl. In some embodiments is a compound of Formula (IV), wherein each R$^{21}$ is independently selected from H, Cl, —CN, —CH$_3$, —OCH$_3$, and —CF$_3$. In some embodiments is a compound of Formula (IV), wherein each R$^{21}$ is independently selected from H, Cl, —CN, and —CH$_3$. In some embodiments is a compound of Formula (IV), wherein each R$^{21}$ is H. In some embodiments is a compound of Formula (IV), wherein each R$^{21}$ is Cl.

In some embodiments is a compound of Formula (IV), wherein R$^4$ is halogen. In some embodiments is a compound of Formula (IV), wherein R$^4$ is F. In some embodiments is a compound of Formula (IV), wherein R$^4$ is Cl. In some embodiments is a compound of Formula (IV), wherein R$^4$ is alkyl. In some embodiments is a compound of Formula (IV), wherein R$^4$ is methyl. In some embodiments is a compound of Formula (IV), wherein R$^4$ is ethyl. In some embodiments is a compound of Formula (IV), wherein R$^4$ is

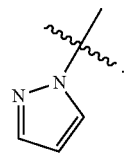

In some embodiments is a compound of Formula (IV), wherein R$^4$ is

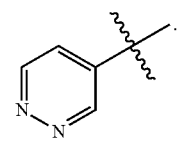

In some embodiments is a compound of Formula (IV), wherein R$^4$ is

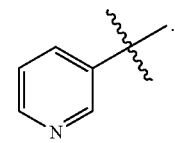

In some embodiments is a compound of Formula (IV), wherein R$^4$ is

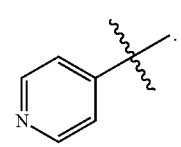

In some embodiments is a compound of Formula (IV), wherein R$^4$ is

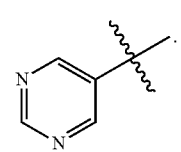

In some embodiments is a compound of Formula (IV), wherein R$^4$ is

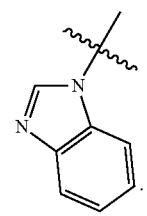

In some embodiments is a compound of Formula (IV), wherein R$^4$ is

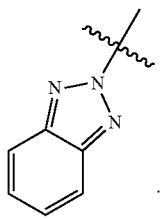 [SMILES: *n1nc2ccccc2n1]

In some embodiments is a compound of Formula (IV), wherein $R^4$ is

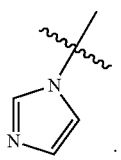

In some embodiments is a compound of Formula (IV), wherein $R^4$ is

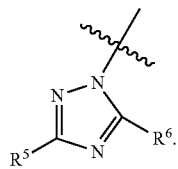

In some embodiments is a compound of Formula (IV), wherein $R^4$ is

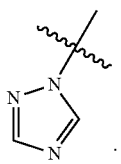

In some embodiments is a compound of Formula (IV), wherein $R^1$ is

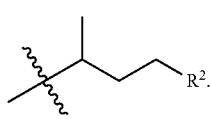

In some embodiments is a compound of Formula (IV), wherein $R^1$ is

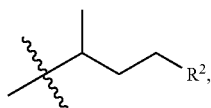

and $R^2$ is H. In some embodiments is a compound of Formula (IV), wherein $R^1$ is

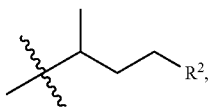

and $R^2$ is alkyl. In some embodiments is a compound of Formula (IV), wherein $R^1$ is

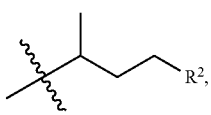

and $R^2$ is methyl. In some embodiments is a compound of Formula (IV), wherein $R^1$ is

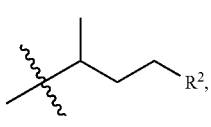

and $R^2$ is ethyl. In some embodiments is a compound of Formula (IV), wherein $R^1$ is

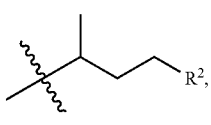

and $R^2$ is isopropyl. In some embodiments is a compound of Formula (IV), wherein $R^1$ is

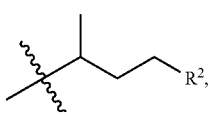

and $R^2$ is —$NR^{13}R^{14}$. In some embodiments is a compound of Formula (IV), wherein $R^1$ is

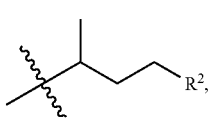

and $R^2$ is —$NH_2$. In some embodiments is a compound of Formula (IV), wherein $R^1$ is

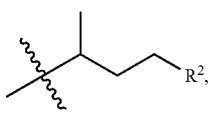

and $R^2$ is —$NHCH_3$. In some embodiments is a compound of Formula (IV), wherein $R^1$ is

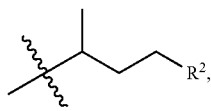

and R² is —N(CH₃)₂.

In some embodiments is a compound of Formula (IV), wherein R¹ is

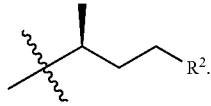

In some embodiments is a compound of Formula (IV), wherein R¹ is

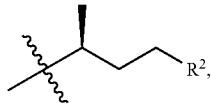

and R² is H. In some embodiments is a compound of Formula (IV), wherein R¹ is

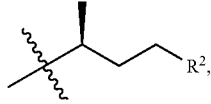

and R² is alkyl. In some embodiments is a compound of Formula (IV), wherein R¹ is

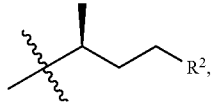

and R² is methyl. In some embodiments is a compound of Formula (IV), wherein R¹ is

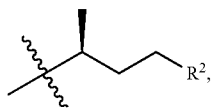

and R² is ethyl. In some embodiments is a compound of Formula (IV), wherein R¹ is

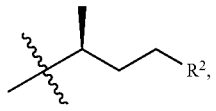

and R² is isopropyl. In some embodiments is a compound of Formula (IV), wherein R¹ is

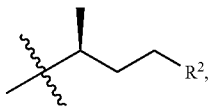

and R² is —NR¹³R¹⁴. In some embodiments is a compound of Formula (IV), wherein R¹ is

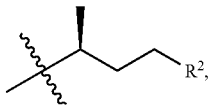

and R² is —NH₂. In some embodiments is a compound of Formula (IV), wherein R¹ is

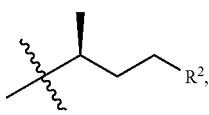

and R² is —NHCH₃. In some embodiments is a compound of Formula (IV), wherein R¹ is

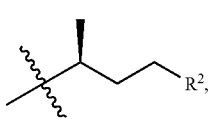

and R² is —N(CH₃)₂.

In some embodiments is a compound of Formula (IV), wherein R¹ is

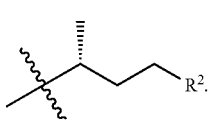

In some embodiments is a compound of Formula (IV), wherein R¹ is

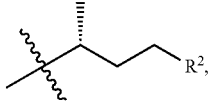

and R² is H. In some embodiments is a compound of Formula (IV), wherein R¹ is

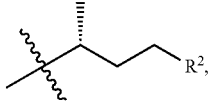

and R² is alkyl. In some embodiments is a compound of Formula (IV), wherein R¹ is

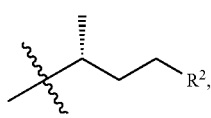

and R² is methyl. In some embodiments is a compound of Formula (IV), wherein R¹ is

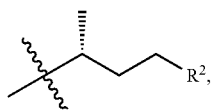

and R² is ethyl. In some embodiments is a compound of Formula (IV), wherein R¹ is

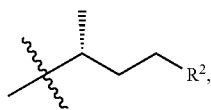

and R² is isopropyl. In some embodiments is a compound of Formula (IV), wherein R¹ is

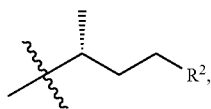

and R² is —NR$^{13}$R$^{14}$. In some embodiments is a compound of Formula (IV), wherein R¹ is

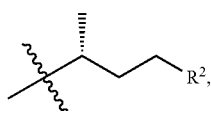

and R² is —NH$_2$. In some embodiments is a compound of Formula (IV), wherein R¹ is

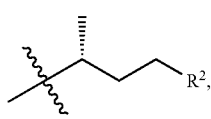

and R² is —NHCH$_3$. In some embodiments is a compound of Formula (IV), wherein R¹ is

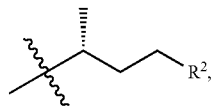

and R² is —N(CH$_3$)$_2$.

In some embodiments is a compound of Formula (IV), wherein R¹ is —CH(CH$_2$CH$_3$)$_2$. In some embodiments is a compound of Formula (IV), wherein R¹ is —CH(CH$_3$)$_2$. In some embodiments is a compound of Formula (IV), wherein R¹ is —CH(CH$_2$CH$_3$)CH(R$^3$)CH$_3$. In some embodiments is a compound of Formula (IV), wherein R¹ is —CH(CH$_2$CH$_3$)CH(R$^3$)CH$_3$, and R$^3$ is —OH. In some embodiments is a compound of Formula (IV), wherein R¹ is —CH(CH$_2$CH$_3$)CH(R$^3$)CH$_3$, and R$^3$ is alkyl. In some embodiments is a compound of Formula (IV), wherein R¹ is —CH(CH$_2$CH$_3$)CH(R$^3$)CH$_3$, and R$^3$ is methyl. In some embodiments is a compound of Formula (IV), wherein R¹ is —CH(CH$_2$CH$_3$)CH(R$^3$)CH$_3$, and R$^3$ is ethyl. In some embodiments is a compound of Formula (IV), wherein R¹ is —CH(CH$_2$CH$_3$)CH(R$^3$)CH$_3$, and R$^3$ is —NR$^{13}$R$^{14}$. In some embodiments is a compound of Formula (IV), wherein R¹ is —CH(CH$_2$CH$_3$)CH(R$^3$)CH$_3$, and R$^3$ is —NH$_2$. In some embodiments is a compound of Formula (IV), wherein R¹ is —CH(CH$_2$CH$_3$)CH(R$^3$)CH$_3$, and R$^3$ is —NHCH$_3$. In some embodiments is a compound of Formula (IV), wherein R¹ is —CH(CH$_2$CH$_3$)CH(R$^3$)CH$_3$, and R$^3$ is —N(CH$_3$)$_2$. In some embodiments is a compound of Formula (IV), wherein R¹ is -alkylene(cycloalkyl). In some embodiments is a compound of Formula (IV), wherein R¹ is —CH$_2$CH$_2$(cycloalkyl). In some embodiments is a compound of Formula (IV), wherein R¹ is —CH$_2$(cycloalkyl). In some embodiments is a compound of Formula (IV), wherein R¹ is —CH$_2$(cyclobutyl). In some embodiments is a compound of Formula (IV), wherein R¹ is —CH$_2$(cyclopentyl). In some embodiments is a compound of Formula (IV), wherein R¹ is —CH$_2$(cyclohexyl). In some embodiments is a compound of Formula (IV), wherein R¹ is

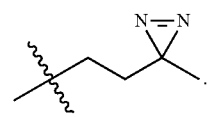

In another embodiment is a compound of Formula (IV) having the structure:

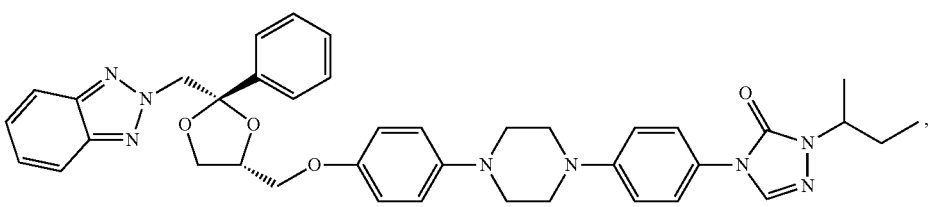

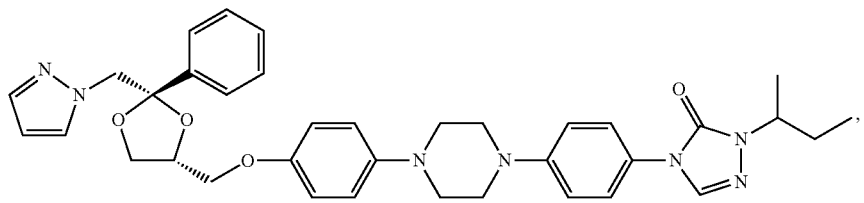
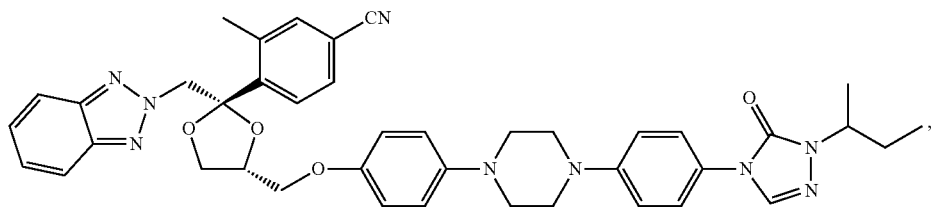
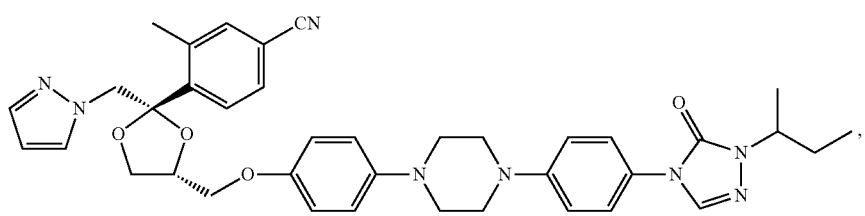
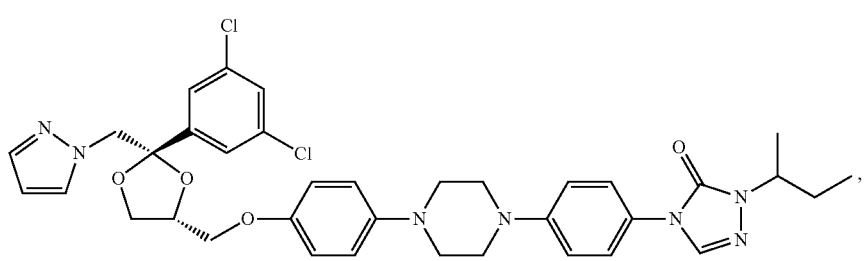
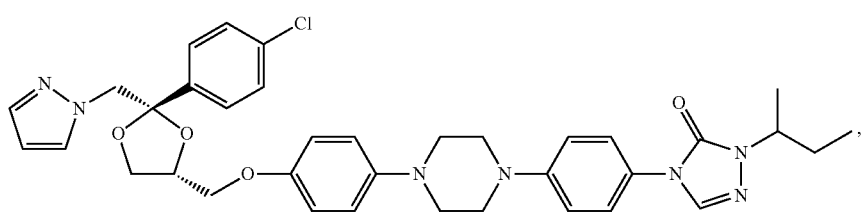
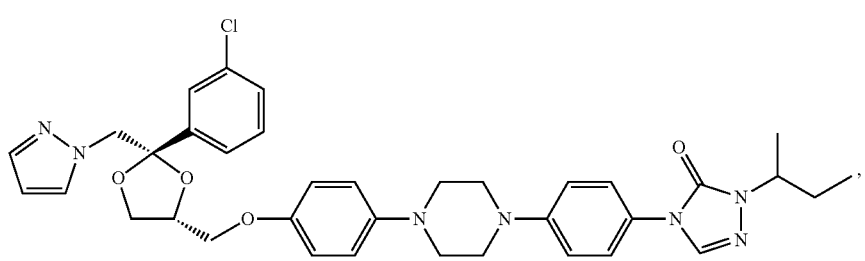
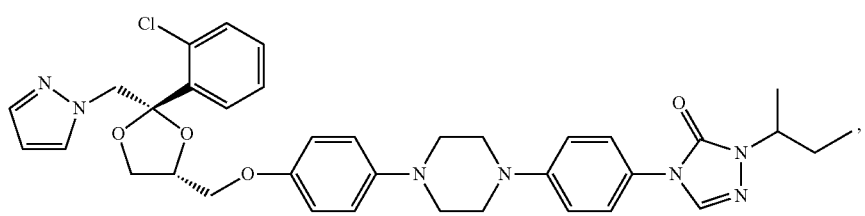

-continued
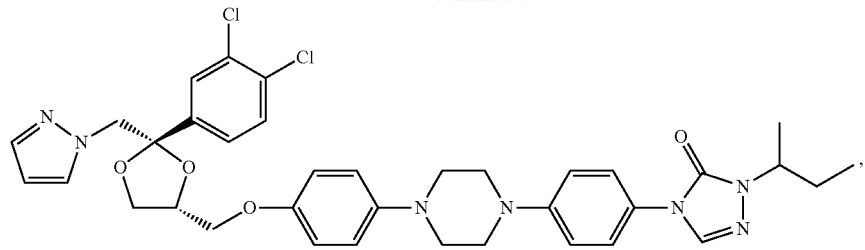
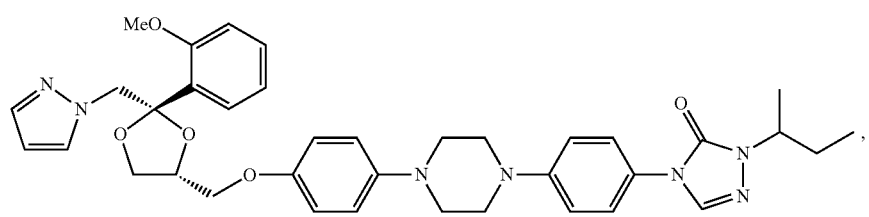
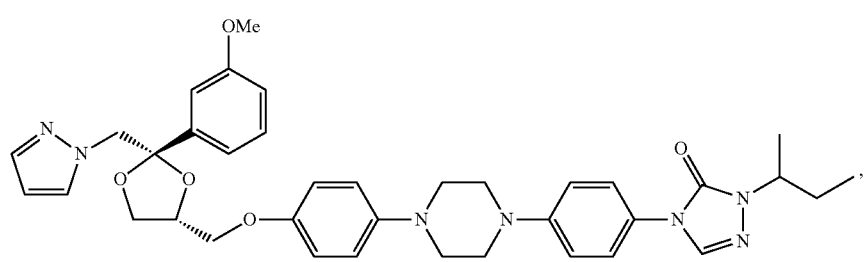
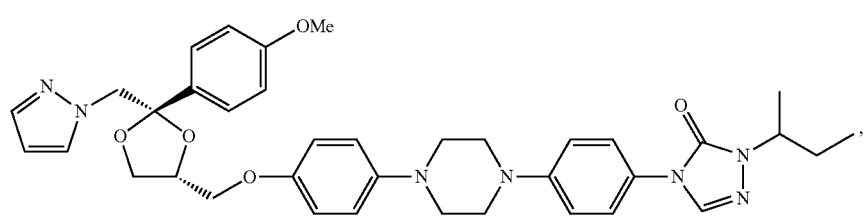
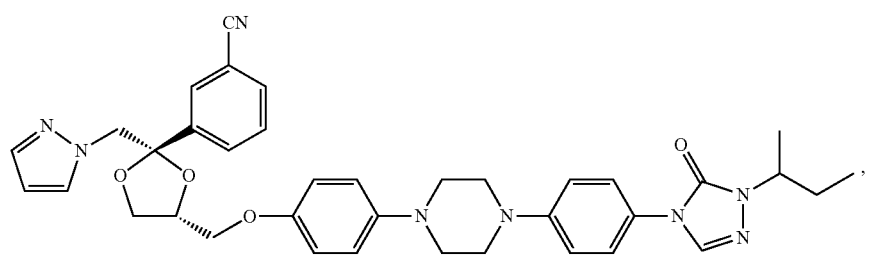
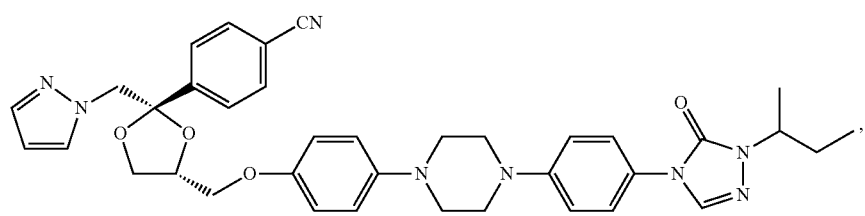
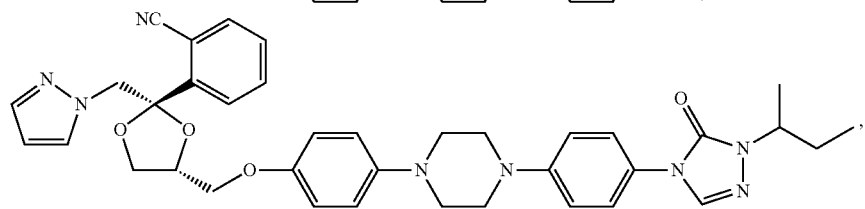

-continued
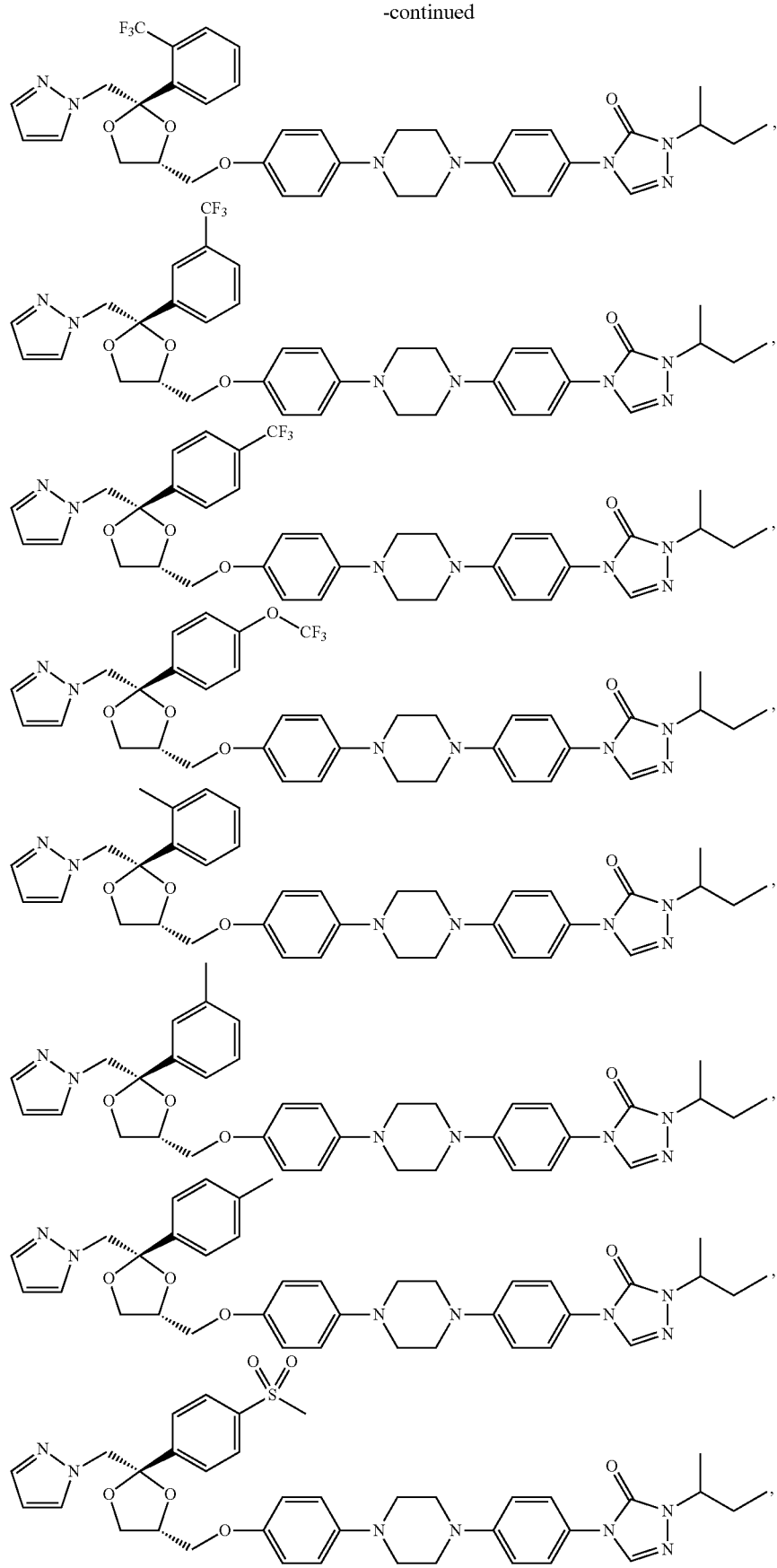

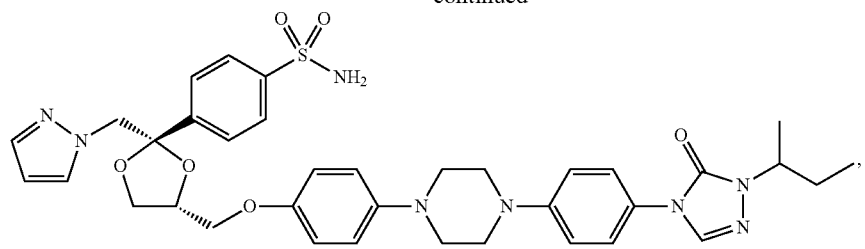
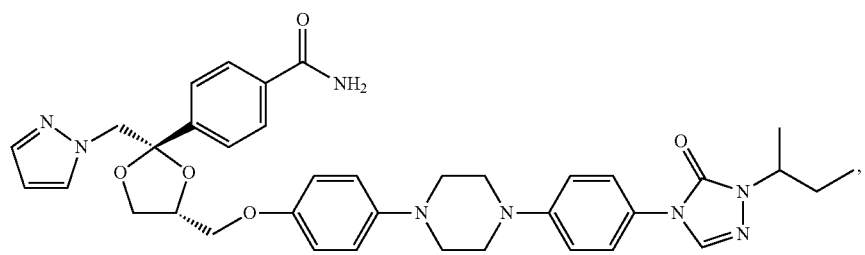
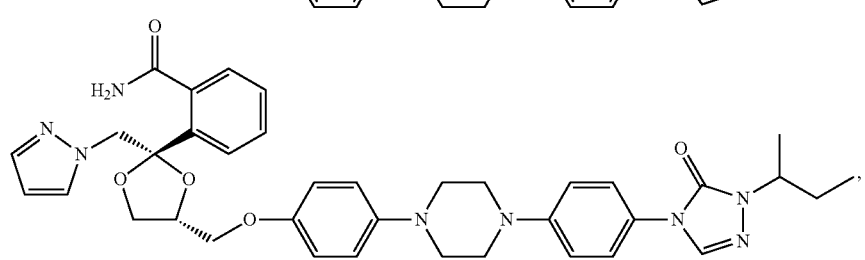
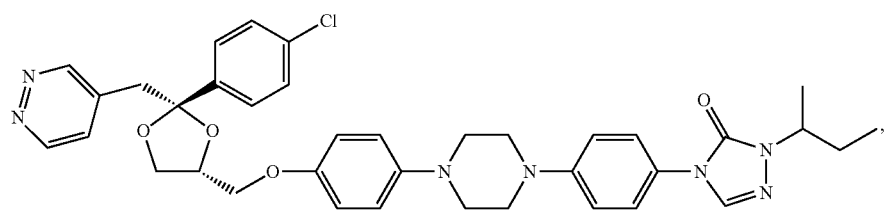
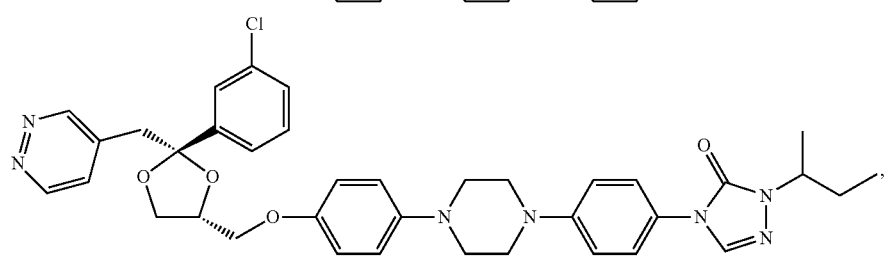
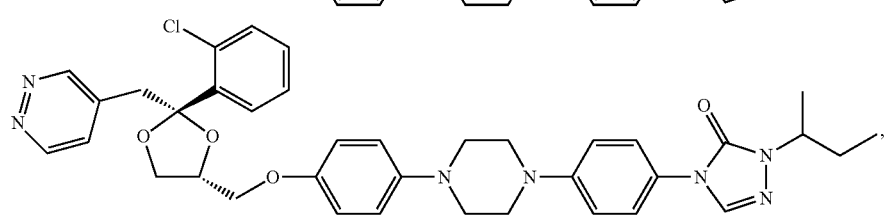
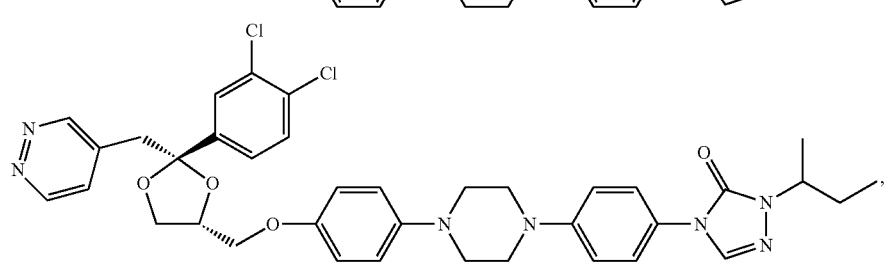

-continued
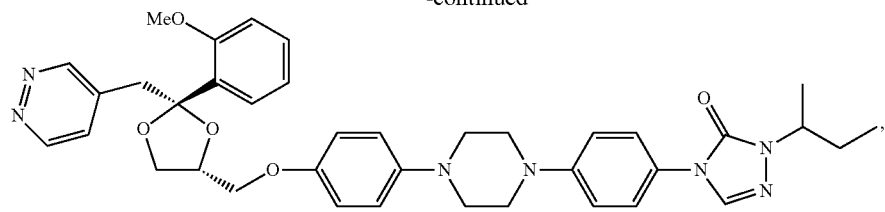
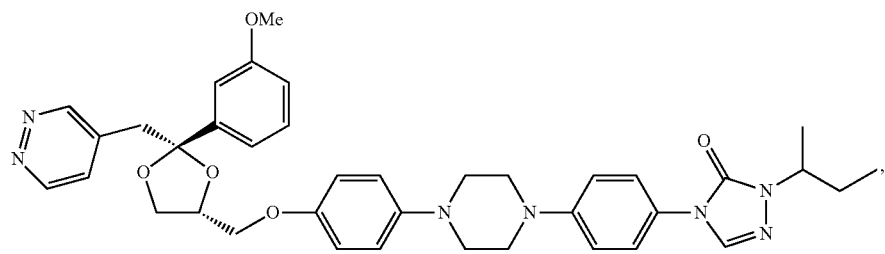
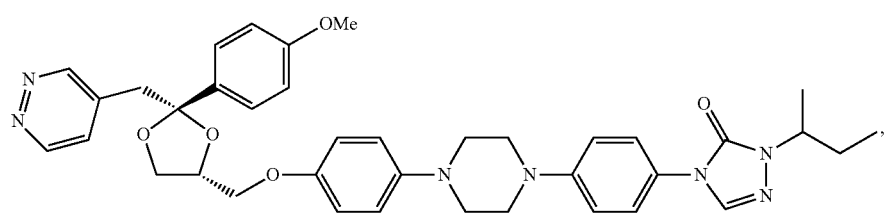
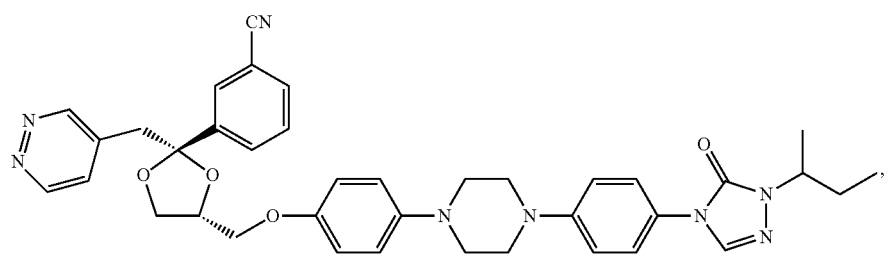
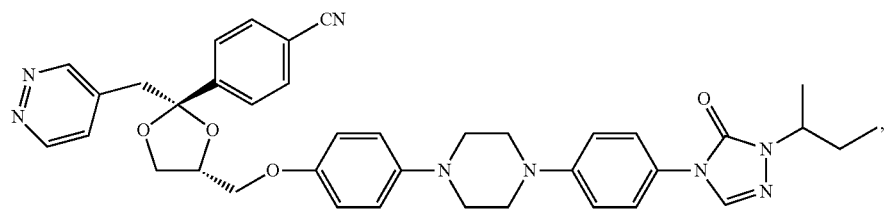
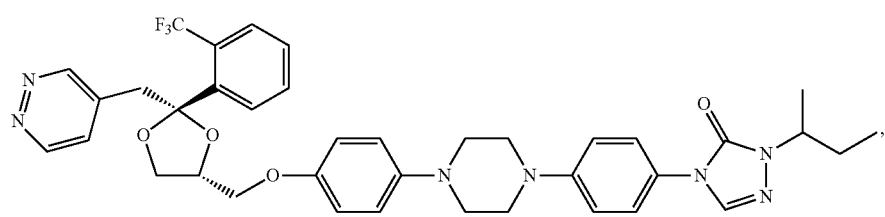
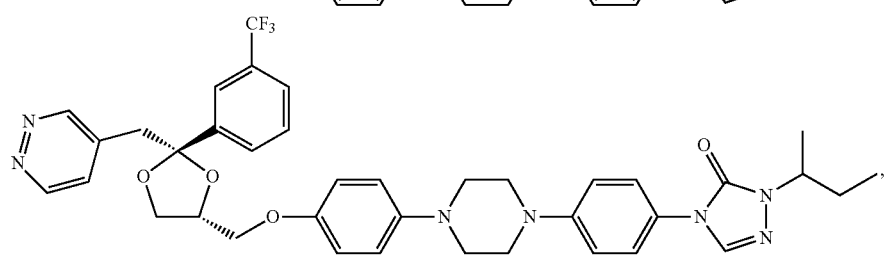

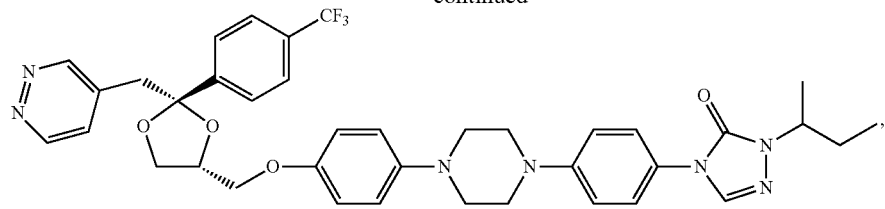
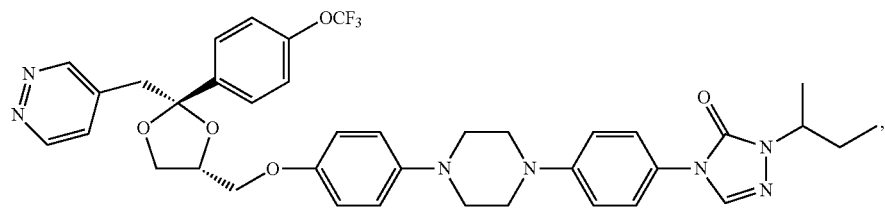
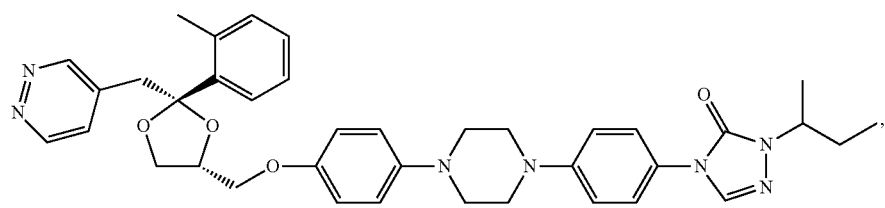
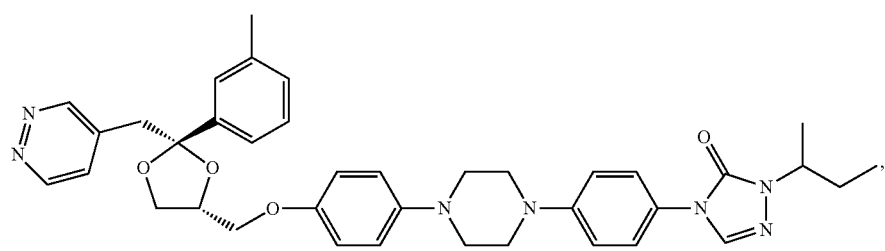
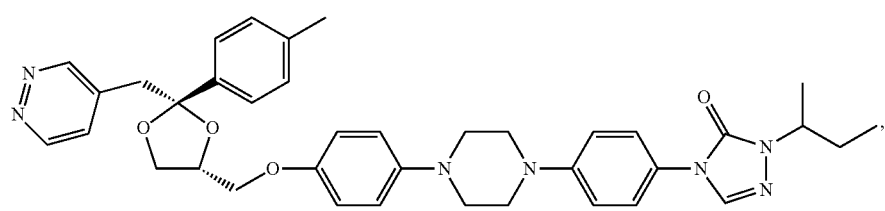
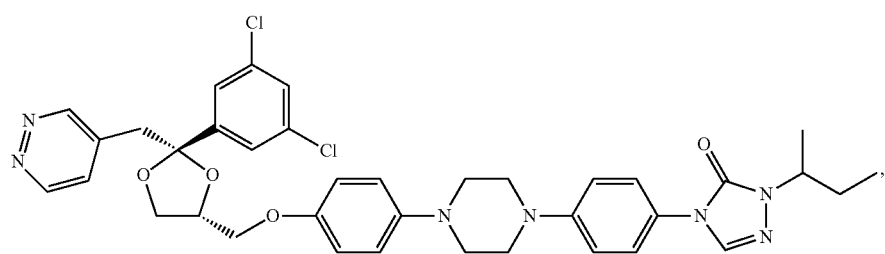
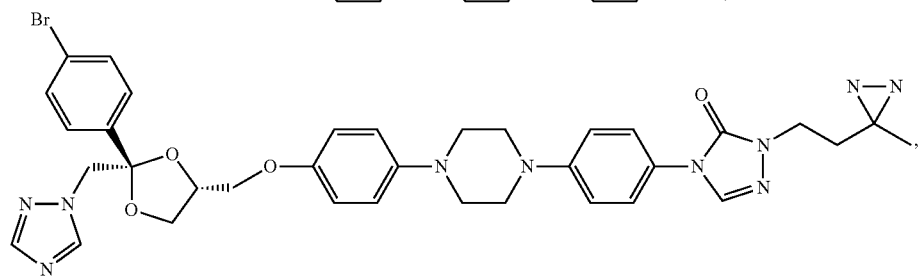

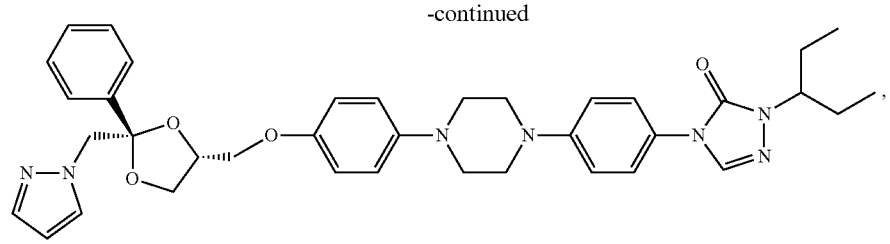
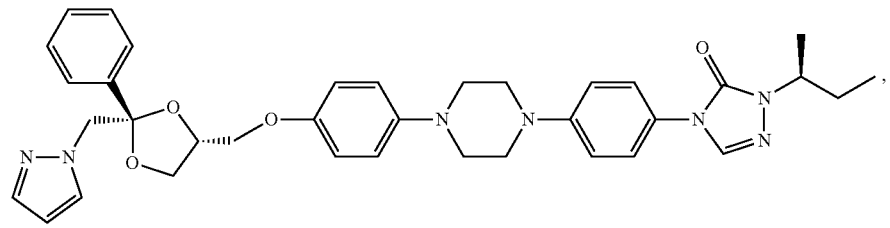
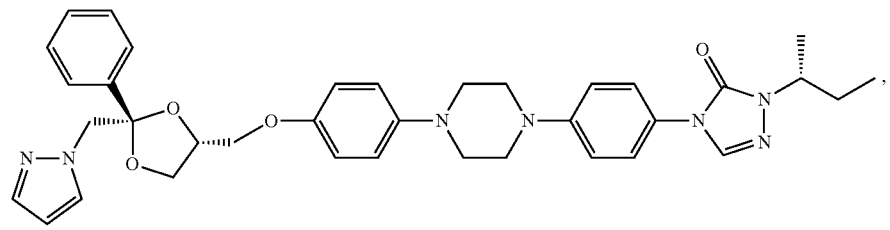
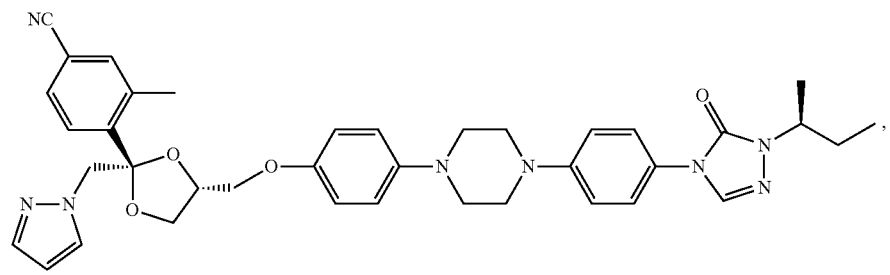
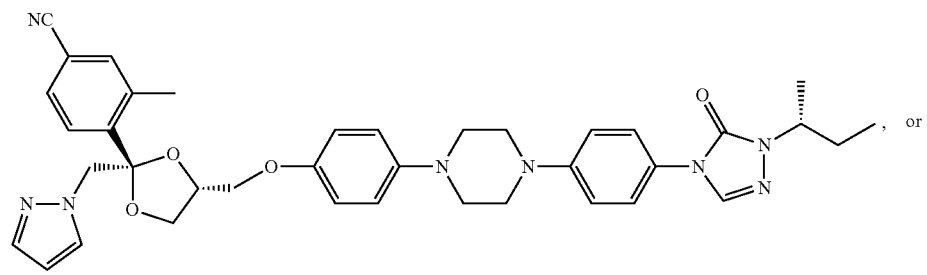
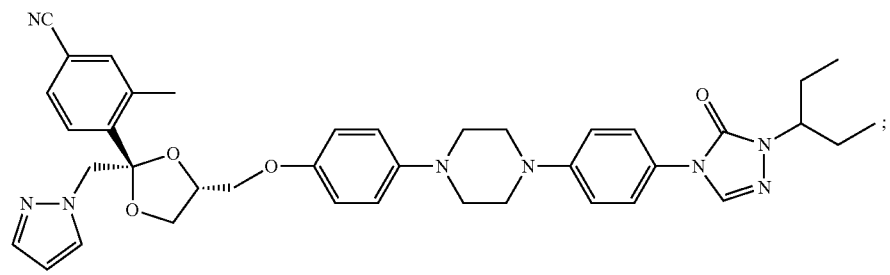
or a pharmaceutically acceptable salt, pharmaceutically acceptable solvate, or pharmaceutically acceptable prodrug thereof.

In another aspect, provided herein are compounds of Formula (IVa) having the structure:

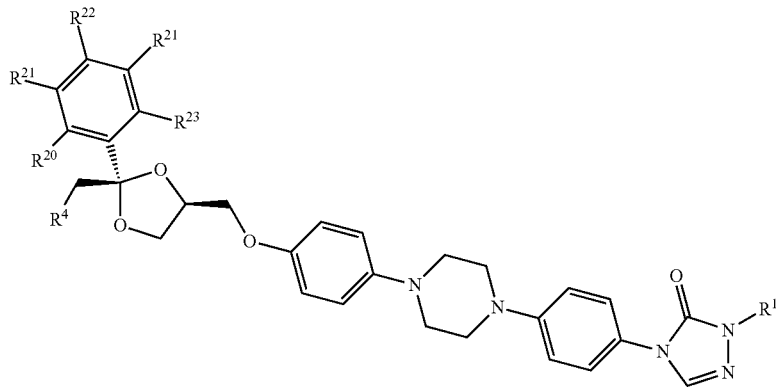

Formula (IVa)

wherein:

R¹ is

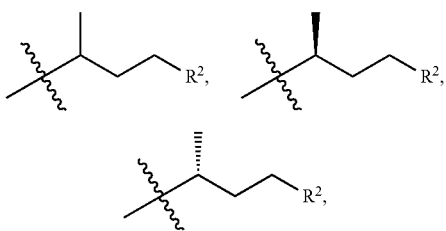

—CH(CH₂CH₃)₂, —CH(CH₃)₂, —CH₂CH(CH₃)₂, —CH(CH₂CH₃)CH(R³)CH₃, -alkylene(cycloalkyl), or

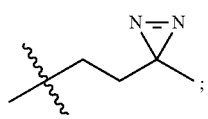 [SMILES: *CCC1(C)N=N1]

$R^2$ is H, alkyl, or —NR¹³R¹⁴;
$R^3$ is —OH, alkyl, or —NR¹³R¹⁴;
$R^4$ is halogen, alkyl,

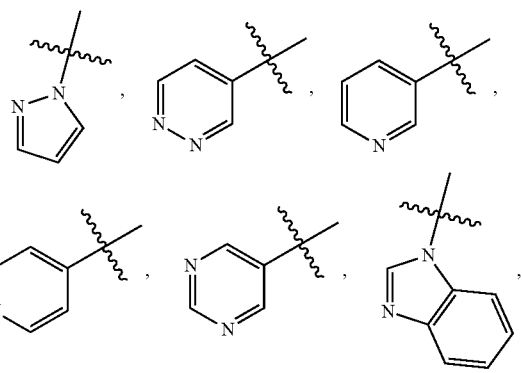

-continued

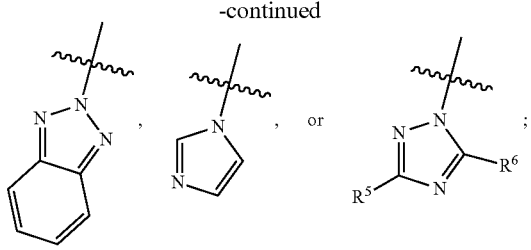

$R^5$ and $R^6$ are independently selected from H, alkyl, halo, and haloalkyl;

each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;

$R^{20}$ and $R^{22}$ are independently selected from H, halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴, wherein at least one of $R^{20}$ and $R^{22}$ is not F or Cl;

each $R^{21}$ is independently selected from H, halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; and $R^{23}$ is H;

or a pharmaceutically acceptable salt, pharmaceutically acceptable solvate, or pharmaceutically acceptable prodrug thereof.

In some embodiments is a compound of Formula (IVa), wherein $R^{20}$ and $R^{22}$ are independently selected from H, halogen, —CN, alkyl, alkoxy, haloalkoxy, haloalkyl, —SO$_2$R$^{13}$, —SO$_2$NR$^{13}$R$^{14}$, and —C(O)NR$^{13}$R$^{14}$; wherein at least one of R$^{20}$ and R$^{22}$ is not F or Cl. In some embodiments is a compound of Formula (IVa), wherein R$^{20}$ and R$^{22}$ are independently selected from H and halogen; wherein at least one of R$^{20}$ and R$^{22}$ is not F or Cl. In some embodiments is a compound of Formula (IVa), wherein R$^{20}$ and R$^{22}$ are independently selected from H and —CN. In some embodiments is a compound of Formula (IVa), wherein R$^{20}$ and R$^{22}$ are independently selected from H and alkyl. In some embodiments is a compound of Formula (IVa), wherein R$^{20}$ and R$^{22}$ are independently selected from H and alkoxy. In some embodiments is a compound of Formula (IVa), wherein R$^{20}$ and R$^{22}$ are independently selected from H and haloalkoxy. In some embodiments is a compound of Formula (IVa), wherein R$^{20}$ and R$^{22}$ are independently selected from H and haloalkyl. In some embodiments is a compound of Formula (IVa), wherein R$^{20}$ and R$^{22}$ are independently selected from H and —SO$_2$R$^{13}$. In some embodiments is a compound of Formula (IVa), wherein R$^{20}$ and R$^{22}$ are independently selected from H and —SO$_2$NR$^{13}$R$^{14}$. In some embodiments is a compound of Formula (IVa), wherein R$^{20}$ and R$^{22}$ are independently selected from H and —C(O)NR$^{13}$R$^{14}$. In some embodiments is a compound of Formula (IVa), wherein R$^{20}$ and R$^{22}$ are independently selected from —CN and alkyl. In some embodiments is a compound of Formula (IVa), wherein R$^{20}$ and R$^{22}$ are independently selected from H, Cl, —CN, —CH$_3$, —OCH$_3$, and —CF$_3$; wherein at least one of R$^{20}$ and R$^{22}$ is not Cl.

In some embodiments is a compound of Formula (IVa), wherein R$^{20}$ and R$^{22}$ are each H.

In some embodiments is a compound of Formula (IVa), wherein each R$^{21}$ is independently selected from H, halogen, —CN, alkyl, alkoxy, and haloalkyl. In some embodiments is a compound of Formula (IVa), wherein each R$^{21}$ is independently selected from H and —CN. In some embodiments is a compound of Formula (IVa), wherein each R$^{21}$ is independently selected from H and alkyl. In some embodiments is a compound of Formula (IVa), wherein each R$^{21}$ is independently selected from H and alkoxy. In some embodiments is a compound of Formula (IVa), wherein each R$^{21}$ is independently selected from H and haloalkoxy. In some embodiments is a compound of Formula (IVa), wherein each R$^{21}$ is independently selected from H and haloalkyl. In some embodiments is a compound of Formula (IVa), wherein each R$^{21}$ is independently selected from H and —SO$_2$R$^{13}$. In some embodiments is a compound of Formula (IVa), wherein each R$^{21}$ is independently selected from H and —SO$_2$NR$^{13}$R$^{14}$. In some embodiments is a compound of Formula (IVa), wherein each R$^{21}$ is independently selected from H and —C(O)NR$^{13}$R$^{14}$. In some embodiments is a compound of Formula (IVa), wherein each R$^{21}$ is independently selected from —CN and alkyl. In some embodiments is a compound of Formula (IVa), wherein each R$^{21}$ is independently selected from H, Cl, —CN, —CH$_3$, —OCH$_3$, and —CF$_3$. In some embodiments is a compound of Formula (IVa), wherein each R$^{21}$ is independently selected from H, Cl, —CN, and —CH$_3$. In some embodiments is a compound of Formula (IVa), wherein each R$^{21}$ is H. In some embodiments is a compound of Formula (IVa), wherein each R$^{21}$ is Cl.

In some embodiments is a compound of Formula (IVa), wherein R$^4$ is halogen. In some embodiments is a compound of Formula (IVa), wherein R$^4$ is F. In some embodiments is a compound of Formula (IVa), wherein R$^4$ is Cl. In some embodiments is a compound of Formula (IVa), wherein R$^4$ is alkyl. In some embodiments is a compound of Formula (IVa), wherein R$^4$ is methyl. In some embodiments is a compound of Formula (IVa), wherein R$^4$ is ethyl. In some embodiments is a compound of Formula (IVa), wherein R$^4$ is

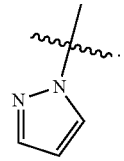

In some embodiments is a compound of Formula (IVa), wherein R$^4$ is

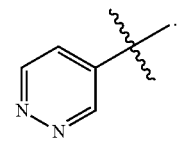 [SMILES: *c1ccnnc1]

In some embodiments is a compound of Formula (IVa), wherein R$^4$ is

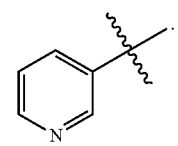 [SMILES: *c1cccnc1]

In some embodiments is a compound of Formula (IVa), wherein R$^4$ is

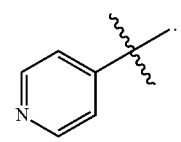 [SMILES: *c1ccncc1]

In some embodiments is a compound of Formula (IVa), wherein R$^4$ is

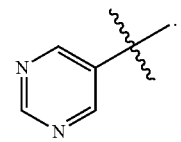 [SMILES: *c1cncnc1]

In some embodiments is a compound of Formula (IVa), wherein R$^4$ is

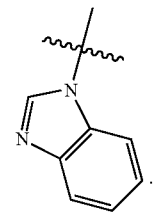 [SMILES: *n1cnc2ccccc21]

In some embodiments is a compound of Formula (IVa), wherein R$^4$ is

In some embodiments is a compound of Formula (IVa), wherein R⁴ is

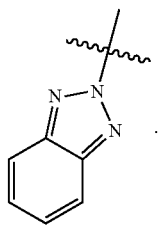 [SMILES: *n1nc2ccccc2n1]

In some embodiments is a compound of Formula (IVa), wherein R⁴ is

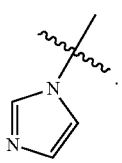

In some embodiments is a compound of Formula (IVa), wherein R⁴ is

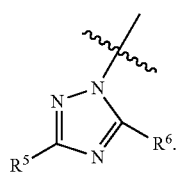

In some embodiments is a compound of Formula (IVa), wherein R⁴ is

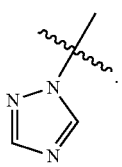

In some embodiments is a compound of Formula (IVa), wherein R¹ is

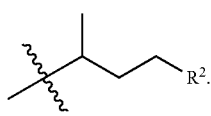

and R² is H. In some embodiments is a compound of Formula (IVa), wherein R¹ is

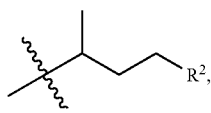

and R² is alkyl. In some embodiments is a compound of Formula (IVa), wherein R¹ is

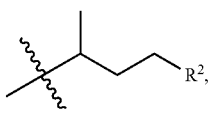

and R² is methyl. In some embodiments is a compound of Formula (IVa), wherein R¹ is

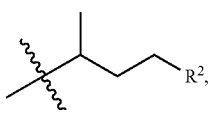

and R² is ethyl. In some embodiments is a compound of Formula (IVa), wherein R¹ is

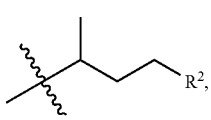

and R² is isopropyl. In some embodiments is a compound of Formula (IVa), wherein R¹ is

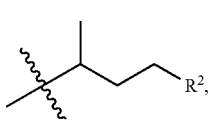

and R² is —NR¹³R¹⁴. In some embodiments is a compound of Formula (IVa), wherein R¹ is

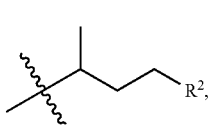

and R² is —NH₂. In some embodiments is a compound of Formula (IVa), wherein R¹ is

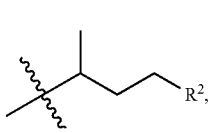

and R² is —NHCH₃. In some embodiments is a compound of Formula (IVa), wherein R¹ is

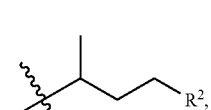

119

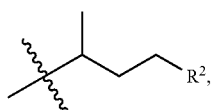

and R² is —N(CH₃)₂.

In some embodiments is a compound of Formula (IVa), wherein R¹ is

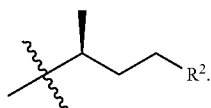

In some embodiments is a compound of Formula (IVa), wherein R¹ is

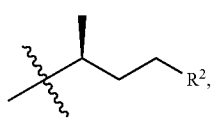

and R² is H. In some embodiments is a compound of Formula (IVa), wherein R¹ is

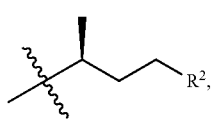

and R² is alkyl. In some embodiments is a compound of Formula (IVa), wherein R¹ is

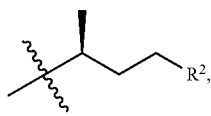

and R² is methyl. In some embodiments is a compound of Formula (IVa), wherein R¹ is

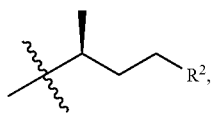

and R² is ethyl. In some embodiments is a compound of Formula (IVa), wherein R¹ is

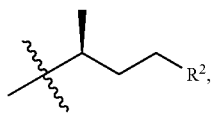

and R² is isopropyl. In some embodiments is a compound of Formula (IVa), wherein R¹ is

120

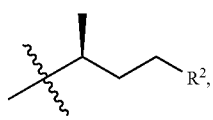

and R² is —NR¹³R¹⁴. In some embodiments is a compound of Formula (IVa), wherein R¹ is

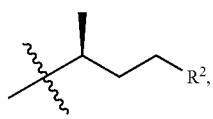

and R² is —NH₂. In some embodiments is a compound of Formula (IVa), wherein R¹ is

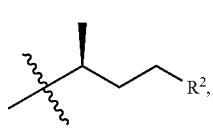

and R² is —NHCH₃. In some embodiments is a compound of Formula (IVa), wherein R¹ is

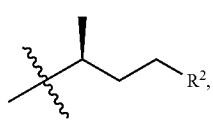

and R² is —N(CH₃)₂.

In some embodiments is a compound of Formula (IVa), wherein R¹ is

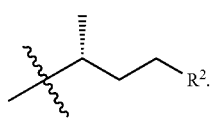

In some embodiments is a compound of Formula (IVa), wherein R¹ is

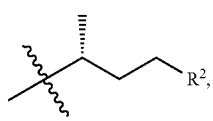

and R² is H. In some embodiments is a compound of Formula (IVa), wherein R¹ is

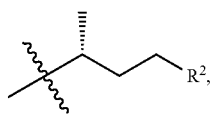

and R² is alkyl. In some embodiments is a compound of Formula (IVa), wherein R¹ is

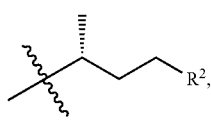

and R² is methyl. In some embodiments is a compound of Formula (IVa), wherein R¹ is

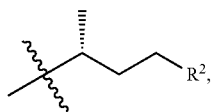

and R² is ethyl. In some embodiments is a compound of Formula (IVa), wherein R¹ is

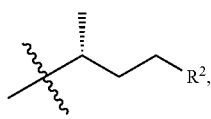

and R² is isopropyl. In some embodiments is a compound of Formula (IVa), wherein R¹ is

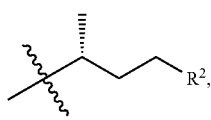

and R² is —NR¹³R¹⁴. In some embodiments is a compound of Formula (IVa), wherein R¹ is

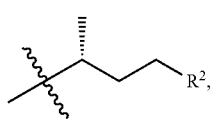

and R² is —NH₂. In some embodiments is a compound of Formula (IVa), wherein R¹ is

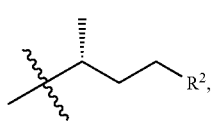

and R² is —NHCH₃. In some embodiments is a compound of Formula (IVa), wherein R¹ is

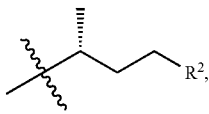

and R² is —N(CH₃)₂.

In some embodiments is a compound of Formula (IVa), wherein R¹ is —CH(CH₂CH₃)₂. In some embodiments is a compound of Formula (IVa), wherein R¹ is —CH(CH₃)₂. In some embodiments is a compound of Formula (IVa), wherein R¹ is —CH(CH₂CH₃)CH(R³)CH₃. In some embodiments is a compound of Formula (IVa), wherein R¹ is —CH(CH₂CH₃)CH(R³)CH₃, and R³ is —OH. In some embodiments is a compound of Formula (IVa), wherein R¹ is —CH(CH₂CH₃)CH(R³)CH₃, and R³ is alkyl. In some embodiments is a compound of Formula (IVa), wherein R¹ is —CH(CH₂CH₃)CH(R³)CH₃, and R³ is methyl. In some embodiments is a compound of Formula (IVa), wherein R¹ is —CH(CH₂CH₃)CH(R³)CH₃, and R³ is ethyl. In some embodiments is a compound of Formula (IVa), wherein R¹ is —CH(CH₂CH₃)CH(R³)CH₃, and R³ is —NR¹³R¹⁴. In some embodiments is a compound of Formula (IVa), wherein R¹ is —CH(CH₂CH₃)CH(R³)CH₃, and R³ is —NH₂. In some embodiments is a compound of Formula (IVa), wherein R¹ is —CH(CH₂CH₃)CH(R³)CH₃, and R³ is —NHCH₃. In some embodiments is a compound of Formula (IVa), wherein R¹ is —CH(CH₂CH₃)CH(R³)CH₃, and R³ is —N(CH₃)₂. In some embodiments is a compound of Formula (IVa), wherein R¹ is -alkylene(cycloalkyl). In some embodiments is a compound of Formula (IVa), wherein R¹ is —CH₂CH₂(cycloalkyl). In some embodiments is a compound of Formula (IVa), wherein R¹ is —CH₂(cycloalkyl). In some embodiments is a compound of Formula (IVa), wherein R¹ is —CH₂(cyclobutyl). In some embodiments is a compound of Formula (IVa), wherein R¹ is —CH₂(cyclopentyl). In some embodiments is a compound of Formula (IVa), wherein R¹ is —CH₂(cyclohexyl). In some embodiments is a compound of Formula (IVa), wherein R¹ is

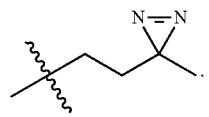

In another embodiment is a compound of Formula (IVa) having the structure:

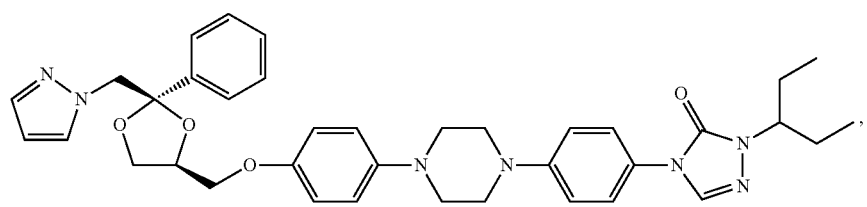

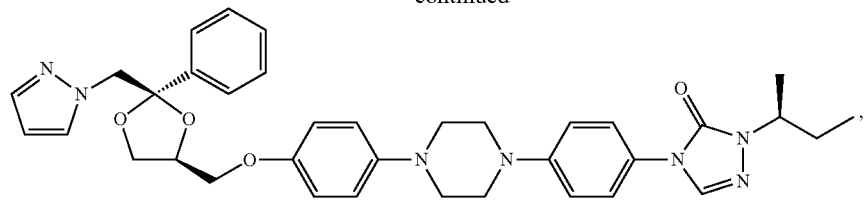
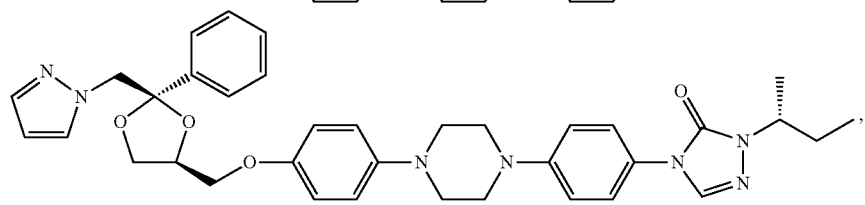
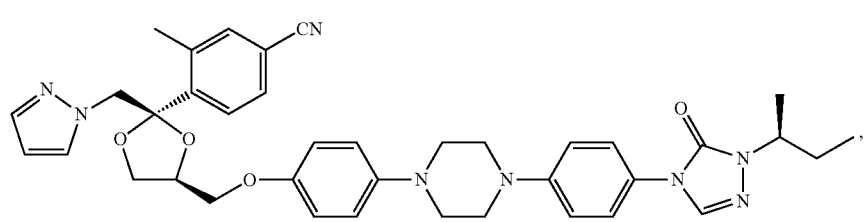
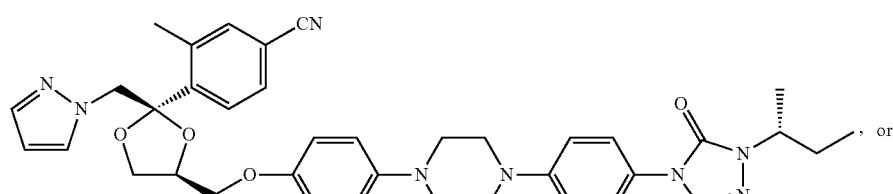, or
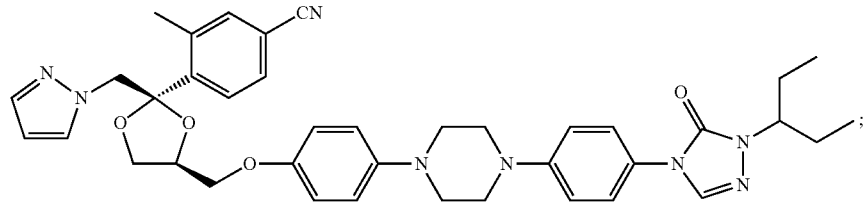
or a pharmaceutically acceptable salt, pharmaceutically acceptable solvate, or pharmaceutically acceptable prodrug thereof.
In another aspect, provided herein are compounds of Formula (IVb) having the structure:
Formula (IVb)
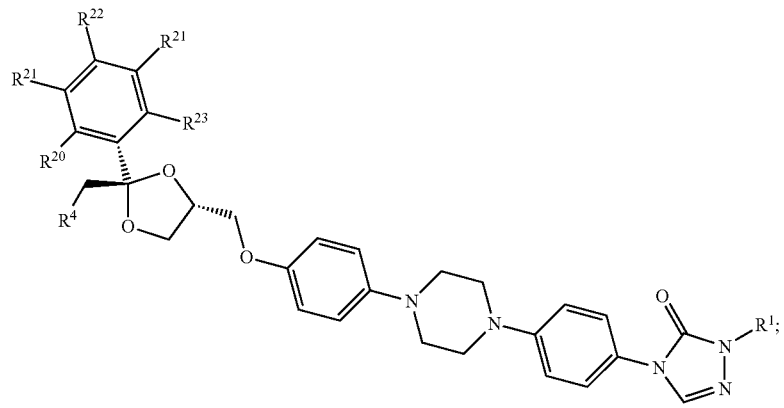

wherein:
R¹ is

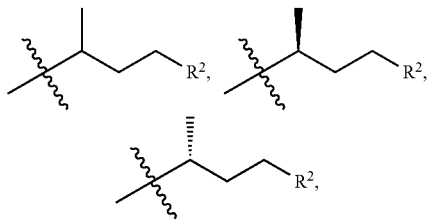

—CH(CH₂CH₃)₂, —CH(CH₃)₂, —CH₂CH(CH₃)₂, —CH(CH₂CH₃)CH(R³)CH₃, -alkylene(cycloalkyl), or

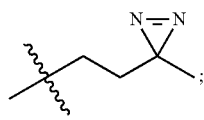

R² is H, alkyl, or —NR¹³R¹⁴;
R³ is —OH, alkyl, or —NR¹³R¹⁴;
R⁴ is halogen, alkyl,

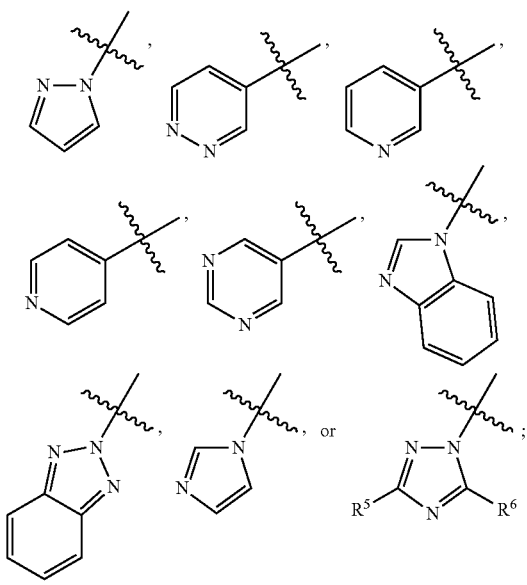

R⁵ and R⁶ are independently selected from H, alkyl, halo, and haloalkyl;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;
R²⁰ and R²² are independently selected from H, halogen, —OH, —NO₂, —N₃, —CN, alkyl, alkoxy, haloalkoxy, haloalkyl, hydroxyalkyl, alkoxyalkyl, -alkylene (NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴, wherein at least one of R²⁰ and R²² is not F or Cl;
each R²¹ is independently selected from H, halogen, —OH, —NO₂, —N₃, —CN, alkyl, alkoxy, haloalkoxy, haloalkyl, hydroxyalkyl, alkoxyalkyl, -alkylene (NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; and
R²³ is H;
or a pharmaceutically acceptable salt, pharmaceutically acceptable solvate, or pharmaceutically acceptable prodrug thereof.

In some embodiments is a compound of Formula (IVb), wherein R²⁰ and R²² are independently selected from H, halogen, —CN, alkyl, alkoxy, haloalkoxy, haloalkyl, —SO₂R¹³, —SO₂NR¹³R¹⁴, and —C(O)NR¹³R¹⁴; wherein at least one of R²⁰ and R²² is not F or Cl. In some embodiments is a compound of Formula (IVb), wherein R²⁰ and R²² are independently selected from H and halogen; wherein at least one of R²⁰ and R²² is not F or Cl. In some embodiments is a compound of Formula (IVb), wherein R²⁰ and R²² are independently selected from H and —CN. In some embodiments is a compound of Formula (IVb), wherein R²⁰ and R²² are independently selected from H and alkyl. In some embodiments is a compound of Formula (IVb), wherein R²⁰ and R²² are independently selected from H and alkoxy. In some embodiments is a compound of Formula (IVb), wherein R²⁰ and R²² are independently selected from H and haloalkoxy. In some embodiments is a compound of Formula (IVb), wherein R²⁰ and R²² are independently selected from H and haloalkyl. In some embodiments is a compound of Formula (IVb), wherein R²⁰ and R²² are independently selected from H and —SO₂R¹³. In some embodiments is a compound of Formula (IVb), wherein R²⁰ and R²² are independently selected from H and —SO₂NR¹³R¹⁴. In some embodiments is a compound of Formula (IVb), wherein R²⁰ and R²² are independently selected from H and —C(O)NR¹³R¹⁴. In some embodiments is a compound of Formula (IVb), wherein R²⁰ and R²² are independently selected from —CN and alkyl. In some embodiments is a compound of Formula (IVb), wherein R²⁰ and R²² are independently selected from H, Cl, —CN, —CH₃, —OCH₃, and —CF₃; wherein at least one of R²⁰ and R²² is not Cl.

In some embodiments is a compound of Formula (IVb), wherein R²⁰ and R²² are each H.

In some embodiments is a compound of Formula (IVb), wherein each R²¹ is independently selected from H, halogen, —CN, alkyl, alkoxy, and haloalkyl. In some embodiments is a compound of Formula (IVb), wherein each R²¹ is independently selected from H and —CN. In some embodiments is a compound of Formula (IVb), wherein each R²¹ is independently selected from H and alkyl. In some embodiments is a compound of Formula (IVb), wherein each R²¹ is independently selected from H and alkoxy. In some embodiments is a compound of Formula (IVb), wherein each R²¹ is independently selected from H and haloalkoxy. In some embodiments is a compound of Formula (IVb), wherein each R²¹ is independently selected from H and haloalkyl. In some embodiments is a compound of Formula (IVb), wherein each R²¹ is independently selected from H and —SO₂R¹³. In some embodiments is a compound of Formula (IVb), wherein each R²¹ is independently selected from H and —SO$_2$NR$^{13}$R$^{14}$. In some embodiments is a compound of Formula (IVb), wherein each R$^{21}$ is independently selected from H and —C(O)NR$^{13}$R$^{14}$. In some embodiments is a compound of Formula (IVb), wherein each R$^{21}$ is independently selected from —CN and alkyl. In some embodiments is a compound of Formula (IVb), wherein each R$^{21}$ is independently selected from H, Cl, —CN, —CH$_3$, —OCH$_3$, and —CF$_3$. In some embodiments is a compound of Formula (IVb), wherein each R$^{21}$ is independently selected from H, Cl, —CN, and —CH$_3$. In some embodiments is a compound of Formula (IVb), wherein each R$^{21}$ is H. In some embodiments is a compound of Formula (IVb), wherein each R$^{21}$ is Cl.

In some embodiments is a compound of Formula (IVb), wherein R$^4$ is halogen. In some embodiments is a compound of Formula (IVb), wherein R$^4$ is F. In some embodiments is a compound of Formula (IVb), wherein R$^4$ is Cl. In some embodiments is a compound of Formula (IVb), wherein R$^4$ is alkyl. In some embodiments is a compound of Formula (IVb), wherein R$^4$ is methyl. In some embodiments is a compound of Formula (IVb), wherein R$^4$ is ethyl. In some embodiments is a compound of Formula (IVb), wherein R$^4$ is

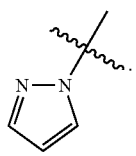

In some embodiments is a compound of Formula (IVb), wherein R$^4$ is

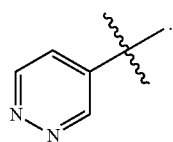

In some embodiments is a compound of Formula (IVb), wherein R$^4$ is

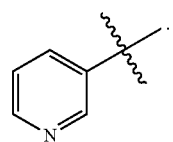

In some embodiments is a compound of Formula (IVb), wherein R$^4$ is

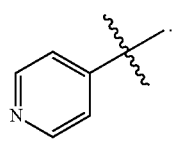

In some embodiments is a compound of Formula (IVb), wherein R$^4$ is

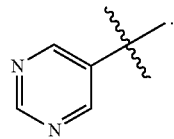

In some embodiments is a compound of Formula (IVb), wherein R$^4$ is

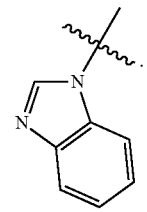

In some embodiments is a compound of Formula (IVb), wherein R$^4$ is

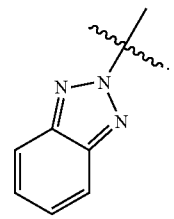 [SMILES: *n1nc2ccccc2n1 ; "."]

In some embodiments is a compound of Formula (IVb), wherein R$^4$ is

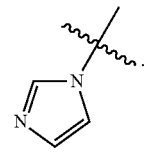

In some embodiments is a compound of Formula (IVb), wherein R$^4$ is

In some embodiments is a compound of Formula (IVb), wherein R$^4$ is

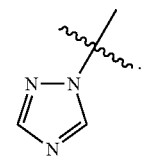 [SMILES: *n1cncn1 ; "."]

In some embodiments is a compound of Formula (IVb), wherein R$^1$ is

129

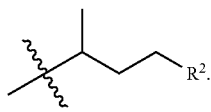

In some embodiments is a compound of Formula (IVb), wherein $R^1$ is

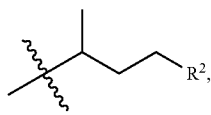

and $R^2$ is H. In some embodiments is a compound of Formula (IVb), wherein $R^1$ is

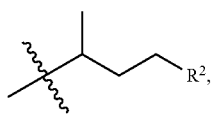

and $R^2$ is alkyl. In some embodiments is a compound of Formula (IVb), wherein $R^1$ is

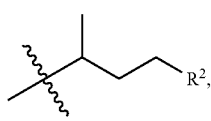

and $R^2$ is methyl. In some embodiments is a compound of Formula (IVb), wherein $R^1$ is

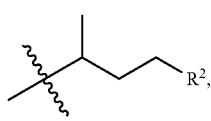

and $R^2$ is ethyl. In some embodiments is a compound of Formula (IVb), wherein $R^1$ is

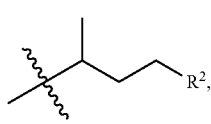

and $R^2$ is isopropyl. In some embodiments is a compound of Formula (IVb), wherein $R^1$ is

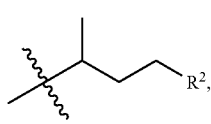

and $R^2$ is —$NR^{13}R^{14}$. In some embodiments is a compound of Formula (IVb), wherein $R^1$ is

130

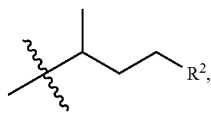

and $R^2$ is —$NH_2$. In some embodiments is a compound of Formula (IVb), wherein $R^1$ is

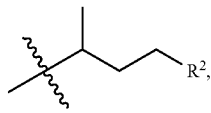

and $R^2$ is —$NHCH_3$. In some embodiments is a compound of Formula (IVb), wherein $R^1$ is

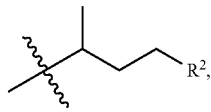

and $R^2$ is —$N(CH_3)_2$.

In some embodiments is a compound of Formula (IVb), wherein $R^1$ is

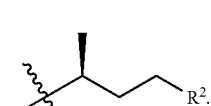

In some embodiments is a compound of Formula (IVb), wherein $R^1$ is

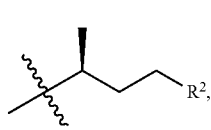

and $R^2$ is H. In some embodiments is a compound of Formula (IVb), wherein $R^1$ is

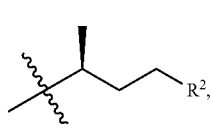

and $R^2$ is alkyl. In some embodiments is a compound of Formula (IVb), wherein $R^1$ is

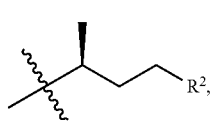

and $R^2$ is methyl. In some embodiments is a compound of Formula (IVb), wherein $R^1$ is

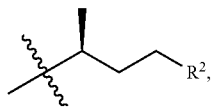

and $R^2$ is ethyl. In some embodiments is a compound of Formula (IVb), wherein $R^1$ is

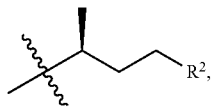

and $R^2$ is isopropyl. In some embodiments is a compound of Formula (IVb), wherein $R^1$ is

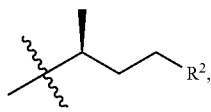

and $R^2$ is $-NR^{13}R^{14}$. In some embodiments is a compound of Formula (IVb), wherein $R^1$ is

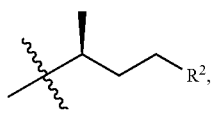

and $R^2$ is $-NH_2$. In some embodiments is a compound of Formula (IVb), wherein $R^1$ is

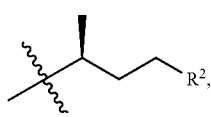

and $R^2$ is $-NHCH_3$. In some embodiments is a compound of Formula (IVb), wherein $R^1$ is

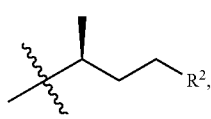

and $R^2$ is $-N(CH_3)_2$.

In some embodiments is a compound of Formula (IVb), wherein $R^1$ is

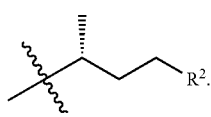

In some embodiments is a compound of Formula (IVb), wherein $R^1$ is

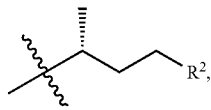

and $R^2$ is H. In some embodiments is a compound of Formula (IVb), wherein $R^1$ is

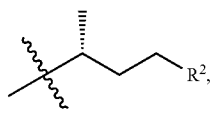

and $R^2$ is alkyl. In some embodiments is a compound of Formula (IVb), wherein $R^1$ is

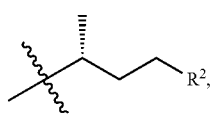

and $R^2$ is methyl. In some embodiments is a compound of Formula (IVb), wherein $R^1$ is

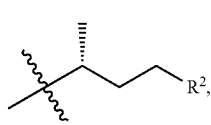

and $R^2$ is ethyl. In some embodiments is a compound of Formula (IVb), wherein $R^1$ is

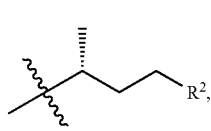

and $R^2$ is isopropyl. In some embodiments is a compound of Formula (IVb), wherein $R^1$ is

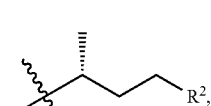

and $R^2$ is $-NR^{13}R^{14}$. In some embodiments is a compound of Formula (IVb), wherein $R^1$ is

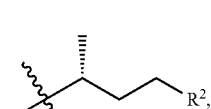

and $R^2$ is $-NH_2$. In some embodiments is a compound of Formula (IVb), wherein $R^1$ is

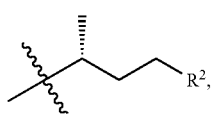

and $R^2$ is —$NHCH_3$. In some embodiments is a compound of Formula (IVb), wherein $R^1$ is

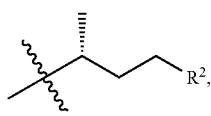

and $R^2$ is —$N(CH_3)_2$.

In some embodiments is a compound of Formula (IVb), wherein $R^1$ is —$CH(CH_2CH_3)_2$. In some embodiments is a compound of Formula (IVb), wherein $R^1$ is —$CH(CH_3)_2$. In some embodiments is a compound of Formula (IVb), wherein $R^1$ is —$CH(CH_2CH_3)CH(R^3)CH_3$. In some embodiments is a compound of Formula (IVb), wherein $R^1$ is —$CH(CH_2CH_3)CH(R^3)CH_3$, and $R^3$ is —OH. In some embodiments is a compound of Formula (IVb), wherein $R^1$ is —$CH(CH_2CH_3)CH(R^3)CH_3$, and $R^3$ is alkyl. In some embodiments is a compound of Formula (IVb), wherein $R^1$ is —$CH(CH_2CH_3)CH(R^3)CH_3$, and $R^3$ is methyl. In some embodiments is a compound of Formula (IVb), wherein $R^1$ is —$CH(CH_2CH_3)CH(R^3)CH_3$, and $R^3$ is ethyl. In some embodiments is a compound of Formula (IVb), wherein $R^1$ is —$CH(CH_2CH_3)CH(R^3)CH_3$, and $R^3$ is —$NR^{13}R^{14}$. In some embodiments is a compound of Formula (IVb), wherein $R^1$ is —$CH(CH_2CH_3)CH(R^3)CH_3$, and $R^3$ is —$NH_2$. In some embodiments is a compound of Formula (IVb), wherein $R^1$ is —$CH(CH_2CH_3)CH(R^3)CH_3$, and $R^3$ is —$NHCH_3$. In some embodiments is a compound of Formula (IVb), wherein $R^1$ is —$CH(CH_2CH_3)CH(R^3)CH_3$, and $R^3$ is —$N(CH_3)_2$. In some embodiments is a compound of Formula (IVb), wherein $R^1$ is -alkylene(cycloalkyl). In some embodiments is a compound of Formula (IVb), wherein $R^1$ is —$CH_2CH_2$(cycloalkyl). In some embodiments is a compound of Formula (IVb), wherein $R^1$ is —$CH_2$(cycloalkyl). In some embodiments is a compound of Formula (IVb), wherein $R^1$ is —$CH_2$(cyclobutyl). In some embodiments is a compound of Formula (IVb), wherein $R^1$ is —$CH_2$(cyclopentyl). In some embodiments is a compound of Formula (IVb), wherein $R^1$ is —$CH_2$(cyclohexyl). In some embodiments is a compound of Formula (IVb), wherein $R^1$ is

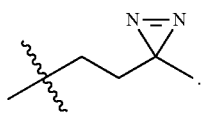 [SMILES: *CCC1(C)N=N1]

In another embodiment is a compound of Formula (IVb) having the structure:

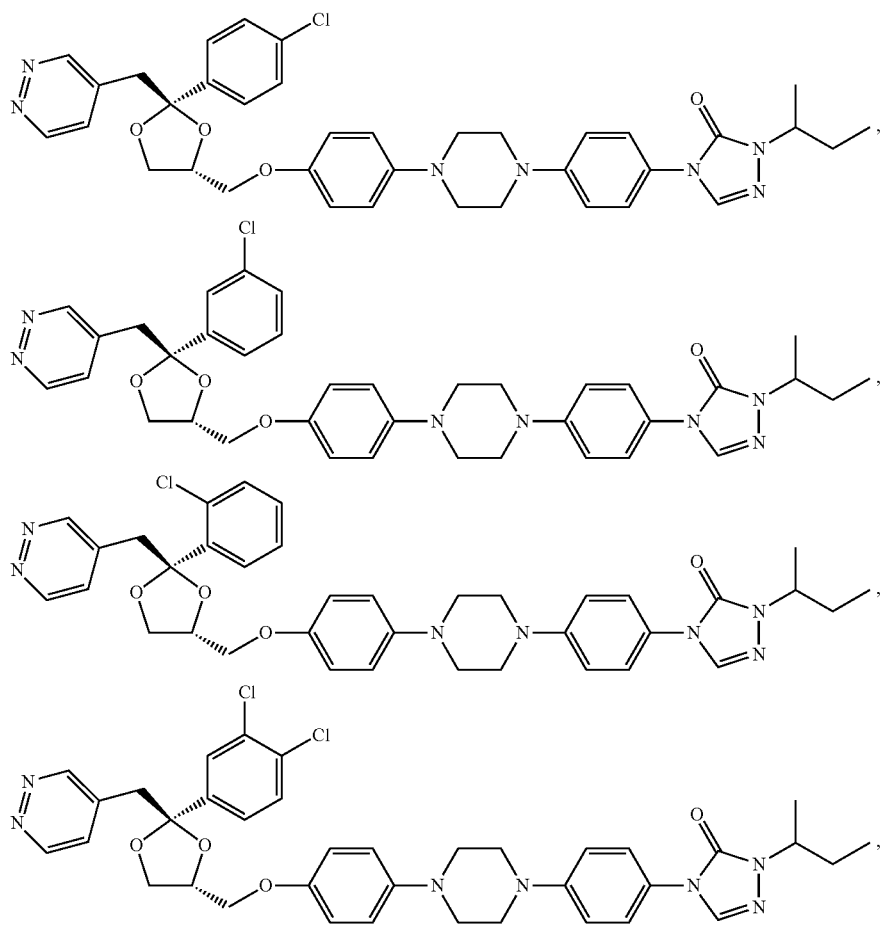

-continued
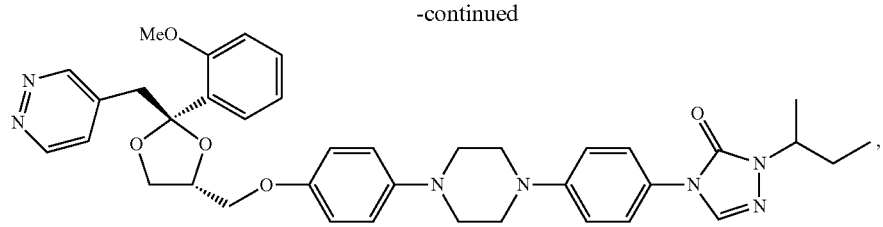,
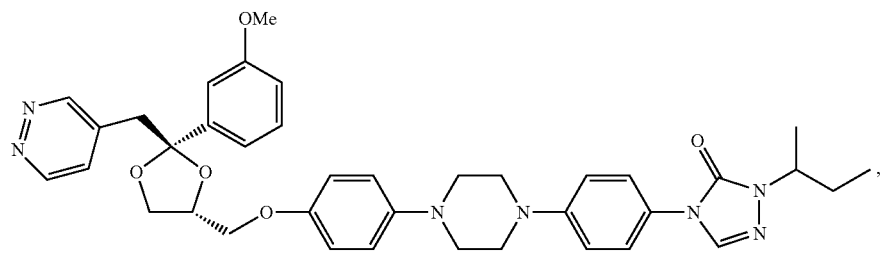,
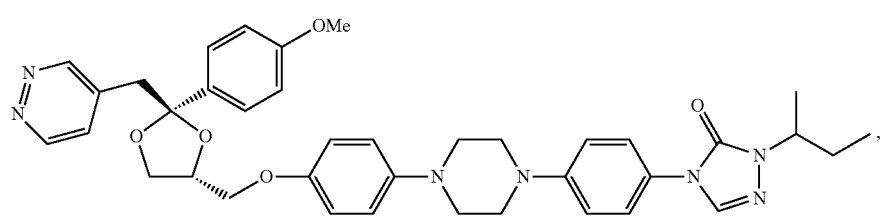,
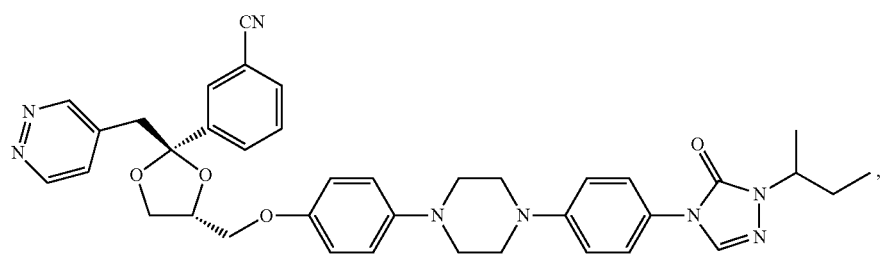,
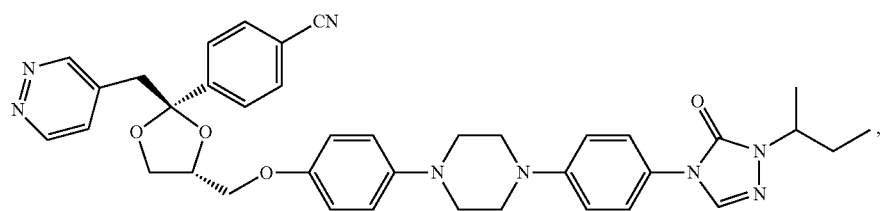,
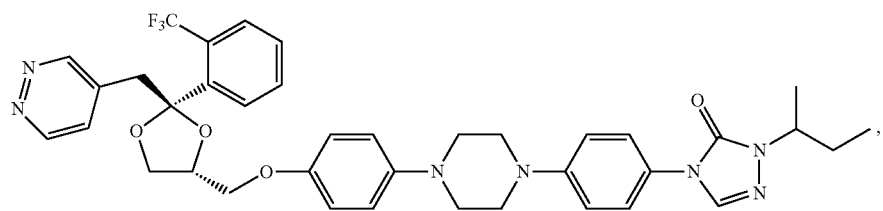,
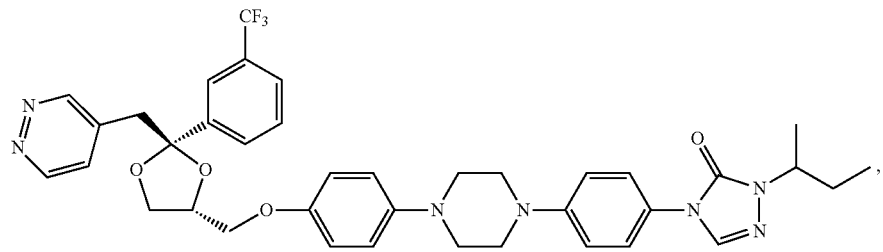, -continued
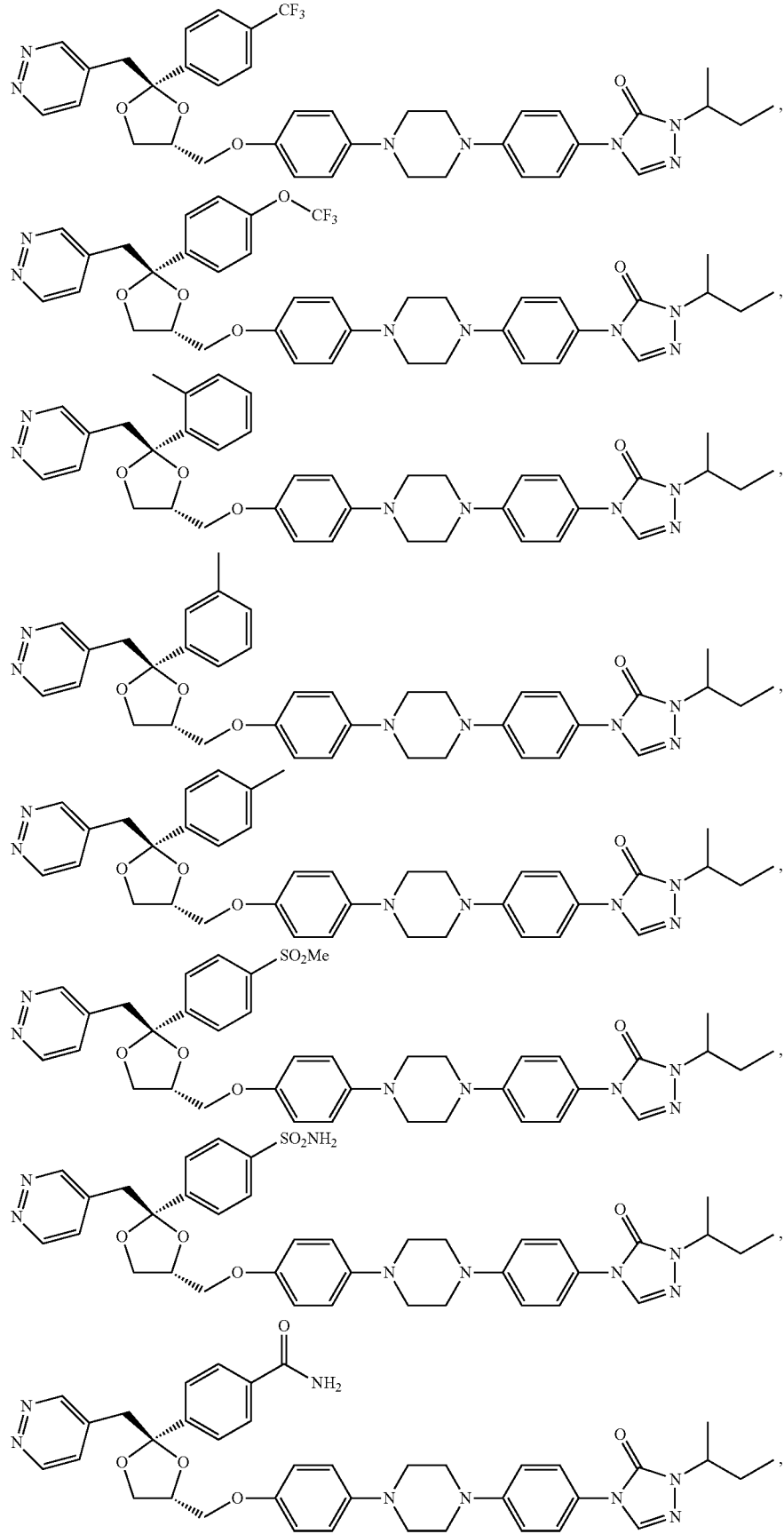

-continued

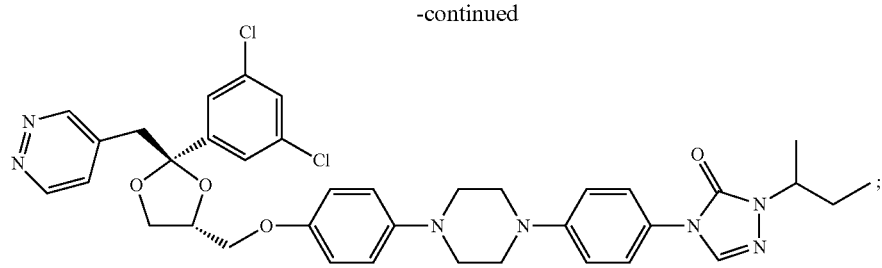

or a pharmaceutically acceptable salt, pharmaceutically acceptable solvate, or pharmaceutically acceptable prodrug thereof.

In another aspect, provided herein are compounds of Formula (V) having the structure:

Formula (V)

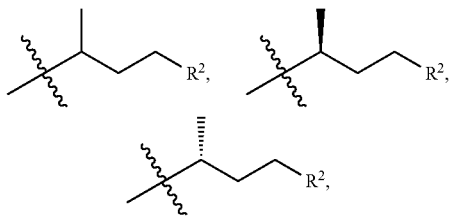

wherein:
R$^1$ is

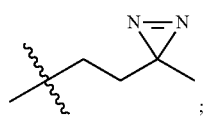 [SMILES: *CCC1(C)N=N1]

—CH(CH$_3$)CH(R$^3$)CH$_3$—CH(CH$_3$)C(O)CH$_3$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or R$^2$ is H, alkyl, or —NR$^{13}$R$^{14}$;
R$^3$ is —OH, alkyl, or —NR$^{13}$R$^{14}$;
R$^{10}$ is H or alkyl;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;

R$^{20}$ is selected from H, Cl, Br, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$;

R$^{21}$, R$^{22}$, and R$^{23}$ are independently selected from H, halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; and R$^{24}$ is H;

or a pharmaceutically acceptable salt, pharmaceutically acceptable solvate, or pharmaceutically acceptable prodrug thereof.

In some embodiments is a compound of Formula (V), wherein R$^{10}$ is H. In some embodiments is a compound of Formula (V), wherein R$^{10}$ is alkyl. In some embodiments is a compound of Formula (V), wherein R$^{10}$ is methyl. In some embodiments is a compound of Formula (V), wherein R$^{10}$ is ethyl.

In some embodiments is a compound of Formula (V), wherein R$^{21}$, R$^{22}$, and R$^{23}$ are independently selected from H, halogen, —CN, alkyl, alkoxy, haloalkoxy, haloalkyl, —SO$_2$R$^{13}$, —SO$_2$NR$^{13}$R$^{14}$, and —C(O)NR$^{13}$R$^{14}$. In some embodiments is a compound of Formula (V), wherein R$^{21}$, R$^{22}$, and R$^{23}$ are independently selected from H, halogen, —CN, alkyl, alkoxy, and haloalkyl. In some embodiments is a compound of Formula (V), wherein R$^{21}$, R$^{22}$, and R$^{23}$ are independently selected from H and halogen. In some embodiments is a compound of Formula (V), wherein R$^{21}$, R$^{22}$, and R$^{23}$ are independently selected from H and —CN. In some embodiments is a compound of Formula (V), wherein R$^{21}$, R$^{22}$, and R$^{23}$ are independently selected from H and alkyl. In some embodiments is a compound of Formula (V), wherein R$^{21}$, R$^{22}$, and R$^{23}$ are independently selected from H and alkoxy. In some embodiments is a compound of Formula (V), wherein R$^{21}$, R$^{22}$, and R$^{23}$ are independently selected from H and haloalkoxy. In some embodiments is a compound of Formula (V), wherein R$^{21}$, R$^{22}$, and R$^{23}$ are independently selected from H and haloalkyl. In some embodiments is a compound of Formula (V), wherein R$^{21}$, R$^{22}$, and R$^{23}$ are independently selected from H and —SO$_2$R$^{13}$. In some embodiments is a compound of Formula (V), wherein R$^{21}$, R$^{22}$, and R$^{23}$ are independently selected from H and —SO$_2$NR$^{13}$R$^{14}$. In some embodiments is a compound of Formula (V), wherein R$^{21}$, R$^{22}$, and R$^{23}$ are independently selected from H and —C(O)NR$^{13}$R$^{14}$. In some embodiments is a compound of Formula (V), wherein R$^{21}$, R$^{22}$, and R$^{23}$ are independently selected from —CN and alkyl. In some embodiments is a compound of Formula (V), wherein R$^{21}$, R$^{22}$, and R$^{23}$ are independently selected from H, Cl, —CN, —CH$_3$, —OCH$_3$, and —CF$_3$.

In some embodiments is a compound of Formula (V), wherein R$^{21}$, R$^{22}$, and R$^{23}$ are each H.

In some embodiments is a compound of Formula (V), wherein R$^{20}$ is selected from H, halogen, —CN, alkyl, alkoxy, and haloalkyl. In some embodiments is a compound of Formula (V), wherein R$^{20}$ is selected from H and —CN. In some embodiments is a compound of Formula (V), wherein R$^{20}$ is selected from H and alkyl. In some embodiments is a compound of Formula (V), wherein R$^{20}$ is selected from H and alkoxy. In some embodiments is a compound of Formula (V), wherein R$^{20}$ is selected from H and haloalkoxy. In some embodiments is a compound of Formula (V), wherein R$^{20}$ is selected from H and haloalkyl. In some embodiments is a compound of Formula (V), wherein R$^{20}$ is selected from H and —SO$_2$R$^{13}$. In some embodiments is a compound of Formula (V), wherein R$^{20}$ is selected from H and —SO$_2$NR$^{13}$R$^{14}$. In some embodiments is a compound of Formula (V), wherein R$^{20}$ is selected R$^{20}$ is selected from —CN and alkyl. In some embodiments is a compound of Formula (V), wherein R$^{20}$ is selected from H, Cl, —CN, —CH$_3$, —OCH$_3$, and —CF$_3$. In some embodiments is a compound of Formula (V), wherein R$^{20}$ is selected from H, Cl, —CN, and —CH$_3$. In some embodiments is a compound of Formula (V), wherein R$^{20}$ is H. In some embodiments is a compound of Formula (V), wherein R$^{20}$ is Cl.

In some embodiments is a compound of Formula (V), wherein R$^1$ is

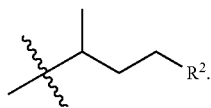

In some embodiments is a compound of Formula (V), wherein R$^1$ is

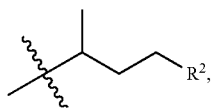

and R$^2$ is H. In some embodiments is a compound of Formula (V), wherein R$^1$ is

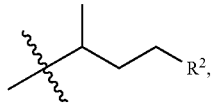

and R$^2$ is alkyl. In some embodiments is a compound of Formula (V), wherein R$^1$ is

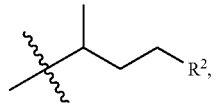

and R$^2$ is methyl. In some embodiments is a compound of Formula (V), wherein R$^1$ is

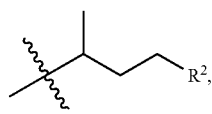

and R$^2$ is ethyl. In some embodiments is a compound of Formula (V), wherein R$^1$ is

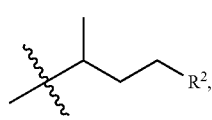

and R$^2$ is isopropyl. In some embodiments is a compound of Formula (V), wherein R$^1$ is

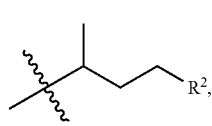

and R$^2$ is —NR$^{13}$R$^{14}$. In some embodiments is a compound of Formula (V), wherein R$^1$ is

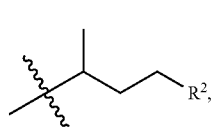

and R$^2$ is —NH$_2$. In some embodiments is a compound of Formula (V), wherein R$^1$ is

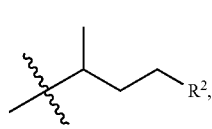

and R$^2$ is —NHCH$_3$. In some embodiments is a compound of Formula (V), wherein R$^1$ is

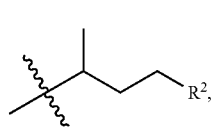

and R$^2$ is —N(CH$_3$)$_2$.

In some embodiments is a compound of Formula (V), wherein R$^1$ is

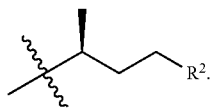

In some embodiments is a compound of Formula (V), wherein R¹ is

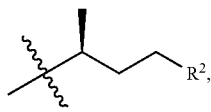

and R² is H. In some embodiments is a compound of Formula (V), wherein R¹ is

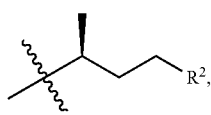

and R² is alkyl. In some embodiments is a compound of Formula (V), wherein R¹ is

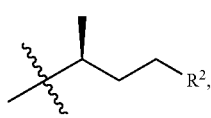

and R² is methyl. In some embodiments is a compound of Formula (V), wherein R¹ is

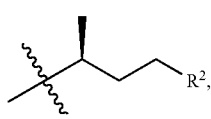

and R² is ethyl. In some embodiments is a compound of Formula (V), wherein R¹ is

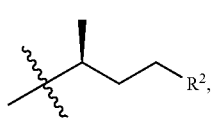

and R² is isopropyl. In some embodiments is a compound of Formula (V), wherein R¹ is

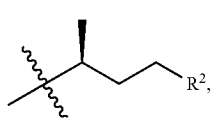

and R² is —NR¹³R¹⁴. In some embodiments is a compound of Formula (V), wherein R¹ is

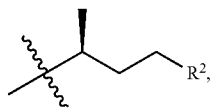

and R² is —NH₂. In some embodiments is a compound of Formula (V), wherein R¹ is

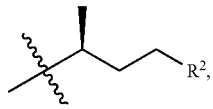

and R² is —NHCH₃. In some embodiments is a compound of Formula (V), wherein R¹ is

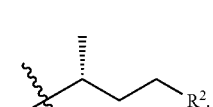

and R² is —N(CH₃)₂.

In some embodiments is a compound of Formula (V), wherein R¹ is

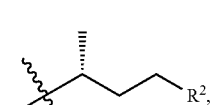

In some embodiments is a compound of Formula (V), wherein R¹ is

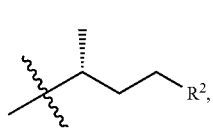

and R² is H. In some embodiments is a compound of Formula (V), wherein R¹ is

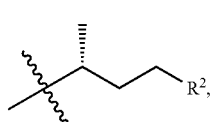

and R² is alkyl. In some embodiments is a compound of Formula (V), wherein R¹ is

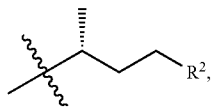

and R² is ethyl. In some embodiments is a compound of Formula (V), wherein R¹ is

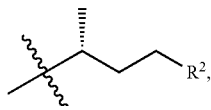

and R² is isopropyl. In some embodiments is a compound of Formula (V), wherein R¹ is

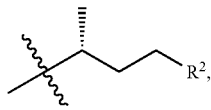

and R² is —NR$^{13}$R$^{14}$. In some embodiments is a compound of Formula (V), wherein R¹ is

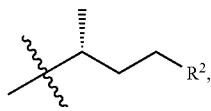

and R² is —NH₂. In some embodiments is a compound of Formula (V), wherein R¹ is

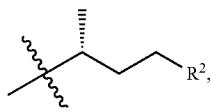

and R² is —NHCH₃. In some embodiments is a compound of Formula (V), wherein R¹ is and R² is —N(CH₃)₂.

In some embodiments is a compound of Formula (V), wherein R¹ is —CH(CH₂CH₃)₂. In some embodiments is a compound of Formula (V), wherein R¹ is —CH(CH₃)₂. In some embodiments is a compound of Formula (V), wherein R¹ is —CH(CH₂CH₃)CH(R³)CH₃. In some embodiments is a compound of Formula (V), wherein R¹ is —CH(CH₂CH₃)CH(R³)CH₃, and R³ is —OH. In some embodiments is a compound of Formula (V), wherein R¹ is —CH(CH₂CH₃)CH(R³)CH₃, and R³ is alkyl. In some embodiments is a compound of Formula (V), wherein R¹ is —CH(CH₂CH₃)CH(R³)CH₃, and R³ is methyl. In some embodiments is a compound of Formula (V), wherein R¹ is —CH(CH₂CH₃)CH(R³)CH₃, and R³ is ethyl. In some embodiments is a compound of Formula (V), wherein R¹ is —CH(CH₂CH₃)CH(R³)CH₃, and R³ is —NR$^{13}$R$^{14}$. In some embodiments is a compound of Formula (V), wherein R¹ is —CH(CH₂CH₃)CH(R³)CH₃, and R³ is —NH₂. In some embodiments is a compound of Formula (V), wherein R¹ is —CH(CH₂CH₃)CH(R³)CH₃, and R³ is —NHCH₃. In some embodiments is a compound of Formula (V), wherein R¹ is —CH(CH₂CH₃)CH(R³)CH₃, and R³ is —N(CH₃)₂. In some embodiments is a compound of Formula (V), wherein R¹ is -alkylene(cycloalkyl). In some embodiments is a compound of Formula (V), wherein R¹ is —CH₂CH₂(cycloalkyl). In some embodiments is a compound of Formula (V), wherein R¹ is —CH₂(cycloalkyl). In some embodiments is a compound of Formula (V), wherein R¹ is —CH₂(cyclobutyl). In some embodiments is a compound of Formula (V), wherein R¹ is —CH₂(cyclopentyl). In some embodiments is a compound of Formula (V), wherein R¹ is —CH₂(cyclohexyl). In some embodiments is a compound of Formula (V), wherein R¹ is

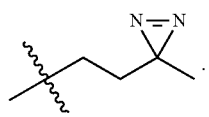 [SMILES: *CCC1(C)N=N1]

In another embodiment is a compound of Formula (V) having the structure:

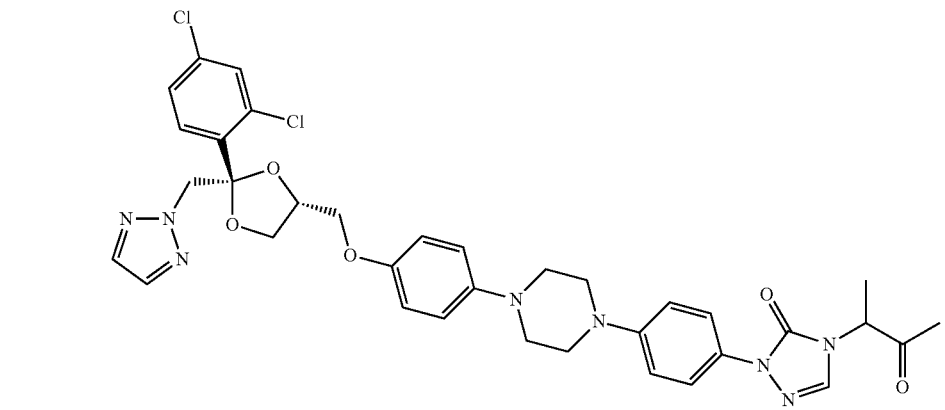

-continued
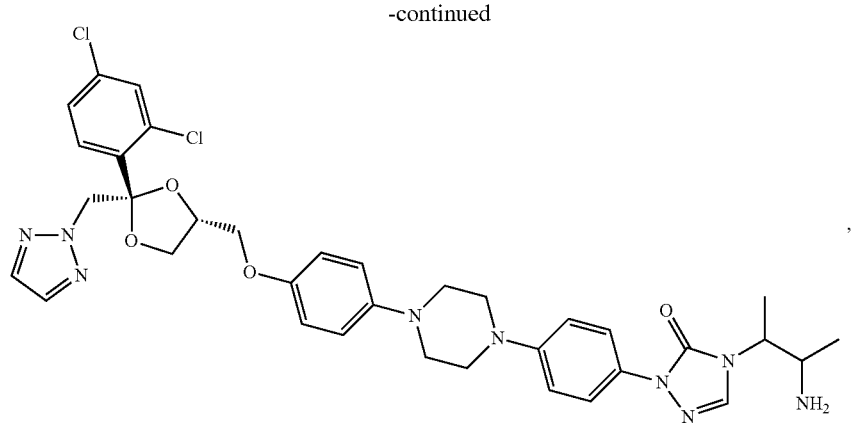
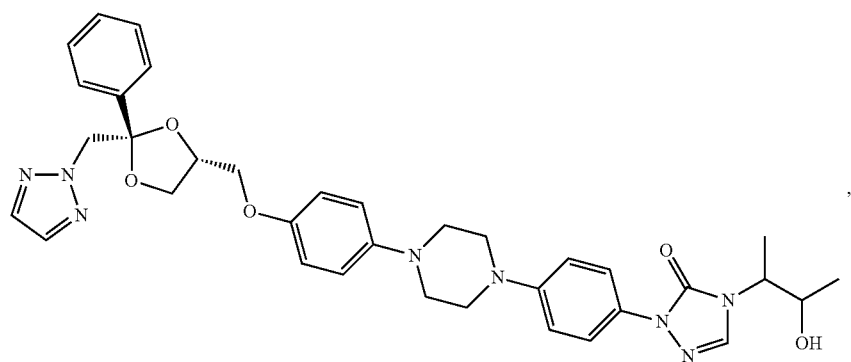
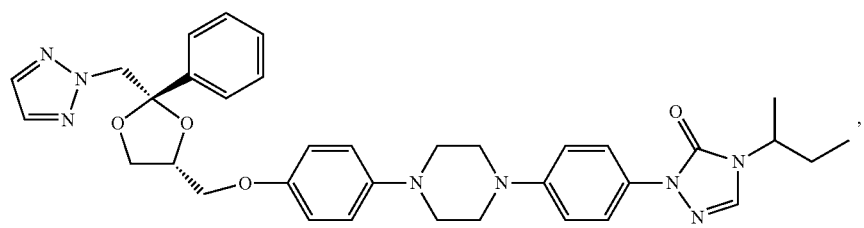
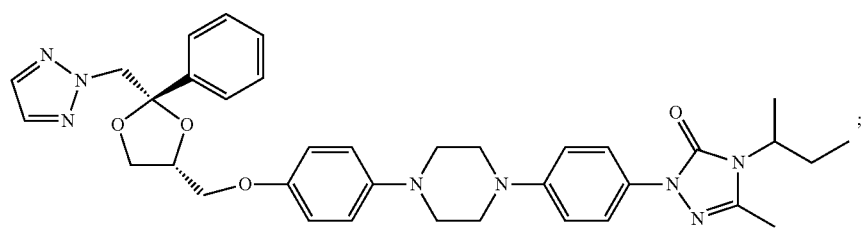
or a pharmaceutically acceptable salt, pharmaceutically acceptable solvate, or pharmaceutically acceptable prodrug thereof.

In another aspect, provided herein are compounds of Formula (Va) having the structure:

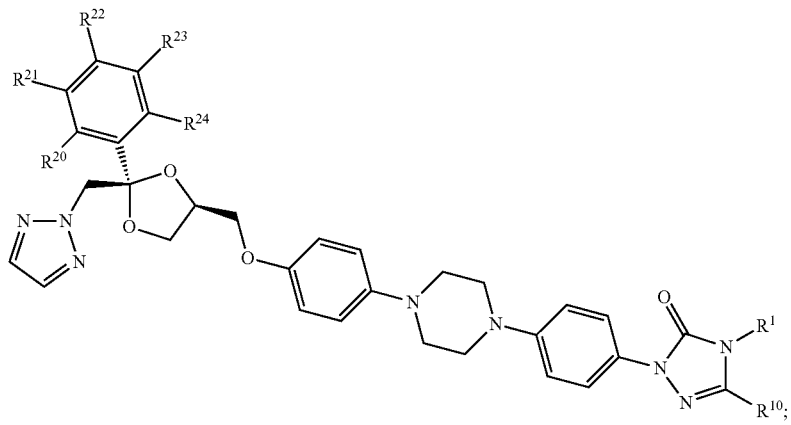

Formula (Va)

wherein:
R$^1$ is

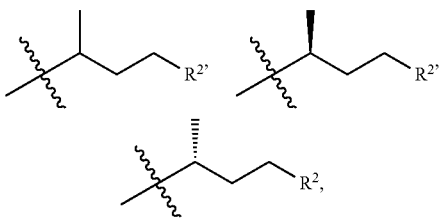

—CH(CH$_3$)CH(R$^3$)CH$_3$, —CH(CH$_3$)C(O)CH$_3$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

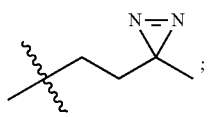 [SMILES: *CCC1(C)N=N1]

R$^2$ is H, alkyl, or —NR$^{13}$R$^{14}$;
R$^3$ is —OH, alkyl, or —NR$^{13}$R$^{14}$;
R$^{10}$ is H or alkyl;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;
R$^{20}$ is selected from H, Cl, Br, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$;
R$^{21}$, R$^{22}$, and R$^{23}$ are independently selected from H, halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; and R$^{24}$ is H;

or a pharmaceutically acceptable salt, pharmaceutically acceptable solvate, or pharmaceutically acceptable prodrug thereof.

In some embodiments is a compound of Formula (Va), wherein R$^{10}$ is H. In some embodiments is a compound of Formula (Va), wherein R$^{10}$ is alkyl. In some embodiments is a compound of Formula (Va), wherein R$^{10}$ is methyl. In some embodiments is a compound of Formula (Va), wherein R$^{10}$ is ethyl.

In some embodiments is a compound of Formula (Va), wherein R$^{21}$, R$^{22}$, and R$^{23}$ are independently selected from H, halogen, —CN, alkyl, alkoxy, haloalkoxy, haloalkyl, —SO$_2$R$^{13}$, —SO$_2$NR$^{13}$R$^{14}$, and —C(O)NR$^{13}$R$^{14}$. In some embodiments is a compound of Formula (Va), wherein R$^{21}$, R$^{22}$, and R$^{23}$ are independently selected from H, halogen, —CN, alkyl, alkoxy, and haloalkyl. In some embodiments is a compound of Formula (Va), wherein R$^{21}$, R$^{22}$, and R$^{23}$ are independently selected from H and halogen. In some embodiments is a compound of Formula (Va), wherein R$^{21}$, R$^{22}$, and R$^{23}$ are independently selected from H and —CN. In some embodiments is a compound of Formula (Va), wherein R$^{21}$, R$^{22}$, and R$^{23}$ are independently selected from H and alkyl. In some embodiments is a compound of Formula (Va), wherein R$^{21}$, R$^{22}$, and R$^{23}$ are independently selected from H and alkoxy. In some embodiments is a compound of Formula (Va), wherein R$^{21}$, R$^{22}$, and R$^{23}$ are independently selected from H and haloalkoxy. In some embodiments is a compound of Formula (Va), wherein R$^{21}$, R$^{22}$, and R$^{23}$ are independently selected from H and haloalkyl. In some embodiments is a compound of Formula (Va), wherein R$^{21}$, R$^{22}$, and R$^{23}$ are independently selected from H and —SO$_2$R$^{13}$. In some embodiments is a compound of Formula (Va), wherein R$^{21}$, R$^{22}$, and R$^{23}$ are independently selected from H and —SO$_2$NR$^{13}$R$^{14}$. In some embodiments is a compound of Formula (Va), wherein R$^{21}$, R$^{22}$, and R$^{23}$ are independently selected from H and —C(O)NR$^{13}$R$^{14}$. In some embodiments is a compound of Formula (Va), wherein R$^{21}$, R$^{22}$, and R$^{23}$ are independently selected from —CN and alkyl. In some embodiments is a compound of Formula (Va), wherein $R^{21}$, $R^{22}$, and $R^{23}$ are independently selected from H, Cl, —CN, —CH$_3$, —OCH$_3$, and —CF$_3$.

In some embodiments is a compound of Formula (Va), wherein $R^{21}$, $R^{22}$, and $R^{23}$ are each H. In some embodiments is a compound of Formula (Va), wherein $R^{20}$ is selected from H, halogen, —CN, alkyl, alkoxy, and haloalkyl. In some embodiments is a compound of Formula (Va), wherein $R^{20}$ is selected from H and —CN. In some embodiments is a compound of Formula (Va), wherein $R^{20}$ is selected from H and alkyl. In some embodiments is a compound of Formula (Va), wherein $R^{20}$ is selected from H and alkoxy. In some embodiments is a compound of Formula (Va), wherein $R^{20}$ is selected from H and haloalkoxy. In some embodiments is a compound of Formula (Va), wherein $R^{20}$ is selected from H and haloalkyl. In some embodiments is a compound of Formula (Va), wherein $R^{20}$ is selected from H and —SO$_2$R$^{13}$. In some embodiments is a compound of Formula (Va), wherein $R^{20}$ is selected from H and —SO$_2$NR$^{13}$R$^{14}$. In some embodiments is a compound of Formula (Va), wherein $R^{20}$ is selected $R^{20}$ is selected from —CN and alkyl. In some embodiments is a compound of Formula (Va), wherein $R^{20}$ is selected from H, Cl, —CN, —CH$_3$, —OCH$_3$, and —CF$_3$. In some embodiments is a compound of Formula (Va), wherein $R^{20}$ is selected from H, Cl, —CN, and —CH$_3$. In some embodiments is a compound of Formula (Va), wherein $R^{20}$ is H. In some embodiments is a compound of Formula (Va), wherein $R^{20}$ is Cl.

In some embodiments is a compound of Formula (Va), wherein $R^1$ is

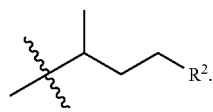

In some embodiments is a compound of Formula (Va), wherein $R^1$ is

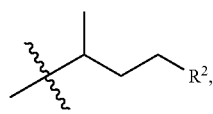

and $R^2$ is H. In some embodiments is a compound of Formula (Va), wherein $R^1$ is

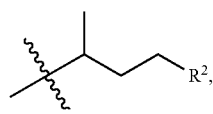

and $R^2$ is alkyl. In some embodiments is a compound of Formula (Va), wherein $R^1$ is

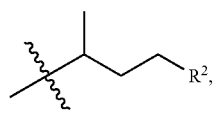

and $R^2$ is methyl. In some embodiments is a compound of Formula (Va), wherein $R^1$ is

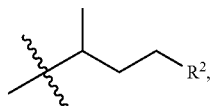

and $R^2$ is ethyl. In some embodiments is a compound of Formula (Va), wherein $R^1$ is

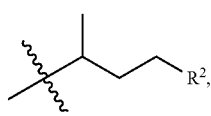

and $R^2$ is isopropyl. In some embodiments is a compound of Formula (Va), wherein $R^1$ is

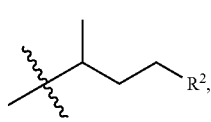

and $R^2$ is —NR$^{13}$R$^{14}$. In some embodiments is a compound of Formula (Va), wherein $R^1$ is

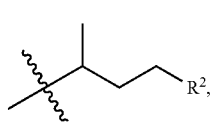

and $R^2$ is —NH$_2$. In some embodiments is a compound of Formula (Va), wherein $R^1$ is

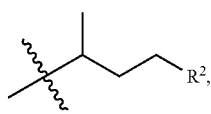

and $R^2$ is —NHCH$_3$. In some embodiments is a compound of Formula (Va), wherein $R^1$ is

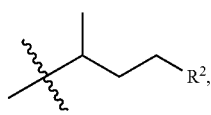

and $R^2$ is —N(CH$_3$)$_2$.

In some embodiments is a compound of Formula (Va), wherein $R^1$ is

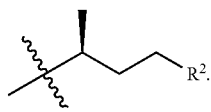

In some embodiments is a compound of Formula (Va), wherein $R^1$ is

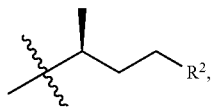

and $R^2$ is H. In some embodiments is a compound of Formula (Va), wherein $R^1$ is

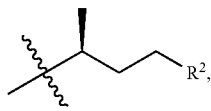

and $R^2$ is alkyl. In some embodiments is a compound of Formula (Va), wherein $R^1$ is

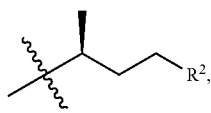

and $R^2$ is methyl. In some embodiments is a compound of Formula (Va), wherein $R^1$ is

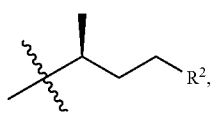

and $R^2$ is ethyl. In some embodiments is a compound of Formula (Va), wherein $R^1$ is

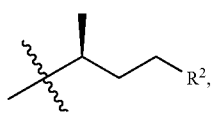

and $R^2$ is isopropyl. In some embodiments is a compound of Formula (Va), wherein $R^1$ is

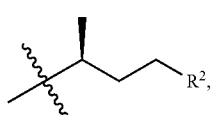

and $R^2$ is —$NR^{13}R^{14}$. In some embodiments is a compound of Formula (Va), wherein $R^1$ is

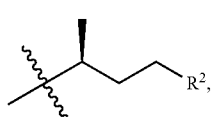

and $R^2$ is —$NH_2$. In some embodiments is a compound of Formula (Va), wherein $R^1$ is

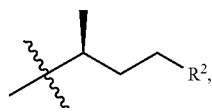

and $R^2$ is —$NHCH_3$. In some embodiments is a compound of Formula (Va), wherein $R^1$ is

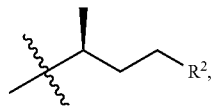

and $R^2$ is —$N(CH_3)_2$.

In some embodiments is a compound of Formula (Va), wherein $R^1$ is

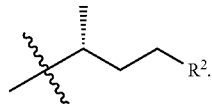

In some embodiments is a compound of Formula (Va), wherein $R^1$ is

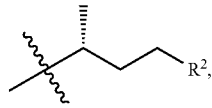

and $R^2$ is H. In some embodiments is a compound of Formula (Va), wherein $R^1$ is

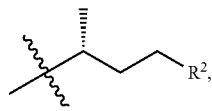

and $R^2$ is alkyl. In some embodiments is a compound of Formula (Va), wherein $R^1$ is

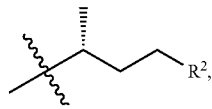

and $R^2$ is methyl. In some embodiments is a compound of Formula (Va), wherein $R^1$ is

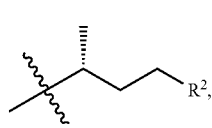

and $R^2$ is ethyl. In some embodiments is a compound of Formula (Va), wherein $R^1$ is

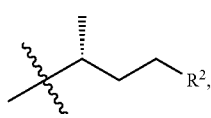

and R² is isopropyl. In some embodiments is a compound of Formula (Va), wherein R¹ is

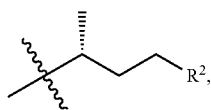

and R² is —NR¹³R¹⁴. In some embodiments is a compound of Formula (Va), wherein R¹ is

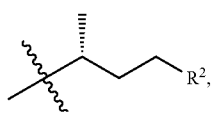

and R² is —NH₂. In some embodiments is a compound of Formula (Va), wherein R¹ is

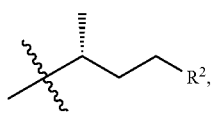

and R² is —NHCH₃. In some embodiments is a compound of Formula (Va), wherein R¹ is

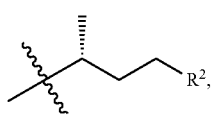

and R² is —N(CH₃)₂.

In some embodiments is a compound of Formula (Va), wherein R¹ is —CH(CH₂CH₃)₂. In some embodiments is a compound of Formula (Va), wherein R¹ is —CH(CH₃)₂. In some embodiments is a compound of Formula (Va), wherein R¹ is —CH(CH₂CH₃)CH(R³)CH₃. In some embodiments is a compound of Formula (Va), wherein R¹ is —CH(CH₂CH₃)CH(R³)CH₃, and R³ is —OH. In some embodiments is a compound of Formula (Va), wherein R¹ is —CH(CH₂CH₃)CH(R³)CH₃, and R³ is alkyl. In some embodiments is a compound of Formula (Va), wherein R¹ is —CH(CH₂CH₃)CH(R³)CH₃, and R³ is methyl. In some embodiments is a compound of Formula (Va), wherein R¹ is —CH(CH₂CH₃)CH(R³)CH₃, and R³ is ethyl. In some embodiments is a compound of Formula (Va), wherein R¹ is —CH(CH₂CH₃)CH(R³)CH₃, and R³ is —NR¹³R¹⁴. In some embodiments is a compound of Formula (Va), wherein R¹ is —CH(CH₂CH₃)CH(R³)CH₃, and R³ is —NH₂. In some embodiments is a compound of Formula (Va), wherein R¹ is —CH(CH₂CH₃)CH(R³)CH₃, and R³ is —NHCH₃. In some embodiments is a compound of Formula (Va), wherein R¹ is —CH(CH₂CH₃)CH(R³)CH₃, and R³ is —N(CH₃)₂. In some embodiments is a compound of Formula (Va), wherein R¹ is -alkylene(cycloalkyl). In some embodiments is a compound of Formula (Va), wherein R¹ is —CH₂CH₂(cycloalkyl). In some embodiments is a compound of Formula (Va), wherein R¹ is —CH₂(cycloalkyl). In some embodiments is a compound of Formula (Va), wherein R¹ is —CH₂(cyclobutyl). In some embodiments is a compound of Formula (Va), wherein R¹ is —CH₂(cyclopentyl). In some embodiments is a compound of Formula (Va), wherein R¹ is —CH₂(cyclohexyl). In some embodiments is a compound of Formula (Va), wherein R¹ is

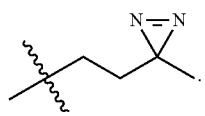 [SMILES: *CCC1(C)N=N1]

In another aspect, provided herein are compounds of Formula (VI) having the structure:

Formula (VI)

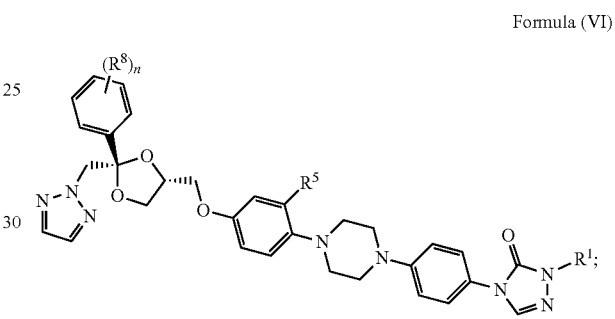

wherein:

R¹ is

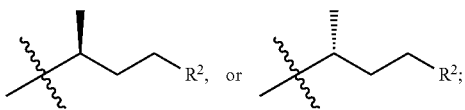

R² is H;

R⁵ is H, —CN, halogen, haloalkyl, alkyl, —NR¹³R¹⁴, -alkylene(NR¹³R¹⁴), and —SO₂R¹³;

each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl),-alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;

each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached; and n is selected from 0, 1, 2, 3, and 4;

or a pharmaceutically acceptable salt, pharmaceutically acceptable solvate, or pharmaceutically acceptable prodrug thereof.

In some embodiments described above or below is a compound of Formula (VI), wherein n is 0.

In some embodiments is a compound of Formula (VI), wherein n is 1. In some embodiments is a compound of Formula (VI), wherein n is 1 and $R^8$ is selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, or —C(O)NR$^{13}$R$^{14}$. In some embodiments is a compound of Formula (VI), wherein n is 1 and $R^8$ is selected from halogen, —CN, alkyl, alkoxy, haloalkoxy, or haloalkyl. In some embodiments is a compound of Formula (VI), wherein n is 1 and $R^8$ is halogen. In some embodiments is a compound of Formula (VI), wherein n is 1 and $R^8$ is F. In some embodiments is a compound of Formula (VI), wherein n is 1 and $R^8$ is Cl. In some embodiments is a compound of Formula (VI), wherein n is 1 and $R^8$ is —CN. In some embodiments is a compound of Formula (VI), wherein n is 1 and $R^8$ is alkyl. In some embodiments is a compound of Formula (VI), wherein n is 1 and $R^8$ is methyl. In some embodiments is a compound of Formula (VI), wherein n is 1 and $R^8$ is ethyl. In some embodiments is a compound of Formula (VI), wherein n is 1 and $R^8$ is alkoxy. In some embodiments is a compound of Formula (VI), wherein n is 1 and $R^8$ is methoxy. In some embodiments is a compound of Formula (VI), wherein n is 1 and $R^8$ is ethoxy. In some embodiments is a compound of Formula (VI), wherein n is 1 and $R^8$ is haloalkoxy. In some embodiments is a compound of Formula (VI), wherein n is 1 and $R^8$ is —OCF$_3$. In some embodiments is a compound of Formula (VI), wherein n is 1 and $R^8$ is haloalkyl. In some embodiments is a compound of Formula (VI), wherein n is 1 and $R^8$ is —CF$_3$.

In some embodiments is a compound of Formula (VI), wherein n is 2. In some embodiments is a compound of Formula (VI), wherein n is 2 and $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$. In some embodiments is a compound of Formula (VI), wherein n is 2 and $R^8$ is independently selected from halogen, —CN, alkyl, alkoxy, haloalkoxy, and haloalkyl. In some embodiments is a compound of Formula (VI), wherein n is 2 and $R^8$ is halogen. In some embodiments is a compound of Formula (VI), wherein n is 2 and each $R^8$ is F. In some embodiments is a compound of Formula (VI), wherein n is 2 and each $R^8$ is Cl. In some embodiments is a compound of Formula (VI), wherein n is 2 and $R^8$ is independently selected from halogen and —CN. In some embodiments is a compound of Formula (VI), wherein n is 2 and $R^8$ is independently selected from halogen and alkyl. In some embodiments is a compound of Formula (VI), wherein n is 2 and $R^8$ is independently selected from —CN and alkyl. In some embodiments is a compound of Formula (VI), wherein n is 2 and two adjacent $R^8$ form a heterocyclyl ring.

In some embodiments described above or below is a compound of Formula (VI), wherein $R^5$ is H. In some embodiments described above or below is a compound of Formula (VI), wherein $R^5$ is —CN. In some embodiments described above or below is a compound of Formula (VI), wherein $R^5$ is halogen. In some embodiments described above or below is a compound of Formula (VI), wherein $R^5$ is F. In some embodiments described above or below is a compound of Formula (VI), wherein $R^5$ is Cl. In some embodiments described above or below is a compound of Formula (VI), wherein $R^5$ is alkyl. In some embodiments described above or below is a compound of Formula (VI), wherein $R^5$ is methyl. In some embodiments described above or below is a compound of Formula (VI), wherein $R^5$ is ethyl. In some embodiments described above or below is a compound of Formula (VI), wherein $R^5$ is —NR$^{13}$R$^{14}$. In some embodiments described above or below is a compound of Formula (VI), wherein $R^5$ is —NH$_2$. In some embodiments described above or below is a compound of Formula (VI), wherein $R^5$ is -alkylene(NR$^{13}$R$^{14}$). In some embodiments described above or below is a compound of Formula (I), wherein $R^5$ is -alkylene(NH$_2$). In some embodiments described above or below is a compound of Formula (VI), wherein $R^5$ is —CH$_2$NH$_2$.

In some embodiments is a compound of Formula (VI), wherein $R^1$ is

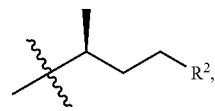

and $R^2$ is H.

In some embodiments is a compound of Formula (VI), wherein $R^1$ is

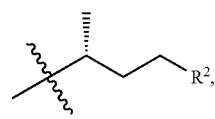

and $R^2$ is H.

In another embodiment is a compound of Formula (VI) having the structure:

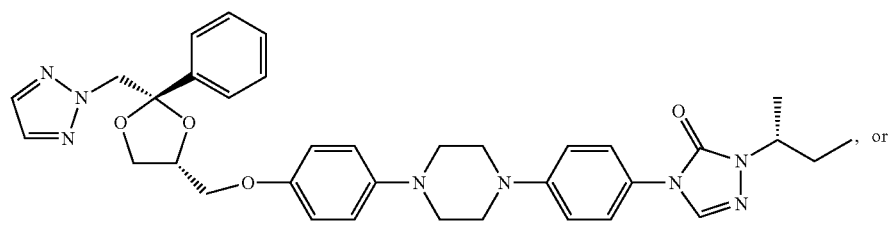

, or

-continued

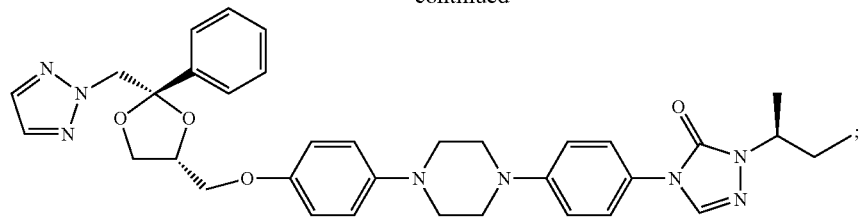

or a pharmaceutically acceptable salt, pharmaceutically acceptable solvate, or pharmaceutically acceptable prodrug thereof.

In another aspect, provided herein are compounds of Formula (VIa) having the structure:

Formula (VIa)

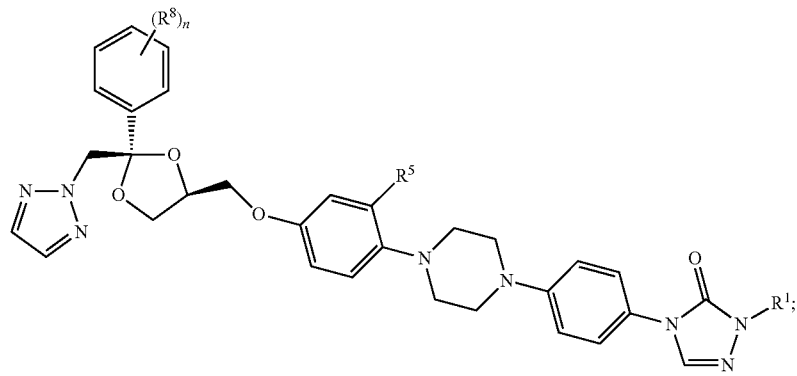

wherein:
R$^1$ is

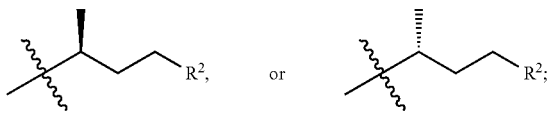

R$^2$ is H;
R$^5$ is H, —CN, halogen, haloalkyl, alkyl, —NR$^{13}$R$^{14}$, -alkylene(NR$^{13}$R$^{14}$), and —SO$_2$R$^{13}$;
each R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene (NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached; and
n is selected from 0, 1, 2, 3, and 4;

or a pharmaceutically acceptable salt, pharmaceutically acceptable solvate, or pharmaceutically acceptable prodrug thereof.

In some embodiments described above or below is a compound of Formula (VIa), wherein n is 0.

In some embodiments is a compound of Formula (VIa), wherein n is 1. In some embodiments is a compound of Formula (VIa), wherein n is 1 and R$^8$ is selected from halogen, —OH, —NO$_2$, —N$_3$, —CN, alkyl, alkoxy, haloalkoxy, haloalkyl, hydroxyalkyl, alkoxyalkyl, -alkylene (NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O) NR$^{13}$R$^{14}$, —C(O)R$^{14}$, —C(O)OR$^{14}$, or —C(O)NR$^{13}$R$^{14}$. In some embodiments is a compound of Formula (VIa), wherein n is 1 and R$^8$ is selected from halogen, —CN, alkyl, alkoxy, haloalkoxy, or haloalkyl. In some embodiments is a compound of Formula (VIa), wherein n is 1 and R$^8$ is halogen. In some embodiments is a compound of Formula (VIa), wherein n is 1 and R$^8$ is F. In some embodiments is a compound of Formula (VIa), wherein n is 1 and R$^8$ is Cl. In some embodiments is a compound of Formula (VIa), wherein n is 1 and R$^8$ is —CN. In some embodiments is a compound of Formula (VIa), wherein n is 1 and R$^8$ is alkyl. In some embodiments is a compound of Formula (VIa), wherein n is 1 and R$^8$ is methyl. In some embodiments is a compound of Formula (VIa), wherein n is 1 and R$^8$ is ethyl. In some embodiments is a compound of Formula (VIa), wherein n is 1 and R$^8$ is alkoxy. In some embodiments is a compound of Formula (VIa), wherein n is 1 and R$^8$ is methoxy. In some embodiments is a compound of Formula (VIa), wherein n is 1 and R⁸ is ethoxy. In some embodiments is a compound of Formula (VIa), wherein n is 1 and R⁸ is haloalkoxy. In some embodiments is a compound of Formula (VIa), wherein n is 1 and R⁸ is —OCF₃. In some embodiments is a compound of Formula (VIa), wherein n is 1 and R⁸ is haloalkyl. In some embodiments is a compound of Formula (VIa), wherein n is 1 and R⁸ is —CF₃.

In some embodiments is a compound of Formula (VIa), wherein n is 2. In some embodiments is a compound of Formula (VIa), wherein n is 2 and R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴. In some embodiments is a compound of Formula (VIa), wherein n is 2 and R⁸ is independently selected from halogen, —CN, alkyl, alkoxy, haloalkoxy, and haloalkyl. In some embodiments is a compound of Formula (VIa), wherein n is 2 and R⁸ is halogen. In some embodiments is a compound of Formula (VIa), wherein n is 2 and each R⁸ is F. In some embodiments is a compound of Formula (VIa), wherein n is 2 and each R⁸ is Cl. In some embodiments is a compound of Formula (VIa), wherein n is 2 and R⁸ is independently selected from halogen and —CN. In some embodiments is a compound of Formula (VIa), wherein n is 2 and R⁸ is independently selected from halogen and alkyl. In some embodiments is a compound of Formula (VIa), wherein n is 2 and R⁸ is independently selected from —CN and alkyl. In some embodiments is a compound of Formula (VIa), wherein n is 2 and two adjacent R⁸ form a heterocyclyl ring.

In some embodiments described above or below is a compound of Formula (VIa), wherein R⁵ is H. In some embodiments described above or below is a compound of Formula (VIa), wherein R⁵ is —CN. In some embodiments described above or below is a compound of Formula (VIa), wherein R⁵ is halogen. In some embodiments described above or below is a compound of Formula (VIa), wherein R⁵ is F. In some embodiments described above or below is a compound of Formula (VIa), wherein R⁵ is Cl. In some embodiments described above or below is a compound of Formula (VIa), wherein R⁵ is alkyl. In some embodiments described above or below is a compound of Formula (VIa), wherein R⁵ is methyl. In some embodiments described above or below is a compound of Formula (VIa), wherein R⁵ is ethyl. In some embodiments described above or below is a compound of Formula (VIa), wherein R⁵ is —NR¹³R¹⁴. In some embodiments described above or below is a compound of Formula (VIa), wherein R⁵ is —NH₂. In some embodiments described above or below is a compound of Formula (VIa), wherein R⁵ is -alkylene(NR¹³R¹⁴). In some embodiments described above or below is a compound of Formula (I), wherein R⁵ is -alkylene(NH₂). In some embodiments described above or below is a compound of Formula (VIa), wherein R⁵ is —CH₂NH₂.

In some embodiments is a compound of Formula (VIa), wherein R¹ is

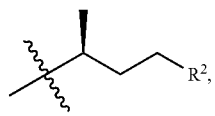

and R² is H.

In some embodiments is a compound of Formula (VIa), wherein R¹ is

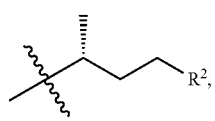

and R² is H.

In another embodiment is a compound of Formula (VIa) having the structure:

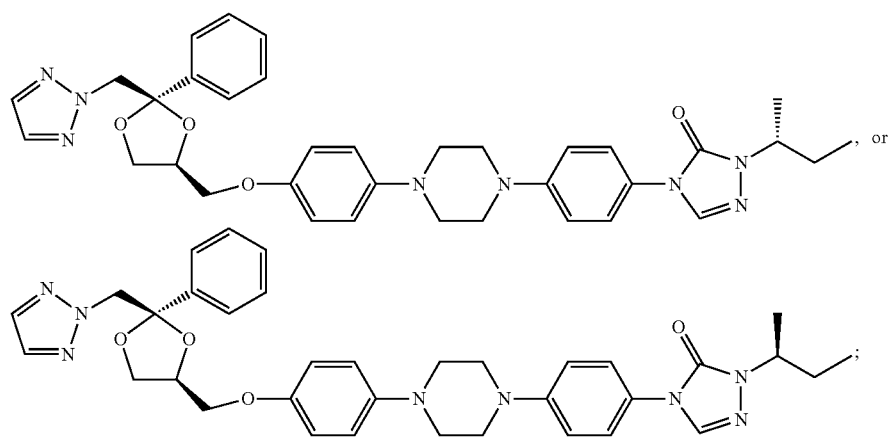

or a pharmaceutically acceptable salt, pharmaceutically acceptable solvate, or pharmaceutically acceptable prodrug thereof.

In another aspect, provided herein are compounds of Formula (VIb) having the structure:

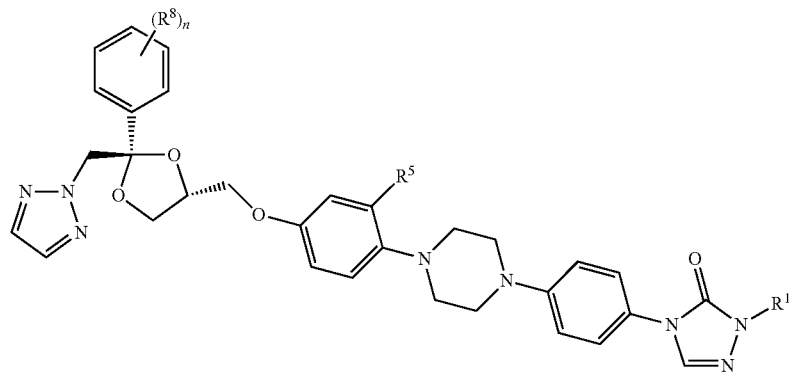

Formula (VIb)

wherein:

R¹ is

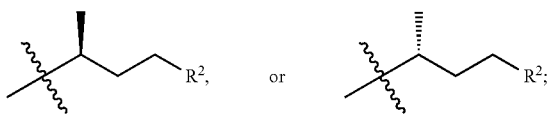

R² is H;
R⁵ is H, —CN, halogen, haloalkyl, alkyl, —NR¹³R¹⁴, -alkylene(NR¹³R¹⁴), and —SO₂R¹³;
each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

In some embodiments described above or below is a compound of Formula (VIb), wherein n is 0.

In some embodiments is a compound of Formula (VIb), wherein n is 1. In some embodiments is a compound of Formula (VIb), wherein n is 1 and R⁸ is selected from halogen, —OH, —NO₂, —N₃, —CN, alkyl, alkoxy, haloalkoxy, haloalkyl, hydroxyalkyl, alkoxyalkyl, -alkylene (NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, or —C(O)NR¹³R¹⁴. In some embodiments is a compound of Formula (VIb), wherein n is 1 and R⁸ is selected from halogen, —CN, alkyl, alkoxy, haloalkoxy, or haloalkyl. In some embodiments is a compound of Formula (VIb), wherein n is 1 and R⁸ is halogen. In some embodiments is a compound of Formula (VIb), wherein n is 1 and R⁸ is F. In some embodiments is a compound of Formula (VIb), wherein n is 1 and R⁸ is Cl. In some embodiments is a compound of Formula (VIb), wherein n is 1 and R⁸ is —CN. In some embodiments is a compound of Formula (VIb), wherein n is 1 and R⁸ is alkyl. In some embodiments is a compound of Formula (VIb), wherein n is 1 and R⁸ is methyl. In some embodiments is a compound of Formula (VIb), wherein n is 1 and R⁸ is ethyl. In some embodiments is a compound of Formula (VIb), wherein n is 1 and R⁸ is alkoxy. In some embodiments is a compound of Formula (VIb), wherein n is 1 and R⁸ is methoxy. In some embodiments is a compound of Formula (VIb), wherein n is 1 and R⁸ is ethoxy. In some embodiments is a compound of Formula (VIb), wherein n is 1 and R⁸ is haloalkoxy. In some embodiments is a compound of Formula (VIb), wherein n is 1 and R⁸ is —OCF₃. In some embodiments is a compound of Formula (VIb), wherein n is 1 and R⁸ is haloalkyl. In some embodiments is a compound of Formula (VIb), wherein n is 1 and R⁸ is —CF₃.

In some embodiments is a compound of Formula (VIb), wherein n is 2. In some embodiments is a compound of Formula (VIb), wherein n is 2 and R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴. In some embodiments is a compound of Formula (VIb), wherein n is 2 and R⁸ is independently selected from halogen, —CN, alkyl, alkoxy, haloalkoxy, and haloalkyl. In some embodiments is a compound of Formula (VIb), wherein n is 2 and R⁸ is halogen. In some embodiments is a compound of Formula (VIb), wherein n is 2 and each R⁸ is F. In some embodiments is a compound of Formula (VIb), wherein n is 2 and each R⁸ is Cl. In some embodiments is a compound of Formula (VIb), wherein n is 2 and R⁸ is independently selected from halogen and —CN. In some embodiments is a compound of Formula (VIb), wherein n is 2 and R⁸ is independently selected from halogen and alkyl. In some embodiments is a compound of Formula (VIb), wherein n is 2 and R⁸ is independently selected from —CN and alkyl. In some embodiments is a compound of Formula (VIb), wherein n is 2 and two adjacent R⁸ form a heterocyclyl ring.

In some embodiments described above or below is a compound of Formula (VIb), wherein R⁵ is H. In some embodiments described above or below is a compound of Formula (VIb), wherein R⁵ is —CN. In some embodiments described above or below is a compound of Formula (VIb), wherein R⁵ is halogen. In some embodiments described above or below is a compound of Formula (VIb), wherein R⁵ is F. In some embodiments described above or below is a compound of Formula (VIb), wherein R⁵ is Cl. In some embodiments described above or below is a compound of Formula (VIb), wherein R⁵ is alkyl. In some embodiments described above or below is a compound of Formula (VIb), wherein R⁵ is methyl. In some embodiments described above or below is a compound of Formula (VIb), wherein R⁵ is ethyl. In some embodiments described above or below is a compound of Formula (VIb), wherein R⁵ is —NR¹³R¹⁴. In some embodiments described above or below is a compound of Formula (VIb), wherein R⁵ is —NH₂. In some embodiments described above or below is a compound of Formula (VIb), wherein R⁵ is -alkylene(NR¹³R¹⁴). In some embodiments described above or below is a compound of Formula (I), wherein R⁵ is -alkylene(NH₂). In some embodiments described above or below is a compound of Formula (VIb), wherein R⁵ is —CH₂NH₂.

In some embodiments is a compound of Formula (VIb), wherein R¹ is

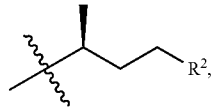

and R² is H.

In some embodiments is a compound of Formula (VIb), wherein R¹ is

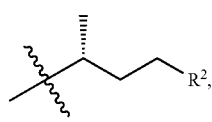

and R² is H.

In another embodiment is a compound of Formula (VIb) having the structure:

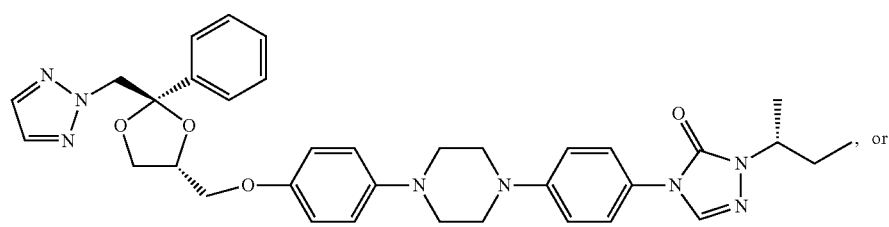

, or

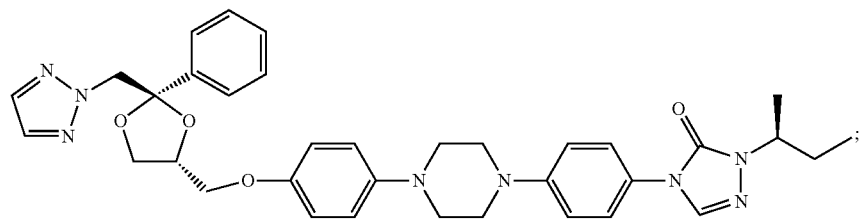

;

or a pharmaceutically acceptable salt, pharmaceutically acceptable solvate, or pharmaceutically acceptable prodrug thereof.

In another aspect, provided herein are compounds of Formula (VIc) having the structure:

Formula (VIc)

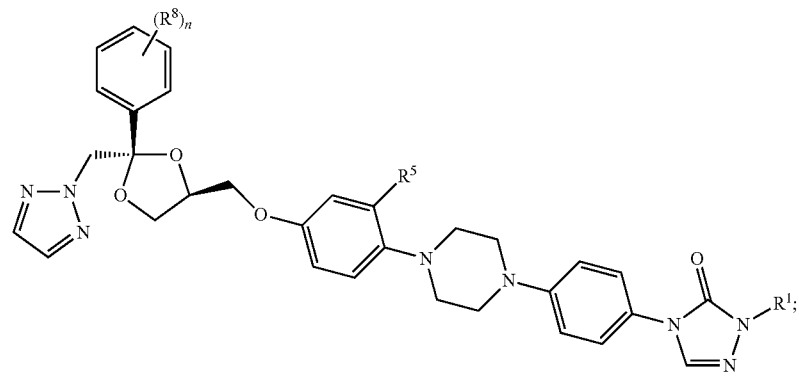

wherein:

R$^1$ is

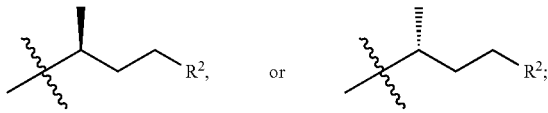

R$^2$ is H;
R$^5$ is H, —CN, halogen, haloalkyl, alkyl, —NR$^{13}$R$^{14}$, -alkylene(NR$^{13}$R$^{14}$), and —SO$_2$R$^{13}$;
each R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene (NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —N$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

In some embodiments described above or below is a compound of Formula (VIc), wherein n is 0.

In some embodiments is a compound of Formula (VIc), wherein n is 1. In some embodiments is a compound of Formula (VIc), wherein n is 1 and R$^8$ is selected from halogen, —OH, —NO$_2$, —N$_3$, —CN, alkyl, alkoxy, haloalkoxy, haloalkyl, hydroxyalkyl, alkoxyalkyl, -alkylene (NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$R$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, NR$^{13}$R$^{14}$, —C(O)R$^{14}$, —C(O)OR$^{14}$, or —C(O)NR$^{13}$R$^{14}$. In some embodiments is a compound of Formula (VIc), wherein n is 1 and R$^8$ is selected from halogen, —CN, alkyl, alkoxy, haloalkoxy, or haloalkyl. In some embodiments is a compound of Formula (VIc), wherein n is 1 and R$^8$ is halogen. In some embodiments is a compound of Formula (VIc), wherein n is 1 and R$^8$ is F. In some embodiments is a compound of Formula (VIc), wherein n is 1 and R$^8$ is Cl. In some embodiments is a compound of Formula (VIc), wherein n is 1 and R$^8$ is —CN. In some embodiments is a compound of Formula (VIc), wherein n is 1 and R$^8$ is alkyl. In some embodiments is a compound of Formula (VIc), wherein n is 1 and R$^8$ is methyl. In some embodiments is a compound of Formula (VIc), wherein n is 1 and R$^8$ is ethyl. In some embodiments is a compound of Formula (VIc), wherein n is 1 and R$^8$ is alkoxy. In some embodiments is a compound of Formula (VIc), wherein n is 1 and R$^8$ is methoxy. In some embodiments is a compound of Formula (VIc), wherein n is 1 and R$^8$ is ethoxy. In some embodiments is a compound of Formula (VIc), wherein n is 1 and R$^8$ is haloalkoxy. In some embodiments is a compound of Formula (VIc), wherein n is 1 and R$^8$ is —OCF$_3$. In some embodiments is a compound of Formula (VIc), wherein n is 1 and R$^8$ is haloalkyl. In some embodiments is a compound of Formula (VIc), wherein n is 1 and R$^8$ is —CF$_3$.

In some embodiments is a compound of Formula (VIc), wherein n is 2. In some embodiments is a compound of Formula (VIc), wherein n is 2 and R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$. In some embodiments is a compound of Formula (VIc), wherein n is 2 and R$^8$ is independently selected from halogen, —CN, alkyl, alkoxy, haloalkoxy, and haloalkyl. In some embodiments is a compound of Formula (VIc), wherein n is 2 and R$^8$ is halogen. In some embodiments is a compound of Formula (VIc), wherein n is 2 and each R$^8$ is F. In some embodiments is a compound of Formula (VIc), wherein n is 2 and each R$^8$ is Cl. In some embodiments is a compound of Formula (VIc), wherein n is 2 and R$^8$ is independently selected from halogen and —CN. In some embodiments is a compound of Formula (VIc), wherein n is 2 and R$^8$ is independently selected from halogen and alkyl. In some embodiments is a compound of Formula (VIc), wherein n is 2 and R$^8$ is independently selected from —CN and alkyl. In some embodiments is a compound of Formula (VIc), wherein n is 2 and two adjacent R$^8$ form a heterocyclyl ring.

In some embodiments described above or below is a compound of Formula (VIc), wherein R$^5$ is H. In some embodiments described above or below is a compound of Formula (VIc), wherein R$^5$ is —CN. In some embodiments described above or below is a compound of Formula (VIc), wherein R$^5$ is halogen. In some embodiments described above or below is a compound of Formula (VIc), wherein R$^5$ is F. In some embodiments described above or below is a compound of Formula (VIc), wherein R$^5$ is Cl. In some embodiments described above or below is a compound of Formula (VIc), wherein R$^5$ is alkyl. In some embodiments described above or below is a compound of Formula (VIc), wherein R$^5$ is methyl. In some embodiments described above or below is a compound of Formula (VIc), wherein R$^5$ is ethyl. In some embodiments described above or below is a compound of Formula (VIc), wherein R$^5$ is —NR$^{13}$R$^{14}$. In some embodiments described above or below is a compound of Formula (VIc), wherein R$^5$ is —NH$_2$. In some embodiments described above or below is a compound of Formula (VIc), wherein R$^5$ is -alkylene(NR$^{13}$R$^{14}$). In some embodiments described above or below is a compound of Formula (I), wherein R$^5$ is -alkylene(NH$_2$). In some embodiments described above or below is a compound of Formula (VIc), wherein R$^5$ is —CH$_2$NH$_2$.

In some embodiments is a compound of Formula (VIc), wherein R$^1$ is

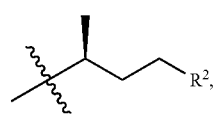

and R$^2$ is H.

In some embodiments is a compound of Formula (VIc), wherein R$^1$ is

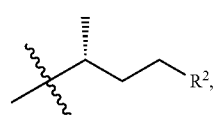

and R$^2$ is H.

In another embodiment is a compound of Formula (VIc) having the structure:

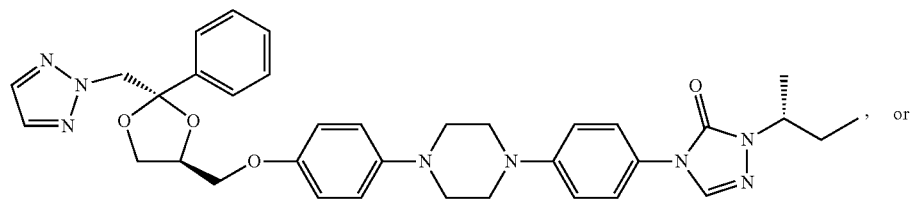, or

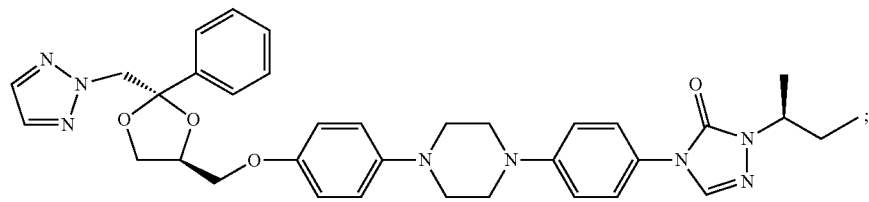;

or a pharmaceutically acceptable salt, pharmaceutically acceptable solvate, or pharmaceutically acceptable prodrug thereof.

In another aspect, provided herein are compounds of Formula (VII) having the structure:

Formula (VII)

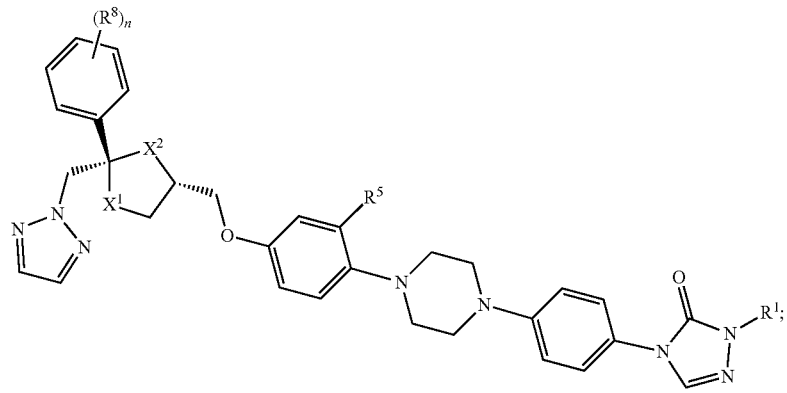

wherein:

R¹ is

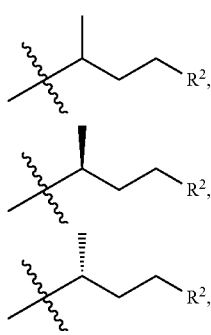

—CH(CH₂CH₃)₂, —CH(CH₃)₂, —CH₂CH(CH₃)₂, —CH(CH₂CH₃)CH(R³)CH₃, -alkylene(cycloalkyl), or R² is H, alkyl, or —NR¹³R¹⁴;
R³ is —OH, alkyl, or —NR¹³R¹⁴;
R⁵ is H, —CN, halogen, haloalkyl, alkyl, —NR¹³R¹⁴, -alkylene(NR¹³R¹⁴), and —SO₂R¹³;
each R⁸ is independently selected from halogen, —OH, —NO₂, —N₃, —CN, alkyl, alkoxy, haloalkoxy, haloalkyl, hydroxyalkyl, alkoxyalkyl, -alkylene (NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;

n is selected from 0, 1, 2, 3, and 4;

$X^1$ and $X^2$ are each independently selected from —O—, —S—, —S(O)$_2$—, —N(R$^{15}$)—, and —(CH$_2$)—, wherein at least one $X^1$ or $X^2$ is not —O—; and $R^{15}$ is H or alkyl;

or a pharmaceutically acceptable salt, pharmaceutically acceptable solvate, or pharmaceutically acceptable prodrug thereof.

In some embodiments is a compound of Formula (VII), wherein $R^1$ is

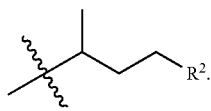

In some embodiments is a compound of Formula (VII), wherein $R^1$ is

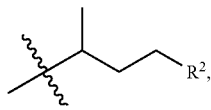

and $R^2$ is H. In some embodiments is a compound of Formula (VII), wherein $R^1$ is

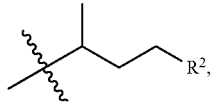

and $R^2$ is alkyl. In some embodiments is a compound of Formula (VII), wherein $R^1$ is

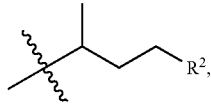

and $R^2$ is methyl. In some embodiments is a compound of Formula (VII), wherein $R^1$ is

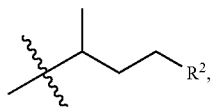

and $R^2$ is ethyl. In some embodiments is a compound of Formula (VII), wherein $R^1$ is

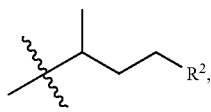

and $R^2$ is isopropyl. In some embodiments is a compound of Formula (VII), wherein $R^1$ is

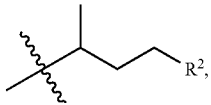

and $R^2$ is —NR$^{13}$R$^{14}$. In some embodiments is a compound of Formula (VII), wherein $R^1$ is

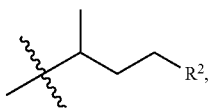

and $R^2$ is —NH$_2$. In some embodiments is a compound of Formula (VII), wherein $R^1$ is

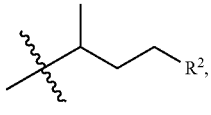

and $R^2$ is —NHCH$_3$. In some embodiments is a compound of Formula (VII), wherein $R^1$ is

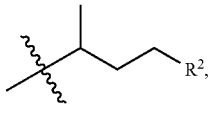

and $R^2$ is —N(CH$_3$)$_2$.

In some embodiments is a compound of Formula (VII), wherein $R^1$ is

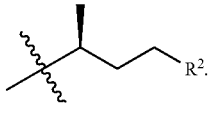

In some embodiments is a compound of Formula (VII), wherein $R^1$ is

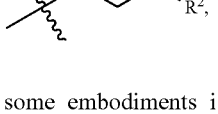

and $R^2$ is H. In some embodiments is a compound of Formula (VII), wherein $R^1$ is

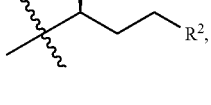

and $R^2$ is alkyl. In some embodiments is a compound of Formula (VII), wherein $R^1$ is

173

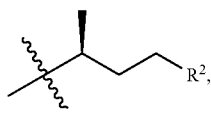

and $R^2$ is methyl. In some embodiments is a compound of Formula (VII), wherein $R^1$ is

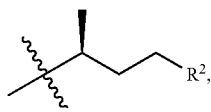

$R^2$ is ethyl. In some embodiments is a compound of Formula (VII), wherein $R^1$ is

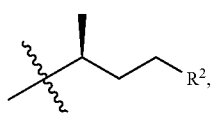

and $R^2$ is isopropyl. In some embodiments is a compound of Formula (VII), wherein $R^1$ is

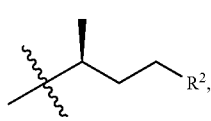

and $R^2$ is —$NR^{13}R^{14}$. In some embodiments is a compound of Formula (VII), wherein $R^1$ is

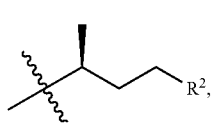

and $R^2$ is —$NH_2$. In some embodiments is a compound of Formula (VII), wherein $R^1$ is

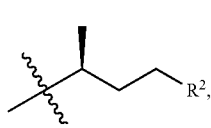

and $R^2$ is —$NHCH_3$. In some embodiments is a compound of Formula (VII), wherein $R^1$ is

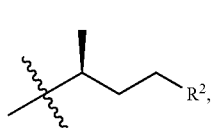

and $R^2$ is —$N(CH_3)_2$.

In some embodiments is a compound of Formula (VII), wherein $R^1$ is

174

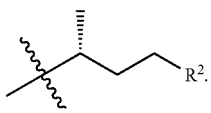

In some embodiments is a compound of Formula (VII), wherein $R^1$ is

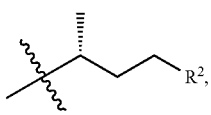

and $R^2$ is H. In some embodiments is a compound of Formula (VII), wherein $R^1$ is

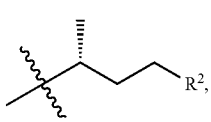

and $R^2$ is alkyl, In some embodiments is a compound of Formula (VII), where $R^1$ is

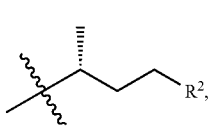

and $R^2$ is methyl. In some embodiments is a compound of Formula (VII), wherein $R^1$ is

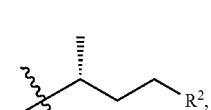

and $R^2$ is ethyl. In some embodiments is a compound of Formula (VII), wherein $R^1$ is

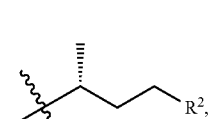

and $R^2$ is isopropyl. In some embodiments is a compound of Formula (VII), wherein $R^1$ is

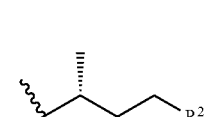

and $R^2$ is —$NR^{13}R^{14}$. In some embodiments is a compound of Formula (VII), wherein $R^1$ is

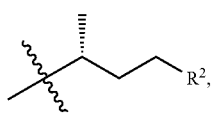

and $R^2$ is —$NH_2$. In some embodiments is a compound of Formula (VII), wherein $R^1$ is

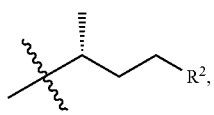

and $R^2$ is —$NHCH_3$. In some embodiments is a compound of Formula (VII), wherein $R^1$ is

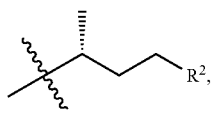

and $R^2$ is —$N(CH_3)_2$.

In some embodiments is a compound of Formula (VII), wherein $R^1$ is —$CH(CH_2CH_3)_2$. In some embodiments is a compound of Formula (VII), wherein $R^1$ is —$CH(CH_3)_2$. In some embodiments is a compound of Formula (VII), wherein $R^1$ is —$CH(CH_2CH_3)CH(R^3)CH_3$. In some embodiments is a compound of Formula (VII), wherein $R^1$ is —$CH(CH_2CH_3)CH(R^3)CH_3$, and $R^3$ is —OH. In some embodiments is a compound of Formula (VII), wherein $R^1$ is —$CH(CH_2CH_3)CH(R^3)CH_3$, and $R^3$ is alkyl. In some embodiments is a compound of Formula (VII), wherein $R^1$ is —$CH(CH_2CH_3)CH(R^3)CH_3$, and $R^3$ is methyl. In some embodiments is a compound of Formula (VII), wherein $R^1$ is —$CH(CH_2CH_3)CH(R^3)CH_3$, and $R^3$ is ethyl. In some embodiments is a compound of Formula (VII), wherein $R^1$ is —$CH(CH_2CH_3)CH(R^3)CH_3$, and $R^3$ is —$NR^{13}R^{14}$. In some embodiments is a compound of Formula (VII), wherein $R^1$ is —$CH(CH_2CH_3)CH(R^3)CH_3$, and $R^3$ is —$NH_2$. In some embodiments is a compound of Formula (VII), wherein $R^1$ is —$CH(CH_2CH_3)CH(R^3)CH_3$, and $R^3$ is —$NHCH_3$. In some embodiments is a compound of Formula (VII), wherein $R^1$ is —$CH(CH_2CH_3)CH(R^3)CH_3$, and $R^3$ is —$N(CH_3)_2$. In some embodiments is a compound of Formula (VII), wherein $R^1$ is -alkylene(cycloalkyl). In some embodiments is a compound of Formula (VII), wherein $R^1$ is —$CH_2CH_2$(cycloalkyl). In some embodiments is a compound of Formula (VII), wherein $R^1$ is —$CH_2$(cycloalkyl). In some embodiments is a compound of Formula (VII), wherein $R^1$ is —$CH_2$(cyclobutyl). In some embodiments is a compound of Formula (VII), wherein $R^1$ is —$CH_2$(cyclopentyl). In some embodiments is a compound of Formula (VII), wherein $R^1$ is —$CH_2$(cyclohexyl). In some embodiments is a compound of Formula (VII), wherein $R^1$ is

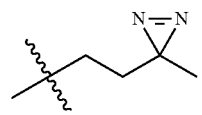

In some embodiments described above or below is a compound of Formula (VII), wherein $R^5$ is H. In some embodiments described above or below is a compound of Formula (VII), wherein $R^5$ is —CN. In some embodiments described above or below is a compound of Formula (VII), wherein $R^5$ is halogen. In some embodiments described above or below is a compound of Formula (VII), wherein $R^5$ is F. In some embodiments described above or below is a compound of Formula (VII), wherein $R^5$ is Cl. In some embodiments described above or below is a compound of Formula (VII), wherein $R^5$ is alkyl. In some embodiments described above or below is a compound of Formula (VII), wherein $R^5$ is methyl. In some embodiments described above or below is a compound of Formula (VII), wherein $R^5$ is ethyl. In some embodiments described above or below is a compound of Formula (VII), wherein $R^5$ is —$NR^{13}R^{14}$. In some embodiments described above or below is a compound of Formula (VII), wherein $R^5$ is —$NH_2$. In some embodiments described above or below is a compound of Formula (VII), wherein $R^5$ is -alkylene($NR^{13}R^{14}$). In some embodiments described above or below is a compound of Formula (VII), wherein $R^5$ is -alkylene($NH_2$). In some embodiments described above or below is a compound of Formula (VII), wherein $R^5$ is —$CH_2NH_2$.

In some embodiments described above or below is a compound of Formula (VII), wherein n is 0.

In some embodiments described above or below is a compound of Formula (VII), wherein n is 1. In some embodiments described above or below is a compound of Formula (VII), wherein n is 1 and $R^8$ is selected from halogen, —OH, —$NO_2$, —$N_3$, —CN, alkyl, alkoxy, haloalkoxy, haloalkyl, hydroxyalkyl, alkoxyalkyl, -alkylene($NR^{13}R^{14}$), -alkylene(cycloalkyl), -alkylene(heterocyclyl), cycloalkyl, heterocyclyl, aryl, heteroaryl, —$SR^{13}$, —$SOR^{13}$, —$SO_2R^{13}$, —$SO_2NR^{13}R^{14}$, —$NR^{13}R^{14}$, —$NR^{13}SO_2R^{14}$, —$NR^{13}C(O)R^{14}$, —$NR^{13}C(O)OR^{14}$, —$NR^{13}C(O)NR^{13}R^{14}$, —$C(O)R^{14}$, —$C(O)OR^{14}$, or —$C(O)NR^{13}R^{14}$. In some embodiments described above or below is a compound of Formula (VII), wherein n is 1 and $R^8$ is selected from halogen, —CN, alkyl, alkoxy, haloalkoxy, or haloalkyl. In some embodiments described above or below is a compound of Formula (VII), wherein n is 1 and $R^8$ is halogen. In some embodiments described above or below is a compound of Formula (VII), wherein n is 1 and $R^8$ is F. In some embodiments described above or below is a compound of Formula (VII), wherein n is 1 and $R^8$ is Cl. In some embodiments described above or below is a compound of Formula (VII), wherein n is 1 and $R^8$ is —CN. In some embodiments described above or below is a compound of Formula (VII), wherein n is 1 and $R^8$ is alkyl. In some embodiments described above or below is a compound of Formula (VII), wherein n is 1 and $R^8$ is methyl. In some embodiments described above or below is a compound of Formula (VII), wherein n is 1 and $R^8$ is ethyl. In some embodiments described above or below is a compound of Formula (VII), wherein n is 1 and $R^8$ is alkoxy. In some embodiments described above or below is a compound of Formula (VII), wherein n is 1 and $R^8$ is methoxy. In some embodiments described above or below is a compound of Formula (VII), wherein n is 1 and $R^8$ is ethoxy. In some embodiments described above or below is a compound of Formula (VII), wherein n is 1 and $R^8$ is haloalkoxy. In some embodiments described above or below is a compound of Formula (VII), wherein n is 1 and $R^8$ is —$OCF_3$. In some embodiments described above or below is a compound of Formula (VII), wherein n is 1 and $R^8$ is haloalkyl. In some embodiments described above or below is a compound of Formula (VII), wherein n is 1 and $R^8$ is —$CF_3$.

In some embodiments described above or below is a compound of Formula (VII), wherein n is 2. In some embodiments described above or below is a compound of Formula (VII), wherein n is 2 and $R^8$ is independently selected from halogen, —OH, —$NO_2$, —$N_3$, —CN, alkyl, alkoxy, haloalkoxy, haloalkyl, hydroxyalkyl, alkoxyalkyl, -alkylene($NR^{13}R^{14}$), -alkylene(cycloalkyl), -alkylene(heterocyclyl), cycloalkyl, heterocyclyl, aryl, heteroaryl, —$SR^{13}$, —$SOR^{13}$, —$SO_2R^{13}$, —$SO_2NR^{13}R^{14}$, —$NR^{13}R^{14}$, —$NR^{13}SO_2R^{14}$, —$NR^{13}C(O)R^{14}$, —$NR^{13}C(O)OR^{14}$, —$NR^{13}C(O)NR^{13}R^{14}$, —$C(O)R^{14}$, —$C(O)OR^{14}$, and —C(O)NR¹³R¹⁴. In some embodiments described above or below is a compound of Formula (VII), wherein n is 2 and R⁸ is independently selected from halogen, —CN, alkyl, alkoxy, haloalkoxy, and haloalkyl. In some embodiments described above or below is a compound of Formula (VII), wherein n is 2 and R⁸ is halogen. In some embodiments described above or below is a compound of Formula (VII), wherein n is 2 and each R⁸ is F. In some embodiments described above or below is a compound of Formula (VII), wherein n is 2 and each R⁸ is Cl. In some embodiments described above or below is a compound of Formula (VII), wherein n is 2 and R⁸ is independently selected from halogen and —CN. In some embodiments described above or below is a compound of Formula (VII), wherein n is 2 and R⁸ is independently selected from halogen and alkyl. In some embodiments described above or below is a compound of Formula (VII), wherein n is 2 and R⁸ is independently selected from —CN and alkyl. In some embodiments described above or below is a compound of Formula (VII), wherein n is 2 and two adjacent R⁸ form a heterocyclyl ring.

In another embodiment is a compound of Formula (VII) having the structure:

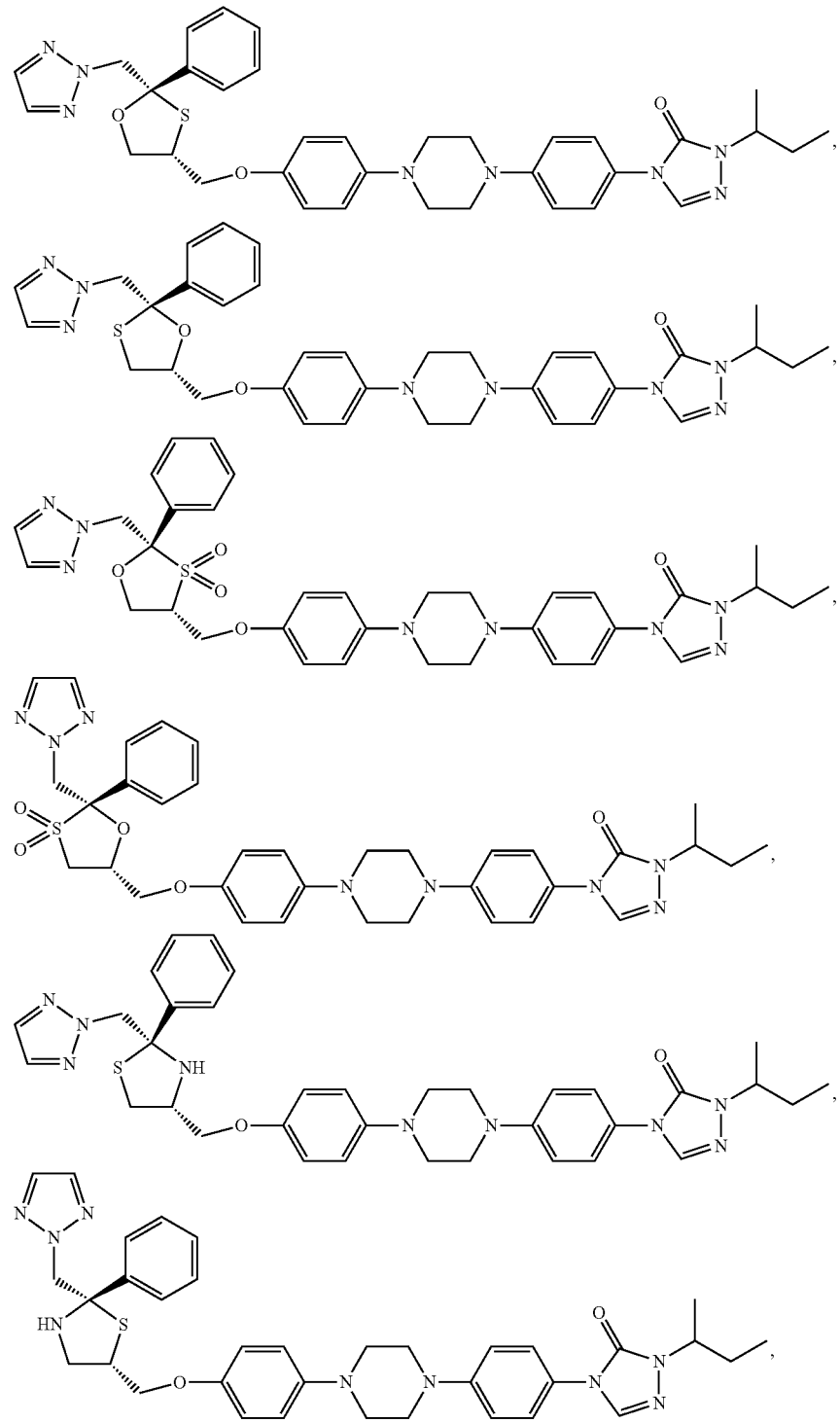

-continued
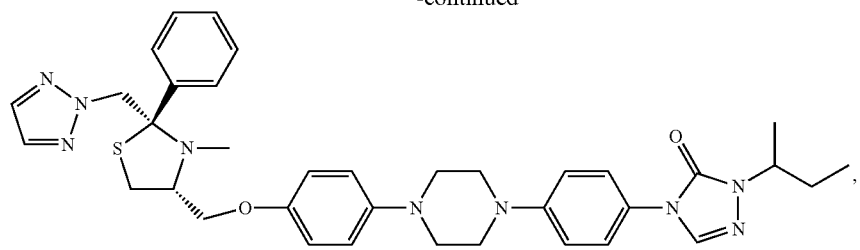
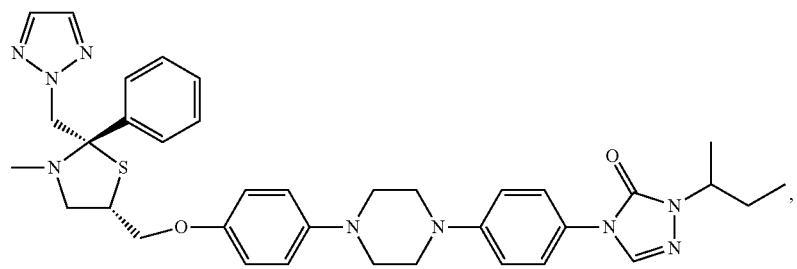
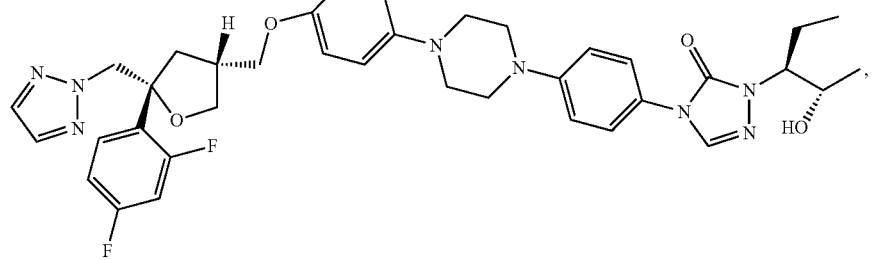
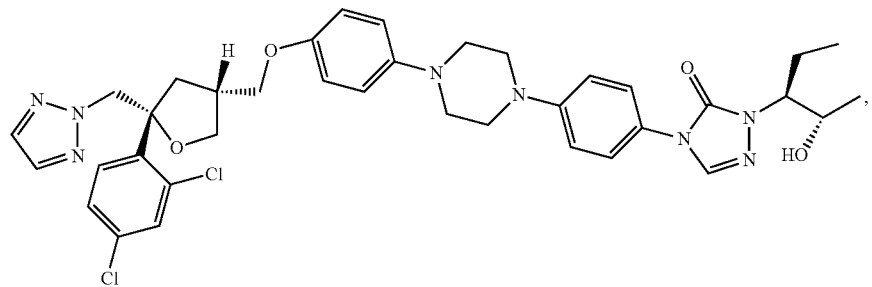
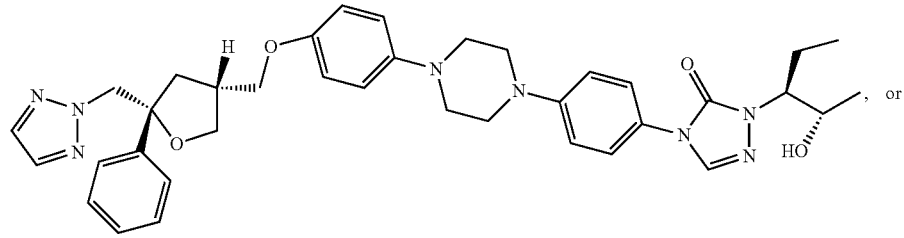
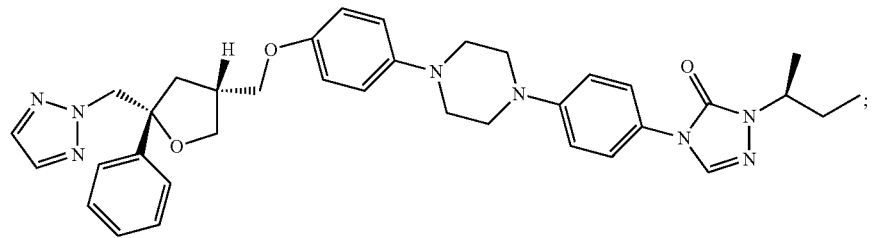
or a pharmaceutically acceptable salt, pharmaceutically acceptable solvate, or pharmaceutically acceptable prodrug thereof.

In another aspect, provided herein are compounds of Formula (VIIa) having the structure:

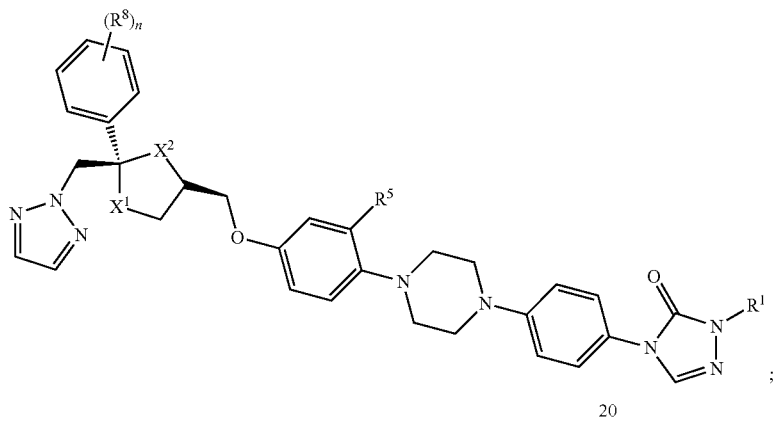

Formula (VIIa)

wherein:
R¹ is

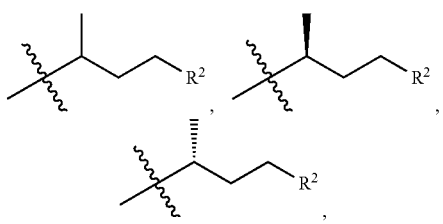

—CH(CH₂CH₃)₂, —CH(CH₃)₂, —CH₂CH(CH₃)₂, —CH(CH₂CH₃)CH(R³)CH₃, -alkylene(cycloalkyl), or

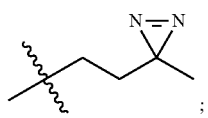

R² is H, alkyl, or —NR¹³R¹⁴;
R³ is —OH, alkyl, or —NR¹³R¹⁴;
R⁵ is H, —CN, halogen, haloalkyl, alkyl, —NR¹³R¹⁴, -alkylene(NR¹³R¹⁴), and —SO₂R¹³;
each R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴; or two adjacent R⁸ form a heterocyclyl ring;
each R¹³ and each R¹⁴ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R¹³ and R¹⁴ taken together form a heterocycle with the atoms to which they are attached;
n is selected from 0, 1, 2, 3, and 4;
X¹ and X² are each independently selected from —O—, —S—, —S(O)₂—, —N(R¹⁵)—, and —(CH₂)—; wherein at least one X¹ or X² is not —O—; and
R¹⁵ is H or alkyl;

or a pharmaceutically acceptable salt, pharmaceutically acceptable solvate, or pharmaceutically acceptable prodrug thereof.

In some embodiments is a compound of Formula (VIIA), wherein R¹ is

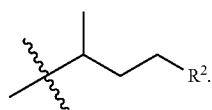

In some embodiments is a compound of Formula (VIIA), wherein R¹ is

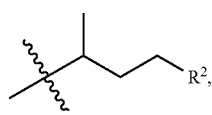

and R² is H. In some embodiments is a compound of Formula (VIIA), wherein R¹ is

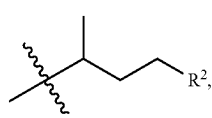

and R² is alkyl. In some embodiments is a compound of Formula (VIIA), wherein R¹ is and R² is methyl. In some embodiments is a compound of Formula (VIIA), wherein R¹ is

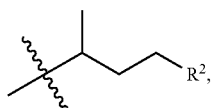

and R² is ethyl. In some embodiments is a compound of Formula (VIIA), wherein R¹ is

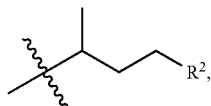

and R² is isopropyl. In some embodiments is a compound of Formula (VIIA), wherein R¹ is

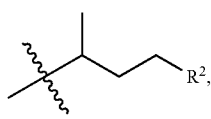

and R² is —NR¹³R¹⁴. In some embodiments is a compound of Formula (VIIA), wherein R¹ is

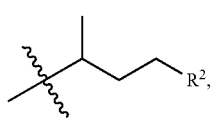

and R² is —NH₂. In some embodiments is a compound of Formula (VIIA), wherein R¹ is

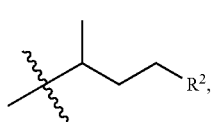

and R² is —NHCH₃. In some embodiments is a compound of Formula (VIIA), wherein R¹ is

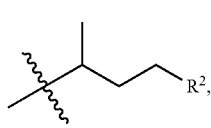

and R² is —N(CH₃)₂.

In some embodiments is a compound of Formula (VIIA), wherein R¹ is

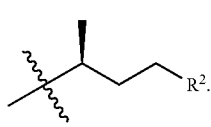

In some embodiments is a compound of Formula (VIIA), wherein R¹ is

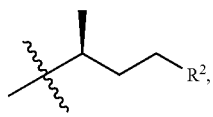

and R² is H. In some embodiments is a compound of Formula (VIIA), wherein R¹ is

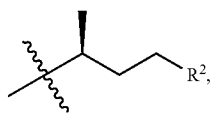

and R² is alkyl. In some embodiments is a compound of Formula (VIIA), wherein R¹ is

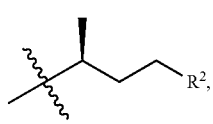

and R² is methyl. In some embodiments is a compound of Formula (VIIA), wherein R¹ is

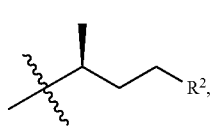

and R² is ethyl. In some embodiments is a compound of Formula (VIIA), wherein R¹ is

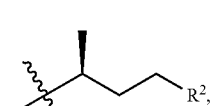

and R² is isopropyl. In some embodiments is a compound of Formula (VIIA), wherein R¹ is

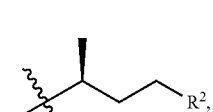

and R² is —NR¹³R¹⁴. In some embodiments is a compound of Formula (VIIA), wherein R¹ is

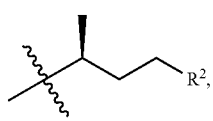

and R² is —NH₂. In some embodiments is a compound of Formula (VIIA), wherein R¹ is

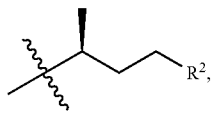

and $R^2$ is —NHCH$_3$. In some embodiments is a compound of Formula (VIIA), wherein $R^1$ is

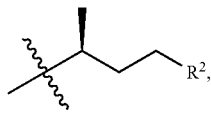

and $R^2$ is —N(CH$_3$)$_2$.

In some embodiments is a compound of Formula (VIIA), wherein $R^1$ is

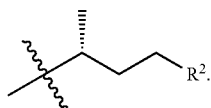

In some embodiments is a compound of Formula (VIIA), wherein $R^1$ is

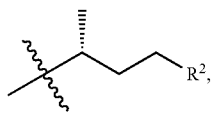

and $R^2$ is H. In some embodiments is a compound of Formula (VIIA), wherein $R^1$ is

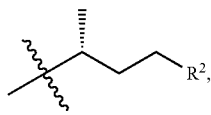

and $R^2$ is alkyl. In some embodiments is a compound of Formula (VIIA), wherein $R^1$ is

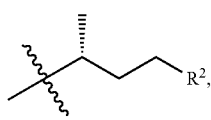

and $R^2$ is methyl. In some embodiments is a compound of Formula (VIIA), wherein $R^1$ is

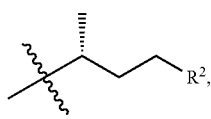

and $R^2$ is ethyl. In some embodiments is a compound of Formula (VIIA), wherein $R^1$ is

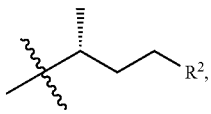

and $R^2$ is isopropyl. In some embodiments is a compound of Formula (VIIA), wherein $R^1$ is

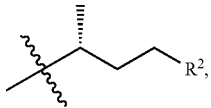

and $R^2$ is —NR$^{13}$R$^{14}$. In some embodiments is a compound Formula (VIIA), wherein $R^1$ is

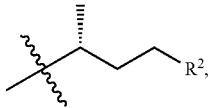

and $R^2$ is —NH$_2$. In some embodiments is a compound of Formula (VIIA), wherein $R^1$ is

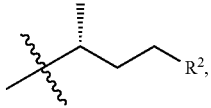

and $R^2$ is —NHCH$_3$. In some embodiments is a compound of Formula (VIIA), wherein $R^1$ is

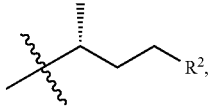

and $R^2$ is —N(CH$_3$)$_2$.

In some embodiments is a compound of Formula (VIIA), wherein $R^1$ is —CH(CH$_2$CH$_3$)$_2$. In some embodiments is a compound of Formula (VIIA), wherein $R^1$ is —CH(CH$_3$)$_2$. In some embodiments is a compound of Formula (VIIA), wherein $R^1$ is —CH(CH$_2$CH$_3$)CH(R$^3$)CH$_3$. In some embodiments is a compound of Formula (VIIA), wherein $R^1$ is —CH(CH$_2$CH$_3$)CH(R$^3$)CH$_3$, and $R^3$ is —OH. In some embodiments is a compound of Formula (VIIA), wherein $R^1$ is —CH(CH$_2$CH$_3$)CH(R$^3$)CH$_3$, and $R^3$ is alkyl. In some embodiments is a compound of Formula (VIIA), wherein $R^1$ is —CH(CH$_2$CH$_3$)CH(R$^3$)CH$_3$, and $R^3$ is methyl. In some embodiments is a compound of Formula (VIIA), wherein $R^1$ is —CH(CH$_2$CH$_3$)CH(R$^3$)CH$_3$, and $R^3$ is ethyl. In some embodiments is a compound of Formula (VIIA), wherein $R^1$ is —CH(CH$_2$CH$_3$)CH(R$^3$)CH$_3$, and $R^3$ is —NR$^{13}$R$^{14}$. In some embodiments is a compound of Formula (VIIA), wherein $R^1$ is —CH(CH$_2$CH$_3$)CH(R$^3$)CH$_3$, and $R^3$ is —NH$_2$. In some embodiments is a compound of Formula (VIIA), wherein $R^1$ is —CH(CH$_2$CH$_3$)CH(R$^3$)CH$_3$, and $R^3$ is —NHCH$_3$. In some embodiments is a compound of Formula (VIIA), wherein $R^1$ is —CH(CH$_2$CH$_3$)CH(R$^3$)CH$_3$, and $R^3$ is —N(CH$_3$)$_2$. In some embodiments is a compound of Formula (VIIA), wherein R¹ is -alkylene (cycloalkyl). In some embodiments is a compound of Formula (VIIA), wherein R¹ is —CH₂CH₂(cycloalkyl). In some embodiments is a compound of Formula (VIIA), wherein R¹ is —CH₂(cycloalkyl). In some embodiments is a compound of Formula (VIIA), wherein R¹ is —CH₂(cyclobutyl). In some embodiments is a compound of Formula (VIIA), wherein R¹ is —CH₂(cyclopentyl). In some embodiments is a compound of Formula (VIIA), wherein R¹ is —CH₂(cyclohexyl). In some embodiments is a compound of Formula (VIIA), wherein R¹ is

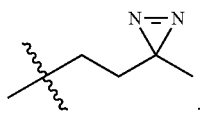 [SMILES: *CCC1(C)N=N1]

In some embodiments described above or below is a compound of Formula (VIIA), wherein R⁵ is H. In some embodiments described above or below is a compound of Formula (VIIA), wherein R⁵ is —CN. In some embodiments described above or below is a compound of Formula (VIIA), wherein R⁵ is halogen. In some embodiments described above or below is a compound of Formula (VIIA), wherein R⁵ is F. In some embodiments described above or below is a compound of Formula (VIIA), wherein R⁵ is Cl. In some embodiments described above or below is a compound of Formula (VIIA), wherein R⁵ is alkyl. In some embodiments described above or below is a compound of Formula (VIIA), wherein R⁵ is methyl. In some embodiments described above or below is a compound of Formula (VIIA), wherein R⁵ is ethyl. In some embodiments described above or below is a compound of Formula (VIIA), wherein R⁵ is —NR¹³R¹⁴. In some embodiments described above or below is a compound of Formula (VIIA), wherein R⁵ is —NH₂. In some embodiments described above or below is a compound of Formula (VIIA), wherein R⁵ is -alkylene (NR¹³R¹⁴). In some embodiments described above or below is a compound of Formula (VIIA), wherein R⁵ is -alkylene (NH₂). In some embodiments described above or below is a compound of Formula (VIIA), wherein R⁵ is —CH₂NH₂.

In some embodiments described above or below is a compound of Formula (VIIA), wherein n is 0.

In some embodiments described above or below is a compound of Formula (VIIA), wherein n is 1. In some embodiments described above or below is a compound of Formula (VIIA), wherein n is 1 and R⁸ is selected from halogen, —OH, —NO₂, —N₃, —CN, alkyl, alkoxy, haloalkoxy, haloalkyl, hydroxyalkyl, alkoxyalkyl, -alkylene (NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, or —C(O)NR¹³R¹⁴. In some embodiments described above or below is a compound of Formula (VIIA), wherein n is 1 and R⁸ is selected from halogen, —CN, alkyl, alkoxy, haloalkoxy, or haloalkyl. In some embodiments described above or below is a compound of Formula (VIIA), wherein n is 1 and R⁸ is halogen. In some embodiments described above or below is a compound of Formula (VIIA), wherein n is 1 and R⁸ is F. In some embodiments described above or below is a compound of Formula (VIIA), wherein n is 1 and R⁸ is Cl. In some embodiments described above or below is a compound of Formula (VIIA), wherein n is 1 and R⁸ is —CN. In some embodiments described above or below is a compound of Formula (VIIA), wherein n is 1 and R⁸ is alkyl. In some embodiments described above or below is a compound of Formula (VIIA), wherein n is 1 and R⁸ is methyl. In some embodiments described above or below is a compound of Formula (VIIA), wherein n is 1 and R⁸ is ethyl. In some embodiments described above or below is a compound of Formula (VIIA), wherein n is 1 and R⁸ is alkoxy. In some embodiments described above or below is a compound of Formula (VIIA), wherein n is 1 and R⁸ is methoxy. In some embodiments described above or below is a compound of Formula (VIIA), wherein n is 1 and R⁸ is ethoxy. In some embodiments described above or below is a compound of Formula (VIIA), wherein n is 1 and R⁸ is haloalkoxy. In some embodiments described above or below is a compound of Formula (VIIA), wherein n is 1 and R⁸ is —OCF₃. In some embodiments described above or below is a compound of Formula (VIIA), wherein n is 1 and R⁸ is haloalkyl. In some embodiments described above or below is a compound of Formula (VIIA), wherein n is 1 and R⁸ is —CF₃.

In some embodiments described above or below is a compound of Formula (VIIA), wherein n is 2. In some embodiments described above or below is a compound of Formula (VIIA), wherein n is 2 and R⁸ is independently selected from halogen, —OH, —NO₂, —N₃, —CN, alkyl, alkoxy, haloalkoxy, haloalkyl, hydroxyalkyl, alkoxyalkyl, -alkylene (NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O) NR¹³R¹⁴, —C(O)R¹⁴, —C(O)OR¹⁴, and —C(O)NR¹³R¹⁴. In some embodiments described above or below is a compound of Formula (VIIA), wherein n is 2 and R⁸ is independently selected from halogen, —CN, alkyl, alkoxy, haloalkoxy, and haloalkyl. In some embodiments described above or below is a compound of Formula (VIIA), wherein n is 2 and R⁸ is halogen. In some embodiments described above or below is a compound of Formula (VIIA), wherein n is 2 and each R⁸ is F. In some embodiments described above or below is a compound of Formula (VIIA), wherein n is 2 and each R⁸ is Cl. In some embodiments described above or below is a compound of Formula (VIIA), wherein n is 2 and R⁸ is independently selected from halogen and —CN. In some embodiments described above or below is a compound of Formula (VIIA), wherein n is 2 and R⁸ is independently selected from halogen and alkyl. In some embodiments described above or below is a compound of Formula (VIIa), wherein n is 2 and R⁸ is independently selected from —CN and alkyl. In some embodiments described above or below is a compound of Formula (VIIa), wherein n is 2 and two adjacent R⁸ form a heterocyclyl ring.

In another embodiment is a compound of Formula (VIIa) having the structure:

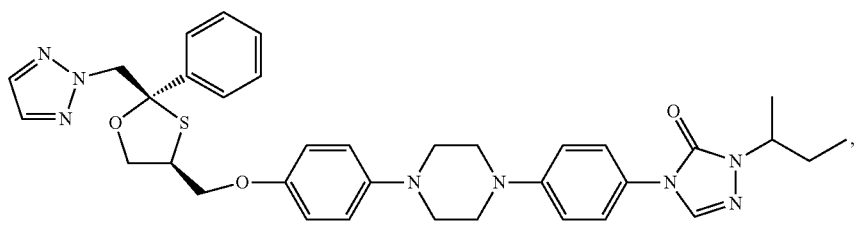

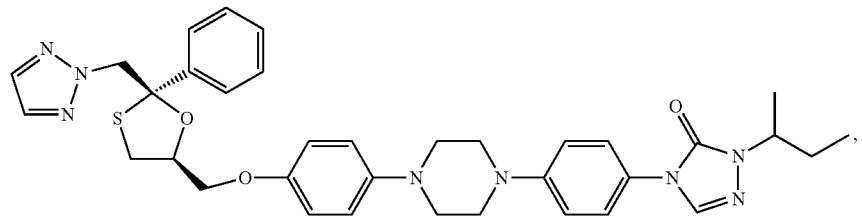
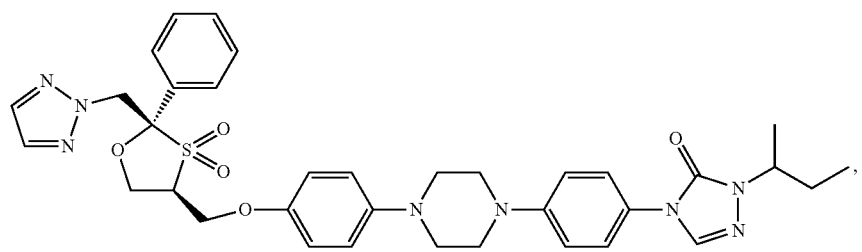
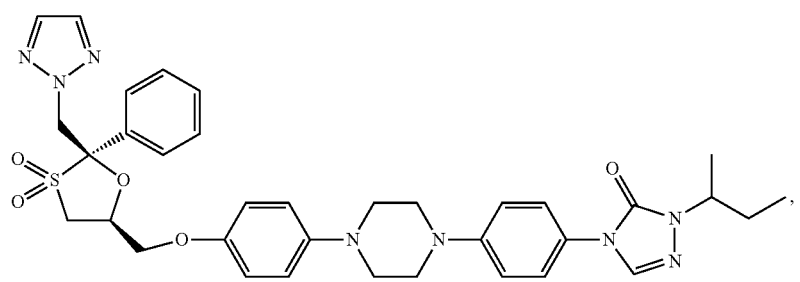
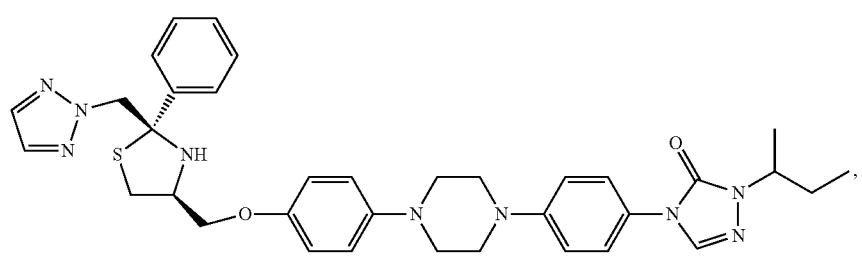
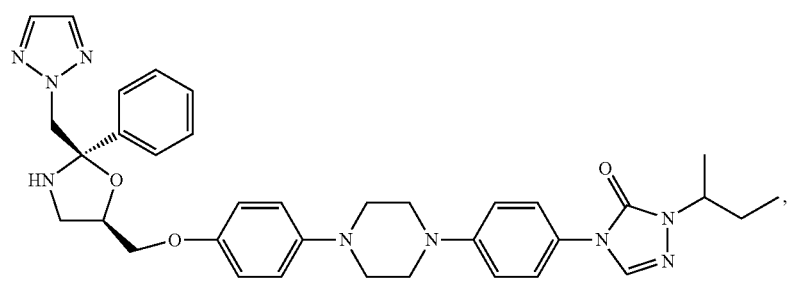
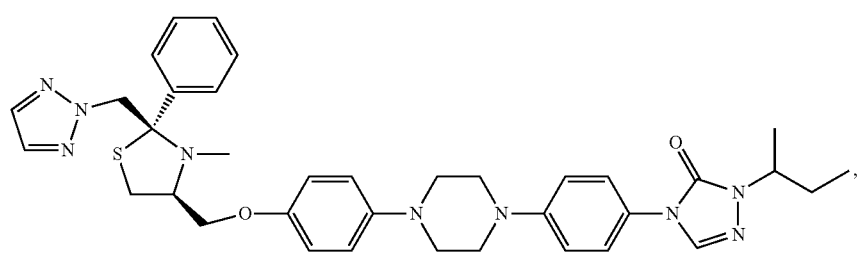

-continued
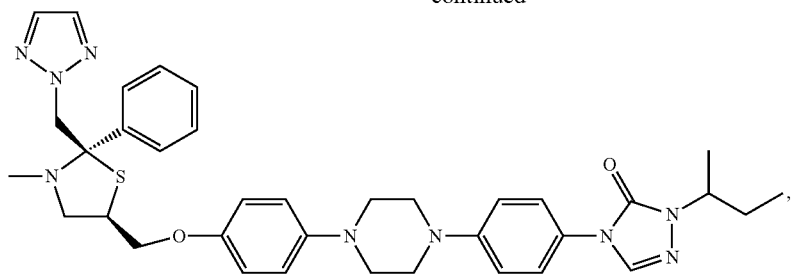
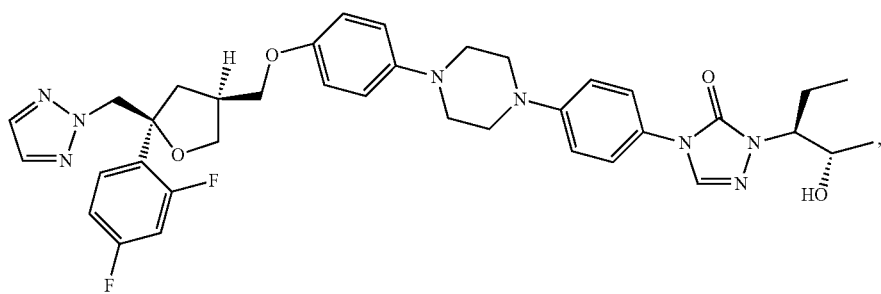
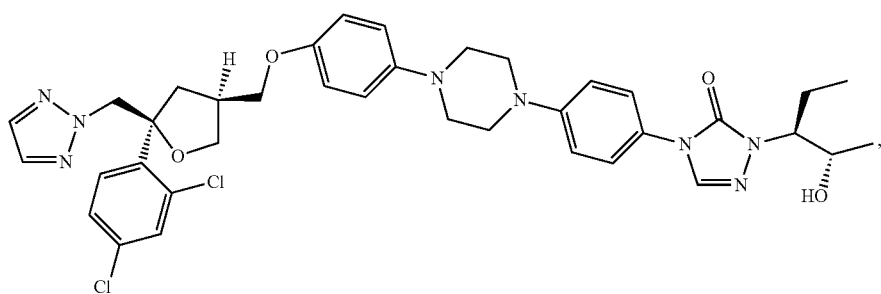
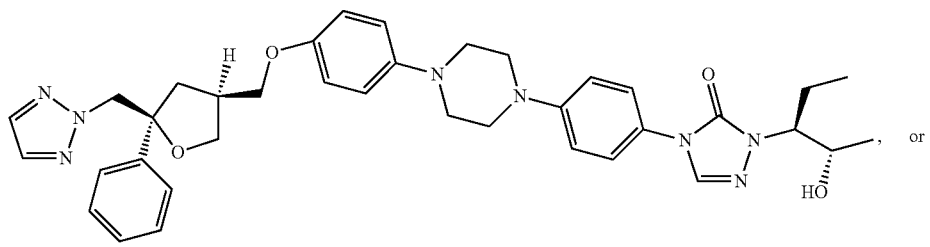, or
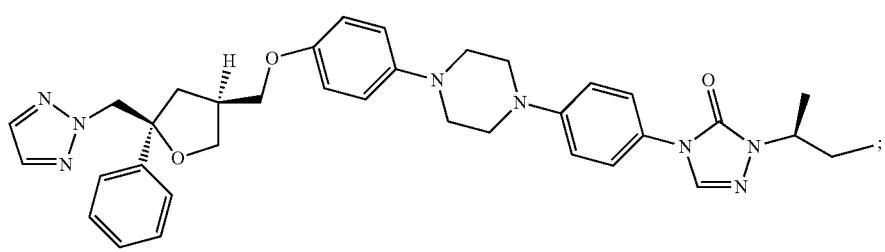;

or a pharmaceutically acceptable salt, pharmaceutically acceptable solvate, or pharmaceutically acceptable prodrug thereof.

In another aspect, provided herein are compounds of Formula (VIII) having the structure:

Formula (VIII)

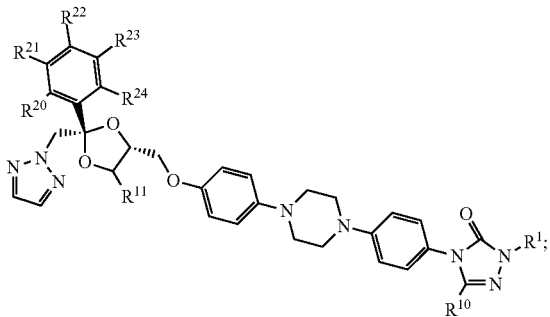

wherein:
$R^1$ is

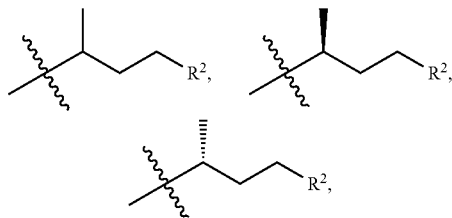

—CH(CH$_3$)CH(R$^3$)CH$_3$, —CH(CH$_3$)C(O)CH$_3$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

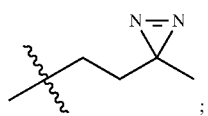 [SMILES: *CCC1(C)N=N1]

$R^2$ is H, alkyl, or —NR$^{13}$R$^{14}$;
$R^3$ is —OH, alkyl, or —NR$^{13}$R$^{14}$;
$R^{10}$ and $R^{11}$ are independently selected from H or alkyl, wherein at least one of $R^{10}$ and $R^{11}$ is alkyl;
each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;
$R^{20}$ is selected from H, F, Cl, Br, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$;
$R^{21}$, $R^{22}$, and $R^{23}$ are independently selected from H, halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; and
$R^{24}$ is H;

or a pharmaceutically acceptable salt, pharmaceutically acceptable solvate, or pharmaceutically acceptable prodrug thereof.

In some embodiments is a compound of Formula (VIII), wherein $R^{10}$ is H and $R^{11}$ is alkyl. In some embodiments is a compound of Formula (VIII), wherein $R^{10}$ is H and $R^{11}$ is methyl. In some embodiments is a compound of Formula (VIII), wherein $R^{10}$ is H and $R^{11}$ is ethyl. In some embodiments is a compound of Formula (VIII), wherein $R^{10}$ is H and $R^{11}$ is isopropyl. In some embodiments is a compound of Formula (VIII), wherein $R^{10}$ is alkyl and $R^{11}$ is H. In some embodiments is a compound of Formula (VIII), wherein $R^{10}$ is methyl and $R^{11}$ is H. In some embodiments is a compound of Formula (VIII), wherein $R^{10}$ is ethyl and $R^{11}$ is H. In some embodiments is a compound of Formula (VIII), wherein $R^{10}$ is isopropyl and $R^{11}$ is H. In some embodiments is a compound of Formula (VIII), wherein $R^{10}$ is alkyl and $R^{11}$ is alkyl. In some embodiments is a compound of Formula (VIII), wherein $R^{10}$ is methyl and $R^{11}$ is methyl.

In some embodiments is a compound of Formula (VIII), wherein $R^{21}$, $R^{22}$, and $R^{23}$ are independently selected from H, halogen, —CN, alkyl, alkoxy, haloalkoxy, haloalkyl, —SO$_2$R$^{13}$, —SO$_2$NR$^{13}$R$^{14}$, and —C(O)NR$^{13}$R$^{14}$. In some embodiments is a compound of Formula (VIII), wherein $R^{21}$, $R^{22}$, and $R^{23}$ are independently selected from H, halogen, —CN, alkyl, alkoxy, and haloalkyl. In some embodiments is a compound of Formula (VIII), wherein $R^{21}$, $R^{22}$, and $R^{23}$ are independently selected from H and halogen. In some embodiments is a compound of Formula (VIII), wherein $R^{21}$, $R^{22}$, and $R^{23}$ are independently selected from H and —CN. In some embodiments is a compound of Formula (VIII), wherein $R^{21}$, $R^{22}$, and $R^{23}$ are independently selected from H and alkyl. In some embodiments is a compound of Formula (VIII), wherein $R^{21}$, $R^{22}$, and $R^{23}$ are independently selected from H and alkoxy. In some embodiments is a compound of Formula (VIII), wherein $R^{21}$, $R^{22}$, and $R^{23}$ are independently selected from H and haloalkoxy. In some embodiments is a compound of Formula (VIII), wherein $R^{21}$, $R^{22}$, and $R^{23}$ are independently selected from H and haloalkyl. In some embodiments is a compound of Formula (VIII), wherein $R^{21}$, $R^{22}$, and $R^{23}$ are independently selected from H and —SO$_2$R$^{13}$. In some embodiments is a compound of Formula (VIII), wherein $R^{21}$, $R^{22}$, and $R^{23}$ are independently selected from H and —SO$_2$NR$^{13}$R$^{14}$. In some embodiments is a compound of Formula (VIII), wherein $R^{21}$, $R^{22}$, and $R^{23}$ are independently selected from H and —C(O)NR$^{13}$R$^{14}$. In some embodiments is a compound of Formula (VIII), wherein $R^{21}$, $R^{22}$, and $R^{23}$ are independently selected from —CN and alkyl. In some embodiments is a compound of Formula (VIII), wherein $R^{21}$, $R^{22}$, and $R^{23}$ are independently selected from H, Cl, —CN, —CH$_3$, —OCH$_3$, and —CF$_3$.

In some embodiments is a compound of Formula (VIII), wherein $R^{21}$, $R^{22}$, and $R^{23}$ are each H.

In some embodiments is a compound of Formula (VIII), wherein $R^{20}$ is selected from H, halogen, —CN, alkyl, alkoxy, and haloalkyl. In some embodiments is a compound of Formula (VIII), wherein $R^{20}$ is selected from H and —CN. In some embodiments is a compound of Formula (VIII), wherein R²⁰ is selected from H and alkyl. In some embodiments is a compound of Formula (VIII), wherein R²⁰ is selected from H and alkoxy. In some embodiments is a compound of Formula (VIII), wherein R²⁰ is selected from H and haloalkoxy. In some embodiments is a compound of Formula (VIII), wherein R²⁰ is selected from H and haloalkyl. In some embodiments is a compound of Formula (VIII), wherein R²⁰ is selected from H and —SO₂R¹³. In some embodiments is a compound of Formula (VIII), wherein R²⁰ is selected from H and —SO₂NR¹³R¹⁴. In some embodiments is a compound of Formula (VIII), wherein R²⁰ is selected R²⁰ is selected from —CN and alkyl. In some embodiments is a compound of Formula (VIII), wherein R²⁰ is selected from H, Cl, —CN, —CH₃, —OCH₃, and —CF₃. In some embodiments is a compound of Formula (VIII), wherein R²⁰ is selected from H, Cl, —CN, and —CH₃. In some embodiments is a compound of Formula (VIII), wherein R²⁰ is H. In some embodiments is a compound of Formula (VIII), wherein R²⁰ is Cl.

In some embodiments is a compound of Formula (VIII), wherein R¹ is

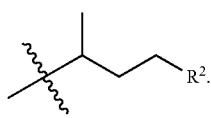

In some embodiments is a compound of Formula (VIII), wherein R¹ is

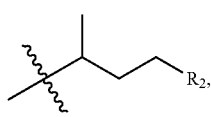

and R² is H. In some embodiments is a compound of Formula (VIII), wherein R¹ is

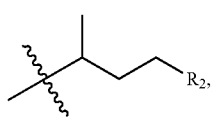

and R² is alkyl. In some embodiments is a compound of Formula (VIII), wherein R¹ is

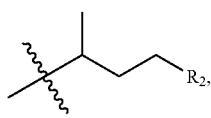

and R² is methyl. In some embodiments is a compound of Formula (VIII), wherein R¹ is

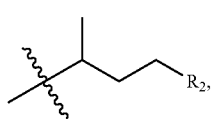

and R² is ethyl. In some embodiments is a compound of Formula (VIII), wherein R¹ is

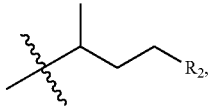

and R² is isopropyl. In some embodiments is a compound of Formula (VIII), wherein R¹ is

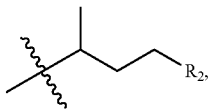

and R² is —NR¹³R¹⁴. In some embodiments is a compound of Formula (VIII), wherein R¹ is

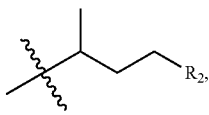

and R² is —NH₂. In some embodiments is a compound of Formula (VIII), wherein R¹ is

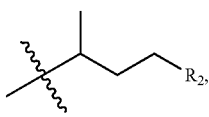

and R² is —NHCH₃. In some embodiments is a compound of Formula (VIII), wherein R¹ is

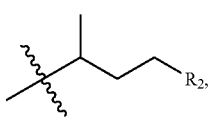

and R² is —N(CH₃)₂.

In some embodiments is a compound of Formula (VIII), wherein R¹ is

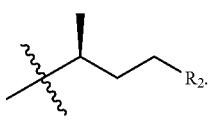

In some embodiments is a compound of Formula (VIII), wherein R¹ is

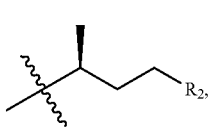

and R² is H. In some embodiments is a compound of Formula (VIII), wherein R¹ is

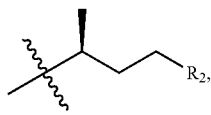

and R² is alkyl. In some embodiments is a compound of Formula (VIII), wherein R¹ is

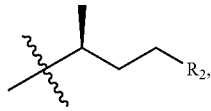

and R² is methyl. In some embodiments is a compound of Formula (VIII), wherein R¹ is

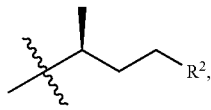

and R² is ethyl. In some embodiments is a compound of Formula (VIII), wherein R¹ is

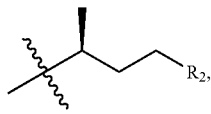

and R² is isopropyl. In some embodiments is a compound of Formula (VIII), wherein R¹ is

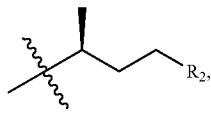

and R² is —NR¹³R¹⁴. In some embodiments is a compound of Formula (VIII), wherein R¹ is

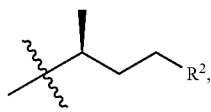

and R² is —NH₂. In some embodiments is a compound of Formula (VIII), wherein R¹ is

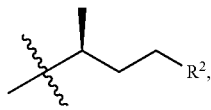

and R² is —NHCH₃. In some embodiments is a compound of Formula (VIII), wherein R¹ is

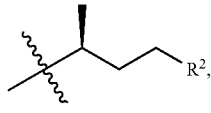

and R² is —N(CH₃)₂.

In some embodiments is a compound of Formula (VIII), wherein R¹ is

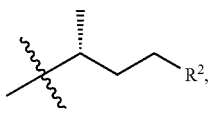

In some embodiments is a compound of Formula (VIII), wherein R¹ is

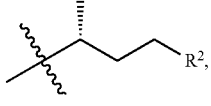

and R² is H. In some embodiments is a compound of Formula (VIII), wherein R¹ is

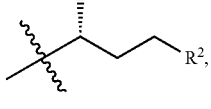

and R² is alkyl. In some embodiments is a compound of Formula (VIII), wherein R¹ is

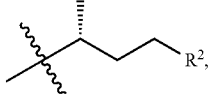

and R² is methyl. In some embodiments is a compound of Formula (VIII), wherein R¹ is

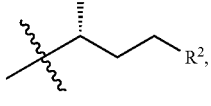

and R² is ethyl. In some embodiments is a compound of Formula (VIII), wherein R¹ is

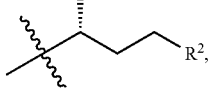

and R² is isopropyl. In some embodiments is a compound of Formula (VIII), wherein R¹ is

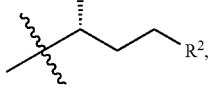

and R² is —NR¹³R¹⁴. In some embodiments is a compound of Formula (VIII), wherein R¹ is

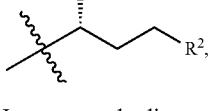

and R² is —NH₂. In some embodiments is a compound of Formula (VIII), wherein R¹ is

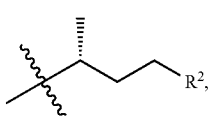

and R² is —NHCH₃. In some embodiments is a compound of Formula (VIII), wherein R¹ is

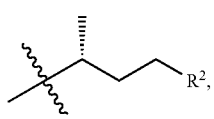

and $R^2$ is —N(CH$_3$)$_2$.

In some embodiments is a compound of Formula (VIII), wherein $R^1$ is —CH(CH$_2$CH$_3$)$_2$. In some embodiments is a compound of Formula (VIII), wherein $R^1$ is —CH(CH$_3$)$_2$. In some embodiments is a compound of Formula (VIII), wherein $R^1$ is —CH(CH$_2$CH$_3$)CH(R$^3$)CH$_3$. In some embodiments is a compound of Formula (VIII), wherein $R^1$ is —CH(CH$_2$CH$_3$)CH(R$^3$)CH$_3$, and $R^3$ is —OH. In some embodiments is a compound of Formula (VIII), wherein $R^1$ is —CH(CH$_2$CH$_3$)CH(R$^3$)CH$_3$, and $R^3$ is alkyl. In some embodiments is a compound of Formula (VIII), wherein $R^1$ is —CH(CH$_2$CH$_3$)CH(R$^3$)CH$_3$, and $R^3$ is methyl. In some embodiments is a compound of Formula (VIII), wherein $R^1$ is —CH(CH$_2$CH$_3$)CH(R$^3$)CH$_3$, and $R^3$ is ethyl. In some embodiments is a compound of Formula (VIII), wherein $R^1$ is —CH(CH$_2$CH$_3$)CH(R$^3$)CH$_3$, and $R^3$ is —NR$^{13}$R$^{14}$. In some embodiments is a compound of Formula (VIII), wherein $R^1$ is —CH(CH$_2$CH$_3$)CH(R$^3$)CH$_3$, and $R^3$ is —NH$_2$. In some embodiments is a compound of Formula (VIII), wherein $R^1$ is —CH(CH$_2$CH$_3$)CH(R$^3$)CH$_3$, and $R^3$ is —NHCH$_3$. In some embodiments is a compound of Formula (VIII), wherein $R^1$ is —CH(CH$_2$CH$_3$)CH(R$^3$)CH$_3$, and $R^3$ is —N(CH$_3$)$_2$. In some embodiments is a compound of Formula (VIII), wherein $R^1$ is -alkylene(cycloalkyl). In some embodiments is a compound of Formula (VIII), wherein $R^1$ is —CH$_2$CH$_2$(cycloalkyl). In some embodiments is a compound of Formula (VIII), wherein $R^1$ is —CH$_2$(cycloalkyl). In some embodiments is a compound of Formula (VIII), wherein $R^1$ is —CH$_2$(cyclobutyl). In some embodiments is a compound of Formula (VIII), wherein $R^1$ is —CH$_2$(cyclopentyl). In some embodiments is a compound of Formula (VIII), wherein $R^1$ is —CH$_2$(cyclohexyl). In some embodiments is a compound of Formula (VIII), wherein $R^1$ is

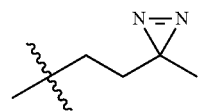

In another embodiment is a compound of Formula (VIII) having the structure:

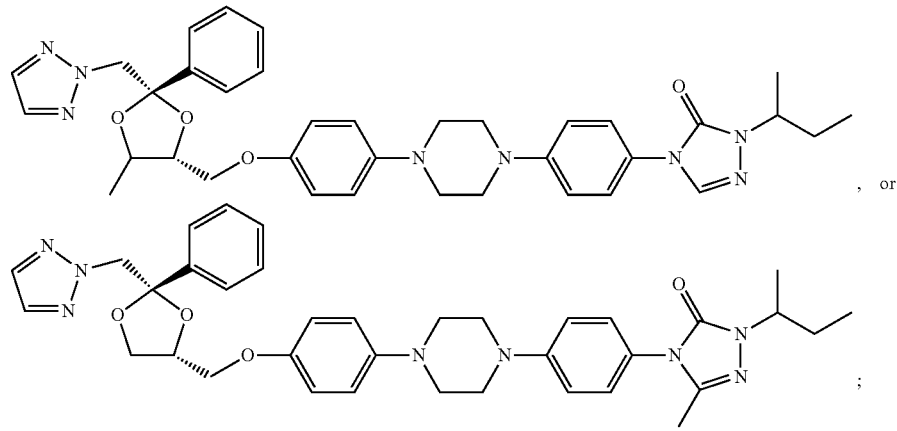

, or or a pharmaceutically acceptable salt, pharmaceutically acceptable solvate, or pharmaceutically acceptable prodrug thereof.

In another aspect, provided herein are compounds of Formula (VIIIa) having the structure:

Formula (VIIIa)

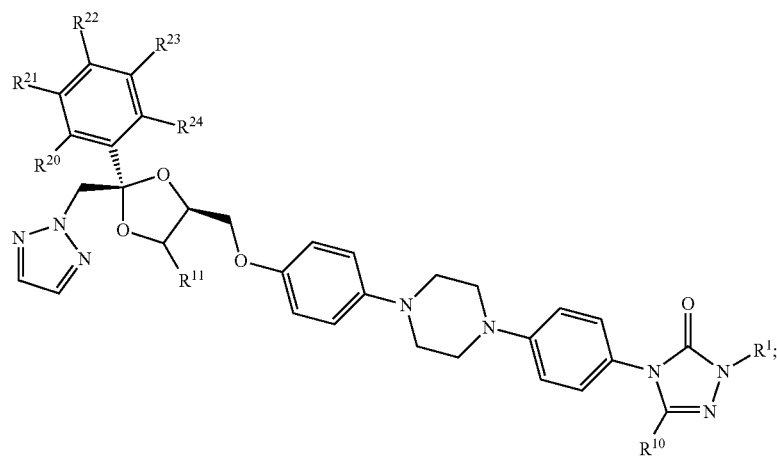

wherein:
R$^1$ is

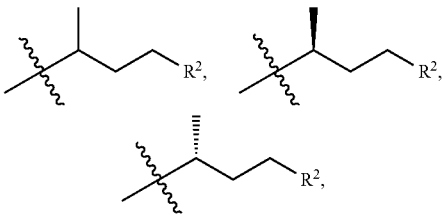

—CH(CH$_3$)CH(R$^3$)CH$_3$, —CH(CH$_3$)C(O)CH$_3$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

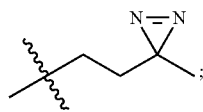

R$^2$ is H, alkyl, or —NR$^{13}$R$^{14}$;
R$^3$ is —OH, alkyl, or —NR$^{13}$R$^{14}$;
R$^{10}$ and R$^{11}$ are independently selected from H or alkyl, wherein at least one of R$^{10}$ and R$^{11}$ is alkyl;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;
R$^{20}$ is selected from H, F, Cl, Br, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$;
R$^{21}$, R$^{22}$, and R$^{23}$ are independently selected from H, halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; and
R$^{24}$ is H;
or a pharmaceutically acceptable salt, pharmaceutically acceptable solvate, or pharmaceutically acceptable prodrug thereof.

In some embodiments is a compound of Formula (VIIIa), wherein R$^{10}$ is H and R$^{11}$ is alkyl. In some embodiments is a compound of Formula (VIIIa), wherein R$^{10}$ is H and R$^{11}$ is methyl. In some embodiments is a compound of Formula (VIIIa), wherein R$^{10}$ is H and R$^{11}$ is ethyl. In some embodiments is a compound of Formula (VIIIa), wherein R$^{10}$ is H and R$^{11}$ is isopropyl. In some embodiments is a compound of Formula (VIIIa), wherein R$^{10}$ is alkyl and R$^{11}$ is H. In some embodiments is a compound of Formula (VIIIa), wherein R$^{10}$ is methyl and R$^{11}$ is H. In some embodiments is a compound of Formula (VIIIa), wherein R$^{10}$ is ethyl and R$^{11}$ is H. In some embodiments is a compound of Formula (VIIIa), wherein R$^{10}$ is isopropyl and R$^{11}$ is H. In some embodiments is a compound of Formula (VIIIa), wherein R$^{10}$ is alkyl and R$^{11}$ is alkyl. In some embodiments is a compound of Formula (VIIIa), wherein R$^{10}$ is methyl and R$^{11}$ is methyl.

In some embodiments is a compound of Formula (VIIIa), wherein R$^{21}$, R$^{22}$, and R$^{23}$ are independently selected from H, halogen, —CN, alkyl, alkoxy, haloalkoxy, haloalkyl, —SO$_2$R$^{13}$, —SO$_2$NR$^{13}$R$^{14}$, and —C(O)NR$^{13}$R$^{14}$. In some embodiments is a compound of Formula (VIIIa), wherein R$^{21}$, R$^{22}$, and R$^{23}$ are independently selected from H, halogen, —CN, alkyl, alkoxy, and haloalkyl. In some embodiments is a compound of Formula (VIIIa), wherein R$^{21}$, R$^{22}$, and R$^{23}$ are independently selected from H and halogen. In some embodiments is a compound of Formula (VIIIa), wherein R$^{21}$, R$^{22}$, and R$^{23}$ are independently selected from H and —CN. In some embodiments is a compound of Formula (VIIIa), wherein R$^{21}$, R$^{22}$, and R$^{23}$ are independently selected from H and alkyl. In some embodiments is a compound of Formula (VIIIa), wherein R$^{21}$, R$^{22}$, and R$^{23}$ are independently selected from H and alkoxy. In some embodiments is a compound of Formula (VIIIa), wherein R$^{21}$, R$^{22}$, and R$^{23}$ are independently selected from H and haloalkoxy. In some embodiments is a compound of Formula (VIIIa), wherein R$^{21}$, R$^{22}$, and R$^{23}$ are independently selected from H and haloalkyl. In some embodiments is a compound of Formula (VIIIa), wherein R$^{21}$, R$^{22}$, and R$^{23}$ are independently selected from H and —SO$_2$R$^{13}$. In some embodiments is a compound of Formula (VIIIa), wherein R$^{21}$, R$^{22}$, and R$^{23}$ are independently selected from H and —SO$_2$NR$^{13}$R$^{14}$. In some embodiments is a compound of Formula (VIIIa), wherein R$^{21}$, R$^{22}$, and R$^{23}$ are independently selected from H and —C(O)NR$^{13}$R$^{14}$. In some embodiments is a compound of Formula (VIIIa), wherein R$^{21}$, R$^{22}$, and R$^{23}$ are independently selected from —CN and alkyl. In some embodiments is a compound of Formula (VIIIa), wherein R$^{21}$, R$^{22}$, and R$^{23}$ are independently selected from H, Cl, —CN, —CH$_3$, —OCH$_3$, and —CF$_3$.

In some embodiments is a compound of Formula (VIIIa), wherein R$^{21}$, R$^{22}$, and R$^{23}$ are each H.

In some embodiments is a compound of Formula (VIIIa), wherein R$^{20}$ is selected from H, halogen, —CN, alkyl, alkoxy, and haloalkyl. In some embodiments is a compound of Formula (VIIIa), wherein R$^{20}$ is selected from H and —CN. In some embodiments is a compound of Formula (VIIIa), wherein R$^{20}$ is selected from H and alkyl. In some embodiments is a compound of Formula (VIIIa), wherein R$^{20}$ is selected from H and alkoxy. In some embodiments is a compound of Formula (VIIIa), wherein R$^{20}$ is selected from H and haloalkoxy. In some embodiments is a compound of Formula (VIIIa), wherein R$^{20}$ is selected from H and haloalkyl. In some embodiments is a compound of Formula (VIIIa), wherein R$^{20}$ is selected from H and —SO$_2$R$^{13}$. In some embodiments is a compound of Formula (VIIIa), wherein R$^{20}$ is selected from H and —SO$_2$NR$^{13}$R$^{14}$. In some embodiments is a compound of Formula (VIIIa), wherein R$^{20}$ is selected R$^{20}$ is selected from —CN and alkyl. In some embodiments is a compound of Formula (VIIIa), wherein R$^{20}$ is selected from H, Cl, —CN, —CH$_3$, —OCH$_3$, and —CF$_3$. In some embodiments is a compound of Formula (VIIIa), wherein R$^{20}$ is selected from H, Cl, —CN, and —CH$_3$. In some embodiments is a compound of Formula (VIIIa), wherein R$^{20}$ is H. In some embodiments is a compound of Formula (VIIIa), wherein R$^{20}$ is Cl.

In some embodiments is a compound of Formula (VIIIa), wherein R$^1$ is

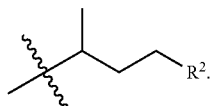

In some embodiments is a compound of Formula (VIIIa), wherein R¹ is

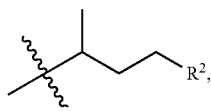

and R² is H. In some embodiments is a compound of Formula (VIIIa), wherein R¹ is

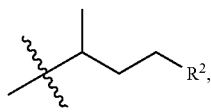

and R² is alkyl. In some embodiments is a compound of Formula (VIIIa), wherein R¹ is

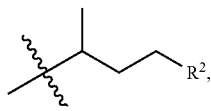

and R² is methyl. In some embodiments is a compound of Formula (VIIIa), wherein R¹ is

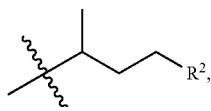

R¹ is

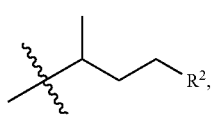

and R² is isopropyl. In some embodiments is a compound of Formula (VIIIa), wherein R¹ is

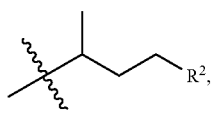

and R² is —NR¹³R¹⁴. In some embodiments is a compound of Formula (VIIIa), wherein R¹ is

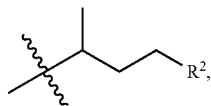

and R² is —NH₂. In some embodiments is a compound of Formula (VIIIa), wherein R¹ is

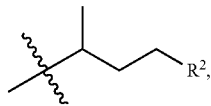

and R² is —NHCH₃. In some embodiments is a compound of Formula (VIIIa), wherein R¹ is

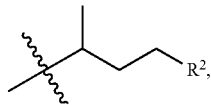

and R² is —N(CH₃)₂.

In some embodiments is a compound of Formula (VIIIa), wherein R¹ is

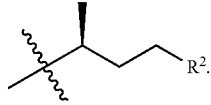

In some embodiments is a compound of Formula (VIIIa), wherein R¹ is

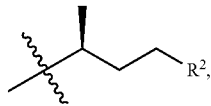

and R² is H. In some embodiments is a compound of Formula (VIIIa), wherein R¹ is

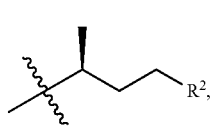

and R² is alkyl. In some embodiments is a compound of Formula (VIIIa), wherein R¹ is

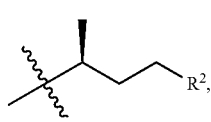

and R² is methyl. In some embodiments is a compound of Formula (VIIIa), wherein R¹ is

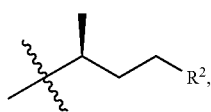

and $R^2$ is ethyl. In some embodiments is a compound of Formula (VIIIa), wherein $R^1$ is

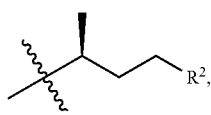

and $R^2$ is isopropyl. In some embodiments is a compound of Formula (VIIIa), wherein $R^1$ is

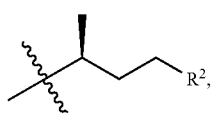

and $R^2$ is $-NR^{13}R^{14}$. In some embodiments is a compound of Formula (VIIIa), wherein $R^1$ is

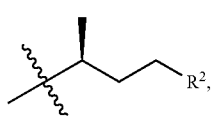

and $R^2$ is $-NH_2$. In some embodiments is a compound of Formula (VIIIa), wherein $R^1$ is

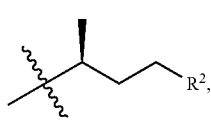

and $R^2$ is $-NHCH_3$. In some embodiments is a compound of Formula (VIIIa), wherein $R^1$ is

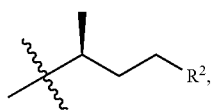

and $R^2$ is $-N(CH_3)_2$.

In some embodiments is a compound of Formula (VIIIa), wherein $R^1$ is

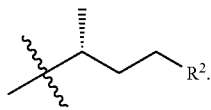

In some embodiments is a compound of Formula (VIIIa), wherein $R^1$ is

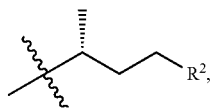

and $R^2$ is H. In some embodiments is a compound of Formula (VIIIa), wherein $R^1$ is

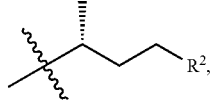

and $R^2$ is alkyl. In some embodiments is a compound of Formula (VIIIa), wherein $R^1$ is

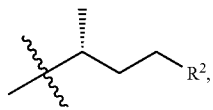

and $R^2$ is methyl. In some embodiments is a compound of Formula (VIIIa), wherein $R^1$ is

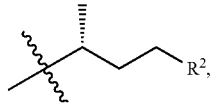

and $R^2$ is ethyl. In some embodiments is a compound of Formula (VIIIa), wherein $R^1$ is

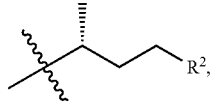

and $R^2$ is isopropyl. In some embodiments is a compound of Formula (VIIIa), wherein $R^1$ is

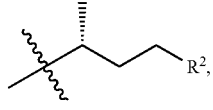

and $R^2$ is $-NR^{13}R^{14}$. In some embodiments is a compound of Formula (VIIIa), wherein $R^1$ is

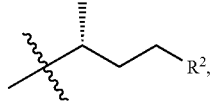

and $R^2$ is $-NH_2$. In some embodiments is a compound of Formula (VIIIa), wherein $R^1$ is

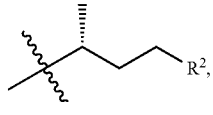

and R² is —NHCH₃. In some embodiments is a compound of Formula (VIIIa), wherein R¹ is

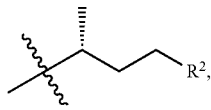

and R² is —N(CH₃)₂. In some embodiments is a compound of Formula (VIIIa), wherein R¹ is —CH(CH₂CH₃)₂. In some embodiments is a compound of Formula (VIIIa), wherein R¹ is —CH(CH₃)₂. In some embodiments is a compound of Formula (VIIIa), wherein R¹ is —CH(CH₂CH₃)CH(R³)CH₃. In some embodiments is a compound of Formula (VIIIa), wherein R¹ is —CH(CH₂CH₃)CH(R³)CH₃, and R³ is —OH. In some embodiments is a compound of Formula (VIIIa), wherein R¹ is —CH(CH₂CH₃)CH(R³)CH₃, and R³ is alkyl. In some embodiments is a compound of Formula (VIIIa), wherein R¹ is —CH(CH₂CH₃)CH(R³)CH₃, and R³ is methyl. In some embodiments is a compound of Formula (VIIIa), wherein R¹ is —CH(CH₂CH₃)CH(R³)CH₃, and R³ is ethyl. In some embodiments is a compound of Formula (VIIIa), wherein R¹ is —CH(CH₂CH₃)CH(R³)CH₃, and R³ is —NR¹³R¹⁴. In some embodiments is a compound of Formula (VIIIa), wherein R¹ is —CH(CH₂CH₃)CH(R³)CH₃, and R³ is —NH₂. In some embodiments is a compound of Formula (VIIIa), wherein R¹ is —CH(CH₂CH₃)CH(R³)CH₃, and R³ is —NHCH₃. In some embodiments is a compound of Formula (VIIIa), wherein R¹ is —CH(CH₂CH₃)CH(R³)CH₃, and R³ is —N(CH₃)₂. In some embodiments is a compound of Formula (VIIIa), wherein R¹ is -alkylene(cycloalkyl). In some embodiments is a compound of Formula (VIIIa), wherein R¹ is —CH₂CH₂(cycloalkyl). In some embodiments is a compound of Formula (VIIIa), wherein R¹ is —CH₂(cycloalkyl). In some embodiments is a compound of Formula (VIIIa), wherein R¹ is —CH₂(cyclobutyl). In some embodiments is a compound of Formula (VIIIa), wherein R¹ is —CH₂(cyclopentyl). In some embodiments is a compound of Formula (VIIIa), wherein R¹ is —CH₂(cyclohexyl). In some embodiments is a compound of Formula (VIIIa), wherein R¹ is

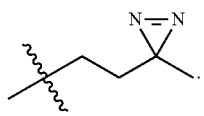 [SMILES: *CCC1(C)N=N1]

In another embodiment is a compound of Formula (VIIIa) having the structure:

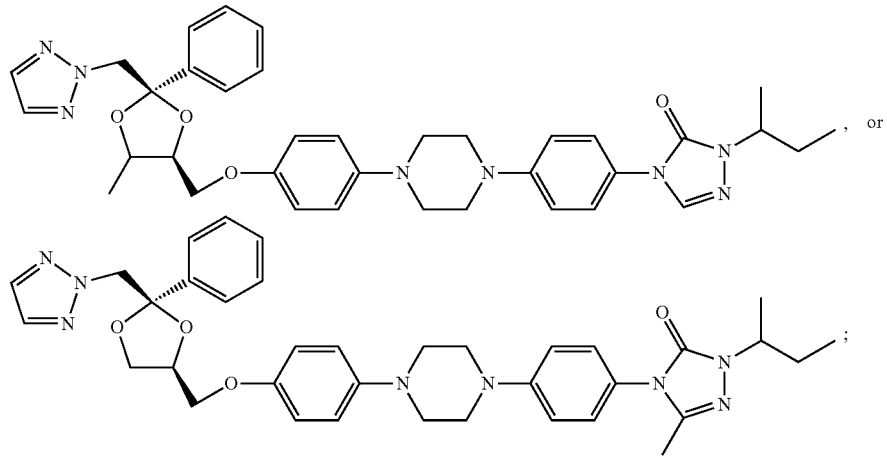

or a pharmaceutically acceptable salt, pharmaceutically acceptable solvate, or pharmaceutically acceptable prodrug thereof.

In another aspect is a compound having the structure:

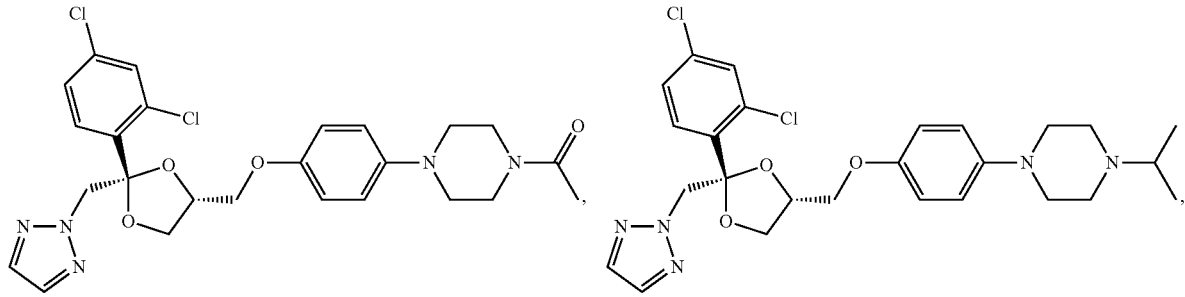

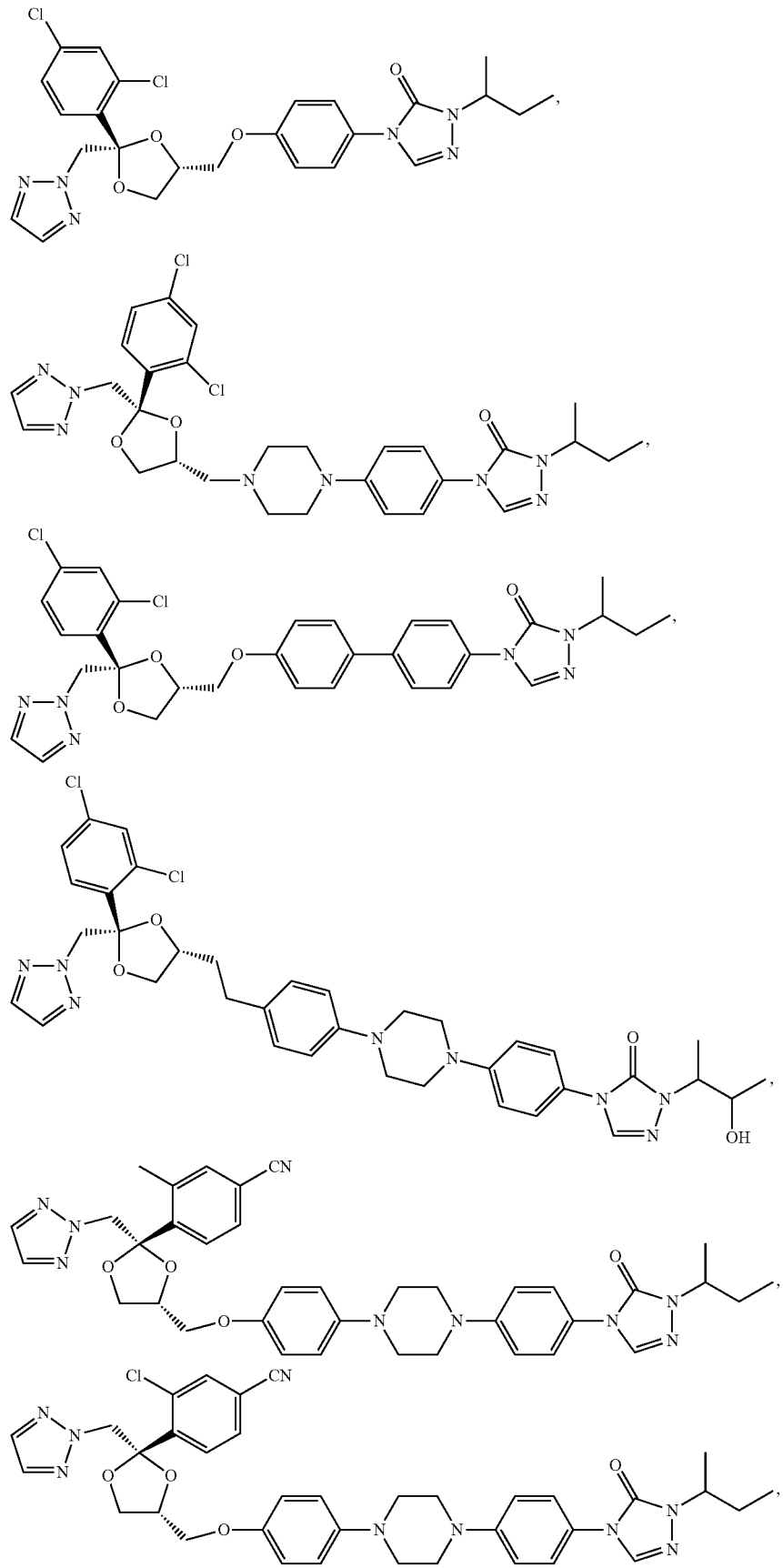

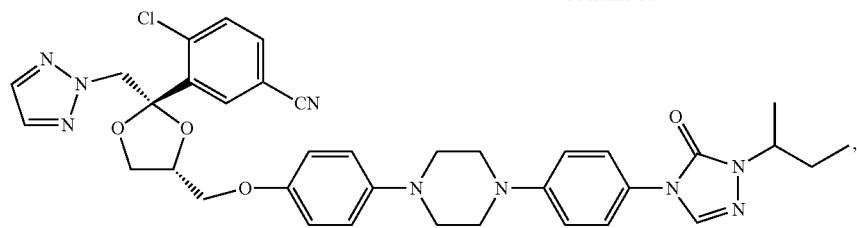
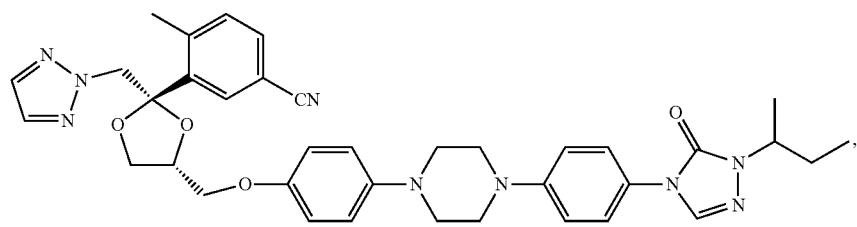
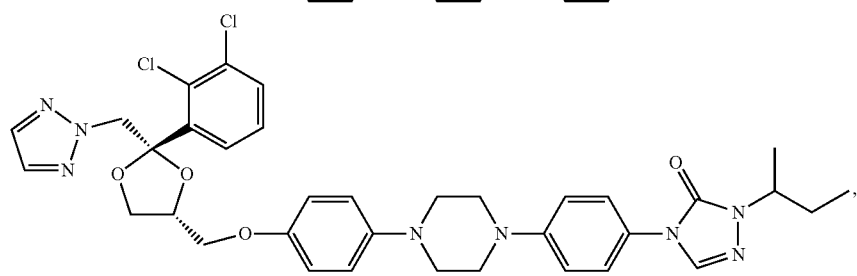
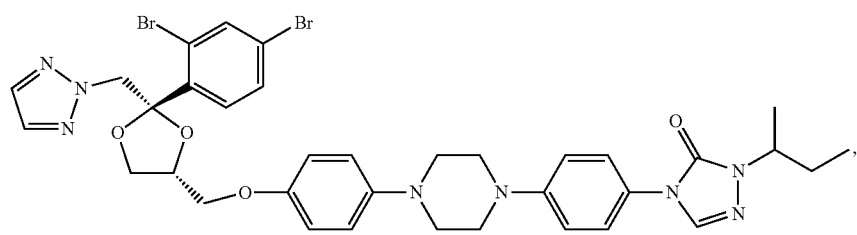
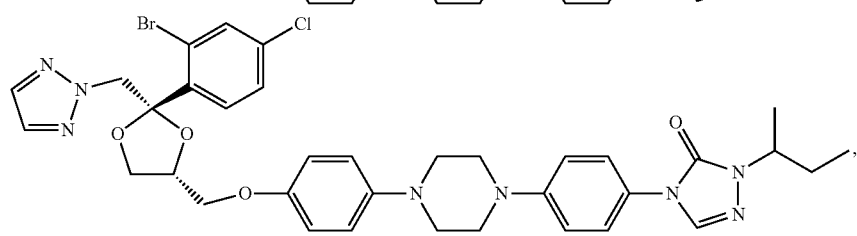
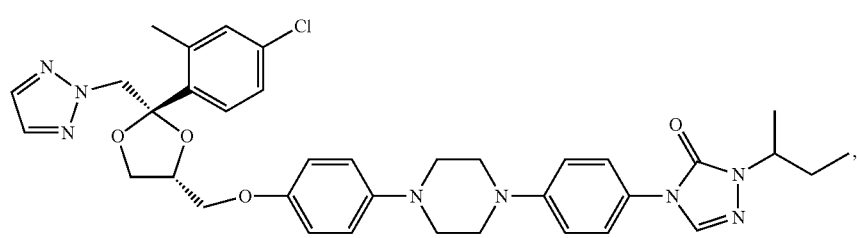
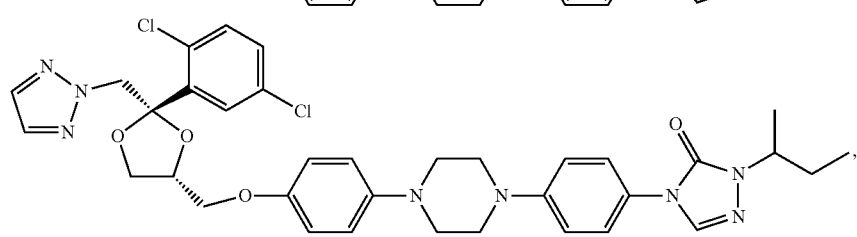

-continued
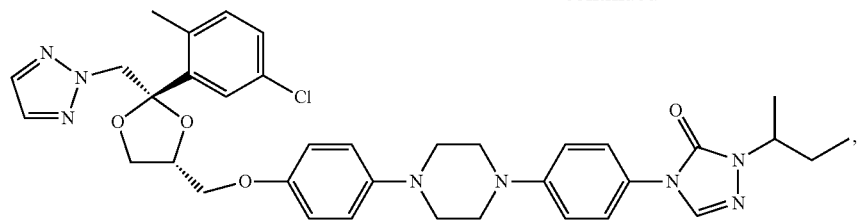
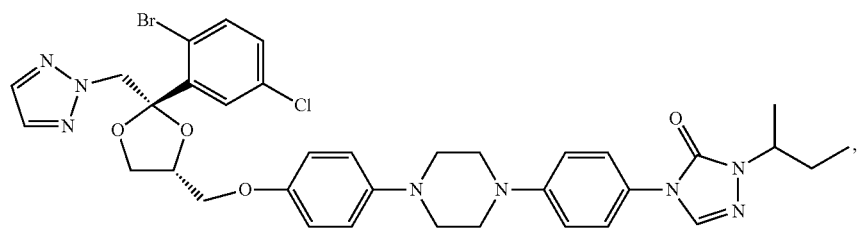
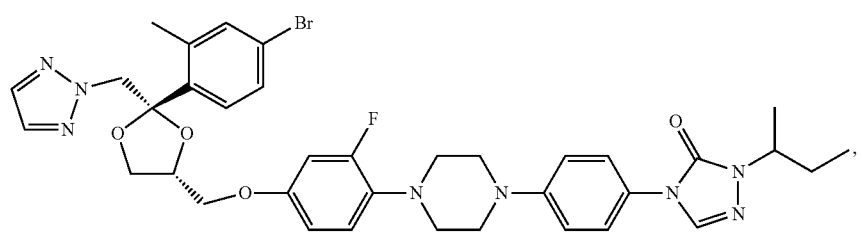
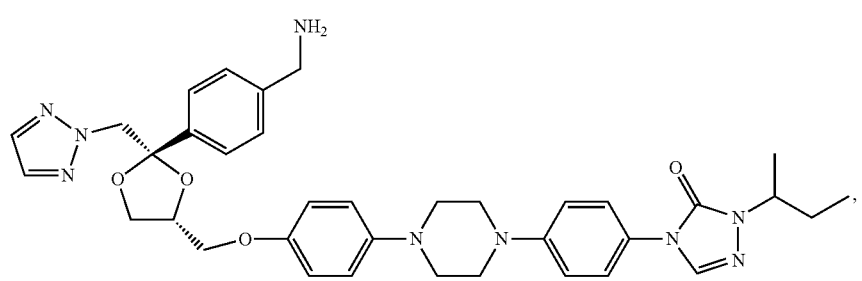
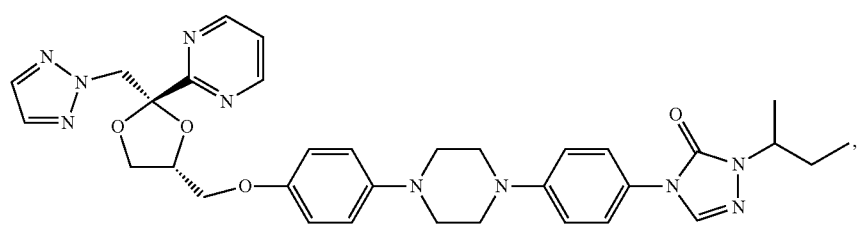
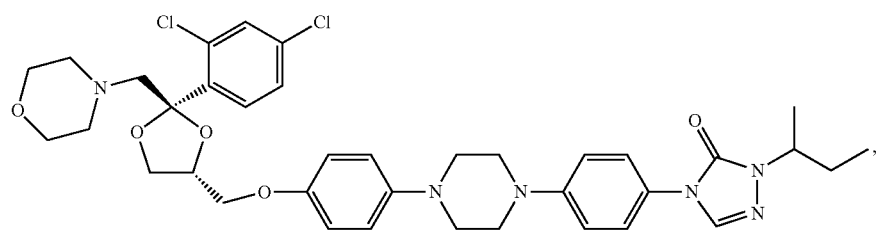

-continued
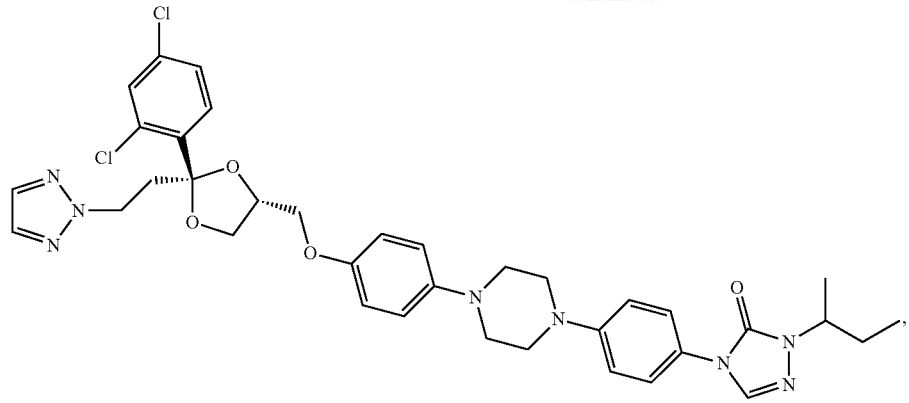
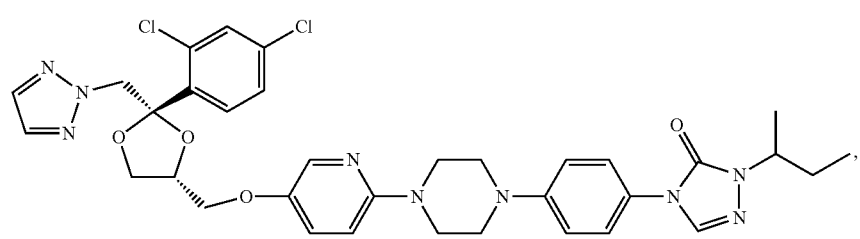
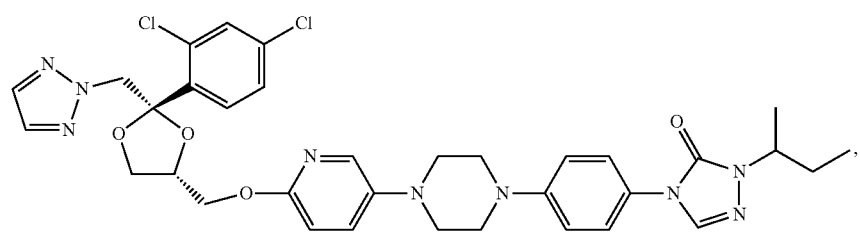
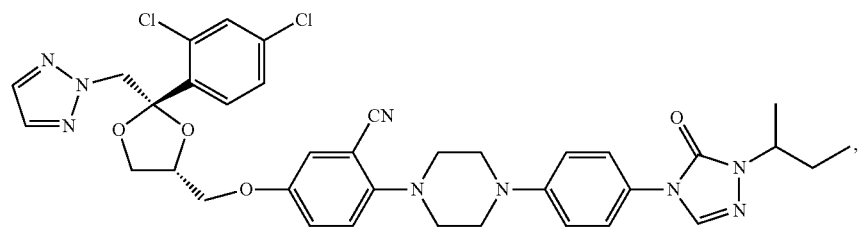
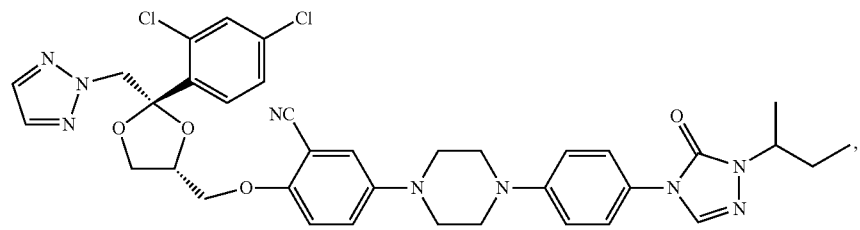
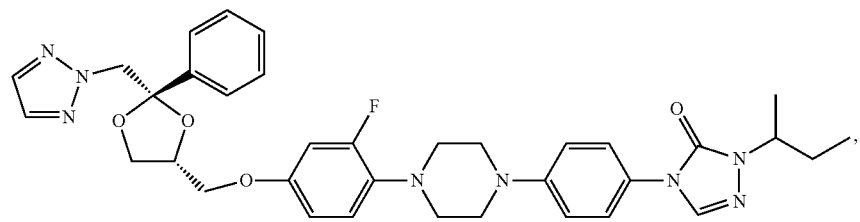

-continued
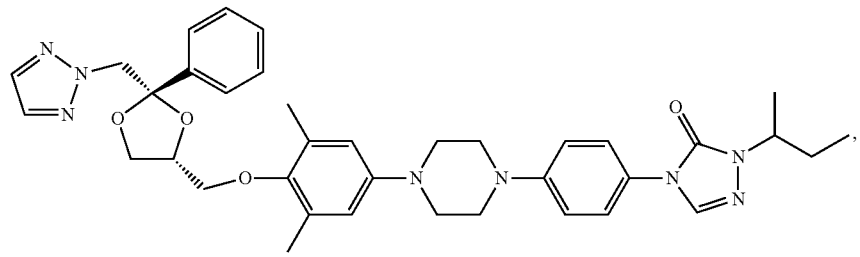
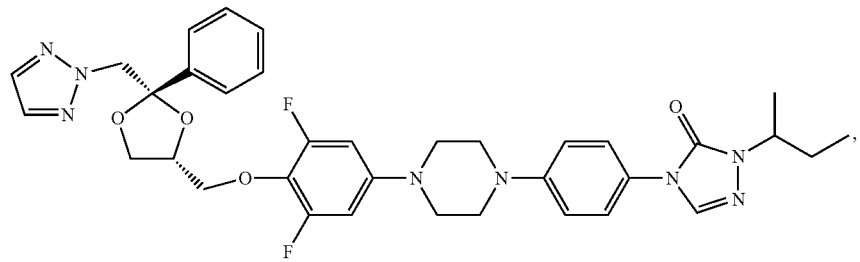
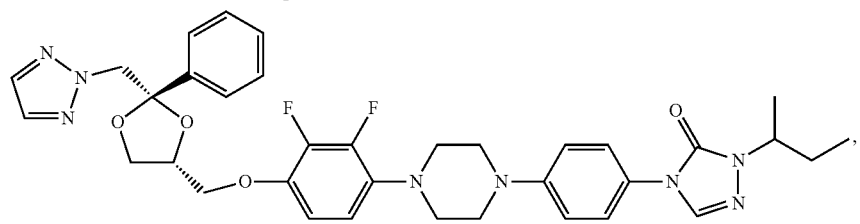
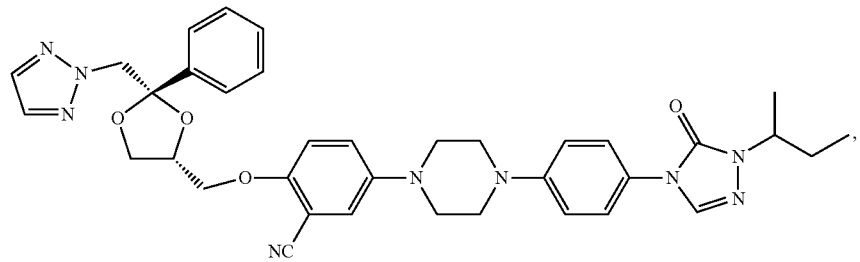
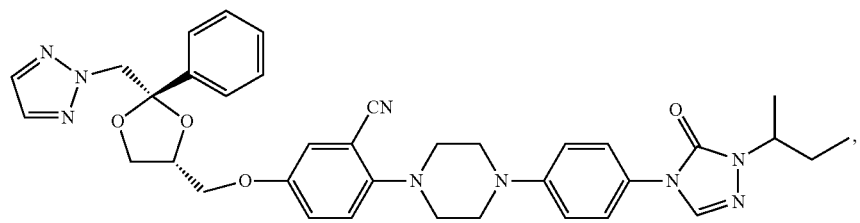
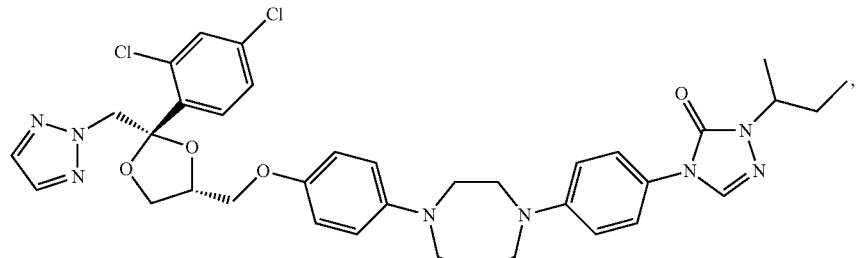
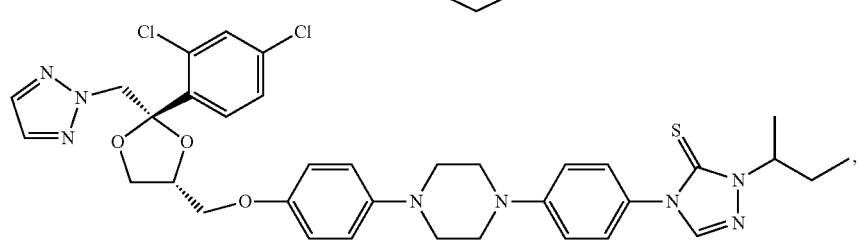

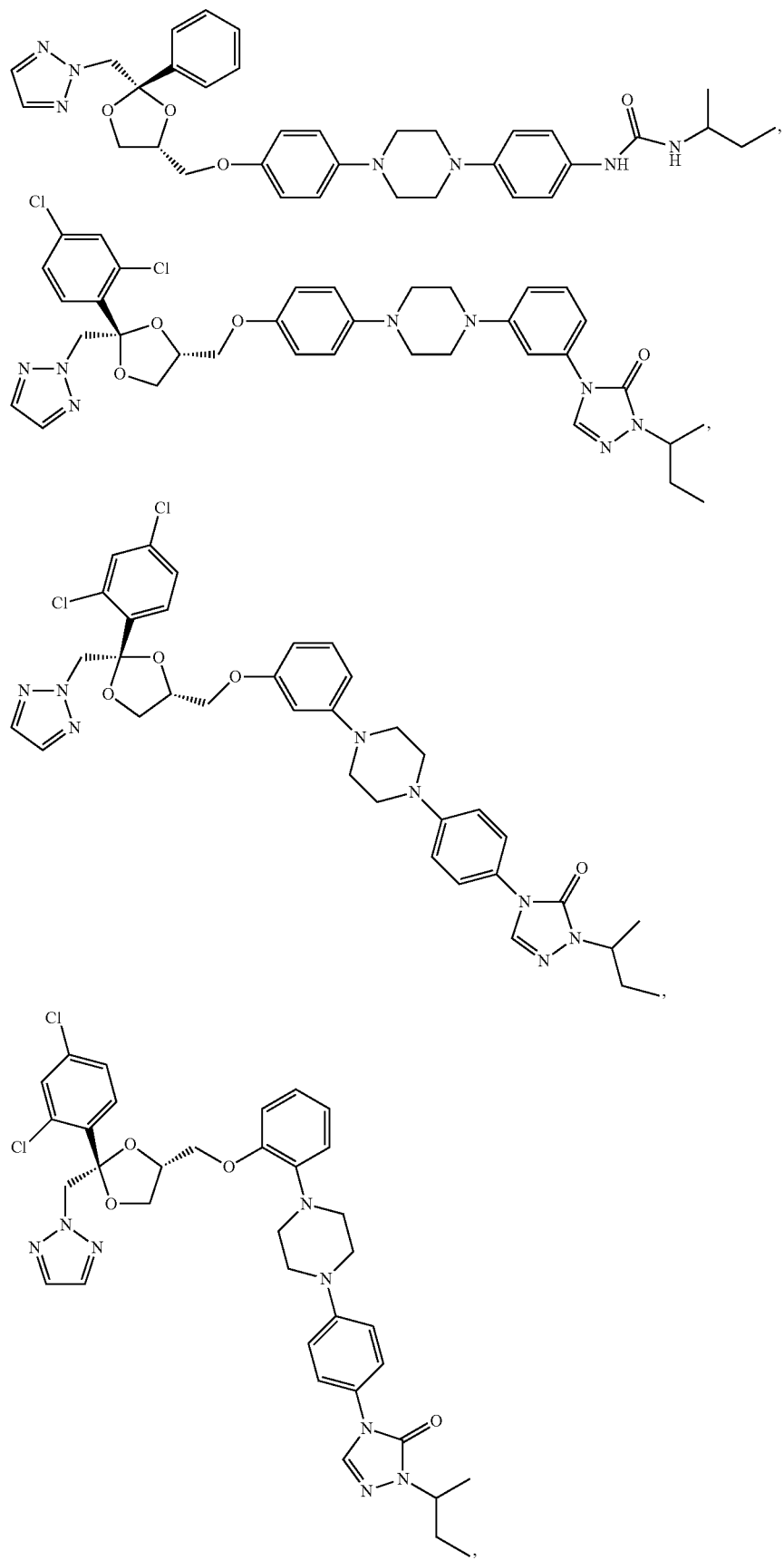

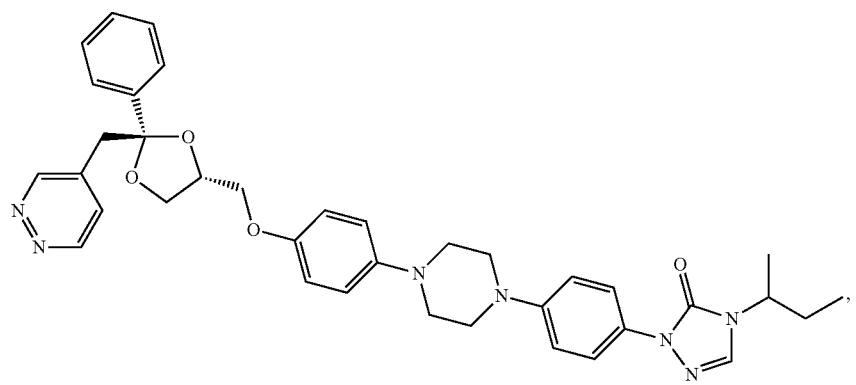
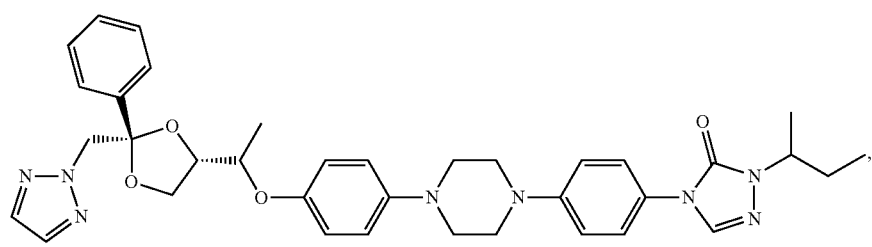
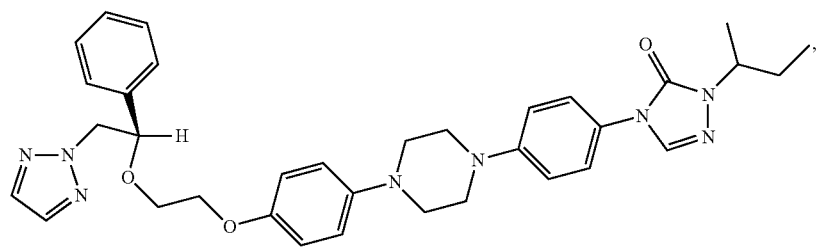
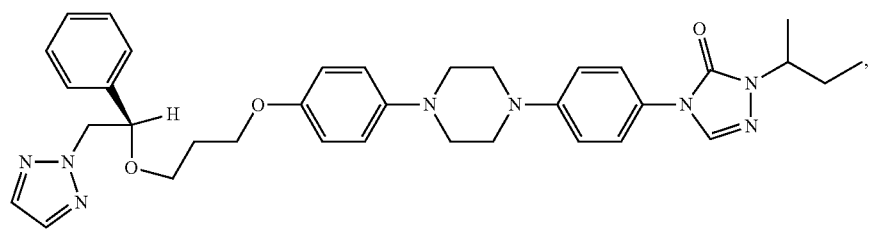
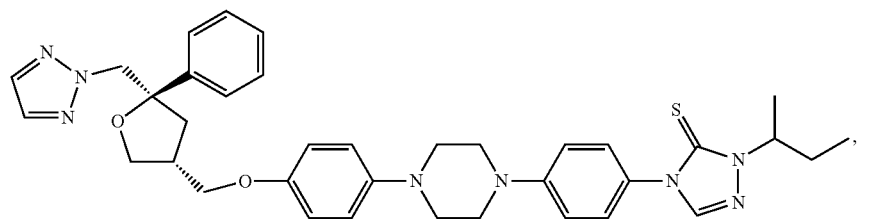
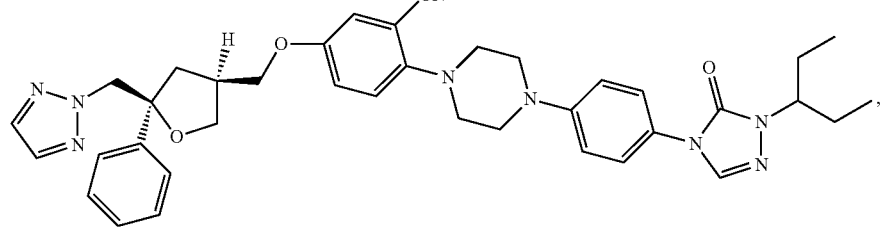

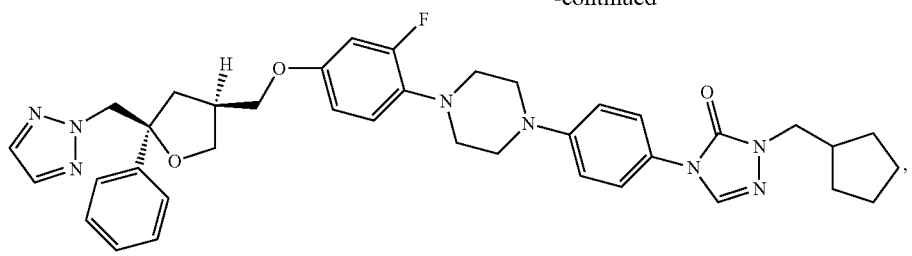
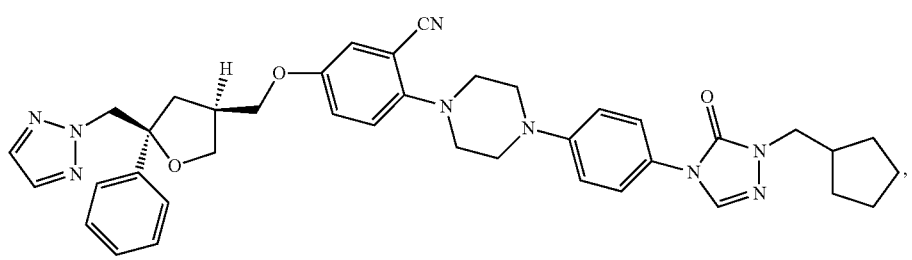
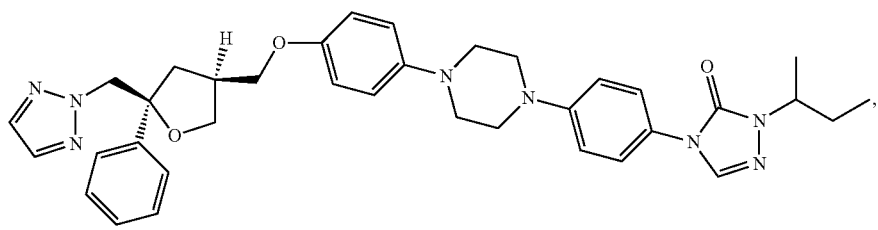
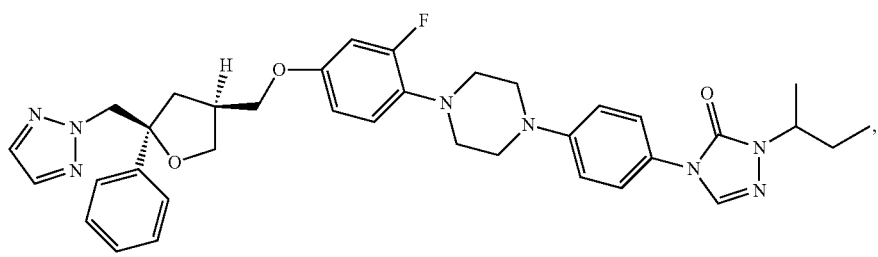
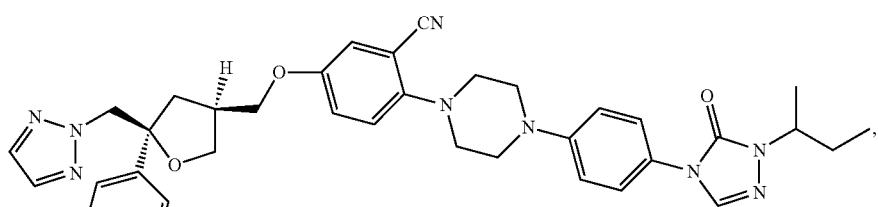
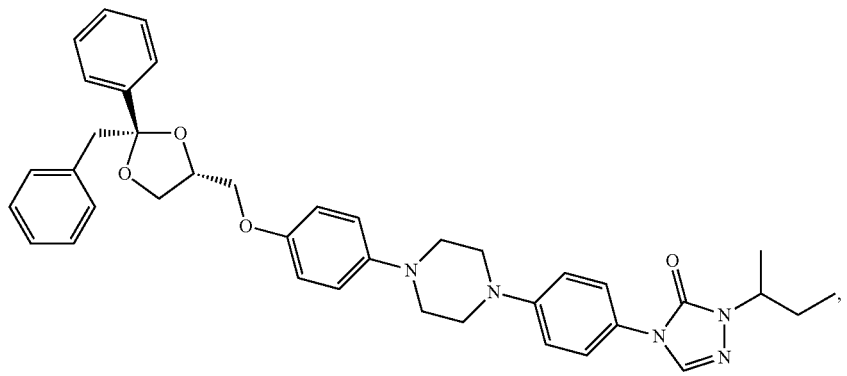

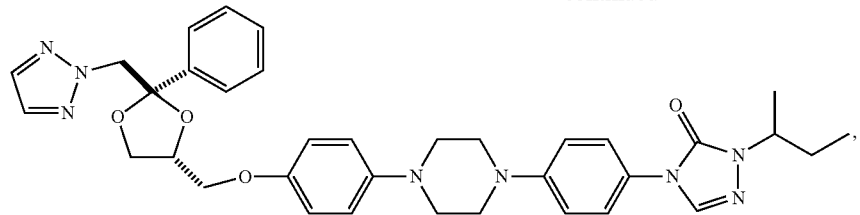
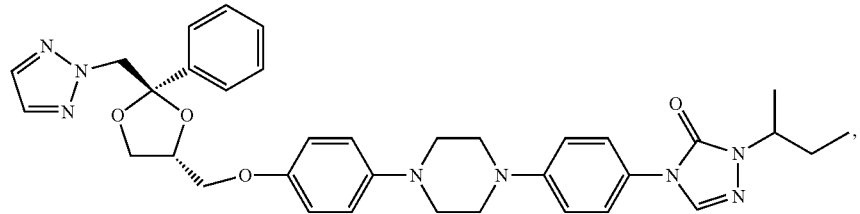
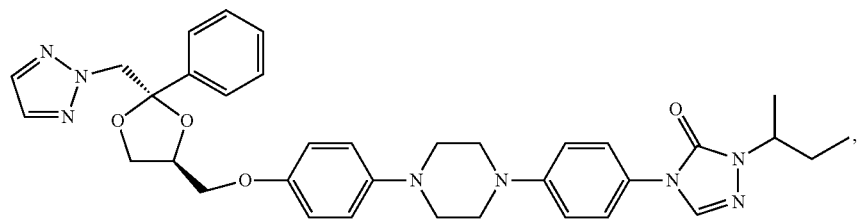
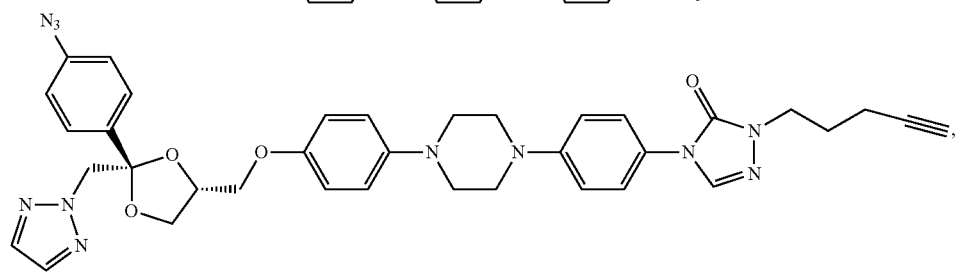
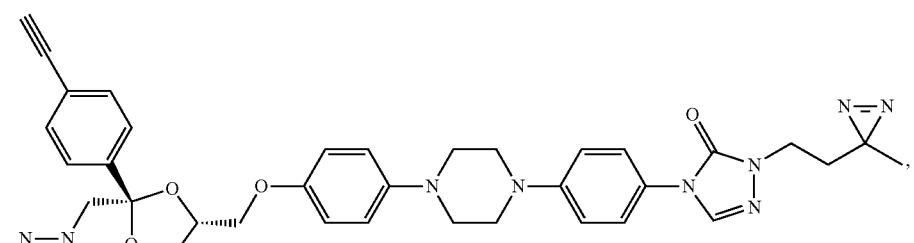
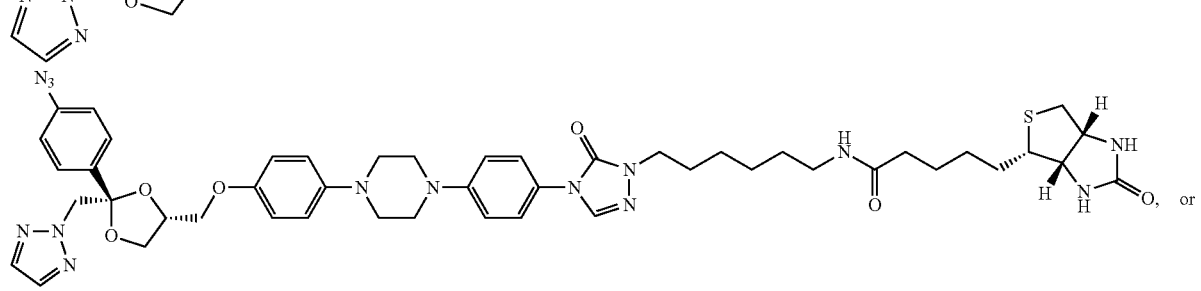
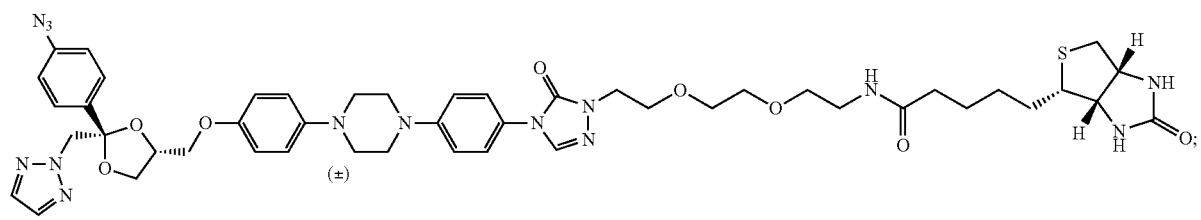

or a pharmaceutically acceptable salt, pharmaceutically acceptable solvate, or pharmaceutically acceptable prodrug thereof.

Formula (IX)

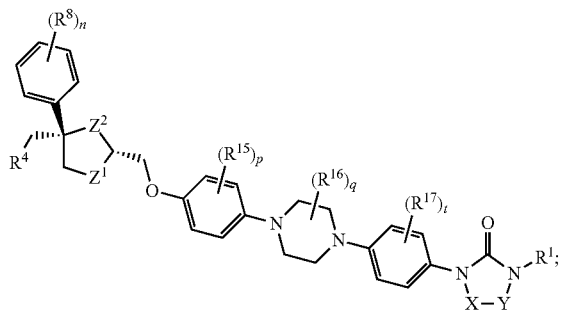

wherein:
—X—Y— is —CH$_2$CH$_2$—, —CH=CH—, —CH=N—, or —N=CH—;
$Z^1$ is selected from O, S, NH, and NR$^{13}$;
$Z^2$ is selected from O, S, CH$_2$, NH, and NR$^{13}$;
$R^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

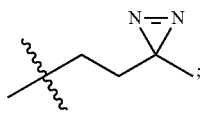

$R^2$ is H, alkyl, or —NR$^{13}$R$^{14}$;
$R^3$ is —OH, alkyl, or —NR$^{13}$R$^{14}$;
$R^4$ is halogen, alkyl,

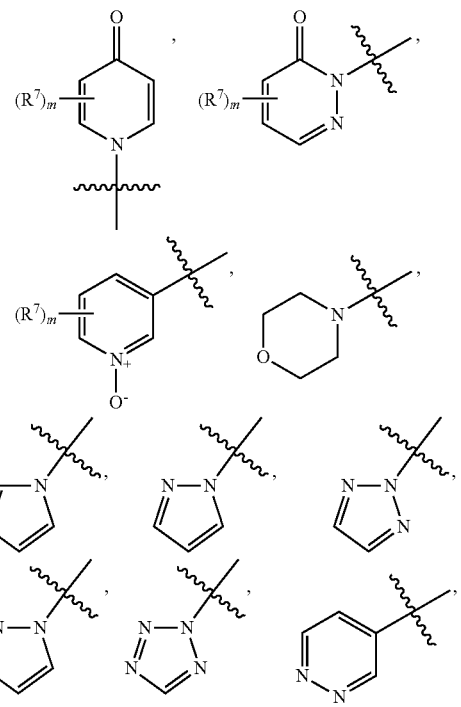

each $R^7$ is independently selected from halogen and alkyl;
each $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;
each $R^{15}$ is independently selected from haloalkyl, -alkylene(NR$^{13}$R$^{14}$), —NR$^{13}$R$^{14}$, and —SO$_2$R$^{13}$;
each $R^{16}$ is independently selected from halogen, alkyl, and haloalkyl;
each $R^{17}$ is independently selected from halogen, alkyl, haloalkyl, and —CN;
n is selected from 0, 1, 2, 3, and 4;
m is selected from 0, 1, and 2;
p is selected from 0, 1, 2, 3, and 4;
q is selected from 0, 1, 2, 3, and 4; and
t is independently selected from 0, 1, 2, 3, and 4;
or a pharmaceutically acceptable salt, pharmaceutically acceptable solvate, pharmaceutically acceptable prodrug, or stereoisomer thereof.

In some embodiments is a compound of Formula (IX), wherein R$^4$ is halogen. In some embodiments is a compound of Formula (IX), wherein R$^4$ is F. In some embodiments is a compound of Formula (IX), wherein R$^4$ is Cl. In some embodiments is a compound of Formula (IX), wherein R$^4$ is alkyl. In some embodiments is a compound of Formula (IX), wherein R$^4$ is methyl. In some embodiments is a compound of Formula (IX), wherein R$^4$ is ethyl. In some embodiments is a compound of Formula (IX), wherein R$^4$ is

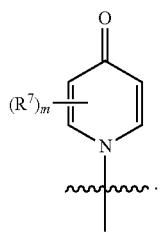

In some embodiments is a compound of Formula (IX), wherein R⁴ is

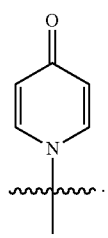

In some embodiments is a compound of Formula (IX), wherein R⁴ is

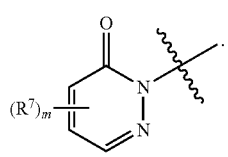

In some embodiments is a compound of Formula (IX), wherein R⁴ is

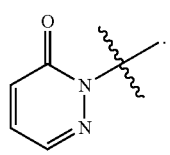

In some embodiments is a compound of Formula (IX), wherein R⁴ is

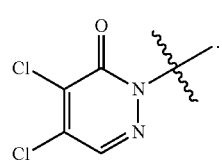 [SMILES: *n1ncc(Cl)c(Cl)c1=O]

In some embodiments is a compound of Formula (IX), wherein R⁴ is

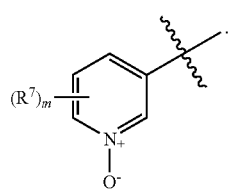

In some embodiments is a compound of Formula (IX), wherein R⁴ is

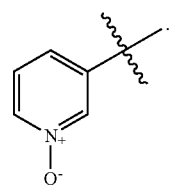 [SMILES: *c1ccc[n+]([O-])c1]

In some embodiments is a compound of Formula (IX), wherein R⁴ is

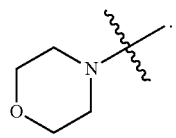 [SMILES: *N1CCOCC1]

In some embodiments is a compound of Formula (IX), wherein R⁴ is

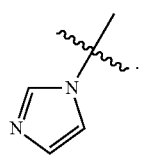

In some embodiments is a compound of Formula (IX), wherein R⁴ is

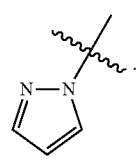

In some embodiments is a compound of Formula (IX), wherein R⁴ is

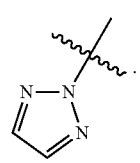

In some embodiments is a compound of Formula (IX), wherein R⁴ is

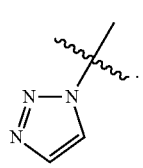

In some embodiments is a compound of Formula (IX), wherein R⁴ is

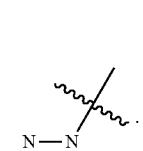
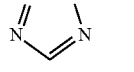

In some embodiments is a compound of Formula (IX), wherein R⁴ is

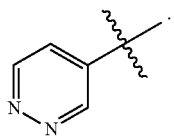

In some embodiments is a compound of Formula (IX), wherein $R^4$ is

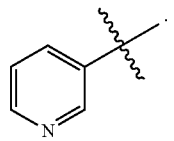 [SMILES: *c1cccnc1]

In some embodiments is a compound of Formula (IX), wherein $R^4$ is

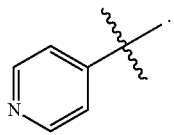

In some embodiments is a compound of Formula (IX), wherein $R^4$ is

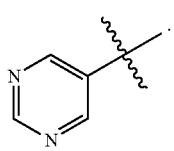

In some embodiments is a compound of Formula (IX), wherein $R^4$ is

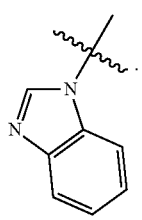

In some embodiments is a compound of Formula (IX), wherein $R^4$ is

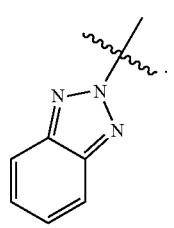 [SMILES: *n1nc2ccccc2n1]

In some embodiments is a compound of Formula (IX), wherein $R^4$ is

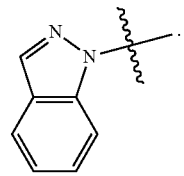 [SMILES: *n1ncc2ccccc21]

In some embodiments is a compound of Formula (IX), wherein $R^1$ is —CH(CH$_3$)CH$_2$CH$_2$R$^2$. In some embodiments is a compound of Formula (IX), wherein $R^1$ is —CH(CH$_3$)CH$_2$CH$_2$R$^2$, and $R^2$ is H. In some embodiments is a compound of Formula (IX), wherein $R^1$ is —CH(CH$_3$)CH$_2$CH$_2$R$^2$, and $R^2$ is alkyl. In some embodiments is a compound of Formula (IX), wherein $R^1$ is —CH(CH$_3$)CH$_2$CH$_2$R$^2$, and $R^2$ is methyl. In some embodiments is a compound of Formula (IX), wherein $R^1$ is —CH(CH$_3$)CH$_2$CH$_2$R$^2$, and $R^2$ is ethyl. In some embodiments is a compound of Formula (IX), wherein $R^1$ is —CH(CH$_3$)CH$_2$CH$_2$R$^2$, and $R^2$ is isopropyl. In some embodiments is a compound of Formula (IX), wherein $R^1$ is —CH(CH$_3$)CH$_2$CH$_2$R$^2$, and $R^2$ is —NR$^{13}$R$^{14}$. In some embodiments is a compound of Formula (IX), wherein $R^1$ is —CH(CH$_3$)CH$_2$CH$_2$R$^2$, and $R^2$ is —NH$_2$. In some embodiments is a compound of Formula (IX), wherein $R^1$ is —CH(CH$_3$)CH$_2$CH$_2$R$^2$, and $R^2$ is —NHCH$_3$. In some embodiments is a compound of Formula (IX), wherein $R^1$ is —CH(CH$_3$)CH$_2$CH$_2$R$^2$, and $R^2$ is —N(CH$_3$)$_2$.

In some embodiments is a compound of Formula (IX), wherein $R^1$ is —CH(CH$_2$CH$_3$)$_2$. In some embodiments is a compound of Formula (IX), wherein $R^1$ is —CH(CH$_3$)$_2$. In some embodiments is a compound of Formula (IX), wherein $R^1$ is —CH(CH$_2$CH$_3$)CH(R$^3$)CH$_3$. In some embodiments is a compound of Formula (IX), wherein $R^1$ is —CH(CH$_2$CH$_3$)CH(R$^3$)CH$_3$, and $R^3$ is —OH. In some embodiments is a compound of Formula (IX), wherein $R^1$ is —CH(CH$_2$CH$_3$)CH(R$^3$)CH$_3$, and $R^3$ is alkyl. In some embodiments is a compound of Formula (IX), wherein $R^1$ is —CH(CH$_2$CH$_3$)CH(R$^3$)CH$_3$, and $R^3$ is methyl. In some embodiments is a compound of Formula (IX), wherein $R^1$ is —CH(CH$_2$CH$_3$)CH(R$^3$)CH$_3$, and $R^3$ is ethyl. In some embodiments is a compound of Formula (IX), wherein $R^1$ is —CH(CH$_2$CH$_3$)CH(R$^3$)CH$_3$, and $R^3$ is —NR$^{13}$R$^{14}$. In some embodiments is a compound of Formula (IX), wherein $R^1$ is —CH(CH$_2$CH$_3$)CH(R$^3$)CH$_3$, and $R^3$ is —NH$_2$. In some embodiments is a compound of Formula (IX), wherein $R^1$ is —CH(CH$_2$CH$_3$)CH(R$^3$)CH$_3$, and $R^3$ is —NHCH$_3$. In some embodiments is a compound of Formula (IX), wherein $R^1$ is —CH(CH$_2$CH$_3$)CH(R$^3$)CH$_3$, and $R^3$ is —N(CH$_3$)$_2$. In some embodiments is a compound of Formula (IX), wherein $R^1$ is -alkylene(cycloalkyl). In some embodiments is a compound of Formula (IX), wherein $R^1$ is —CH$_2$CH$_2$(cycloalkyl). In some embodiments is a compound of Formula (IX), wherein $R^1$ is —CH$_2$(cycloalkyl). In some embodiments is a compound of Formula (IX), wherein $R^1$ is —CH$_2$(cyclobutyl). In some embodiments is a compound of Formula (IX), wherein $R^1$ is —CH$_2$(cyclopentyl). In some embodiments is a compound of Formula (IX), wherein $R^1$ is —CH$_2$(cyclohexyl). In some embodiments is a compound of Formula (IX), wherein $R^1$ is

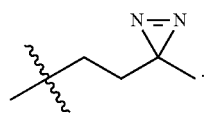

In some embodiments is a compound of Formula (IX), wherein R¹ is

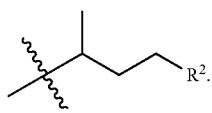

In some embodiments is a compound of Formula (IX), wherein R¹ is

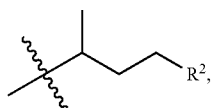

and R² is H. In some embodiments is a compound of Formula (IX), wherein R¹ is

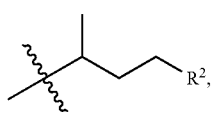

and R² is alkyl. In some embodiments is a compound of Formula (IX), wherein R¹ is

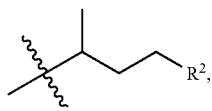

and R² is methyl. In some embodiments is a compound of Formula (IX), wherein R¹ is

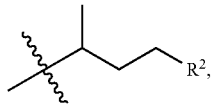

and R² is ethyl. In some embodiments is a compound of Formula (IX), wherein R¹ is

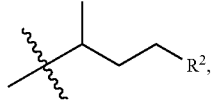

and R² is isopropyl. In some embodiments is a compound of Formula (IX), wherein R¹ is

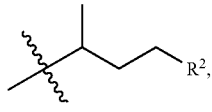

and R² is —NR¹³R¹⁴. In some embodiments is a compound of Formula (IX), wherein R¹ is

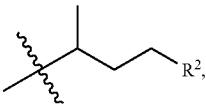

and R² is —NH₂. In some embodiments is a compound of Formula (IX), wherein R¹ is

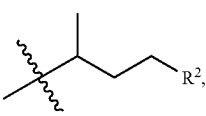

and R² is —NHCH₃. In some embodiments is a compound of Formula (IX), wherein R¹ is

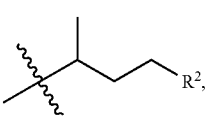

and R² is —N(CH₃)₂.

In some embodiments is a compound of Formula (IX), wherein R¹ is

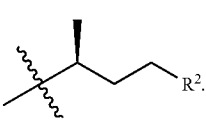

In some embodiments is a compound of Formula (IX), wherein R¹ is

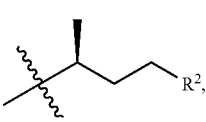

and R² is H. In some embodiments is a compound of Formula (IX), wherein R¹ is

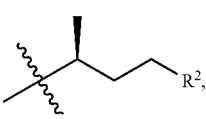

and R² is alkyl. In some embodiments is a compound of Formula (IX), wherein R¹ is

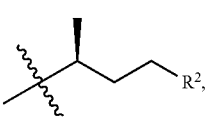

and R² is methyl. In some embodiments is a compound of Formula (IX), wherein R¹ is

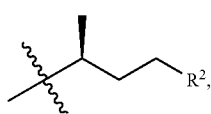

$R^2$, and $R^2$ is ethyl. In some embodiments is a compound of Formula (IX), wherein $R^1$ is

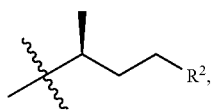

and $R^2$ is isopropyl. In some embodiments is a compound of Formula (IX), wherein $R^1$ is

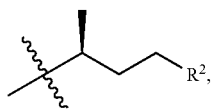

and $R^2$ is —$NR^{13}R^{14}$. In some embodiments is a compound of Formula (IX), wherein $R^1$ is

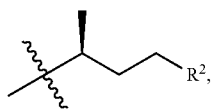

and $R^2$ is —$NH_2$. In some embodiments is a compound of Formula (IX), wherein $R^1$ is

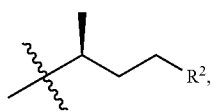

and $R^2$ is —$NHCH_3$. In some embodiments is a compound of Formula (IX), wherein $R^1$ is

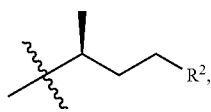

and $R^2$ is —$N(CH_3)_2$.

In some embodiments is a compound of Formula (IX), wherein $R^1$ is

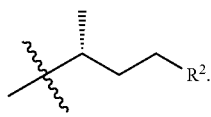

In some embodiments is a compound of Formula (IX), wherein $R^1$ is

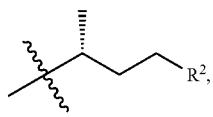

and $R^2$ is H. In some embodiments is a compound of Formula (IX), wherein $R^1$ is

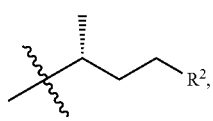

and $R^2$ is alkyl. In some embodiments is a compound of Formula (IX), wherein $R^1$ is

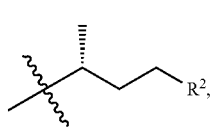

and $R^2$ is methyl. In some embodiments is a compound of Formula (IX), wherein $R^1$ is

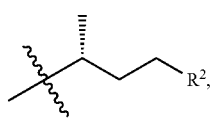

and $R^2$ is ethyl. In some embodiments is a compound of Formula (IX), wherein $R^1$ is

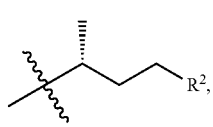

and $R^2$ is isopropyl. In some embodiments is a compound of Formula (IX), wherein $R^1$ is

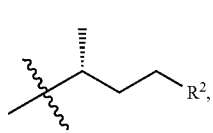

and $R^2$ is —$NR^{13}R^{14}$. In some embodiments is a compound of Formula (IX), wherein $R^1$ is

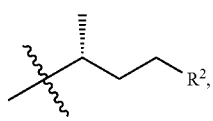

and $R^2$ is —$NH_2$. In some embodiments is a compound of Formula (IX), wherein $R^1$ is

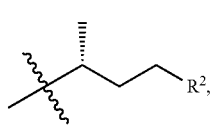

and $R^2$ is —$NHCH_3$. In some embodiments is a compound of Formula (IX), wherein $R^1$ is

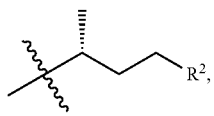

and $R^2$ is —$N(CH_3)_2$.

In some embodiments described above or below is a compound of Formula (IX), wherein n is 0.

In some embodiments described above or below is a compound of Formula (IX), wherein n is 1. In some embodiments described above or below is a compound of Formula (IX), wherein n is 1 and $R^8$ is selected from halogen, —OH, —$NO_2$, —$N_3$, —CN, alkyl, alkoxy, haloalkoxy, haloalkyl, hydroxyalkyl, alkoxyalkyl, -alkylene($NR^{13}R^{14}$), -alkylene (cycloalkyl), -alkylene(heterocyclyl), cycloalkyl, heterocyclyl, aryl, heteroaryl, —$SR^{13}$, —$SOR^{13}$, —$SO_2R^{13}$, —$SO_2NR^{13}R^{14}$, —$NR^{13}R^{14}$, —$NR^{13}SO_2R^{14}$, —$NR^{13}C(O)R^{14}$, —$NR^{13}C(O)OR^{14}$, —$NR^{13}C(O)NR^{13}R^{14}$, —$C(O)R^{14}$, —$C(O)OR^{14}$, or —$C(O)NR^{13}R^{14}$. In some embodiments described above or below is a compound of Formula (IX), wherein n is 1 and $R^8$ is selected from halogen, —CN, alkyl, alkoxy, haloalkoxy, or haloalkyl. In some embodiments described above or below is a compound of Formula (IX), wherein n is 1 and $R^8$ is halogen. In some embodiments described above or below is a compound of Formula (IX), wherein n is 1 and $R^8$ is F. In some embodiments described above or below is a compound of Formula (IX), wherein n is 1 and $R^8$ is Cl. In some embodiments described above or below is a compound of Formula (IX), wherein n is 1 and $R^8$ is —CN. In some embodiments described above or below is a compound of Formula (IX), wherein n is 1 and $R^8$ is alkyl. In some embodiments described above or below is a compound of Formula (IX), wherein n is 1 and $R^8$ is methyl. In some embodiments described above or below is a compound of Formula (IX), wherein n is 1 and $R^8$ is ethyl. In some embodiments described above or below is a compound of Formula (IX), wherein n is 1 and $R^8$ is alkoxy. In some embodiments described above or below is a compound of Formula (IX), wherein n is 1 and $R^8$ is methoxy. In some embodiments described above or below is a compound of Formula (IX), wherein n is 1 and $R^8$ is ethoxy. In some embodiments described above or below is a compound of Formula (IX), wherein n is 1 and $R^8$ is haloalkoxy. In some embodiments described above or below is a compound of Formula (IX), wherein n is 1 and $R^8$ is —$OCF_3$. In some embodiments described above or below is a compound of Formula (IX), wherein n is 1 and $R^8$ is haloalkyl. In some embodiments described above or below is a compound of Formula (IX), wherein n is 1 and $R^8$ is —$CF_3$.

In some embodiments described above or below is a compound of Formula (IX), wherein n is 2. In some embodiments described above or below is a compound of Formula (IX), wherein n is 2 and $R^8$ is independently selected from halogen, —OH, —$NO_2$, —$N_3$, —CN, alkyl, alkoxy, haloalkoxy, haloalkyl, hydroxyalkyl, alkoxyalkyl, -alkylene ($NR^{13}R^{14}$), -alkylene(cycloalkyl), -alkylene(heterocyclyl), cycloalkyl, heterocyclyl, aryl, heteroaryl, —$SR^{13}$, —$SOR^{13}$, —$SO_2R^{13}$, —$SO_2NR^{13}R^{14}$, —$NR^{13}R^{14}$, —$NR^{13}SO_2R^{14}$, —$NR^{13}C(O)R^{14}$, —$NR^{13}C(O)OR^{14}$, —$NR^{13}C(O)NR^{13}R^{14}$, —$C(O)R^{14}$, —$C(O)OR^{14}$, and —$C(O)NR^{13}R^{14}$.

In some embodiments described above or below is a compound of Formula (IX), wherein n is 2 and $R^8$ is independently selected from halogen, —CN, alkyl, alkoxy, haloalkoxy, and haloalkyl. In some embodiments described above or below is a compound of Formula (IX), wherein n is 2 and $R^8$ is halogen. In some embodiments described above or below is a compound of Formula (IX), wherein n is 2 and each $R^8$ is F. In some embodiments described above or below is a compound of Formula (IX), wherein n is 2 and each $R^8$ is Cl. In some embodiments described above or below is a compound of Formula (IX), wherein n is 2 and $R^8$ is independently selected from halogen and —CN. In some embodiments described above or below is a compound of Formula (IX), wherein n is 2 and $R^8$ is independently selected from halogen and alkyl. In some embodiments described above or below is a compound of Formula (IX), wherein n is 2 and $R^8$ is independently selected from —CN and alkyl. In some embodiments described above or below is a compound of Formula (IX), wherein n is 2 and two adjacent $R^8$ form a heterocyclyl ring.

In some embodiments described above or below is a compound of Formula (IX), wherein $Z^1$ is O. In some embodiments described above or below is a compound of Formula (IX), wherein $Z^1$ is S. In some embodiments described above or below is a compound of Formula (IX), wherein $Z^1$ is $NR^{13}$. In some embodiments described above or below is a compound of Formula (IX), wherein $Z^1$ is $N(CH_3)$. In some embodiments described above or below is a compound of Formula (IX), wherein $Z^1$ is NH.

In some embodiments described above or below is a compound of Formula (IX), wherein $Z^2$ is O. In some embodiments described above or below is a compound of Formula (IX), wherein $Z^2$ is S. In some embodiments described above or below is a compound of Formula (IX), wherein $Z^2$ is $NR^{13}$. In some embodiments described above or below is a compound of Formula (IX), wherein $Z^2$ is $N(CH_3)$. In some embodiments described above or below is a compound of Formula (IX), wherein $Z^2$ is NH. In some embodiments described above or below is a compound of Formula (IX), wherein $Z^2$ is $CH_2$.

In some embodiments described above or below is a compound of Formula (IX), wherein $Z^1$ and $Z^2$ are each O.

In some embodiments described above or below is a compound of Formula (IX), wherein —X—Y— is —$CH_2CH_2$—. In some embodiments described above or below is a compound of Formula (IX), wherein —X—Y— is —CH═CH—. In some embodiments described above or below is a compound of Formula (IX), wherein —X—Y— is —CH═N—. In some embodiments described above or below is a compound of Formula (IX), wherein —X—Y— is —N═CH—.

In another embodiment is a compound of Formula (IX) having the structure:

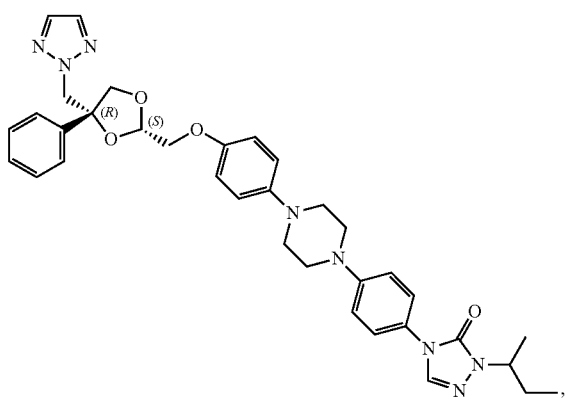

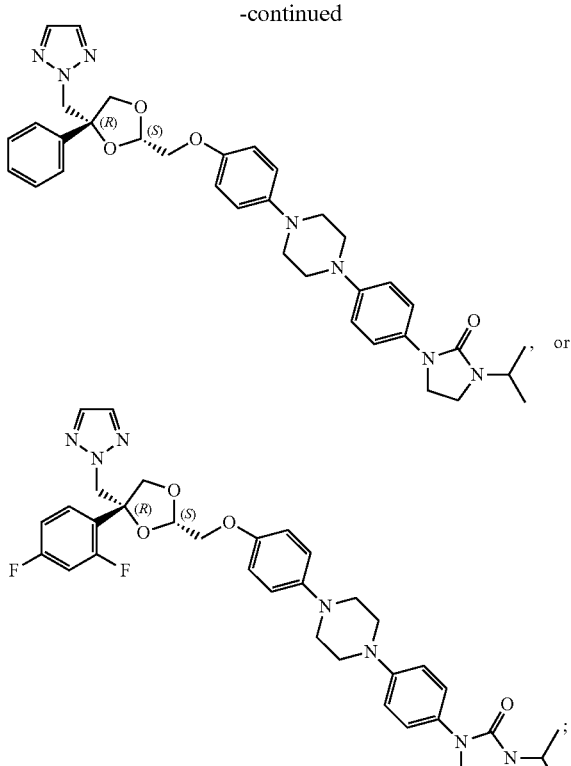

or a pharmaceutically acceptable salt, pharmaceutically acceptable solvate, or pharmaceutically acceptable prodrug thereof.

In another aspect, provided herein are compounds of Formula (IXa) having the structure:

Formula (IXa)

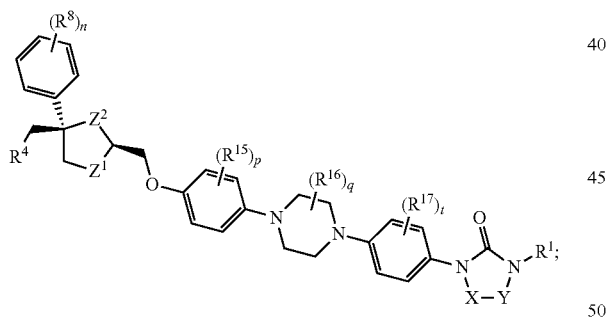

wherein:
—X—Y— is —CH$_2$CH$_2$—, —CH=CH—, —CH=N—, or —N=CH—;
Z$^1$ is selected from O, S, NH, and NR$^{13}$;
Z$^2$ is selected from O, S, CH$_2$, NH, and NR$^{13}$;
R$^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

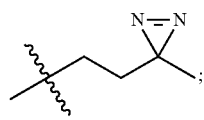

R$^2$ is H, alkyl, or —NR$^{13}$R$^{14}$;
R$^3$ is —OH, alkyl, or —NR$^{13}$R$^{14}$;
R$^4$ is halogen, alkyl,

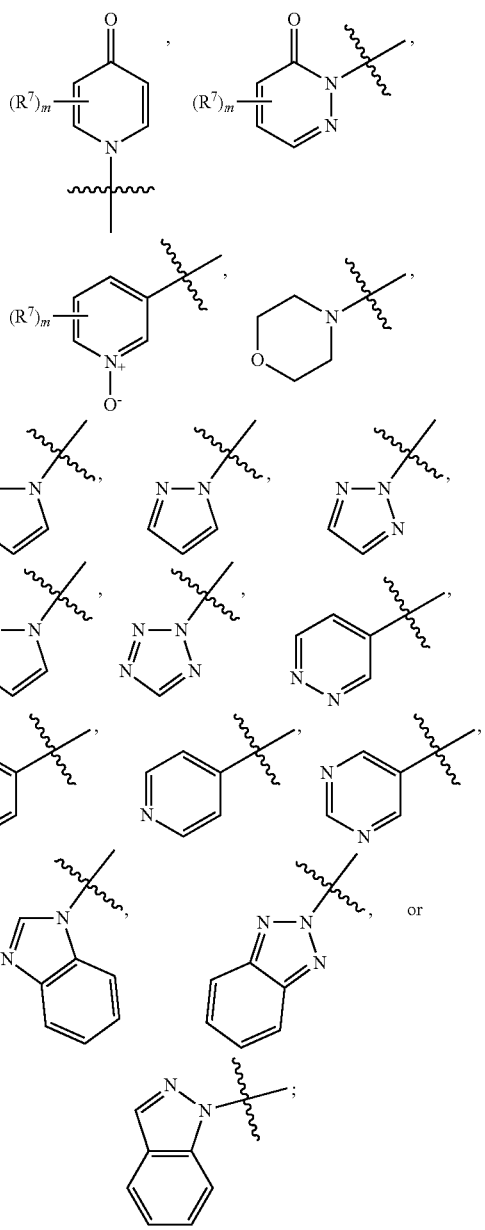

each R$^7$ is independently selected from halogen and alkyl;
each R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;
each R$^{15}$ is independently selected from haloalkyl, -alkylene(NR$^{13}$R$^{14}$), —NR$^{13}$R$^{14}$, and —SO$_2$R$^{13}$;

each $R^{16}$ is independently selected from halogen, alkyl, and haloalkyl;
each $R^{17}$ is independently selected from halogen, alkyl, haloalkyl, and —CN;
n is selected from 0, 1, 2, 3, and 4;
m is selected from 0, 1, and 2;
p is selected from 0, 1, 2, 3, and 4;
q is selected from 0, 1, 2, 3, and 4; and
t is independently selected from 0, 1, 2, 3, and 4;
or a pharmaceutically acceptable salt, pharmaceutically acceptable solvate, pharmaceutically acceptable prodrug, or stereoisomer thereof.

In some embodiments is a compound of Formula (IXa), wherein $R^4$ is halogen. In some embodiments is a compound of Formula (IXa), wherein $R^4$ is F. In some embodiments is a compound of Formula (IXa), wherein $R^4$ is Cl. In some embodiments is a compound of Formula (IXa), wherein $R^4$ is alkyl. In some embodiments is a compound of Formula (IXa), wherein $R^4$ is methyl. In some embodiments is a compound of Formula (IXa), wherein $R^4$ is ethyl. In some embodiments is a compound of Formula (IXa), wherein $R^4$ is

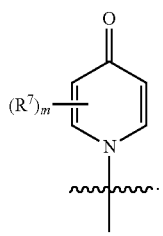

In some embodiments is a compound of Formula (IXa), wherein $R^4$ is

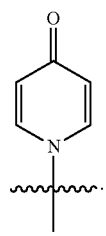

In some embodiments is a compound of Formula (IXa), wherein $R^4$ is

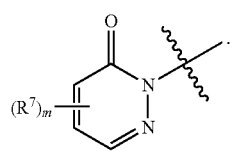

In some embodiments is a compound of Formula (IXa), wherein $R^4$ is

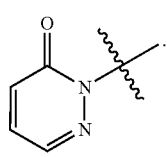

In some embodiments is a compound of Formula (IXa), wherein $R^4$ is

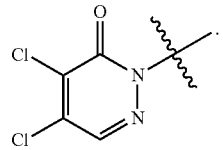 [SMILES: *n1ncc(Cl)c(Cl)c1=O]

In some embodiments is a compound of Formula (IXa), wherein $R^4$ is

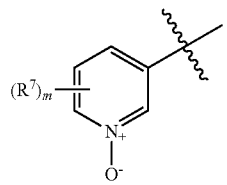

In some embodiments is a compound of Formula (IXa), wherein $R^4$ is

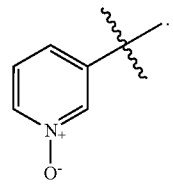 [SMILES: *c1ccc[n+]([O-])c1]

In some embodiments is a compound of Formula (IXa), wherein $R^4$ is

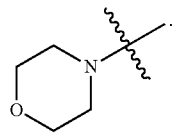 [SMILES: *N1CCOCC1]

In some embodiments is a compound of Formula (IXa), wherein $R^4$ is

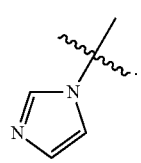

In some embodiments is a compound of Formula (IXa), wherein $R^4$ is

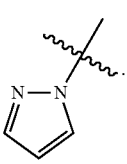 [SMILES: *n1cccn1]

In some embodiments is a compound of Formula (IXa), wherein $R^4$ is

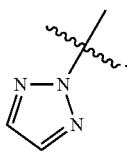 [SMILES: *n1nccn1]

In some embodiments is a compound of Formula (IXa), wherein $R^4$ is

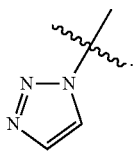

In some embodiments is a compound of Formula (IXa), wherein $R^4$ is

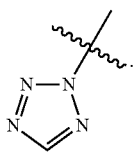

In some embodiments is a compound of Formula (IXa), wherein $R^4$ is

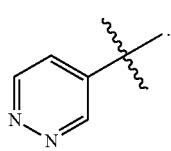

In some embodiments is a compound of Formula (IXa), wherein $R^4$ is

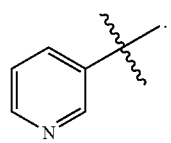 [SMILES: *c1cccnc1]

In some embodiments is a compound of Formula (IXa), wherein $R^4$ is

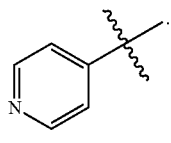

In some embodiments is a compound of Formula (IXa), wherein $R^4$ is

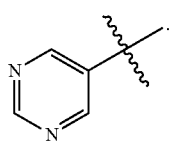

In some embodiments is a compound of Formula (IXa), wherein $R^4$ is

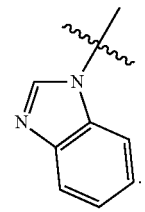

In some embodiments is a compound of Formula (IXa), wherein $R^4$ is

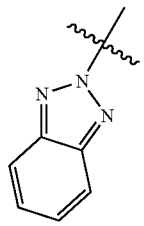

In some embodiments is a compound of Formula (IXa), wherein $R^4$ is

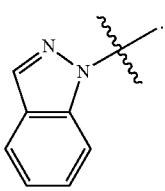 [SMILES: *n1ncc2ccccc21]

In some embodiments is a compound of Formula (IXa), wherein $R^1$ is —CH(CH$_3$)CH$_2$CH$_2$R$^2$. In some embodiments is a compound of Formula (IXa), wherein $R^1$ is —CH(CH$_3$)CH$_2$CH$_2$R$^2$, and $R^2$ is H. In some embodiments is a compound of Formula (IXa), wherein $R^1$ is —CH(CH$_3$)CH$_2$CH$_2$R$^2$, and $R^2$ is alkyl. In some embodiments is a compound of Formula (IXa), wherein $R^1$ is —CH(CH$_3$)CH$_2$CH$_2$R$^2$, and $R^2$ is methyl. In some embodiments is a compound of Formula (IXa), wherein $R^1$ is —CH(CH$_3$)CH$_2$CH$_2$R$^2$, and $R^2$ is ethyl. In some embodiments is a compound of Formula (IXa), wherein $R^1$ is —CH(CH$_3$)CH$_2$CH$_2$R$^2$, and $R^2$ is isopropyl. In some embodiments is a compound of Formula (IXa), wherein $R^1$ is —CH(CH$_3$)CH$_2$CH$_2$R$^2$, and $R^2$ is —NR$^{13}$R$^{14}$. In some embodiments is a compound of Formula (IXa), wherein $R^1$ is —CH(CH$_3$)CH$_2$CH$_2$R$^2$, and $R^2$ is —NH$_2$. In some embodiments is a compound of Formula (IXa), wherein $R^1$ is —CH(CH$_3$)CH$_2$CH$_2$R$^2$, and $R^2$ is —NHCH$_3$. In some embodiments is a compound of Formula (IXa), wherein $R^1$ is —CH(CH$_3$)CH$_2$CH$_2$R$^2$, and $R^2$ is —N(CH$_3$)$_2$.

In some embodiments is a compound of Formula (IXa), wherein $R^1$ is —CH(CH$_2$CH$_3$)$_2$. In some embodiments is a compound of Formula (IXa), wherein $R^1$ is —CH(CH$_3$)$_2$. In some embodiments is a compound of Formula (IXa), wherein $R^1$ is —CH(CH$_2$CH$_3$)CH(R$^3$)CH$_3$. In some embodiments is a compound of Formula (IXa), wherein $R^1$ is —CH(CH$_2$CH$_3$)CH(R$^3$)CH$_3$, and $R^3$ is —OH. In some embodiments is a compound of Formula (IXa), wherein $R^1$ is —CH(CH$_2$CH$_3$)CH(R$^3$)CH$_3$, and $R^3$ is alkyl. In some embodiments is a compound of Formula (IXa), wherein $R^1$ is —CH(CH$_2$CH$_3$)CH(R$^3$)CH$_3$, and R$^3$ is methyl. In some embodiments is a compound of Formula (IXa), wherein R$^1$ is —CH(CH$_2$CH$_3$)CH(R$^3$)CH$_3$, and R$^3$ is ethyl. In some embodiments is a compound of Formula (IXa), wherein R$^1$ is —CH(CH$_2$CH$_3$)CH(R$^3$)CH$_3$, and R$^3$ is —NR$^{13}$R$^{14}$. In some embodiments is a compound of Formula (IXa), wherein R$^1$ is —CH(CH$_2$CH$_3$)CH(R$^3$)CH$_3$, and R$^3$ is —NH$_2$. In some embodiments is a compound of Formula (IXa), wherein R$^1$ is —CH(CH$_2$CH$_3$)CH(R$^3$)CH$_3$, and R$^3$ is —NHCH$_3$. In some embodiments is a compound of Formula (IXa), wherein R$^1$ is —CH(CH$_2$CH$_3$)CH(R$^3$)CH$_3$, and R$^3$ is —N(CH$_3$)$_2$. In some embodiments is a compound of Formula (IXa), wherein R$^1$ is -alkylene(cycloalkyl). In some embodiments is a compound of Formula (IXa), wherein R$^1$ is —CH$_2$CH$_2$(cycloalkyl). In some embodiments is a compound of Formula (IXa), wherein R$^1$ is —CH$_2$(cycloalkyl). In some embodiments is a compound of Formula (IXa), wherein R$^1$ is —CH$_2$(cyclobutyl). In some embodiments is a compound of Formula (IXa), wherein R$^1$ is —CH$_2$(cyclopentyl). In some embodiments is a compound of Formula (IXa), wherein R$^1$ is —CH$_2$(cyclohexyl). In some embodiments is a compound of Formula (IXa), wherein R$^1$ is

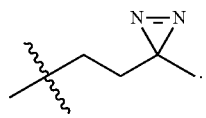 [SMILES: *CCC1(C)N=N1]

In some embodiments is a compound of Formula (IXa), wherein R$^1$ is

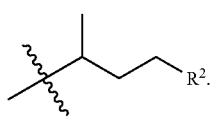

In some embodiments is a compound of Formula (IXa), wherein R$^1$ is

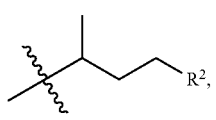

and R$^2$ is H. In some embodiments is a compound of Formula (IXa), wherein R$^1$ is

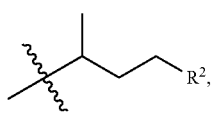

and R$^2$ is alkyl. In some embodiments is a compound of Formula (IXa), wherein R$^1$ is

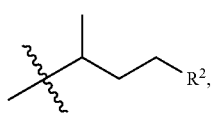

and R$^2$ is methyl. In some embodiments is a compound of Formula (IXa), wherein R$^1$ is

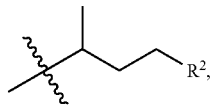

and R$^2$ ethyl. In some embodiments is a compound of Formula (IXa), wherein R$^1$ is

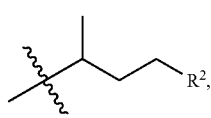

and R$^2$ is isopropyl. In some embodiments is a compound of Formula (IXa), wherein R$^1$ is

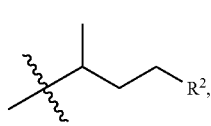

and R$^2$ is —NR$^{13}$R$^{14}$. In some embodiments is a compound of Formula (IXa), wherein R$^1$ is

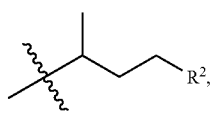

and R$^2$ is —NH$_2$. In some embodiments is a compound of Formula (IXa), wherein R$^1$ is

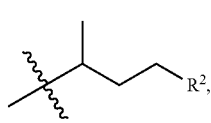

and R$^2$ is —NHCH$_3$. In some embodiments is a compound of Formula (IXa), wherein R$^1$ is

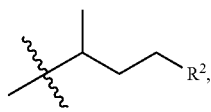

and R$^2$ is —N(CH$_3$)$_2$.

In some embodiments is a compound of Formula (IXa), wherein R$^1$ is

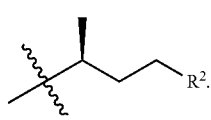

In some embodiments is a compound of Formula (IXa), wherein R$^1$ is

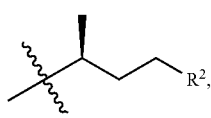

and R² is H. In some embodiments is a compound of Formula (IXa), wherein R¹ is


and R² is alkyl. In some embodiments is a compound of Formula (IXa), wherein R¹ is

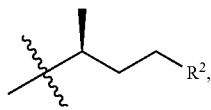

and R² is methyl. In some embodiments is a compound of Formula (IXa), wherein R¹ is

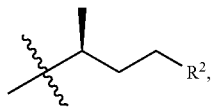

and R² is ethyl. In some embodiments is a compound of Formula (IXa), wherein R¹ is

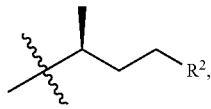

and R² is isopropyl. In some embodiments is a compound of Formula (IXa), wherein R¹ is

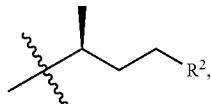

and R² is —NR¹³R¹⁴. In some embodiments is a compound of Formula (IXa), wherein R¹ is

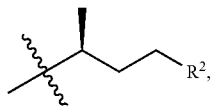

and R² is —NH₂. In some embodiments is a compound of Formula (IXa), wherein R¹ is

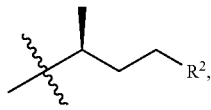

and R² is —NHCH₃. In some embodiments is a compound of Formula (IXa), wherein R¹ is

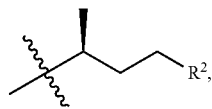

and R² is —N(CH₃)₂.

In some embodiments is a compound of Formula (IXa), wherein R¹ is

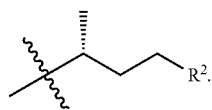

In some embodiments is a compound of Formula (IXa), wherein R¹ is

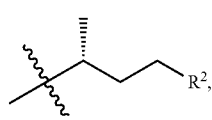

and R² is H. In some embodiments is a compound of Formula (IXa), wherein R¹ is

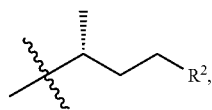

and R² is alkyl. In some embodiments is a compound of Formula (IXa), wherein R¹ is

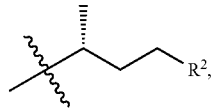

and R² is methyl. In some embodiments is a compound of Formula (IXa), wherein R¹ is

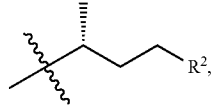

and R² is ethyl. In some embodiments is a compound of Formula (IXa), wherein R¹ is

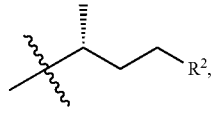

and R² is isopropyl. In some embodiments is a compound of Formula (IXa), wherein R¹ is

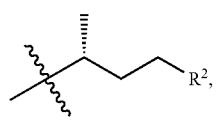

and R² is —NR¹³R¹⁴. In some embodiments is a compound of Formula (IXa), wherein R¹ is

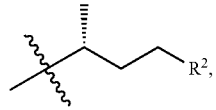

and R² is —NH₂. In some embodiments is a compound of Formula (IXa), wherein R¹ is

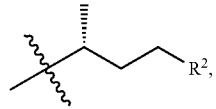

and R² is —NHCH₃. In some embodiments is a compound of Formula (IXa), wherein R¹ is

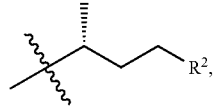

and R² is —N(CH₃)₂.

In some embodiments described above or below is a compound of Formula (IXa), wherein n is 0.

In some embodiments described above or below is a compound of Formula (IXa), wherein n is 1. In some embodiments described above or below is a compound of Formula (IXa), wherein n is 1 and R⁸ is selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, or —C(O)NR¹³R¹⁴. In some embodiments described above or below is a compound of Formula (IXa), wherein n is 1 and R⁸ is selected from halogen, —CN, alkyl, alkoxy, haloalkoxy, or haloalkyl. In some embodiments described above or below is a compound of Formula (IXa), wherein n is 1 and R⁸ is halogen. In some embodiments described above or below is a compound of Formula (IXa), wherein n is 1 and R⁸ is F. In some embodiments described above or below is a compound of Formula (IXa), wherein n is 1 and R⁸ is Cl. In some embodiments described above or below is a compound of Formula (IXa), wherein n is 1 and R⁸ is —CN. In some embodiments described above or below is a compound of Formula (IXa), wherein n is 1 and R⁸ is alkyl. In some embodiments described above or below is a compound of Formula (IXa), wherein n is 1 and R⁸ is methyl. In some embodiments described above or below is a compound of Formula (IXa), wherein n is 1 and R⁸ is ethyl. In some embodiments described above or below is a compound of Formula (IXa), wherein n is 1 and R⁸ is alkoxy. In some embodiments described above or below is a compound of Formula (IXa), wherein n is 1 and R⁸ is methoxy. In some embodiments described above or below is a compound of Formula (IXa), wherein n is 1 and R⁸ is ethoxy. In some embodiments described above or below is a compound of Formula (IXa), wherein n is 1 and R⁸ is haloalkoxy. In some embodiments described above or below is a compound of Formula (IXa), wherein n is 1 and R⁸ is —OCF₃. In some embodiments described above or below is a compound of Formula (IXa), wherein n is 1 and R⁸ is haloalkyl. In some embodiments described above or below is a compound of Formula (IXa), wherein n is 1 and R⁸ is —CF₃.

In some embodiments described above or below is a compound of Formula (IXa), wherein n is 2. In some embodiments described above or below is a compound of Formula (IXa), wherein n is 2 and R⁸ is independently selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, and —C(O)NR¹³R¹⁴. In some embodiments described above or below is a compound of Formula (IXa), wherein n is 2 and R⁸ is independently selected from halogen, —CN, alkyl, alkoxy, haloalkoxy, and haloalkyl. In some embodiments described above or below is a compound of Formula (IXa), wherein n is 2 and R⁸ is halogen. In some embodiments described above or below is a compound of Formula (IXa), wherein n is 2 and each R⁸ is F. In some embodiments described above or below is a compound of Formula (IXa), wherein n is 2 and each R⁸ is Cl. In some embodiments described above or below is a compound of Formula (IXa), wherein n is 2 and R⁸ is independently selected from halogen and —CN. In some embodiments described above or below is a compound of Formula (IXa), wherein n is 2 and R⁸ is independently selected from halogen and alkyl. In some embodiments described above or below is a compound of Formula (IXa), wherein n is 2 and R⁸ is independently selected from —CN and alkyl. In some embodiments described above or below is a compound of Formula (IXa), wherein n is 2 and two adjacent R⁸ form a heterocyclyl ring.

In some embodiments described above or below is a compound of Formula (IXa), wherein Z¹ is O. In some embodiments described above or below is a compound of Formula (IXa), wherein Z¹ is S. In some embodiments described above or below is a compound of Formula (IXa), wherein Z¹ is NR¹³. In some embodiments described above or below is a compound of Formula (IXa), wherein Z¹ is N(CH₃). In some embodiments described above or below is a compound of Formula (IXa), wherein Z¹ is NH.

In some embodiments described above or below is a compound of Formula (IXa), wherein Z² is O. In some embodiments described above or below is a compound of Formula (IXa), wherein Z² is S. In some embodiments described above or below is a compound of Formula (IXa), wherein Z² is NR¹³. In some embodiments described above or below is a compound of Formula (IXa), wherein Z² is N(CH₃). In some embodiments described above or below is a compound of Formula (IXa), wherein Z² is NH. In some embodiments described above or below is a compound of Formula (IXa), wherein Z² is CH₂.

In some embodiments described above or below is a compound of Formula (IXa), wherein Z¹ and Z² are each O.

In some embodiments described above or below is a compound of Formula (IXa), wherein —X—Y— is —CH₂CH₂—. In some embodiments described above or below is a compound of Formula (IXa), wherein —X—Y— is —CH=CH—. In some embodiments described above or below is a compound of Formula (IXa), wherein —X—Y— is —CH=N—. In some embodiments described above or below is a compound of Formula (IXa), wherein —X—Y— is —N=CH—.

In another embodiment is a compound of Formula (IXa) having the structure:
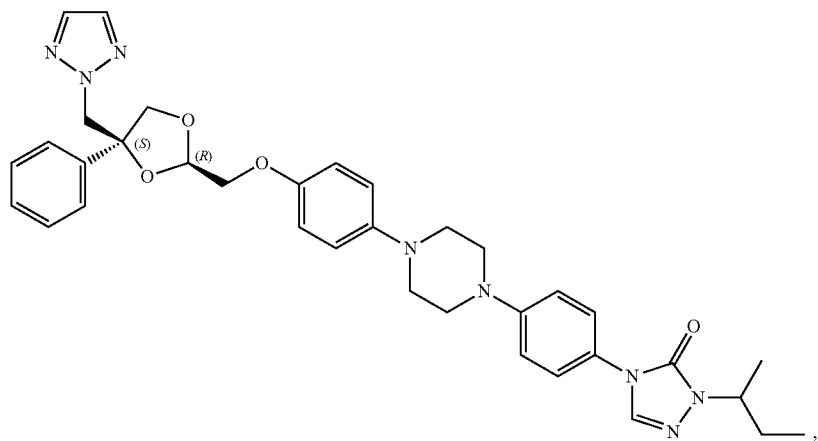
,
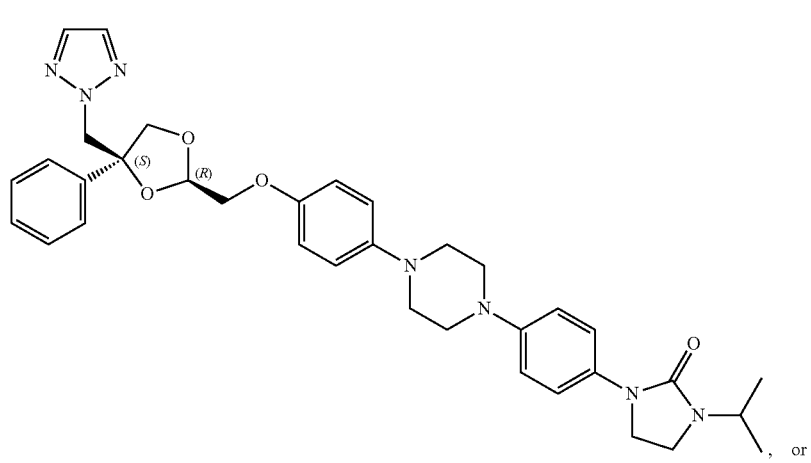
, or
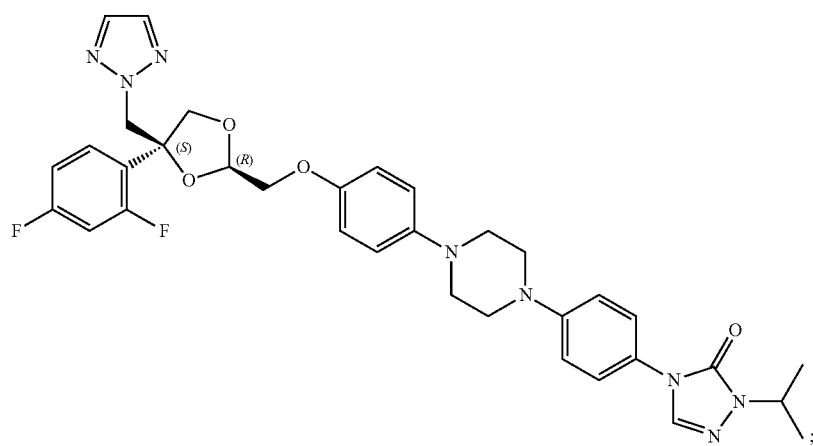
;
or a pharmaceutically acceptable salt, pharmaceutically acceptable solvate, or pharmaceutically acceptable prodrug thereof.

In another aspect, provided herein are compounds of Formula (X) having the structure:

Formula (X)

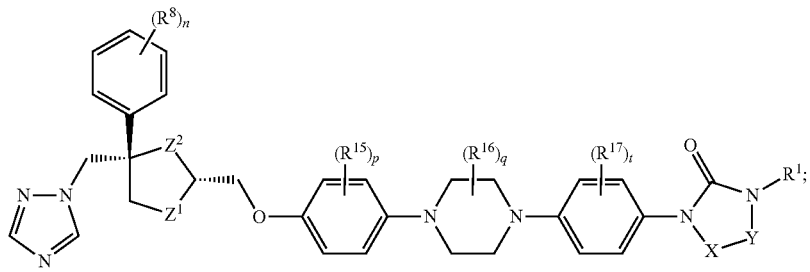

wherein:
—X—Y— is —CH$_2$CH$_2$—, —CH=CH—, —CH=N—, or —N=CH—;
Z$^1$ is selected from O, S, NH, and NR$^{13}$;
Z$^2$ is selected from O, S, CH$_2$, NH, and NR$^{13}$;
R$^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

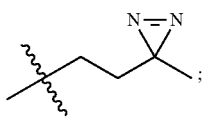 [SMILES: *CCC1(C)N=N1]

R$^2$ is H, alkyl, or —NR$^{13}$R$^{14}$;
R$^3$ is —OH, alkyl, or —NR$^{13}$R$^{14}$;
each R$^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;
each R$^{13}$ and each R$^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;
each R$^{15}$ is independently selected from haloalkyl, -alkylene(NR$^{13}$R$^{14}$), —NR$^{13}$R$^{14}$, and —SO$_2$R$^{13}$;
each R$^{16}$ is independently selected from halogen, alkyl, and haloalkyl;
each R$^{17}$ is independently selected from halogen, alkyl, haloalkyl, and —CN;
n is selected from 0, 1, 2, 3, and 4;
p is selected from 0, 1, 2, 3, and 4;
q is selected from 0, 1, 2, 3, and 4; and
t is independently selected from 0, 1, 2, 3, and 4;
wherein when Z$^1$ and Z$^2$ are both O then —X—Y— is —CH=CH—, —CH=N—, or —N=CH—; or a pharmaceutically acceptable salt, pharmaceutically acceptable solvate, pharmaceutically acceptable prodrug, or stereoisomer thereof.

In some embodiments is a compound of Formula (X), wherein R$^1$ is —CH(CH$_3$)CH$_2$CH$_2$R$^2$. In some embodiments is a compound of Formula (X), wherein R$^1$ is —CH(CH$_3$)CH$_2$CH$_2$R$^2$, and R$^2$ is H. In some embodiments is a compound of Formula (X), wherein R$^1$ is —CH(CH$_3$)CH$_2$CH$_2$R$^2$, and R$^2$ is alkyl. In some embodiments is a compound of Formula (X), wherein R$^1$ is —CH(CH$_3$)CH$_2$CH$_2$R$^2$, and R$^2$ is methyl. In some embodiments is a compound of Formula (X), wherein R$^1$ is —CH(CH$_3$)CH$_2$CH$_2$R$^2$, and R$^2$ is ethyl. In some embodiments is a compound of Formula (X), wherein R$^1$ is —CH(CH$_3$)CH$_2$CH$_2$R$^2$, and R$^2$ is isopropyl. In some embodiments is a compound of Formula (X), wherein R$^1$ is —CH(CH$_3$)CH$_2$CH$_2$R$^2$, and R$^2$ is —NR$^{13}$R$^{14}$. In some embodiments is a compound of Formula (X), wherein R$^1$ is —CH(CH$_3$)CH$_2$CH$_2$R$^2$, and R$^2$ is —NH$_2$. In some embodiments is a compound of Formula (X), wherein R$^1$ is —CH(CH$_3$)CH$_2$CH$_2$R$^2$, and R$^2$ is —NHCH$_3$. In some embodiments is a compound of Formula (X), wherein R$^1$ is —CH(CH$_3$)CH$_2$CH$_2$R$^2$, and R$^2$ is —N(CH$_3$)$_2$.

In some embodiments is a compound of Formula (X), wherein R$^1$ is —CH(CH$_2$CH$_3$)$_2$. In some embodiments is a compound of Formula (X), wherein R$^1$ is —CH(CH$_3$)$_2$. In some embodiments is a compound of Formula (X), wherein R$^1$ is —CH(CH$_2$CH$_3$)CH(R$^3$)CH$_3$. In some embodiments is a compound of Formula (X), wherein R$^1$ is —CH(CH$_2$CH$_3$)CH(R$^3$)CH$_3$, and R$^3$ is —OH. In some embodiments is a compound of Formula (X), wherein R$^1$ is —CH(CH$_2$CH$_3$)CH(R$^3$)CH$_3$, and R$^3$ is alkyl. In some embodiments is a compound of Formula (X), wherein R$^1$ is —CH(CH$_2$CH$_3$)CH(R$^3$)CH$_3$, and R$^3$ is methyl. In some embodiments is a compound of Formula (X), wherein R$^1$ is —CH(CH$_2$CH$_3$)CH(R$^3$)CH$_3$, and R$^3$ is ethyl. In some embodiments is a compound of Formula (X), wherein R$^1$ is —CH(CH$_2$CH$_3$)CH(R$^3$)CH$_3$, and R$^3$ is —NR$^{13}$R$^{14}$. In some embodiments is a compound of Formula (X), wherein R$^1$ is —CH(CH$_2$CH$_3$)CH(R$^3$)CH$_3$, and R$^3$ is —NH$_2$. In some embodiments is a compound of Formula (X), wherein R$^1$ is —CH(CH$_2$CH$_3$)CH(R$^3$)CH$_3$, and R$^3$ is —NHCH$_3$. In some embodiments is a compound of Formula (X), wherein R$^1$ is —CH(CH$_2$CH$_3$)CH(R$^3$)CH$_3$, and R$^3$ is —N(CH$_3$)$_2$. In some embodiments is a compound of Formula (X), wherein R$^1$ is -alkylene(cycloalkyl). In some embodiments is a compound of Formula (X), wherein R$^1$ is —CH$_2$CH$_2$(cycloalkyl). In some embodiments is a compound of Formula (X), wherein R$^1$ is —CH$_2$(cycloalkyl). In some embodiments is a compound of Formula (X), wherein R$^1$ is —CH$_2$(cyclobutyl). In some embodiments is a compound of Formula (X), wherein R$^1$ is —CH$_2$(cyclopentyl). In some embodiments is a compound of Formula (X), wherein R$^1$ is —CH$_2$(cyclohexyl). In some embodiments is a compound of Formula (X), wherein R$^1$ is In some embodiments is a compound of Formula (X), wherein R¹ is

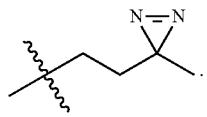

In some embodiments is a compound of Formula (X), wherein R¹ is

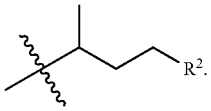

and R² is H. In some embodiments is a compound of Formula (X), wherein R¹ is

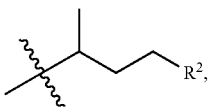

and R² is alkyl. In some embodiments is a compound of Formula (X), wherein R¹ is

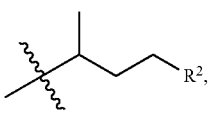

and R² is methyl. In some embodiments is a compound of Formula (X), wherein R¹ is

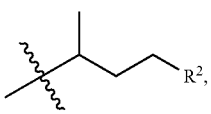

and R² is ethyl. In some embodiments is a compound of Formula (X), wherein R¹ is

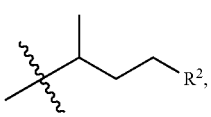

and R² is isopropyl. In some embodiments is a compound of Formula (X), wherein R¹ is

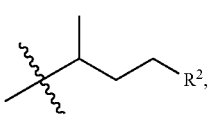

and R² is —NR¹³R¹⁴. In some embodiments is a compound of Formula (X), wherein R¹ is

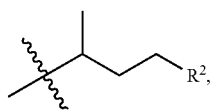

and R² is —NH₂. In some embodiments is a compound of Formula (X), wherein R¹ is

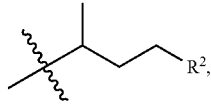

and R² is —NHCH₃. In some embodiments is a compound of Formula (X), wherein R¹ is

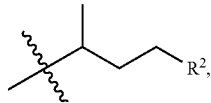

and R² is —N(CH₃)₂.

In some embodiments is a compound of Formula (X), wherein R¹ is

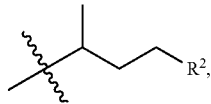

In some embodiments is a compound of Formula (X), wherein R¹ is

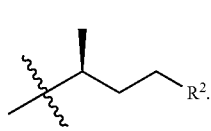

and R² is H. In some embodiments is a compound of Formula (X), wherein R¹ is

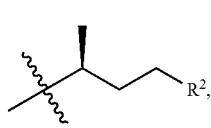

and R² is alkyl. In some embodiments is a compound of Formula (X), wherein R¹ is

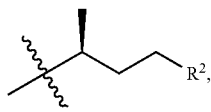

and $R^2$ is methyl. In some embodiments is a compound of Formula (X), wherein $R^1$ is

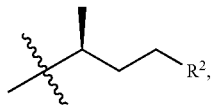

and $R^2$ is ethyl. In some embodiments is a compound of Formula (X), wherein $R^1$ is

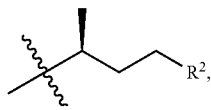

and $R^2$ is isopropyl. In some embodiments is a compound of Formula (X), wherein $R^1$ is

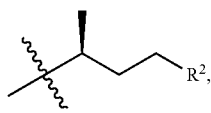

and $R^2$ is —$NR^{13}R^{14}$. In some embodiments is a compound of Formula (X), wherein $R^1$ is

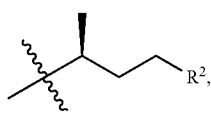

and $R^2$ is —$NH_2$. In some embodiments is a compound of Formula (X), wherein $R^1$ is

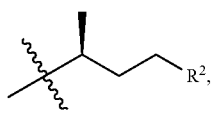

and $R^2$ is —$NHCH_3$. In some embodiments is a compound of Formula (X), wherein $R^1$ is

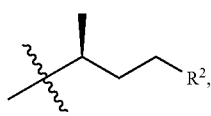

and $R^2$ is —$N(CH_3)_2$.

In some embodiments is a compound of Formula (X), wherein $R^1$ is

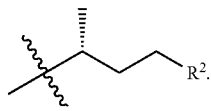

In some embodiments is a compound of Formula (X), wherein $R^1$ is

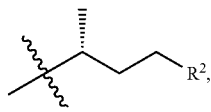

and $R^2$ is H. In some embodiments is a compound of Formula (X), wherein $R^1$ is

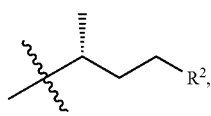

and $R^2$ is alkyl. In some embodiments is a compound of Formula (X), wherein $R^1$ is

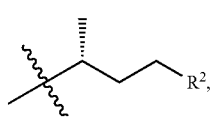

and $R^2$ is methyl. In some embodiments is a compound of Formula (X), wherein $R^1$ is

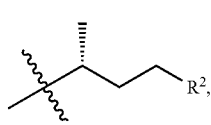

and $R^2$ is ethyl. In some embodiments is a compound of Formula (X), wherein $R^1$ is

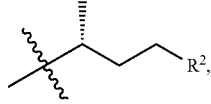

and $R^2$ is isopropyl. In some embodiments is a compound of Formula (X), wherein $R^1$ is

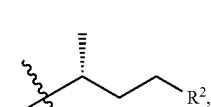

and $R^2$ is —$NR^{13}R^{14}$. In some embodiments is a compound of Formula (X), wherein $R^1$ is

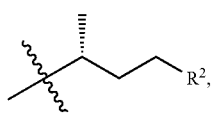

and $R^2$ is —NH$_2$. In some embodiments is a compound of Formula (X), wherein $R^1$ is

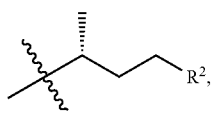

and $R^2$ is —NHCH$_3$. In some embodiments is a compound of Formula (X), wherein $R^1$ is

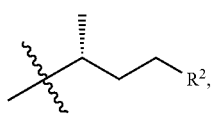

and $R^2$ is —N(CH$_3$)$_2$.

In some embodiments described above or below is a compound of Formula (X), wherein n is 0.

In some embodiments described above or below is a compound of Formula (X), wherein n is 1. In some embodiments described above or below is a compound of Formula (X), wherein n is 1 and $R^8$ is selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, or —C(O)NR$^{13}$R$^{14}$. In some embodiments described above or below is a compound of Formula (X), wherein n is 1 and $R^8$ is selected from halogen, —CN, alkyl, alkoxy, haloalkoxy, or haloalkyl. In some embodiments described above or below is a compound of Formula (X), wherein n is 1 and $R^8$ is halogen. In some embodiments described above or below is a compound of Formula (X), wherein n is 1 and $R^8$ is F. In some embodiments described above or below is a compound of Formula (X), wherein n is 1 and $R^8$ is Cl. In some embodiments described above or below is a compound of Formula (X), wherein n is 1 and $R^8$ is —CN. In some embodiments described above or below is a compound of Formula (X), wherein n is 1 and $R^8$ is alkyl. In some embodiments described above or below is a compound of Formula (X), wherein n is 1 and $R^8$ is methyl. In some embodiments described above or below is a compound of Formula (X), wherein n is 1 and $R^8$ is ethyl. In some embodiments described above or below is a compound of Formula (X), wherein n is 1 and $R^8$ is alkoxy. In some embodiments described above or below is a compound of Formula (X), wherein n is 1 and $R^8$ is methoxy. In some embodiments described above or below is a compound of Formula (X), wherein n is 1 and $R^8$ is ethoxy. In some embodiments described above or below is a compound of Formula (X), wherein n is 1 and $R^8$ is haloalkoxy. In some embodiments described above or below is a compound of Formula (X), wherein n is 1 and $R^8$ is —OCF$_3$. In some embodiments described above or below is a compound of Formula (X), wherein n is 1 and $R^8$ is haloalkyl. In some embodiments described above or below is a compound of Formula (X), wherein n is 1 and $R^8$ is —CF$_3$.

In some embodiments described above or below is a compound of Formula (X), wherein n is 2. In some embodiments described above or below is a compound of Formula (X), wherein n is 2 and $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$. In some embodiments described above or below is a compound of Formula (X), wherein n is 2 and $R^8$ is independently selected from halogen, —CN, alkyl, alkoxy, haloalkoxy, and haloalkyl. In some embodiments described above or below is a compound of Formula (X), wherein n is 2 and $R^8$ is halogen. In some embodiments described above or below is a compound of Formula (X), wherein n is 2 and each $R^8$ is F. In some embodiments described above or below is a compound of Formula (X), wherein n is 2 and each $R^8$ is Cl. In some embodiments described above or below is a compound of Formula (X), wherein n is 2 and $R^8$ is independently selected from halogen and —CN. In some embodiments described above or below is a compound of Formula (X), wherein n is 2 and $R^8$ is independently selected from halogen and alkyl. In some embodiments described above or below is a compound of Formula (X), wherein n is 2 and $R^8$ is independently selected from —CN and alkyl. In some embodiments described above or below is a compound of Formula (X), wherein n is 2 and two adjacent $R^8$ form a heterocyclyl ring.

In some embodiments described above or below is a compound of Formula (X), wherein $Z^1$ is O. In some embodiments described above or below is a compound of Formula (X), wherein $Z^1$ is S. In some embodiments described above or below is a compound of Formula (X), wherein $Z^1$ is NR$^{13}$. In some embodiments described above or below is a compound of Formula (X), wherein $Z^1$ is N(CH$_3$). In some embodiments described above or below is a compound of Formula (X), wherein $Z^1$ is NH.

In some embodiments described above or below is a compound of Formula (X), wherein $Z^2$ is O. In some embodiments described above or below is a compound of Formula (X), wherein $Z^2$ is S. In some embodiments described above or below is a compound of Formula (X), wherein $Z^2$ is NR$^{13}$. In some embodiments described above or below is a compound of Formula (X), wherein $Z^2$ is N(CH$_3$). In some embodiments described above or below is a compound of Formula (X), wherein $Z^2$ is NH. In some embodiments described above or below is a compound of Formula (X), wherein $Z^2$ is CH$_2$.

In some embodiments described above or below is a compound of Formula (X), wherein $Z^1$ and $Z^2$ are each O.

In some embodiments described above or below is a compound of Formula (X), wherein —X—Y— is —CH$_2$CH$_2$—. In some embodiments described above or below is a compound of Formula (X), wherein —X—Y— is —CH=CH—. In some embodiments described above or below is a compound of Formula (X), wherein —X—Y— is —CH=N—. In some embodiments described above or below is a compound of Formula (X), wherein —X—Y— is —N=CH—.

In another embodiment is a compound of Formula (X) having the structure:

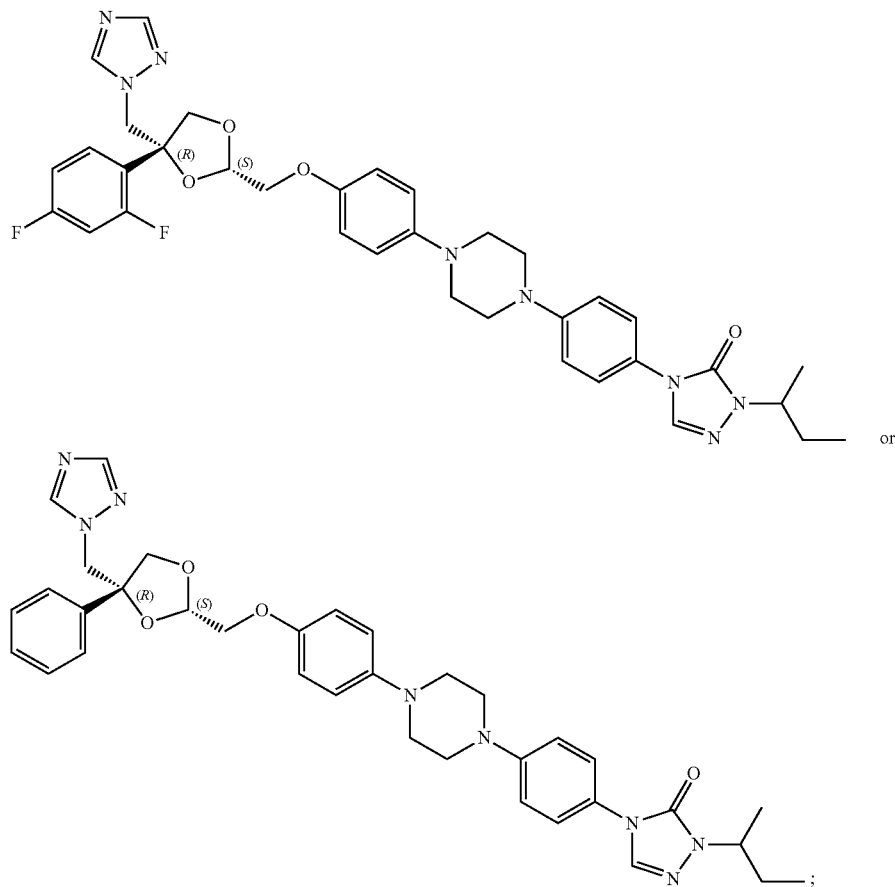

or

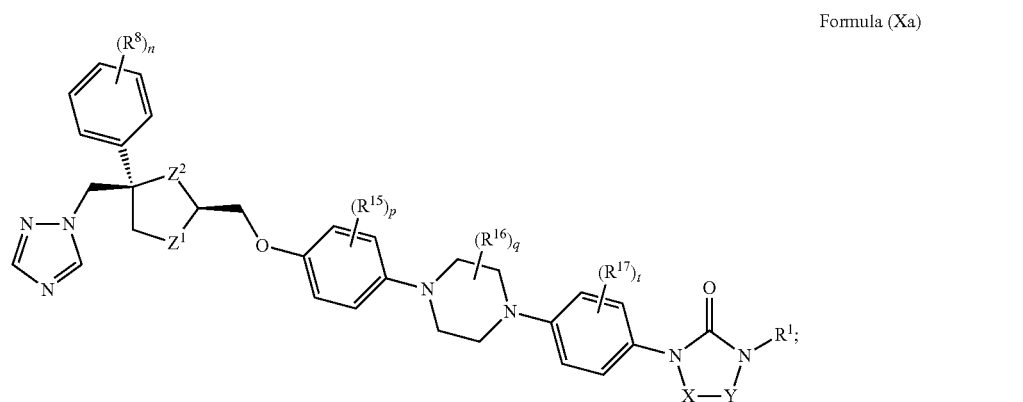

In another aspect, provided herein are compounds of Formula (Xa) having the structure:

Formula (Xa)

wherein:

—X—Y— is —CH$_2$CH$_2$—, —CH=CH—, —CH=N—, or —N=CH—;

Z$^1$ is selected from O, S, NH, and NR$^{13}$;

Z$^2$ is selected from O, S, CH$_2$, NH, and NR$^{13}$;

R$^1$ is —CH(CH$_3$)CH$_2$CH$_2$R$^2$, —CH(CH$_2$CH$_3$)$_2$, —CH(CH$_3$)$_2$, —CH$_2$CH(CH$_3$)$_2$, —CH(CH$_2$CH$_3$)CH(R$^3$)CH$_3$, -alkylene(cycloalkyl), or

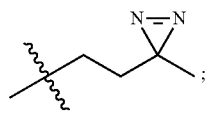

R$^2$ is H, alkyl, or —NR$^{13}$R$^{14}$;

R$^3$ is —OH, alkyl, or —NR$^{13}$R$^{14}$;

each $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent R$^8$ form a heterocyclyl ring;

each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or R$^{13}$ and R$^{14}$ taken together form a heterocycle with the atoms to which they are attached;

each $R^{15}$ is independently selected from haloalkyl, -alkylene(NR$^{13}$R$^{14}$), —NR$^{13}$R$^{14}$, and —SO$_2$R$^{13}$;

each $R^{16}$ is independently selected from halogen, alkyl, and haloalkyl;

each $R^{17}$ is independently selected from halogen, alkyl, haloalkyl, and —CN;

n is selected from 0, 1, 2, 3, and 4;

p is selected from 0, 1, 2, 3, and 4;

q is selected from 0, 1, 2, 3, and 4; and t is independently selected from 0, 1, 2, 3, and 4;

wherein when Z$^1$ and Z$^2$ are both O then —X—Y— is —CH═CH—, —CH═N—, or —N═CH—;

or a pharmaceutically acceptable salt, pharmaceutically acceptable solvate, pharmaceutically acceptable prodrug, or stereoisomer thereof.

In some embodiments is a compound of Formula (Xa), wherein R$^1$ is —CH(CH$_3$)CH$_2$CH$_2$R$^2$. In some embodiments is a compound of Formula (Xa), wherein R$^1$ is —CH(CH$_3$)CH$_2$CH$_2$R$^2$, and R$^2$ is H. In some embodiments is a compound of Formula (Xa), wherein R$^1$ is —CH(CH$_3$)CH$_2$CH$_2$R$^2$, and R$^2$ is alkyl. In some embodiments is a compound of Formula (Xa), wherein R$^1$ is —CH(CH$_3$)CH$_2$CH$_2$R$^2$, and R$^2$ is methyl. In some embodiments is a compound of Formula (Xa), wherein R$^1$ is —CH(CH$_3$)CH$_2$CH$_2$R$^2$, and R$^2$ is ethyl. In some embodiments is a compound of Formula (Xa), wherein R$^1$ is —CH(CH$_3$)CH$_2$CH$_2$R$^2$, and R$^2$ is isopropyl. In some embodiments is a compound of Formula (Xa), wherein R$^1$ is —CH(CH$_3$)CH$_2$CH$_2$R$^2$, and R$^2$ is —NR$^{13}$R$^{14}$. In some embodiments is a compound of Formula (Xa), wherein R$^1$ is —CH(CH$_3$)CH$_2$CH$_2$R$^2$, and R$^2$ is —NH$_2$. In some embodiments is a compound of Formula (Xa), wherein R$^1$ is —CH(CH$_3$)CH$_2$CH$_2$R$^2$, and R$^2$ is —NHCH$_3$. In some embodiments is a compound of Formula (Xa), wherein R$^1$ is —CH(CH$_3$)CH$_2$CH$_2$R$^2$, and R$^2$ is —N(CH$_3$)$_2$.

In some embodiments is a compound of Formula (Xa), wherein R$^1$ is —CH(CH$_2$CH$_3$)$_2$. In some embodiments is a compound of Formula (Xa), wherein R$^1$ is —CH(CH$_3$)$_2$. In some embodiments is a compound of Formula (Xa), wherein R$^1$ is —CH(CH$_2$CH$_3$)CH(R$^3$)CH$_3$. In some embodiments is a compound of Formula (Xa), wherein R$^1$ is —CH(CH$_2$CH$_3$)CH(R$^3$)CH$_3$, and R$^3$ is —OH. In some embodiments is a compound of Formula (Xa), wherein R$^1$ is —CH(CH$_2$CH$_3$)CH(R$^3$)CH$_3$, and R$^3$ is alkyl. In some embodiments is a compound of Formula (Xa), wherein R$^1$ is —CH(CH$_2$CH$_3$)CH(R$^3$)CH$_3$, and R$^3$ is methyl. In some embodiments is a compound of Formula (Xa), wherein R$^1$ is —CH(CH$_2$CH$_3$)CH(R$^3$)CH$_3$, and R$^3$ is ethyl. In some embodiments is a compound of Formula (Xa), wherein R$^1$ is —CH(CH$_2$CH$_3$)CH(R$^3$)CH$_3$, and R$^3$ is —NR$^{13}$R$^{14}$. In some embodiments is a compound of Formula (Xa), wherein R$^1$ is —CH(CH$_2$CH$_3$)CH(R$^3$)CH$_3$, and R$^3$ is —NH$_2$. In some embodiments is a compound of Formula (Xa), wherein R$^1$ is —CH(CH$_2$CH$_3$)CH(R$^3$)CH$_3$, and R$^3$ is —NHCH$_3$. In some embodiments is a compound of Formula (Xa), wherein R$^1$ is —CH(CH$_2$CH$_3$)CH(R$^3$)CH$_3$, and R$^3$ is —N(CH$_3$)$_2$. In some embodiments is a compound of Formula (Xa), wherein R$^1$ is -alkylene(cycloalkyl). In some embodiments is a compound of Formula (Xa), wherein R$^1$ is —CH$_2$CH$_2$(cycloalkyl). In some embodiments is a compound of Formula (Xa), wherein R$^1$ is —CH$_2$(cycloalkyl). In some embodiments is a compound of Formula (Xa), wherein R$^1$ is —CH$_2$(cyclobutyl). In some embodiments is a compound of Formula (Xa), wherein R$^1$ is —CH$_2$(cyclopentyl). In some embodiments is a compound of Formula (Xa), wherein R$^1$ is —CH$_2$(cyclohexyl). In some embodiments is a compound of Formula (Xa), wherein R$^1$ is

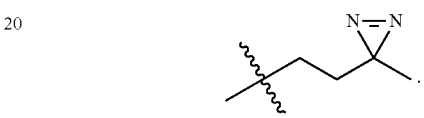

In some embodiments is a compound of Formula (Xa), wherein R$^1$ is

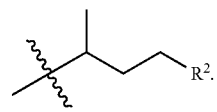

In some embodiments is a compound of Formula (Xa), wherein R$^1$ is

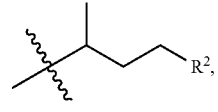

and R$^2$ is H. In some embodiments is a compound of Formula (Xa), wherein R$^1$ is

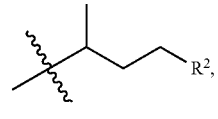

and R$^2$ is alkyl. In some embodiments is a compound of Formula (Xa), wherein R$^1$ is

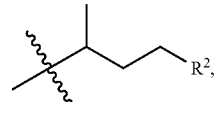

and R$^2$ is methyl. In some embodiments is a compound of Formula (Xa), wherein R$^1$ is

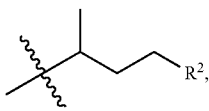

and $R^2$ is ethyl. In some embodiments is a compound of Formula (Xa), wherein $R^1$ is

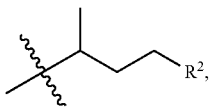

and $R^2$ is isopropyl. In some embodiments is a compound of Formula (Xa), wherein $R^1$ is

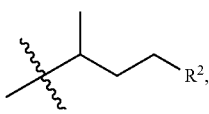

and $R^2$ is —$NR^{13}R^{14}$. In some embodiments is a compound of Formula (Xa), wherein $R^1$ is

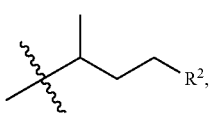

and $R^2$ is —$NH_2$. In some embodiments is a compound of Formula (Xa), wherein $R^1$ is

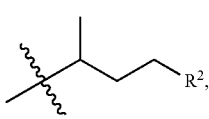

and $R^2$ is —$NHCH_3$. In some embodiments is a compound of Formula (Xa), wherein $R^1$ is

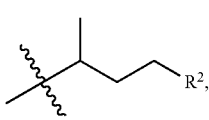

and $R^2$ is —$N(CH_3)_2$.

In some embodiments is a compound of Formula (Xa), wherein $R^1$ is

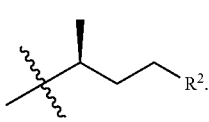

In some embodiments is a compound of Formula (Xa), wherein $R^1$ is

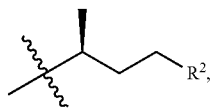

and $R^2$ is H. In some embodiments is a compound of Formula (Xa), wherein $R^1$ is

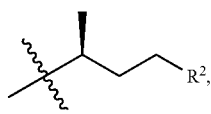

and $R^2$ is alkyl. In some embodiments is a compound of Formula (Xa), wherein $R^1$ is

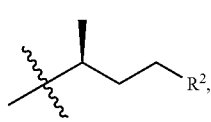

and $R^2$ is methyl. In some embodiments is a compound of Formula (Xa), wherein $R^1$ is

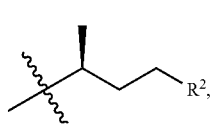

and $R^2$ is ethyl. In some embodiments is a compound of Formula (Xa), wherein $R^1$ is

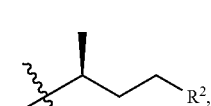

and $R^2$ is isopropyl. In some embodiments is a compound of Formula (Xa), wherein $R^1$ is

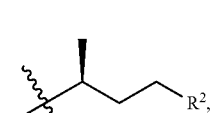

and $R^2$ is —$NR^{13}R^{14}$. In some embodiments is a compound of Formula (Xa), wherein $R^1$ is

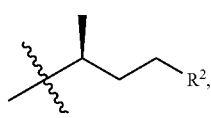

and $R^2$ is —$NH_2$. In some embodiments is a compound of Formula (Xa), wherein $R^1$ is

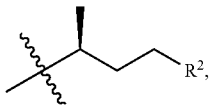

and R² is —NHCH₃. In some embodiments is a compound of Formula (Xa), wherein R¹ is

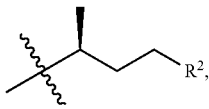

and R² is —N(CH₃)₂.

In some embodiments is a compound of Formula (Xa), wherein R¹ is

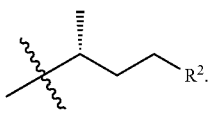

In some embodiments is a compound of Formula (Xa), wherein R¹ is

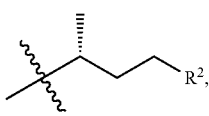

and R² is H. In some embodiments is a compound of Formula (Xa), wherein R¹ is

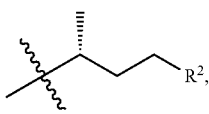

and R² is alkyl. In some embodiments is a compound of Formula (Xa), wherein R¹ is

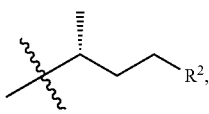

and R² is methyl. In some embodiments is a compound of Formula (Xa), wherein R¹ is

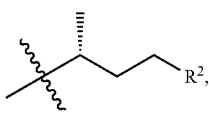

and R² is ethyl. In some embodiments is a compound of Formula (Xa), wherein R¹ is

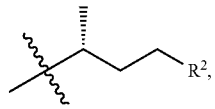

and R² is isopropyl. In some embodiments is a compound of Formula (Xa), wherein R¹ is

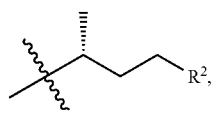

and R² is —NR¹³R¹⁴. In some embodiments is a compound of Formula (Xa), wherein R¹ is

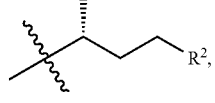

and R² is —NH₂. In some embodiments is a compound of Formula (Xa), wherein R¹ is

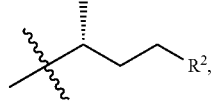

and R² is —NHCH₃. In some embodiments is a compound of Formula (Xa), wherein R¹ is

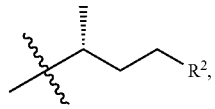

and R² is —N(CH₃)₂.

In some embodiments described above or below is a compound of Formula (Xa), wherein n is 0.

In some embodiments described above or below is a compound of Formula (Xa), wherein n is 1. In some embodiments described above or below is a compound of Formula (Xa), wherein n is 1 and R⁸ is selected from halogen, —OH, —NO₂, —N₃, —CN, alkyl, alkoxy, haloalkoxy, haloalkyl, hydroxyalkyl, alkoxyalkyl, -alkylene(NR¹³R¹⁴), -alkylene(cycloalkyl), -alkylene(heterocyclyl), cycloalkyl, heterocyclyl, aryl, heteroaryl, —SR¹³, —SOR¹³, —SO₂R¹³, —SO₂NR¹³R¹⁴, —NR¹³R¹⁴, —NR¹³SO₂R¹⁴, —NR¹³C(O)R¹⁴, —NR¹³C(O)OR¹⁴, —NR¹³C(O)NR¹³R¹⁴, —C(O)R¹⁴, —C(O)OR¹⁴, or —C(O)NR¹³R¹⁴. In some embodiments described above or below is a compound of Formula (Xa), wherein n is 1 and R⁸ is selected from halogen, —CN, alkyl, alkoxy, haloalkoxy, or haloalkyl. In some embodiments described above or below is a compound of Formula (Xa), wherein n is 1 and R⁸ is halogen. In some embodiments described above or below is a compound of Formula (Xa), wherein n is 1 and $R^8$ is F. In some embodiments described above or below is a compound of Formula (Xa), wherein n is 1 and $R^8$ is Cl. In some embodiments described above or below is a compound of Formula (Xa), wherein n is 1 and $R^8$ is —CN. In some embodiments described above or below is a compound of Formula (Xa), wherein n is 1 and $R^8$ is alkyl. In some embodiments described above or below is a compound of Formula (Xa), wherein n is 1 and $R^8$ is methyl. In some embodiments described above or below is a compound of Formula (Xa), wherein n is 1 and $R^8$ is ethyl. In some embodiments described above or below is a compound of Formula (Xa), wherein n is 1 and $R^8$ is alkoxy. In some embodiments described above or below is a compound of Formula (Xa), wherein n is 1 and $R^8$ is methoxy. In some embodiments described above or below is a compound of Formula (Xa), wherein n is 1 and $R^8$ is ethoxy. In some embodiments described above or below is a compound of Formula (Xa), wherein n is 1 and $R^8$ is haloalkoxy. In some embodiments described above or below is a compound of Formula (Xa), wherein n is 1 and $R^8$ is —OCF$_3$. In some embodiments described above or below is a compound of Formula (Xa), wherein n is 1 and $R^8$ is haloalkyl. In some embodiments described above or below is a compound of Formula (Xa), wherein n is 1 and $R^8$ is —CF$_3$.

In some embodiments described above or below is a compound of Formula (Xa), wherein n is 2. In some embodiments described above or below is a compound of Formula (Xa), wherein n is 2 and $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene (NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O) NR$^{13}$R$^{14}$, —C(O)R$^{14}$, —C(O)OR$^{14}$, and —C(O)NR$^{13}$R$^{14}$. In some embodiments described above or below is a compound of Formula (Xa), wherein n is 2 and $R^8$ is independently selected from halogen, —CN, alkyl, alkoxy, haloalkoxy, and haloalkyl. In some embodiments described above or below is a compound of Formula (Xa), wherein n is 2 and $R^8$ is halogen. In some embodiments described above or below is a compound of Formula (Xa), wherein n is 2 and each $R^8$ is F. In some embodiments described above or below is a compound of Formula (Xa), wherein n is 2 and each $R^8$ is Cl. In some embodiments described above or below is a compound of Formula (Xa), wherein n is 2 and $R^8$ is independently selected from halogen and —CN. In some embodiments described above or below is a compound of Formula (Xa), wherein n is 2 and $R^8$ is independently selected from halogen and alkyl. In some embodiments described above or below is a compound of Formula (Xa), wherein n is 2 and $R^8$ is independently selected from —CN and alkyl. In some embodiments described above or below is a compound of Formula (Xa), wherein n is 2 and two adjacent $R^8$ form a heterocyclyl ring.

In some embodiments described above or below is a compound of Formula (Xa), wherein $Z^1$ is O. In some embodiments described above or below is a compound of Formula (Xa), wherein $Z^1$ is S. In some embodiments described above or below is a compound of Formula (Xa), wherein $Z^1$ is NR$^{13}$. In some embodiments described above or below is a compound of Formula (Xa), wherein $Z^1$ is N(CH$_3$). In some embodiments described above or below is a compound of Formula (Xa), wherein $Z^1$ is NH.

In some embodiments described above or below is a compound of Formula (Xa), wherein $Z^2$ is O. In some embodiments described above or below is a compound of Formula (Xa), wherein $Z^2$ is S. In some embodiments described above or below is a compound of Formula (Xa), wherein $Z^2$ is NR$^{13}$. In some embodiments described above or below is a compound of Formula (Xa), wherein $Z^2$ is N(CH$_3$). In some embodiments described above or below is a compound of Formula (Xa), wherein $Z^2$ is NH. In some embodiments described above or below is a compound of Formula (Xa), wherein $Z^2$ is CH$_2$.

In some embodiments described above or below is a compound of Formula (Xa), wherein $Z^1$ and $Z^2$ are each O.

In some embodiments described above or below is a compound of Formula (Xa), wherein —X—Y— is —CH$_2$CH$_2$—. In some embodiments described above or below is a compound of Formula (Xa), wherein —X—Y— is —CH=CH—. In some embodiments described above or below is a compound of Formula (Xa), wherein —X—Y— is —CH=N—. In some embodiments described above or below is a compound of Formula (Xa), wherein —X—Y— is —N=CH—.

In another embodiment is a compound of Formula (Xa) having the structure:

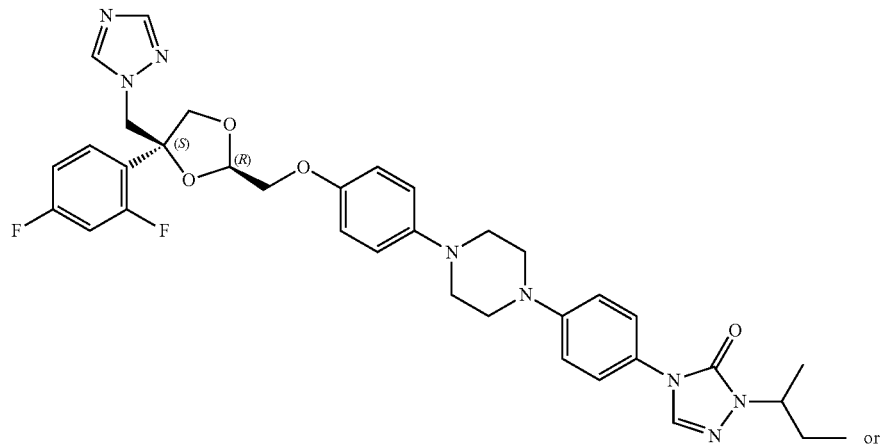

or

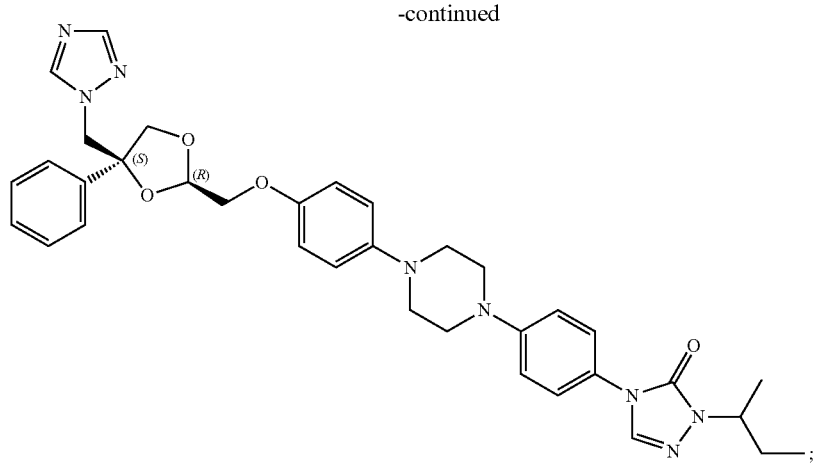

pharmaceutically acceptable salt, pharmaceutically acceptable solvate, or pharmaceutically acceptable prodrug thereof.

Further provided here is a method of treating a disease or condition in a subject in need thereof, the method comprising administering to the subject one or more compounds identified herein. The disease or condition may be a fibrosis. The fibrosis may be liver fibrosis. The liver fibrosis may be idiopathic pulmonary fibrosis.

Further provided here is a method of treating a disease or condition in a subject in need thereof, the method comprising administering to the subject one or more compounds identified here. The disease or condition may be a fibrosis. The fibrosis may be a chronic autoimmune disease. The chronic autoimmune disease may be rheumatoid arthritis, scleroderma, Crohn's disease, or systemic lupus erythematosus.

Preparation of Compounds

Described herein are compounds that treat fibrosis, a disorder characterized by fibrosis, or a disease characterized by fibrosis, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Compounds of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) described herein may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. Bioorganic & Medicinal Chemistry Letters 10 (2000) 2167-2170; Burchat et al. Bioorganic & Medicinal Chemistry Letters 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i. e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e. g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

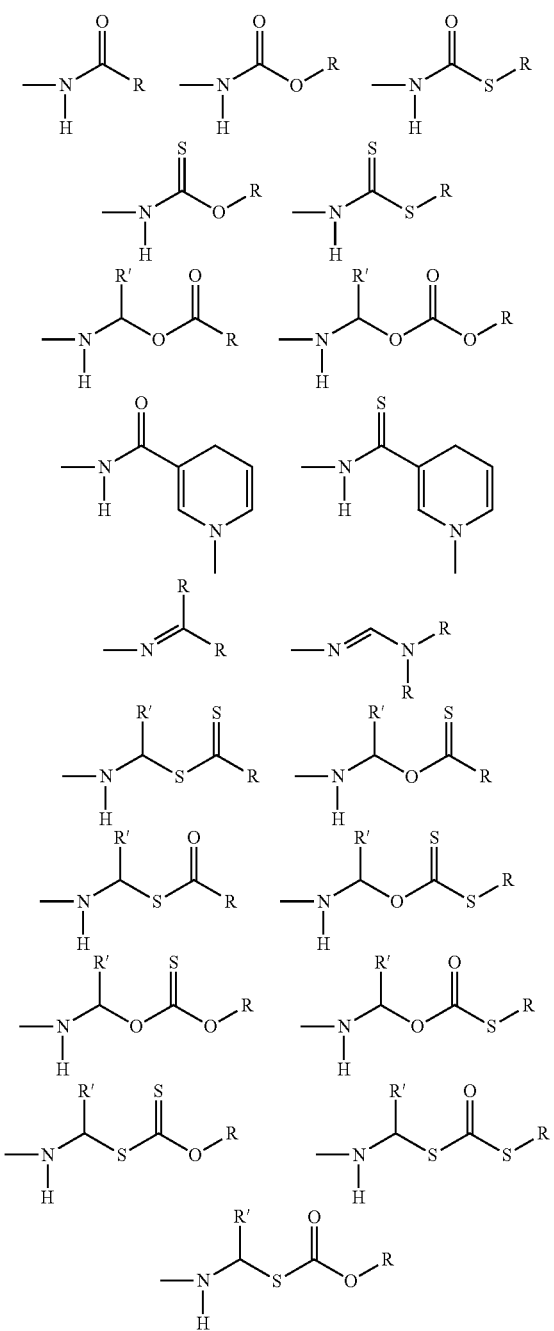

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Metabolites

In some embodiments, compounds of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) described herein are metabolized upon administration to an organism in need to produce a metabolite that is then used to produce a desired effect, including a desired therapeutic effect.

Pharmaceutical Compositions/Formulations

In another aspect, provided herein are pharmaceutical composition comprising a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein, or a pharmaceutically acceptable salt, pharmaceutically acceptable solvate, or pharmaceutically acceptable prodrug thereof, and a pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) and at least one pharmaceutically acceptable inactive ingredient. In some embodiments, the compounds described herein are administered as pharmaceutical compositions in which a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIa), (IX), (IXa), (X), or (Xa) are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Combination Treatment

The compounds according to Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) described herein may be used in combination with one or more additional antifibrotic agents. The antifibrotic agent may be a lysophosphatidic acid 1 (LPA1) antagonist. The antifibrotic agent may be selected from pirfenidone, nintedanib, thalidomide, carlumab, FG-3019, fresolimumab, interferon alpha, lecithinized superoxide dismutase, simtuzumab, tanzisertib, tralokinumab, hu3G9, huTBTl3_2_1, 2126458, AM-152, IFN-gamma-1b, IW-001, PRM-151, PXS-25, pentoxifylline/N-acetyl-cysteine, pentoxifylline/vitamin E, salbutamol sulfate, [Sar9,Met(O2)11]-Substance P, pentoxifylline, mercaptamine bitartrate, obeticholic acid, aramchol, GFT-505, icosapent ethyl ester, metformin hydrochloride, metreleptin, muromonab-CD3, oltipraz, IMM-124-E, MK-4074, PX-102, and RO-5093151.

The compounds according to Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) described herein may be used in combination with one or more additional azole antifungal agents. The azole antifungal agent may be selected from an imidazole antifungal, a triazole antifungal, or a thiazole antifungal. Examples of such antifungal agents include, but are not limited to, Imidazole derivatives like miconazole, ketoconazole, clotrimazole, clomidazole, croconazole, econazole, omoconazole, bifonazole, butoconazole, fenticonazole, isoconazole, miconazole, neticonazole, oxiconazole, sertaconazole, sulconazole, tioconazole; Triazole derivatives like fluconazole, fosfluconazole, hexaconazole, itraconazole, isavuconazole, posaconazole, voriconzaole, terconazole, albaconazole; and Thiazole derivatives like abafungin.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Method of Treatment

Also provided herein is a method of treating fibrosis, a disorder characterized by fibrosis, or a disorder characterized by fibrosis in a subject comprising administering to the subject a therapeutically effective amount of a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein, or a pharmaceutically acceptable salt, pharmaceutically acceptable solvate, or pharmaceutically acceptable prodrug thereof, and a pharmaceutically acceptable excipient.

Further provided herein is a method to treat fibrosis using a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein wherein the fibrosis is liver fibrosis, idiopathic pulmonary fibrosis, kidney fibrosis, or cardiac fibrosis.

Further provided herein is a method to treat liver fibrosis using a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein wherein the liver fibrosis is associated with the later stages of alcoholic or nonalcoholic liver cirrhosis.

Further provided herein is a method to treat fibrosis using a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein, or a pharmaceutically acceptable salt, pharmaceutically acceptable solvate, or pharmaceutically acceptable prodrug thereof wherein the fibrosis is idiopathic pulmonary fibrosis.

Further provided herein is a method to treat a disease using a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein wherein the disease or disorder characterized by fibrosis is a chronic autoimmune disease.

Further provided herein is a method to treat chronic autoimmune disease using a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein wherein the chronic autoimmune disease is rheumatoid arthritis, scleroderma, Crohn's disease or systemic lupus erythematosus.

Further provided herein is a method to treat chronic autoimmune disease using a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein wherein the chronic autoimmune disease is scleroderma.

Further provided herein is a method to treat fibrosis using a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein wherein the fibrosis is keloid formation resulting from abnormal wound healing.

Further provided herein is a method to treat fibrosis using a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein wherein the fibrosis occurs after organ transplantation.

Also provided herein is a method to treat fibrosis, a disorder characterized by fibrosis, or a disease characterized by fibrosis, the method comprising administering a composition comprising a therapeutically effective amount of a compound of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) as described herein in combination with one or more pharmaceutical agents. In certain embodiments described above, the one or more pharmaceutical agents are antifibrotic agents. In certain embodiments described above, the one or more pharmaceutical agents are antifungal agents.

In another aspect, provided herein is a method to treat fibrosis, a disorder characterized by fibrosis, or a disease characterized by fibrosis, the method comprising administering a composition comprising a therapeutically effective amount of a compound of Formula (XI), a pharmaceutically acceptable salt, solvate, polymorph, prodrug, metabolite, N-oxide, stereoisomer, or isomer thereof:

Formula (XI)

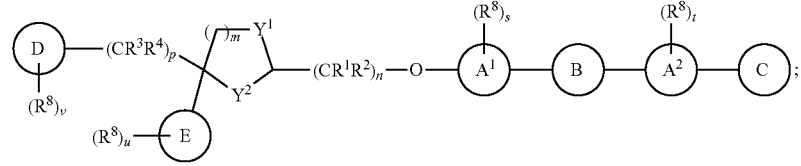

wherein:
A¹ and A² are independently selected from aryl or heteroaryl;
B is

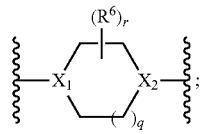

C is optionally substituted 5- or 6-membered heterocyclyl or optionally substituted 5- or 6-membered heteroaryl, wherein the heterocyclyl or the heteroaryl contains 1 to 4 nitrogen atoms;
D is aryl or heteroaryl;
E is aryl, heteroaryl, carbocyclyl, hetercyclyl, or alkyl;
each $R^1$, $R^2$, $R^3$, and $R^4$ is independently selected from H, alkyl, haloalkyl, or alkoxy;
$X_1$ and $X_2$ are independently selected from N and $CR^5$;
$R^5$ is H, OH, alkyl, or alkoxy;
each $R^6$ is independently alkyl, haloalkyl, halo, alkoxy, -alkylene($NR^{13}R^{14}$), or aryl;
each $R^8$ is independently selected from alkyl, cycloalkyl, heterocyclyl, halo, hydroxy, nitrile, azido, nitro, alkoxy, haloalkoxy, haloalkyl, hydroxyalkyl, alkoxyalkyl, -alkylene($NR^{13}R^{14}$), -alkylene(cycloalkyl), -alkylene(heterocyclyl), aryl, heteroaryl, —$SR^{13}$, —$SOR^{13}$, —$SO_2R^{13}$, —$SO_2NR^{13}R^{14}$, —$NR^{13}R^{14}$, —$NR^{13}SO_2R^{14}$, —$NR^{13}C(O)R^{14}$, —$NR^{13}C(O)OR^{14}$, —$NR^{13}C(O)NR^{13}R^{14}$, —$C(O)R^{14}$, —$C(O)OR^{14}$, and —$C(O)NR^{13}R^{14}$; or two adjacent $R^8$ form a heterocyclyl ring;
each $R^{13}$ and $R^{14}$ is independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached;
$Y^1$ is selected from O, NH, and $NR^{13}$;
$Y^2$ is selected from O, $CH_2$, NH, and $NR^{13}$;
n is 1, 2, or 3;
m is 1 or 2;
p is 1, 2, 3, or 4;
q is 1, 2, or 3;
r is 0, 1, 2, 3, 4, 5, 6, 7, or 8;
s is 0, 1, 2, 3, or 4;
t is 0, 1, 2, 3, or 4;
u is 0, 1, 2, 3, 4 or 5; and
v is 0, 1, 2, 3, or 4.
In some embodiments described above or below of a compound of Formula (XI), $X_1$ and $X_2$ are N
In some embodiments described above or below of a compound of Formula (XI), $X_1$ is $CR^5$ and $X_2$ is N.
In some embodiments described above or below of a compound of Formula (XI), $X_1$ is N and $X_2$ is $CR^5$.
In some embodiments described above or below of a compound of Formula (XI), q is 1 and r is 0.
In some embodiments described above or below of a compound of Formula (XI), $A^1$ is aryl.
In some embodiments described above or below of a compound of Formula (XI), $A^1$ is

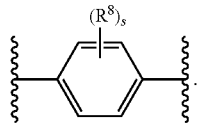

In some embodiments described above or below of a compound of Formula (XI), $A^1$ is

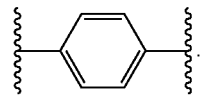

In some embodiments described above or below of a compound of Formula (XI), $A^1$ is heteroaryl.
In some embodiments described above or below of a compound of Formula (XI), $A^2$ is aryl.
In some embodiments described above or below of a compound of Formula (XI), $A^2$ is

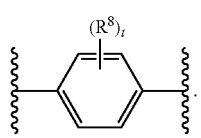

In some embodiments described above or below of a compound of Formula (XI), $A^2$ is

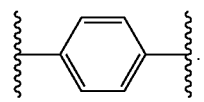

In some embodiments described above or below of a compound of Formula (XI), $A^2$ is heteroaryl.
In some embodiments described above or below of a compound of Formula (XI), $A^2$ is pyridine, pyrazine, pyrimidine, pyridazine, or triazine.
In some embodiments described above or below of a compound of Formula (XI), C is optionally substituted 5- or 6-membered heteroaryl. In other embodiments described above or below of a compound of Formula (XI), C is optionally substituted 5- or 6-membered heterocyclyl.
In some embodiments described above or below of a compound of Formula (XI), C is

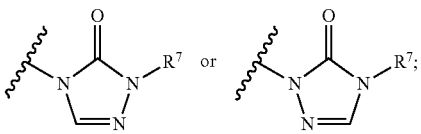

and
$R^7$ is alkyl, haloalkyl, hydroxyalkyl, alkoxyalkyl, -alkylene($NR^{13}R^{14}$), cycloalkyl, heterocyclyl, -alkylene(cycloalkyl), or -alkylene(heterocyclyl).
In some embodiments described above or below of a compound of Formula (XI), C is

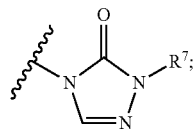

and R[7] is alkyl, haloalkyl, hydroxyalkyl, alkoxyalkyl, -alkylene(NR[13]R[14]), cycloalkyl, heterocyclyl, -alkylene(cycloalkyl), or -alkylene(heterocyclyl).

In some embodiments described above or below of a compound of Formula (XI), C is

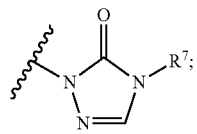

and R[7] is alkyl, haloalkyl, hydroxyalkyl, alkoxyalkyl, -alkylene(NR[13]R[14]), cycloalkyl, heterocyclyl, -alkylene(cycloalkyl), or -alkylene(heterocyclyl).

In some embodiments described above or below of a compound of Formula (XI), E is alkyl.

In some embodiments described above or below of a compound of Formula (XI), E is cycloalkyl.

In some embodiments described above or below of a compound of Formula (XI), E is cyclopropyl, cyclobutyl, cyclopentyl, or cyclohexyl.

In some embodiments described above or below of a compound of Formula (XI), E is heterocyclyl.

In some embodiments described above or below of a compound of Formula (XI), E is aryl.

In some embodiments described above or below of a compound of Formula (XI), E is

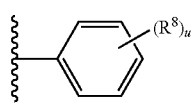

and u is 0, 1, 2, 3, 4, or 5.

In some embodiments described above or below of a compound of Formula (XI), E is heteroaryl.

In some embodiments described above or below of a compound of Formula (XI), E is selected from:

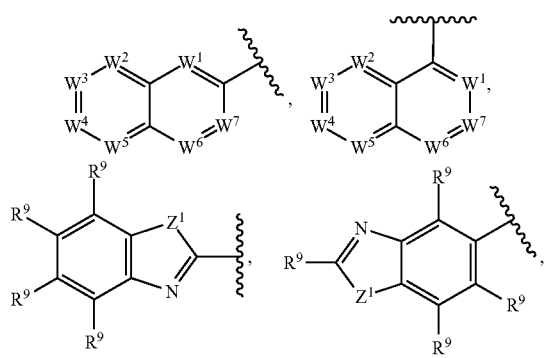

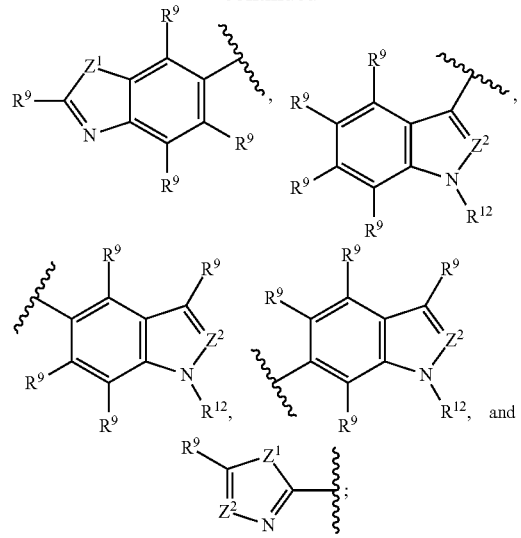

$W^1$, $W^2$, $W^3$, $W^4$, $W^5$, $W^6$, and $W^7$ are independently selected from N and $CR^9$;

$Z^1$ is $NR^{12}$, S, or O;

$Z^2$ is N or $CR^9$;

each $R^9$ is independently selected from H, halogen, CN, $NO_2$, alkyl, —$SR^{10}$, —$OR^1$, —$NR^{10}R^{11}$, $NR^{10}C(O)$(alkyl), —$NR^{10}C(O)$(cycloalkyl), —$NR^{10}C(O)$(heterocycloalkyl), —$NR^{10}C(O)$(aryl), —$NR^{10}C(O)$(heteroaryl), —$C(O)NR^{10}R^{11}$, —$C(O)NR^{10}$(cycloalkyl), —$C(O)NR^{10}$(heterocycloalkyl), —$C(O)NR^{10}$(aryl), —$C(O)NR^{10}$(heteroaryl), —$NR^{10}C(O)NR^{10}R^{11}$, —$NR^{10}C(O)NR^{11}$(cycloalkyl), —$NR^{10}C(O)NR^{11}$(heterocycloalkyl), —$NR^{10}C(O)NR^{11}$(aryl), —$NR^{10}C(O)NR^{11}$(heteroaryl), —$NR^{10}C(O)O$(alkyl), —$NR^{10}C(O)O$(cycloalkyl), —$NR^{10}C(O)O$(heterocycloalkyl), —$NR^{10}C(O)O$(aryl), —$NR^{10}C(O)O$(heteroaryl), —$NR^{10}SO_2$(alkyl), —$NR^{10}SO_2$(cycloalkyl), —$NR^{10}SO_2$(heterocycloalkyl), —$NR^{10}SO_2$(aryl), —$NR^{10}SO_2$(heteroaryl), —$SO_2NR^{10}R^{11}$, —$SO_2NR^{10}$(cycloalkyl), —$SO_2NR^{10}$(heterocycloalkyl), —$SO_2NR^{10}$(aryl), —$SO_2NR^{10}$(heteroaryl), haloalkyl, aryl, and heteroaryl;

each $R^{10}$ and $R^{11}$ is independently selected from H and alkyl; or $R^{10}$ and $R^{11}$ taken together form a heterocycle with the nitrogen to which they are attached; and $R^{12}$ is H, alkyl or haloalkyl.

In some embodiments described above or below of a compound of Formula (XI), D is aryl.

In some embodiments described above or below of a compound of Formula (XI), E is heteroaryl.

In some embodiments described above or below of a compound of Formula (XI), D is selected from:

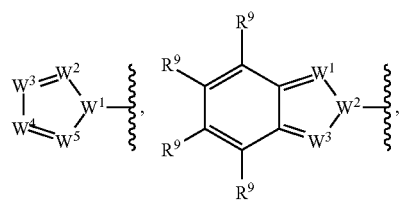

-continued

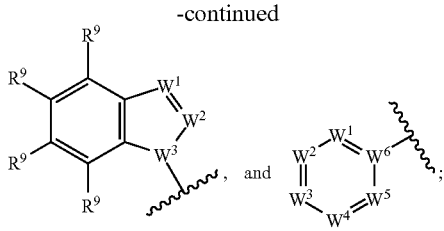

$W^1$, $W^2$, $W^3$, $W^4$, and $W^5$ are independently selected from N and $CR^9$;

$W^6$ is N or C; and each $R^9$ is independently selected from H, halogen, CN, $NO_2$, alkyl, $-SR^{10}$, $-OR^1$, $-NR^{10}R^{11}$, $NR^{10}C(O)(alkyl)$, $-NR^{10}C(O)(cycloalkyl)$, $-NR^{10}C(O)(heterocycloalkyl)$, $-NR^{10}C(O)(aryl)$, $-NR^{10}C(O)(heteroaryl)$, $-C(O)NR^{10}R^{11}$, $-C(O)NR^{10}(cycloalkyl)$, $-C(O)NR^{10}(heterocyclo\ alkyl)$, $-C(O)NR^{10}(aryl)$, $-C(O)NR^{10}(heteroaryl)$, $-NR^{10}C(O)NR^{10}R^{11}$, $-NR^{10}C(O)NR^{11}(cycloalkyl)$, $-NR^{10}C(O)NR^{11}(heterocycloalkyl)$, $-NR^{10}C(O)NR^{11}(aryl)$, $-NR^{10}C(O)NR^{11}(heteroaryl)$, $-NR^{10}C(O)O(alkyl)$, $-NR^{10}C(O)O(cycloalkyl)$, $-NR^{10}C(O)O(heterocloalkyl)$, $-NR^{10}C(O)O(aryl)$, $-NR^{10}C(O)O(heteroaryl)$, $-NR^{10}SO_2(alkyl)$, $-NR^{10}SO_2(cycloalkyl)$, $-NR^{10}SO_2(heterocycloalkyl)$, $-NR^{10}SO_2(aryl)$, $-NR^{10}SO_2(heteroaryl)$, $-SO_2NR^{10}R^{11}$, $-SO_2NR^{10}(cycloalkyl)$, $-SO_2NR^{10}(heterocycloalkyl)$, $-SO_2NR^{10}(aryl)$, $-SO_2NR^{10}(heteroaryl)$, haloalkyl, aryl, and heteroaryl.

In certain embodiments described above or below of a compound of Formula (XI), D is

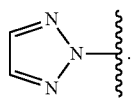

In certain embodiments described above or below of a compound of Formula (XI), D is

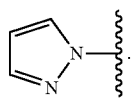

In certain embodiments described above or below of a compound of Formula (XI), D is

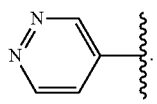

In some embodiments described above or below of a compound of Formula (XI), $Y^1$ and $Y^2$ are O.

In some embodiments described above or below of a compound of Formula (XI), m is 1.

In some embodiments described above or below of a compound of Formula (XI), p is 1, 2, or 3.

In some embodiments described above or below of a compound of Formula (XI), p is 1.

In some embodiments described above or below of a compound of Formula (XI), $R^1$, $R^2$, $R^3$, and $R^4$ are hydrogen.

Further provided herein is a method to treat fibrosis using a compound described herein wherein the fibrosis is liver fibrosis, idiopathic pulmonary fibrosis, kidney fibrosis, or cardiac fibrosis.

Further provided herein is a method to treat liver fibrosis using a compound described herein wherein the liver fibrosis is associated with the later stages of alcoholic or nonalcoholic liver cirrhosis.

Further provided herein is a method to treat fibrosis using a compound described herein wherein the fibrosis is idiopathic pulmonary fibrosis.

Further provided herein is a method to treat a disease using a compound described herein wherein the disease or disorder characterized by fibrosis is a chronic autoimmune disease.

Further provided herein is a method to treat chronic autoimmune disease using a compound described herein wherein the chronic autoimmune disease is rheumatoid arthritis, scleroderma, Crohn's disease or systemic lupus erythematosus.

Further provided herein is a method to treat chronic autoimmune disease using a compound described herein wherein the chronic autoimmune disease is scleroderma.

Further provided herein is a method to treat fibrosis using a compound described herein wherein the fibrosis is keloid formation resulting from abnormal wound healing.

Further provided herein is a method to treat fibrosis using a compound described herein wherein the fibrosis occurs after organ transplantation.

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
BOP benzotriazol-1-yl-oxytris (dimethylamino) phosphonium
t-Bu tert-butyl
Cbz benzyl carbamate
Cy Cyclohexyl
DBU 1,8-Diazabicyclo[5.4.0]undec-7-ene
DCC dicyclohexylcarbodiimide
DCM dichloromethane ($CH_2Cl_2$)
DIC 1,3-diisopropylcarbodiimide
DEAD diethyl azodicarboxylate
DIAD diisopropyl azodicarboxylate
DIEA diisopropylethylamine
DMAP 4-(N,N-dimethylamino)pyridine
DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI 1-ethyl-3-(3-dimethylaminopropyl) carbodiimide HCl
eq equivalent(s)
Et ethyl Et₂O diethyl ether
EtOH ethanol
EtOAc ethyl acetate
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
Me methyl
MeI methyliodide
MeOH methanol
MOMCl methoxymethylchloride
MOM methoxymethyl
MS mass spectroscopy
NMP N-methyl-pyrrolidin-2-one
NMR nuclear magnetic resonance
PyBOP benzotriazole-1-yl-oxytris-pyrrolidino-phosphonium Hexafluorophosphate
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
RT room temperature
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
Tf₂O triflate anhydride
TMG 1,1,3,3-Tetramethylguanidine
THF tetrahydrofuran
THP tetrahydropyran
TLC thin layer chromatography
XPHOS 2-Dicyclohexylphosphino-2',4',6'-triisopropylbiphenyl General Examples for the Preparation of Compounds of the Invention The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as Scifinder (www.cas.org) or Reaxys (www.reaxys.com).

The following reaction schemes A, B, and C detail the synthesis of intermediates involved in the synthesis of compounds described herein.

Scheme A: Synthesis of Racemic Diol (E):

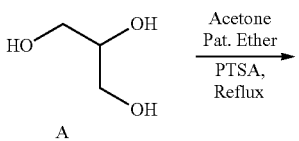

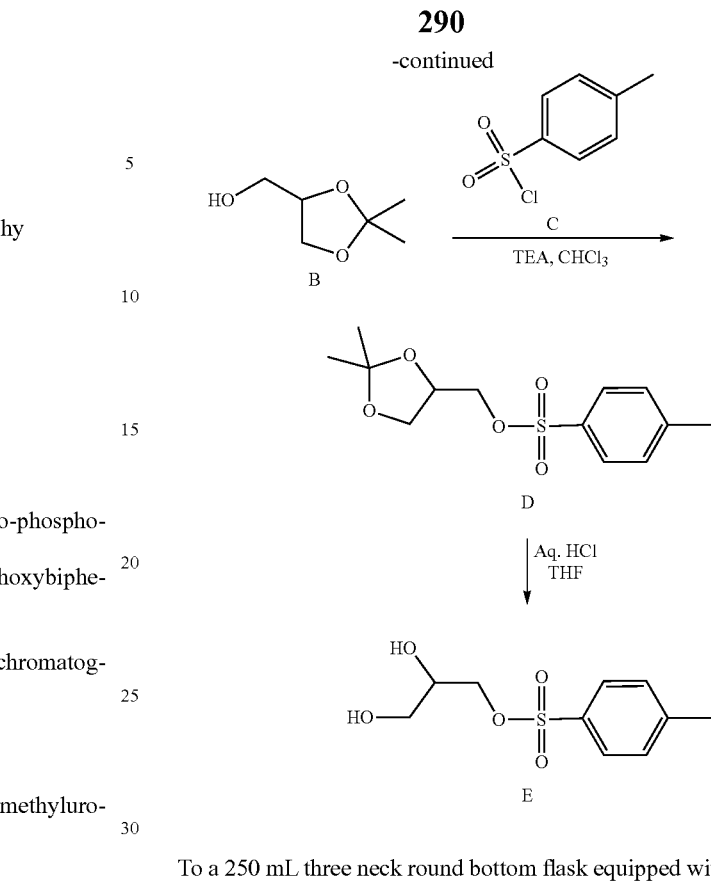

To a 250 mL three neck round bottom flask equipped with condenser and a Dean-stark was added Intermediate-A (25.0 g), acetone (75.0 mL), PTSA.H₂O (0.75 g) and petroleum ether (75.0 mL). The mixture was stirred at reflux temperature for 12 h and monitored by TLC (Hexane:Ethyl acetate (5:5)). The reaction mixture was cooled to room temperature and 0.75 g sodium acetate was added. The mixture was stirred at room temperature for 30 minutes. The organic layer was decanted and concentrated under reduced pressure to give crude liquid, Intermediate-B (27.0 g, 75.2%).

To a 500 mL three neck round bottom flask equipped with calcium chloride guard tube was added Intermediate-B (25.0 g) in chloroform (185 mL). TEA (79.0 mL) was added and the reaction cooled to 0° C. Intermediate-C (47.0 g) was charged lot wise to the mixture and allowed to stir at room temperature for 5 h. The reaction was monitored by TLC (Hexane:Ethyl acetate (5:5)). The reaction mixture was washed with water (200 mL) and the aqueous layer back extracted with CHCl₃ (50 mL×2). The organic layers were combined, dried over Na₂SO₄ and concentrated under reduced pressure to give a crude oil. The oil was purified by column chromatography (6% ethyl acetate in hexanes) to afford Intermediate-D (21.0 g, 38.6%).

To a 250 mL three neck round bottom flask equipped with magnetic stirrer was added Intermediate-D (21.0 g) in THF (100 mL). The reaction solution was cooled to 0° C., mixed with 6N HCl (25.0 mL) and stirred at room temperature for 6 h. The reaction was monitored by TLC (Hexane:Ethyl acetate (5:5)). The reaction mixture was diluted with water (100 mL) and neutralized with saturated sodium bicarbonate solution. The product was extracted with CHCl₃ (50 mL*2). The organic layers were combined, dried over Na₂SO₄ and concentrated under reduced pressure to give a thick oil, Intermediate-E (16.0 g, 88.8%). Intermediate-E was used in the next stage of synthesis without further purification.

Intermediate Spectral Data:

| Intermediate | Characterization Data (NMR/LCMS) |
|---|---|
| B | $^1$HNMR (400 MHz, CDCl$_3$): 1.23 (s, 3H), 1.3 (s, 3H), 3.44-3.55 (m, 3H), 3.61-3.64 (m, 1H), 3.89-3.92 (m, 1H), 4.05-4.10 (m, 1H). |
| D | LCMS: 98.1%; m/z: 304 (M + H$_2$0). |
| E | $^1$HNMR (400 MHz, CDCl$_3$): 2.46 (s, 3H), 2.85 (s, 1H), 3.4 (s, 1H), 3.57-3.61 (m, 1H), 3.66-3.70 (m, 1H), 3.93-3.96 (m, 1H), 4.04-4.10 (m, 2H), 7.36-7.38 (dd, J = 8.0 Hz, 2H), 7.79-7.81 (dd, J = 8.0 Hz, 2H). |

Scheme B: Synthesis of Intermediate-K:

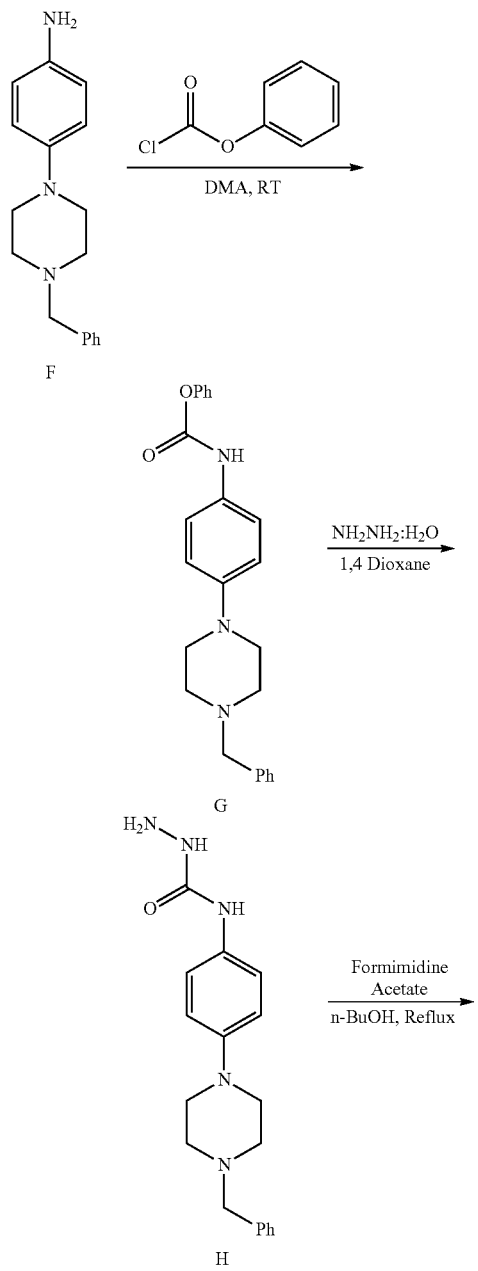

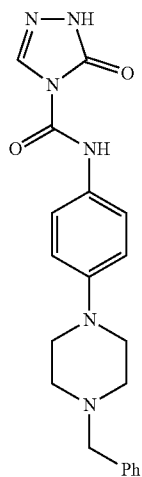

To a 100 mL three neck round bottom flask equipped with calcium chloride tube was added Intermediate-F (5.0 g) in DMA (25.0 mL). Phenyl chloroformate (2.8 ml) was added dropwise and the reaction mixture stirred at RT for 30 minutes. The reaction was monitored by TLC (Hexane:Ethyl acetate (5:5)). The reaction mixture was poured into ice water. The resulting precipitate was collected by filtration, washed with water and dried under vacuum to obtain pure product, Intermediate-G (4.4 g, 61.1%).

To a 100 mL three neck round bottom flask equipped with calcium chloride tube was added Intermediate-G (4.4 g) in 1,4 Dioxane (20.0 mL). Hydrazine hydrate (1.37 mL) was added dropwise and the reaction mixture was stirred at RT for 24 h. The reaction was monitored by TLC (Hexane:Ethyl acetate (5:5)). The reaction mixture was poured into ice water. The resulting precipitate was collected by filtration, washed with water and dried under vacuum to obtain pure product, Intermediate-H (2.80 g, 53.8%).

To a 100 mL three neck round bottom flask equipped with condenser was added Intermediate-H (2.80 g) in n-BuOH (25.0 mL). Formimidine acetate (4.47 g) was added and the reaction mixture was stirred at 90° C. for 4 h. The reaction was monitored by TLC (EtOAc). The reaction mixture was cooled to room temperature and the precipitate collected by filtration, washed with ethyl acetate and dried to get pure product, Intermediate-I (2.5 g, 86.8%).

To a 100 mL three neck round bottom flask equipped with condenser was added Intermediate-I (2.50 g) in DMF (30.0 mL). NaOH (1.50 g) and sec-bromo butane (5.11 g) were added and the reaction mixture stirred at 90° C. for 8 h. The reaction was monitored by TLC (EtOAc). The reaction mixture was poured into ice water. The resulting precipitate was collected by filtration, washed with water and dried under vacuum to obtain pure product, Intermediate-J (1.45 g, 49.8%).

To a 100 mL Hydrogenator vessel was added Intermediate-J (1.45 g) in MeOH (25.0 mL). 10% Pd/C (0.15 g) was added and the reaction mixture was hydrogenated at RT under 10 kg of $H_2$ pressure overnight. The reaction was monitored by TLC (EtOAc). After completion of the reaction, the catalyst was removed by filtration and the solvent was evaporated to give a thick oil. The crude product was purified by column chromatography (5% MeOH in MDC) to give Intermediate-K (0.75 g, 67.5%).

Intermediate Spectral Data:

| Intermediate # | Characterization Data (NMR/LCMS) |
|---|---|
| G | LCMS: 99.16% @ 256 nm; m/z: 388 (M + H). <br> $^1$HNMR (400 MHz, CDCl$_3$): 2.94-3.05 (m, 2H), 3.13-3.20 (m, 2H), 3.72-3.75 (d, 2H), 4.39-4.40 (d, 2H), 6.95-6.97 (d, J = 8.0 Hz, 2H), 7.19-7.27 (m, 3H), 7.38-7.44 (m, 4H), 7.49-7.50 (m, 3H), 7.59-7.60 (d, J = 4.0 Hz, 2H). |
| H | LCMS: 97.61% @ 254 nm; m/z: 326 (M + H). |
| I | LCMS: 98.34% @ 256 nm; m/z: 336 (M + H). |
| J | LCMS: 96.95% @ 258 nm; m/z: 392 (M + H). |
| K | LCMS: 95.78% @ 257 nm; m/z: 302 (M + H). |

Scheme C: Synthesis of Intermediate-N

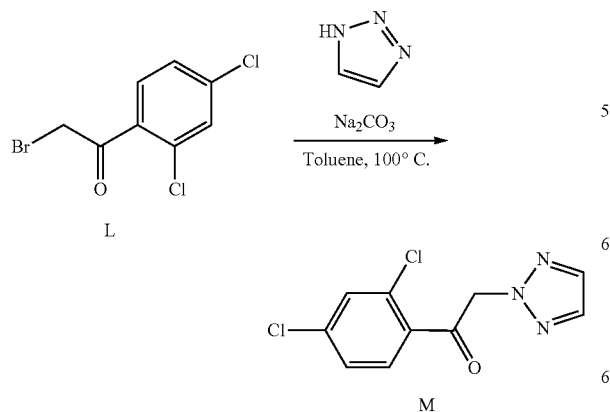

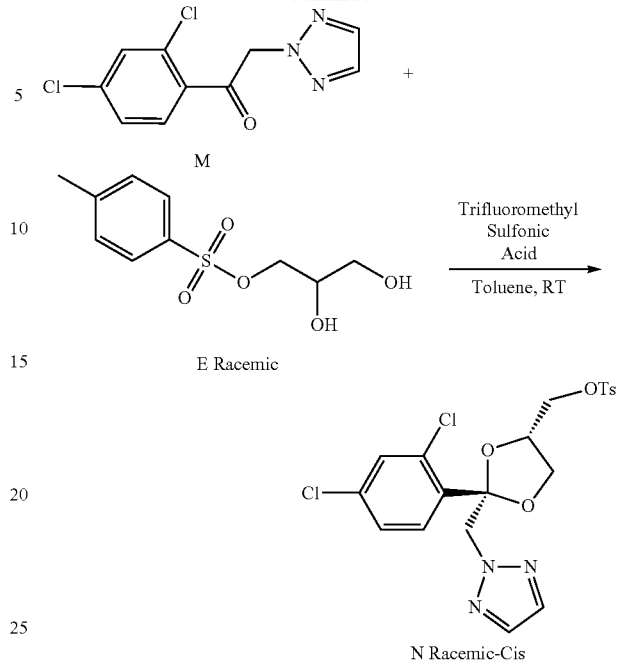

To a stirred solution of Intermediate-L (2.0 g) in toluene (30.0 mL) was charged 1H-1,2,3 triazole (1.96 g) and Na$_2$CO$_3$ (3.01 g) at RT. The reaction mixture was stirred at 100° C. for 3 h. The completion of the reaction was monitored via TLC (Hexane:Ethyl acetate (5:5)). After reaction completion, the mixture was cooled to RT and diluted with ethyl acetate (50 mL). The obtained organic layer was washed with water (50 mL×2). The organic layer was separated, dried over Na$_2$SO$_4$ and concentrated under reduced pressure. The crude product was purified by column chromatograph (20% ethyl acetate in hexanes) to give Intermediate-M (0.70 g, 19.2%).

To a stirred solution of Intermediate-M (1.30 g) in toluene (15.0 ml) was charged Intermediate-E (1.50 g) at RT under argon atmosphere. The resulting mixture was cooled to 0° C. and to it was added dropwise triflic acid (1.80 mL). The mixture was warmed to RT and stirred for 60 h. The completion of the reaction was monitored via TLC (Hexane: Ethyl acetate (5:5)). After reaction completion, the resulting mixture was poured into water (25 mL) and neutralized with saturated sodium bicarbonate solution. The aqueous layer was extracted with ethyl acetate (25 mL×2). The organic layer was combined, dried over Na$_2$SO$_4$ and concentrated under reduced pressure to give a thick oil. The crude product was purified by column chromatography (10% ethyl acetate in hexanes) to give Intermediate-N (0.32 g, 24.6%).

Intermediate Spectral Data:

| Intermediate # | Characterization Data (NMR/LCMS) |
|---|---|
| M | LCMS: 96.62% @ 252 nm; m/z 258 (M + H). <br> $^1$HNMR (400 MHz, CDCl$_3$): 5.91 (s, 2H), 7.36-7.39 (dd, J$_1$ = 12.0 Hz and J$_2$ = 4.0 Hz, 1H), 7.51-7.52 (d, J = 4.0 Hz, 1H), 7.64-7.66 (d, J = 8.0 Hz, 1H), 7.73 (s, 2H). |
| N | LCMS: 100% @ 225 nm; m/z 486 (M + 2). <br> $^1$HNMR (400 MHz, CDCl$_3$): 2.49 (s, 3H), 3.41-3.45 (m, 1H), 3.75-3.82 (m, 1H), 3.84-3.89 (m, 2H), 4.23-4.26 (m, 1H), 4.94-4.98 (d, J = 14.4 Hz, 1H), 5.06-5.09 (d, J = |

| Intermediate # | Characterization Data (NMR/LCMS) |
|---|---|
| | 14.0 Hz, 1H), 7.18-7.21 (dd, $J_1$ = 10.4 Hz and $J_2$ = 2.0 Hz, 1H), 7.38-7.40 (d, $J_1$ = 12.0 Hz and $J_2$ = 8.0 Hz, 2H), 7.44-7.46 (m, 2H), 7.55 (s, 2H), 7.77-7.79 (d, $J_1$ = 12.0 Hz and $J_2$ = 8.4 Hz, 2H). |

Scheme D: Synthesis of Intermediate-O

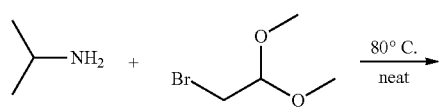

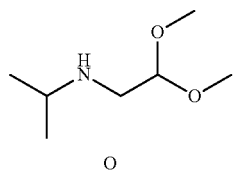

A mixture of isopropyl amine and 2-bromo-1,1-dimethoxyethane in a sealed tube were heated at 80° C. The reaction mixture was cooled and purified to give Intermediate-O (92%).

Example 1

Synthesis of 4-(4-(4-(4-(((2S,4R)-2-((2H-1,2,3-triazol-2-yl)methyl)-2-phenyl-1,3-dioxolan-4-yl)methoxy)phenyl)piperazin-1-yl)phenyl)-(S)-1-sec-butyl-1H-1,2,4-triazol-5(4H)-one (180)

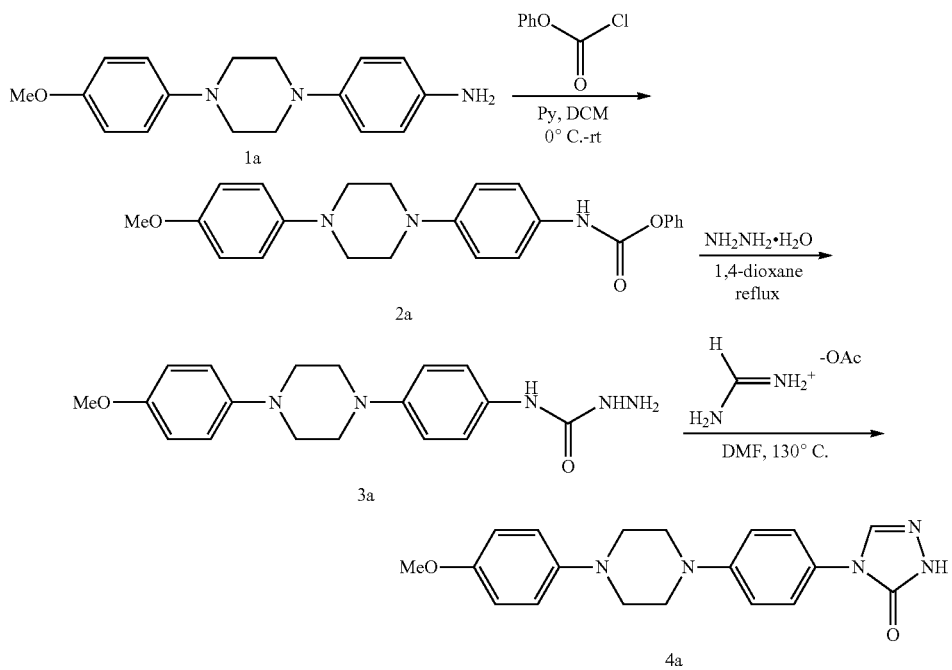

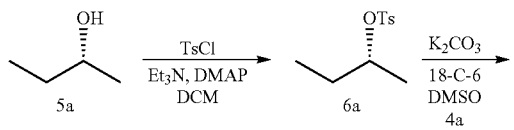

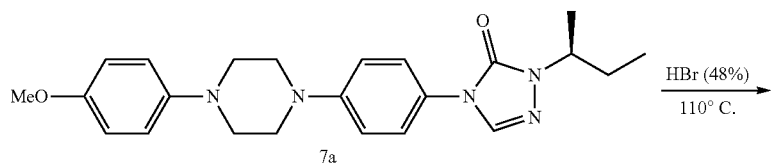

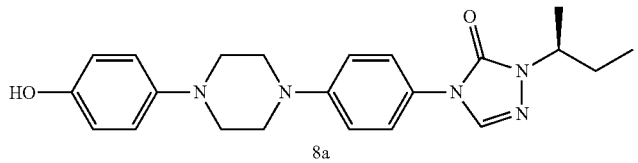

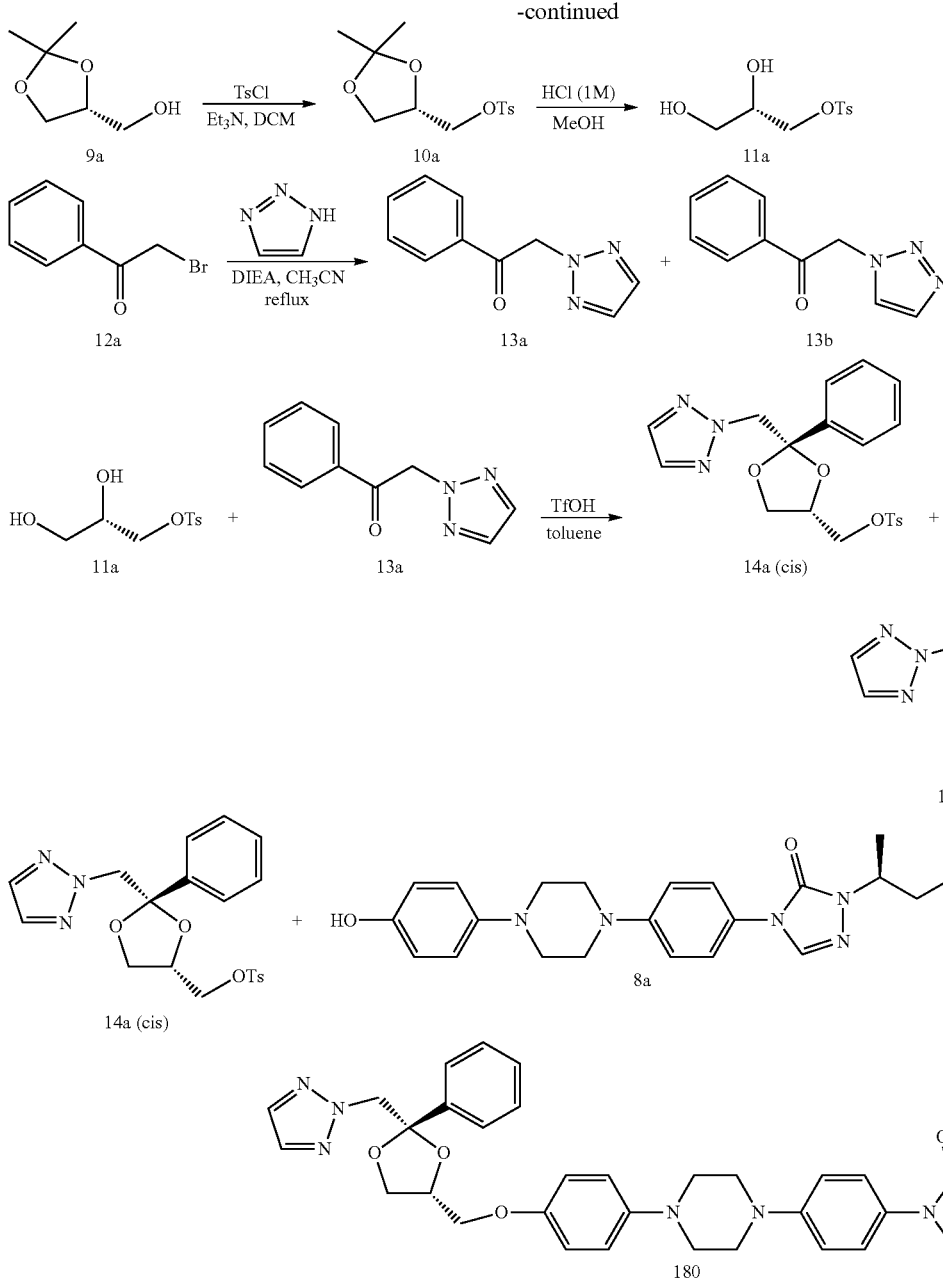

To a solution of compound 1a (10 g, 35.3 mmol) and pyridine (3.12 mL, 38.8 mmol) in anhydrous DCM (40 mL) at 0° C. was added phenylchloroformate (4.87 mL, 38.8 mmol) dropwise. The reaction was warmed to room temperature and stirred for additional 2 h. After completion of the reaction, reaction mixture was poured into ice water (100 mL). Resulting precipitates were collected by filtration, washed with water and dried to afford compound 2a as a brown solid (13.1 g, 92%), which was used directly in next step without further purification. LC-MS: m/z 404.1 (M+H); $^1$H NMR (400 MHz, CDCl$_3$): δ 7.32-7.43 (m, 4H), 7.16-7.26 (m, 3H), 6.97 (d, J=8.4 Hz, 4H), 6.87 (d, J=8.8 Hz, 2H), 6.81 (s, 1H), 3.79 (s, 3H), 3.31 (br s, 4H), 3.24 (br s, 4H).

To a solution of compound 2a (13.1 g, 32.4 mmol) in 1,4-dioxane (50 mL) was added hydrazine hydrate (50-60%, 9.72 mL, 97.2 mmol). The reaction mixture was heated to reflux (110° C.) for 1 h, cooled to room temperature and then poured into water (150 mL). The obtained precipitate was collected by filtration, washed with water and dried to give compound 3a (10.5 g, 95%) as a brown solid, which was used directly in next step without further purification. LC-MS: m/z 342.2 (M+H); $^1$H NMR (400 MHz, DMSO-d$_6$) δ 8.41 (s, 1H), 7.46-7.30 (m, 2H), 7.25 (s, 1H), 6.99-6.92 (m, 2H), 6.93-6.88 (m, 2H), 6.88-6.81 (m, 2H), 4.31 (s, 2H), 3.70 (s, 3H), 3.18-3.17 (m, 8H).

To a solution of compound 3a (7.65 g, 22 mmol) in anhydrous DMF (25 mL) was added formamidine acetate (7.0 g, 67.0 mmol). The reaction mixture was heated at 130° C. for 3 h, cooled to room temperature and then water (100 mL) was added. The precipitate was collected by filtration, washed with water and dried to give product 4a (6.70 g, 85%) as a brown solid, which was used directly in next step without further purification. LC-MS: m/z 352.0 (M+H); $^1$H NMR (400 MHz, DMSO-d$_6$) δ 8.25 (s, 1H), 7.55-7.42 (m, 2H), 7.14-7.05 (m, 2H), 7.03-6.91 (m, 2H), 6.91-6.81 (m, 2H), 3.70 (s, 3H), 3.35-3.29 (m, 4H), 3.21 (br s, 1H), 3.20-3.11 (m, 4H).

To a solution of (R)-2-butanol 5a (5 g, 67.3 mmol), Et$_3$N (18.8 mL, 134.6 mmol) and DMAP (822 mg, 6.73 mmol) in DCM (30 mL) at 0° C., was slowly added a solution of p-toluenesulfonic chloride (TsCl) (15.4 g, 80.7 mmol) in DCM. The reaction mixture was warmed to room temperature and stirred overnight. After diluting with water, the reaction mixture was extracted with DCM. The combined organic layers were dried over Na$_2$SO$_4$, filtered, and concentrated. The crude product was purified by column chromatography on silica gel (eluent: hexanes/EtOAc=10/1) to give product 6a (10.5 g, 69%) as a colorless liquid. $^1$H NMR (400 MHz, CDCl$_3$) δ 7.90-7.74 (m, 2H), 7.43-7.31 (m, 2H), 4.58 (m, 1H), 2.46 (s, 3H), 1.68-1.49 (m, 2H), 1.27 (d, J=6.3 Hz, 3H), 0.83 (t, J=7.5 Hz, 3H).

To a solution of compound 4a (5 g, 14.2 mmol) in DMSO (50 mL), was added K$_2$CO$_3$ (3.9 g, 28.4 mmol), 18-Crown-6 (3.4 g, 14.2 mmol) and 6a (3.89 g, 17.0 mmol) in order. The reaction mixture was stirred at room temperature overnight, followed by the dilution with water and the extraction with DCM. The combined organic layer was dried over Na$_2$SO$_4$, filtered and concentrated. The crude product was purified by column chromatography on silica gel (eluent: hexanes/EtOAc=1/1) to give product 7a as an off-white solid (2.1 g, 36%). LC-MS: m/z 408.2 (M+H); $^1$H NMR (400 MHz, CDCl$_3$): δ 7.62 (s, 1H), 7.42 (d, J=7.2 Hz, 2H), 7.03 (d, J=7.2 Hz, 2H), 6.98 (br s, 2 H), 6.86 (d, J=7.2 Hz, 2H), 4.29 (m, 1H), 3.79 (s, 3H), 3.37 (br s, 4H), 3.23 (br s, 4H), 1.89 (m, 1H), 1.70 (m, 1H), 1.39 (d, J=5.6 Hz, 3H), 0.90 (t, J=6.0 Hz, 3H).

A mixture of 7a (2.0 g, 4.91 mmol) and 48% HBr solution (10 mL) was heated at reflux overnight and then the reaction mixture was cooled to room temperature. The reaction mixture was diluted DCM, and neutralized with sat. NaHCO$_3$. The mixture was extracted with DCM. The combined organic layer was washed with brine, dried over Na$_2$SO$_4$, filtered, and concentrated. The crude product was purified by column chromatography on silica gel (eluent: hexanes/EtOAc=1/3) to give product 8a as an off-white solid (1.26 g, 65%). LC-MS: m/z 394.2 (M+H); $^1$H NMR (400 MHz, CDCl$_3$): δ 7.64 (s, 1H), 7.41 (d, J=8.8 Hz, 2H), 7.00 (d, J=9.2 Hz, 2H), 6.86 (d, J=9.2 Hz, 2H), 6.74 (d, J=8.8 Hz, 2H), 5.77 (br s, 1H), 4.33 (m, 1H), 3.48-3.31 (m, 4H), 3.31-3.07 (m, 4H), 1.89 (m, 1H), 1.75 (m, 1H), 1.42 (d, J=6.7 Hz, 3H), 0.93 (t, J=7.4 Hz, 3H).

To a solution of (R)-2,2-Dimethyl-1,3-dioxolane-4-methanol 9a (5 g, 37.8 mmol), Et$_3$N (10.5 mL, 75.6 mmol) and DMAP (462 mg, 3.78 mmol) in DCM (20 mL) at 0° C., was slowly added a solution of p-toluenesulfonic chloride (TsCl) (10.8 g, 56.7 mmol) in DCM. The reaction mixture was warmed to room temperature and stirred overnight. After diluting with water, the reaction mixture was extracted with DCM. The combined organic layers was dried over Na$_2$SO$_4$, filtered, and concentrated. The crude produce was purified by column chromatography on silica gel (eluent: hexanes/EtOAc=5/1) to give product 10a (9.39 g, 87%) as colorless liquid. $^1$H NMR (400 MHz, CDCl$_3$) δ 7.82 (d, J=8.4 Hz, 2H), 7.40 (d, J=8.4 Hz, 2H), 4.30 (tt, J=6.0, 5.1 Hz, 1H), 4.12-3.91 (m, 3H), 3.79 (ddd, J=8.8, 5.1, 0.7 Hz, 1H), 2.47 (s, 3H), 1.36 (s, 3H), 1.33 (s, 3H).

A mixture of 10a (9.39 g, 32.7 mmol) in methanol (20 mL) and 1M aq HCl (31 mL) was stirred at room temperature for 3 h. The solvent was partially removed in vacuo, diluted with EtOAc, and neutralized with sat. NaHCO$_3$. The mixture was extracted with EtOAc. The combined organic layer was washed with brine, dried over Na$_2$SO$_4$, filtered, and concentrated. The crude product was purified by column chromatography on silica gel (eluent: hexanes/EtOAc=1/3) to give product 11a (6.9 g, 85%) as a white solid. $^1$H NMR (400 MHz, CDCl$_3$) δ 7.82 (d, J=8.4 Hz, 2H), 7.39 (d, J=8.4 Hz, 2H), 4.18-4.06 (m, 2H), 4.96 (m, 1H), 3.78-3.59 (m, 2H), 2.48 (s, 3H), 2.26 (br s, 2H).

To a solution of 2-bromoacetophenone 12a (10 g, 50 mmol) in CH$_3$CN (50 mL) was added 1,2,3-triazole (3.48 mL, 60 mmol) and DIEA (13.2 mL, 75 mmol). The mixture was heated to reflux for 1 h, cooled to room temperature, and then the solvent was removed in vacuo. The residue was redissolved in EtOAc (150 mL), washed with water (50 mL), 10% citric acid (50 mL), and brine, then dried over Na$_2$SO$_4$, filtered and concentrated. The crude product was purified by flash chromatography on silica gel (eluent: hexanes/EtOAc=3/1) to give product 13a as a yellow solid (1.50 g, 8.0%) and (eluent: hexanes/EtOAc=1/3) to give product 13b as a yellow solid (7.05 g, 75%). 13a: $^1$H NMR (400 MHz, CDCl$_3$): δ 8.05-7.93 (m, 2H), 7.76 (s, 2H), 7.72-7.60 (m, 1H), 7.60-7.51 (m, 2H), 5.95 (s, 2H). 13b: $^1$H NMR (400 MHz, CDCl$_3$): δ 8.03 (dd, J=8.0, 1.5 Hz, 2H), 7.83 (s, 1H), 7.77 (s, 1H), 7.72-7.68 (m, 1H), 7.59-7.55 (m, 2H), 5.92 (s, 2H).

Under nitrogen, to a solution of ketone 13a (0.5 g, 2.67 mmol) and compound 11a (0.72 g, 2.93 mmol) in anhydrous toluene (10 mL) at 0° C. was added TfOH (0.93 mL, 10.6 mmol) slowly. After addition, the mixture was warmed to room temperature and stirred for 60 h. The reaction was quenched by adding sat. NaHCO$_3$ at 0° C. The mixture was extracted with EtOAc. The combined organic layer was washed with brine and dried over Na$_2$SO$_4$, filtered and concentrated in vacuo. The crude material was purified by flash chromatography on silica gel (eluent: hexanes/EtOAc=3/1) to obtain cis product 14a as a white solid (0.52 g g, 47.2%), and (eluent: hexanes/EtOAc=1/1) to obtain trans product 14b as a slight yellow liquid (0.15 g, 14.0%). 14a: LC-MS: m/z 416.0 (M+H); $^1$H NMR (400 MHz, CDCl$_3$): δ 107.82-7.75 (m, 2H), 7.57 (s, 2H), 7.50-7.44 (m, 2H), 7.43-7.34 (m, 5H), 4.77 (dd, J=17.6, 14.4 Hz, 2H), 4.21 (m, 1H), 3.85-3.75 (m, 2H), 3.70 (dd, J=8.8, 4.0 Hz, 1H), 3.37 (dd, J=10.0, 7.2 Hz, 1H), 2.50 (s, 3H). ee (>98%) was determined by chiral HPLC analysis with Phenomenex Lux Cellulose-3 column: 5 uL inj. 1 mg/mL (ethanol); flow rate, 1.0 mL/min; mobile phase, water:CH$_3$CN:acetic acid (40:60:0.1); RT=3.24 min. 14b: LC-MS: m/z 416.1 (M+H); $^1$H NMR (400 MHz, CDCl$_3$): δ 7.67-7.59 (m, 2H), 7.58 (s, 2H), 7.44-7.32 (m, 2H), 7.31-7.23 (m, 5H), 4.70 (s, 2H), 4.06 (m, 1H), 3.90 (dd, J=10.3, 5.3 Hz, 1H), 3.81 (dd, J=8.6, 6.2 Hz, 1H), 3.72 (dd, J=10.3, 6.3 Hz, 1H), 3.55 (dd, J=8.6, 6.5 Hz, 1H), 2.42 (s, 3H).

To a solution of tosylate 14a (49 mg, 0.12 mmol) and phenol 8a (43 mg, 0.11 mmol) in anhydrous DMF (2 mL) was added KOH (25 mg, 0.44 mmol). The reaction mixture was stirred at 50° C. overnight. After cooling to room temperature, the reaction mixture was diluted with water and DCM, and the organic phase was separated. The aqueous phase was extracted with DCM. The combined organic layer was washed with brine and dried over Na$_2$SO$_4$, filtered, and concentrated under rotovap. The crude product was purified by column chromatography on silica gel (eluent: hexanes/EtOAc=1/1 to 1/3) to give 180 as an off-white solid (32 mg, 46%). LC-MS: m/z 637.2 (M+H); $^1$H NMR (400 MHz, CDCl$_3$) δ 7.64-7.63 (m, 3H), 7.62-7.54 (m, 2H), 7.50-7.43 (m, 2H), 7.43-7.36 (m, 3H), 7.11-7.03 (m, 2H), 6.96 (br s, 2H), 6.84-6.78 (m, 2H), 4.87 (s, 2H), 4.38 (m, 1H), 4.31 (m, 1H), 3.92 (dd, J=8.5, 6.5 Hz, 1H), 3.85 (dd, J=8.5, 4.4 Hz, 1H), 3.78 (dd, J=9.4, 5.1 Hz, 1H), 3.49-3.33 (m, 5H), 3.27 (br s, 4H), 1.89 (m, 1H), 1.75 (m, 1H), 1.41 (d, J=6.8 Hz, 3H), 0.93 (t, J=7.4 Hz, 3H); Elemental analysis: theory (C, 66.02; H, 6.33; N, 17.60); found (C, 65.95; H, 6.39; N, 17.40).

Example 2

Synthesis of 4-(4-(4-(4-(((2S,4R)-2-((2H-1,2,3-triazol-2-yl)methyl)-2-phenyl-1,3-dioxolan-4-yl)methoxy)phenyl)piperazin-1-yl)phenyl)-(R)-1-sec-butyl-1H-1,2,4-triazol-5(4H)-one (179)

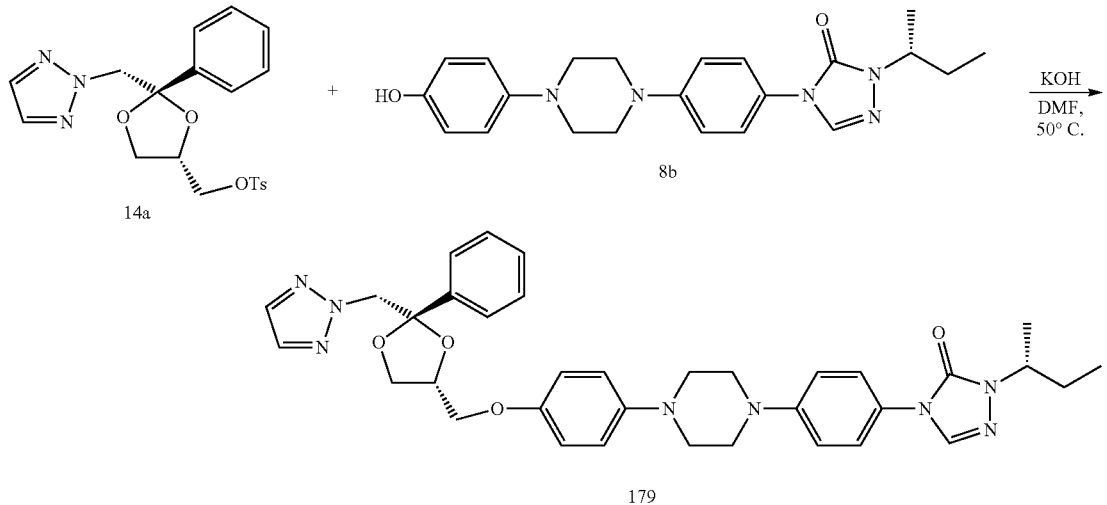

In a similar manner as described in Example 1 for the preparation of compound 8a, compound 8b was obtained as an off-white solid in 18.6% yield over 3 steps, starting from (S)-2-butanol 5b. LC-MS: m/z 394.2 (M+H); $^1$H NMR (400 MHz, CDCl$_3$): δ 7.64 (s, 1H), 7.40 (d, J=8.8 Hz, 2H), 7.00 (d, J=9.2 Hz, 2H), 6.89 (d, J=9.2 Hz, 2H), 6.74 (d, J=8.8 Hz, 2H), 5.81 (br s, 1H), 4.33 (m, 1H), 3.43-3.29 (m, 4H), 3.29-3.14 (m, 4H), 1.90 (m, 1H), 1.75 (m, 1H), 1.41 (d, J=6.8 Hz, 3H), 0.93 (t, J=7.4 Hz, 3H).

In a similar manner as described in Example 1 for the preparation of compound 180, compound 179 was obtained from tosylate 14a and phenol 8b. LC-MS: m/z 637.2 (M+H); $^1$H NMR (400 MHz, CDCl$_3$) δ 7.64 (m, 3H), 7.57 (dt, J=10.1, 5.5 Hz, 2H), 7.50-7.34 (m, 5H), 7.05 (t, J=9.8 Hz, 2H), 6.94 (m, 2H), 6.80 (d, J=8.8 Hz, 2H), 4.87 (s, 2H), 4.42-4.28 (m, 2H), 3.92 (dd, J=17.5, 8.8 Hz, 1H), 3.85 (m, 1H), 3.78 (dd, J=9.4, 5.0 Hz, 1H), 3.37 (m, 5H), 3.27 (m, 4H), 1.94-1.82 (m, 1H), 1.82-1.70 (m, 1H), 1.42 (d, J=6.7 Hz, 3H), 0.95 (t, J=7.4 Hz, 3H).

Example 3

Synthesis of 4-(4-(4-(4-(((2R,4S)-2-((2H-1,2,3-triazol-2-yl)methyl)-2-phenyl-1,3-dioxolan-4-yl)methoxy)phenyl)piperazin-1-yl)phenyl)-(R)-1-sec-butyl-1H-1,2,4-triazol-5(4H)-one (182)

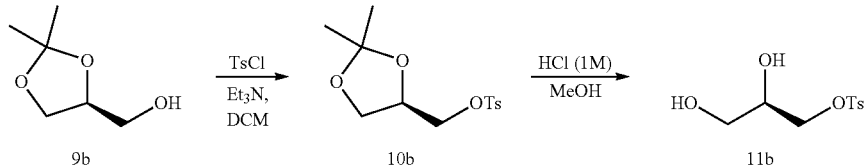

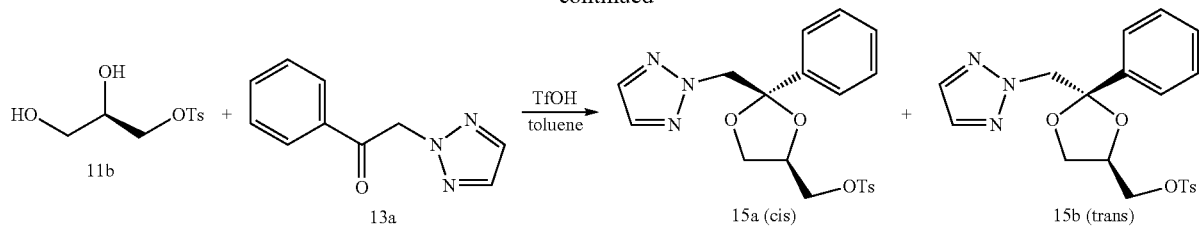

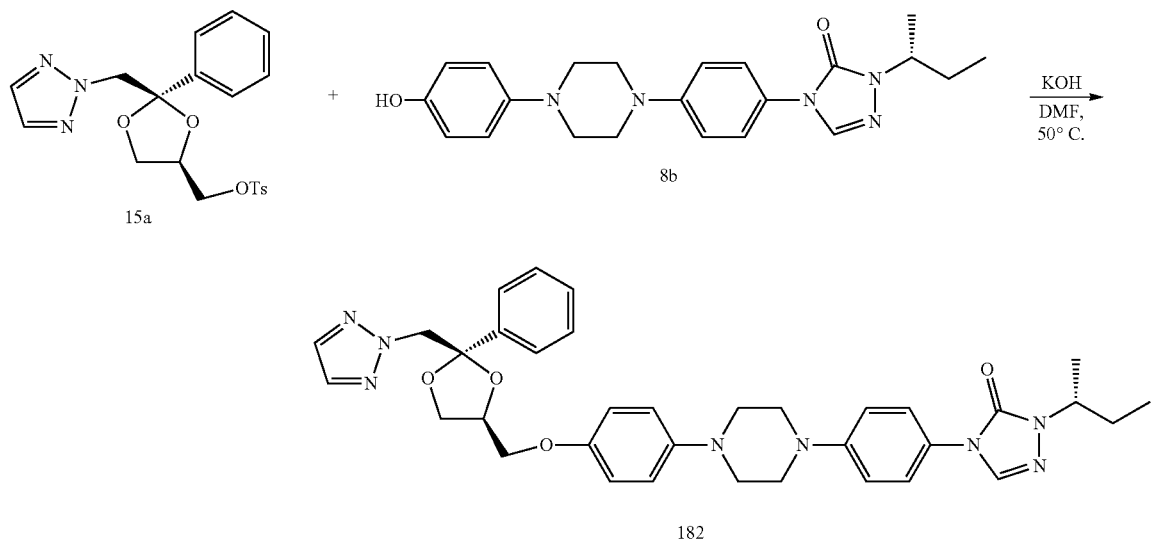

In a similar manner as described in Example 1 for the preparation of compound 11a, 11b was obtained as a white solid in 72.2% yield over 2 steps, starting from (S)-2,2-Dimethyl-1,3-dioxolane-4-methanol 9b. $^1$H NMR (400 MHz, CDCl$_3$) δ 7.83 (d, J=8.4 Hz, 2H), 7.39 (d, J=8.4 Hz, 2H), 4.16-4.04 (m, 2H), 3.99 (m, 1H), 3.78-3.60 (m, 2H), 2.48 (s, 3H), 2.17 (br s, 2H).

In a similar manner as described in Example 1 for the preparation of compounds 14a and 14b, compounds 15a and 15b were prepared. 15a was obtained as a white solid in 45.4% yield. LC-MS: m/z 416.1 (M+H); $^1$H NMR (400 MHz, CDCl$_3$) δ 7.81-7.74 (m, 2H), 7.57 (s, 2H), 7.50-7.43 (m, 2H), 7.42-7.33 (m, 5H), 4.77 (dd, J=17.6, 14.4 Hz, 2H), 4.21 (m, 1H), 3.85-3.75 (m, 2H), 3.70 (dd, J=8.8, 4.0 Hz, 1H), 3.37 (dd, J=10.0, 7.2 Hz, 1H), 2.50 (s, 3H); ee (>98%) was determined by chiral HPLC analysis with Phenomenex Lux Cellulose-3 column: 5 uL inj. 1 mg/mL (ethanol); flow rate, 1.0 mL/min; mobile phase, water:CH$_3$CN:acetic acid (40:60:0.1); RT=2.86 min. 15b was obtained as a slight yellow solid in 13.5% yield. LC-MS: m/z 416.1 (M+H); $^1$H NMR (400 MHz, CDCl$_3$) δ 7.72-7.65 (m, 2H), 7.63 (s, 2H), 7.44-7.38 (m, 2H), 7.36-7.29 (m, 5H), 4.74 (s, 2H), 4.11 (m, 1H), 3.96 (dd, J=10.3, 5.2 Hz, 1H), 3.86 (dd, J=8.6, 6.2 Hz, 1H), 3.75 (dd, J=10.2, 6.5 Hz, 1H), 3.60 (dd, J=8.6, 6.6 Hz, 1H), 2.47 (s, 3H).

In a similar manner as described in Example 1 for the preparation of compound 180, compound 182 was obtained from tosylate 15a and phenol 8b. LC-MS: m/z 637.1 (M+H); $^1$H NMR (400 MHz, CDCl$_3$) δ 7.70-7.62 (m, 3H), 7.63-7.53 (m, 2H), 7.53-7.32 (m, 5H), 7.04 (t, J=9.3 Hz, 2H), 6.95 (d, J=7.5 Hz, 2H), 6.79 (d, J=9.0 Hz, 2H), 4.88 (s, 2H), 4.43-4.25 (m, 2H), 3.92 (dd, J=8.4, 6.6 Hz, 1H), 3.88-3.81 (m, 1H), 3.77 (dd, J=9.4, 5.0 Hz, 1H), 3.45-3.31 (m, 5H), 3.26 (m, 4H), 1.96-1.82 (m, 1H), 1.82-1.71 (m, 1H), 1.42 (d, J=6.7 Hz, 3H), 0.93 (t, J=7.4 Hz, 3H).

Example 4

Synthesis of 4-(4-(4-(4-(((2R,4S)-2-((2H-1,2,3-triazol-2-yl)methyl)-2-phenyl-1,3-dioxolan-4-yl)methoxy)phenyl)piperazin-1-yl)phenyl)-(S)-1-sec-butyl-1H-1,2,4-triazol-5(4H)-one (182)

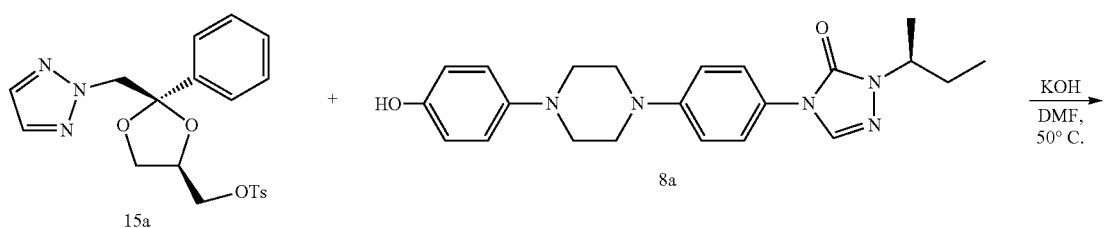

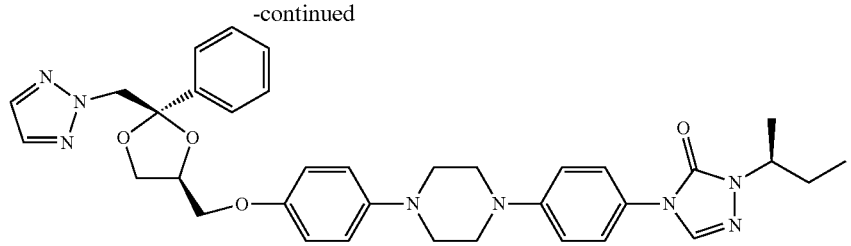
183
In a similar manner as described in Examples 1-3, compound 183 was obtained from tosylate 15a and phenol 8a. LC-MS: m/z 637.1 (M+H); $^1$H NMR (400 MHz, CDCl$_3$) δ 7.67-7.61 (m, 3H), 7.57 (m, 2H), 7.47-7.33 (m, 5H), 7.04 (t, J=9.2 Hz, 2H), 6.95 (d, J=8.2 Hz, 2H), 6.79 (d, J=9.0 Hz, 2H), 4.86 (s, 2H), 4.42-4.26 (m, 2H), 3.92 (dd, J=8.4, 6.6 Hz, 1H), 3.85 (dd, J=8.5, 4.4 Hz, 1H), 3.78 (dd, J=9.4, 5.0 Hz, 1H), 3.37 (m, 5H), 3.26 (m, 4H), 1.96-1.82 (m, 1H), 1.74 (m, 1H), 1.42 (d, J=6.7 Hz, 3H), 0.93 (t, J=7.4 Hz, 3H).
Example 5
Synthesis of 4-((2S,4R)-4-((4-(4-(4-(1-sec-butyl-5-oxo-1H-1,2,4-triazol-4(5H)-yl)phenyl)piperazin-1-yl)phenoxy)methyl)-2-(pyridazin-4-ylmethyl)-1,3-dioxolan-2-yl)benzamide (121)
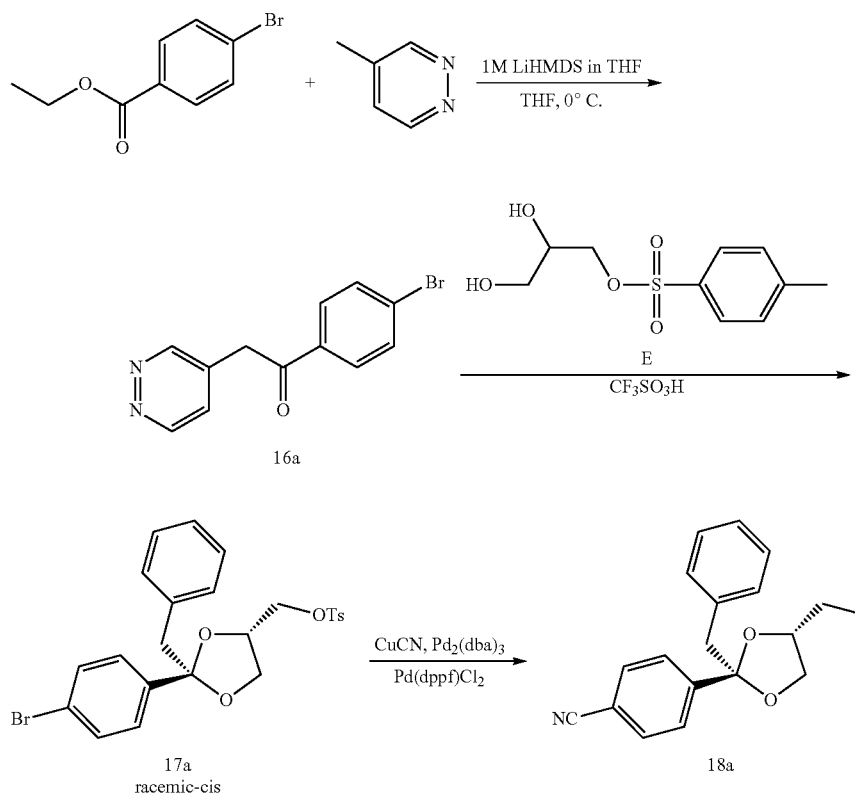
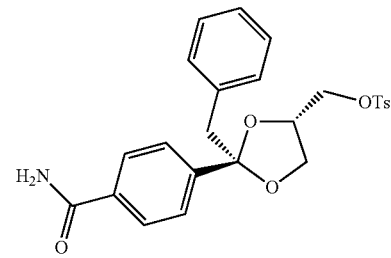

-continued

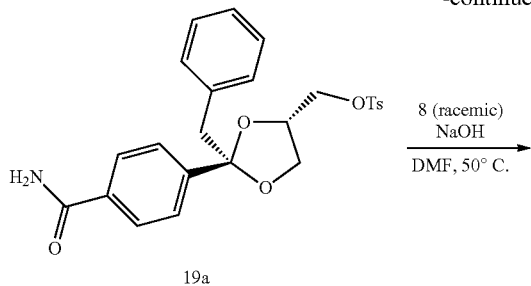

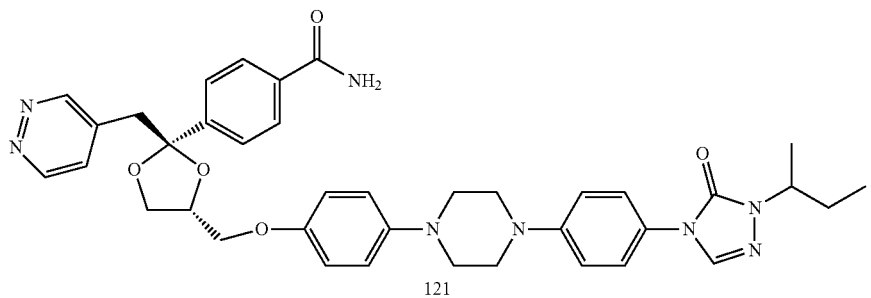

In a similar manner as described in Examples 1-4, compound 121 was obtained starting from ethyl 4-bromobenzoate and 4-methylpyridazine. LC-MS: m/z 691.4 (M+H); $^1$H NMR (400 MHz, CDCl$_3$) δ 0.90-0.94 (t, 3H), 1.40-1.42 (d, 3H), 1.70-1.77 (m, 1H), 1.86-1.88 (m, 1H), 3.17-3.27 (m, 5H), 3.35-3.40 (m, 4H), 3.55-3.72 (m, 1H), 3.67-3.69 (m, 1H), 3.81-3.84 (m, 2H), 4.29-4.32 (m, 3H), 5.51-5.68 (m, 1H), 6.09-6.21 (m, 1H), 6.66-6.77. (m, 2H), 6.88-6.97 (m, 2H), 7.02-7.06 (m, 2H), 7.32-7.33 (m, 1H), 7.53-7.59 (m, 2H), 7.63-7.64 (m, 1H), 7.78-7.85 (m, 2H), 9.02-9.08 (m, 2H).

The compounds in Table 1 were prepared using analogous procedures as described in Examples 1-5.

TABLE 1

| Cmpd # | Structure | Characterization Data |
|---|---|---|
| 4 | 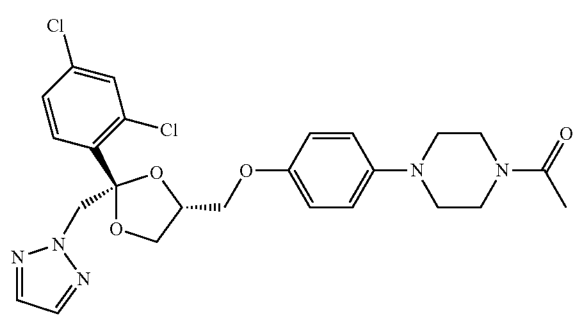 [SMILES: CC(=O)N1CCN(c2ccc(OC[C@@H]3CO[C@@](Cn4nccn4)(c4ccc(Cl)cc4Cl)O3)cc2)CC1] | LC-MS: m/z 532.0 (M + H) $^1$H NMR (400 MHz, CDCl$_3$) δ 7.61 (br s, 2H), 7.55 (d, J = 8.5 Hz, 1H), 7.47 (dd, J = 5.7, 2.8 Hz, 1H), 7.27-7.19 (m, 1H), 6.95-6.86 (m, 2H), 6.85-6.76 (m, 2H), 5.26-5.00 (m, 2H), 4.38 (m, 1H), 3.98-3.82 (m, 3H), 3.78 (dd, J = 11.5, 6.2 Hz, 2H), 3.70-3.59 (m, 2H), 3.46 (dd, J = 9.5, 7.1 Hz, 1H), 3.13-3.00 (m, 4H), 2.16 (s, 3H). |

| Cm pd # | Structure | Characterization Data |
|---|---|---|
| 5 | 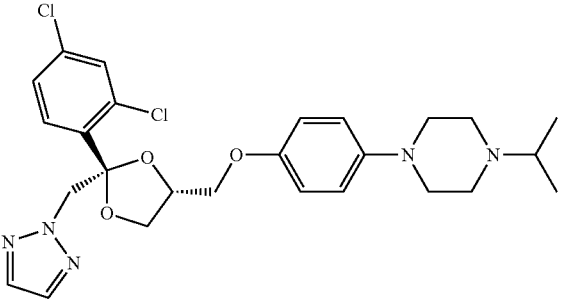 [SMILES: CC(C)N1CCN(c2ccc(OC[C@@H]3CO[C@@](Cn4nccn4)(c4ccc(Cl)cc4Cl)O3)cc2)CC1] | LC-MS: m/z 532.0 (M + H) $^1$H NMR (400 MHz, CDCl$_3$) δ 7.61 (s, 2H), 7.55 (t, J = 5.3 Hz, 1H), 7.48 (d, J = 2.1 Hz, 1H), 7.22 (dd, J = 8.4, 2.1 Hz, 1H), 6.92-6.88 (m, 2H), 6.81-6.74 (m, 2H), 5.12 (dd, J = 53.7, 14.3 Hz, 2H), 4.37 (m, 1H), 3.98-3.74 (m, 4H), 3.45 (dd, J = 9.5, 7.2 Hz, 1H), 3.13 (m, 4H), 2.73 (m, 4H), 1.12 (d, J = 6.5 Hz, 6H). |
| 6 | 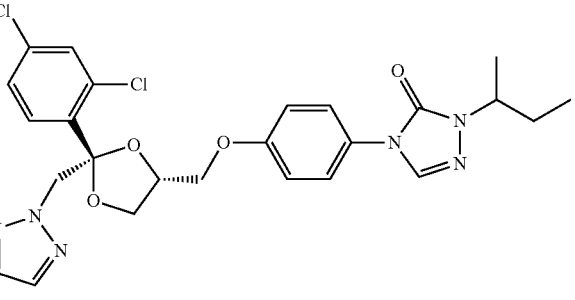 | LC-MS: m/z 545.0 (M + H) $^1$H NMR (400 MHz, CDCl$_3$) δ 7.65 (s, 1H), 7.62 (s, 2H), 7.58 (d, J = 8.4 Hz, 1H), 7.48 (dd, J = 4.6, 2.1 Hz, 2H), 7.47-7.45 (m, 1H), 7.24 (dd, J = 8.4. 2.1 Hz, 1H), 6.95-6.90 (m, 2H), 5.13 (dd, J = 51.6, 14.3 Hz, 2H), 4.49-4.35 (m, 1H), 4.31 (m, 1H), 3.99-3.81 (m, 4H), 3.52 (dd, J = 9.5, 6.8 Hz, 1H), 1.95-1.83 (m, 1H), 1.75 (m, 1H), 1.41 (d, J = 6.7 Hz, 3H), 0.93 (t, J = 7.4 Hz, 3H). |
| 7 | 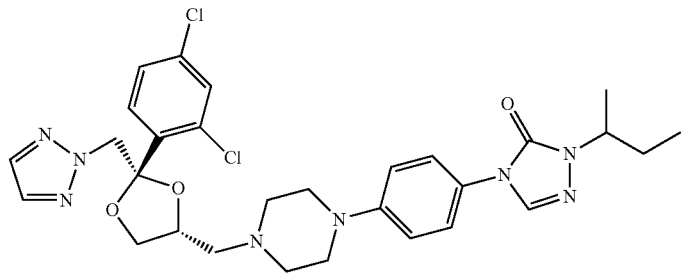 [SMILES: CCC(C)n1ncn(-c2ccc(N3CCN(C[C@@H]4CO[C@@](Cn5nccn5)(c5ccc(Cl)cc5Cl)O4)CC3)cc2)c1=O] | LC-MS: m/z 613.2 (M + H) |

TABLE 1-continued
| Cmpd # | Structure | Characterization Data |
|---|---|---|
| 8 | 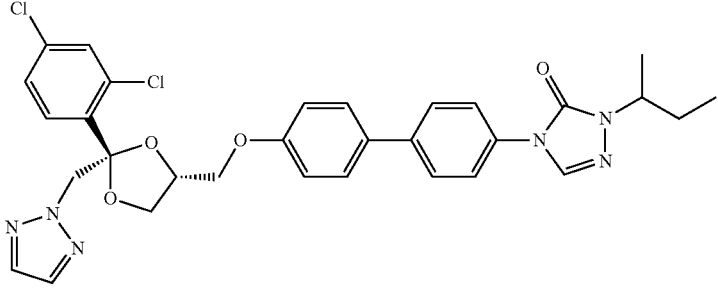 [SMILES: CCC(C)n1ncn(-c2ccc(-c3ccc(OC[C@@H]4CO[C@@](Cn5nccn5)(c5ccc(Cl)cc5Cl)O4)cc3)cc2)c1=O] | LC-MS: m/z 621.3 (M + H) ¹H NMR (400 MHz, CDCl₃) δ 7.75 (s, 1H), 7.65-7.48 (m, 6H), 7.49 (dd, J = 3.3, 2.0 Hz, 2H), 7.37 (dd, J = 8.3, 2.0 Hz, 2H), 7.24 (dd, J = 8.4, 2.0 Hz, 1H), 6.93 (d, J = 8.8 Hz, 2H), 5.15 (dd, J = 50.1, 14.3 Hz, 2H), 4.44 (m, 1H), 4.34 (m, 1H), 4.01-3.82 (m, 3H), 3.55 (dd, J = 9.5, 7.0 Hz, 1H), 1.90 (m, 1H), 1.80-1.69 (m, 1H), 1.43 (d, J = 6.7 Hz, 3H), 0.93 (t, J = 7.4 Hz, 3H). |
| 10 | 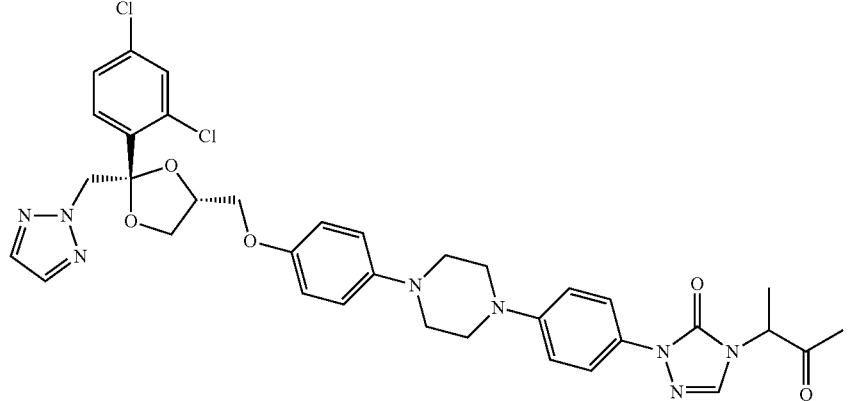 [SMILES: CC(=O)C(C)n1cnn(-c2ccc(N3CCN(c4ccc(OC[C@@H]5CO[C@@](Cn6nccn6)(c6ccc(Cl)cc6Cl)O5)cc4)CC3)cc2)c1=O] | LC-MS: m/z 718.9 (M+) ¹H NMR (400 MHz, CDCl₃) δ 7.71 (s, 1H), 7.61 (s, 2H), 7.56 (d, J = 5.8 Hz, 1H), 7.48 (d, J = 2.1 Hz, 1H), 7.47-7.42 (m, 2H), 7.23 (dd, J = 8.4, 2.1 Hz, 1H), 7.09-7.04 (m, 2H), 7.00-6.92 (m, 2H), 6.84-6.77 (m, 2H), 5.13 (dd, J = 52.1, 14.3 Hz, 2H), 4.94 (m, 1H), 4.39 (m, 1H), 4.02-3.76 (m, 3H), 3.53-3.44 (m, 1H), 3.40 (m, 4H), 3.26 (m, 4H), 2.21 (s, 3H), 1.66 (d, J = 8.3 Hz, 7H). |

TABLE 1-continued
| Cmpd # | Structure | Characterization Data |
|---|---|---|
| 11 | 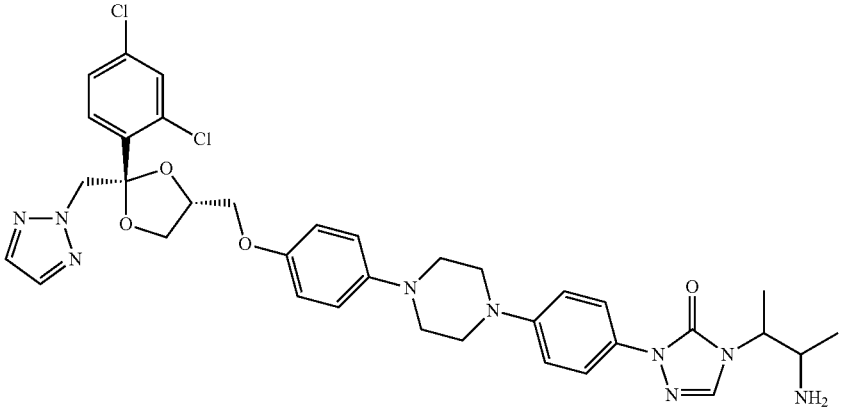 [SMILES: CC(N)C(C)n1cnn(-c2ccc(N3CCN(c4ccc(OC[C@@H]5CO[C@@](Cn6nccn6)(c6ccc(Cl)cc6Cl)O5)cc4)CC3)cc2)c1=O] | LC-MS: m/z 720.1 (M + H) |
| 12 | 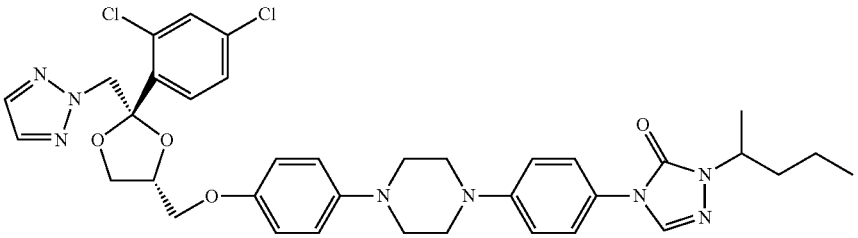 [SMILES: CCCC(C)n1ncn(-c2ccc(N3CCN(c4ccc(OC[C@@H]5CO[C@@](Cn6nccn6)(c6ccc(Cl)cc6Cl)O5)cc4)CC3)cc2)c1=O] | LC-MS: m/z 719.1 (M + H) $^1$H NMR (400 MHz, CDCl$_3$) δ 7.64 (s, 1H), 7.61 (s, 2H), 7.56 (d, J = 8.4 Hz, 1H), 7.47 (m, 3H), 7.23 (dd, J = 8.4, 2.1 Hz, 1H), 7.04 (t, J = 8.9 Hz, 2H), 6.95 (br s, 2H), 6.81 (d, J = 8.8 Hz, 2H), 5.13 (dd, J = 51.8, 14.3 Hz, 2H), 4.47-4.36 (m, 2H), 3.91 (m, 3H), 3.47 (dd, J = 15.8, 7.9 Hz, 1H), 3.39 (br s, 4H), 3.27 (br s, 4H), 1.94-1.80 (m, 1H), 1.78-1.57 (m, 1H), 1.40 (t, J = 8.4 Hz, 3H), 1.36-1.21 (m, 2H), 0.91 (t J = 7.4 Hz, 3H). |
| 13 | 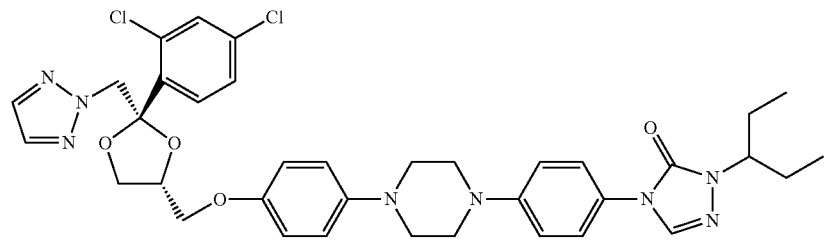 [SMILES: CCC(CC)n1ncn(-c2ccc(N3CCN(c4ccc(OC[C@@H]5CO[C@@](Cn6nccn6)(c6ccc(Cl)cc6Cl)O5)cc4)CC3)cc2)c1=O] | LC-MS: m/z 719.1 (M + H) $^1$H NMR (400 MHz, CDCl$_3$) δ 7.67 (s, 1H), 7.62 (s, 2H), 7.56 (d, J = 6.3 Hz, 1H), 7.51-7.39 (m, 3H), 7.23 (dd, J = 8.4, 2.1 Hz, 1H), 7.06 (d, J = 8.8 Hz, 2H), 6.98 (d, J = 28.3 Hz, 2H), 6.83 (m, 2H), 5.13 (dd, J = 51.4, 14.3 Hz, 2H), 4.39 (m, 1H), 4.09 (m, 1H), 3.99-3.80 (m, 3H), 3.47 (m, 1H), 3.39 (br s, 4H), 3.27 |

TABLE 1-continued

| Cmpd # | Structure | Characterization Data |
|---|---|---|
| | | (br s, 4H), 1.97-1.66 (m, 4H), 0.91 (t, J = 7.4 Hz, 6H). |
| 14 | 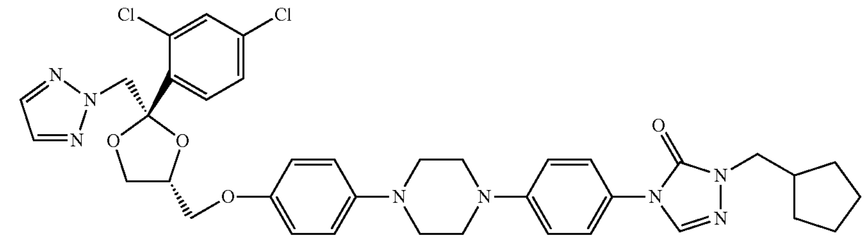 [SMILES: O=c1n(-c2ccc(N3CCN(c4ccc(OC[C@@H]5CO[C@@](Cn6nccn6)(c6ccc(Cl)cc6Cl)O5)cc4)CC3)cc2)cnn1CC1CCCC1] | LC-MS: m/z 731.3 (M + H) $^1$H NMR (400 MHz, CDCl$_3$) δ 7.63 (s, 1H), 7.61 (s, 2H), 7.56 (d, J = 8.4 Hz, 1H), 7.50-7.42 (m, 3H), 7.23 (dd, J = 8.5, 2.1 Hz, 1H), 7.09-7.03 (m, 2H), 6.99 (br s, 2H), 6.86-6.76 (m, 2H), 5.25-5.03 (m, 2H), 4.39 (m, 1H), 4.03-3.83 (m, 3H), 3.80 (d, J = 7.5 Hz, 2H), 3.63-3.34 (m, 5H), 3.29 (br s, 4H), 2.46 (m, 1H), 1.87-1.50 (m, 6H), 1.49-1.22 (m, 2H). |
| 15 | 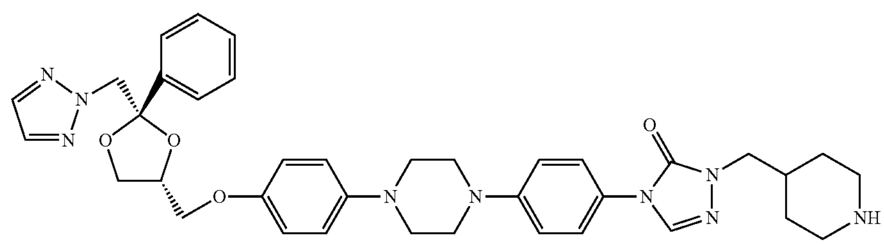 [SMILES: O=c1n(-c2ccc(N3CCN(c4ccc(OC[C@@H]5CO[C@@](Cn6nccn6)(c6ccccc6)O5)cc4)CC3)cc2)cnn1CC1CCNCC1] | LC-MS: m/z 678.2 (M + H) |
| 16 | 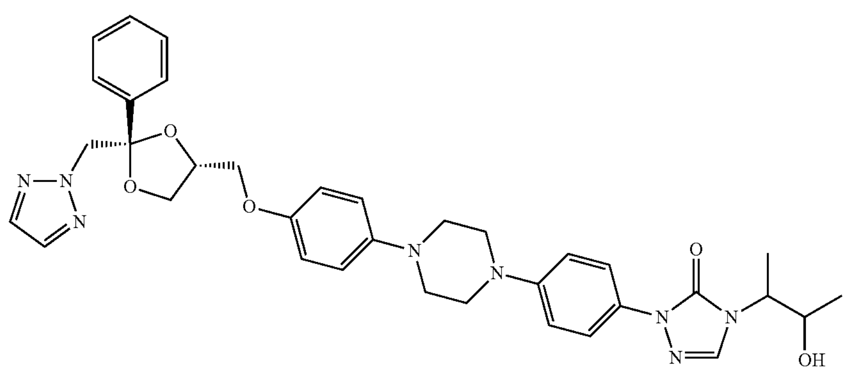 [SMILES: CC(O)C(C)n1cnn(-c2ccc(N3CCN(c4ccc(OC[C@@H]5CO[C@@](Cn6nccn6)(c6ccccc6)O5)cc4)CC3)cc2)c1=O] | LC-MS: m/z 653.2 (M + H) |
| 17 | 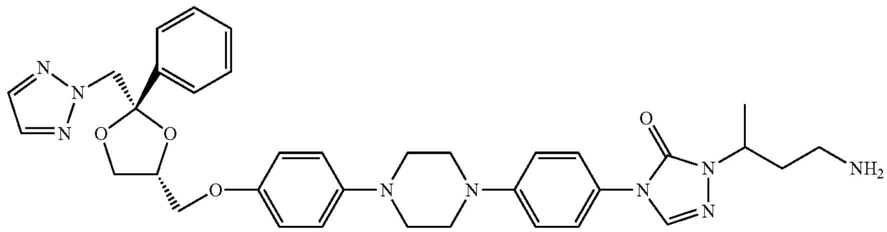 [SMILES: CC(CCN)n1ncn(-c2ccc(N3CCN(c4ccc(OC[C@@H]5CO[C@@](Cn6nccn6)(c6ccccc6)O5)cc4)CC3)cc2)c1=O] | LC-MS: m/z 652.2 (M + H) |

TABLE 1-continued

| Cmpd # | Structure | Characterization Data |
|---|---|---|
| 18 | 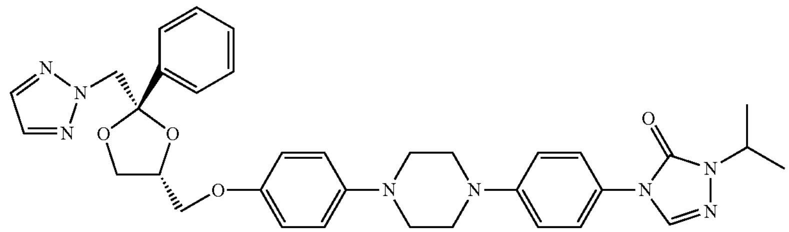 [SMILES: CC(C)n1ncn(-c2ccc(N3CCN(c4ccc(OC[C@@H]5CO[C@@](Cn6nccn6)(c6ccccc6)O5)cc4)CC3)cc2)c1=O] | LC-MS: m/z 623.3 (M + H) |
| 19 | 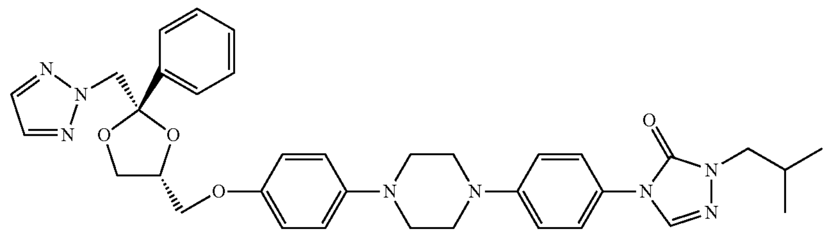 [SMILES: CC(C)Cn1ncn(-c2ccc(N3CCN(c4ccc(OC[C@@H]5CO[C@@](Cn6nccn6)(c6ccccc6)O5)cc4)CC3)cc2)c1=O] | LC-MS: m/z 637.1 (M + H) |
| 20 | 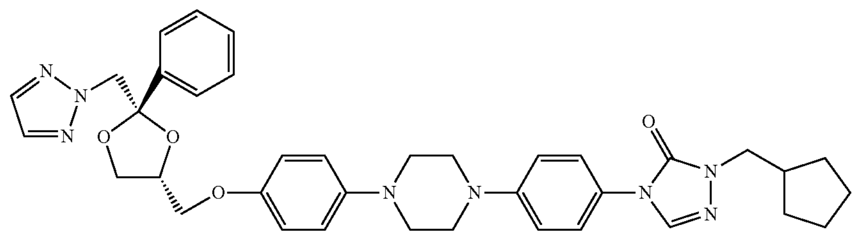 [SMILES: O=c1n(-c2ccc(N3CCN(c4ccc(OC[C@@H]5CO[C@@](Cn6nccn6)(c6ccccc6)O5)cc4)CC3)cc2)cnn1CC1CCCC1] | LC-MS: m/z 663.3 (M + H) |
| 21 | 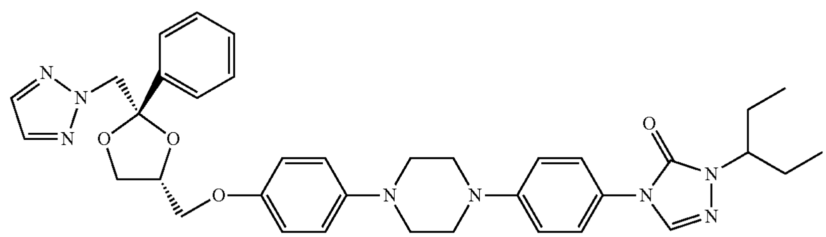 [SMILES: CCC(CC)n1ncn(-c2ccc(N3CCN(c4ccc(OC[C@@H]5CO[C@@](Cn6nccn6)(c6ccccc6)O5)cc4)CC3)cc2)c1=O] | LC-MS: m/z 651.2 (M + H) |
| 22 | 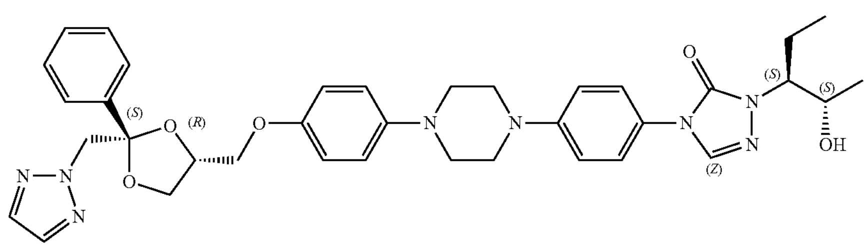 | LC-MS: m/z 667.2 (M + H) |
| 23 | 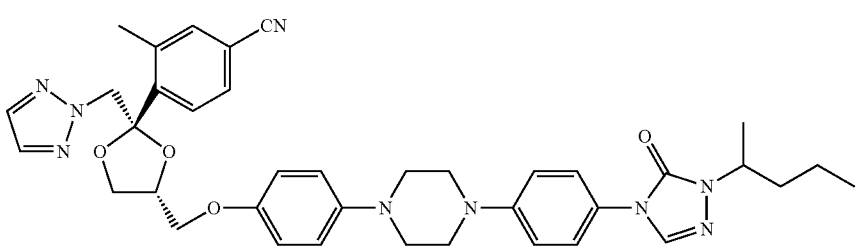 [SMILES: CCCC(C)n1ncn(-c2ccc(N3CCN(c4ccc(OC[C@@H]5CO[C@@](Cn6nccn6)(c6ccc(C#N)cc6C)O5)cc4)CC3)cc2)c1=O] | LC-MS: m/z 690.2 (M + H) |

TABLE 1-continued

| Cmpd # | Structure | Characterization Data |
|---|---|---|
| 24 | 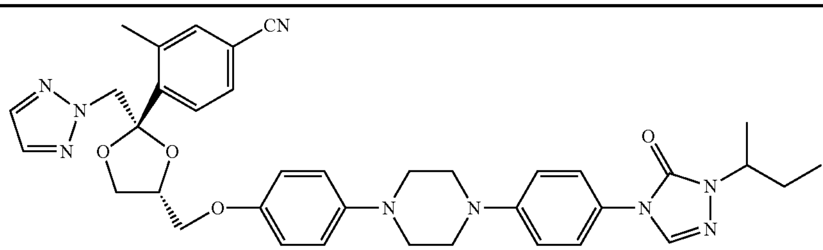 | LC-MS: m/z 676.2 (M + H) |
| 25 | 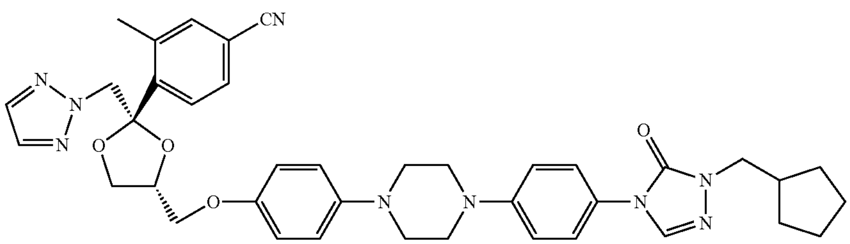 | LC-MS: m/z 702.2 (M + H) |
| 26 | 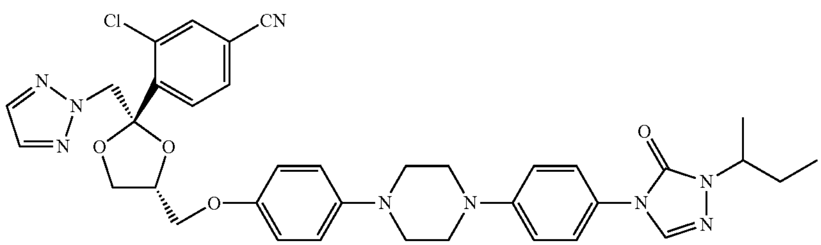 [SMILES: CCC(C)n1ncn(-c2ccc(N3CCN(c4ccc(OC[C@@H]5CO[C@@](Cn6nccn6)(c6ccc(C#N)cc6Cl)O5)cc4)CC3)cc2)c1=O] | LC-MS: m/z 696.1 (M + H) |
| 27 | 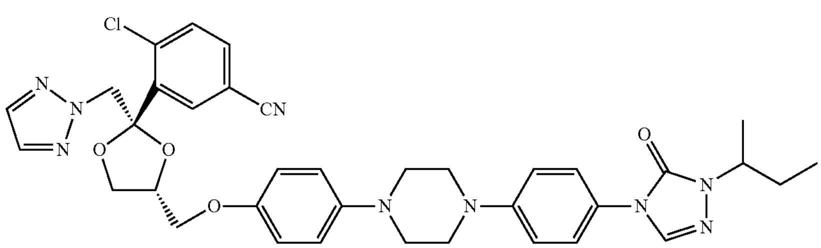 [SMILES: CCC(C)n1ncn(-c2ccc(N3CCN(c4ccc(OC[C@@H]5CO[C@@](Cn6nccn6)(c6cc(C#N)ccc6Cl)O5)cc4)CC3)cc2)c1=O] | LC-MS: m/z 696.1 (M + H) |
| 28 | 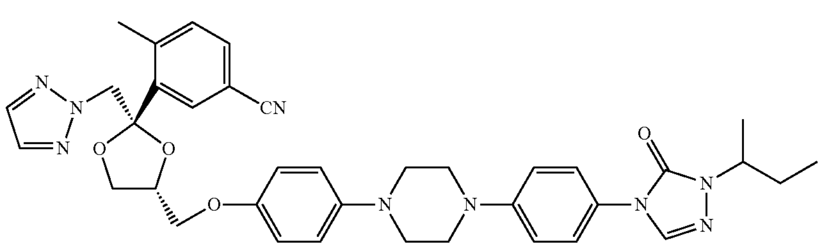 | LC-MS: m/z 676.2 (M + H) |
| 29 | 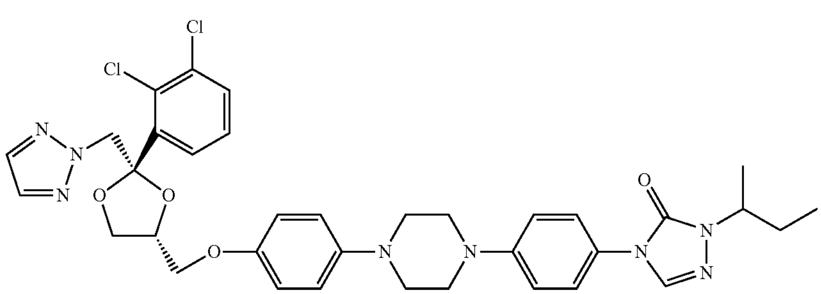 [SMILES: CCC(C)n1ncn(-c2ccc(N3CCN(c4ccc(OC[C@@H]5CO[C@@](Cn6nccn6)(c6cccc(Cl)c6Cl)O5)cc4)CC3)cc2)c1=O] | LC-MS: m/z 705.2 (M + H) <sup>1</sup>H NMR (400 MHz, CDCl<sub>3</sub>) δ 7.64 (s, 1H), 7.63 (s, 2H), 7.59 (dt, J = 5.4, 2.7 Hz, 1H), 7.52 (dt, J = 8.0, 3.9 Hz, 1H), 7.44 (dd, J = 7.2, 5.1 Hz, 2H), 7.25-7.13 (m, 1H), 7.10-7.01 (m, 3H), 6.95 (d, J = 6.1 Hz, |

TABLE 1-continued
| Cmpd # | Structure | Characterization Data |
|---|---|---|
| | | 2H), 6.85-6.75 (m, 2H), 5.27-5.02 (m, 2H), 4.48-4.22 (m, 2H), 4.00-3.90 (m, 1H), 3.90-3.78 (m, 2H), 3.41 (m, 5H), 3.27 (m, 4H), 1.97-1.81 (m, 1H), 1.81-1.69 (m, 1H), 1.42 (d, J = 6.7 Hz, 3H), 0.93 (t, J = 7.4 Hz, 3H). |
| 30 | 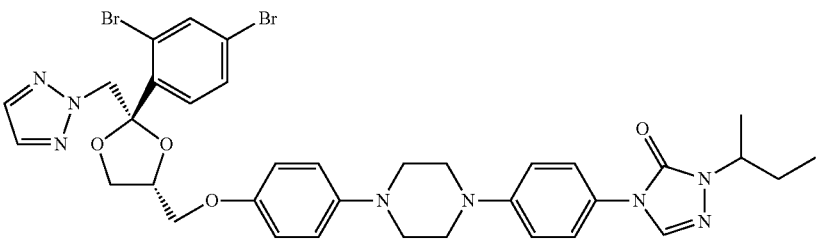 | LCMS: 100% @ 262 nm; m/z 794.7 (M + H). 1H NMR (400 MHz, CDCl3): 0.90-0.94 (t, J = 7.6 Hz, 3H), 1.40-1.42 (d, J = 6.8 Hz, 3H), 1.74-1.77 (m, 1H), 1.85-1.89 (m, 1H), 3.24-3.27 (m, 4H), 3.37-3.46 (m, 5H), 3.83-3.91 (m, 3H), 4.30-4.37 (m, 2H), 5.05-5.09 (d, 1H), 5.20-5.24 (d, 1H), 6.79-6.81 (d, J = 9.2 Hz, 2H), 6.94-6.96 (d, J = 8.8 Hz, 2H), 7.04-7.06 (d, J = 9.2 Hz, 2H) 7.42-7.46 (m, 3H), 7.51-7.54 (m, 1H), 7.62 (s, 2H), 7.64 (s, 1H), 7.84-7.85 (d, J = 4 Hz, 1H). |
| 31 | 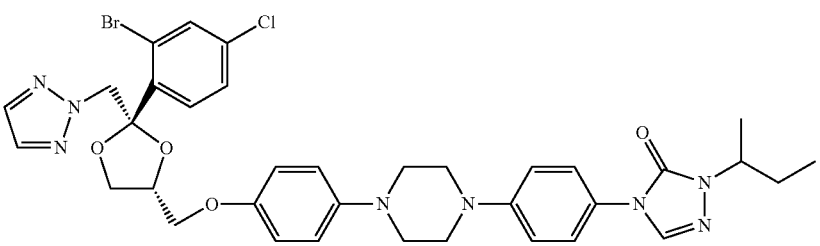 [SMILES: CCC(C)n1ncn(-c2ccc(N3CCN(c4ccc(OC[C@@H]5CO[C@@](Cn6nccn6)(c6ccc(Cl)cc6Br)O5)cc4)CC3)cc2)c1=O] | LCMS: 100% @ 262 nm; m/z 750.8 (M + H). 1H NMR (400 MHz, CDCl3): 0.91-0.94 (t, J = 7.6 Hz, 3H), 1.40-1.42 (d, J = 6.4 Hz, 3H), 1.74-1.76 (m, 1H), 1.87-1.89 (m, 1H), 3.24-3.27 (m, 4H), 3.37-3.47 (m, 5H), 3.84-3.91 (m, 3H), 4.31-4.34 (m, 1H), 4.36-4.39 (m, 1H), 5.05-5.09 (d, 1H), 5.20-5.24 (d, 1H), 6.79-6.81 (d, J = 8.8 Hz, 2H), 6.94-6.96 (d, J = 9.2 Hz, 2H), 7.04-7.06 (d, J = 9.2 Hz, 2H), |

TABLE 1-continued

| Cmpd # | Structure | Characterization Data |
|---|---|---|
| | | 7.28 (m, 1H), 7.44-7.46 (d, J = 8.8 Hz, 2H), 7.57-7.64 (m, 4H), 7.69 (m, 1H). |
| 32 | 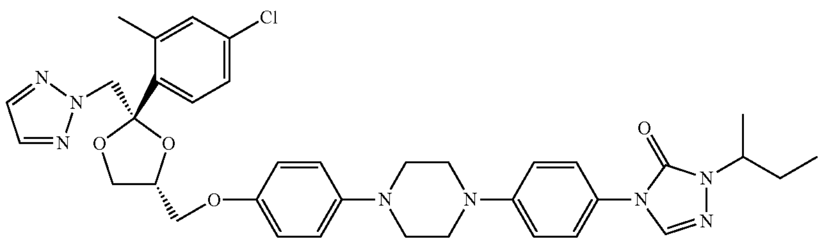 | LC-MS: m/z 705.1 (M + H) |
| 33 | 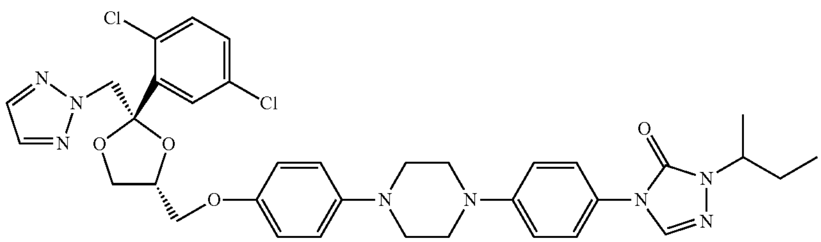 | LCMS: 98.08% @ 262 nm; m/z 705.01 (M + H). 1H NMR (400 MHz, CDCl3): 0.91-0.94 (t, J = 7.6 Hz, 3H), 1.42-1.47 (d, J = 6.8 Hz, 3H), 1.70-1.77 (m, 1H), 1.85-1.88 (m, 1H), 3.26-3.27 (m, 4H), 3.37-3.49 (m, 5H), 3.85-3.99 (m, 3H), 4.29-4.33 (m, 1H), 4.41-4.43 (m, 1H), 5.05-5.09 (d, 1H), 5.18-5.22 (d, 1H), 6.80-6.82 (d, J = 8.8 Hz, 2H), 6.94-6.97 (d, J = 8.8 Hz, 2H), 7.04-7.06 (d, J = 8.8 Hz, 2H), 7.28-7.30 (m, 1H), 7.38-7.40 (m, 1H), 7.44-7.46 (m, 2H), 7.62-7.64 (m, 4H). |
| 34 | 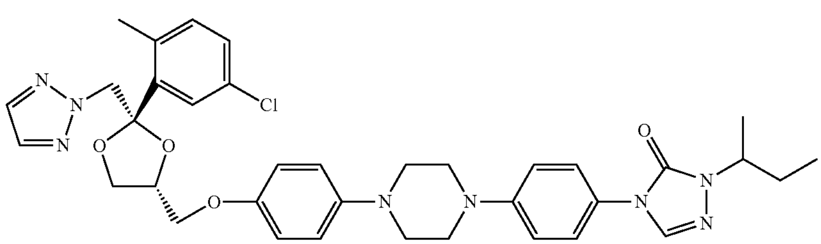 | LCMS: 96.48% @ 262 nm; m/z 684.96 (M + H). 1H NMR (400 MHz, CDCl3): 0.90-0.94 (t, J = 7.2 Hz, 3H), 1.40-1.42 (d, J = 6.8 Hz, 3H), 1.74-1.77 (m, 1H), 1.85-1.89 (m, 1H), 2.59 (s, 3H), 3.24-3.27 (m, 4H), 3.36-3.40 (m, 5H), 3.79-3.84 (m, 2H), 3.89-3.93 (m, 1H), 4.33-4.36 (m, 2H), 4.88-4.89 (q, 2H), 6.78-6.80 (d, J = 9.2 Hz, 2H), 6.94-6.96 (d, J = 9.2 Hz, 2H), 7.04- |

| Cmpd # | Structure | Characterization Data |
|---|---|---|
| | | 7.06 (d, J = 8.8 Hz, 2H), 7.14-7.16 (d, J = 8.8 Hz, 1H), 7.22-7.23 (d, J = 2 Hz, 1H), 7.43-7.46 (d, J = 9.2 Hz, 2H), 7.59-7.60 (d, J = 2.4 Hz, 1H), 7.64 (s, 3H). |
| 35 | 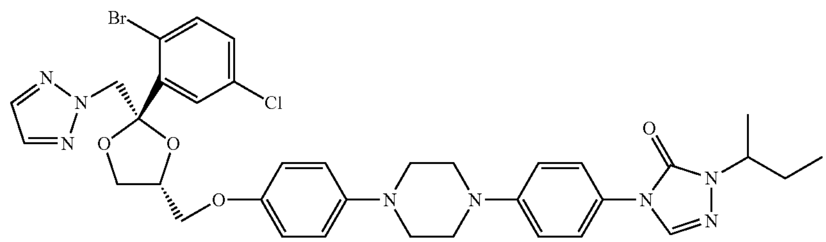 | LCMS: 97.47% @ 262 nm; m/z 750.6 (M + H). 1H NMR (400 MHz, CDCl3): 0.88-0.92 (t, J = 7.2 Hz, 3H), 1.40-1.42 (d, J = 6.8 Hz, 3H), 1.70-1.77 (m, 1H), 1.85-1.90 (m, 1H), 3.24-3.27 (m, 4H), 3.39-3.46 (m, 5H), 3.84-3.90 (m, 2H), 3.92-3.96 (m, 1H), 4.29-4.34 (m, 1H), 4.39-4.42 (m, 1H), 5.09-5.09 (d, 1H), 5.21-5.24 (d, 1H), 6.79-6.81 (d, J = 9.2 Hz, 2H), 6.94-6.96 (d, J = 9.2 Hz, 2H), 7.04-7.06 (d, J = 9.2 Hz, 2H), 7.19-7.22 (dd, J = 2.4 Hz, 1H), 7.44-7.46 (d, J = 8.8 Hz, 2H), 7.59-7.66 (m, 5H). |
| 36 | 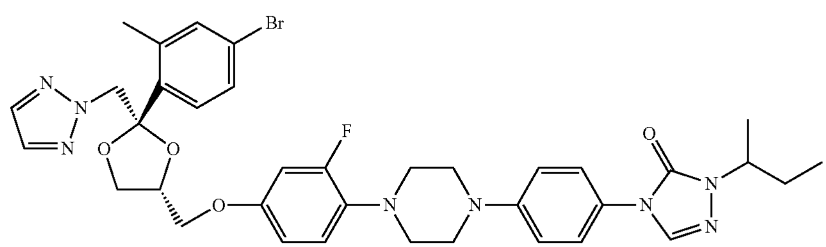 [SMILES: CCC(C)n1ncn(-c2ccc(N3CCN(c4ccc(OC[C@@H]5CO[C@@](Cn6nccn6)(c6ccc(Br)cc6C)O5)cc4F)CC3)cc2)c1=O] | LC-MS: m/z 729.3 (M + H) |
| 37 | 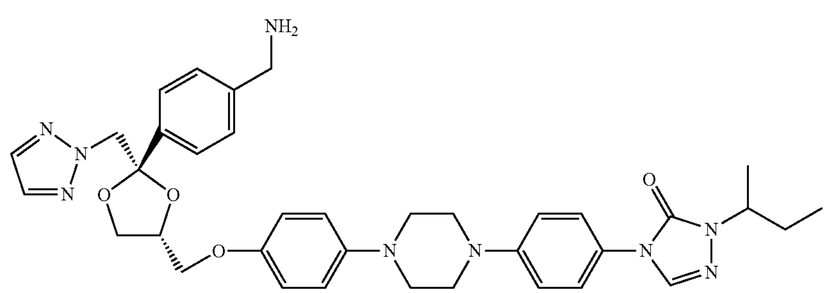 [SMILES: CCC(C)n1ncn(-c2ccc(N3CCN(c4ccc(OC[C@@H]5CO[C@@](Cn6nccn6)(c6ccc(CN)cc6)O5)cc4)CC3)cc2)c1=O] | LC-MS: m/z 666.2 (M + H) 1H NMR (400 MHz, CDCl3) δ 7.63 (m, 3H), 7.58-7.47 (m, 2H), 7.49-7.35 (m, 4H), 7.12-7.01 (m, 2H), 6.95 (d, J = 8.9 Hz, 2H), 6.79 (d, J = 8.8 Hz, 2H), 4.84 (m, 2H), 4.43-4.18 (m, 3H), 3.90 (m, 2H), 3.78 (m, 1H), 3.39 (m, 4H), 3.25 (m, |

TABLE 1-continued

| Cm pd # | Structure | Characterization Data |
|---|---|---|
| | | 4H), 1.90 (m, 1H), 1.74 (m, 1H), 1.42 (d, J = 6.7 Hz, 3H), 0.92 (t, J = 7.5 Hz, 3H). |
| 38 | 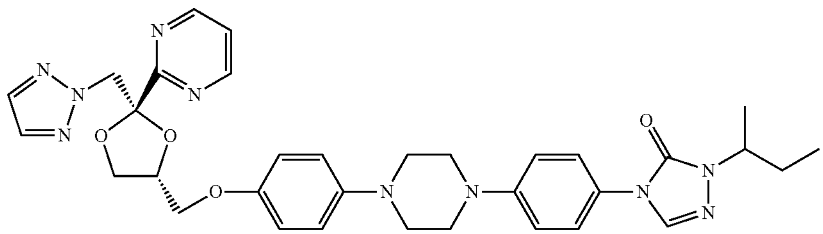 [SMILES: CCC(C)n1ncn(-c2ccc(N3CCN(c4ccc(OC[C@@H]5CO[C@@](Cn6nccn6)(c6ncccn6)O5)cc4)CC3)cc2)c1=O] | LC-MS: m/z 639.1 (M + H) |
| 39 | 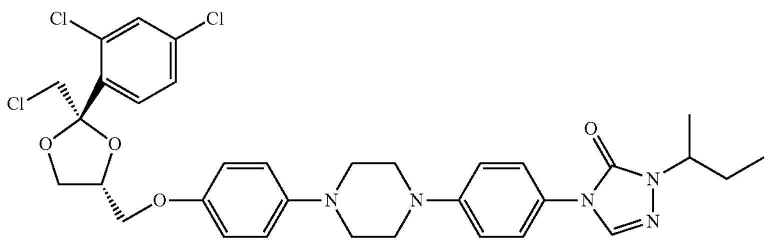 [SMILES: CCC(C)n1ncn(-c2ccc(N3CCN(c4ccc(OC[C@@H]5CO[C@@](CCl)(c6ccc(Cl)cc6Cl)O5)cc4)CC3)cc2)c1=O] | LC-MS: m/z 672.1 (M + H) |
| 40 | 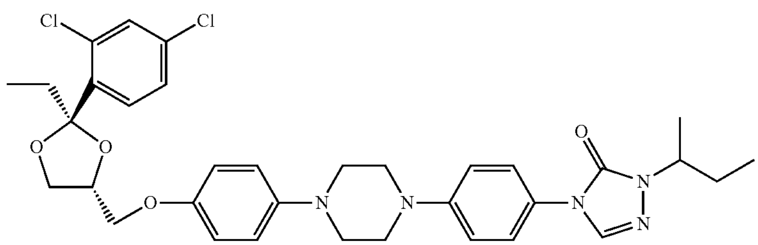 [SMILES: CCC(C)n1ncn(-c2ccc(N3CCN(c4ccc(OC[C@@H]5CO[C@@](CC)(c6ccc(Cl)cc6Cl)O5)cc4)CC3)cc2)c1=O] | LC-MS: m/z 652.1 (M + H ¹H NMR (400 MHz, CDCl₃) δ 7.68 (s, 1H), 7.59 (d, J = 8.4 Hz, 1H), 7.54-7.48 (m, 4H), 7.43 (d, J = 2.1 Hz, 1H), 7.26 (dd, J = 8.4, 2.1 Hz, 1H), 7.07 (dd, J = 13.1, 9.0 Hz, 4H), 4.34 (m, 2H), 4.17 (m, 1H), 4.04 (m, 2H), 3.96-3.84 (m, 1H), 3.69 (m, 8H), 2.21-2.07 (m, 2H), 1.97-1.83 (m, 1H), 1.83-1.62 (m, 1H), 1.42 (d, J = 6.7 Hz, 3H), 0.92 (m, 6H |
| 41 | 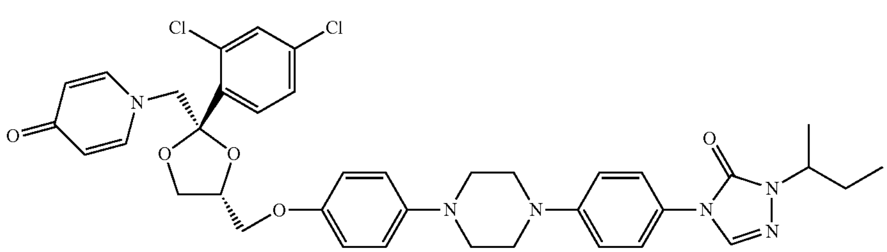 [SMILES: CCC(C)n1ncn(-c2ccc(N3CCN(c4ccc(OC[C@@H]5CO[C@@](Cn6ccc(=O)cc6)(c6ccc(Cl)cc6Cl)O5)cc4)CC3)cc2)c1=O] | LC-MS: m/z 731.2 (M + H) |

TABLE 1-continued

| Cmpd # | Structure | Characterization Data |
|---|---|---|
| 42 | 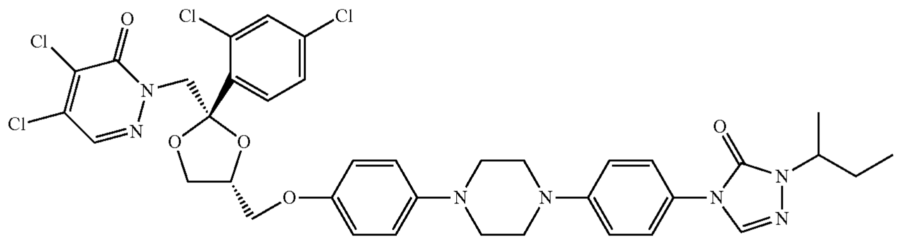 [SMILES: CCC(C)n1ncn(-c2ccc(N3CCN(c4ccc(OC[C@@H]5CO[C@@](Cn6ncc(Cl)c(Cl)c6=O)(c6ccc(Cl)cc6Cl)O5)cc4)CC3)cc2)c1=O] | LC-MS: m/z 800.1 (M + H) |
| 43 | 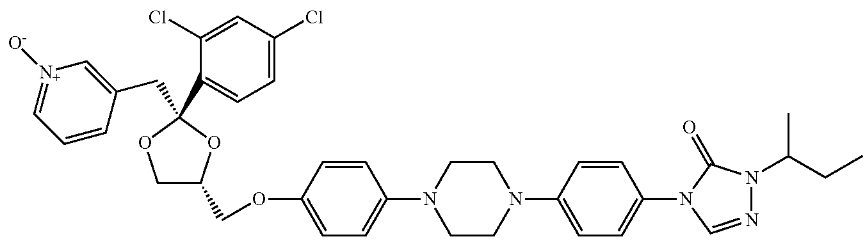 | LC-MS: m/z 747.2 (M + H) |
| 44 | 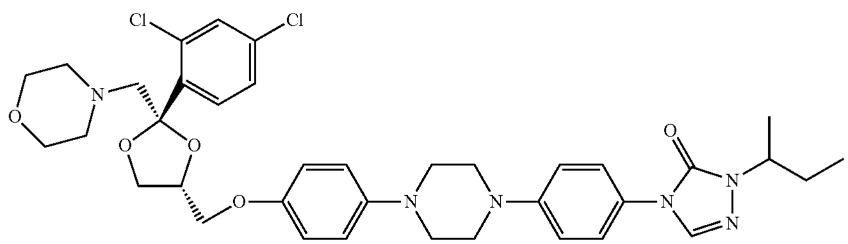 [SMILES: CCC(C)n1ncn(-c2ccc(N3CCN(c4ccc(OC[C@@H]5CO[C@@](CN6CCOCC6)(c6ccc(Cl)cc6Cl)O5)cc4)CC3)cc2)c1=O] | LC-MS: m/z 723.1 (M + H) |
| 45 | 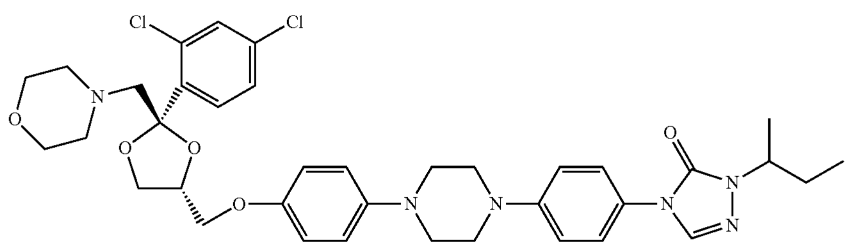 [SMILES: CCC(C)n1ncn(-c2ccc(N3CCN(c4ccc(OC[C@@H]5CO[C@](CN6CCOCC6)(c6ccc(Cl)cc6Cl)O5)cc4)CC3)cc2)c1=O] | LC-MS: m/z 723.1 (M + H) |
| 46 | 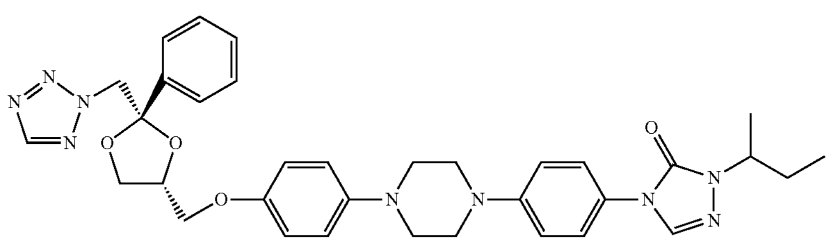 | LC-MS: m/z 687.2 (M + H) |
| 47 | 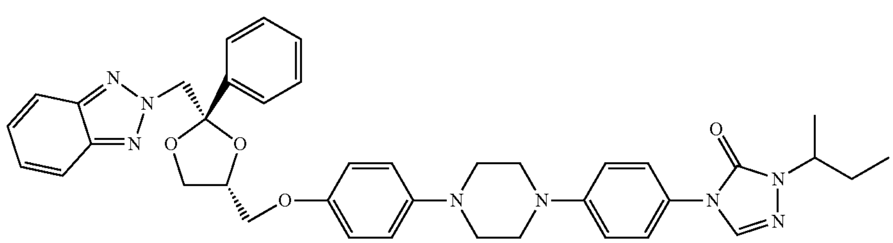 | LC-MS: m/z 678.2 (M + H) |

TABLE 1-continued

| Cmpd # | Structure | Characterization Data |
|---|---|---|
| 48 | 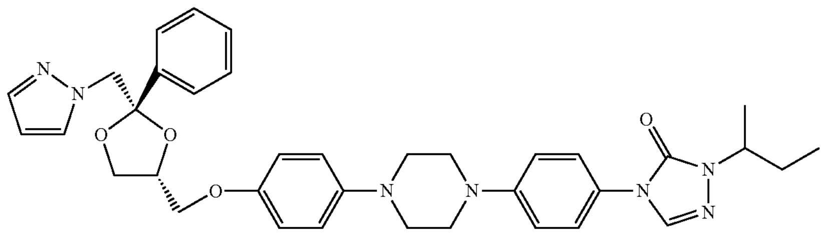 | LCMS: 100% @ 261 nm; m/z 636.10 (M + H). $^1$H NMR (400 MHz, CDCl$_3$): 0.91-0.94 (t, J = 7.6 Hz, 3H), 1.40-1.42 (d, J = 6.8 Hz, 3H), 1.72-1.76 (m, 1H), 1.85-1.89 (m, 1H), 3.25-3.37 (m, 5H), 3.37-3.40 (m, 4H), 3.70-3.74 (m, 1H), 3.77-3.80 (m, 1H), 3.86-3.90 (m, 1H), 4.31-4.38 (m, 2H), 4.46-4.55 (q, 2H), 6.25-6.26 (t, J = 2.0 Hz, 1H), 6.78-6.80 (d, J = 8.8 Hz, 2H), 6.94-6.96 (d, J = 8.8 Hz, 2H), 7.04-7.07 (d, J = 8.8 Hz, 2H), 7.39-7.46 (m, 5H), 7.51-7.54 (m, 2H), 7.56-7.58 (m-2H), 7.64 (s, 1H). |
| 49 | 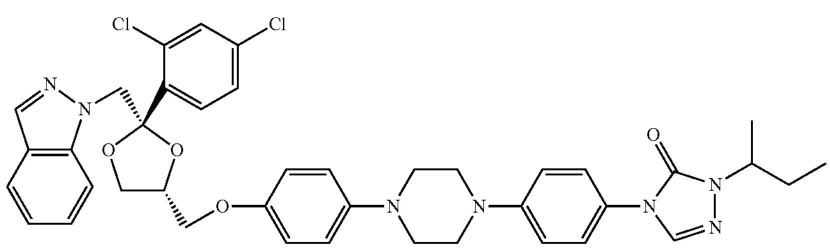 [SMILES: CCC(C)n1ncn(-c2ccc(N3CCN(c4ccc(OC[C@@H]5CO[C@@](Cn6ncc7ccccc76)(c6ccc(Cl)cc6Cl)O5)cc4)CC3)cc2)c1=O] | LC-MS: m/z 754.1 (M + H) |
| 50 | 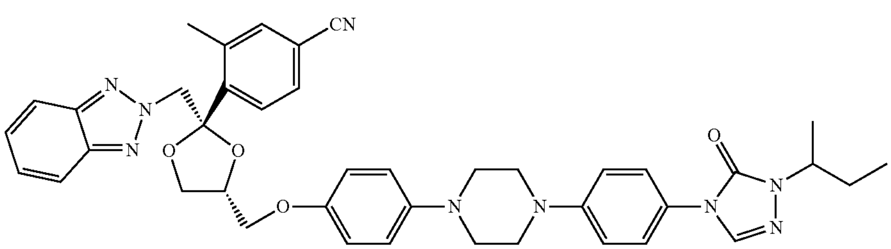 [SMILES: CCC(C)n1ncn(-c2ccc(N3CCN(c4ccc(OC[C@@H]5CO[C@@](Cn6nc7ccccc7n6)(c6ccc(C#N)cc6C)O5)cc4)CC3)cc2)c1=O] | LC-MS: m/z 726.2 (M + H) |
| 51 | 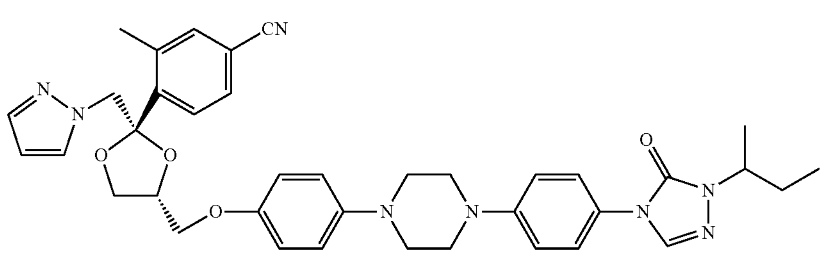 | LC-MS: m/z 675.2 (M + H) |

TABLE 1-continued
| Cmpd # | Structure | Characterization Data |
|---|---|---|
| 52 | 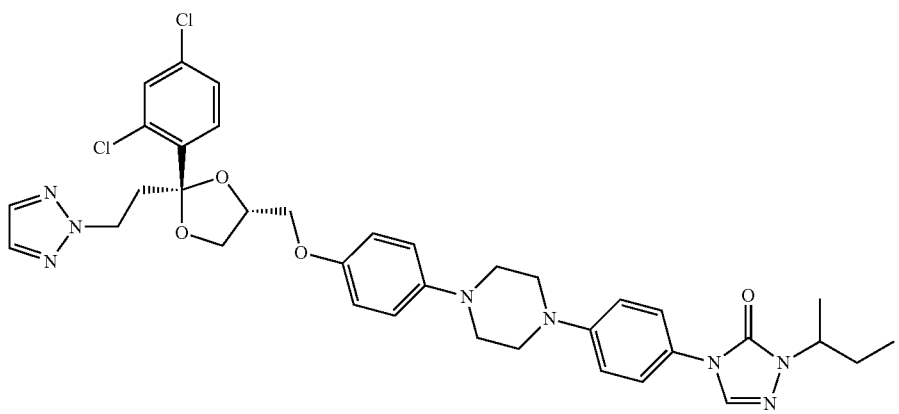 [SMILES: CCC(C)n1ncn(-c2ccc(N3CCN(c4ccc(OC[C@@H]5CO[C@@](CCn6nccn6)(c6ccc(Cl)cc6Cl)O5)cc4)CC3)cc2)c1=O] | LC-MS: m/z 719.2(M + H) $^1$H NMR (400 MHz, CDCl$_3$) δ 7.64 (d, J = 0.7 Hz, 1H), 7.61 (d, J = 8.4 Hz, 1H), 7.56 (s, 2H), 7.48-7.40 (m, 3H), 7.25 (dd, J = 8.4, 2.1 Hz, 1H), 7.09-7.01 (m, 2H), 6.99 (d, J = 8.8 Hz, 2H), 6.95-6.87 (m, 2H), 4.78-4.57 (m, 2H), 4.41-4.23 (m, 2H), 4.22-4.11 (m, 1H), 4.10-3.97 (m, 2H), 3.90 (dd, J = 8.3, 7.1 Hz, 1H), 3.39 (m, 4H), 3.32-3.12 (m, 4H), 2.86 (m, 2H), 1.89 (m, 1H), 1.74 (m, 1H), 1.41 (d, J = 6.7 Hz, 3H), 0.94 (t, J = 7.4 Hz, 3H). |
| 53 | 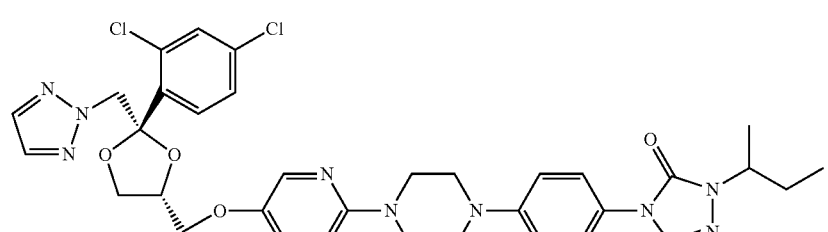 | LC-MS: m/z 706.0 (M + H) $^1$H NMR (400 MHz, CDCl$_3$) δ 7.69 (s, 1H), 7.64 (m, 3H), 7.62-7.56 (m, 2H), 7.52-7.42 (m, 3H), 7.25 (m, 2H), 7.08-7.01 (m, 2H), 5.27-5.01 (m, 2H), 4.39 (m, 1H), 4.32 (m, 1H), 4.27-4.13 (m, 1H), 4.01-3.75 (m, 3H), 3.67 (m, 4H), 3.38 (m, 4H), 1.88 (m, 1H), 1.75 (m, 1H), 1.42 (d, J = 6.7 Hz, 3H), (t, J = 7.4 Hz, 3H). |
| 54 | 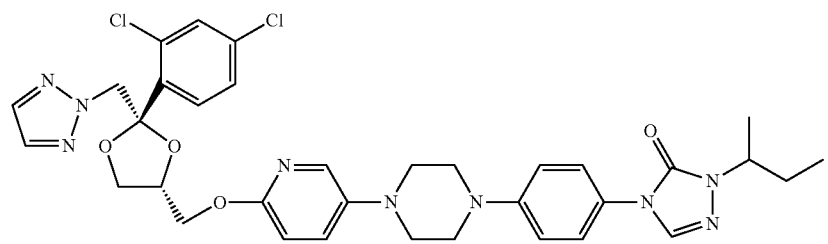 [SMILES: CCC(C)n1ncn(-c2ccc(N3CCN(c4ccc(OC[C@@H]5CO[C@@](Cn6nccn6)(c6ccc(Cl)cc6Cl)O5)nc4)CC3)cc2)c1=O] | LC-MS: m/z 706.1 (M + H) |

TABLE 1-continued

| Cmpd # | Structure | Characterization Data |
|---|---|---|
| 55 | 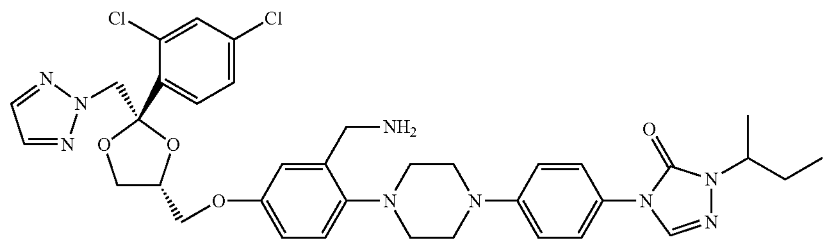 [SMILES: CCC(C)n1ncn(-c2ccc(N3CCN(c4ccc(OC[C@@H]5CO[C@@](Cn6nccn6)(c6ccc(Cl)cc6Cl)O5)cc4CN)CC3)cc2)c1=O] | LC-MS: m/z 734.0 (M + H) |
| 56 | 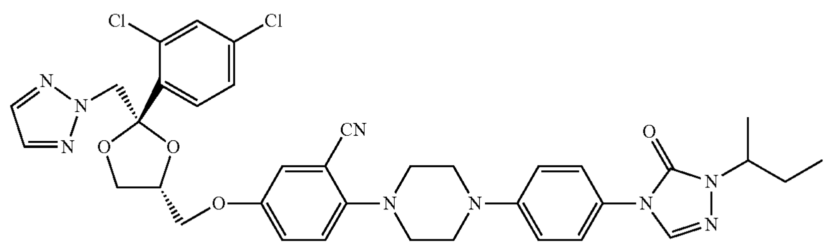 [SMILES: CCC(C)n1ncn(-c2ccc(N3CCN(c4ccc(OC[C@@H]5CO[C@@](Cn6nccn6)(c6ccc(Cl)cc6Cl)O5)cc4C#N)CC3)cc2)c1=O] | LC-MS: m/z 730.0 (M + H) |
| 57 | 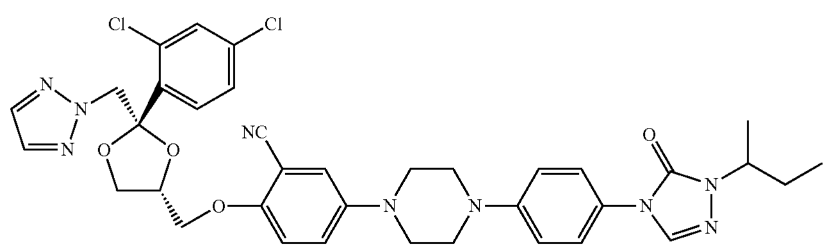 [SMILES: CCC(C)n1ncn(-c2ccc(N3CCN(c4ccc(OC[C@@H]5CO[C@@](Cn6nccn6)(c6ccc(Cl)cc6Cl)O5)c(C#N)c4)CC3)cc2)c1=O] | LC-MS: m/z 730.2 (M + H) |
| 58 | 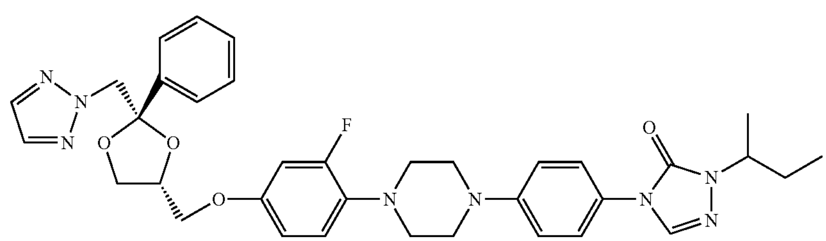 [SMILES: CCC(C)n1ncn(-c2ccc(N3CCN(c4ccc(OC[C@@H]5CO[C@@](Cn6nccn6)(c6ccccc6)O5)cc4F)CC3)cc2)c1=O] | LC-MS: m/z 655.1 (M + H) $^1$H NMR (400 MHz, CDCl$_3$) δ 7.64 (m, 3H), 7.57 (m, 2H), 7.48-7.36 (m, 5H), 7.04 (t, J = 9.2 Hz, 2H), 6.95 (t, J = 9.2 Hz, 1H), 6.66-6.53 (m, 2H), 4.87 (s, 2H), 4.44-4.25 (m, 2H), 3.91 (dd, J = 8.5, 6.5 Hz, 1H), 3.83 (dd, J = 8.5, 4.3 Hz, 1H), 3.73 (dd, J = 9.4, 5.1 Hz, 1H), 3.45-3.28 (m, 5H), 3.24-3.12 (m, 4H), 1.96-1.80 (m, 1H), 1.81-1.68 (m, 1H), 1.41 (d, J = 6.7 Hz, 3H), 0.93 (t, J = 7.4 Hz, 3H). |

TABLE 1-continued

| Cmpd # | Structure | Characterization Data |
|---|---|---|
| 59 | 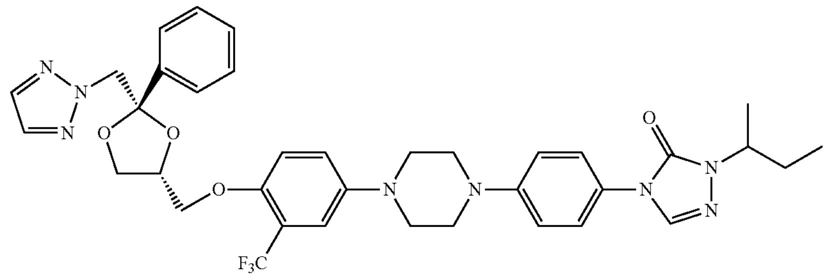 [SMILES: CCC(C)n1ncn(-c2ccc(N3CCN(c4ccc(OC[C@@H]5CO[C@@](Cn6nccn6)(c6ccccc6)O5)c(C(F)(F)F)c4)CC3)cc2)c1=O] | LC-MS: m/z 705.2 (M + H) |
| 60 | 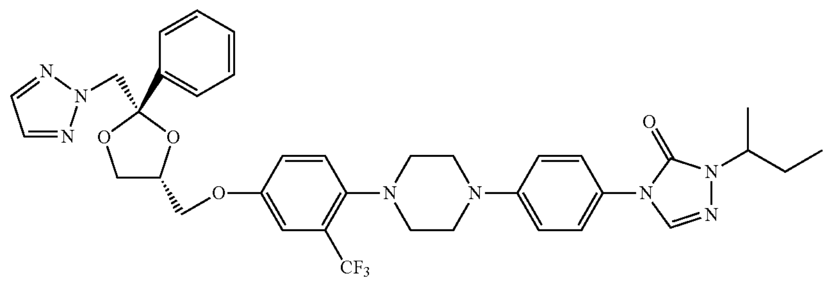 [SMILES: CCC(C)n1ncn(-c2ccc(N3CCN(c4ccc(OC[C@@H]5CO[C@@](Cn6nccn6)(c6ccccc6)O5)cc4C(F)(F)F)CC3)cc2)c1=O] | LC-MS: m/z 705.2 (M + H) |
| 61 | 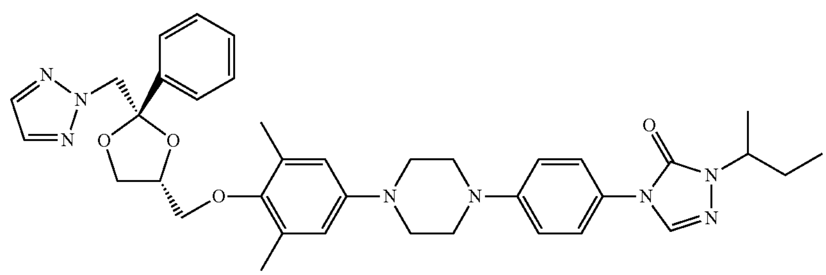 [SMILES: CCC(C)n1ncn(-c2ccc(N3CCN(c4cc(C)c(OC[C@@H]5CO[C@@](Cn6nccn6)(c6ccccc6)O5)c(C)c4)CC3)cc2)c1=O] | LC-MS: m/z 665.3 (M + H) |
| 62 | 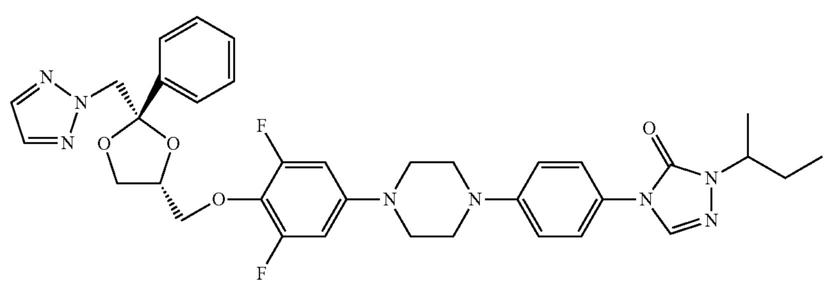 [SMILES: CCC(C)n1ncn(-c2ccc(N3CCN(c4cc(F)c(OC[C@@H]5CO[C@@](Cn6nccn6)(c6ccccc6)O5)c(F)c4)CC3)cc2)c1=O] | LC-MS: m/z 673.2 (M + H) |
| 63 | 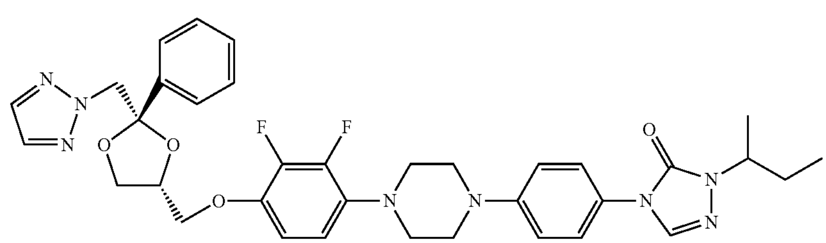 | LC-MS: m/z 673.2 (M + H) |

TABLE 1-continued

| Cmpd # | Structure | Characterization Data |
|---|---|---|
| 64 | 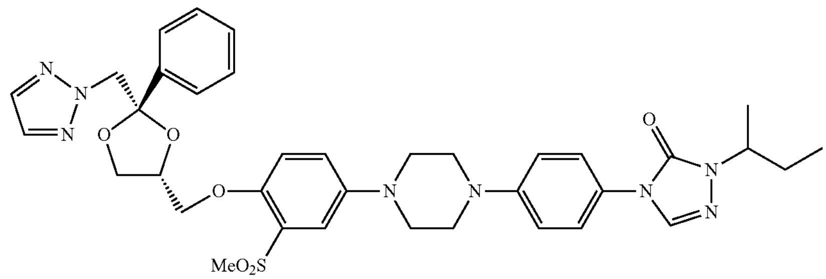 [SMILES: CCC(C)n1ncn(-c2ccc(N3CCN(c4ccc(OC[C@@H]5CO[C@@](Cn6nccn6)(c6ccccc6)O5)c(S(C)(=O)=O)c4)CC3)cc2)c1=O] | LC-MS: m/z 715.1 (M + H) |
| 65 | 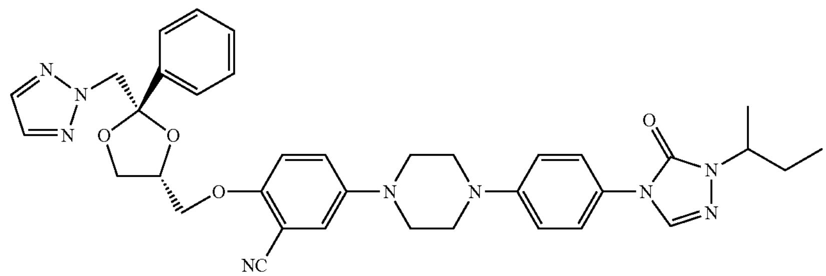 [SMILES: CCC(C)n1ncn(-c2ccc(N3CCN(c4ccc(OC[C@@H]5CO[C@@](Cn6nccn6)(c6ccccc6)O5)c(C#N)c4)CC3)cc2)c1=O] | LC-MS: m/z 662.2 (M + H) |
| 66 | 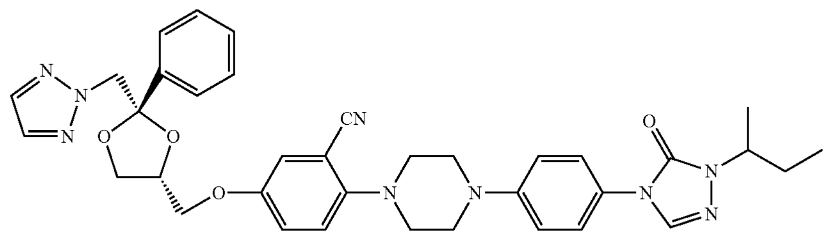 [SMILES: CCC(C)n1ncn(-c2ccc(N3CCN(c4ccc(OC[C@@H]5CO[C@@](Cn6nccn6)(c6ccccc6)O5)cc4C#N)CC3)cc2)c1=O] | LC-MS: m/z 662.2 (M + H) |
| 67 | 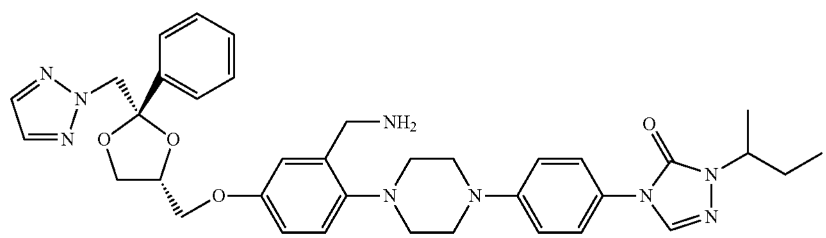 [SMILES: CCC(C)n1ncn(-c2ccc(N3CCN(c4ccc(OC[C@@H]5CO[C@@](Cn6nccn6)(c6ccccc6)O5)cc4CN)CC3)cc2)c1=O] | LC-MS: m/z 666.1 (M + H) |
| 68 | 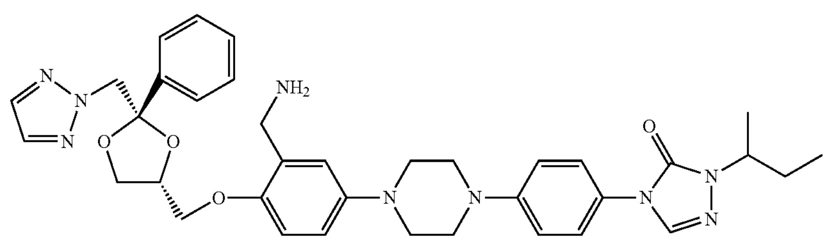 [SMILES: CCC(C)n1ncn(-c2ccc(N3CCN(c4ccc(OC[C@@H]5CO[C@@](Cn6nccn6)(c6ccccc6)O5)c(CN)c4)CC3)cc2)c1=O] | LC-MS: m/z 666.1 (M + H) |
| 69 | 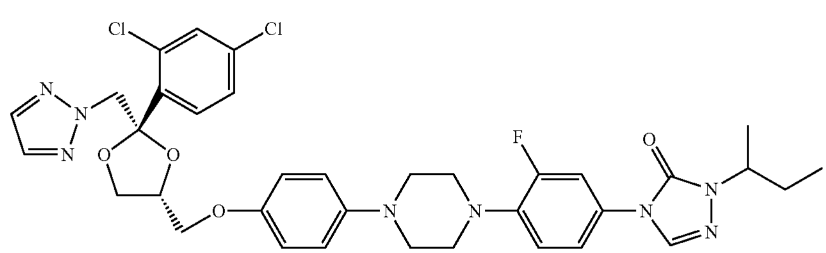 [SMILES: CCC(C)n1ncn(-c2ccc(N3CCN(c4ccc(OC[C@@H]5CO[C@@](Cn6nccn6)(c6ccc(Cl)cc6Cl)O5)cc4)CC3)c(F)c2)c1=O] | LC-MS: m/z 723.1 (M + H) $^1$H NMR (400 MHz, CDCl$_3$) δ 7.70 (s, 1H), 7.64 (s, 2H), 7.62-7.51 (m, 4H), 7.50 (d, J = 2.1 Hz, 2H), 7.25 (dd, J = 8.5, 2.1 Hz, 1H), 7.13 (t, J = 8.9 Hz, 1H), 6.96 (t, J = 8.8 |

| Cmpd # | Structure | Characterization Data |
|---|---|---|
| | | Hz, 2H), 5.14 (dd, J = 43.9, 14.3 Hz, 2H), 4.47-4.39 (m, 1H), 4.32 (m, 1H), 4.05-3.92 (m, 1H), 3.92-3.82 (m, 2H), 3.75 (m, 4H), 3.61 (m, 4H), 3.53 (dd, J = 9.7, 6.5 Hz, 1H), 1.96-1.82 (m, 1H), 1.82-1.72 (m, 1H), 1.42 (d, J = 6.7 Hz, 3H), 0.92 (t, J = 7.4 Hz, 3H). |
| 70 | 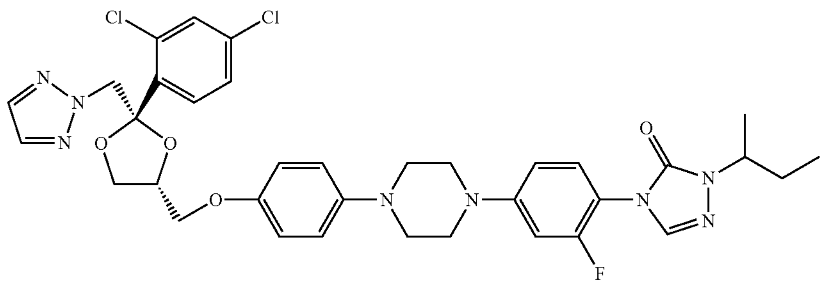 [SMILES: CCC(C)n1ncn(-c2ccc(N3CCN(c4ccc(OC[C@@H]5CO[C@@](Cn6nccn6)(c6ccc(Cl)cc6Cl)O5)cc4)CC3)cc2F)c1=O] | LC-MS: m/z 723.2 (M + H) $^1$H NMR (400 MHz, CDCl$_3$) δ 7.66-7.61 (m, 3H), 7.60-7.52 (m, 2H), 7.49 (d, J = 2.1 Hz, 1H), 7.37 (d, J = 9.1 Hz, 2H), 7.25-7.22 (m, 1H), 6.92 (t, J = 6.4 Hz, 2H), 6.88-6.75 (m, 2H), 5.13 (dd, J = 46.4, 14.3 Hz, 2H), 4.48-4.37 (m, 1H), 4.31 (dt, J = 13.4, 6.7 Hz, 1H), 3.95 (dd, J = 8.5, 6.5 Hz, 1H), 3.92-3.79 (m, 2H), 3.68-3.60 (m, 4H), 3.58-3.45 (m, 5H), 1.89 (m, 1H), 1.81-1.69 (m, 1H), 1.43 (d, J = 6.7 Hz, 3H), 0.93 (t, J = 7.4 Hz, 3H). |
| 71 | 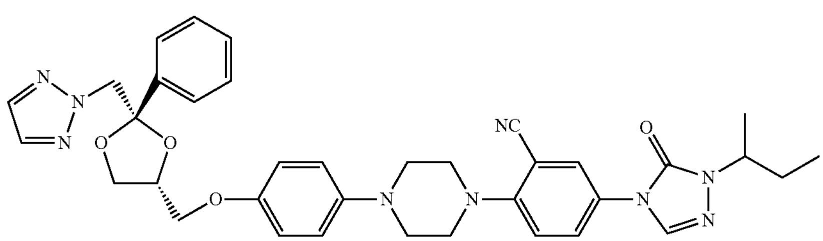 [SMILES: CCC(C)n1ncn(-c2ccc(N3CCN(c4ccc(OC[C@@H]5CO[C@@](Cn6nccn6)(c6ccccc6)O5)cc4)CC3)c(C#N)c2)c1=O] | LC-MS: m/z 662.1 (M + H) |
| 72 | 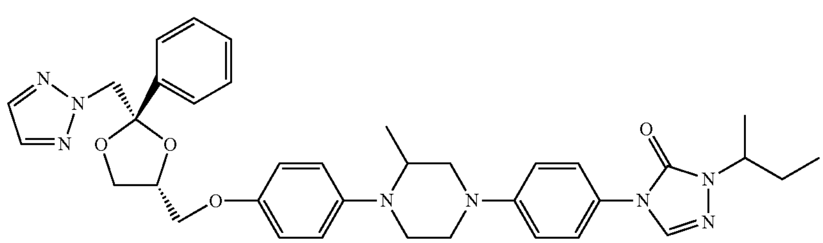 | LC-MS: m/z 651.2 (M + H) |

TABLE 1-continued

| Cm pd # | Structure | Characterization Data |
|---|---|---|
| 73 | 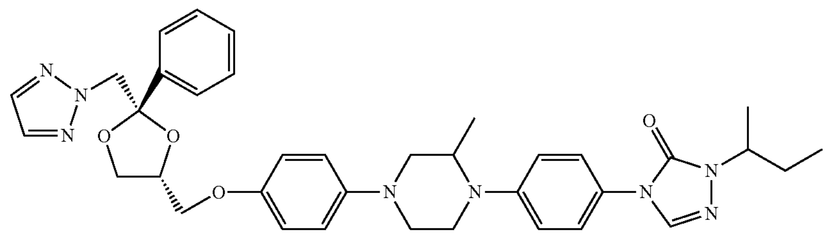 [SMILES: CCC(C)n1ncn(-c2ccc(N3CCN(c4ccc(OC[C@@H]5CO[C@@](Cn6nccn6)(c6ccccc6)O5)cc4)CC3C)cc2)c1=O] | LC-MS: m/z 651.2 (M + H) |
| 74 | 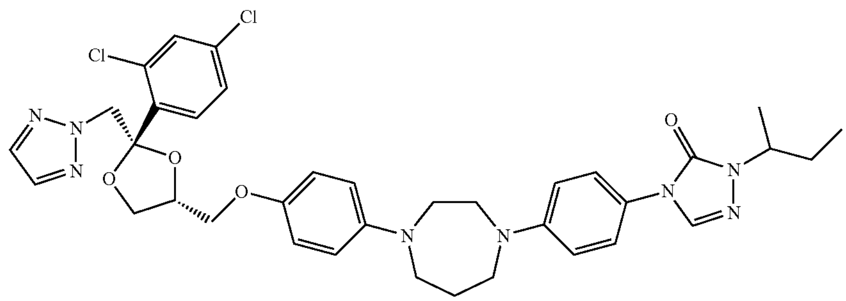 [SMILES: CCC(C)n1ncn(-c2ccc(N3CCCN(c4ccc(OC[C@@H]5CO[C@@](Cn6nccn6)(c6ccc(Cl)cc6Cl)O5)cc4)CC3)cc2)c1=O] | LC-MS: m/z 719.3 (M + H) |
| 75 | 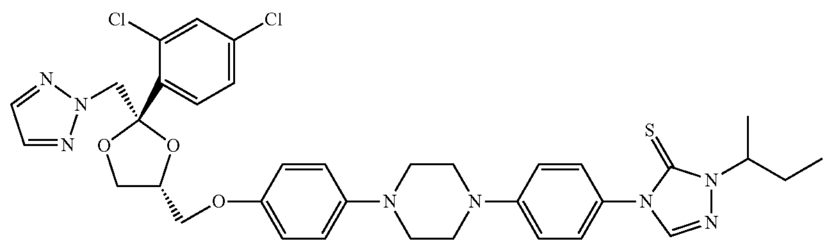 [SMILES: CCC(C)n1ncn(-c2ccc(N3CCN(c4ccc(OC[C@@H]5CO[C@@](Cn6nccn6)(c6ccc(Cl)cc6Cl)O5)cc4)CC3)cc2)c1=S] | LC-MS: m/z 721.0 (M + H)<br>$^1$H NMR (400 MHz, MeOD) δ 8.70 (s, 1H), 7.65 (s, 2H), 7.55 (t, J = 5.5 Hz, 2H), 7.36 (d, J = 8.9 Hz, 2H), 7.30 (m, 2H), 7.20 (m, 3H), 6.96 (d, J = 9.1 Hz, 2H), 5.11 (m, 2H), 4.47-4.32 (m, 2H), 4.05-3.93 (m, 2H), 3.91-3.82 (m, 2H), 3.76 (dd, J = 10.1, 5.2 Hz, 2H), 3.61-3.47 (m, 4H), 3.42 (m, 4H), 1.78-1.53 (m, 2H), 1.33 (d, J = 7.8 Hz, 3H), 0.96 (t, J = 7.4 Hz, 3H). |
| 76 | 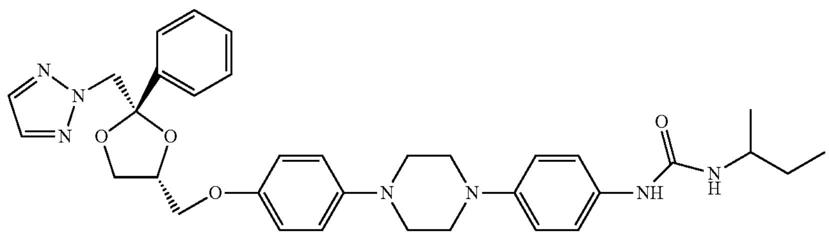 | LC-MS: m/z 638.3 (M + H) |

TABLE 1-continued

| Cmpd # | Structure | Characterization Data |
|---|---|---|
| 77 | 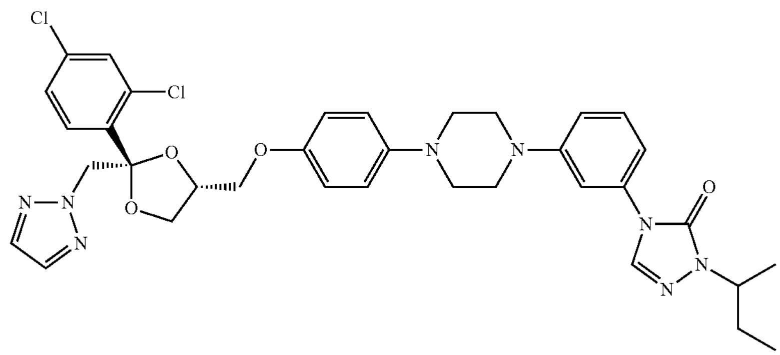 [SMILES: CCC(C)n1ncn(-c2cccc(N3CCN(c4ccc(OC[C@@H]5CO[C@@](Cn6nccn6)(c6ccc(Cl)cc6Cl)O5)cc4)CC3)c2)c1=O] | LC-MS: m/z 705.3 (M + H) |
| 78 | 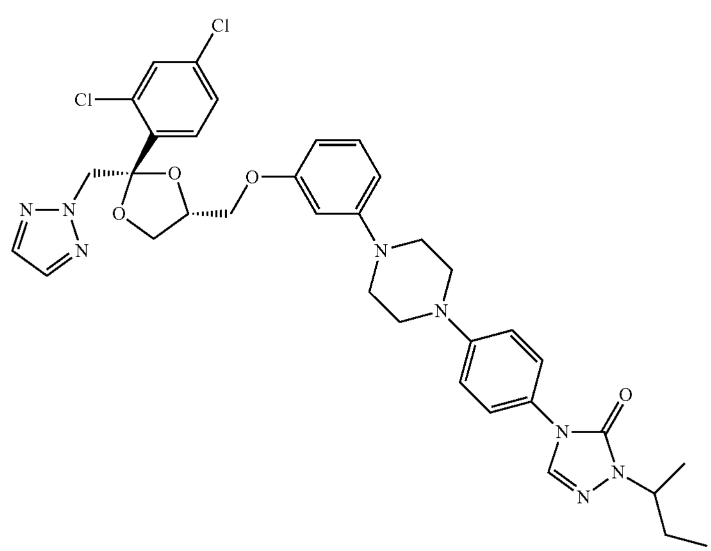 [SMILES: CCC(C)n1ncn(-c2ccc(N3CCN(c4cccc(OC[C@@H]5CO[C@@](Cn6nccn6)(c6ccc(Cl)cc6Cl)O5)c4)CC3)cc2)c1=O] | LC-MS: m/z 705.3 (M + H) <sup>1</sup>H NMR (400 MHz, CDCl$_3$) δ 7.65 (s, 1H), 7.62 (s, 2H), 7.56 (d, J = 8.5 Hz, 1H), 7.53-7.49 (m, 3H), 7.32 (m, 1H), 7.24 (dd, J = 8.4, 2.1 Hz, 1H), 7.19-7.09 (m, 2H), 6.85 (dd, J = 8.1, 2.1 Hz, 1H), 6.77 (br s, 1H), 6.60 (dd, J = 8.2, 2.0 Hz, 1H), 5.14 (dd, J = 45.3, 14.3 Hz, 2H), 4.47-4.38 (m, 1H), 4.32 (m, 1H), 3.99-3.82 (m, 3H), 3.65-3.55 (m, 1H), 3.54 (m, 8H), 1.98-1.81 (m, 1H), 1.74 (m, 1H), 1.42 (d, J = 6.7 Hz, 3H), 0.93 (t, J = 7.4 Hz, 3H). |

TABLE 1-continued

| Cmpd # | Structure | Characterization Data |
|---|---|---|
| 79 | 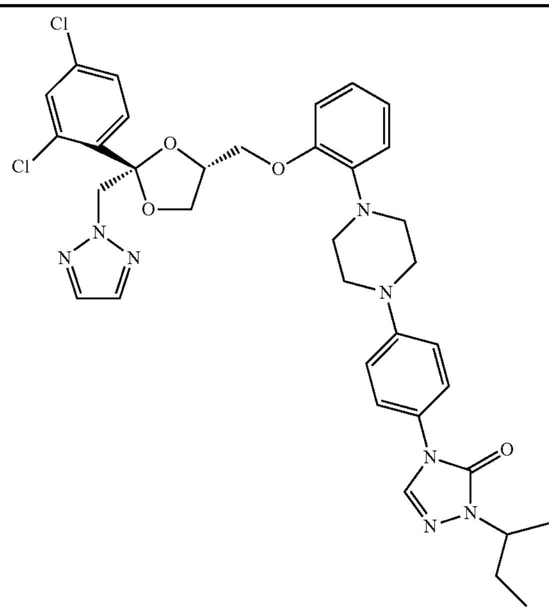 | LC-MS: m/z 705.1 (M + H) |
| 80 | 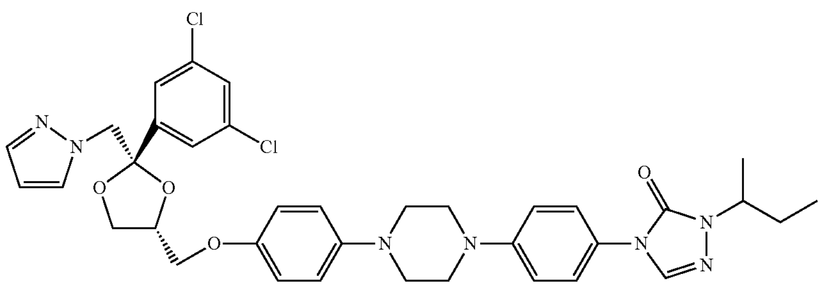 [SMILES: CCC(C)n1ncn(-c2ccc(N3CCN(c4ccc(OC[C@@H]5CO[C@@](Cn6cccn6)(c6cc(Cl)cc(Cl)c6)O5)cc4)CC3)cc2)c1=O] | LCMS: 99.31% @ 261 nm; m/z 703.9 (M + H). ¹H NMR (400 MHz, CDCl₃): 0.91-0.94 (t, J = 7.2 Hz, 3H), 1.40-1.42 (d, J = 6.4 Hz, 3H), 1.74-1.76 (m, 1H), 1.85-1.92 (m, 1H), 3.25-3.39 (m, 4H), 3.35-3.40 (m, 5H), 3.72-3.76 (m, 1H), 3.82-3.91 (m, 2H), 4.29-4.34 (m, 1H), 4.38-4.42 (m, 1H), 4.46-4.47 (d, J = 1.6 Hz, 2H), 6.26-6.27 (t, J = 2.0 Hz, 1H), 6.78-6.81 (d, J = 9.2 Hz, 2H), 6.95-6.97 (d, J = 9.2 Hz, 2H) 7.04-7.07 (d, J = 9.2 Hz, 2H), 7.36-7.37 (m, 1H), 7.40-7.46 (m, 4H), 7.49-7.53 (m, 2H), 7.64 (s, 1H). |
| 81 | 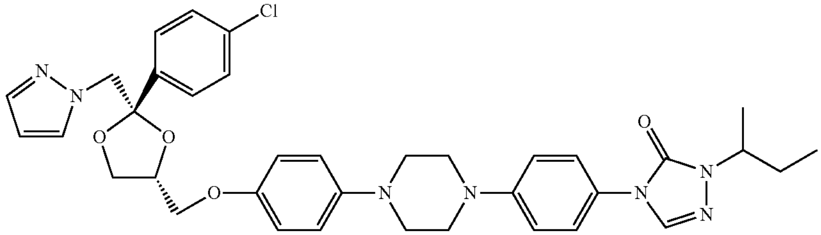 [SMILES: CCC(C)n1ncn(-c2ccc(N3CCN(c4ccc(OC[C@@H]5CO[C@@](Cn6cccn6)(c6ccc(Cl)cc6)O5)cc4)CC3)cc2)c1=O] | LCMS: 100% @ 261 nm; m/z 670.11 (M + H). 1H NMR (400 MHz, CDCl3): 0.91-0.94 (t, J = 7.2 Hz, 3H), 1.40-1.42 (d, J = 6.4 Hz, 3H), 1.74-1.76 (m, 1H), 1.85-1.92 (m, 1H), |

TABLE 1-continued

| Cmpd # | Structure | Characterization Data |
|---|---|---|
| | | 3.25-3.39 (m, 4H), 3.35-3.40 (m, 5H), 3.73-3.79 (m, 1H), 3.80-3.87 (m, 2H), 4.32-4.48 (m, 2H), 4.486 (s, 1H), 6.24-6.26 (t, J = 2.0 Hz, 1H), 6.78-6.80 (d, 2H), 6.94-6.96 (d, J = 9.2 Hz, 2H) 7.04-7.06 (d, J = 8.8 Hz, 2H), 7.36-7.38 (m, 2H), 7.43-7.52 (m, 6H), 7.64 (s, 1H). |
| 82 | 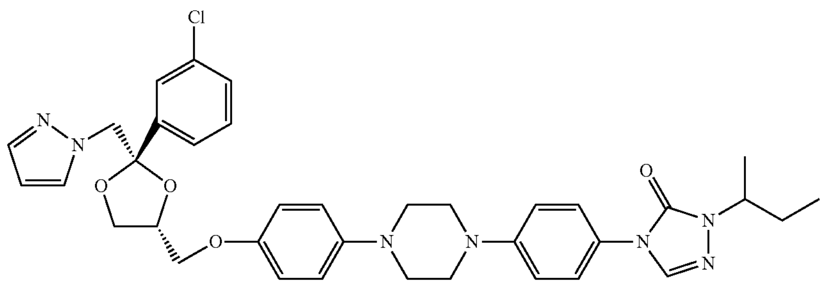 [SMILES: CCC(C)n1ncn(-c2ccc(N3CCN(c4ccc(OC[C@@H]5CO[C@@](Cn6cccn6)(c6cccc(Cl)c6)O5)cc4)CC3)cc2)c1=O] | LCMS: 100% @ 261 nm; m/z 669.9 (M + H). 1H NMR (400 MHz, CDCl3 δ ppm) 0.91-0.94 (t, J = 1.6 Hz, 3H), 1.40-1.42 (d, J = 6.8 Hz, 3H), 1.72-1.77 (m, 1H), 1.86-1.89 (m, 1H), 3.24-3.40 (m, 9H), 3.71-3.75 (m, 1H), 3.79-3.86 (m, 1H), 3.86-3.89 (m, 1H), 4.31-4.33 (m, 1H), 4.37-4.39 (m, 1H), 4.48-4.49 (d, J = 3.2 Hz, 2H), 6.26-6.27 (t, J = 2.0 Hz, 1H), 6.78-6.80 (d, J = 9.2 Hz, 2H), 6.94-6.97 (m, J = 9.2 Hz, 2H), 7.04-7.07 (m, J = 9.2 Hz, 2H), 7.33-7.36 (m, 3H), 7.42-7.46 (m, 3H), 7.50-7.55 (m, 3H), 7.64 (s, 1H). |
| 83 | 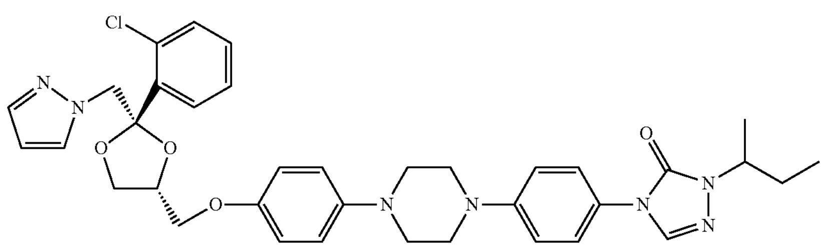 | LCMS: 100% @ 262 nm; m/z 670.1 (M + H). 1H NMR (400 MHz, CDCl3): 0.87-0.94 (t, J = 7.6 Hz, 3H), 1.40-1.42 (d, J = 6.8 Hz, 3H), 1.74-1.76 (m, 1H), 1.87-1.89 (m, 1H), 3.24-3.30 (m, 5H), 3.37-3.39 (m, 4H), 3.77-3.82 (m, 2H), 3.89-3.92 (t, 1H), 4.31-4.38 (m, 2H), 4.72-4.76 (d, J = 14.8 Hz 1H), 4.85-4.88 (d, J = |

TABLE 1-continued
| Cmpd # | Structure | Characterization Data |
|---|---|---|
| | | 14.8 Hz, 1H), 6.25-6.26 (t, 1H) 6.78-6.80 (d, J = 8.8 Hz, 2H), 6.94-6.96 (d, J = 8.8 Hz, 2H), 7.30-7.34 (m, 2H), 7.44-7.47 (m, 3H), 7.54- (d, J = 2.4 Hz, 2H), 7.64 (s, 1H), 7.76-7.71 (m-1H). |
| 84 | 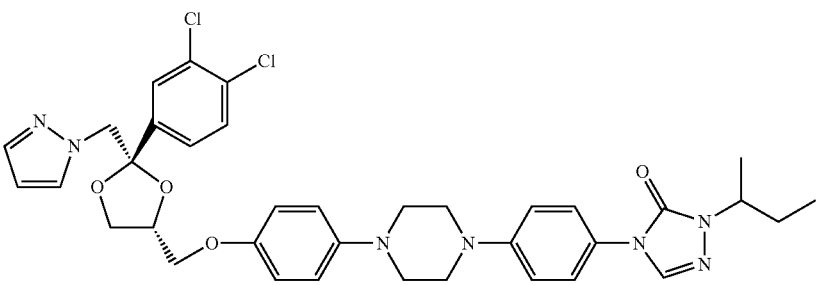 [SMILES: CCC(C)n1ncn(-c2ccc(N3CCN(c4ccc(OC[C@@H]5CO[C@@](Cn6cccn6)(c6ccc(Cl)c(Cl)c6)O5)cc4)CC3)cc2)c1=O] | LCMS: 99.57% @ 260 nm; m/z 703.91 (M + H). 1H NMR (400 MHz, CDCl3): 0.91-0.94 (t, J = 7.2 Hz, 3H), 1.40-1.42 (d, J = 6.4 Hz,3H), 1.72-1.77 (m, 1H), 1.85-1.90 (m, 1H), 3.25-3.27 (m, 4H), 3.36-3.40 (m, 5H), 3.73-3.76 (m, 1H), 3.82-3.90 (m, 2H), 4.30-4.33 (m, 1H), 4.37-4.39 (m, 1H), 4.47-4.48 (d, J = 1.6 Hz, 2H), 6.26-6.27 (t, J = 2.0 Hz, 1H), 6.78-6.81 (d, J = 7.2 Hz, 2H), 6.95-6.97 (d, J = 7.2 Hz, 2H) 7.04-7.06 (d, J = 7.2 Hz, 2H), 7.33-7.36 (m, 1H), 7.44-7.47 (m, 3H), 7.49-7.52 (m, 2H), 7.61-7.62 (d, 1H), 7.64 (s, 1H). |
| 85 | 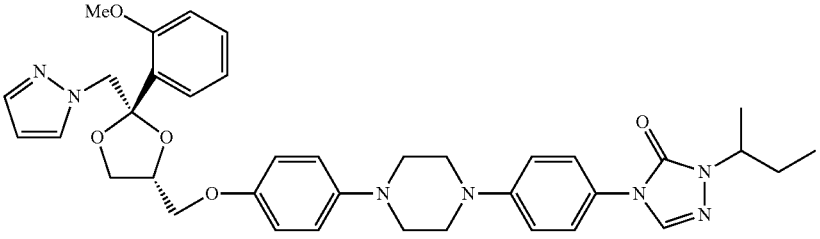 | LCMS: 100% @ 261 nm; m/z 665.9 (M + H). 1H NMR (400 MHz, CDCl3): 0.90-0.94 (t, J = 7.2 Hz, 3H) 1.40-1.42 (d, J = 6.4 Hz,3H), 1.70-1.75 (m, 1H), 1.85-1.90 (m, 1H), 3.21-3.27 (m, 5H), 3.37-3.40 (m, 4H), 3.72-3.76 (m, 2H), 3.92-3.96 (m, 1H), 3.98 (s, 3H), 4.30-4.33 (m, 1H), 4.37-4.41 (m, 1H), 4.71-4.75 (d, 2H), 4.88-4.92 (d, 1H), 6.24-6.25 (t, J = 2.0 Hz, 1H), 6.77-6.79 (d, J = 9.2 Hz, |

TABLE 1-continued

| Cmpd # | Structure | Characterization Data |
|---|---|---|
| | | 2H), 6.94-7.01 (m, 4H), 7.04-7.06 (d, J = 8.8 Hz, 2H), 7.35 7.40 (m, 1H), 7.43-7.46 (d, 2H), 7.52-7.58 (m, 3H), 7.64 (s, 1H). |
| 86 | 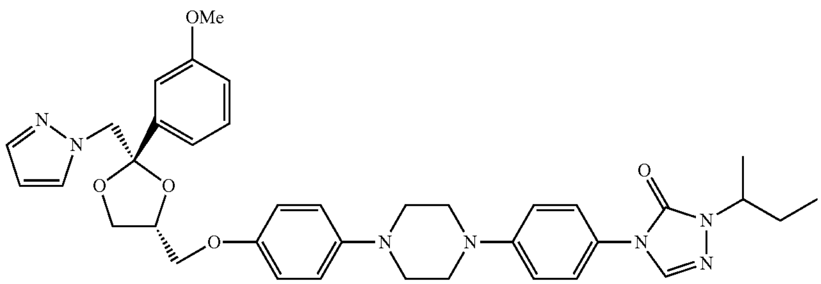 [SMILES: CCC(C)n1ncn(-c2ccc(N3CCN(c4ccc(OC[C@@H]5CO[C@@](Cn6cccn6)(c6cccc(OC)c6)O5)cc4)CC3)cc2)c1=O] | LCMS: 99.82% @ 262 nm; m/z 666.05 (M + H). 1H NMR (400 MHz, CDCl3): 0.90-0.94 (t, J = 7.6 Hz, 3H), 1.40-1.42 (d, J = 6.8 Hz, 3H), 1.74-1.76 (m, 1H), 1.87-1.89 (m, 1H), 3.24-3.28 (m, 5H), 3.37-3.40 (m, 4H), 3.68-3.72 (m, 1H), 3.77-3.79 (t, 1H), 3.80 (s, 3H), 3.84-3.90 (m, 1H), 4.30-4.42 (m, 2H), 4.50-4.51 (d, J = 4.0 Hz, 2H), 6.25-6.26 (t, J = 2.0 Hz, 1H), 6.77-6.79 (d, J = 8.8 Hz, 2H), 6.91-6.96 (m, 3H), 7.04-7.07 (d, J = 8.8 Hz, 2H), 7.10-7.11 (t, J = 2.4 Hz, 1H), 7.30-7.34 (t, 1H), 7.43-7.46 (d, J = 8.8 Hz, 2H), 7.51-7.56 (d, J = 2.4 Hz, 1H), 7.54-7.55 (d, 1H), 7.64 (s, 1H). |
| 87 | 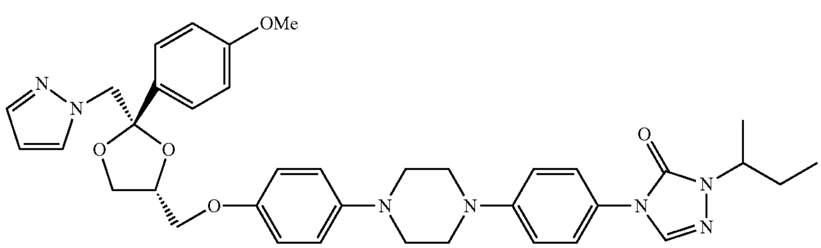 | LCMS: 100% @ 202 nm; m/z 666.96(M + H). 1H NMR (400 MHz, CDCl3): 0.91-0.94 (t, J = 7.6 Hz, 3H), 1.40-1.42 (d, J = 6.8 Hz, 3H), 1.74-1.76 (m, 1H), 1.87-1.89 (m, 1H), 3.24-3.28 (m, 5H), 3.37-3.40 (m, 4H), 3.69-3.73 (m, 1H), 3.77-3.79 (t, 1H), 3.80 (s, 3H), 3.84-3.89 (m, 1H), 4.33-4.36 (m, 2H), 4.48-4.49(d, J = 4.0 Hz, 2H), 6.24-6.25 (t, J = 2.0 Hz, 1H), 6.77-6.80 (d, J = 8.8 Hz, 2H), 6.91- |

TABLE 1-continued
| Cmpd # | Structure | Characterization Data |
|---|---|---|
| | | 6.96 (m, 4H), 7.04-7.07 (d, J = 8.8 Hz, 2H), 7.43-7.48 (m, 4H), 7.50-7.563 (m, 2H), 7.64 (s, 1H). |
| 88 | 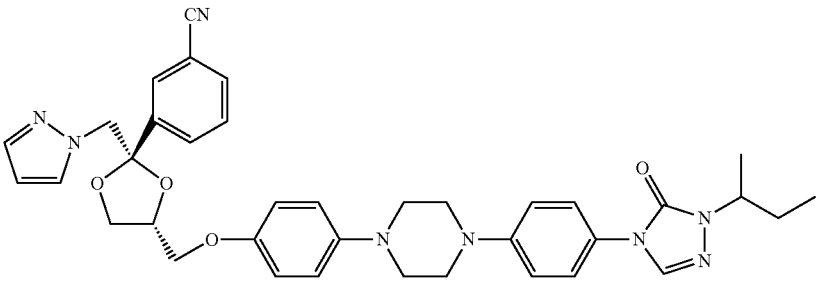 | LCMS: 100% @ 261 nm; m/z 661.05 (M + H). 1H NMR (400 MHz, CDCl3): 0.91-0.94 (t, J = 7.6 Hz, 3H), 1.40-1.42 (d, J = 6.8 Hz, 3H), 1.71-1.77 (m, 1H), 1.85-1.90 (m, 1H), 3.22-3.27 (m, 4H), 3.39-3.40 (m, 5H), 3.78-3.82 (m, 1H), 3.87-3.88 (d, J = 5.6 Hz, 2H), 4.29-4.40 (m, 2H), 4.99(s, 2H), 6.26-6.27 (t, J = 2.0 Hz, 1H), 6.80-6.82 (d, J = 9.2 Hz, 2H), 6.95-6.98 (d, J = 9.2 Hz, 2H), 7.04-7.07 (d, J = 9.2 Hz, 2H), 7.43-7.46 (d, 2H), 7.49-7.55 (m, 3H), 7.64-7.68 (m, 2H), 7.73-7.76(m, 1H), 7.80(s, 1H). |
| 89 | 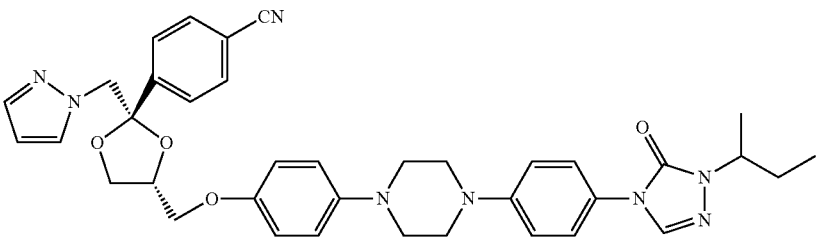 [SMILES: CCC(C)n1ncn(-c2ccc(N3CCN(c4ccc(OC[C@@H]5CO[C@@](Cn6cccn6)(c6ccc(C#N)cc6)O5)cc4)CC3)cc2)c1=O] | LCMS: 98.37% @ 262 nm; m/z 660.95 (M + H). 1H NMR (400 MHz, CDCl3): 0.91-0.94 (t, J = 7.6 Hz, 3H), 1.40-1.43 (d, J = 6.8 Hz, 3H), 1.71-1.77 (m, 1H), 1.85-1.90 (m, 1H), 2.90 (s, 3H),2.98 (s, 3H), 3.40-3.44 (m, 3H), 3.20-3.30(m, 1H), 3.86-3.88 (d, J = 5.2 Hz, 2H),4.28-4.45 (m, 2H),4.50 (s, 1H), 6.26-6.27 (t, 1H), 6.851(m, 2H), 7.06-7.08 (d, 2H), 7.29-7.33 (m, 2H), 7.45-7.53 (m, 3H), 7.60-7.80 (m, 5H), 8.04 (s, 1H). |

| Cm pd # | Structure | Characterization Data |
|---|---|---|
| 90 | 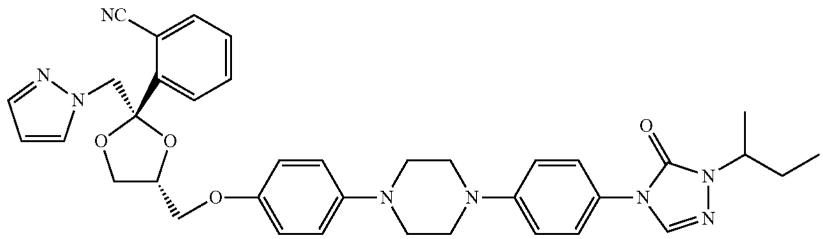 [SMILES: CCC(C)n1ncn(-c2ccc(N3CCN(c4ccc(OC[C@@H]5CO[C@@](Cn6cccn6)(c6ccccc6C#N)O5)cc4)CC3)cc2)c1=O] | LCMS: 99.91 @ 262 nm; m/z 661.2 (M + H). 1H NMR (400 MHz, CDCl3): 0.91-0.94 (t, J = 7.6 Hz, 3H), 1.40-1.42 (d, J = 6.8 Hz, 3H), 1.70-1.76 (m, 1H), 1.87-1.89 (m, 1H), 3.24-3.27 (m, 4H), 3.37-3.41 (m, 4H), 3.52 (m, 1H), 3.83-3.86 (m, 1H), 3.91-3.92 (d, 2H), 4.31-4.34 (m, 1H), 4.40-4.41 (m, 1H), 4.66-4.75 (d, J = 4.0 Hz, 2H), 6.27-6.28 (t, 1H), 6.79-6.81 (d, J = 8.8 Hz, 2H), 6.95-6.97 (d, J = 8.8 Hz, 2H), 7.04-7.07 (d, J = 8.8 Hz, 2H), 7.43-7.46 (d, 2H),7.49-7.51 (m, 2H), 7.59-7.60 (m, 2H), 7.64 (s, 1H), 7.72-7.74 (m, 1H), 7.77-7.79 (m, 1H). |
| 91 | 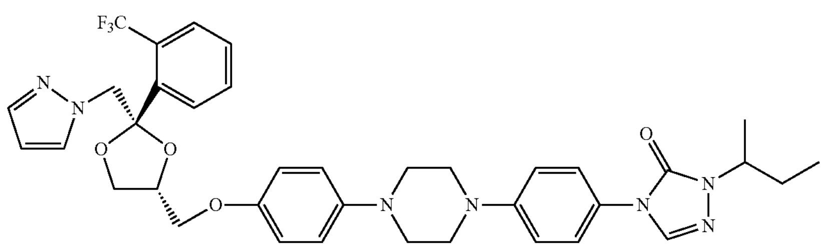 | LCMS: 100% @ 262 nm; m/z 704.90 (M + H). 1H NMR (400 MHz, CDCl3): 0.91-0.94 (t, J = 7.6 Hz, 3H), 1.40-1.42 (d, J = 6.8 Hz, 3H), 1.70-1.77 (m, 1H), 1.87-1.90 (m, 1H), 3.22-3.28 (m, 5H), 3.37-3.40 (m, 4H), 3.73-3.86 (m, 3H), 4.27-4.34 (m, 2H), 4.57-4.67 (m, 2H), 6.26-6.27 (t, J = 2.0 Hz, 1H), 6.75-6.77 (d, J = 9.2 Hz, 2H), 6.93-6.96 (d, J = 9.2 Hz, 2H), 7.04-7.07 (d, J = 9.2 Hz, 2H), 7.43-7.48 (d, 2H),7.48-7.59 (m, 4H), 7.64 (s, 1H), 7.80-7.83 (t, 2H). |

TABLE 1-continued
| Cmpd # | Structure | Characterization Data |
|---|---|---|
| 92 | 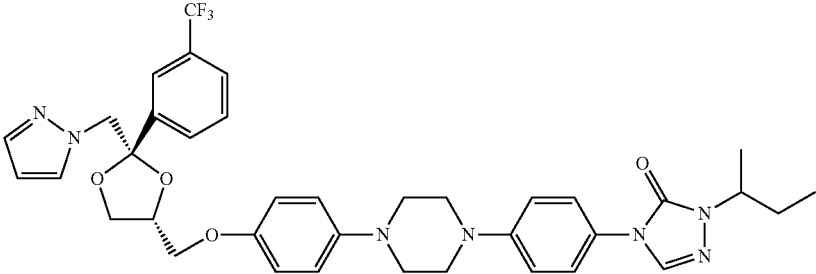 | LCMS: 100% @ 262 nm; m/z 704.01 (M + H). 1H NMR (400 MHz, CDCl3): 0.91-0.94 (t, J = 7.6 Hz, 3H), 1.40-1.42 (d, J = 6.8 Hz, 3H), 1.70-1.76 (m, 1H), 1.87-1.90 (m, 1H), 3.25-3.27 (m, 4H), 3.37-3.40 (m, 5H), 3.74-3.76 (m, 1H), 3.84-3.88 (m, 2H), 4.30-4.40 (m, 2H), 4.50-4.51(m, 2H), 6.26-6.27 (t, J = 2.0 Hz, 1H), 6.79-6.81 (d, J = 8.8 Hz, 2H), 6.95-6.97 (d, J = 8.8 Hz, 2H), 7.04-7.07 (d, J = 9.2 Hz, 2H), 7.44-7.46 (d, 2H),7.50-7.52 (m, 2H),7.64-7.65 (m, 2H), 7.72-7.74 (d, 1H), 7.79 (s, 1H). |
| 93 | 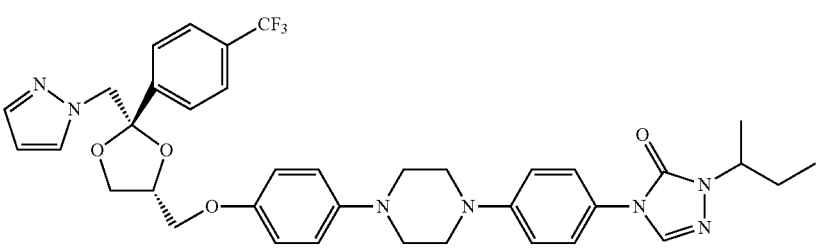 | LCMS: 100% @ 262 nm; m/z 704.01 (M + H). 1H NMR (400 MHz, CDCl3): 0.91-0.94 (t, J = 7.6 Hz, 3H), 1.40-1.42 (d, J = 6.8 Hz, 3H), 1.72-1.76 (m, 1H), 1.85-1.89 (m, 1H), 3.25-3.27 (m, 4H), 3.35-3.40 (m, 5H), 3.73-3.77 (m, 1H),3.82-3.89 (m, 2H), 4.31-4.39 (m, 2H), 4.50-4.51 (q, 2H), 6.26-6.27 (t, J = 2.0 Hz, 1H), 6.78-6.81 (d, J = 9.2 Hz, 2H), 6.95-6.97 (d, J = 9.2 Hz, 2H), 7.04-7.07 (d, J = 9.2 Hz, 2H), 7.44-7.46 (d, 2H), 7.51-7.53 (m, 2H),7.64-7.67 (m, 5H). |

TABLE 1-continued
| Cmpd # | Structure | Characterization Data |
|---|---|---|
| 94 | 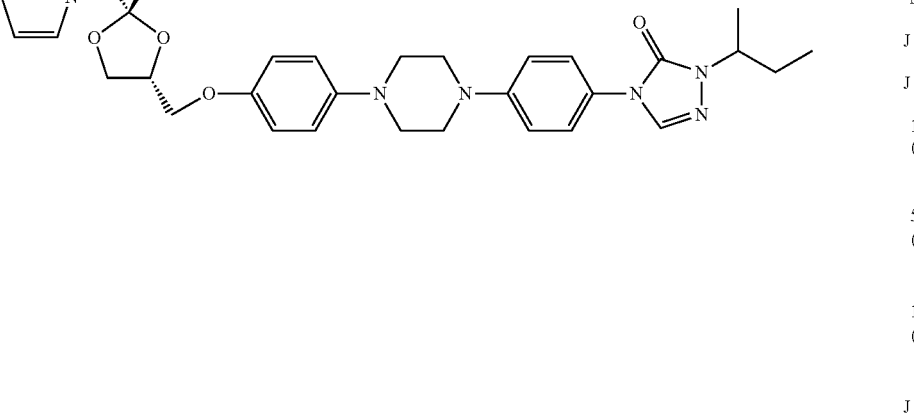 | LCMS: 100% @ 262 nm; m/z 719.96 (M + H). 1H NMR (400 MHz, CDCl3): 0.90-0.94 (t, J = 7.6 Hz, 3H), 1.40-1.42 (d, J = 6.8 Hz, 3H), 1.72-1.76 (m, 1H), 1.87-1.89 (m, 1H), 3.24-3.27 (m, 4H), 3.33-3.40 (m, 5H), 3.72-3.75 (m, 1H), 3.79-3.80 (m, 1H), 3.81-3.90 (m, 1H), 4.30-4.38 (m, 2H), 4.49-4.55 (q, 2H), 6.25-6.26 (t, J = 2.0 Hz, 1H), 6.78-6.80 (m, 2H), 6.94-6.97 (d, J = 8.8 Hz, 2H), 7.04-7.07 (d, J = 8.8 Hz, 2H), 7.23-7.25 (d, 2H), 7.43-7.46 (d, 2H),7.51-7.53 (m, 2H), 7.56-7.59 (m, 2H), 7.64 (s, 1H). |
| 95 | 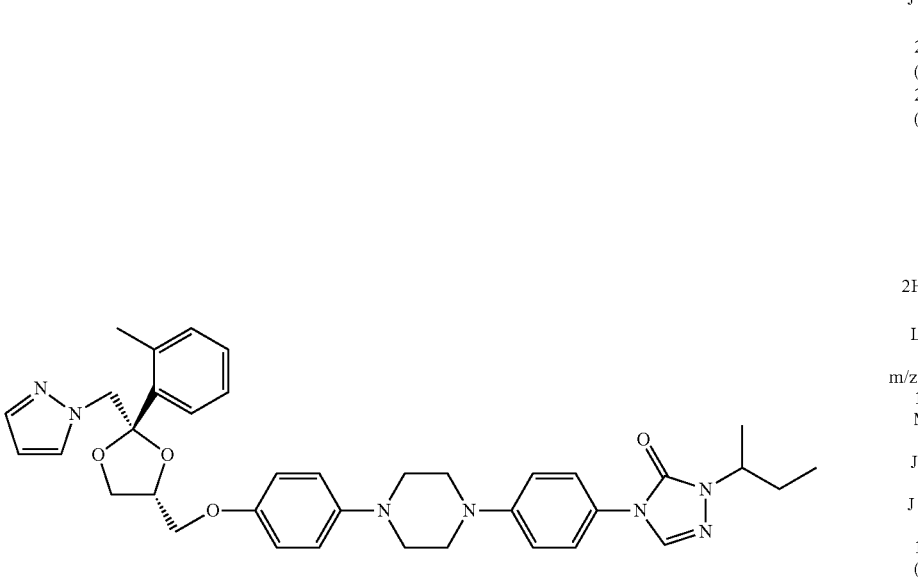 | LCMS: 99.51% @ 262 nm; m/z 650.05 (M + H). 1H NMR (400 MHz, CDCl3): 0.91-0.94 (t, J = 7.6 Hz,3H), 1.40-1.42 (d, J = 6.8 Hz, 3H), 1.70-1.77 (m, 1H), 1.85-1.90 (m, 1H), 2.624 (s, 3H), 3.24-3.29 (m, 4H), 3.37-3.40 (m, 4H), 3.71-3.77 (m, 2H), 3.84-3.88(m, 1H), 4.31-4.34 (m, 2H), 4.50-4.60 (q, 2H), 6.26-6.27 (t, J = 2.0 Hz, 1H), 6.77-6.79 (d, J = 9.2 Hz, 2H), 6.96-6.94 (d, J = 9.2 Hz, 2H), 7.04-7.07 (d, J = 9.2 Hz, 2H), 7.23-7.24 (d, 2H), 7.43-7.46 (d, 2H),7.52-7.55 (m, 2H),7.63-7.64 (m, 2H). |

TABLE 1-continued
| Cmpd # | Structure | Characterization Data |
|---|---|---|
| 96 | 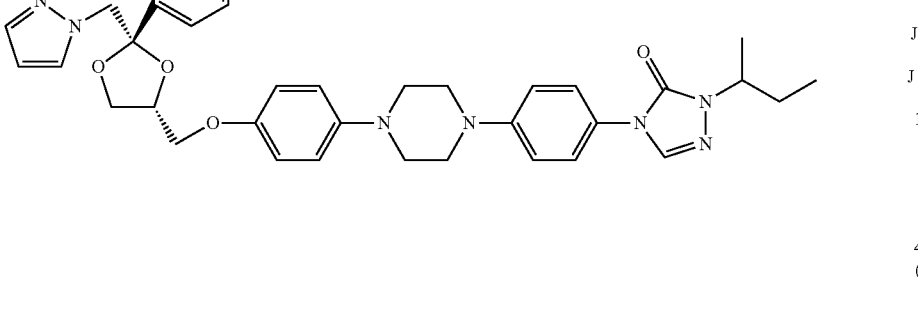 | LCMS: 98.90% @ 262 nm; m/z 650.9 (M + H). 1H NMR (400 MHz, CDCl3): 0.90-0.94 (t, J = 7.6 Hz,3H), 1.40-1.42 (d, J = 6.8 Hz, 3H), 1.70-1.77 (m, 1H), 1.85-1.90 (m, 1H), 2.40 (s, 3H), 2.64 (s, 1H), 3.24-3.32 (m, 4H), 3.37-3.42 (m, 4H), 3.67-3.71 (m, 1H), 3.75-3.78 (m, 1H), 3.86-3.89 (t, 1H), 4.29-4.40 (m, 2H), 4.44-4.50 (q, 2H), 6.25-6.26 (t, J = 2.0 Hz, 1H), 6.77-6.79 (d, J = 9.2 Hz, 2H), 6.96-6.94 (d, J = 9.2 Hz, 2H), 7.04-7.06 (d, J = 9.2 Hz, 2H), 7.18-7.20 (d, 2H), 7.29-7.31 (m, 1H), 7.36-7.38 (d, 2H), 7.43-7.45 (d, 2H), 7.51-7.54 (m, 2H), 7.64 (s, 1H). |
| 97 | 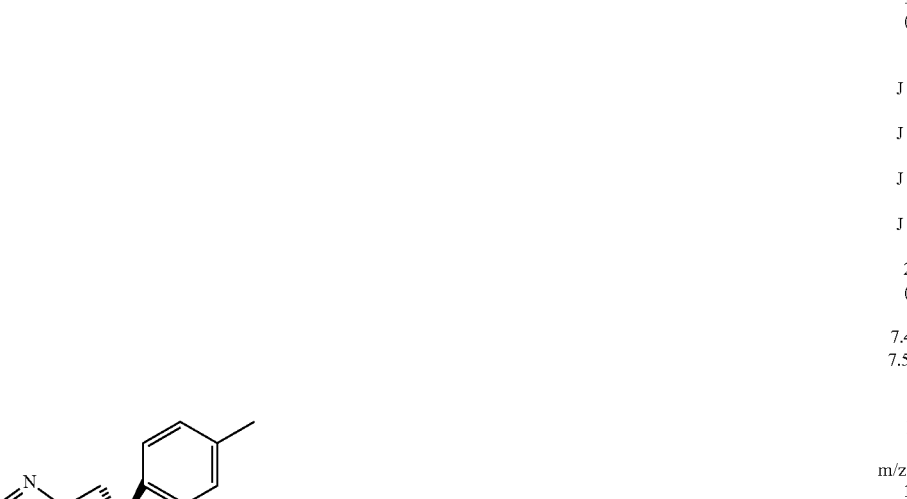 | LCMS: 100% @ 262 nm; m/z 650.01 (M + H). 1H NMR (400 MHz, CDCl3): 0.90-0.94 (t, J = 7.6 Hz,3H), 1.40-1.42 (d, J = 6.8 Hz, 3H), 1.70-1.77 (m, 1H), 1.85-1.89 (m, 1H), 2.39 (s, 3H), 3.24-3.30 (m, 5H), 3.37-3.40 (m, 4H), 3.68-3.72 (m, 1H), 3.76-3.79 (m, 1H), 3.85-3.89 (t, 1H), 4.30-4.37 (m, 2H), 4.45-4.53 (q, 2H), 6.25-6.26 (t, J = 2.0 Hz, 1H), 6.77-6.79 (d, J = 9.2 Hz, 2H), 6.94-6.96 (d, J = 9.2 Hz, 2H), 7.04-7.06 (d, J = 9.2 Hz, 2H), 7.20-7.22 (d, 2H), 7.43-7.46 (m, 4H), 7.52-7.53 (m, 2H), 7.64 (s, 1H). |

TABLE 1-continued

| Cmpd # | Structure | Characterization Data |
|---|---|---|
| 98 | 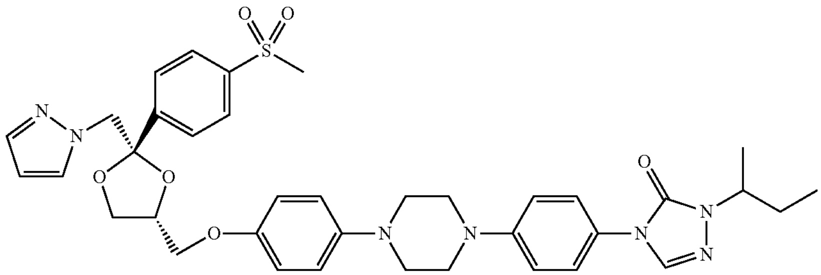 [SMILES: CCC(C)n1ncn(-c2ccc(N3CCN(c4ccc(OC[C@@H]5CO[C@@](Cn6cccn6)(c6ccc(S(C)(=O)=O)cc6)O5)cc4)CC3)cc2)c1=O] | LCMS: 99.03% @ 262 nm; m/z 713.9 (M + H). 1H NMR (400 MHz, CDCl3): 0.90-0.94 (t, J = 7.6 Hz, 3H), 1.40-1.42 (d, J = 6.8 Hz, 3H), 1.70-1.77 (m, 1H), 1.85-1.89 (m, 1H), 3.09 (s, 3H), 3.23-3.27 (m, 4H), 3.35-3.44 (m, 4H), 3.75-3.79 (m, 1H), 3.86-3.88 (m, 2H), 4.29-4.40 (m, 2H), 4.47-4.52 (q, 2H), 6.26-6.27 (t, J = 2.0 Hz, 1H), 6.79-6.81 (d, J = 8.8 Hz, 2H), 6.95-6.97 (d, J = 8.8 Hz, 2H), 7.04-7.07 (d, J = 9.2 Hz, 2H), 7.20-7.22 (d, 2H), 7.42-7.46 (m, 2H), 7.51-7.52 (m, 2H), 7.63-7.64 (d, 1H), 7.70-7.75 (m, 2H) 7.91-7.98 (m, 2H). |
| 99 | 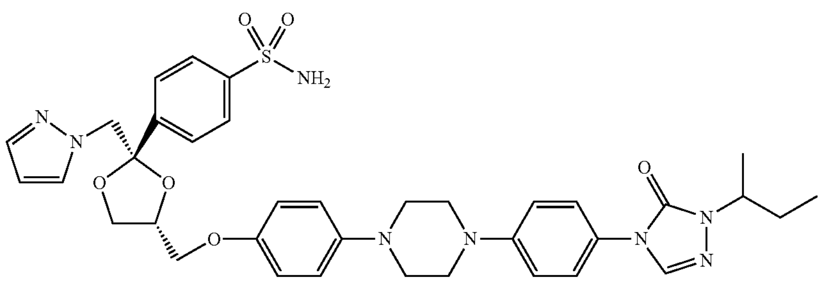 [SMILES: CCC(C)n1ncn(-c2ccc(N3CCN(c4ccc(OC[C@@H]5CO[C@@](Cn6cccn6)(c6ccc(S(N)(=O)=O)cc6)O5)cc4)CC3)cc2)c1=O] | LCMS: 100% @ 262 nm; m/z 714.9 (M + H). 1H NMR (400 MHz, CDCl3): 0.90-0.94 (t, J = 7.6 Hz, 3H), 1.40-1.42 (d, J = 6.8 Hz, 3H), 1.70-1.77 (m, 1H), 1.85-1.89 (m, 1H), 3.09 (s, 3H), 3.26-3.31 (m, 4H), 3.34-3.44 (m, 4H), 3.75-3.79 (m, 1H), 3.86-3.90 (m, 1H), 4.29-4.34 (m, 1H), 4.36-4.39 (m, 1H), 4.45-4.50 (m, 2H), 4.89 (s, 1H), 5.00 (m, 1H), 6.27-6.29 (m, 1H), 6.65-6.67 (d, J = 9.2 Hz, 2H), 6.79-6.81 (d, J = 9.2 Hz, 2H), 6.96-6.98 (m, 2H), 7.03-7.07 (m, 2H), 7.44-7.46 (m, 2H), 7.51-7.52 (m, 2H), 7.62-7.64 (d, 2H), 7.68-7.70 (m, 2H) 7.85-7.96 (m, 2H). |

TABLE 1-continued
| Cmpd # | Structure | Characterization Data |
|---|---|---|
| 100 | 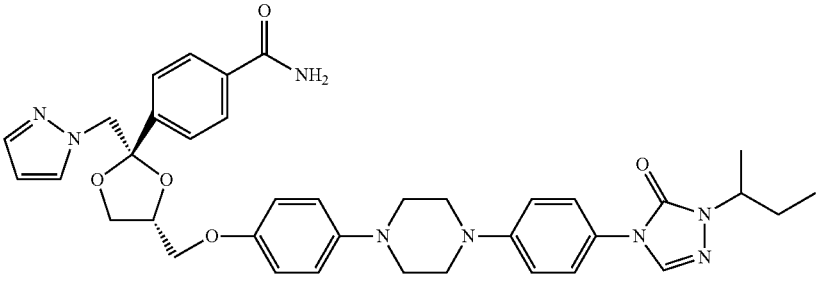 [SMILES: CCC(C)n1ncn(-c2ccc(N3CCN(c4ccc(OC[C@@H]5CO[C@@](Cn6cccn6)(c6ccc(C(N)=O)cc6)O5)cc4)CC3)cc2)c1=O] | LCMS: 99.76% @ 260 nm; m/z 679.91 (M + H). 1H NMR (400 MHz, CDCl3): 0.91-0.94 (t, J = 7.6 Hz,3H). 1.40-1.42 (d, J = 6.8 Hz, 3H), 1.70-1.77 (m, 1H), 1.85-1.89 (m, 1H), 3.25-3.27 (m, 4H), 3.38-3.41 (m, 4H), 3.75-3.78 (m, 1H), 3.82-3.89 (m, 2H), 4.31-4.39 (m, 2H), 4.51-4.52 (q, 2H), 5.65 (s, 1H), 6.15 (s, 1H), 6.25-6.26 (t, 1H), 6.79-6.81 (d, J = 9.2 Hz, 2H), 6.95-6.97 (d, 2H), 7.03-7.07 (d, 2H), 7.44-7.46 (d, 2H), 7.50-7.52 (m, 2H), 7.62-7.64 (m, 2H),7.83-7.85 (d, 2H). |
| 101 | 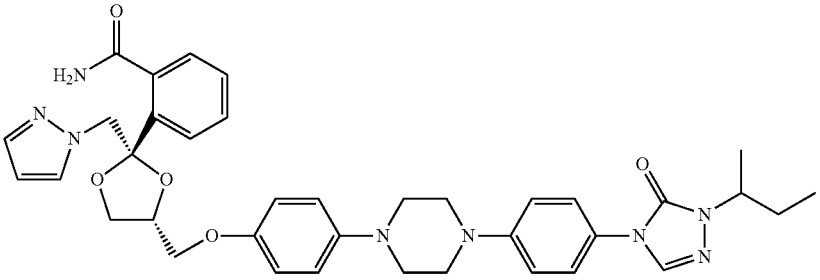 [SMILES: CCC(C)n1ncn(-c2ccc(N3CCN(c4ccc(OC[C@@H]5CO[C@@](Cn6cccn6)(c6ccccc6C(N)=O)O5)cc4)CC3)cc2)c1=O] | LCMS: 100% @ 260 nm; m/z 678.8 (M + H). 1H NMR (400 MHz, CDCl3): 0.91-0.94 (t, J = 7.6 Hz,3H), 1.40-1.42 (d, J = 6.8 Hz, 3H), 1.72-1.77 (m, 1H), 1.85-1.90 (m, 1H), 3.22-3.27(m, 4H), 3.31-3.39 (m, 5H), 3.79-3.85 (m, 3H), 4.31 (m, 2H), 4.89 (s, 2H), 5.64-5.72 (m, 1H), 6.09-6.17 (m, 1H), 6.21-6.23 (m, 1H), 6.78-6.80 (d, 2H), 6.94-6.97 (d, J = 8.8 Hz, 4H), 7.02-7.07 (d, J = 8.8 Hz, 2H), 7.33-7.41 (m, 3H),7.43-7.49 (m, 4H), 7.57-7.61 (m, 1H), 7.64 (s, 1H). |

TABLE 1-continued

| Cmpd # | Structure | Characterization Data |
|---|---|---|
| 102 | 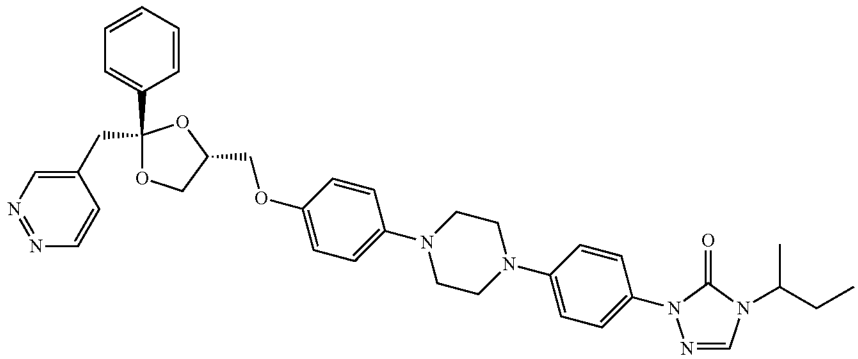 [SMILES: CCC(C)n1cnn(-c2ccc(N3CCN(c4ccc(OC[C@@H]5CO[C@@](Cc6ccnnc6)(c6ccccc6)O5)cc4)CC3)cc2)c1=O] | Trans racemate LC-MS: m/z 648.2 (M + H) $^1$H NMR (400 MHz, CDCl$_3$) δ 9.13 (m, 2H), 7.65 (s, 1H), 7.53-7.41 (m, 4H), 7.41-7.27 (m, 4H), 7.17 (d, J = 9.0 Hz, 2H), 7.06 (d, J = 9.0 Hz, 2H), 6.76 (d, J = 9.0 Hz, 2H), 4.30 (m, 2H), 4.16 (dd, J = 8.4, 6.4 Hz, 1H), 3.91 (dd, J = 9.8, 5.5 Hz, 1H), 3.73-3.63 (m, 2H), 3.52 (m, 4H), 3.43 (m, 4H), 3.23 (s, 2H), 1.89 (m, 1H), 1.70 (m, 1H), 1.42 (d, J = 6.7 Hz, 3H), 0.93 (t, J = 7.4 Hz, 3H). |
| 103 | 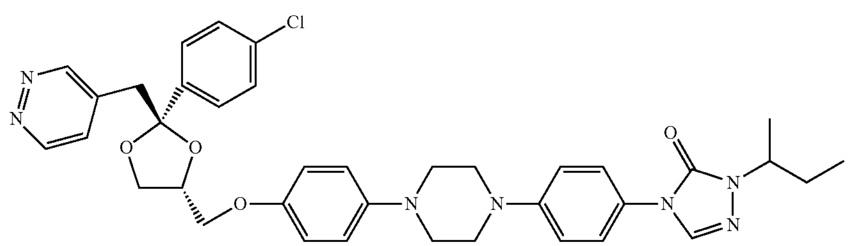 | LCMS: 98.50% @ 261 nm; m/z 681.86 (M + H). 1H NMR (400 MHz, CDCl3) δ 0.90-0.94 (m, J = 7.6 Hz, 3H), 1.40-1.42 (m, J = 6.4 Hz, 3H), 1.70-1.77 (m, 1H), 1.86-1.88 (m, 1H), 3.16 (s, 2H), 3.21-3.27 (m, 4H), 3.38-3.40 (m, 4H), 3.51-3.55 (m, 1H), 3.69-3.71 (m, 1H), 3.76-3.85 (m, 2H), 4.10-4.14 (m, 1H), 4.29-4.34 (m, 2H) 6.68-6.71 (d, J = 8.8 Hz, 2H), 6.90-6.92 (d, J = 9.2 Hz, 2H), 7.03-7.05 (d, J = 8.8 Hz, 2H), 7.28-7.32 (m, 4H), 7.37-7.45 (m, 4H), 7.63 (s, 1H), 9.07-9.09 (m, 2H). |

TABLE 1-continued

| Cmpd # | Structure | Characterization Data |
|---|---|---|
| 104 | 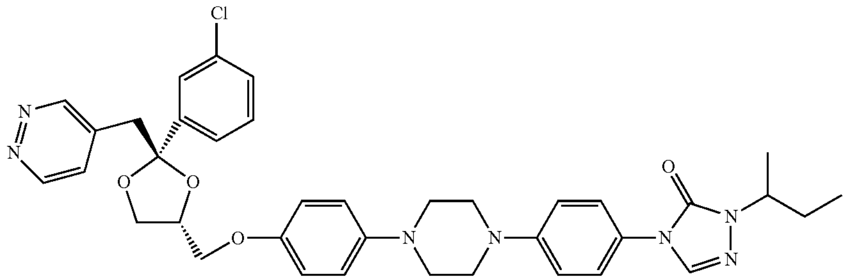 | LCMS: 100% @ 261 nm; m/z 681.96 (M + H). 1H NMR (400 MHz, CDCl3) δ 0.90-0.94 (m, J = 7.6 Hz, 3H), 1.40-1.42 (m, J = 6.4 Hz, 3H), 1.70-1.77 (m, 1H), 1.86-1.88 (m, 1H), 3.15 (s, 2H), 3.22-3.24 (m, 4H), 3.35-3.38 (m, 5H), 3.64-3.73 (m, 2H), 3.88-3.91 (m, 1H), 4.10-4.14 (m, 1H), 4.25-4.34 (m, 2H), 6.70-6.72 (d, J = 8.8 Hz, 2H), 6.90-6.92 (d, J = 9.2 Hz, 2H), 7.03-7.05 (d, J = 8.8 Hz, 2H), 7.33-7.34 (m, 3H), 7.43-7.45 (d, 2H), 7.50 (s, 1H) 7.63 (s, 1H), 9.09-9.10 (m, 2H). |
| 105 | 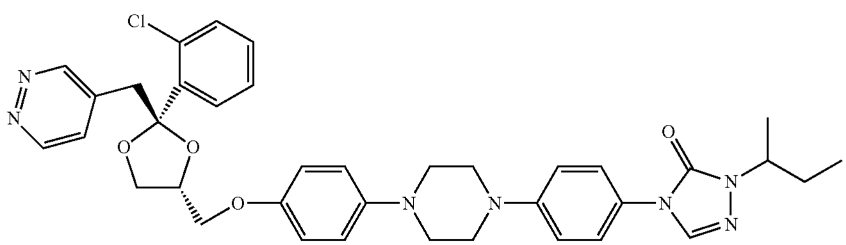 [SMILES: CCC(C)n1ncn(-c2ccc(N3CCN(c4ccc(OC[C@@H]5CO[C@](Cc6ccnnc6)(c6ccccc6Cl)O5)cc4)CC3)cc2)c1=O] | LCMS: 98.06% @ 261 nm; m/z 681.91 (M + H). 1H NMR (400 MHz, CDCl3): δ 0.90-0.94 (m, J = 7.6 Hz, 3H), 1.40-1.42 (m, J = 6.4 Hz, 3H), 1.70-1.77 (m, 1H), 1.86-1.88 (m, 1H), 3.21-3.24 (m, 5H), 3.35-3.38 (m, 4H), 3.46 (s, 2H), 3.69-3.75 (m, J = 6.4 Hz, 2H), 3.91-3.94 (m, 1H), 4.11-4.14 (m, 1H), 4.27-4.30 (m, 2H), 6.68-6.70 (d, J = 8.8 Hz, 2H), 6.89-6.91 (d, J = 9.2 Hz, 2H), 7.03-7.05 (d, J = 8.8 Hz, 2H), 7.17-7.19 (m, 1H), 7.33-7.34 (m, 1H), 7.41-7.44 (m, 3H), 7.53-7.55 (m, 1H), 7.63 (s, 1H), 9.06-9.12 (m, 2H), 9.06-9.07 (m, 2H). |

TABLE 1-continued

| Cm pd # | Structure | Characterization Data |
|---|---|---|
| 106 | 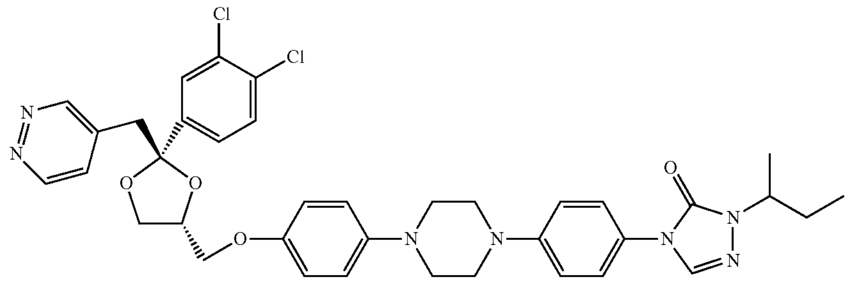 [SMILES: CCC(C)n1ncn(-c2ccc(N3CCN(c4ccc(OC[C@@H]5CO[C@](Cc6ccnnc6)(c6ccc(Cl)c(Cl)c6)O5)cc4)CC3)cc2)c1=O] | LCMS: 100% @ 261 nm; m/z 715.86 (M + H). 1H NMR (400 MHz, CDCl3): δ 0.88-0.94 (m, J = 7.6 Hz, 3H), 1.40-1.42 (m, J = 6.4 Hz, 3H), 1.70-1.77 (m, 1H), 1.86-1.88 (m, 1H), 3.13 (s, 2H), 3.23-3.24 (m, 4H), 3.36-3.37 (m, 4H), 3.65-3.69 (m, 1H), 3.73-3.77 (m, 1H), 3.86-3.90 (m, 1H), 4.07-4.11 (m, 1H), 4.20-4.21 (m, 1H) 4.30-4.32 (m, 1H), 6.68-6.71 (d, J = 8.8 Hz, 2H), 6.90-6.92 (d, J = 9.2 Hz, 2H), 7.03-7.05 (d, J = 8.8 Hz, 2H), 7.28 (m, 1H), 7.34-7.35 (m, 1H), 7.41-7.45 (m, 3H), 7.60-7.63 (m, 2H), 9.10-9.12 (d, J = 5.2 Hz, 1H). |
| 107 | 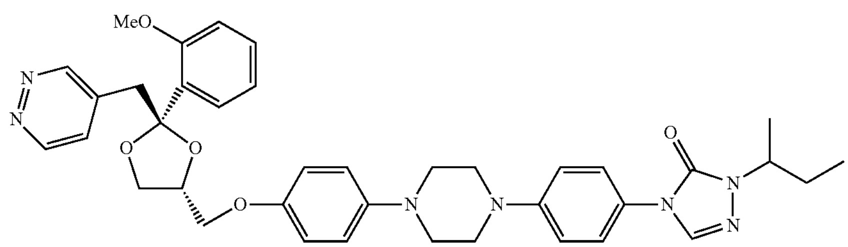 [SMILES: CCC(C)n1ncn(-c2ccc(N3CCN(c4ccc(OC[C@@H]5CO[C@](Cc6ccnnc6)(c6ccccc6OC)O5)cc4)CC3)cc2)c1=O] | LCMS: 99.50% @ 261 nm; m/z 678.06 (M + H). 1H NMR (400 MHz, CDCl3): δ 0.90-0.94 (m, J = 7.6 Hz, 3H), 1.40-1.42 (m, J = 6.4 Hz, 3H) ,1.70-1.77 (m, 1H), 1.86-1.88 (m, 1H), 3.21-3.24 (m, 4H), 3.35-3.38 (m, 4H), 3.42-3.52 (q, 3H), 3.72-3.81 (m, 3H), 3.95 (s, 3H), 4.11-4.15 (m, 1H), 4.29-4.32 (m, 2H), 6.72-6.75 (d, J = 8.8 Hz, 2H), 6.89-6.92 (d, 3H), 6.97-6.99 (d, 1H), 7.03-7.05 (d, J = 8.8 Hz, 2H), 7.31-7.32 (m, 2H), 7.40-7.45 (m, 3H), 7.63 (s, 1H), 9.03 (m, 2H). |

TABLE 1-continued
| Cmpd # | Structure | Characterization Data |
|---|---|---|
| 108 | 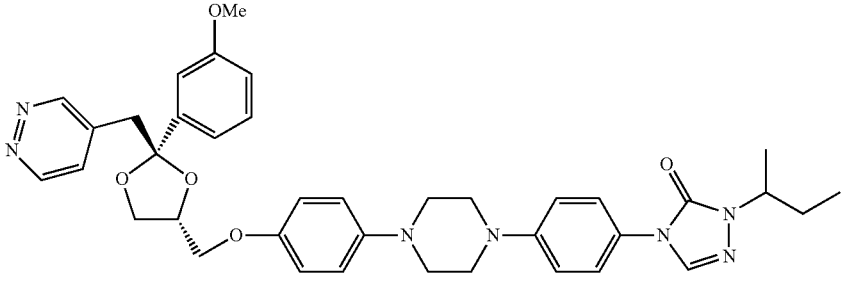 [SMILES: CCC(C)n1ncn(-c2ccc(N3CCN(c4ccc(OC[C@@H]5CO[C@](Cc6ccnnc6)(c6cccc(OC)c6)O5)cc4)CC3)cc2)c1=O] | LCMS: 97.87% @ 261 nm; m/z 678.01 (M + H). 1H NMR (400 MHz, CDCl3): δ 0.90-0.94 (m, J = 7.6 Hz, 3H), 1.40-1.42 (m, J = 6.4 Hz, 3H), 1.70-1.77 (m, 1H), 1.86-1.88 (m, 1H), 3.176 (s, 2H), 3.22-3.24 (m, 4H), 3.35-3.37 (m, 4H), 3.64-3.68 (t, 2H), 3.77 (s, 3H), 3.90-3.93 (m, 1H), 4.11-4.15 (m, 1H), 4.29-4.32 (m, 2H), 6.71-6.74 (d, J = 8.8 Hz, 2H), 6.86-6.91 (m, 3H), 6.98-7.05 (m, 4H), 7.31-7.32 (m, 1H), 7.43-7.45 (m, 2H), 7.63 (s, 2H), 9.06 (m, 2H). |
| 109 | 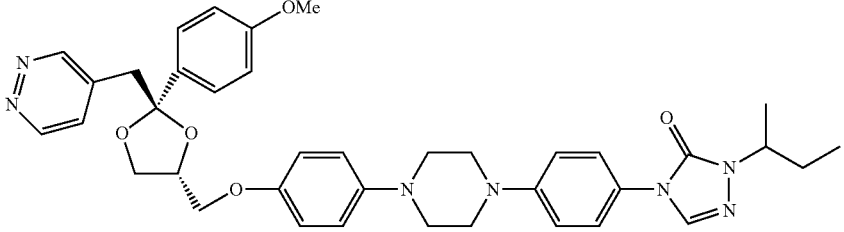 [SMILES: CCC(C)n1ncn(-c2ccc(N3CCN(c4ccc(OC[C@@H]5CO[C@](Cc6ccnnc6)(c6ccc(OC)cc6)O5)cc4)CC3)cc2)c1=O] | LCMS: 100% @ 260 nm; m/z 677.96 (M + H). 1H NMR (400 MHz, CDCl3): δ 0.90-0.94 (m, J = 7.6 Hz, 3H), 1.40-1.42 (m, J = 6.4 Hz, 3H), 1.68-1.77 (m, 1H), 1.86-1.89 (m, 1H), 3.16 (s, 2H), 3.21-3.24 (m, 4H), 3.35-3.38 (m, 4H), 3.63-3.67 (t, 2H), 3.82 (s, 3H), 3.87-3.92 (m, 1H), 4.12-4.16 (m, 1H), 4.29-4.34 (m, 2H), 6.72-6.74 (d, J = 8.8 Hz, 2H), 6.84-6.86 (d, 2H), 6.90-6.92 (d, 2H), 7.03-7.05 (d, 2H), 7.32-7.35 (m, 3H), 7.43-7.45 (m, 2H), 7.63 (s, 1H), 9.04-9.07 (m, 2H). |

TABLE 1-continued
| Cmpd # | Structure | Characterization Data |
|---|---|---|
| 110 | 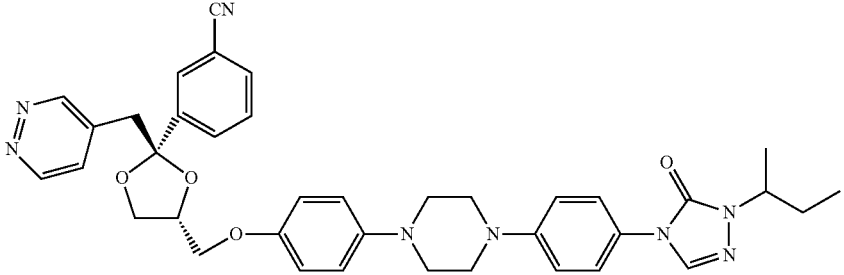 | LCMS: 99.23% @ 261 nm; m/z 673.01 (M + H). 1H NMR (400 MHz, CDCl3): 0.90-0.94 (t, J = 7.6 Hz, 3H), 1.40-1.42 (d, J = 6.4 Hz, 3H), 1.70-1.77 (m, 1H), 1.84-1.88 (m, 1H), 3.12 (s, 2H), 3.22-3.24 (m, 4H), 3.35-3.38 (m, 4H), 3.66-3.68 (t, 1H), 3.76-3.88 (m, 2H), 4.09-4.12 (m, 1H), 4.30-4.32 (m, 2H), 6.65-6.67 (d, J = 9.2 Hz, 2H), 6.89-6.92 (d, J = 9.2 Hz, 2H), 7.03-7.05 (d, J = 9.2 Hz, 2H), 7.35-7.37 (m, 1H), 7.43-7.49 (m, 3H), 7.63-7.71 (m, 3H), 7.84 (s, 1H), 9.10-9.13 (m, 2H). |
| 111 | 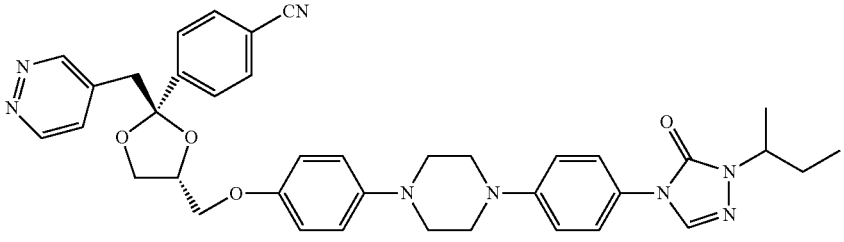 [SMILES: CCC(C)n1ncn(-c2ccc(N3CCN(c4ccc(OC[C@@H]5CO[C@](Cc6ccnnc6)(c6ccc(C#N)cc6)O5)cc4)CC3)cc2)c1=O] | LCMS: 96.01% @ 262 nm; m/z 673.01 (M + H). 1H NMR (400 MHz, CDCl3): δ 0.90-0.94 (t, J = 7.6 Hz, 3H), 1.40-1.42 (d, J = 6.4 Hz, 3H), 1.70-1.77 (m, 1H), 1.84-1.88 (m, 1H), 3.14 (s, 2H), 3.23-3.24 (m, 4H), 3.36-3.37 (m, 4H), 3.66-3.70 (t, 1H), 3.75-3.77 (m, 1H), 3.91-3.85 (m, 1H), 4.09-4.12 (m, 1H), 4.24-4.32 (m, 2H), 6.62-6.64 (d, J = 8.8 Hz, 2H), 6.89-6.91 (d, J = 8.8 Hz, 2H), 7.03-7.05 (d, J = 8.8 Hz, 2H), 7.35-7.37 (m, 1H), 7.43-7.45 (m, 2H), 7.58-7.60 (m, 2H), 7.64-7.67 (m, 3H), 9.10-9.13 (m, 2H). |

TABLE 1-continued
| Cmpd # | Structure | Characterization Data |
|---|---|---|
| 112 | 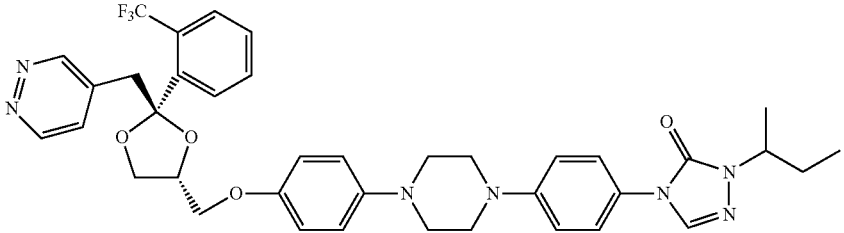 [SMILES: CCC(C)n1ncn(-c2ccc(N3CCN(c4ccc(OC[C@@H]5CO[C@](Cc6ccnnc6)(c6ccccc6C(F)(F)F)O5)cc4)CC3)cc2)c1=O] | LCMS: 98.76% @ 261 nm; m/z 715.96 (M + H). 1H NMR (400 MHz, CDCl3): δ 0.90-0.94 (t, J = 7.6 Hz, 3H), 1.40-1.42 (d, J = 6.4 Hz, 3H), 1.70-1.77 (m, 1H), 1.85-1.90 (m, 1H), 3.20-3.23 (m, 5H), 3.329 (s, 1H), 3.35-3.37 (m, 4H), 3.56-3.64 (m, 2H), 3.86-3.90 (m, 1H), 4.06-4.11 (m, 2H), 4.30-4.32 (m, 2H), 6.60-6.63 (d, J = 9.2 Hz, 2H), 6.86-6.89 (d, J = 9.2 Hz, 2H), 7.02-7.05 (d, J = 9.2 Hz, 2H), 7.42-7.45 (m, 3H), 7.46-7.53 (m, 2H), 7.75-7.79 (m, 2H), 9.12-9.18 (m, 2H). |
| 113 | 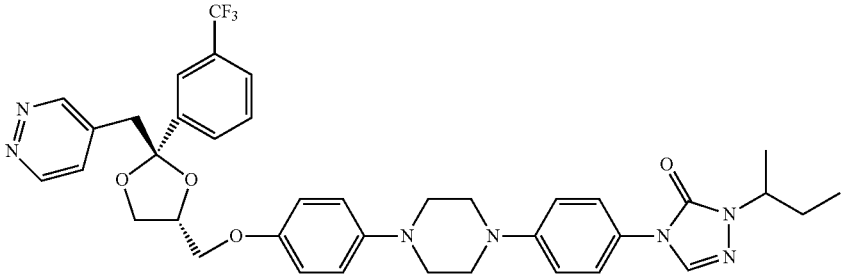 | LCMS: 99.45% @ 262 nm; m/z 715.96 M + H). 1H NMR (400 MHz, CDCl3): δ 0.91-0.94 (t, J = 7.6 Hz, 3H), 1.40-1.42 (d, J = 6.4 Hz, 3H), 1.70-1.77 (m, 1H), 1.84-1.88 (m, 1H), 2.98 (s, 1H), 2.17 (s, 1H), 3.22-3.23 (m, 3H), 3.35-3.38 (m, 3H), 3.69-3.74 (m, 2H), 3.86-3.88 (m, 1H), 4.09-4.13 (m, 1H), 4.22-4.24 (m, 1H), 4.30-4.32 (m, 1H), 6.66-6.68 (d, J = 9.2 Hz, 2H), 6.88-6.90 (d, J = 9.2 Hz, 2H), 7.03-7.05 (d, J = 9.2 Hz, 2H), 7.33-7.36 (m, 1H), 7.43-7.50 (m, 3H), 7.61-7.67 (m, 3H), 7.83 (s, 1H), 9.10-9.11 (m, 2H). |

TABLE 1-continued

| Cmpd # | Structure | Characterization Data |
|---|---|---|
| 114 | 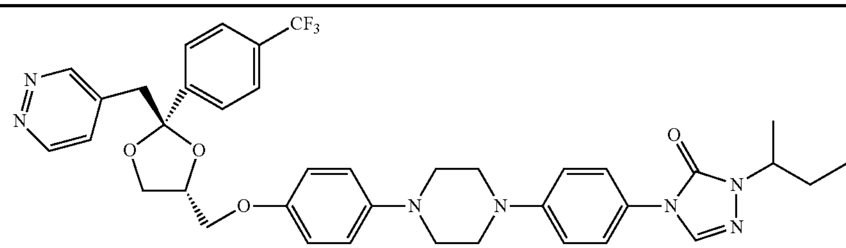 | LCMS: 99.76% @ 261 nm; m/z 716.46 (M + H). 1H NMR (400 MHz, CDCl3): δ 0.90-0.94 (t, J = 7.6 Hz, 3H), 1.40-1.42 (d, J = 6.4 Hz, 3H), 1.70-1.77 (m, 1H), 1.84-1.88 (m, 1H), 3.16 (s, 2H), 3.21-3.24 (m, 4H), 3.35-3.38 (m, 4H), 3.65-3.74 (m, 2H), 3.84-3.88 (m, 1H), 4.10-4.14 (m, 1H), 4.25-4.32 (m, 2H), 6.63-6.65 (d, J = 8.8 Hz, 2H), 6.88-6.90 (d, J = 8.8 Hz, 2H), 7.03-7.05 (d, J = 9.2 Hz, 2H), 7.33-7.35 (m, 1H), 7.43-7.45 (m, 2H), 7.58-7.63 (m, 5H), 9.10-9.11 (m, 2H). |
| 115 | 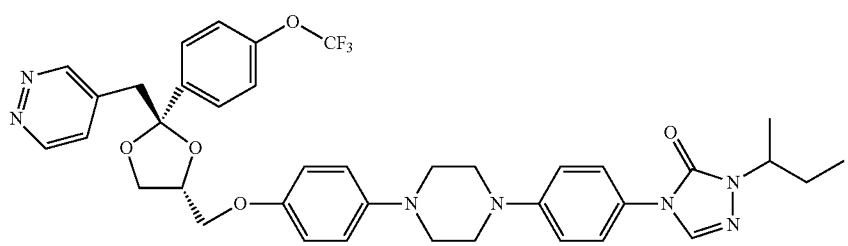 | LCMS: 99.36% @ 260 nm; m/z 732.36 (M + H). 1H NMR (400 MHz, CDCl3): δ 0.91-0.94 (t, J = 7.6 Hz, 3H), 1.40-1.42 (d, J = 6.8 Hz 3H), 1.70-1.77 (m, 1H), 1.86-1.90 (m, 1H), 3.16 (s, 2H), 3.25-3.28 (m, 4H), 3.39-3.45 (m, 4H), 3.66-3.75 (m, 2H), 3.85-3.89 (m, 1H), 4.09-4.13 (m, 1H), 4.24-4.32 (m, 2H), 6.66-6.69 (d, J = 8.8 Hz, 2H), 6.90-6.98 (m, 2H), 7.03-7.06 (d, J = 8.8 Hz, 2H), 7.18-7.23 (d, 2H), 7.33 (m, 1H), 7.44-7.51 (m, 4H), 7.64 (s, 1H), 9.10-9.19 (m, 2H). |
| 116 | 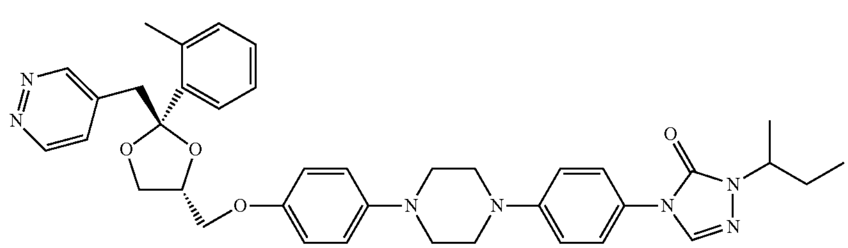 [SMILES: CCC(C)n1ncn(-c2ccc(N3CCN(c4ccc(OC[C@@H]5CO[C@](Cc6ccnnc6)(c6ccccc6C)O5)cc4)CC3)cc2)c1=O] | LCMS: 99.40% @ 261 nm; m/z 661.95 (M + H). 1H NMR (400 MHz, CDCl3): δ 0.90-0.94 (t, J = 7.6 Hz, 3H), 1.40-1.42 (d, J = 6.8 Hz 3H), 1.70-1.77 (m, 1H), 1.86- |

US 10,336,735 B2
383          384
TABLE 1-continued
| Cmpd # | Structure | Characterization Data |
|---|---|---|
| | | 1.88 (m, 1H), 2.57 (s, 3H), 3.21-3.23 (m, 5H), 3.35-3.38 (m, 4H), 3.62-3.66 (m, 2H), 3.84-3.88 (m, 1H), 4.08-4.11 (m, 1H), 4.23-4.30 (m, 2H), 6.67-6.69 (m, 2H), 6.88-6.90 (m, 2H), 7.03-7.05 (m, 2H), 7.11-7.27 (m, 3H), 7.30-7.35 (m, 1H), 7.42-7.45 (m, 3H), 7.63 (s, 1H), 9.06-9.08 (m, 2H). |
| 117 | 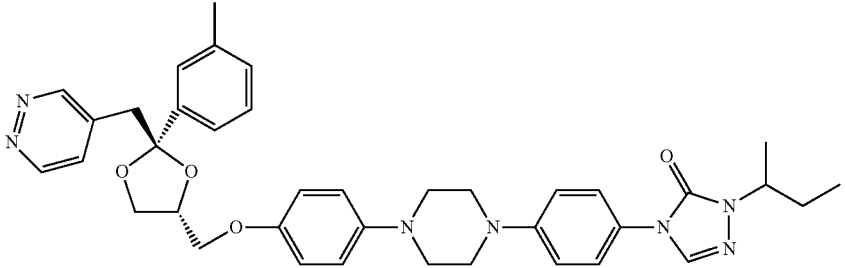 [SMILES: CCC(C)n1ncn(-c2ccc(N3CCN(c4ccc(OC[C@@H]5CO[C@](Cc6ccnnc6)(c6cccc(C)c6)O5)cc4)CC3)cc2)c1=O] | LCMS: 100% @ 260 nm; m/z 662.0 (M + H). 1H NMR (400 MHz, CDCl3): δ 0.90-0.94 (t, J = 7.6 Hz, 3H), 1.40-1.42 (d, J = 6.8 Hz 3H), 1.70-1.77 (m, 1H), 1.86-1.88 (m, 1H), 2.34 (s, 3H), 3.169 (s, 2H), 3.21-3.24 (m, 4H), 3.35-3.38 (m, 4H), 3.63-3.68 (m, 2H), 3.89-3.93 (m, 1H), 4.10-4.13 (m, 1H), 4.25-4.30 (m, 2H), 6.70-6.7. (d, J = 9.2 Hz, 2H), 6.89-6.92 (d, J = 9.2 Hz, 2H), 7.03-7.05 (d, J = 9.2 Hz, 2H), 7.15-7.18 (m, 1H), 7.22-7.25 (m, 2H), 7.30-7.33 (m, 2H) 7.43-7.45 (m, 2H), 7.63 (s, 1H), 9.06-9.08 (m, 2H). |
| 118 | 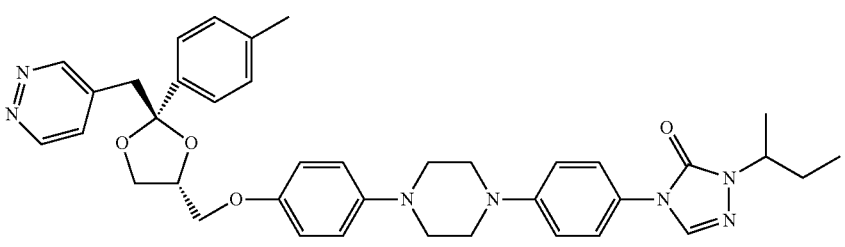 [SMILES: CCC(C)n1ncn(-c2ccc(N3CCN(c4ccc(OC[C@@H]5CO[C@](Cc6ccnnc6)(c6ccc(C)cc6)O5)cc4)CC3)cc2)c1=O] | LCMS: 100% @ 262 nm; m/z 661.95 (M + H). 1H NMR (400 MHz, CDCl3): δ 0.90-0.94 (t, J = 7.6 Hz, 3H), 1.40-1.42 (d, J = 6.8 Hz 3H), 1.70-1.77 (m, 1H), 1.86-1.88 (m, 1H), 2.36 (s, 3H), 3.17 (s, 2H), 3.22-3.24 (m, 4H), 3.36-3.38 (m, 4H), 3.62-3.66 (m, 2H), 3.89-3.93 (m, |

| Cmpd # | Structure | Characterization Data |
|---|---|---|
| | | 1H), 4.12-4.15 (m, 1H), 4.27-4.32 (m, 2H), 6.72-6.74. (d, J = 9.2 Hz, 2H), 6.90-6.92 (d, J = 9.2 Hz, 2H), 7.03-7.05 (d, J = 9.2 Hz, 2H), 7.13-7.15 (d, 2H), 7.30-7.32 (m, 3H), 7.43-7.45 (m, 2H), 7.63 (s, 1H), 9.04-9.06 (m, 2H). |
| 119 | 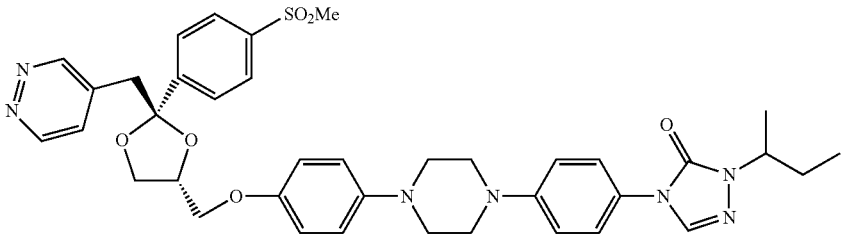 | LCMS: 100% @ 260 nm; m/z 725.86 (M + H). 1H NMR (400 MHz, CDCl3): δ 0.90-0.94 (t, J = 7.6 Hz, 3H), 1.40-1.42 (d, J = 6.8 Hz 3H), 1.70-1.77 (m, 1H), 1.86-1.88 (m, 1H), 3.09-3.16 (m, 3H), 3.16-3.18 (m, 2H), 3.22-3.27 (m, 4H), 3.37-3.40 (m, 4H), 3.52-3.54 (m, 1H), 3.67-3.69 (m, 1H), 3.80-3.86 (m, 2H), 4.31-4.32 (m, 3H), 6.63-6.76. (m, 2H), 6.88-6.97 (m, 2H), 7.03-7.06 (m, 2H), 7.35-7.37 (m, 1H), 7.43-7.46 (m, 2H), 7.63-7.64 (m, 1H), 7.69-7.75 (m, 2H), 7.93-8.00 (m, 2H), 9.04-9.11 (m, 2H). |
| 120 | 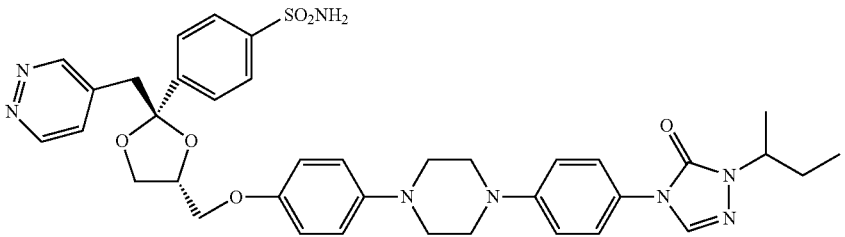 [SMILES: CCC(C)n1ncn(-c2ccc(N3CCN(c4ccc(OC[C@@H]5CO[C@](Cc6ccnnc6)(c6ccc(S(N)(=O)=O)cc6)O5)cc4)CC3)cc2)c1=O] | LCMS: 100% @ 260 nm; m/z 727.01 (M + H). 1H NMR (400 MHz, CDCl3): δ 0.91-0.94 (t, J = 7.6 Hz, 3H), 1.40-1.42 (d, J = 6.8 Hz 3H), 1.70-1.77 (m, 1H), 1.86-1.89 (m, 1H), 3.14-3.25 (m, 5H), 3.36-3.44 (m, 4H), 3.52-3.56 (m, 1H), 3.69-3.79 (m, 2H), 3.81-3.86 (m, 1H), 4.09-4.12 (m, 1H), 4.29-4.34 (m, 2H), 4.90-4.93 (m, 2H), 6.64-6.77. (m, 2H), 6.87-6.97 (m, 2H), 7.02-7.06 |

TABLE 1-continued
| Cmpd # | Structure | Characterization Data |
|---|---|---|
| | | (m, 2H), 7.33-7.36 (m, 1H), 7.43-7.46 (m, 2H), 7.58-7.68 (m, 3H), 7.87-7.97 (m, 2H), 9.04-9.12 (m, 2H). |
| 122 | 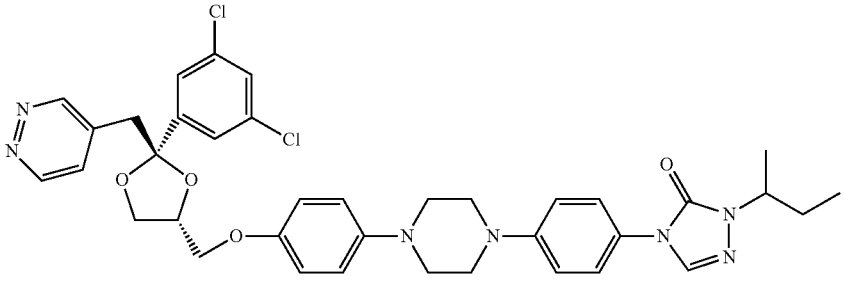 [SMILES: CCC(C)n1ncn(-c2ccc(N3CCN(c4ccc(OC[C@@H]5CO[C@](Cc6ccnnc6)(c6cc(Cl)cc(Cl)c6)O5)cc4)CC3)cc2)c1=O] | LCMS: 100% @ 261 nm; m/z 715.76 (M + H). 1H NMR (400 MHz, CDCl3): δ 0.90-0.94 (t, J = 7.6 Hz, 3H), 1.40-1.42 (d, J = 6.8 Hz 3H), 1.70-1.77 (m, 1H), 1.86-1.88 (m, 1H), 3.13 (s, 2H), 3.18-3.25 (m, 4H), 3.36-3.38 (m, 4H), 3.66-3.70 (m, 1H), 3.76-3.79 (m, 1H), 3.88-3.91 (m, 1H), 4.09-4.18 (m, 1H), 4.28-4.32 (m, 1H), 6.70-6.72 (d, J = 9.2 Hz, 2H), 6.90-6.92 (d, J = 9.2 Hz, 2H), 7.03-7.05 (d, J = 9.2 Hz, 2H), 7.33-7.45 (m, 6H), 7.63 (s, 1H), 9.12-9.13 (m, 2H). |
| 123 | 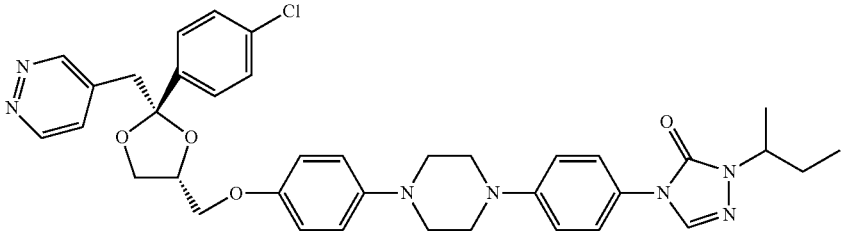 | LCMS: 100% @ 261 nm; m/z 681.86 (M + H). 1H NMR (400 MHz, CDCl3): δ 0.90-0.94 (m, J = 7.6 Hz, 3H), 1.40-1.42 (m, J = 6.4 Hz, 3H), 1.70-1.77 (m, 1H), 1.86-1.88 (m, 1H), 3.15 (s, 2H), 3.22-3.24 (m, 4H), 3.36-3.38 (m, 4H), 3.63-3.71 (m, 2H), 3.85-3.89 (m, 1H), 4.10-4.14 (m, 1H), 4.26-4.32 (m, 1H) 4.30-4.32 (m, 1H), 6.75-6.78 (d, J = 8.8 Hz, 2H), 6.95-6.97 (d, J = 9.2 Hz, 2H), 7.30-7.46 (m, 6H), 7.64 (s, 1H), 9.01-9.08 (m, 2H). |

TABLE 1-continued
| Cmpd # | Structure | Characterization Data |
|---|---|---|
| 124 | 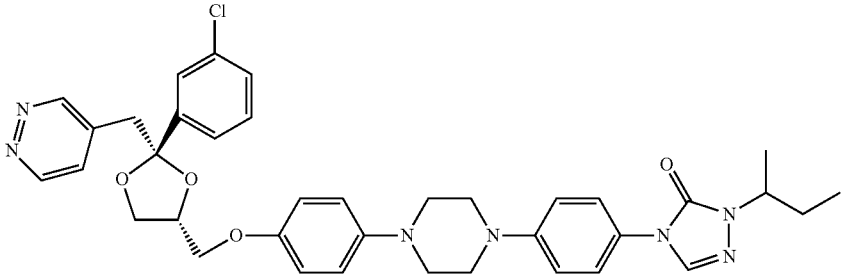 | LCMS: 100% @ 261 nm; m/z 681.91 (M + H). 1H NMR (400 MHz, CDCl3): δ 0.90-0.94 (m, J = 7.6 Hz, 3H), 1.40-1.42 (m, J = 6.4 Hz, 3H), 1.70-1.77 (m, 1H), 1.86-1.88 (m, 1H), 3.17 (s, 2H), 3.26-3.27 (m, 5H), 3.38-3.39 (m, 4H), 3.48-3.51 (m, 1H), 3.67-3.70 (m, 1H), 3.77-3.87 (m, 2H), 4.31-4.34 (m, 2H), 6.74-6.76 (d, J = 8.8 Hz, 2H), 6.95-6.98 (d, J = 9.2 Hz, 2H), 7.03-7.07 (d, 2H), 7.33-7.36 (m, 4H), 7.44-7.46 (d, 2H), 7.52 (s, 1H), 7.64 (s, 1H), 9.02-9.10 (m, 2H). |
| 125 | 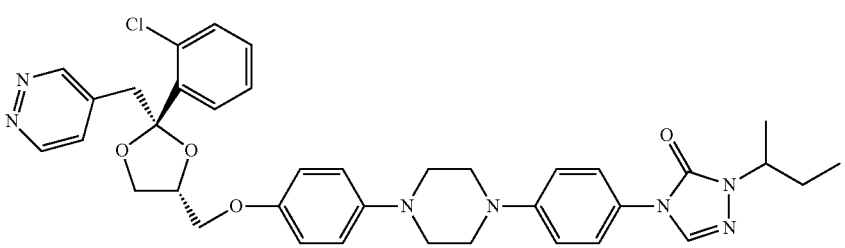 | LCMS: 98.06% @ 261 nm; m/z 681.91 (M + H). 1H NMR (400 MHz, CDCl3): 0.90-0.94 (m, J = 7.6 Hz, 3H), 1.40-1.42 (m, J = 6.4 Hz, 3H), 1.70-1.77 (m, 1H), 1.86-1.88 (m, 1H), 3.21-3.24 (m, 4H), 3.35-3.38 (m, 4H), 3.46 (s, 2H), 3.51-3.54 (m, 2H), 3.73-3.80 (m, 2H), 3.85-3.88 (m, 1H), 4.29-4.34 (m, 2H), 6.75-6.78 (d, J = 8.8 Hz, 2H), 6.96-6.98 (d, J = 9.2 Hz, 2H), 7.04-7.07 (d, J = 8.8 Hz, 2H), 7.23-7.25 (m, 1H), 7.33-7.37 (m, 2H), 7.44-7.48 (t, 3H), 7.56-7.57 (m, 1H), 7.64 (s, 1H), 9.01-9.13 (m, 2H). |

TABLE 1-continued
| Cmpd # | Structure | Characterization Data |
|---|---|---|
| 126 | 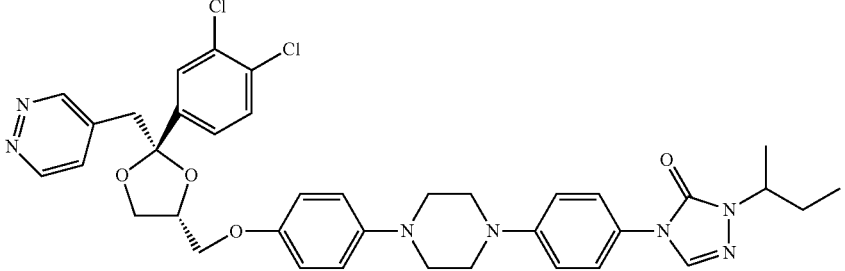 [SMILES: CCC(C)n1ncn(-c2ccc(N3CCN(c4ccc(OC[C@@H]5CO[C@@](Cc6ccnnc6)(c6ccc(Cl)c(Cl)c6)O5)cc4)CC3)cc2)c1=O] | LCMS: 97.0% @ 261 nm; m/z 715.86 (M + H). 1H NMR (400 MHz, CDCl3): δ 0.88-0.94 (m, J = 7.6 Hz, 3H), 1.40-1.48 (m, J = 6.4 Hz, 3H), 1.72-1.77 (m, 1H), 1.86-1.89 (m, 1H), 3.15 (s, 2H), 3.25-3.27 (m, 4H), 3.37-3.40 (m, 4H), 3.48-3.52 (m, 1H), 3.65-3.69 (m, 1H), 3.76-3.79 (m, 1H), 3.82-3.86 (m, 1H) 4.30-4.33 (m, 2H), 6.73-6.75 (d, J = 8.8 Hz, 2H), 6.95-6.97 (d, J = 9.2 Hz, 2H), 7.04-7.06 (d, J = 8.8 Hz, 2H), 7.31-7.33 (m, 2H), 7.43-7.48 (m, 3H), 7.63-7.64 (m, 2H), 9.03-9.04 (d, J = 5.2 Hz, 1H), 9.11 (s, 1H). |
| 127 | 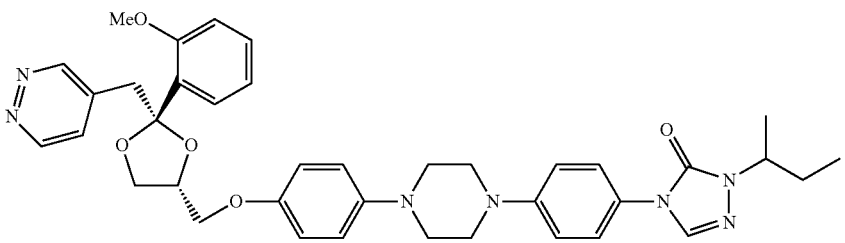 [SMILES: CCC(C)n1ncn(-c2ccc(N3CCN(c4ccc(OC[C@@H]5CO[C@@](Cc6ccnnc6)(c6ccccc6OC)O5)cc4)CC3)cc2)c1=O] | LCMS: 100% @ 260 nm; m/z 678.01 (M + H). 1H NMR (400 MHz, CDCl3): δ 0.90-0.94 (m, J = 7.6 Hz, 3H), 1.40-1.42 (m, J = 6.4 Hz, 3H), 1.70-1.77 (m, 1H), 1.86-1.88 (m, 1H), 3.24-3.27 (m, 4H), 3.37-3.46 (m, 5H), 3.51-3.58 (m, 2H), 3.74-3.80 (m, 2H), 3.90-3.93 (m, 1H), 3.98 (s, 3H), 4.30-4.34 (m, 1H), 4.38-4.41 (m, 1H), 6.76-6.79 (d, J = 8.8 Hz, 2H), 6.91-7.07 (m, 5H), 7.32-7.46 (m, 6H), 7.64 (s, 1H), 8.98-9.08 (m, 2H). |

TABLE 1-continued
| Cmpd # | Structure | Characterization Data |
|---|---|---|
| 128 | 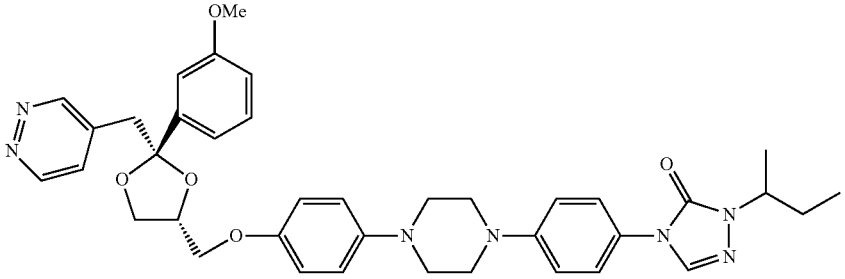 | LCMS: 999.85% @ 261 nm; m/z 678.1 (M + H). 1H NMR (400 MHz, CDCl3): δ 0.91-0.94 (m, J = 7.6 Hz, 3H). 1.40-1.42 (m, J = 6.4 Hz, 3H), 1.70-1.77 (m, 1H), 1.86-1.90 (m, 1H), 3.19 (s, 2H), 3.24-3.27 (m, 4H), 3.37-3.40 (m, 4H), 3.50-3.54 (m, 1H), 3.70-3.74 (m, 1H), 3.76-3.79 (m, 1H), 3.77-3.79 (m, 1H), 3.83 (s, 1H), 3.85-3.88 (m, 1H), 4.30-4.34 (m, 2H), 6.75-6.77 (d, J = 8.8 Hz, 2H), 6.89-6.97 (m, 3H), 7.01-7.07 (m, 4H), 7.31-7.34 (m, 2H), 7.44-7.46 (d, 2H), 7.64 (s, 1H), 9.01-9.08 (m, 2H). |
| 129 | 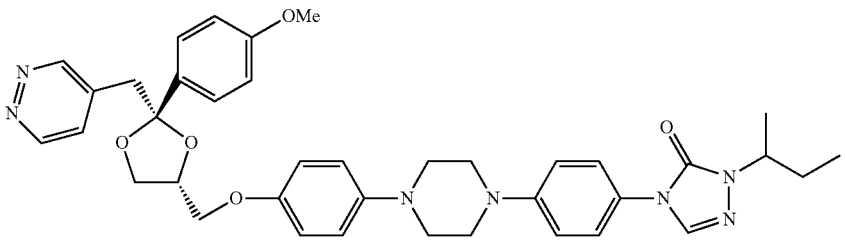 [SMILES: CCC(C)n1ncn(-c2ccc(N3CCN(c4ccc(OC[C@@H]5CO[C@@](Cc6ccnnc6)(c6ccc(OC)cc6)O5)cc4)CC3)cc2)c1=O] | LCMS: 99.82% @ 261 nm; m/z 677.9 (M + H). 1H NMR (400 MHz, CDCl3): δ 0.90-0.94 (m, J = 7.6 Hz, 3H), 1.39-1.42 (m, J = 6.4 Hz, 3H), 1.70-1.76 (m, 1H), 1.86-1.89 (m, 1H), 3.18 (s, 2H), 3.24-3.27 (m, 4H), 3.3-3.40 (m, 4H), 3.52-3.56 (m, 1H), 3.71-3.79 (m, 2H), 3.84 (s, 3H), 3.8-3.87 (m, 1H), 4.29-4.34 (m, 2H), 6.76-6.78 (d, J = 8.8 Hz, 2H), 6.88-6.91 (d, 2H), 6.95-6.97 (d, 2H), 7.04-7.06 (d, 2H), 7.32-7.39 (m, 3H), 7.43-7.46 (m, 2H), 7.64 (s, 1H), 9.06 (m, 2H). |

TABLE 1-continued

| Cmpd # | Structure | Characterization Data |
|---|---|---|
| 130 | 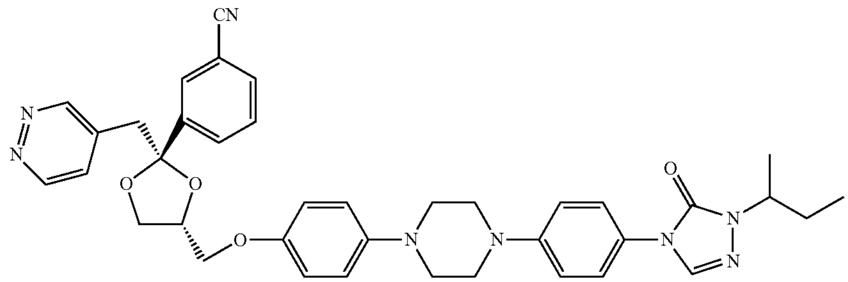 | LCMS: 100% @ 261 nm; m/z 672.86 (M + H). 1H NMR (400 MHz, CDCl3): δ 0.90-0.94 (t, J = 7.6 Hz, 3H), 1.40-1.43 (d, J = 6.4 Hz, 3H), 1.70-1.77 (m, 1H), 1.84-1.90 (m, 1H), 3.17 (s, 2H), 3.25-3.27 (m, 4H), 3.37-3.40 (m, 4H), 3.49-3.53 (m, 1H), 3.67-3.71 (m, 1H), 3.78-3.83 (m, 2H), 4.29-4.32 (m, 2H), 6.73-6.76 (d, J = 8.8 Hz, 2H), 6.95-6.97 (d, J = 8.8 Hz, 2H), 7.04-7.04 (d, J = 8.8 Hz, 2H), 7.34-7.36 (m, 1H), 7.44-7.46 (d, 2H), 7.51-7.55 (t, 1H), 7.64 (s, 1H), 7.67-7.74 (m, 2H), 7.87 (s, 1H), 9.04-9.11 (m, 2H). |
| 131 | 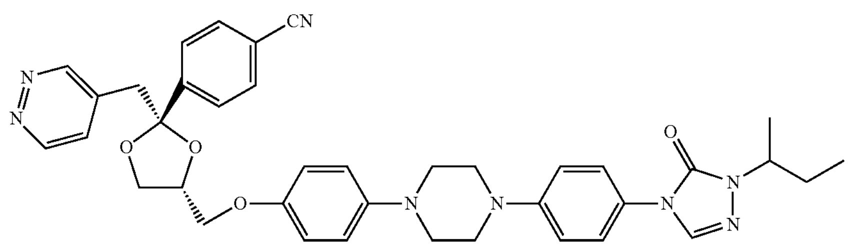 [SMILES: CCC(C)n1ncn(-c2ccc(N3CCN(c4ccc(OC[C@@H]5CO[C@@](Cc6ccnnc6)(c6ccc(C#N)cc6)O5)cc4)CC3)cc2)c1=O] | LCMS: 98.53% @ 262 nm; m/z 673.06 (M + H). 1H NMR (400 MHz, CDCl3): δ 0.91-0.94 (t, J = 7.6 Hz, 3H), 1.40-1.42 (d, J = 6.4 Hz, 3H), 1.70-1.77 (m, 1H), 1.84-1.88 (m, 1H), 3.17 (s, 2H), 3.24-3.27 (m, 4H), 3.37-3.40 (m, 4H), 3.51-3.54 (m, 1H), 3.67-3.71 (m, 1H), 3.80-3.83 (m, 1H), 4.29-4.32 (m, 2H), 6.73-6.76 (d, J = 9.2 Hz, 2H), 6.95-6.97 (d, J = 8.8 Hz, 2H), 7.04-7.07 (d, J = 9.2 Hz, 2H), 7.35-7.37 (m, 1H), 7.32-7.33 (m, 1H), 7.44-7.46 (m, 2H), 7.62-7.64 (m, 2H), 7.70-7.72 (m, 2H), 9.03-9.10 (m, 2H). |

TABLE 1-continued
| Cmpd # | Structure | Characterization Data |
|---|---|---|
| 132 | 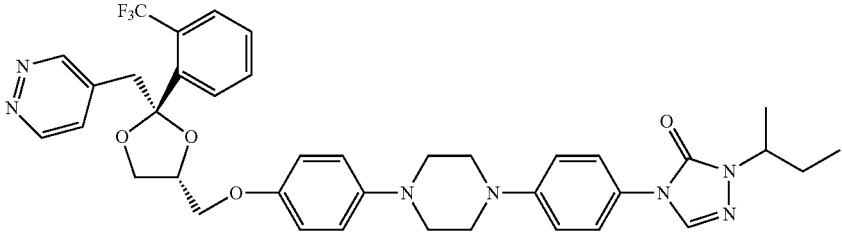 [SMILES: CCC(C)n1ncn(-c2ccc(N3CCN(c4ccc(OC[C@@H]5CO[C@@](Cc6ccnnc6)(c6ccccc6C(F)(F)F)O5)cc4)CC3)cc2)c1=O] | LCMS: 98.97% @ 261 nm; m/z 715.9 (M + H). 1H NMR (400 MHz, CDCl3): δ 0.91-0.94 (t, J = 7.6 Hz, 3H), 1.40-1.42 (d, J = 6.4 Hz, 3H), 1.70-1.77 (m, 1H), 1.85-1.90 (m, 1H), 3.24-3.29 (m, 4H), 3.37-3.39 (m, 5H), 3.73-3.78 (m, 4H), 4.19-4.37 (m, 3H), 4.30-4.32 (m, 2H), 6.69-6.71 (d, J = 8.8 Hz, 2H), 6.93-6.95 (d, J = 9.2 Hz, 2H), 7.04-7.06 (d, J = 9.2 Hz, 2H), 7.40-7.46 (m, 3H), 7.51-7.59 (m, 2H), 7.64 (s, 1H), 7.79-7.83 (t, 2H), 9.04-9.16 (m, 2H). |
| 133 | 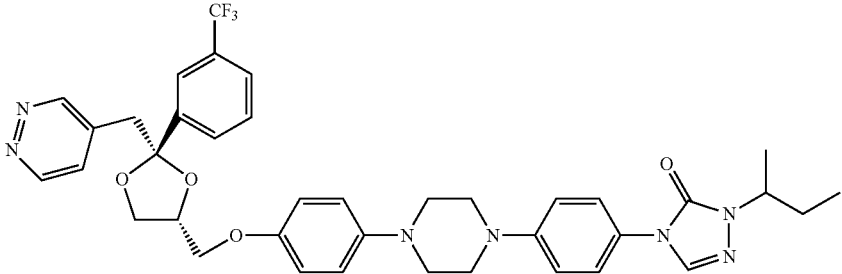 | LCMS: 100% @ 261 nm; m/z 716.01 (M + H). $^1$H NMR (400 MHz, CDCl$_3$): δ 0.91-0.94 (t, J = 7.6 Hz, 3H), 1.40-1.42 (d, J = 6.4 Hz, 3H), 1.70-1.77 (m, 1H), 1.84-1.88 (m, 1H), 2.19 (s, 2H), 3.24-3.27 (m, 4H), 3.37-3.40 (m, 4H), 3.50-3.51 (m, 1H), 3.67-3.70 (m, 1H), 3.77-3.86 (m, 2H), 4.31-4.34 (m, 2H), 6.74-6.76 (d, J = 9.2 Hz, 2H), 6.95-6.97 (d, J = 9.2 Hz, 2H), 7.04-7.07 (d, J = 9.2 Hz, 2H), 7.34-7.36 (m, 1H), 7.44-7.46 (m, 2H), 7.53-7.55 (m, 1H), 7.64-7.66 (m, 2H), 7.68-7.70 (m, 1H), 7.80(s, 1H), 9.02-9.12 (m, 2H). |

TABLE 1-continued

| Cmpd # | Structure | Characterization Data |
|---|---|---|
| 134 | 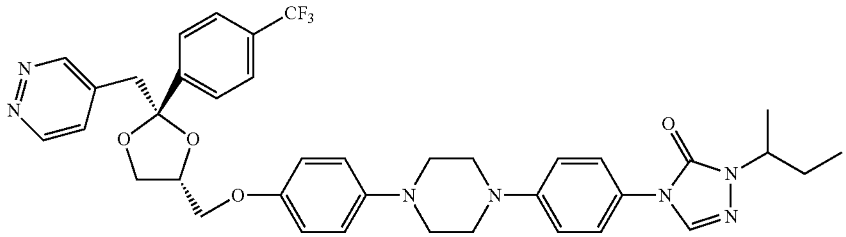 | LCMS: 100% @ 261 nm; m/z 715.81 (M + H). 1H NMR (400 MHz, CDCl3): δ 0.91-0.94 (t, J = 7.6 Hz, 3H), 1.40-1.42 (d, J = 6.4 Hz, 3H), 1.70-1.77 (m, 1H), 1.84-1.89 (m, 1H), 3.13 (s, 2H), 3.21-3.24 (m, 4H), 3.32-3.40 (m, 4H), 3.50-3.54 (m, 2H), 3.68-3.72 (m, 1H), 3.78-3.86 (m, 2H), 4.29-4.32 (m, 2H), 6.74-6.76 (d, J = 9.2 Hz, 2H), 6.95-6.97 (d, J = 8.8 Hz, 2H), 7.0-7.07 (d, J = 8.8 Hz, 2H), 7.34-7.35 (m, 1H), 7.43-7.49 (m, 2H), 7.59-7.71 (m, 5H), 9.03-9.04 (m, 1H), 9.11 (m, 1H). |
| 135 | 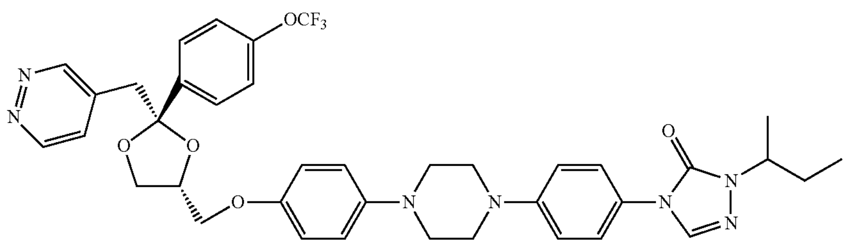 [SMILES: CCC(C)n1ncn(-c2ccc(N3CCN(c4ccc(OC[C@@H]5CO[C@@](Cc6ccnnc6)(c6ccc(OC(F)(F)F)cc6)O5)cc4)CC3)cc2)c1=O] | LCMS: 100% @ 260 nm; m/z 732.76 (M + H). 1H NMR (400 MHz, CDCl3): δ 0.90-0.94 (t, J = 7.6 Hz, 3H), 1.40-1.42 (d, J = 6.8 Hz 3H), 1.70-1.77 (m, 1H), 1.86-1.90 (m, 1H), 3.16 (s, 2H), 3.21-3.27 (m, 4H), 3.33-3.40 (m, 4H), 3.50-3.53 (m, 1H), 3.76-3.79 (m, 1H), 3.83-3.87 (m, 1H), 4.29-4.33 (m, 2H), 6.74-6.76 (d, J = 8.8 Hz, 2H), 6.95-6.97 (d, 2H), 7.04-7.07 (d, J = 8.8 Hz, 2H), 7.23-7.25 (d, 2H), 7.33-7.34 (m, 1H), 7.44-7.46 (m, 2H), 7.49-7.59 (m, 2H), 7.64 (s, 1H), 9.02-9.03 (m, 1H), 9.10-9.11 (m, 1H). |

TABLE 1-continued
| Cmpd # | Structure | Characterization Data |
|---|---|---|
| 136 | 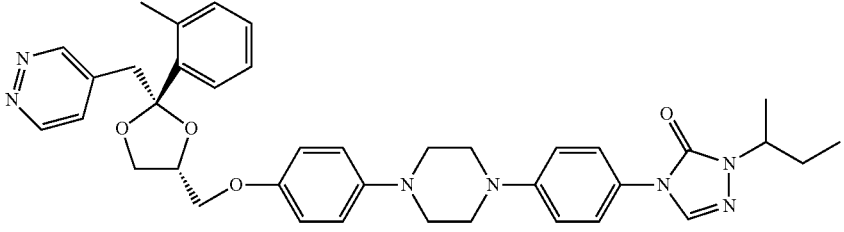 [SMILES: CCC(C)n1ncn(-c2ccc(N3CCN(c4ccc(OC[C@@H]5CO[C@@](Cc6ccnnc6)(c6ccccc6C)O5)cc4)CC3)cc2)c1=O] | LCMS: 100% @ 261 nm; m/z 661.95 (M + H). 1H NMR (400 MHz, CDCl3): δ 0.91-0.94 (t, J = 7.6 Hz, 3H), 1.40-1.42 (d, J = 6.8 Hz 3H), 1.70-1.77 (m, 1H), 1.86-1.90 (m, 1H), 2.60 (s, 2H), 3.19-3.29 (m, 5H), 3.37-3.40 (m, 4H), 3.47-3.51 (m, 1H), 3.69-3.75 (m, 2H), 3.81-3.84 (m, 1H), 4.26-4.34 (m, 2H), 6.74-6.76 (d, J = 8.8 Hz, 2H), 6.93-6.96 (d, 2H), 7.04-7.06 (d, J = 8.8 Hz, 2H), 7.16-7.28 (d, 2H), 7.32-7.34 (m, 1H), 7.43-7.50 (m, 3H), 7.64 (s, 1H), 9.01-9.03 (m, 1H), 9.10-9.11 (m, 1H). |
| 137 | 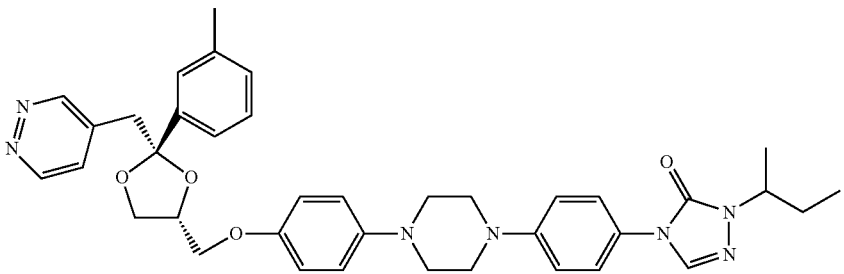 [SMILES: CCC(C)n1ncn(-c2ccc(N3CCN(c4ccc(OC[C@@H]5CO[C@@](Cc6ccnnc6)(c6cccc(C)c6)O5)cc4)CC3)cc2)c1=O] | LCMS: 100% @ 260 nm; m/z 662.0 (M + H). 1H NMR (400 MHz, CDCl3): δ 0.91-0.94 (t, J = 7.6 Hz, 3H), 1.40-1.42 (d, J = 6.8 Hz 3H), 1.70-1.77 (m, 1H), 1.86-1.90 (m, 1H), 2.39 (s, 3H), 3.18 (s, 2H), 3.19-3.29 (m, 4H), 3.38-3.44 (m, 4H), 3.48-3.52 (m, 1H), 3.68-3.72 (m, 1H), 3.74-3.78 (m, 1H), 3.84-3.85 (m, 1H), 4.31-4.34 (m, 2H), 6.75-6.77 (d, J = 8.8 Hz, 2H), 6.97-6.98 (m, 2H), 7.04-7.06 (d, J = 8.8 Hz, 2H), 7.15-7.25 (d, 3H), 7.32-7.35 (m, 2H), 7.64 (s, 1H), 9.00-9.01 (m, 1H), 9.08 (m, 1H). |

TABLE 1-continued
| Cmpd # | Structure | Characterization Data |
|---|---|---|
| 138 | 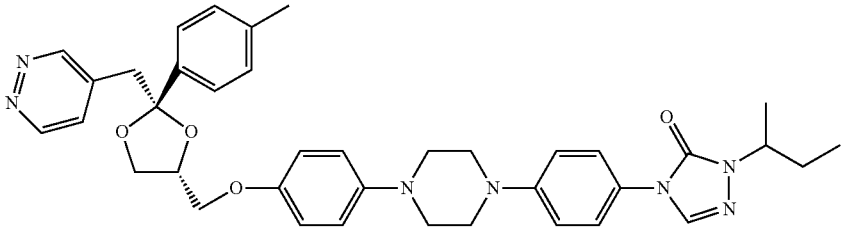 [SMILES: CCC(C)n1ncn(-c2ccc(N3CCN(c4ccc(OC[C@@H]5CO[C@@](Cc6ccnnc6)(c6ccc(C)cc6)O5)cc4)CC3)cc2)c1=O] | LCMS: 99.69% @ 262 nm; m/z 661.95 (M + H). 1H NMR (400 MHz, CDCl3): δ 0.90-0.94 (t, J = 7.6 Hz, 3H), 1.40-1.42 (d, J = 6.8 Hz 3H), 1.70-1.77 (m, 1H), 1.86-1.90 (m, 1H), 2.38 (s, 3H), 3.18 (s, 2H), 3.22-3.27 (m, 4H), 3.37-3.40 (m, 4H), 3.50-3.54 (m, 1H), 3.70-3.78 (m, 2H), 3.83-3.87 (m, 1H), 4.29-4.33 (m, 2H), 6.77-6.75 (d, J = 8.8 Hz, 2H), 6.94-6.96 (d, 2H), 7.04-7.06 (d, J = 8.8 Hz, 2H), 7.18-7.20 (d, 2H), 7.31-7.36 (m, 3H), 7.43-7.46 (m, 2H), 7.64 (s, 1H), 9.00-9.01 (m, 1H), 9.06 (m, 1H). |
| 139 | 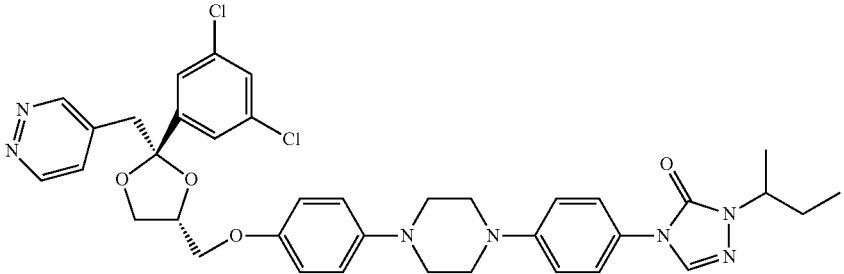 [SMILES: CCC(C)n1ncn(-c2ccc(N3CCN(c4ccc(OC[C@@H]5CO[C@@](Cc6ccnnc6)(c6cc(Cl)cc(Cl)c6)O5)cc4)CC3)cc2)c1=O] | LCMS: 100% @ 261 nm; m/z 715.81(M + H). 1H NMR (400 MHz, CDCl3): δ 0.90-0.94 (t, J = 7.6 Hz, 3H), 1.40-1.42 (d, J = 6.8 Hz 3H), 1.70-1.77 (m, 1H), 1.86-1.88 (m, 1H), 3.14 (s, 2H), 3.24-3.27 (m, 5H), 3.37-3.40 (m, 4H), 3.47-3.49 (m, 1H), 3.62-3.66 (m, 1H), 3.74-3.78 (m, 1H), 3.83-3.87 (m, 1H), 4.31-4.34 (m, 1H), 6.72-6.74 (d, J = 8.8 Hz, 2H), 6.94-6.96 (d, J = 9.2 Hz, 2H), 7.04-7.07 (d, J = 8.8 Hz, 2H), 7.34-7.38 (m, 2H), 7.42-7.46 (m, 4H), 7.64 (s, 1H), 9.03-9.049 (m, 1H), 9.12-9.13 (m, 1H). |

TABLE 1-continued

| Cmpd # | Structure | Characterization Data |
|---|---|---|
| 140 | 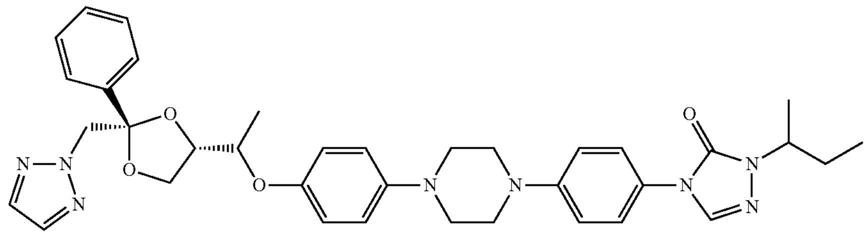 [SMILES: CCC(C)n1ncn(-c2ccc(N3CCN(c4ccc(OC(C)[C@@H]5CO[C@@](Cn6nccn6)(c6ccccc6)O5)cc4)CC3)cc2)c1=O] | LC-MS: m/z 651.2 (M + H) |
| 141 | 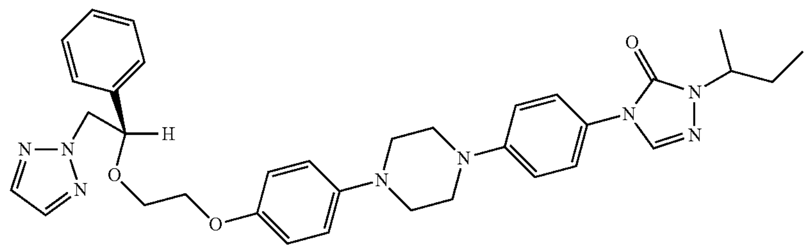 [SMILES: CCC(C)n1ncn(-c2ccc(N3CCN(c4ccc(OCCO[C@@H](Cn5nccn5)c5ccccc5)cc4)CC3)cc2)c1=O] | LC-MS: m/z 609.2 (M + H) |
| 142 | 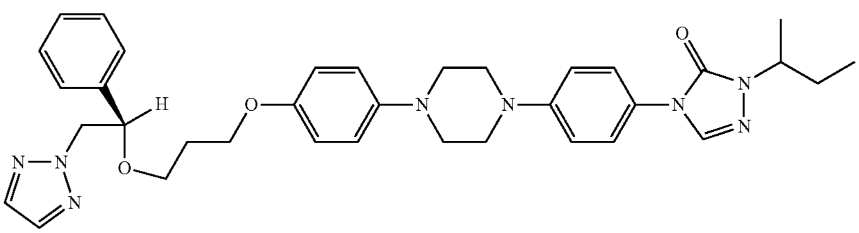 [SMILES: CCC(C)n1ncn(-c2ccc(N3CCN(c4ccc(OCCCO[C@@H](Cn5nccn5)c5ccccc5)cc4)CC3)cc2)c1=O] | LC-MS: m/z 623.3 (M + H) |
| 143 | 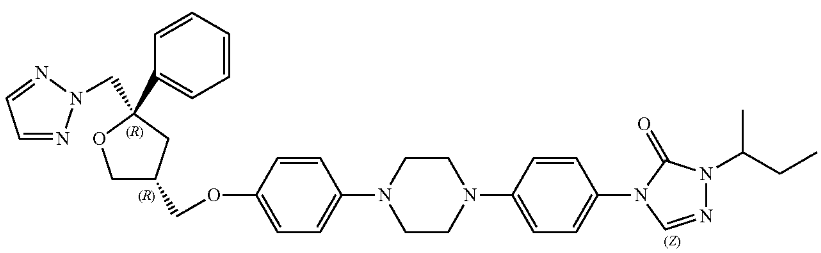 | LC-MS: m/z 635.3 (M + H) |
| 144 | 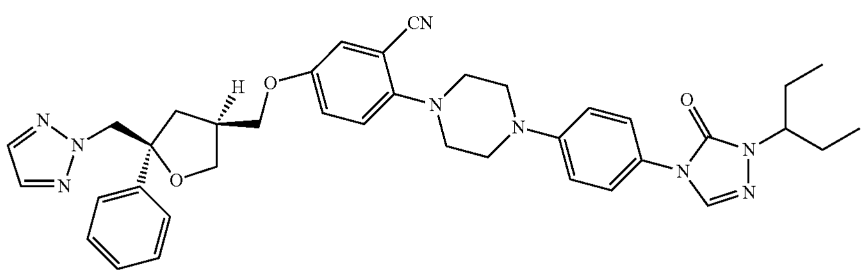 [SMILES: CCC(CC)n1ncn(-c2ccc(N3CCN(c4ccc(OC[C@H]5CO[C@](Cn6nccn6)(c6ccccc6)C5)cc4C#N)CC3)cc2)c1=O] | LC-MS: m/z 674.2 (M + H) |
| 145 | 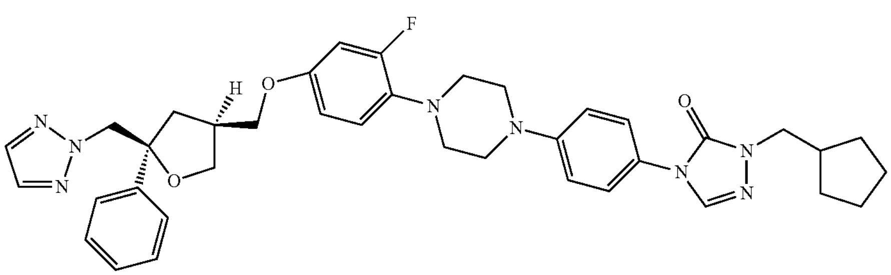 [SMILES: O=c1n(-c2ccc(N3CCN(c4ccc(OC[C@H]5CO[C@](Cn6nccn6)(c6ccccc6)C5)cc4F)CC3)cc2)cnn1CC1CCCC1] | LC-MS: m/z 679.2 (M + H) |

| Cm pd # | Structure | Characterization Data |
|---|---|---|
| 146 | 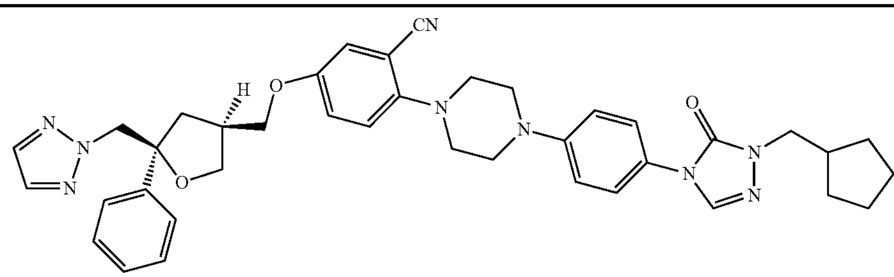 | LC-MS: m/z 686.2 (M + H) |
| 147 | 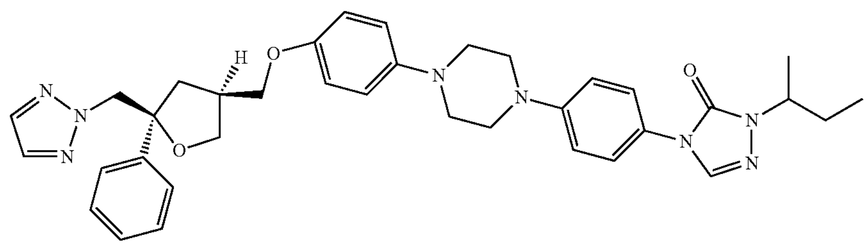 [SMILES: CCC(C)n1ncn(-c2ccc(N3CCN(c4ccc(OC[C@H]5CO[C@](Cn6nccn6)(c6ccccc6)C5)cc4)CC3)cc2)c1=O] | LC-MS: m/z 635.2 (M + H) |
| 148 | 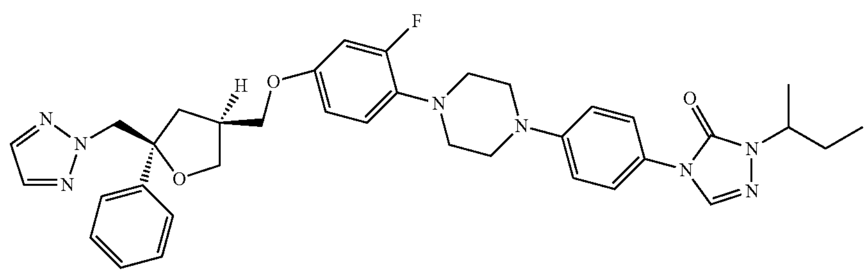 | LC-MS: m/z 653.2 (M + H) |
| 149 | 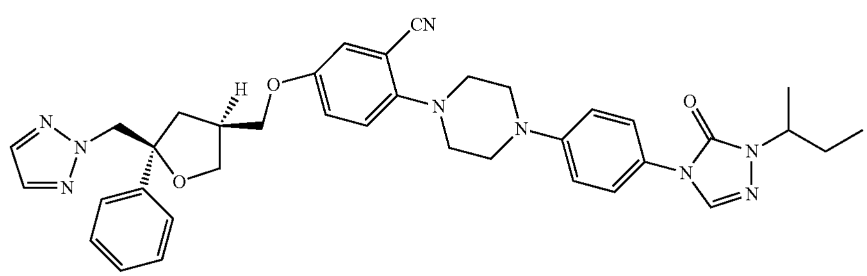 | LC-MS: m/z 660.3 (M + H) |
| 150 | 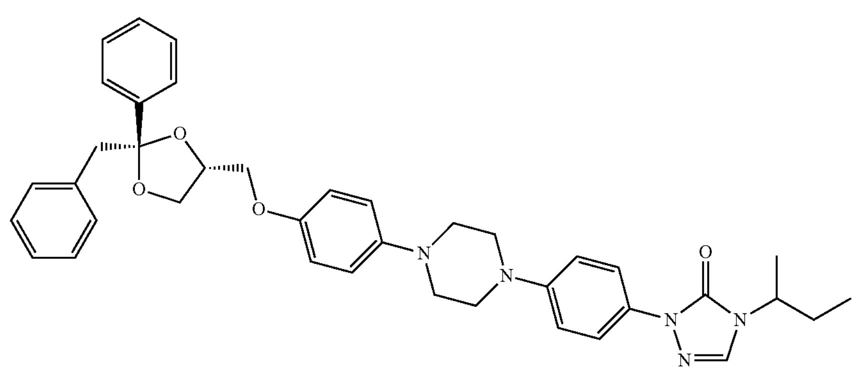 [SMILES: CCC(C)n1cnn(-c2ccc(N3CCN(c4ccc(OC[C@@H]5CO[C@@](Cc6ccccc6)(c6ccccc6)O5)cc4)CC3)cc2)c1=O] | LC-MS: m/z 646.1 (M + H) $^1$H NMR (400 MHz, CDCl$_3$) δ 8.07-8.00 (m, 2H), 7.67 (s, 1H), 7.61-7.54 (m, 1H), 7.55-7.43 (m, 6H), 7.43-7.32 (m, 3H), 7.28-7.20 (m, 2H), 7.14-6.96 (m, 3H), 6.84 (d, J = 7.9 Hz, 1H), 4.32 (m, 2H), 4.12 (m, 1H), 3.93-3.73 (m, 3H), 3.67 (m, 8H), 3.33-3.08 (m, 2H), 1.89 (m, 1H), 1.75 (m, 1H), 1.42 |

TABLE 1-continued

| Cmpd # | Structure | Characterization Data |
|---|---|---|
| | | (d, J = 6.7 Hz, 3H), 0.93 (t, J = 7.4 Hz, 3H). |
| 151 | 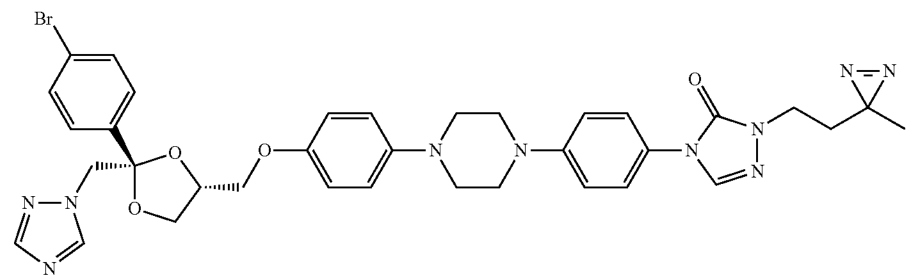 [SMILES: CC1(CCn2ncn(-c3ccc(N4CCN(c5ccc(OC[C@@H]6CO[C@@](Cn7cncn7)(c7ccc(Br)cc7)O6)cc5)CC4)cc3)c2=O)N=N1] | LC-MS: m/z 741.3 (M + H) |
| 152 | 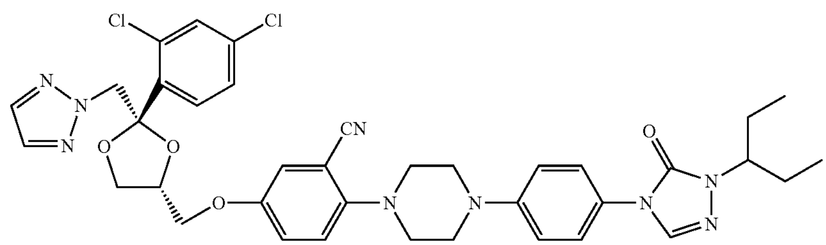 [SMILES: CCC(CC)n1ncn(-c2ccc(N3CCN(c4ccc(OC[C@@H]5CO[C@@](Cn6nccn6)(c6ccc(Cl)cc6Cl)O5)cc4C#N)CC3)cc2)c1=O] | LC-MS: m/z 744.1 (M + H) |
| 154 | 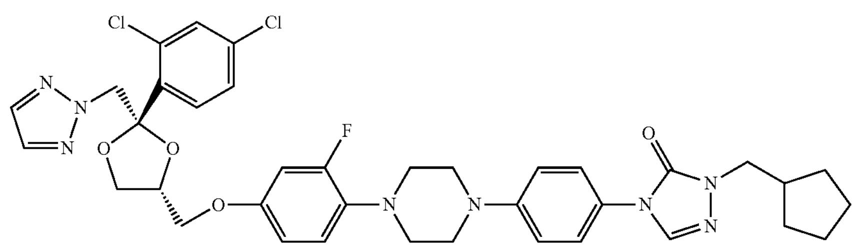 | LC-MS: m/z 749.1 (M + H) |
| 155 | 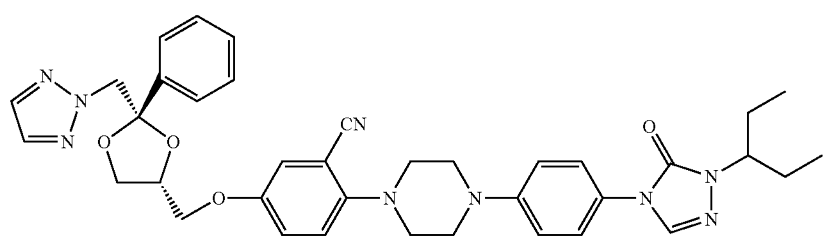 [SMILES: CCC(CC)n1ncn(-c2ccc(N3CCN(c4ccc(OC[C@@H]5CO[C@@](Cn6nccn6)(c6ccccc6)O5)cc4C#N)CC3)cc2)c1=O] | LC-MS: m/z 676.2 (M + H) |
| 156 | 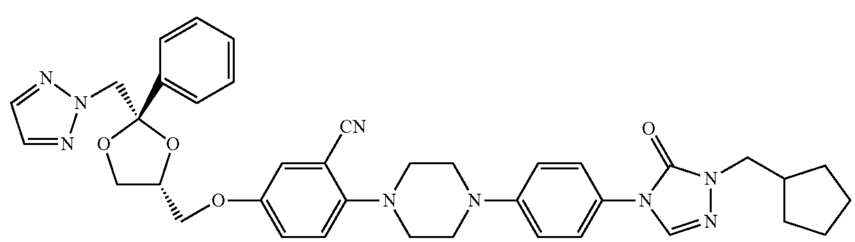 [SMILES: N#Cc1cc(OC[C@@H]2CO[C@@](Cn3nccn3)(c3ccccc3)O2)ccc1N1CCN(c2ccc(-n3cnn(CC4CCCC4)c3=O)cc2)CC1] | LC-MS: m/z 688.3 (M + H) |
| 157 | 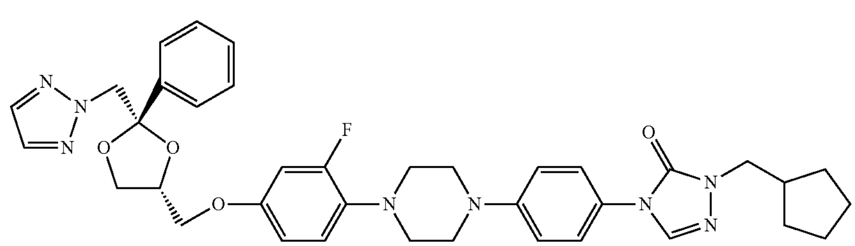 [SMILES: O=c1n(-c2ccc(N3CCN(c4ccc(OC[C@@H]5CO[C@@](Cn6nccn6)(c6ccccc6)O5)cc4F)CC3)cc2)cnn1CC1CCCC1] | LC-MS: m/z 681.2 (M + H) |

TABLE 1-continued

| Cmpd # | Structure | Characterization Data |
|---|---|---|
| 158 | 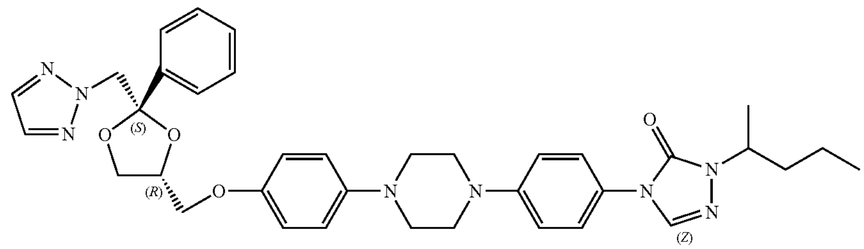 | LC-MS: m/z 651.2 (M + H) |
| 159 | 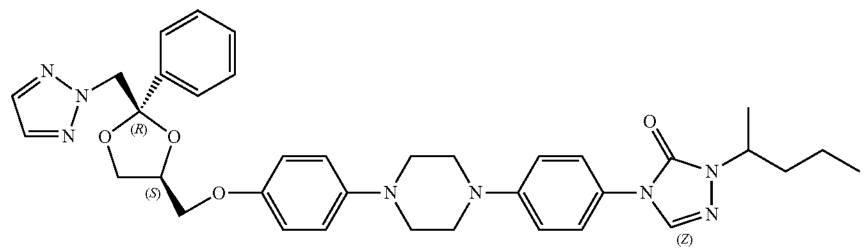 | LC-MS: m/z 651.2 (M + H) |
| 160 | 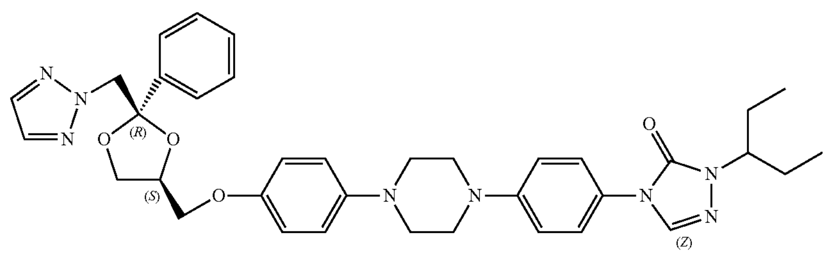 | LC-MS: m/z 651.3 (M + H) |
| 161 | 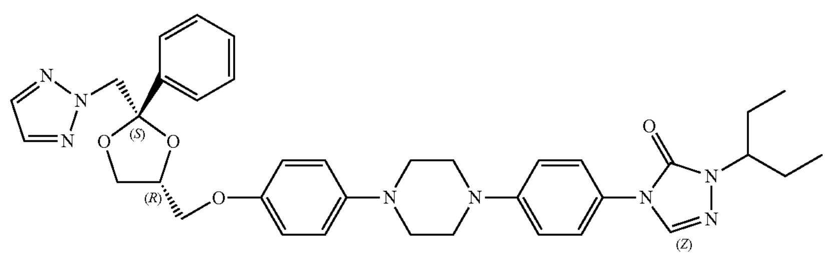 | LC-MS: m/z 651.3 (M + H) |
| 162 | 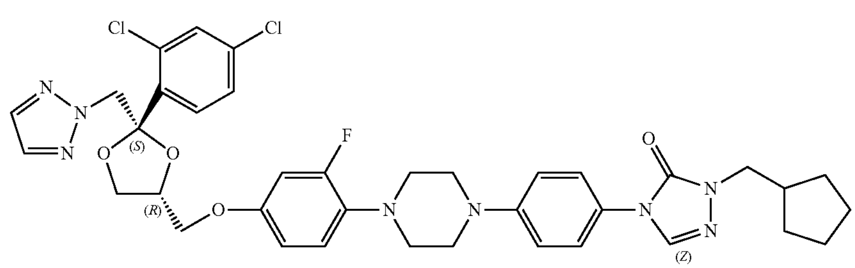 | LC-MS: m/z 749.1 (M + H) |
| 163 | 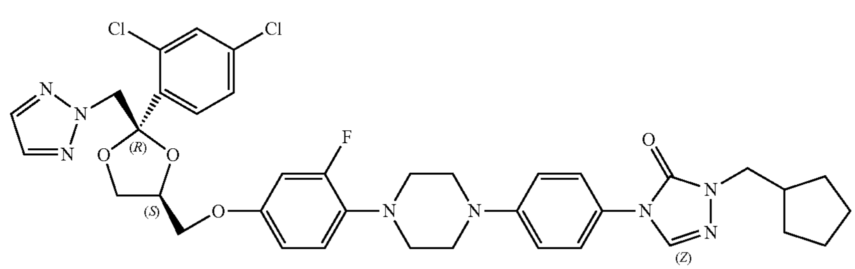 | LC-MS: m/z 749.1 (M + H) |

TABLE 1-continued

| Cmpd # | Structure | Characterization Data |
|---|---|---|
| 164 | 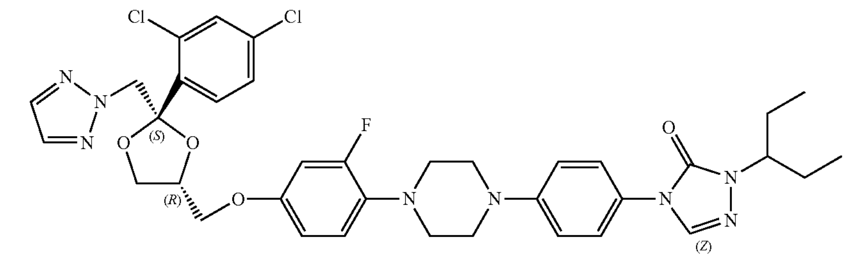 | LC-MS: m/z 737.2 (M + H) |
| 165 | 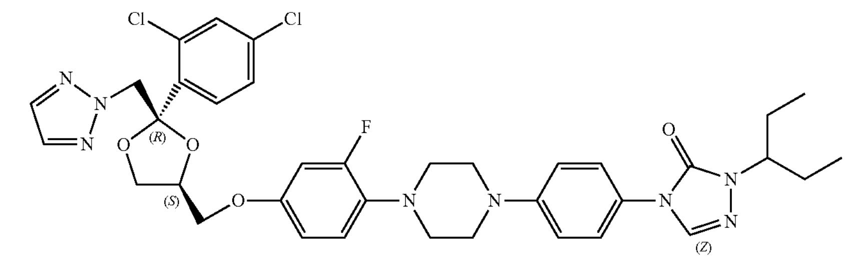 | LC-MS: m/z 737.2 (M + H) |
| 166 | 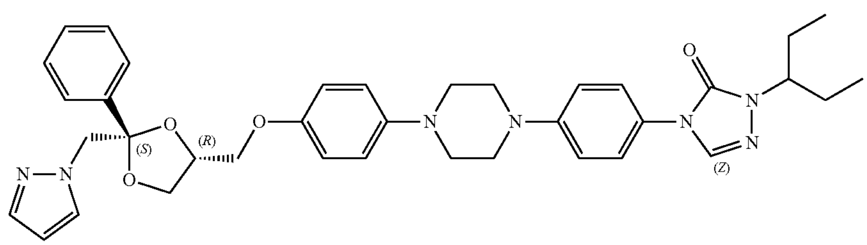 | LC-MS: m/z 650.2 (M + H) |
| 167 | 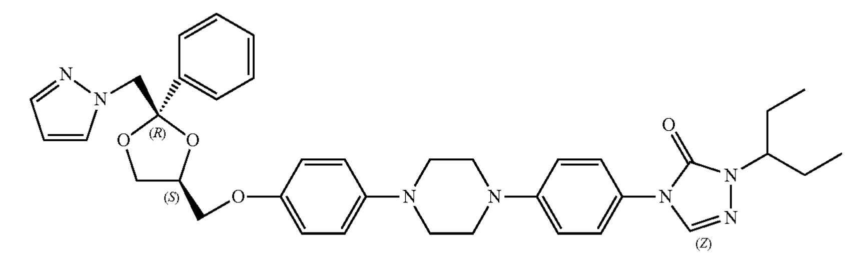 | LC-MS: m/z 650.2 (M + H) |
| 168 | 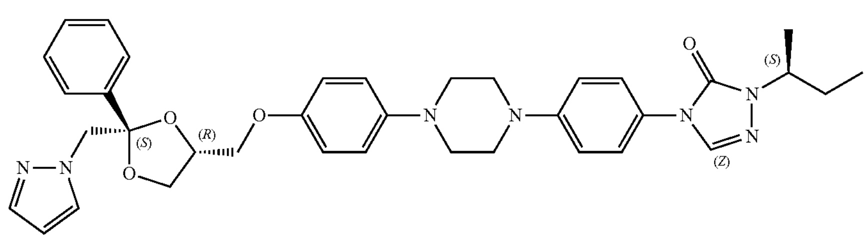 | LC-MS: m/z 636.2 (M + H) |
| 169 | 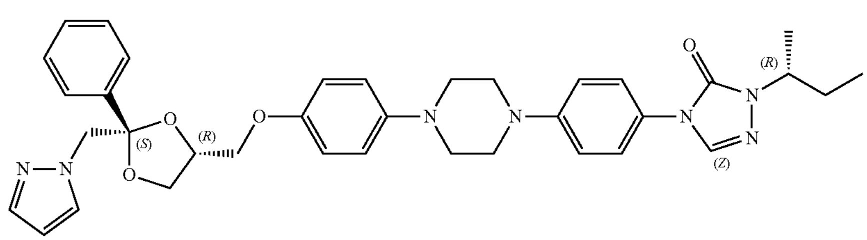 | LC-MS: m/z 636.2 (M + H) |

TABLE 1-continued

| Cm pd # | Structure | Characterization Data |
|---|---|---|
| 170 | 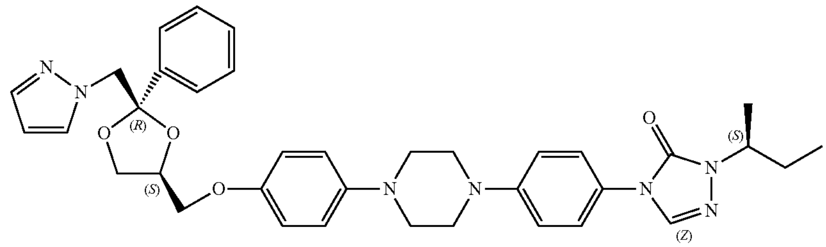 | LC-MS: m/z 636.2 (M + H) |
| 171 | 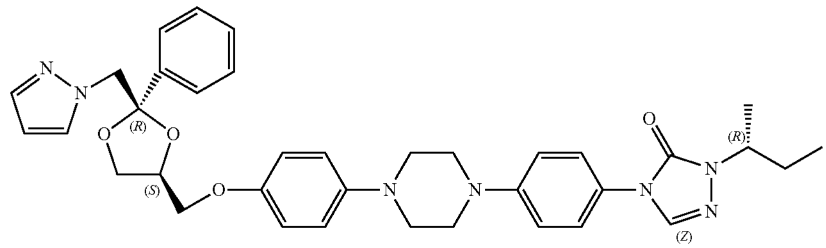 | LC-MS: m/z 636.2 (M + H) |
| 172 | 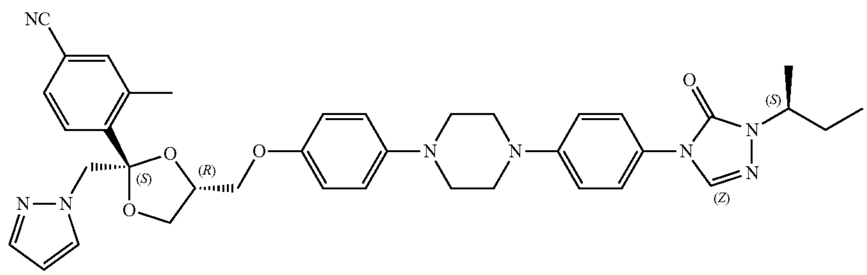 | LC-MS: m/z 675.2 (M + H) |
| 173 | 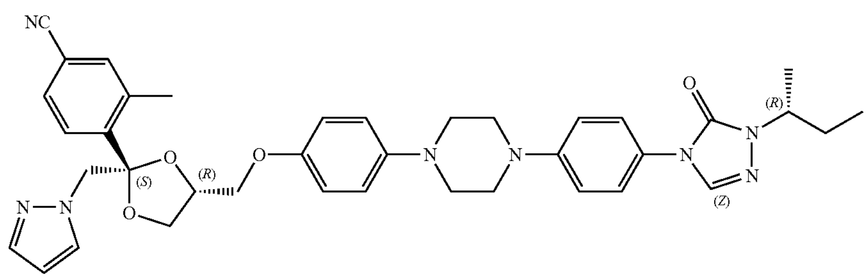 | LC-MS: m/z 675.2 (M + H) |
| 174 | 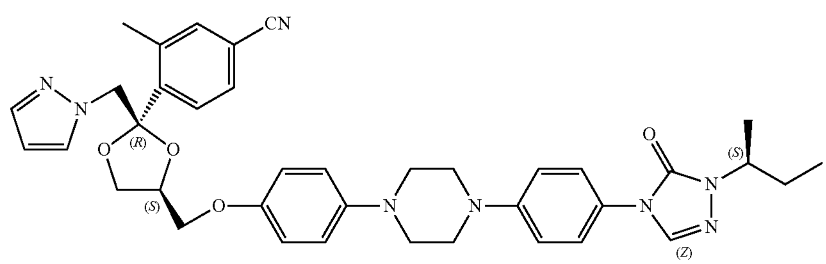 | LC-MS: m/z 675.2 (M + H) |
| 175 | 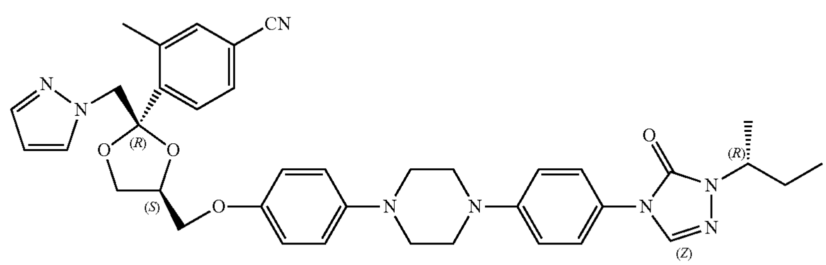 | LC-MS: m/z 675.2 (M + H) |

TABLE 1-continued

| Cmpd # | Structure | Characterization Data |
|---|---|---|
| 176 | 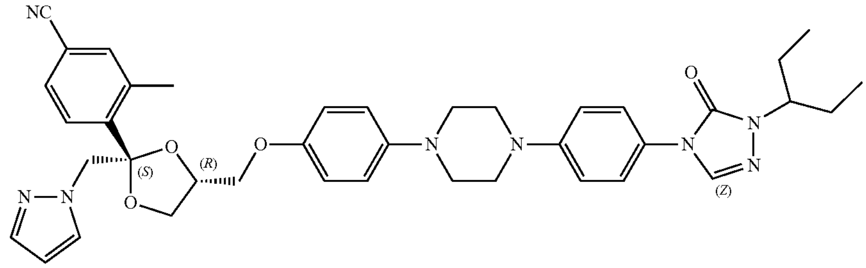 | LC-MS: m/z 689.2 (M + H) |
| 177 | 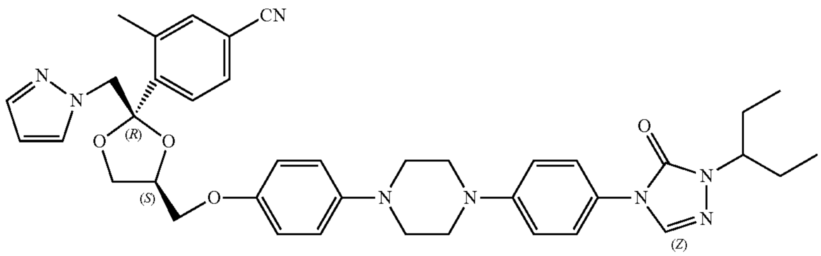 | LC-MS: m/z 689.2 (M + H) |
| 178 | 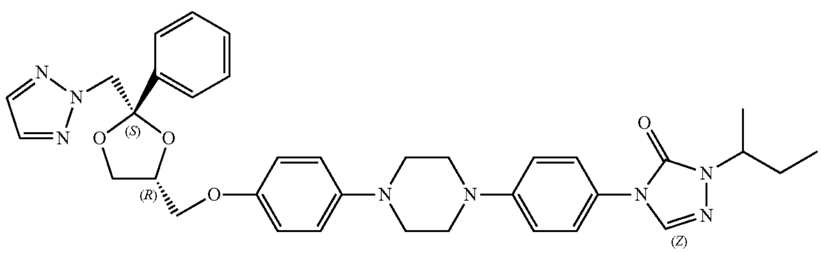 | LC-MS: m/z 637.1 (M + H) $^1$H NMR (400 MHz, CDCl$_3$) δ 7.64 (m, 3H), 7.58 (dd, J = 7.4, 2.2 Hz, 2H), 7.49-7.36 (m, 5H), 7.05 (t, J = 9.7 Hz, 2H), 6.95 (d, J = 6.6 Hz, 2H), 6.79 (d, J = 8.8 Hz, 2H), 4.87 (s, 2H), 4.43-4.25 (m, 2H), 3.92 (dd, J = 8.4, 6.5 Hz, 1H), 3.89-3.80 (m, 1H), 3.77 (dd, J = 9.4, 5.0 Hz, 1H), 3.37 (m, 5H), 3.26 (m, 4H), 1.89 (m, 1H), 1.75 (m, 1H), 1.42 (d, J = 6.7 Hz, 3H), 0.95 (t, J = 7.4 Hz, 3H). |
| 181 | 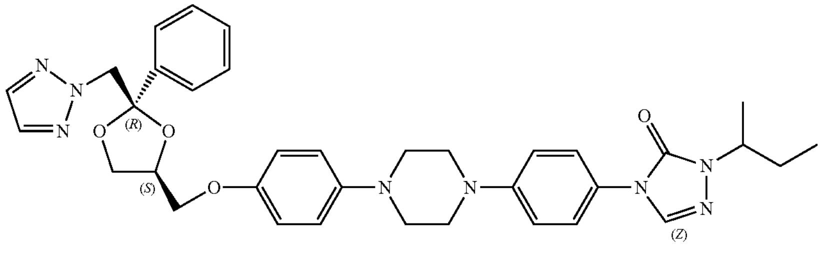 | LC-MS: m/z 637.2 (M + H) $^1$H NMR (400 MHz, CDCl$_3$) δ 7.64 (m, 3H), 7.61-7.53 (m, 2H), 7.50-7.33 (m, 5H), 7.16-7.01 (m, 2H), 6.94 (d, J = 7.3 Hz, 2H), 6.79 (d, J = 9.0 Hz, 2H),, 4.87 (s, 2H), 4.44-4.25 (m, 2H), 3.92 (dd, J = 8.4, 6.5 Hz, 1H), 3.89-3.82 (m, 1H), 3.78 (dd, J = |

TABLE 1-continued

| Cmpd # | Structure | Characterization Data |
|---|---|---|
| | | 9.4, 5.0 Hz, 1H), 3.37 (m, 5H), 3.26 (m, 4H), 1.88 (m, 1H), 1.82-1.67 (m, 1H), 1.42 (d, J = 6.7 Hz, 3H), 0.93 (t, J = 7.4 Hz, 3H). |
| 184 | 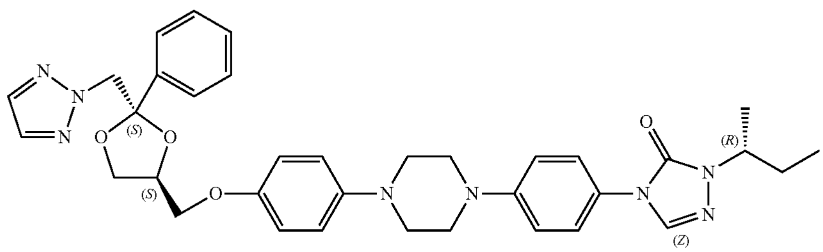 | LC-MS: m/z 637.3 (M + H) |
| 185 | 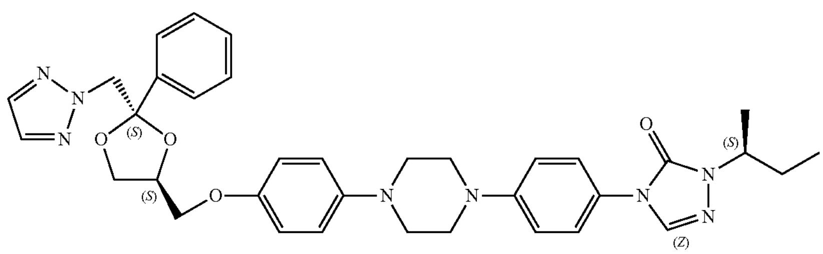 | LC-MS: m/z 637.3 (M + H) |
| 186 | 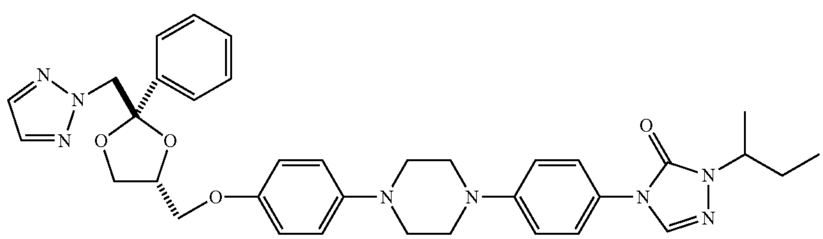 [SMILES: CCC(C)n1ncn(-c2ccc(N3CCN(c4ccc(OC[C@@H]5CO[C@](Cn6nccn6)(c6ccccc6)O5)cc4)CC3)cc2)c1=O] | LC-MS: m/z 637.3 (M + H) |
| 187 | 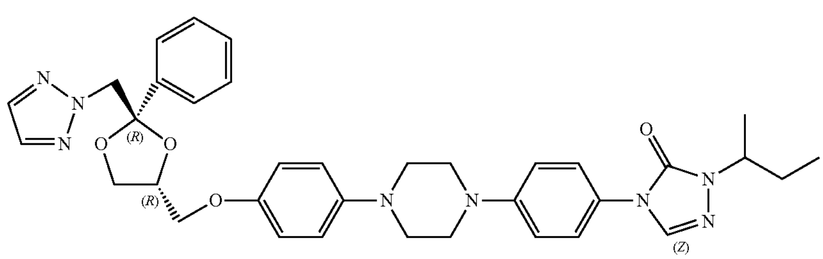 | LC-MS: m/z 637.3 (M + H) |
| 188 | 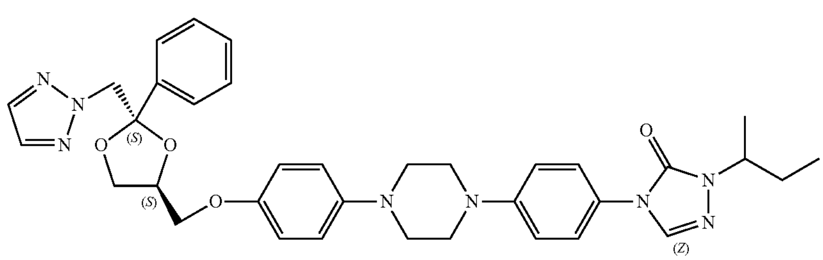 | LC-MS: m/z 637.3 (M + H) |

TABLE 1-continued

| Cm pd # | Structure | Characterization Data |
|---|---|---|
| 189 | 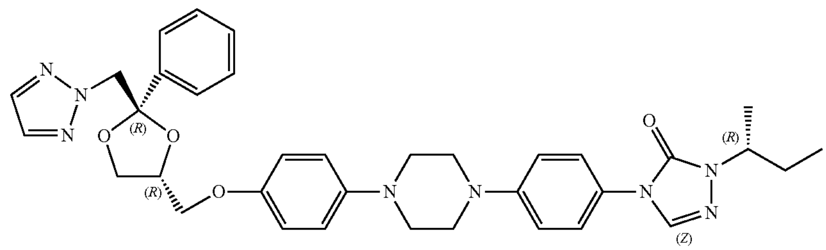 | LC-MS: m/z 637.3 (M + H) |
| 190 | 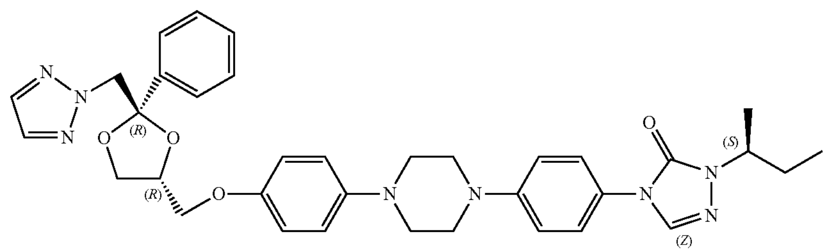 | LC-MS: m/z 637.3 (M + H) |
| 191 | 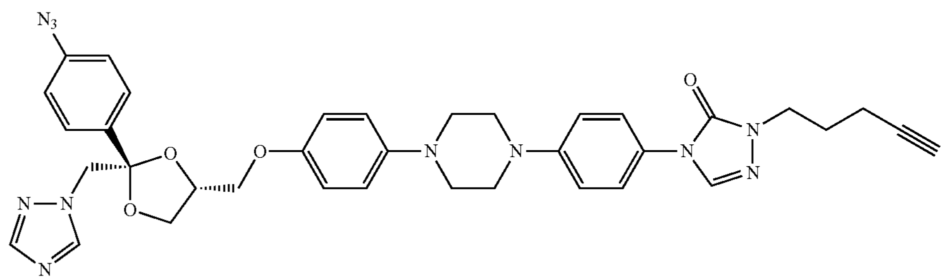 [SMILES: C#CCCCn1ncn(-c2ccc(N3CCN(c4ccc(OC[C@@H]5CO[C@@](Cn6cncn6)(c6ccc(N=[N+]=[N-])cc6)O5)cc4)CC3)cc2)c1=O] | LC-MS: m/z 688.1 (M + H). |
| 192 | 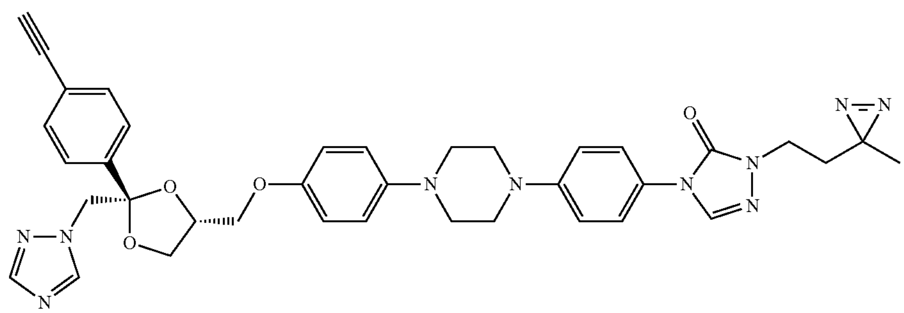 [SMILES: C#Cc1ccc([C@]2(Cn3cncn3)OC[C@@H](COc3ccc(N4CCN(c5ccc(-n6cnn(CCC7(C)N=N7)c6=O)cc5)CC4)cc3)O2)cc1] | LC-MS: m/z 687.3 (M + H) |
| 193 | 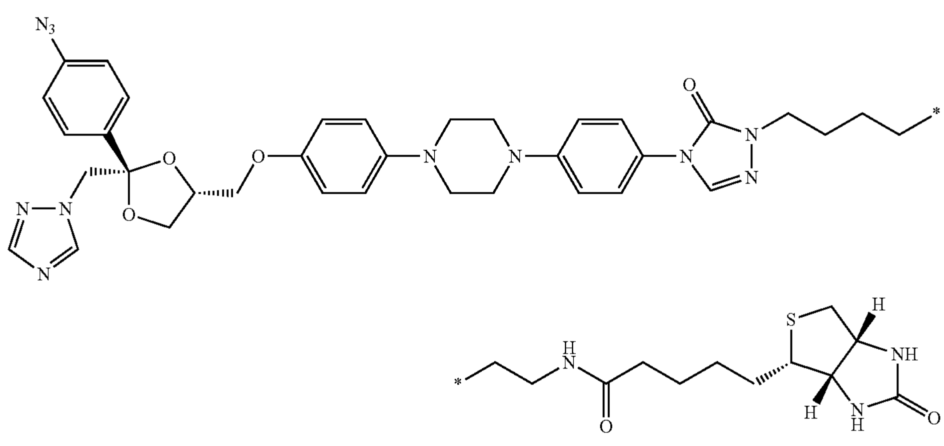 [SMILES: *CCCCn1ncn(-c2ccc(N3CCN(c4ccc(OC[C@@H]5CO[C@@](Cn6cncn6)(c6ccc(N=[N+]=[N-])cc6)O5)cc4)CC3)cc2)c1=O ; *CCNC(=O)CCCC[C@@H]1SC[C@@H]2NC(=O)N[C@@H]21] | LC-MS: m/z 947.3 (M + H) |

| Cmpd # | Structure | Characterization Data |
|---|---|---|
| 194 | 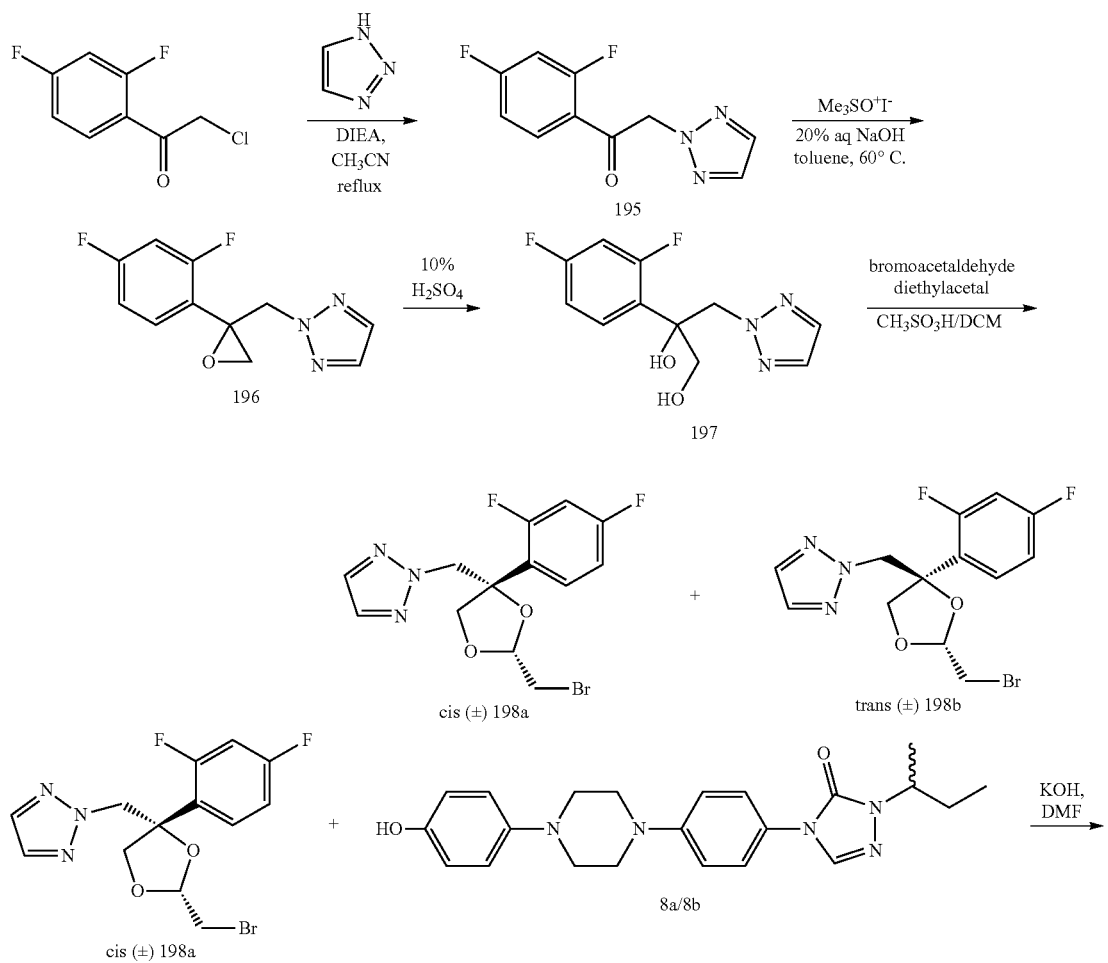 (±) | LC-MS: m/z 979.3 (M + H) |
Example 6
Synthesis of cis (±)-4-(4-(4-(4-((4-((2H-1,2,3-triazol-2-yl)methyl)-4-(2,4-difluorophenyl)-1,3-dioxolan-2-yl)methoxy)phenyl)piperazin-1-yl)phenyl)-1-sec-butyl-1H-1,2,4-triazol-5(4H)-one (199)

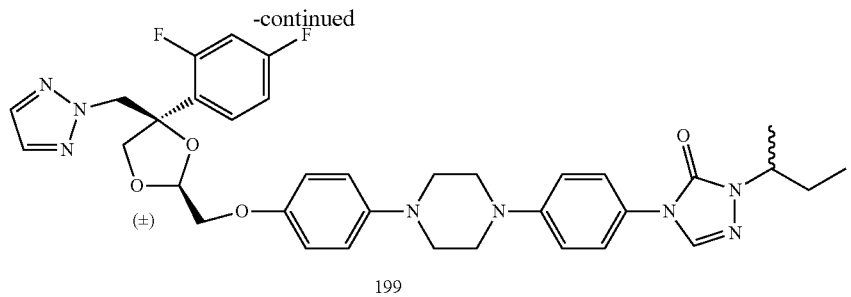

199

To a solution of 2-chloro-2',4'-difluoroacetophenone (20 g, 10.5 mol) in CH₃CN (100 mL) was added 1,2,3-triazole (9.12 mL, 15.7 mol) and DIEA (18.0 mL, 21 mol). The reaction mixture was heated to reflux for 1 h, then cooled to rt. The reaction mixture was concentrated and the residue was redissolved in EtOAc (150 mL), and washed with water (50 mL), 10% citric acid (50 mL), and brine, then dried over Na₂SO₄, filtered and concentrated. The crude product was purified by flash chromatography on silica gel (eluent: hexanes/EtOAc=3/1) to give compound 195 as a yellow solid (3.97 g, 17.2%). LC-MS: m/z 224.0 (M+H); ¹H NMR (400 MHz, CDCl₃) δ 8.06 (td, J=8.5, 6.5 Hz, 1H), 7.77 (s, 2H), 7.12-7.04 (m, 1H), 7.04-6.94 (m, 1H), 5.87 (d, J=3.8 Hz, 2H).

To a solution of 195 (3.97 g, 17.7 mmol) in toluene (40 mL) was added trimethylsulfoxonium iodide (5.19 g, 23 mmol) followed by the addition of 20% sodium hydroxide solution (4.6 mL). The reaction mixture was then heated at 60° C. for 4 h. After the reaction was over, it was diluted with ethyl acetate (60 mL) and poured into chilled water. The organic layer was washed with water and brine, dried over Na₂SO₄ and filtered. The filtrate was concentrated under reduced pressure and the residue was purified by flash silica gel column (eluent: hexanes/EtOAc=3/1) to give compound 196 (3.68 g, 87.6%) as a yellow solid. LC-MS: m/z 238.01 (M+H); ¹H NMR (400 MHz, CDCl₃) δ 7.52 (s, 2 H), 7.55 (m, 1H), 6.80-6.65 (m, 2H), 4.77 (dd, J=14.8, 1.4 Hz, 1H), 4.45 (dd, J=14.8, 1.3 Hz, 1H), 2.89 (dd, J=4.7, 1.4 Hz, 1H), 2.81 (dd, J=4.7, 1.5 Hz, 1H).

To compound 196 (3.68 g, 15.5 mmol) was added a solution of 10% v/v H₂SO₄/H₂O (20 mL) at 0° C. The reaction solution was stirred at rt overnight. The solution was basified by adding sat. NaHCO₃ and then extracted from EtOAc. The combined organic extracts were washed with brine, then dried over Na₂SO₄, filtered and concentrated. The crude product was purified by flash chromatography on silica gel (eluent: hexanes/EtOAc=1/1) to give compound 197 as a light yellow solid (2.24 g, 56.7%). LC-MS: m/z 256.0 (M+H); ¹H NMR (400 MHz, CDCl₃): δ 7.52 (s, 2H), 7.50-7.42 (m, 1H), 6.78 (ddt, J=9.7, 8.4, 1.5 Hz, 2H), 5.18 (dd, J=14.1, 1.2 Hz, 1H), 4.98 (d, J=14.1 Hz, 1H), 4.03 (dt, J=11.7, 1.4 Hz, 1H), 3.79 (dd, J=11.7, 0.6 Hz, 1H), 2.22 (br s, 1H).

Bromoacetaldehyde diethylacetal (1.70 mL, 11.0 mmol) was added dropwise to a stirred solution of 197 (2.24 g, 8.78 mmol) in methanesulfonic acid (5.7 mL) and DCM (50 mL) at 0° C. After addition, the mixture was allowed to warm at room temperature, stirred for 3 h, then poured into a mixture of ice/Sat NaHCO₃. The mixture was extracted with DCM. The combined organic solvent was dried over Na₂SO₄ and filtered. The filtrate was concentrated under reduced pressure and the residue was purified by flash silica gel column (eluent: hexanes/EtOAc=10/1) to give 198a as colorless oil (1.72 g, 54.5%). LC-MS: m/z 360.0 (M+H); ¹H NMR (400 MHz, CDCl₃): δ ¹H NMR (400 MHz, CDCl3) δ 7.61 (s, 2H), 7.55 (td, J=8.7, 6.4 Hz, 1H), 6.91 (m, 1H), 6.85 (m, 1H), 5.16 (dd, J=5.1, 3.6 Hz, 1H), 4.96-4.90 (m, 1H), 4.86-4.70 (m, 2H), 4.05 (dd, J=9.3, 1.8 Hz, 1H), 3.45 (dd, J=11.0, 3.6 Hz, 1H), 3.28 (dd, J=11.0, 5.1 Hz, 1H).

To a solution of 198a (55 mg, 0.15 mmol) and racemic 8a/8b (60 mg, 0.15 mmol) in anhydrous DMF (1.5 mL) was added KOH (25 mg, 0.44 mmol). The reaction mixture was stirred at 50° C. for 2 h. After cooling to rt, the reaction mixture was diluted with water and DCM, and the organic phase was separated. The aqueous phase was extracted with DCM. The combined organic layer was washed with brine and dried over Na₂SO₄, filtered, and concentrated under reduced pressure. The crude product was purified by column chromatography on silica gel (eluent: hexanes/EtOAc=1/3) to give the title compound 199 as an off-white solid (22 mg, 21%). LC-MS: m/z 637.2 (M+H); 1H NMR (400 MHz, CDCl3) δ 7.81 (s, 1H), 7.65 (s, 2H), 7.51-7.43 (m, 2H), 7.43-7.32 (m, 1H), 7.26 (s, 1H), 7.07 (d, J=8.9 Hz, 2H), 6.99 (d, J=8.6 Hz, 2H), 6.93-6.80 (m, 2H), 5.33 (t, J=3.1 Hz, 1H), 4.73 (dd, J=9.3, 3.2 Hz, 1H), 4.67 (d, J=14.3 Hz, 1H), 4.55 (d, J=14.3 Hz, 1H), 4.39-4.23 (m, 1H), 4.13 (d, J=3.2 Hz, 2H), 4.05 (dd, J=9.4, 1.4 Hz, 1H), 3.56 (br s, 4H), 3.40 (br s, 4H), 1.89 (m, 1H), 1.74 (m, 1H), 1.41 (d, J=6.8, 3H), 0.92 (t, J=7.4 Hz, 3H).

The compound in Table 2 was prepared using analogous procedures as described in Example 6.

TABLE 2

| Cmpd # | Structure | Characterization Data |
|---|---|---|
| 200 |  cis (±) | LC-MS: m/z 673.3 (M + H) |

Example 7

Synthesis of cis (±)-1-(4-(4-(4-((4-((2H-1,2,3-tri-azol-2-yl)methyl)-4-(2,4-difluorophenyl)-1,3-dioxolan-2-yl)methoxy)phenyl)piperazin-1-yl)phenyl)-3-isopropylimidazolidin-2-one (203)

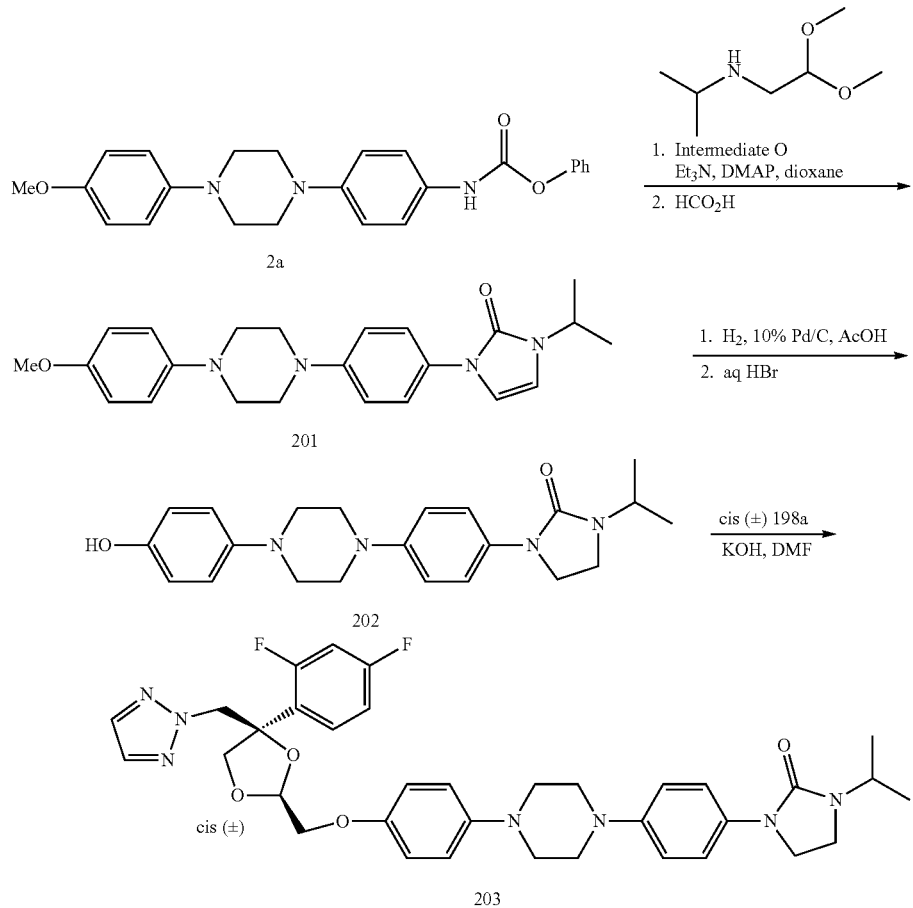

Compound 203 was prepared as outlined in the above scheme using analogous procedures as described in the previous examples. LC-MS: m/z 660.3 (M+H).

The compounds in Table 3 are prepared using analogous procedures as described in Examples 1-7.

TABLE 3

| Cmpd # | Structure |
|---|---|
| 204 | 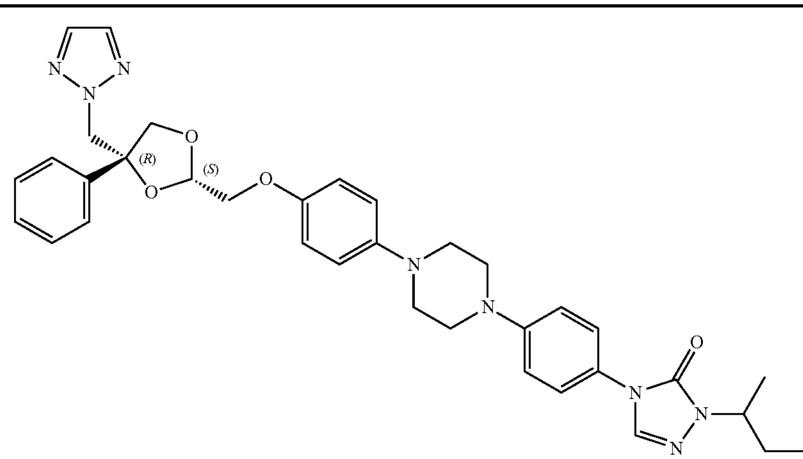 |

TABLE 3-continued

| Cmpd # | Structure |
| --- | --- |
| 205 | *[Chemical structure: triazole-dioxolane-phenyl-piperazine-phenyl-triazolone with sec-butyl group, (R),(S) stereochemistry]* |
| 206 | *[Chemical structure: triazole-dioxolane-phenyl-piperazine-phenyl-imidazolidinone with isopropyl group, (R),(S) stereochemistry]* |

BIOLOGICAL EXAMPLES

Example I

Biological Assays

A high content imaging assay, based on α-SMA staining and cell morphological changes associated with fibroblast to myofibroblast transdifferentiation, was established using primary human lung fibroblasts and primary rodent HSCs. Conditions, involving serum starvation and subsequent TGF-β treatment, were identified that facilitate robust in vitro transdifferentiation in a miniaturized (384 well plate) format that is amenable to high throughput small molecule screening. A selective ALK-5 TGF-β1 receptor inhibitor (SB-431542) was used as a positive control. The 4 day long assay was amenable to screens on the order of 100,000 wells and facilitated the identification of compounds that selectively inhibit fibroblast to myofibroblast transdifferentiation. This assay was used to evaluate compounds of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) generated from medicinal chemistry efforts.

The activity of Itraconazole and compounds of Formula (I), (Ia), (II), (IIa), (III), (IIIa), (IV), (IVa), (IVb), (V), (Va), (VI), (VIa), (VIb), (VIc), (VII), (VIIa), (VIII), (VIIIa), (IX), (IXa), (X), or (Xa) was confirmed by analyzing changes in gene expression of multiple genes associated with fibroblast to myofibroblast transdifferentiation using biochemical methods (i.e., Western blot and RT-PCR). These 4-day assays were used to evaluate sets of 6 compounds at a time in 4-point dose response fashion.

α-SMA Assays

Quiescent rat hepatic stellate cells were seeded in 384 well plates (350 cells per well) coated with Poly-D-lysine in stellate cell medium (Sciencell). After 24 hour incubation, cells were treated with itraconazole for 48 hours in the presence of 10 ng/mL of TGF-β1 in hepatic stellate medium. Following fixation and staining with an anti smooth muscle actin antibody, cell morphology was analyzed with a Cellomics cell insight imaging reader. Cells were analyzed for mean cellular area of α-SMA staining or mean fluorescence intensity of SMA staining. In this assay itraconazole reproducibly induced dose dependent decreases in both mean cellular area and alpha smooth muscle actin staining, indicating the inhibition of myofibroblast transdifferentiation and activation.

Western Blot Analyses of Fibrosis-related Proteins in Cells Exposed to TGFβ and Itraconazole (Itra)

Human lung fibroblasts were seeded at $10^5$ cells per well in 6 well dishes in assay medium (2% fetal bovine serum, DMEM). After 24 incubation, medium was changed to assay medium containing TGF-β1 (10 ng/mL) and simultaneously treated with itraconazole (10 µM), or vehicle control. After incubation for 48 hours, cells were harvested by brief trypsinization and centrifugation. Cells were lysed in Cell Lytic M (Sigma) and lysate concentrations normalized via absorption readings at 260 nm. Samples were boiled in 2× sample buffer and 10% beta-mercaptoethanol. Three micrograms of lysate were loaded into each gel lane and then separated by SDS-PAGE on 10% Bis-Tris gels and then transferred via semi dry transfer to PVDF membranes. After blocking in 5% milk in TRIS buffered saline with Tween-20 (0.1%), membranes were exposed to appropriate primary antibodies. Blots were incubated with HRP-conjugated secondary antibodies and visualized using film and SuperSignal West Dura Chemiluminescent Substrate (Pierce). In this assay itraconazole reproducibly induced dose dependent decreases in levels of induced alpha smooth muscle actin protein levels, indicating the inhibition of myofibroblast transdifferentiation and activation.

Gene Expression Analysis of Human Lung Fibroblasts Treated with Itraconazole

Human lung fibroblasts were seeded at $10^5$ cells per well in 6 well dishes in assay medium (2% fetal bovine serum in DMEM). After 24 hours, medium was changed to assay medium containing TGF-β1 (10 ng/mL) and itraconazole (500 nM). After 48 hours of incubation at 37 C, cells were harvested by brief trypsinization and centrifugation. RNA was extracted using RNeasy kit (Qiagen) and cDNA amplified using SuperScript III First-Strand Synthesis kit (Life Technologies). qPCRs reactions were then performed using a fibrosis focused RT2 Profiler PCR Array kit with supplied plate and reagents. Data was analyzed using N=1 per reaction per treatment condition. Data was expressed as fold regulation relative to a sample not treated with TGF-β1. In this assay itraconazole reproducibly induced dose dependent changes in multiple fibrosis-related genes, indicating the inhibition of myofibroblast transdifferentiation and activation.

Anti-fibrotic activity of itraconazole did not result from P450 inhibition associated with anti-fungal activity. Itraconazole inhibited VEGF and Hedgehog pro-fibrotic signaling pathways.

qPCR Analysis of Hedgehog Related Genes in Rat Hepatic Stellate Cells Treated with Itraconazole Rat hepatic stellate cells were seeded at $10^5$ cells per well in 6 well dishes coated with poly-D-lysine in stellate cell medium (Sciencell) and allowed to proliferate to full confluence (~2 weeks). Medium was then switched to DMEM and 0.5% fetal bovine serum with 1 ug/mL SHH-N (R&D systems). Cells were treated with SHH-N and compounds (cyclopamine 5 µM (positive control), itraconazole 1 µM) for 24 hours. Cells were harvested by brief trypsinization and centrifugation. RNA was extracted using RNeasy kit (Qiagen) and cDNA amplified using SuperScript III First-Strand Synthesis kit (Life Technologies). qPCR was performed using a SYBR green mastermix (Takara). Relative levels of PTCH1 (protein patched homolog 1) and GLI1 (GLI family zinc finger 1) mRNA indicated that itraconazole inhibits Hedgehog signaling in rat hepatic stellate cells.

Western Blot Analyses of COL1-GFP HSCs after Knockdown of Smoothened

COL1-GFP HSCs (an immortalized mouse hepatic stellate cell line with GFP knocked into the collagen locus) were plated at $7.5^5$ cells per well in assay medium (10% fetal bovine serum, DMEM). After 24 hours, cells were transduced with lentiviral particles. After 24 hours of incubation with viral particles, cells were switched to fresh assay medium and incubated for 48 hours. Cells were lysed in Cell Lytic M (Sigma) and lysate concentrations normalized via absorption readings at 260 nm. Samples were boiled in 2× sample buffer and 10% beta-mercaptoethanol. Equal amounts of lysate were loaded into each gel lane and then separated by SDS-PAGE on 10% Bis-Tris gels and then transferred via semi dry transfer to PVDF membranes. After blocking in 5% milk in TRIS buffered saline with Tween-20 (0.1%), membranes were exposed to appropriate primary antibodies. Blots were incubated with HRP-conjugated secondary antibodies and visualized using film and SuperSignal West Dura Chemiluminescent Substrate (Pierce). Constructs for lentivirally delivered shRNAs were obtained from Sigma as MISSION glycerol stocks. Lentiviruses were packaged using 293T cells and packaging vectors pMD2.G and pSPAX2. Clones 71, 12, and 95 correspond to shRNAs to SMO and pLKO is plasmid SCH002 which encodes a non-targeting shRNA. shRNA mediated knockdown of SMO and the resultant inhibition of Hedgehog signaling in rat hepatic stellate cells partially recapitulated the anti-fibrotic activity of itraconazole.

Western Blot Analysis of VEGFR2 Migration Pattern after Treatment with Itraconazole Quiescent rat hepatic stellate cells were seeded at $10^5$ cells per well in 6 well dishes coated with Poly-D-Lysine in stellate cell medium (Sciencell). After 24 hour incubation, cells were then treated with various doses of itraconazole for 24 hours. Cells were harvested by brief trypsinization and centrifugation. Cells were lysed in Cell Lytic M (Sigma) and lysate concentrations normalized via absorption readings at 260 nm. Samples were boiled in 2× sample buffer and 10% beta-mercaptoethanol. Equal amounts of lysate were loaded into each gel lane and then separated by SDS-PAGE on 10% Bis-Tris gels and then transferred via semi dry transfer to PVDF membranes. After blocking in 5% milk in TRIS buffered saline with Tween-20 (0.1%), membranes were exposed to appropriate primary antibodies. Blots were incubated with HRP-conjugated secondary antibodies and visualized using film and SuperSignal West Dura Chemiluminescent Substrate (Pierce). Itraconazole inhibited VEGFR2 glycosylation and trafficking, thereby causing an inhibition of pro-fibrotic VEGF signaling in rat hepatic stellate cells.

Western Blot Analysis of Rat Hepatic Stellate Cells Treated with Combinations of VEGFR and Hedgehog Inhibiting Compounds Quiescent rat hepatic stellate cells were seeded at $10^5$ cells per well in 6 well dishes coated with Poly-D-Lysine in stellate cell medium (Sciencell). After 24 hour incubation, cells were switched to stellate cell medium containing 10 ng/mL TGF-β1 and the indicated combinations of compounds. After 48 hours of treatment, cells were harvested by brief trypsinization and centrifugation. Cells were lysed in Cell Lytic M (Sigma) and lysate concentrations normalized via absorption readings at 260 nm. Samples were boiled in 2× sample buffer and 10% beta-mercaptoethanol. Three micrograms of lysate were loaded into each gel lane and then separated by SDS-PAGE on 10% Bis-Tris gels and then transferred via semi dry transfer to PVDF membranes. After blocking in 5% milk in TRIS buffered saline with Tween-20 (0.1%), membranes were exposed to appropriate primary antibodies. Blots were incubated with HRP-conjugated secondary antibodies and visualized using film and SuperSignal West Dura Chemiluminescent Substrate (Pierce). Dual pharmacological inhibition of VEGF and Hedgehog signaling in rat hepatic stellate cells recapitulated the anti-fibrotic activity of itraconazole.

Western Blot Analyses of LX2 Human Hepatic Stellate Cells after Knockdown of VEFGR1, VEGFR2, or SMO.

LX2 cells (an immortalized human hepatic stellate cells line, Scot Friedman lab) were plated at $10^5$ cells per well in assay medium (10% fetal bovine serum, DMEM). After 24 hours, cells were transduced with lentiviral particles. After 24 hours of incubation with viral particles, cells were switched to fresh assay medium and incubated for 48 hours. Cells were lysed in Cell Lytic M (Sigma) and lysate concentrations normalized via absorption readings at 260 nm. Samples were boiled in 2× sample buffer and 10% beta-mercaptoethanol. Equal amounts of lysate were loaded into each gel lane and then separated by SDS-PAGE on 10% Bis-Tris gels and then transferred via semi dry-transfer to PVDF membranes. After blocking in 5% milk in TRIS buffered saline with Tween-20 (0.1%), membranes were exposed to appropriate primary antibodies. Blots were incubated with HRP-conjugated secondary antibodies and visualized using film and SuperSignal West Dura Chemiluminescent Substrate (Pierce). Constructs for lentivirally delivered shRNAs were obtained from Sigma as MISSION glycerol stocks. Lentiviruses were packaged using 293T cells and packaging vectors pMD2.G and pSPAX2. Clone 65 corresponds to a shRNA targeting SMO, 31 and 32 correspond to a shRNA targeting VEGFR1, clones 86 and 87 correspond to a shRNA targeting VEGFR2, and pLKO is plasmid $SCH_{002}$ which encodes a non-targeting shRNA.

Table 3 below shows biological activity ($EC_{50}$) for compounds described herein. The $EC_{50}$ for (imaging and western based) activity is graded as: +++=<500 nM; ++=500 nM to 5 µM; +=5 to 30 µM; –=>30 µM; NT=Not Tested.

TABLE 3

| Cmpd # | Activity |
|---|---|
| 4 | – |
| 5 | + |
| 6 | – |
| 7 | – |
| 8 | – |
| 10 | ++ |
| 11 | NT |
| 12 | ++ |
| 13 | ++ |
| 14 | +++ |
| 15 | + |
| 16 | + |
| 17 | + |
| 18 | + |
| 19 | ++ |
| 20 | + |
| 21 | +++ |
| 22 | NT |
| 23 | ++ |
| 24 | ++ |
| 25 | ++ |
| 26 | + |
| 27 | + |
| 28 | + |
| 29 | +++ |
| 30 | ++ |
| 31 | +++ |
| 32 | +++ |
| 33 | ++ |
| 34 | ++ |
| 35 | ++ |
| 36 | ++ |
| 37 | ++ |
| 38 | – |
| 39 | ++ |
| 40 | ++ |
| 41 | +++ |
| 42 | + |
| 43 | +++ |
| 44 | – |
| 45 | – |
| 46 | +++ |
| 47 | ++ |
| 48 | +++ |
| 49 | ++ |
| 50 | ++ |
| 51 | +++ |
| 52 | +++ |
| 53 | ++ |
| 54 | ++ |
| 55 | +++ |
| 56 | ++ |
| 57 | +++ |
| 58 | +++ |
| 59 | + |
| 60 | + |
| 61 | + |
| 62 | + |
| 63 | + |
| 64 | ++ |
| 65 | +++ |
| 66 | +++ |
| 67 | ++ |
| 68 | +++ |
| 69 | ++ |
| 70 | ++ |
| 71 | + |
| 72 | + |
| 73 | + |
| 74 | ++ |
| 75 | – |
| 76 | + |
| 77 | – |
| 78 | ++ |
| 79 | – |
| 80 | ++ |
| 81 | +++ |
| 82 | +++ |
| 83 | +++ |
| 84 | ++ |
| 85 | ++ |
| 86 | +++ |
| 87 | +++ |
| 88 | ++ |
| 89 | ++ |
| 90 | ++ |
| 91 | +++ |
| 92 | +++ |
| 93 | +++ |
| 94 | +++ |
| 95 | +++ |
| 96 | +++ |
| 97 | + |
| 98 | ++ |
| 99 | + |
| 100 | ++ |
| 101 | + |
| 102 | ++ |
| 103 | ++ |
| 104 | ++ |
| 105 | +++ |
| 106 | +++ |
| 107 | ++ |
| 108 | ++ |
| 109 | ++ |
| 110 | + |
| 111 | + |
| 112 | ++ |
| 113 | ++ |
| 114 | +++ |
| 115 | ++ |
| 116 | +++ |
| 117 | ++ |
| 118 | + |
| 119 | + |
| 120 | – |
| 121 | + |
| 122 | +++ |

TABLE 3-continued

| Cmpd # | Activity |
|---|---|
| 123 | +++ |
| 124 | +++ |
| 125 | +++ |
| 126 | +++ |
| 127 | +++ |
| 128 | ++ |
| 129 | +++ |
| 130 | ++ |
| 131 | - |
| 132 | +++ |
| 133 | +++ |
| 134 | +++ |
| 135 | +++ |
| 136 | ++ |
| 137 | +++ |
| 138 | +++ |
| 139 | +++ |
| 140 | + |
| 141 | - |
| 142 | - |
| 143 | + |
| 144 | - |
| 145 | + |
| 146 | - |
| 147 | - |
| 148 | - |
| 149 | - |
| 150 | - |
| 151 | ++ |
| 152 | + |
| 154 | +++ |
| 155 | +++ |
| 156 | ++ |
| 157 | +++ |
| 158 | NT |
| 159 | NT |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | ++ |
| 173 | ++ |
| 174 | ++ |
| 175 | + |
| 176 | +++ |
| 177 | ++ |
| 178 | +++ |
| 179 | +++ |
| 180 | +++ |
| 181 | +++ |
| 182 | +++ |
| 183 | +++ |
| 184 | +++ |
| 185 | +++ |
| 186 | + |
| 187 | + |
| 188 | + |
| 189 | + |
| 190 | ++ |
| 191 | ++ |
| 192 | ++ |
| 193 | + |
| 194 | + |
| 199 | +++ |
| 200 | +++ |
| 203 | - |

Cyp Reversible Inhibition Assay

The purpose of this assay is to determine reversible inhibition of Cyp enzyme with a given compound using a substrate probe turnover as the surrogate for inhibition. This assay is done with human liver microsomes rather an isolated enzyme to account for metabolites of parent drug leading to a potential drug-drug interaction through Cyp inhibition. The substrate turnover (for example conversion of midazolam to hydroxyl midazolam) is monitored by LCMSMS (Q1/Q2=342.2/203.2). Test compounds are tested in a 7-point dose response curve starting from 50 µM to 50 nM (~3-fold dilution series). For Cyp 3A4, the positive control compound is ketoconazole.

The detailed protocol is as follows:
Prepare test compounds and standard inhibitors working solution (100×).
Pull microsomes out of the −80° C. freezer to thaw on ice, labeled with the date and put back to freezer immediately after using.
Add 20 µL of the substrate solutions to corresponding wells.
Add 20 µL PB to Blank wells.
Add 2 µL of the test compounds and positive control working solution to corresponding wells.
Add 2 µL MeOH to No Inhibitor wells and Blank wells.
Prepared HLM working solution.
Add 158 µL of the HLM working solution to all wells of incubation plate.
Pre-warm the plate for about 10 min at 37° C. water bath.
Prepare NADPH cofactor solution.
Add 20 µL NADPH cofactor to all incubation wells.
Mix and incubate for 10 minutes at 37° C. water bath.
At the time point, terminate the reaction by adding 400 µL cold stop solution (200 ng/mL Tolbutamide in ACN).
Centrifuge the samples at 4000 rpm for 20 minutes to precipitate protein.
Transfer 200 µL supernatant to 200 µL HPLC water and shook for 10 min.
Analyze samples by LC/MS/MS.

Cyp Time-dependent Inhibition (TDI) Assay

The purpose of this assay is to ascertain the ability for compounds to form irreversibly inhibited cytochrome P450 adducts (also known as mechanism-based inhibition (MBI)) in human liver microsomes. Compared to competitive CYP inhibition, it has been recognized that MBI is a much greater concern in drug discovery and development, because inactivation of CYPs can lead to non-linear pharmacokinetics and underestimate drug-drug interaction potential. The data from this assay is used in conjunction to the reversible inhibition assay. The TDI assay is generally performed in liver microsomes to assess TDI potential of parent drug as well as metabolites. The readout is an $IC_{50}$ shift with NADPH (the inactivation/TDI set) to allow for compound to convert to a reactive species and without NADPH (control set to correct for protein degradation during pre-incubation of 20 minutes). Then both incubation sets are diluted with fresh assay buffer containing NADPH Cyp specific substrates (midazolam for Cyp3A4) and inhibition of midazolam hydroxylation is measured by LC-MS/MS (Q1/Q2=m/z 342.2/203.2). An $IC_{50}$ shift>1.5-fold is considered to be positive for time dependent inhibition where the 20 min pre-incubation leads to an increase in potency. Troleandomycin is used as a positive control compound, exhibiting a TDI $IC_{50}$ shift of >20. Test compounds are tested in a 7-point dose response curve starting from 50 µM to 50 nM (~3-fold dilution series).

The detailed protocol is as follows:
Prepare test compounds and positive control working solution (100×) in 1:1 DMSO/MeOH
Pull microsomes out of the −80° C. freezer to thaw.

Prepare incubation mix and added 147.5 µL to all wells of incubation plate.
Prepare cofactor solution and substrate dilution solution.
  Add 2.5 µL of the test compounds and positive control working solution to corresponding wells. Final compound concentrations in 7-point dose response from 50 µM to 50 nM
  Add 2.5 µL 1:1 DMSO/MeOH to NIC wells
Pre-warm the plate for about 10 min at 37° C.
Add 50 µL cofactor to pre-incubation wells
Add 50 µL substrate dilution solution to incubation wells.
Mix and pre-incubated for 20 minutes at 37° C. water bath.
Add 50 µL cofactor to incubation wells;
  Add 50 µL substrate dilution solution to pre-incubation wells.
Mix and incubated for 5 minutes at 37° C. water bath.
At the time point, terminate the reaction by adding cold 250 µL IS-fortified stop solution to all wells.
Centrifuge the incubation plate at 4000 rpm for 20 min.
Transfer 200 µL supernatant into 200 µL HPLC water and shook for 10 min.
Analyze samples by LCMS.

PXR (Cyp 3A4) Activation Assay

CYP3A4 metabolism is evaluated by using P450-Glo™ CYP3A4 Assay with Luciferin-IPA as the substrate of CYP3A4 and represented as RLU (Relative Luminescence Units). PXR activation is evaluated by using a luciferase detection reagent, ONE-Glo™ and represented as RLU. The luminescence light intensity is directly proportional to the extent of PXR activation and accompanying gene transcription in the DPX2 cells. Compounds are tested at 10, 1, and 0.1 µM in the assay. Fold of induction=(RLU/RFU of compound treated sample)/(RLU/RFU of vehicle treated sample), RFU is the signal of cell viability. RLU is the signal of CYP3A metabolism and PXR activation. 0.1% DMSO is used as vehicle. Cell viability is detected by using CellTiter-Fluor™ and represented as RFU (Relative Fluorescence Units).

Activation potency is defined as negative, weak, moderate and strong. Negative, weak, moderate and strong activators are those that give <15%, <40%, <69% and >70%, respectively, of the response produced by 10 µM RIF at 10 µM.

Candida albicans Anti-fungal MIC Potency Determination

The wild type Candida albicans (ATCC 10231) is used and Fluconazole, amphotericin B, itraconazole and terbinafine are purchased from Sigma and used as positive controls.

The highest assay concentration for all test compounds and fluconazole is 100 µM. Fluconazole is also tested at the highest concentration of 64 µg/ml, and amphotercin B and terbinafine at 16 and 64 µg/ml. The test compounds are in DMSO stock solution at a concentration of 10 mM. Two stock solutions in DMSO are prepared for fluconazole at 10 mM and 6.4 mg/ml. Amphotericin B and terbinafine stock solutions in DMSO are prepared at 1.6 and 6.4 mg/ml.

Serial dilution of 100× stock solutions: 4 µl of stock solution is added into 196 µl of RPMI1640 (MOPS buffered and free of HEPES and sodium bicarbonate) in the first well of a row of a sterile u-bottom 96-well plate. The rest of the wells are filled with 100 µl RPMI1640. The 2-fold serial dilution is made sequentially by transferring 100 µl solution to the next well and mixing by pipetting, until 11th well. The extra 100 µl in 11th well is discarded. Therefore, the compound wells contain 100 µl of 2× of testing concentrations of drugs in RPMI1640. The 12th well is filled with only 100 µl RPMI1640.

C. albicans 3147 (ATCC 10231) glycerol frozen stock is streaked on Sabouraud dextrose agar (SDA). The plate is incubated at 35° C. ambient atmosphere for 20 h. Single colonies are suspended into sterile saline until turbidity reached 0.1 (1-5×10⁶ CFU/ml) using a Siemens turbidity meter. This suspension is diluted 50× in RPMI1640 in a 15 ml conical, and then it is further diluted 20× in RPMI1640 in a 50 ml conical. This gives 1-5×10³ CFU/ml suspension and is used as inoculum. The cell density in inoculum is plate-counted to be 4.94×10³ CFU/ml.

MIC determination: Within 15 min, 100 µl of prepared bacterial inoculum is added into each well of compound/RPMI1640-containing plate. The plates are incubated at 35° C. in ambient atmosphere. The photos are taken at 24 h and 48 h. The MIC end points for fluconazole and amphotericin B are read according to the M27-A3 protocol (Reference Method for Broth Dilution Antifungal Susceptibility Testing of Yeasts; Approved Standard-Third Edition, M27-A3 standard published Jan. 1, 2008 by Clinical and Laboratory Standards Institute). The MIC for compounds for test cmpds and terbinafine (not mentioned in M27-A3 protocol) are read as if they were azoles.

Mouse Pharmacokinetic (PK) Studies

Compounds with suitable in vitro ADME properties are progressed to in vivo PK studies. A snapshot format in mice is used to quickly assess the potential for lead candidates to be orally bioavailable. The snapshot format involves a single dose (typically 20 mg/kg) given orally in a standard vehicle (5% PEG/DMSO in water for example). Compounds are infused directly into MS analysis to determine unique MRM (multiple reaction monitoring) signal that is concentration dependent in either ESI positive or negative modes. HPLC analysis using various solvent gradients is performed from organic and aqueous solution to ensure good peak shape of desired Q1/Q2 masses. Formulations include 45% Cyclodextrin in water (as is used clinically for Itraconazole). Other formulations that may be used are solutol, Eudragit, MC/Tween, etc. Standard curves are generated using plasma spiked with compound at various concentrations (10 ng/mL to 2000 ng/mL) to determine linear range of Q1/Q2 mass signal to compound concentration using female mouse heparinized plasma. Mice are dosed orally with compound, plasma samples collected by retro-orbital bleeds. Five time points are collected (30 min, 1 h, 4 h, 8 h, 24 h) into heparinized collection tubes. Protein precipitation is performed. Compounds are extracted in cold acetonitrile and analyzed by MS. Nonwinlin is used for PK modeling as needed.

Example II

Animal Models

To demonstrate in vivo anti-fibrotic activity, carbon tetrachloride ($CCl_4$) induced liver and bleomycin induced lung and skin rodent fibrosis models are established. These in vivo assays take 6-8 weeks to complete (including full histological analysis). Typical experiments consist of groups of 6-8 animals to be treated with itraconazole (2-4 doses), 1 or 2 test compounds (2-4 doses), vehicle, and benchmark treatments (pirfenidone and AM-152). AM-152 (Amira Pharmaceuticals) is an LPA1 (Lysophosphatidic acid 1) receptor antagonist. This target has been described as relevant to exacerbation of IPF systems in a mouse bleomycin model (British Journal of Pharmacology (2010), 160, 1699-

1713). AM-152 is an advanced compound on this target as has been previously described in more detail in WO 2012/078805.

Bleomycin-induced Lung Fibrosis Model

Nine-week old B6 male mice (Taconic farms) are surgically implanted with osmotic pumps delivering 25 mg/kg bleomycin for seven days. 17 days after surgery mice are treated with drug for 2 weeks. Drug treatments are administered. Previously described anti-fibrotic drugs AM-152 and pirfenidone are used as positive control drugs. Lung sections are stained with Masson's trichrome and following scanning, eight random fields are taken per animal for analysis. Data are represented as mean and s.e.m. Stained lung sections are analyzed according to a modified Ashcroft scoring system and use an unbiased automated image analysis method. Total Masson's trichrome stained area is generated using an automated image analysis macro in Image J. Each image is then converted to an RGB stack, and the threshold for stained area is set such that only lung tissue is included in the analysis while empty spaces such as respiratory ducts and alveoli are excluded. Total stained area is then determined by using the area measurement function within ImageJ. Mean Ashcroft scores and mean percent stained area values are analyzed to determine severity of lung fibrosis.

Carbon Tetrachloride-induced Liver Fibrosis Model

Drug treatments are administered. Liver sections are stained with Sirius Red solution. After scanning, 5 random images per animal are generated. Total percent area positive for Sirius Red staining is generated using an automated image macro in Image J. Briefly, each image is converted to a RGB stack, and the threshold for stained area is set such that no nuclei are included in the analysis. Total red area is quantitatively determined by using the area measurement function within Image J. Pieces of liver from the $CCl_4$-induced liver fibrosis model are homogenized in PBS with a homogenizer and steel balls. Debris is discarded by centrifugation and lysate concentrated determined by Nanodrop absorbance measurements at 260 nm. Equal amounts of lysate are loaded into each gel lane and then separated by SDS-PAGE on 10% Bis-Tris gels and then transferred via semi dry transfer to PVDF membranes. After blocking in 5% milk in TRIS buffered saline with Tween-20 (0.1%), membranes are exposed to appropriate primary antibodies. Blots are incubated with HRP-conjugated secondary antibodies and visualized using film and SuperSignal West Dura Chemiluminescent Substrate (Pierce).

Rodent Wound Healing Model

The effect of itraconazole and test compounds on normal wound healing is evaluated using a rodent wound healing model. Five days prior to the initiation of the model, mice are anesthetized and the back skin hair is removed using Nair. On day 1, mice are weighed and one sterile biopsy punch (5 mm diameter) is made by punching through the full thickness of the folded back skin (2×5 mm dial holes in total). The size of the wounds is measured daily using calipers. Body weight is monitored twice a week thoughout the study. On day land until the end of the study, drug treatment (25 mg/kg, SID of itraconazole, 25 mg/kg SID test compound or vehicle) is administered daily using 5 ml/kg dosing volume. On days 7, 11 and 14, animals are euthanized from each group and wounds are collected for histological analysis. When collecting the wounds, wounds are cut out including a few mm of the surrounding skin. For each animal, two pieces of wound are collected and fixed for histology analysis.

Example III

Phase II Clinical Study for Scleroderma

A phase II placebo controlled randomized double blind clinical trial demonstrates Proof of Concept for an optimized anti-fibrotic itraconazole analogue in patients with diffuse cutaneous scleroderma or systemic scleroderma with diffuse cutaneous involvement. Patients that satisfy the enrollment criteria make up two equal groups of 30. The experimental arm is given a single high dose of drug every day for 6 months and the placebo comparator arm will be given placebo every day for 6 months. The single high dose of drug is determined based on preclinical efficacy, target engagement in a preclinical cynomolgus toxicology study and a phase I safety study. The primary outcome measure is a comparison of the efficacy of drug vs placebo based on percent variation in m-RSS (score 0-51, 17 site) between inclusion and monthly visits. Secondary outcome measures are a comparison of efficacy of drug vs placebo based on variation in m-RSS between inclusion and follow-up time points (1, 3 and 6 months); assessment of target engagement as determined by expression profiling of hedgehog and VEGFR target genes using skin biopsies obtained at inclusion and at 6 months; assessment of skin thickness at inclusion and 6 months using skin biopsies; assessment of treatment of non-cutaneous symptoms in systemic scleroderma patients; assessment of quality of life using a health assessment questionnaire and the Dermatology Quality of Life Index; and assessment of tolerance of treatment using clinical and laboratory monitoring of side effects (including assessment of signs of negative inotropic effects using cardiac ultrasound). Successful Proof of Concept will be established if >40% of patients have m-RSS improvement (defined as decline in m-RSS of ≥5.3 units between baseline and last study visit at 6 months).

The precise target patient population consists of patients diagnosed with diffuse (or severe) cutaneous scleroderma (modified Rodnan skin score, m-RSS≥16/51). Patients diagnosed with localized diffuse cutaneous scleroderma or systemic scleroderma with diffuse cutaneous involvement, as defined by the American College of Rheumatology, are the known patient subsets.

Inclusion and exclusion criteria for patient recruitment of a phase II proof of concept study are as follows. Patients will be 18 years of age or older with documented diagnosis of cutaneous or systemic scleroderma. A baseline m-RSS of ≥16/51 indicative of diffuse cutaneous scleroderma is required. A pre-inclusion cardiac ultrasound ejection fraction score of more than 55% (i.e., normal) is required for inclusion. Patients will be excluded if they have been treated with a drug (e.g., methotrexate, corticosteroids, cyclophosphamide, bosentan) that has the potential to interfere with the course of disease within a 3 month period prior to the start of the trial. Patients suffering from severe organ failure, chronic liver disease (e.g., liver cirrhosis, chronic hepatitis), cancer, chronic illness (e.g., rheumatoid arthritis, systemic lupus erythematosus, diabetes, HIV) or having anomalous blood chemistry will be excluded. Patients having had major surgery less than 4 weeks before inclusion will be excluded. Patients contraindicated to itraconazole, as specified in product specifications, will be excluded. Specifically, patients with evidence of ventricular dysfunction (e.g., congestive heart failure, CHF), at risk of CHF or having been treated with inotropic drugs will be excluded. Patients having suffered myocardial infarction less than 6 months prior to inclusion will be excluded.

Patients included in a phase II proof of concept study are identified and selected for treatment in collaboration with dermatology clinicians at multiple sites within the United States. A coordinating investigator that is a member of the Scleroderma Clinical Trials Consortium oversees patient recruitment and serves as the study chair. Patients are diagnosed with localized diffuse cutaneous scleroderma or systemic scleroderma with diffuse cutaneous involvement. Patients are stratified based on scleroderma diagnosis (i.e., localized or systemic), sex and age to ensure equal distribution within treatment populations. Additionally, patients are stratified based on the severity of cutaneous involvement to ensure an equal number of patients with severe cutaneous involvement (m-RSS≥20/51) within treatment populations. This stratification requires an initial diagnostic test involving cutaneous induration scale and skin biopsy. Patients are required to undergo a cardiac ultrasound diagnostic test prior to inclusion to ensure normal heart function (ejection fraction score>55%).

As there is currently no treatment indicated directly to inhibit fibrosis in scleroderma patients, there is no comparator agent to be used in studies of patients. The new agent is dosed alone. Patients taking any medication are monitored to ensure that the new agent does not alter the pharmacokinetic and metabolism properties of the medication being taken.

The modified Rodnan skin score (m-RSS) is an identified, measurable and validated biomarker used to evaluate clinical efficacy in scleroderma patients. Briefly, total skin surface is arbitrarily divided into 17 sites. In each area, manual palpitation is used to asses a skin score. The skin score varies from 0-3 based on degree of skin thickening (0, uninvolved; 1, mild; 2, moderate; 3, severe). The total skin score is the of sum scores from each of the 17 areas (maximum score of 51). Patients having a score of between 16 and 19 are classified as diffuse and those having a score of ≥20 are classified as severe. This skin scoring system has been demonstrated to correlate very well with the extent of dermal fibrosis and also correlates well with the extent of fibrosis/dysfunction in internal organs (in systemic scleroderma patients). Target engagement in skin can be assessed by monitoring changes in expression of hedgehog and VEGFR target genes using skin biopsies.

Example IV

Phase II Clinical Study for Idiopathic Pulmonary Fibrosis

The purpose of this study is to determine the safety and efficacy of compound of formula (I) and formula (II) for the treatment of idiopathic pulmonary fibrosis, compared with placebo. The clinical trial is interventional. The allocation of the clinical study participants is randomized; the intervention model is parallel assignment; and there is a double blind masking of the study (subject, caregiver, investigator). The present clinical study primarily measures the rate of change of forced vital capacity, and secondarily measures the safety based on AEs, vital signs and clinical laboratory tests.

The inclusion criteria for patient recruitment are as follows:

Both genders between the ages of 40 and 80 years, inclusive, at randomization.

Have clinical symptoms consistent with Idiopathic Pulmonary Fibrosis (IPF).

Have first received a diagnosis of IPF at least 6 months and no more than 48 months before randomization. The date of diagnosis is defined as the date of the first available HRCT or surgical lung biopsy consistent with IPF/UIP.

Have a diagnosis of usual interstitial pulmonary fibrosis (UIP) or IPF by high resolution computed tomography (HRCT) or surgical lung biopsy (SLB)

Extent of fibrotic changes (honeycombing, reticular changes) greater than the extent of emphysema on HRCT scan.

Have no features supporting an alternative diagnosis on transbronchial biopsy, BAL, or SLB, if performed.

Have percent predicted post-bronchodilator FVC between 50% and 80%, inclusive, at screening.

Have a change in post-bronchodilator FVC (measured in liters) between screening and day 1 that is less than a 10% relative difference, calculated as: the absolute value of 100% (screening FVC (L)–day 1 FVC (L))/ screening FVC(L).

Have carbon monoxide diffusing capacity (DLCO) between 30% and 80% (adjusted for hemoglobin and altitude, inclusive, at screening.

Have no evidence of improvement in measures of IPF disease severity over the preceding year, in the investigator's opinion.

Be able to walk 150 meters or more during the 6 minute walk test (6 MWT) at screening.

Demonstrate a decrease in oxygen saturation of 2 percentage points or greater during the 6 MWT at screening (may be performed with supplemental oxygen titrating to keep oxygen saturation levels>88%).

Are able to understand and sign a written informed consent form.

Are able to understand the importance of adherence to study treatment and the study protocol and are willing to comply with all study requirements, including the concomitant medication restrictions, throughout the study.

Women of childbearing potential (WOCBP) and men who are sexually active with WOCBP must use acceptable method(s) of contraception.

The exclusion criteria for patient recruitment are as follows:

i) Target Disease Exclusions
  (1) Has significant clinical worsening of IPF between screening and day 1 (during the screening process), in the opinion of the investigator.
  (2) Has forced expiratory volume in 1 second (FEV1)/ FVC ratio less than 0.8 after administration of bronchodilator at screening.
  (3) Has bronchodilator response, defined by an absolute increase of 12% or greater and an increase of 200 mL in FEV1 or FVC or both after bronchodilator use compared with the values before bronchodilator use at screening.

ii) Medical History and Concurrent Diseases
  (1) Has a history of clinically significant environmental exposure known to cause pulmonary fibrosis.
  (2) Has a known explanation for interstitial lung disease.
  (3) Has a clinical diagnosis of any connective tissue disease.
  (4) Currently has clinically significant asthma or chronic obstructive pulmonary disease.
  (5) Has clinical evidence of active infection.
  (6) Has any history of malignancy likely to result in significant disability or likely to require significant medical or surgical intervention within the next 2 years. This does not include minor surgical procedures for localized cancer (e.g., basal cell carcinoma).
  (7) Has any condition other than IPF that, in the opinion of the investigator, is likely to result in the death of the subject within the next 2 years.

(8) Has a history of end-stage liver disease.
(9) Has a history of end-stage renal disease requiring dialysis.
(10) Has a history of unstable or deteriorating cardiac or pulmonary disease (other than IPF) within the previous 6 months.
(11) Has a history of alcohol or substance abuse in the past 2 years.
(12) Has a family or personal history of long QT syndrome and/or Torsades de Pointes (polymorphic ventricular tachycardia).
(13) Has used any of the following specific therapies within 7 days before screening:
  (a) Investigational therapy, defined as any drug that has not been approved for marketing for any indication in the country of the participating site.
  (b) Any cytotoxic, immunosuppressive, cytokine-modulating, or receptor-antagonist agent, including, but not limited to, azathioprine, bosetan, ambrisentan, cyclophosphamide, cyclosporine, etanercept, iloprost, infliximab, leukotriene antagonists, methotrexate, mycophenolate mofetil, tacrolimus, montelukast, tetrathiomolybdate, tumor necrosis factor alpha inhibitors, NAC, imatinib mesylate, interferon gamma-1b, pirfenidone, and tyrosine kinase inhibitors.
  (c) Colchicine, heparin, and warfarin. Sildenafil (daily use) may be used if given for a non-IPF indication if there is no clinically acceptable alternate therapy for the same indication; intermittent use for erectile dysfunction is allowed.
  (d) Intermittent use of corticosteroids is allowed for acute respiratory worsening.
  (e) Ketoconazole, cyclosporine and steroids for topical and ophthalmic use is permitted.

The invention claimed is:

1. A compound of Formula (I) or Formula (Ia):

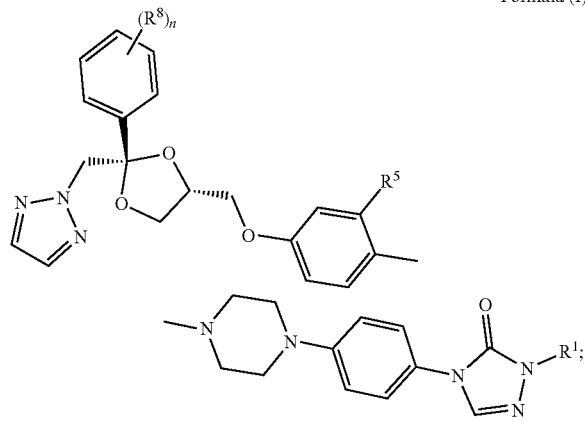

wherein:
$R^1$ is —CH(CH$_3$)CH$_2$CH$_2$CH$_3$ or —CH(CH$_2$CH$_3$)$_2$;
$R^5$ is H, —CN, halogen, haloalkyl, alkyl, —NR$^{13}$R$^{14}$, -alkylene(NR$^{13}$R$^{14}$), and —SO$_2$R$^{13}$;
each $R^8$ is independently selected from halogen, —OH, —NO$_2$, —N$_3$, —CN, alkyl, alkoxy, haloalkoxy, haloalkyl, hydroxyalkyl, alkoxyalkyl, -alkylene(NR$^{13}$R$^{14}$), -alkylene(cycloalkyl), -alkylene(heterocyclyl), cycloalkyl, heterocyclyl, aryl, heteroaryl, —SR$^{13}$, —SOR$^{13}$, —SO$_2$R$^{13}$, —SO$_2$NR$^{13}$R$^{14}$, —NR$^{13}$R$^{14}$, —NR$^{13}$SO$_2$R$^{14}$, —NR$^{13}$C(O)R$^{14}$, —NR$^{13}$C(O)OR$^{14}$, —NR$^{13}$C(O)NR$^{13}$R$^{14}$, —C(O)R$^{14}$, —C(O)OR$^{14}$, and —C(O)NR$^{13}$R$^{14}$; or two adjacent $R^8$ form a heterocyclyl ring;
each $R^{13}$ and each $R^{14}$ is each independently selected from H, alkyl, cycloalkyl, heterocyclylalkyl, haloalkyl, hydroxyalkyl, alkoxyalkyl, arylalkyl, heteroarylalkyl, aryl, and heteroaryl; or $R^{13}$ and $R^{14}$ taken together form a heterocycle with the atoms to which they are attached; and
n is selected from 0, 1, 2, 3, and 4;
or a pharmaceutically acceptable salt, pharmaceutically acceptable solvate, or pharmaceutically acceptable prodrug thereof.

2. The compound of claim 1, wherein $R^1$ is —CH(CH$_2$CH$_3$)$_2$.
3. The compound of claim 1, wherein $R^1$ is —CH(CH$_3$)$_2$—.
4. The compound of claim 1, wherein n is 0.
5. The compound of claim 1, wherein n is 1 or 2.
6. The compound of claim 5, wherein each $R^8$ is independently selected from halogen, —CN, alkyl, alkoxy, haloalkoxy, and haloalkyl.
7. The compound of claim 6, wherein each $R^8$ is halogen.
8. The compound of claim 7, wherein each $R^8$ is Cl.
9. The compound of claim 1, wherein $R^5$ is H.
10. The compound of claim 1, wherein $R^5$ is halogen.
11. The compound of claim 10, wherein $R^5$ is F.
12. The compound of claim 1 having the structure:

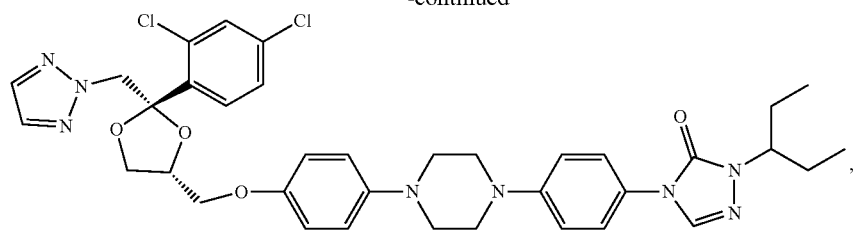
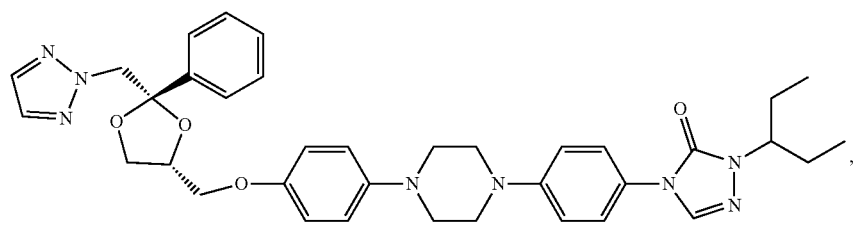
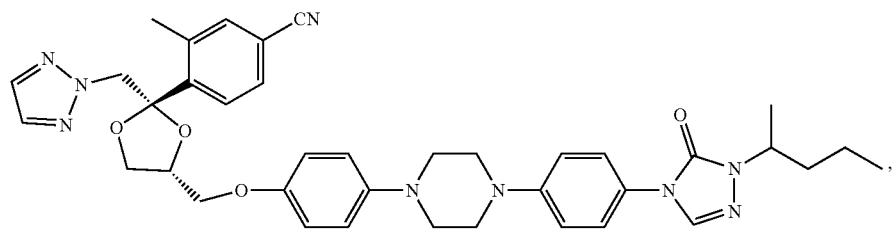
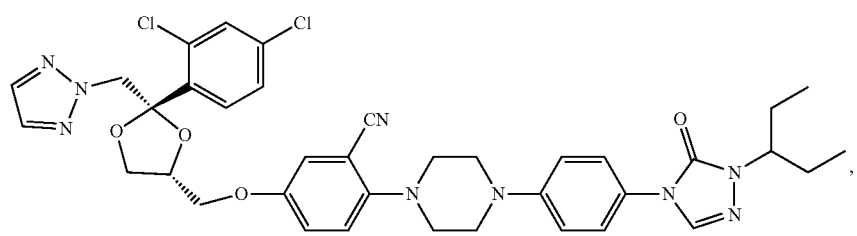
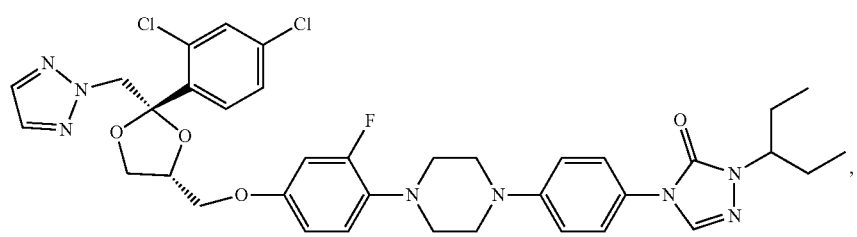
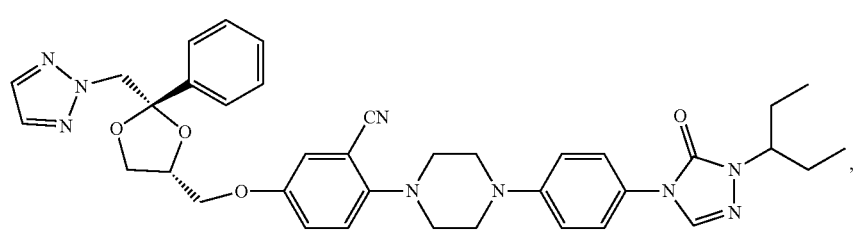
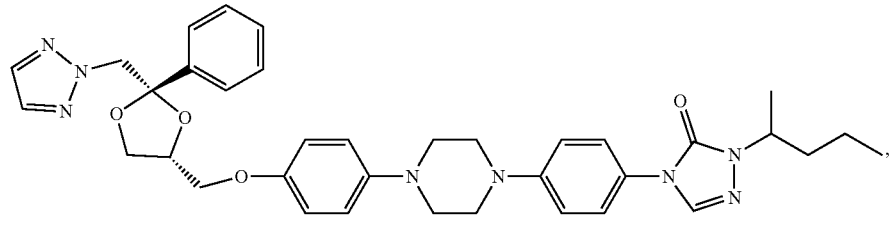

-continued

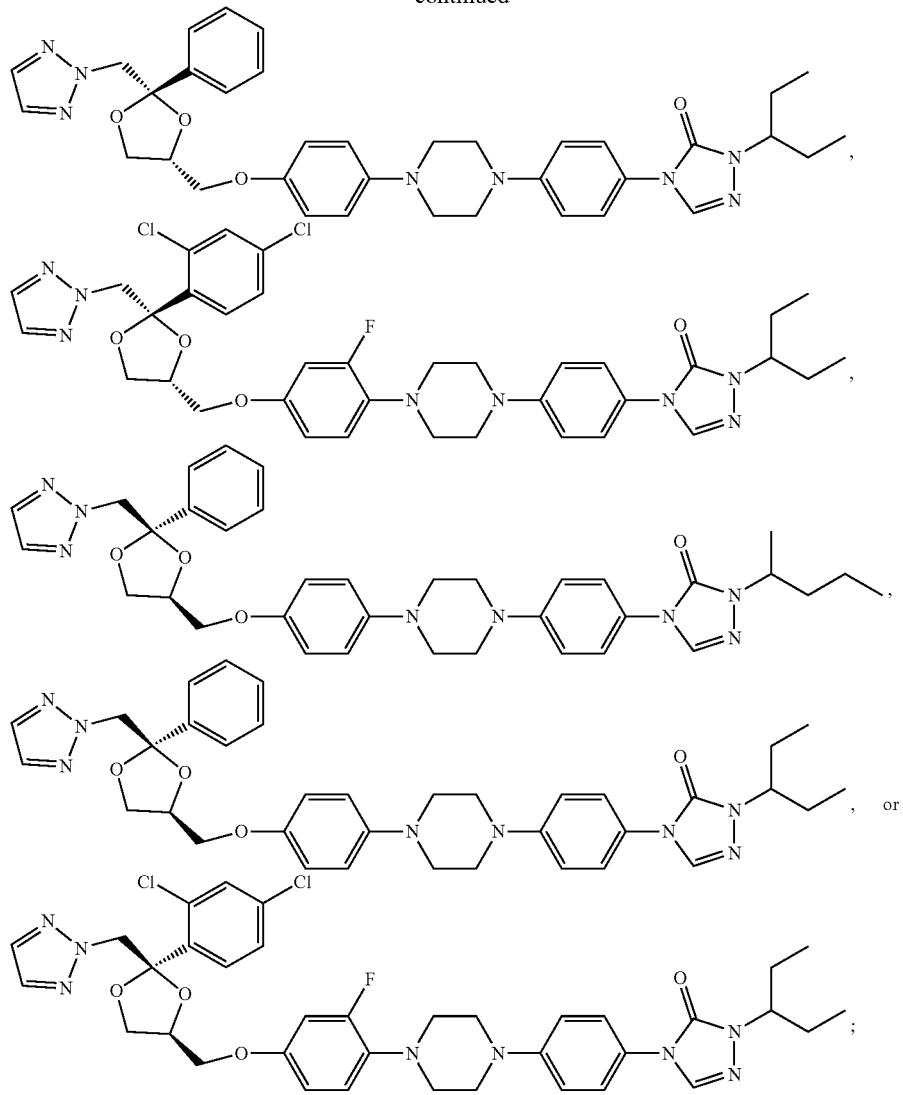

or a pharmaceutically acceptable salt, pharmaceutically acceptable solvate, or pharmaceutically acceptable prodrug thereof.

13. A pharmaceutical composition comprising a compound of claim 1, or a pharmaceutically acceptable salt, pharmaceutically acceptable solvate, or pharmaceutically acceptable prodrug thereof, and a pharmaceutically acceptable excipient.

14. A method of treating fibrosis in a subject comprising administering to the subject a therapeutically effective amount of a compound of claim 1, or a pharmaceutically acceptable salt, pharmaceutically acceptable solvate, or pharmaceutically acceptable prodrug thereof.

15. The method of claim 14 wherein the fibrosis is liver fibrosis, idiopathic pulmonary fibrosis, kidney fibrosis, or cardiac fibrosis.

* * * * *